United States Patent
Dyke et al.

(10) Patent No.: US 9,440,976 B2
(45) Date of Patent: *Sep. 13, 2016

(54) 1,7-DIAZACARBAZOLES AND METHODS OF USE

(71) Applicant: Genentech, Inc., South San Francisco, CA (US)

(72) Inventors: Hazel Joan Dyke, Harlow (GB); Lewis Gazzard, South San Francisco, CA (US); Karen Williams, Harlow (GB); Huifen Chen, South San Francisco, CA (US); Samuel Kintz, South San Francisco, CA (US); Joy Drobnick, South San Francisco, CA (US); Joseph P. Lyssikatos, South San Francisco, CA (US); Simon Goodacre, Harlow (GB); Calum Macleod, Harlow (GB); Charles Ellwood, Harlow (GB)

(73) Assignee: GENENTECH, INC., South San Francisco, CA (US)

( * ) Notice: Subject to any disclaimer, the term of this patent is extended or adjusted under 35 U.S.C. 154(b) by 1 day.

This patent is subject to a terminal disclaimer.

(21) Appl. No.: 14/743,835

(22) Filed: Jun. 18, 2015

(65) Prior Publication Data

US 2015/0328195 A1 Nov. 19, 2015

Related U.S. Application Data

(63) Continuation of application No. 14/182,190, filed on Feb. 17, 2014, now abandoned, which is a continuation of application No. 12/967,864, filed on Dec. 14, 2010, now abandoned.

(60) Provisional application No. 61/287,702, filed on Dec. 17, 2009, provisional application No. 61/284,414, filed on Dec. 16, 2009.

(51) Int. Cl.
*C07D 471/14* (2006.01)
*C07D 453/02* (2006.01)
*A61K 31/5377* (2006.01)
*C07D 519/00* (2006.01)
*A61K 31/4375* (2006.01)
*A61K 31/439* (2006.01)
*A61K 31/4545* (2006.01)
*A61K 31/496* (2006.01)
*A61K 31/55* (2006.01)
*A61K 45/06* (2006.01)

(52) U.S. Cl.
CPC .......... *C07D 471/14* (2013.01); *A61K 31/439* (2013.01); *A61K 31/4375* (2013.01); *A61K 31/4545* (2013.01); *A61K 31/496* (2013.01); *A61K 31/5377* (2013.01); *A61K 31/55* (2013.01); *A61K 45/06* (2013.01); *C07D 453/02* (2013.01); *C07D 519/00* (2013.01)

(58) Field of Classification Search
CPC .............. C07D 471/14; C07D 453/02; A61K 31/5377; A61K 45/06
USPC ............................................. 546/82; 544/126
See application file for complete search history.

(56) References Cited

U.S. PATENT DOCUMENTS

| 8,501,765 B2* | 8/2013 | Chen .................... C07D 471/14 514/248 |
|---|---|---|
| 2006/0009477 A1 | 1/2006 | Matasi et al. |
| 2006/0264493 A1 | 11/2006 | Vanotti et al. |
| 2011/0118230 A1* | 5/2011 | Chen .................... C07D 471/14 514/210.16 |
| 2011/0178053 A1 | 7/2011 | Arendt et al. |
| 2011/0183938 A1 | 7/2011 | Dyke et al. |
| 2012/0208809 A1 | 8/2012 | Babin et al. |
| 2014/0171407 A1 | 6/2014 | Dyke et al. |
| 2015/0087630 A1* | 3/2015 | Chen .................... C07D 471/14 514/210.21 |

FOREIGN PATENT DOCUMENTS

| WO | 0168648 A1 | 9/2001 |
|---|---|---|
| WO | 03039545 A2 | 5/2003 |
| WO | 2007044779 A1 | 4/2007 |
| WO | 2008045834 A2 | 4/2008 |
| WO | 2008054956 A2 | 5/2008 |
| WO | 2009004329 A1 | 1/2009 |
| WO | 2009129401 A1 | 10/2009 |
| WO | 2009150381 A2 | 12/2009 |

(Continued)

OTHER PUBLICATIONS

Bahekar, et al., "Synthesis of 3, 8, 9-trisubstituted-1, 7, 9-triazafluorene-6-carboxylic acid derivatives as a new class of insulin secretagogues", Bioorg Med Chem 15 (17), 5950-5964 (2007).

(Continued)

*Primary Examiner* — Rita Desai
(74) *Attorney, Agent, or Firm* — Viksnins Harris & Padys PLLP

(57) ABSTRACT

The invention relates to 1,7-diazacarbazole compounds of Formula (I), (I-a) and (I-b) which are useful as kinase inhibitors, more specifically useful as checkpoint kinase 1 (chk1) inhibitors, thus useful as cancer therapeutics. The invention also relates to compositions, more specifically pharmaceutical compositions comprising these compounds and methods of using the same to treat various forms of cancer and hyperproliferative disorders, as well as methods of using the compounds for in vitro, in situ, and in vivo diagnosis or treatment of mammalian cells, or associated pathological conditions.

5 Claims, No Drawings

(56) References Cited

FOREIGN PATENT DOCUMENTS

| WO | 2009151598 A1 | 12/2009 |
| WO | 2010015589 A1 | 2/2010 |
| WO | 2010109084 A2 | 9/2010 |

OTHER PUBLICATIONS

Bartek, et al., "Chk1 and Chk2 kinases in checkpoint control and cancer", Cancer Cell 3 (5), 421-429 (2003).
Bartek, et al., "CHK2 kinase—a busy messenger", Nat. Rev. Mol. Cell Biol. 2 (12), 877-886 (2001).
Bhatti, et al., "Pyrolysis of 1-substitued pyrazoles and chloroform at 550 C: formation of a-carboline from 1-benzylpyrazoles", Journal of the Chemical Society, Perkin Transactions I, vol. 1997, 3581-3585 (1997).
Hartwell, et al., "Checkpoints: controls that ensure the order of cell cycle events", Science 246 (4930), 629-634 (1989).
Hayakawa, et al., "Synthesis and biological evaluation of pyrido[3',2-d]pyrimidine derivatives as novel PI3 kinase p100α inhibitors", Bioorg Med Chem Lett 17 (9), 2438-2442 (2007).
Jordan, "Tamoxifen: a most unlikely pioneering medicine", Nature Reviews: Drug Discovery 2, 205-213 (2003).
Patent Cooperation Treaty, International Searching Authority, Search Report and Written Opinion for PCT/EP2010/069771.
Vippagunta, et al., "Crystalline solids", Adv. Drug Delivery Rev. 48, 3-26 (2001).
Yakhontov, "Derivatives of Azaindoles", Caplus English Abstract DN 64:104132 (1966).

* cited by examiner

1,7-DIAZACARBAZOLES AND METHODS OF USE

CROSS REFERENCE TO RELATED APPLICATIONS

This application is a continuation of U.S. patent application Ser. No. 14/182,190, filed Feb. 17, 2014, which is a continuation of U.S. patent application Ser. No. 12/967,864, filed Dec. 14, 2010, which claims the benefit of U.S. Provisional Patent Application Ser. No. 61/287,702, filed Dec. 17, 2009, and U.S. Provisional Patent Application Ser. No. 61/284,414, filed Dec. 16, 2009, the disclosures of which are incorporated herein by reference in its entirety.

BACKGROUND OF THE INVENTION

The invention relates to 1,7-diazacarbazole compounds which are useful as kinase inhibitors, more specifically useful as checkpoint kinase 1 (chk1) inhibitors, thus useful as cancer therapeutics. The invention also relates to compositions, more specifically pharmaceutical compositions comprising these compounds and methods of using the same to treat various forms of cancer and hyperproliferative disorders, as well as methods of using the compounds for in vitro, in situ, and in vivo diagnosis or treatment of mammalian cells, or associated pathological conditions.

Individual cells replicate by making an exact copy of their chromosomes, and then segregating these into separate cells. This cycle of DNA replication, chromosome separation and division is regulated by mechanisms within the cell that maintain the order of the steps and ensure that each step is precisely carried out. Involved in these processes are the cell cycle checkpoints (Hartwell et al., Science, Nov. 3, 1989, 246(4930):629-34) where cells may arrest to ensure DNA repair mechanisms have time to operate prior to continuing through the cycle into mitosis. There are two such checkpoints in the cell cycle—the G1/S checkpoint that is regulated by p53 and the G2/M checkpoint that is monitored by the serine/threonine kinase checkpoint kinase 1 (chk1).

Chk1 and chk2 are structurally unrelated yet functionally overlapping serine/threonine kinases activated in response to genotoxic stimuli (reviewed in Bartek et al., Nat. Rev. Mol. Cell Biol. 2001, vol. 2, pp. 877-886). Chk1 and chk2 relay the checkpoint signals from the ATM and ATR, which phosphorylate and activate them. Chk2 is a stable protein expressed throughout the cell cycle, activated mainly by ATM in response to double-strand DNA breaks (DSBs). In contrast, Chk1 protein expression is largely restricted to S and G2 phases. In response to DNA damage, ChK1 is phosphorylated and activated by ATM/ATR, resulting in cell cycle arrest in the S and G2/M phases to allow for repair of DNA damage (reviewed in Cancer Cell, Bartek and Lukas, Volume 3, Issue 5, May 2003, Pages 421-429. Inhibition of Chk1 has been shown to abrogate cell cycle arrest leading to enhanced tumor cell death following DNA damage by a range of chemotherapeutics. Cells lacking intact G1 checkpoints are particularly dependent on S and G2/M checkpoints and are therefore expected to be more sensitive to chemotherapeutic treatment in the presence of a chk1 inhibitor, whereas normal cells with functional G1 checkpoints would be predicted to undergo less cell death.

SUMMARY OF THE INVENTION

The invention relates to 1,7-diazacarbazoles of Formula (I), (I-a), and/or (I-b) (and/or solvates, hydrates and/or salts thereof) with kinase inhibitory activity, more specifically with chk1 inhibitory activity. The compounds of the present invention are also useful as inhibitors of Glycogen Synthase Kinase-3 (GSK-3), KDR kinase, and FMS-like tyrosine kinase 3 (FLT3). Accordingly, the compounds of the invention and compositions thereof are useful in the treatment of hyperproliferative disorders such as cancer.

One embodiment of the invention provides compounds of formula (I)

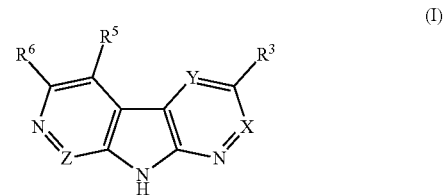

(I)

or pharmaceutically acceptable salts thereof,
wherein:
X is $CR^2$ or N;
Y is $CR^4$ or N;
Z is $CR^8$ or N; provided that no more than one of X, Y and Z is N at the same time;
$R^2$ is H, halo, CN, $CF_3$, —$OCF_3$, OH, —$NO_2$, $C_1$-$C_5$ alkyl, —$O(C_1$-$C_5$ alkyl), —$S(C_1$-$C_5$ alkyl), or $N(R^{22})_2$;
$R^3$ is H, halo, CN, —O—$R^9$, —$N(R^{22})$—$R^9$, —$S(O)_p$—$R^9$, or $R^9$;
p is 0, 1 or 2;
$R^4$ is H, halo, CN, $CF_3$, —$OCF_3$, OH, —$NO_2$, —$(CR^{14}R^{15})_nC(=Y')OR^{11}$, —$(CR^{14}R^{15})_nC(=Y')NR^{11}R^{12}$, —$(CR^{14}R^{15})_nNR^{11}R^{12}$, —$(CR^{14}R^{15})_nOR^{11}$, —$(CR^{14}R^{15})_nS(O)_pR^{11}$, —$(CR^{14}R^{15})_nNR^{12}C(=Y')R^{11}$, —$(CR^{14}R^{15})_nNR^{12}C(=Y')OR^{11}$, —$(CR^{14}R^{15})_nNR^{12}C(=Y')NR^{11}R^{12}$, —$(CR^{14}R^{15})_nNR^{12}SO_2R^{11}$, —$(CR^{14}R^{15})_nOC(=Y')R^{11}$, —$(CR^{14}R^{15})_nOC(=Y')NR^{11}R^{12}$, —$(CR^{14}R^{15})_nS(O)_2NR^{11}R^{12}$, alkyl, alkenyl, alkynyl, cycloalkyl, heterocyclyl, aryl, or heteroaryl wherein said alkyl, alkenyl, alkynyl, cycloalkyl, heterocyclyl, aryl and heteroaryl are optionally substituted with one to four $R^{13}$ groups;
each n is independently 0-5;
$R^5$ is H, halo, CN, $CF_3$, —$OCF_3$, OH, —$NO_2$, —$(CR^{14}R^{15})_nC(=Y')OR^{11}$, —$(CR^{14}R^{15})_nC(=Y')NR^{11}R^{12}$, —$(CR^{14}R^{15})_nNR^{12}C(=Y')R^{11}$, —$(CR^{14}R^{15})_nNR^{11}R^{12}$, —$(CR^{14}R^{15})_nOR^{11}$, —$(CR^{14}R^{15})_nS(O)_pR^{11}$, —$(CR^{14}R^{15})_nNR^{12}C(=Y')OR^{11}$, —$(CR^{14}R^{15})_nNR^{12}C(=Y')NR^{11}R^{12}$, —$(CR^{14}R^{15})_nNR^{12}SO_2R^{11}$, —$(CR^{14}R^{15})_nOC(=Y')R^{11}$, —$(CR^{14}R^{15})_nOC(=Y')NR^{11}R^{12}$, —$(CR^{14}R^{15})_nS(O)_2NR^{11}R^{12}$, alkyl, alkenyl, alkynyl, cycloalkyl, heterocyclyl, aryl, heteroaryl wherein the said alkyl, alkenyl, alkynyl, cycloalkyl, heterocyclyl, aryl and heteroaryl are optionally substituted with one to four $R^{13}$ groups;
$R^6$ is H, CN, —$CF_3$, —$OCF_3$, halo, —$C(=Y')OR^{11}$, —$C(=Y')NR^{11}R^{12}$, —$OR^{11}$, —$OC(=Y')R^{11}$, —$NR^{11}R^{12}$, —$NR^{12}C(=Y')R^{11}$, —$NR^{12}C(=Y')NR^{11}R^{12}$, $NR^{12}S(O)_qR^{11}$, —$SR^{11}$, —$S(O)R^{11}$, —$S(O)_2R^{11}$, —$OC(=Y')NR^{11}R^{12}$, —$S(O)_2NR^{11}R^{12}$, alkyl, alkenyl, alkynyl, cycloalkyl, heterocyclyl, aryl, or heteroaryl wherein said alkyl, alkenyl, alkynyl, cycloalkyl, heterocyclyl, aryl and heteroaryl are optionally substituted by one to four $R^{13}$ groups;

$R^7$ is H, OH, CN, O($C_1$-$C_3$ alkyl), or $C_1$-$C_4$ alkyl, wherein each said alkyl is optionally substituted with one to three groups independently selected from halo, N($R^{22}$)$_2$ or O$R^{22}$;

$R^8$ is H, halo, CN, NO$_2$, N($R^{22}$)$_2$, OH, O($C_1$-$C_3$ alkyl), or $C_1$-$C_3$ alkyl, wherein each said alkyl is optionally substituted with one to three fluoro groups;

each $R^9$ is independently alkyl, alkenyl, alkynyl, cycloalkyl, heterocyclyl, aryl, heteroaryl, wherein each member of $R^9$ is independently substituted with one to three $R^{10}$ groups;

each $R^{10}$ is independently H, CN, —CF$_3$, —OCF$_3$, —NO$_2$, halo, $R^{11}$, —O$R^{11}$, —N$R^{12}$C(=Y')$R^{11}$, —N$R^{12}$C(=N$R^{12}$)$R^{11}$, —N$R^{12}$S(O)$_q$$R^{11}$, —S$R^{11}$, —N$R^{11}$$R^{12}$, oxo, —C(=Y')O$R^{11}$, —C(=Y')N$R^{11}$$R^{12}$, —S(O)$_q$$R^{11}$, —N$R^{12}$C(=Y')O$R^{11}$, —N$R^{12}$C(=Y')N$R^{11}$$R^{12}$, —OC(=Y')$R^{11}$, —OC(=Y')N$R^{11}$$R^{12}$, or —S(O)$_2$N$R^{11}$$R^{12}$;

each q independently is 1 or 2;

$R^{11}$ and $R^{12}$ are independently H, alkyl, cycloalkyl, heterocyclyl, aryl or heteroaryl, wherein said alkyl, cycloalkyl, heterocyclyl, aryl and heteroaryl are optionally substituted with one to four $R^{13}$ groups, wherein two geminal $R^{13}$ groups are optionally taken together with the atom to which they are attached to form a 3-6 membered ring having additional 0-2 heteroatoms selected from O, S, and N, said ring being optionally substituted with one to four $R^{18}$ groups;

$R^{11}$ and $R^{12}$ are optionally taken together with the attached N atom to form a 4-7 membered ring having additional 0-2 heteroatoms selected from O, S, and N, said ring being optionally substituted with one to four $R^{13}$ groups;

each $R^{13}$ is independently halo, CN, CF$_3$, —OCF$_3$, —NO$_2$, oxo, —(C$R^{14}$$R^{15}$)$_n$C(=Y')$R^{16}$, —(C$R^{14}$$R^{15}$)$_n$C(=Y')O$R^{16}$, —(C$R^{14}$$R^{15}$)$_n$C(=Y')N$R^{16}$$R^{17}$, —(C$R^{14}$$R^{15}$)$_n$N$R^{16}$$R^{17}$, —(C$R^{14}$$R^{15}$)$_n$O$R^{16}$, —(C$R^{14}$$R^{15}$)$_n$S$R^{16}$, —(C$R^{14}$$R^{15}$)$_n$N$R^{16}$C(=Y')$R^{17}$, —(C$R^{14}$$R^{15}$)$_n$N$R^{16}$C(=Y')O$R^{17}$, —(C$R^{14}$$R^{15}$)$_n$N$R^{17}$C(=Y')N$R^{16}$$R^{17}$, —(C$R^{14}$$R^{15}$)$_n$N$R^{17}$SO$_2$$R^{16}$, —(C$R^{14}$$R^{15}$)$_n$OC(=Y')$R^{16}$, —(C$R^{14}$$R^{15}$)$_n$OC(=Y')N$R^{16}$$R^{17}$, —(C$R^{14}$$R^{15}$)$_n$S(O)$R^{16}$, —(C$R^{14}$$R^{15}$)$_n$S(O)$_2$$R^{16}$, —(C$R^{14}$$R^{15}$)$_n$S(O)$_2$N$R^{16}$$R^{17}$, or $R^{16}$;

$R^{14}$ and $R^{15}$ are independently selected from H, alkyl, cycloalkyl, heterocyclyl, aryl or heteroaryl, wherein said alkyl, cycloalkyl, heterocyclyl, aryl and heteroaryl are optionally substituted with one to four $R^{18}$ groups;

$R^{16}$ and $R^{17}$ are independently H, alkyl, cycloalkyl, heterocyclyl, aryl or heteroaryl, wherein said alkyl, cycloalkyl, heterocyclyl, aryl and heteroaryl are optionally substituted with one to four $R^{18}$ groups;

$R^{16}$ and $R^{17}$ are optionally taken together with the attached N atom to form a 5-6 membered ring having additional 0-2 heteroatoms selected from O, S, and N, said ring being optionally substituted with one to four $R^{18}$ groups;

each $R^{18}$ is independently H, alkyl, cycloalkyl, heterocyclyl, aryl, heteroaryl, halo, CN, CF$_3$, —OCF$_3$, —NO$_2$, oxo, —(C$R^{19}$$R^{20}$)$_n$C(=Y')$R^{23}$, —(C$R^{19}$$R^{20}$)$_n$C(=Y')O$R^{23}$, —(C$R^{19}$$R^{20}$)$_n$C(=Y')N$R^{23}$$R^{24}$, —(C$R^{19}$$R^{20}$)$_n$N$R^{23}$$R^{24}$, —(C$R^{19}$$R^{20}$)$_n$O$R^{23}$, —(C$R^{19}$$R^{20}$)$_n$—S$R^{23}$, —(C$R^{19}$$R^{20}$)$_n$N$R^{24}$C(=Y')$R^{23}$, —(C$R^{19}$$R^{20}$)$_n$N$R^{24}$C(=Y')O$R^{23}$, —(C$R^{19}$$R^{20}$)$_n$N$R^{22}$C(=Y')N$R^{23}$$R^{24}$, —(C$R^{19}$$R^{20}$)$_n$N$R^{24}$SO$_2$$R^{23}$, —(C$R^{19}$$R^{20}$)$_n$OC(=Y')$R^{23}$, —(C$R^{19}$$R^{20}$)$_n$OC(=Y')N$R^{23}$$R^{24}$, —(C$R^{19}$$R^{20}$)$_n$S(O)$R^{23}$, —(C$R^{19}$$R^{20}$)$_n$S(O)$_2$$R^{23}$, or —(C$R^{19}$$R^{20}$)$_n$S(O)$_2$N$R^{23}$$R^{24}$, wherein said alkyl, cycloalkyl, heterocyclyl, aryl, and heteroaryl are optionally substituted with one to four $R^{21}$ groups;

$R^{19}$ and $R^{20}$ are independently H, alkyl, cycloalkyl, heterocyclyl, aryl or heteroaryl, wherein said alkyl, cycloalkyl, heterocyclyl, aryl and heteroaryl are optionally substituted with one to four $R^{25}$ groups;

$R^{23}$ and $R^{24}$ are independently H, alkyl, cycloalkyl, heterocyclyl, aryl or heteroaryl, wherein said alkyl, cycloalkyl, heterocyclyl, aryl and heteroaryl are optionally substituted with one to four $R^{21}$ groups;

$R^{23}$ and $R^{24}$ are optionally taken together with the attached N atom to form a 5-6 membered ring having additional 0-2 heteroatoms selected from O, S, and N, said ring being optionally substituted with one to four $R^{21}$ groups;

each $R^{21}$ is independently H, alkyl, cycloalkyl, heterocyclyl, aryl, heteroaryl, halo, CN, CF$_3$, —OCF$_3$, —NO$_2$, oxo, —C(=Y')$R^{25}$, —C(=Y')O$R^{25}$, —C(=Y')N$R^{25}$$R^{26}$, —N$R^{25}$$R^{26}$, —O$R^{25}$, —S$R^{25}$, —N$R^{26}$C(=Y')$R^{25}$, —N$R^{26}$C(=Y')O$R^{25}$, —N$R^{22}$C(=Y')N$R^{25}$$R^{26}$, —N$R^{26}$SO$_2$$R^{25}$, —OC(=Y')$R^{25}$, —OC(=Y')N$R^{25}$$R^{26}$, —S(O)$R^{25}$, —S(O)$_2$$R^{25}$, or —S(O)$_2$N$R^{25}$$R^{26}$, wherein said alkyl, cycloalkyl, heterocyclyl, aryl, and heteroaryl are optionally substituted with one to four $R^{25}$ groups;

each $R^{25}$ and $R^{26}$ is independently H, alkyl, cycloalkyl, heterocyclyl, aryl, or heteroaryl, wherein said alkyl, cycloalkyl, heterocyclyl, aryl, or heteroaryl is optionally substituted with one to four groups selected from halo, —CN, —OCF$_3$, —CF$_3$, —NO$_2$, —C$_1$-C$_6$ alkyl, —OH, oxo, —SH, —O(C$_1$-C$_6$ alkyl), —S(C$_1$-C$_6$ alkyl), —NH$_2$, —NH(C$_1$-C$_6$ alkyl), —N(C$_1$-C$_6$ alkyl)$_2$, —SO$_2$(C$_1$-C$_6$ alkyl), —CO$_2$H, —CO$_2$(C$_1$-C$_6$ alkyl), —C(O)NH$_2$, —C(O)NH(C$_1$-C$_6$ alkyl), —C(O)N(C$_1$-C$_6$ alkyl)$_2$, —N(C$_1$-C$_6$ alkyl)C(O)(C$_1$-C$_6$ alkyl), —NHC(O)(C$_1$-C$_6$ alkyl), —NHSO$_2$(C$_1$-C$_6$ alkyl), —N(C$_1$-C$_6$ alkyl)SO$_2$(C$_1$-C$_6$ alkyl), —SO$_2$NH$_2$, —SO$_2$NH(C$_1$-C$_6$ alkyl), —SO$_2$N(C$_1$-C$_6$ alkyl)$_2$, —OC(O)NH$_2$, —OC(O)NH(C$_1$-C$_6$ alkyl), —OC(O)N(C$_1$-C$_6$ alkyl)$_2$, —NHC(O)NH(C$_1$-C$_6$ alkyl), —NHC(O)N(C$_1$-C$_6$ alkyl)$_2$, —N(C$_1$-C$_6$ alkyl)C(O)NH(C$_1$-C$_6$ alkyl), —N(C$_1$-C$_6$ alkyl)C(O)N(C$_1$-C$_6$ alkyl)$_2$, —NHC(O)NH(C$_1$-C$_6$ alkyl), —NHC(O)N(C$_1$-C$_6$ alkyl)$_2$, —NHC(O)O(C$_1$-C$_6$ alkyl), and —N(C$_1$-C$_6$ alkyl)C(O)O(C$_1$-C$_6$ alkyl);

$R^{25}$ and $R^{26}$ are optionally taken together with the attached N atom to form a 5-6 membered ring having additional 0-2 heteroatoms selected from O, S, and N, said ring being optionally substituted with one to four groups selected from halo, —CN, —OCF$_3$, CF$_3$, —NO$_2$, —C$_1$-C$_6$ alkyl, —OH, oxo, —SH, —O(C$_1$-C$_6$ alkyl), —S(C$_1$-C$_6$ alkyl), —NH$_2$, —NH(C$_1$-C$_6$ alkyl), —N(C$_1$-C$_6$ alkyl)$_2$, —SO$_2$(C$_1$-C$_6$ alkyl), —CO$_2$H, —CO$_2$(C$_1$-C$_6$ alkyl), —C(O)NH$_2$, —C(O)NH(C$_1$-C$_6$ alkyl), —C(O)N(C$_1$-C$_6$ alkyl)$_2$, —N(C$_1$-C$_6$ alkyl)C(O)(C$_1$-C$_6$ alkyl), —NHC(O)(C$_1$-C$_6$ alkyl), —NHSO$_2$(C$_1$-C$_6$ alkyl), —N(C$_1$-C$_6$ alkyl)SO$_2$(C$_1$-C$_6$ alkyl), —SO$_2$NH$_2$, —SO$_2$NH(C$_1$-C$_6$ alkyl), —SO$_2$N(C$_1$-C$_6$ alkyl)$_2$, —OC(O)NH$_2$, —OC(O)NH(C$_1$-C$_6$ alkyl), —OC(O)N(C$_1$-C$_6$ alkyl)$_2$, —NHC(O)NH(C$_1$-C$_6$ alkyl), —NHC(O)N(C$_1$-C$_6$ alkyl)$_2$, —N(C$_1$-C$_6$ alkyl)C(O)NH(C$_1$-C$_6$ alkyl), —N(C$_1$-C$_6$ alkyl)C(O)N(C$_1$-C$_6$ alkyl)$_2$, —NHC(O)NH(C$_1$-C$_6$ alkyl), —NHC(O)N(C$_1$-C$_6$ alkyl)$_2$, —NHC(O)O(C$_1$-C$_6$ alkyl), and —N(C$_1$-C$_6$ alkyl)C(O)O(C$_1$-C$_6$ alkyl);

Y' is independently O, N$R^{22}$, or S;

each $R^{22}$ is independently H or C$_1$-C$_5$ alkyl; and provided that (1) $R^2$, $R^3$, $R^4$, $R^5$, $R^6$, and $R^8$ are not H at the same time; and (2) when X is CH, Y is CH, $R^5$ is H, Z is C$R^8$, and $R^3$ is H or alkyl, then $R^6$ is not —C(=Y')O$R^{11}$.

The present invention includes a composition (e.g., a pharmaceutical composition) comprising a compound of Formula (I), (I-a), and/or (I-b) (and/or solvates, hydrates and/or salts thereof) and a carrier (a pharmaceutically acceptable carrier). The present invention also includes a composition (e.g., a pharmaceutical composition) comprising a compound of Formula (I), (I-a), and/or (I-b) (and/or solvates, hydrates and/or salts thereof) and a carrier (a pharmaceutically acceptable carrier), further comprising a second chemotherapeutic agent. The present compositions are therefore useful for inhibiting abnormal cell growth or treating a hyperproliferative disorder in a mammal (e.g., human), such as cancer.

The present invention includes a method of inhibiting abnormal cell growth or treating a hyperproliferative disorder in a mammal (e.g., human) such as cancer comprising administering to said mammal a therapeutically effective amount of a compound of Formula (I), (I-a), and/or (I-b) (and/or solvates, hydrates and/or salts thereof) or a composition thereof, alone or in combination with a second chemotherapeutic agent.

The present invention includes a method of using the present compounds for in vitro, in situ, and in vivo diagnosis or treatment of mammalian cells, organisms, or associated pathological conditions. Also included are methods for making the present compounds.

DETAILED DESCRIPTION OF THE INVENTION

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls.

The term "alkyl" as used herein refers to a saturated linear or branched-chain monovalent hydrocarbon radical of one to twelve carbon atoms. Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, 1-heptyl, 1-octyl, and the like.

The term "alkenyl" refers to linear or branched-chain monovalent hydrocarbon radical of two to twelve carbon atoms with at least one site of unsaturation, i.e., a carbon-carbon, $sp^2$ double bond, wherein the alkenyl radical includes radicals having "cis" and "trans" orientations, or alternatively, "E" and "Z" orientations. Examples include, but are not limited to, ethylenyl or vinyl (—$CH=CH_2$), allyl (—$CH_2CH=CH_2$), and the like.

The term "alkynyl" refers to a linear or branched monovalent hydrocarbon radical of two to twelve carbon atoms with at least one site of unsaturation, i.e., a carbon-carbon, sp triple bond. Examples include, but are not limited to, ethynyl (—$C≡CH$), propynyl (propargyl, —$CH_2C≡CH$), and the like.

The term "cycloalkyl" refers to a monovalent non-aromatic, saturated or partially unsaturated ring having 3 to 12 carbon atoms as a monocyclic ring or 6 to 12 carbon atoms as a bicyclic ring. Bicyclic carbocycles having 6 to 12 atoms can be arranged, for example, as a bicyclo[4,5], [5,5], [5,6] or [6,6] system, and bicyclic carbocycles having 9 or 10 ring atoms can be arranged as a bicyclo[5,6] or [6,6] system, or as bridged systems such as bicyclo[2.2.1]heptane, bicyclo[2.2.2]octane and bicyclo[3.2.2]nonane. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like.

"Aryl" means a monovalent aromatic hydrocarbon radical of 6-14 carbon atoms derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic or heterocyclic ring. Typical aryl groups include, but are not limited to, radicals derived from benzene (phenyl), substituted benzenes, naphthalene, anthracene, indenyl, indanyl, 1,2-dihydronapthalene, 1,2,3,4-tetrahydronapthyl, and the like.

The terms "heterocycle," "heterocyclyl" and "heterocyclic ring" are used interchangeably herein and refer to a saturated or a partially unsaturated (i.e., having one or more double bonds within the ring) carbocyclic radical of 3 to 14 ring atoms in which at least one ring atom is a heteroatom selected from nitrogen, oxygen and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, and S) or a bicycle having 6 to 10 ring members (4 to 9 carbon atoms and 1 to 6 heteroatoms selected from N, O, and S), for example: a bicyclo[4,5], [5,5], [5,6], or [6,6] system or a bridged [2.1.1], [2.2.1], [2.2.2] or [3.2.2] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidinyl, morpholinyl, thiomorpholinyl, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, pyrazolidinylimidazolinyl, imidazolidinyl, 3-azabicyco[3.1.0]hexanyl, 3-azabicyclo[4.1.0]heptanyl, and azabicyclo[2.2.2]hexanyl. Spiro moieties are also included within the scope of this definition. Examples of a heterocyclic group wherein ring atoms are substituted with oxo (=O) moieties are pyrimidinonyl and 1,1-dioxo-thiomorpholinyl.

The term "heteroaryl" refers to a monovalent aromatic radical of 5- or 6-membered rings, and includes fused ring systems (at least one of which is aromatic) of 5-16 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

The heterocycle or heteroaryl groups may be carbon (carbon-linked) or nitrogen (nitrogen-linked) attached where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiophene, tetrahydrothiophene, pyrrole or pyrrolidine, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, 2-oxo-1,2-dihydropyridine, or 4-oxo-1,4-dihydropyridine; position 2 of a isoindole, or isoindoline; position 4 of a morpholine; and position 9 of a carbazole, or β-carboline.

The term "halo" refers to F, Cl, Br or I. The heteroatoms present in heteroaryl or heterocyclyl include the oxidized forms such as $N^+ \rightarrow O^-$, $S(O)$ and $S(O)_2$.

The terms "treat" and "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The terms "abnormal cell growth" and "hyperproliferative disorder" are used interchangeably in this application. "Abnormal cell growth", as used herein, unless otherwise indicated, refers to cell growth that is independent of normal regulatory mechanisms. This includes, for example, the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; (3) any tumors that proliferate by receptor tyrosine kinases; (4) any tumors that proliferate by aberrant serine/threonine kinase activation; and (5) benign and malignant cells of other proliferative diseases in which aberrant serine/threonine kinase activation occurs.

The terms "cancer" and "cancerous" refer to or describe the physiological condition in mammals that is typically characterized by unregulated cell growth. A "tumor" comprises one or more cancerous cells. Tumors include solid and liquid tumors. Examples of cancer include, but are not limited to, carcinoma, lymphoma, blastoma, sarcoma, myeloma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, malignant brain tumors, melanoma, endometrial or uterine carcinoma, salivary gland carcinoma, kidney or renal cancer, prostate cancer, vulval cancer, thyroid cancer, hepatic carcinoma, anal carcinoma, penile carcinoma, head and neck cancer, as well as acute myelogenous leukemia (AML).

A "chemotherapeutic agent" is a chemical compound useful in the treatment of cancer. Examples of chemotherapeutic agents include Erlotinib (TARCEVA®, Genentech/OSI Pharm.), Bortezomib (VELCADE®, Millennium Pharm.), Fulvestrant (FASLODEX®, AstraZeneca), Sutent (SU11248, Pfizer), Letrozole (FEMARA®, Novartis), Imatinib mesylate (GLEEVEC®, Novartis), PTK787/ZK 222584 (Novartis), Oxaliplatin (Eloxatin®, Sanofi), Leucovorin, Rapamycin (Sirolimus, RAPAMUNE®, Wyeth), Lapatinib (TYKERB®, GSK572016, Glaxo Smith Kline), Lonafarnib (SCH 66336), Sorafenib (BAY43-9006, Bayer Labs), and Gefitinib (IRESSA®, AstraZeneca), AG1478, AG1571 (SU 5271; Sugen), alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB 1-TM1); eleutherobin; pancratistatin; a sarcodictyin; spongistatin; folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; bestrabucil; bisantrene; edatraxate; defofamine; demecolcine; diaziquone; elfornithine; elliptinium acetate; an epothilone; etoglucid; gallium nitrate; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2''-trichlorotriethylamine; trichothecenes (especially T-2 toxin, verracurin A, roridin A and anguidine); urethan; dacarbazine; mannomustine; mitobronitol; mitolactol; pipobroman; gacytosine; arabinoside ("Ara-C"); chloranmbucil; 6-thioguanine; mercaptopurine; ifosfamide; mitoxantrone; novantrone; edatrexate; daunomycin; aminopterin; capecitabine (XELODA®); ibandronate; CPT-11; difluoromethylornithine (DMFO); and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; a topoisomerase 1 inhibitor such as LURTOTECAN®; ABARELIX® rmRH; (ix) anti-angiogenic agents such as bevacizumab (AVASTIN®, Genentech); and (x) pharmaceutically acceptable salts, acids and derivatives of any of the above.

Other examples of "chemotherapeutic agents" that can be used in combination with the present compounds include inhibitors of MEK (MAP kinase kinase), such as XL518 (Exelixis, Inc.) and AZD6244 (Astrazeneca); inhibitors of Raf, such as XL281 (Exelixis, Inc.), PLX4032 (Plexxikon), and ISIS5132 (Isis Pharmaceuticals); inhibitors of mTor (mammalian target of rapamycin), such as rapamycin, AP23573 (Ariad Pharmaceuticals), temsirolimus (Wyeth Pharmaceuticals) and RAD001 (Novartis); inhibitors of PI3K (phosphoinositide-3 kinase), such as SF-1126 (PI3K inhibitor, Semafore Pharmaceuticals), BEZ-235 (PI3K inhibitor, Novartis), XL-147 (PI3K inhibitor, Exelixis, Inc.), and GDC-0941 (Genentech); inhibitors of cMet, such as PHA665752 (Pfizer), XL-880 (Exelixis, Inc.), ARQ-197 (ArQule), and CE-355621; and pharmaceutically acceptable salts, acids and derivatives of any of the above.

Examples of a "chemotherapeutic agent" also include a DNA damaging agent such as thiotepa and CYTOXAN® cyclosphosphamide; alkylating agents (for example cisplatin; carboplatin; cyclophosphamide; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; busulphan; nitrosoureas such as carmustine, chlorozotocin, fotemustine, lomustine, nimustine, and ranimnustine; and temozolomide); antimetabolites (for example antifolates such as fluoropyrimidines like 5-fluorouracil (5-FU) and tegafur, raltitrexed, methotrexate, cytosine arabinoside, hydroxyurea and GEMZAR® (gemcitabine); antitumour antibiotics such as the enediyne antibiotics (e.g., calicheamicin, especially calicheamicin gamma1I and calicheamicin omega1I (Angew Chem. Intl. Ed. Engl. (1994) 33:183-186); anthracyclines like adriamycin; dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin, epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, and zorubicin; antimitotic agents (for example vinca alkaloids like vincristine, vinblastine, vindesine and NAVELBINE® (vinorelbine) and taxoids like taxoids, e.g., TAXOL® (paclitaxel; Bristol-Myers Squibb Oncology, Princeton, N.J.), ABRAXANE™ (Cremophorfree), albumin-engineered nanoparticle formulations of paclitaxel (American Pharmaceutical Partners, Schaumberg, Ill.), and TAXOTERE® (doxetaxel; Rhône-Poulenc Rorer, Antony, France); topoisomerase inhibitors (for example RFS 2000, epipodophyllotoxins like etoposide and teniposide, amsacrine, a camptothecin (including the synthetic analog topotecan), and irinotecan and SN-38) and cytodifferentiating agents (for example retinoids such as all-trans retinoic acid, 13-cis retinoic acid and fenretinide); and pharmaceutically acceptable salts, acids and derivatives of any of the above.

A "chemotherapeutic agent" also includes an agent that modulates the apoptotic response including inhibitors of IAP (inhibitor of apoptosis proteins) such as AEG40826 (Aegera Therapeutics); and inhibitors of bcl-2 such as GX15-070 (Gemin X Biotechnologies), CNDO103 (Apogossypol; Coronado Biosciences), HA14-1 (ethyl 2-amino-6-bromo-4-(1-cyano-2-ethoxy-2-oxoethyl)-4H-chromene-3-carboxylate), AT101 (Ascenta Therapeutics), ABT-737 and ABT-263 (Abbott); and pharmaceutically acceptable salts, acids and derivatives of any of the above.

The term "prodrug" as used in this application refers to a precursor or derivative form of a compound of the invention that is capable of being enzymatically or hydrolytically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," *Directed Drug Delivery*, Borchardt et al., (ed.), pp. 247-267, Humana Press (1985). The prodrugs of this invention include, but are not limited to, ester-containing prodrugs, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs, optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, compounds of the invention and chemotherapeutic agents such as described above.

A "metabolite" is a product produced through metabolism in the body of a specified compound or salt thereof. Metabolites of a compound may be identified using routine techniques known in the art and their activities determined using tests such as those described herein. Such products may result for example from the oxidation, hydroxylation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a compound of this invention with a mammal for a period of time sufficient to yield a metabolic product thereof.

A "liposome" is a small vesicle composed of various types of lipids, phospholipids and/or surfactant which is useful for delivery of a drug (such as chk inhibitors disclosed herein and, optionally, a chemotherapeutic agent) to a mammal. The components of the liposome are commonly arranged in a bilayer formation, similar to the lipid arrangement of biological membranes.

The term "package insert" is used to refer to instructions customarily included in commercial packages of therapeutic products, that contain information about the indications, usage, dosage, administration, contraindications and/or warnings concerning the use of such therapeutic products.

The term "chiral" refers to molecules which have the property of non-superimposability of the mirror image partner, while the term "achiral" refers to molecules which are superimposable on their mirror image partner.

The term "stereoisomer" refers to compounds which have identical chemical constitution and connectivity, but different orientations of their atoms in space that cannot be interconverted by rotation about single bonds.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as crystallization, electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons. For example, any reference to a structure of 2-hydroxypyridine include its tautomer 2-oxo-1,2-dihydropyridine, also known as 2-pyridone.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, pamoate (i.e., 1,1'-methylene-bis-(2-hydroxy-3-naphthoate)) salts, alkali metal (e.g., sodium and potassium) salts, alkaline earth metal (e.g., magnesium) salts, and ammonium salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, methanesulfonic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The phrase "pharmaceutically acceptable" indicates that the substance or composition must be compatible chemically and/or toxicologically, with the other ingredients comprising a formulation, and/or the mammal being treated therewith.

A "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

The term "protecting group" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBZ), 2-(trimethylsilyl)ethoxymethyl (SEM) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and t-butyldimethylsilyl. A "carboxy-protecting group" refers to a substituent of the carboxy group that blocks or protects the carboxy functionality. Common carboxy-protecting groups include phenylsulfonylethyl, cyanoethyl, 2-(trimethylsilyl)ethyl, 2-(trimethylsilyl) ethoxymethyl, 2-(p-toluenesulfonyl)ethyl, 2-(p-nitrophenylsulfenyl)ethyl, 2-(diphenylphosphino)-ethyl, nitroethyl and the like. For a general description of protecting groups and their use, see T. W. Greene, Protective Groups in Organic Synthesis, John Wiley & Sons, New York, 1991.

The terms "compound of this invention," and "compounds of the present invention", "compounds of Formula (I), (I-a), or (I-b)" and "compounds of Formula (I), (I-a), and/or (I-b)", unless otherwise indicated, include compounds of Formula (I), (I-a), or (I-b) and stereoisomers, geometric isomers, tautomers, solvates, metabolites, salts (e.g., pharmaceutically acceptable salts) and prodrugs thereof. Unless otherwise stated, structures depicted herein are also meant to include compounds that differ only in the presence of one or more isotopically enriched atoms. For example, compounds of Formula (I), (I-a), or (I-b), wherein one or more hydrogen atoms are replaced deuterium or tritium, or one or more carbon atoms are replaced by a $^{13}$C- or $^{14}$C-enriched carbon are within the scope of this invention.

The present invention provides 1,7-diazacarbazoles of Formula (I), (I-a), and/or (I-b) (and/or solvates, hydrates and/or salts thereof) as described above with kinase inhibitory activity, such as chk1, GSK-3, KDR and/or FLT3 inhibitory activities. The present compounds are particularly useful as chk1 kinase inhibitors.

In certain embodiments of the present invention, compounds are of Formula (I-a) (i.e., X is CH, Y is $CR^4$, Z is CH and $R^5$ is H) wherein $R^3$, $R^4$, and $R^6$ are as defined in Formula (I); and $R^3$, $R^4$, and $R^6$ are not H at the same time; and when $R^4$ is H and $R^3$ is H or alkyl, then $R^6$ is not —C(=Y')$OR^{11}$.

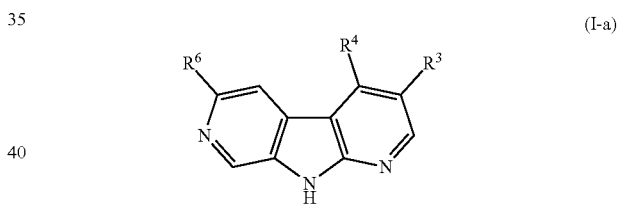

(I-a)

In certain embodiments of the present invention, compounds are of Formula (I-b) (i.e., X is CH, Y is CH, Z is CH) wherein $R^3$, $R^5$ and $R^6$ are as defined in Formula (I); and $R^3$, $R^5$ and $R^6$ are not H at the same time; and when $R^5$ is H and $R^3$ is H or alkyl, then $R^6$ is not —C(=Y')$OR^{11}$.

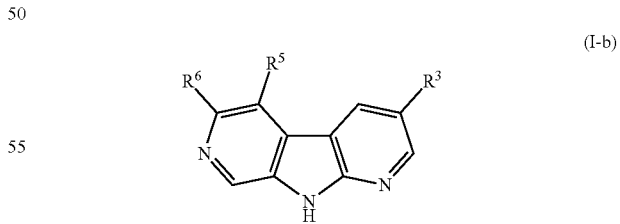

(I-b)

In certain embodiments of the present invention, X is CH (i.e., $R^2$ is H), Y is $CR^4$, and Z is CH (i.e., $R^8$ is H); and all other variables are as defined in Formula (I).

In certain embodiments of the present invention, $R^3$ is H, $CH_3$, or halo; and all other variables are as defined in Formula (I), (I-a), or (I-b), or as defined in any one of the embodiments herein. In certain embodiments of the present invention, $R^3$ is H; and all other variables are as defined in Formula (I), (I-a), or (I-b), or as defined in any one of the embodiments herein. In certain embodiments of the present invention, $R^3$ is halo (for example, F, Cl, or Br); and all other variables are as defined in Formula (I), (I-a), or (I-b), or as defined in any one of the embodiments herein. In certain embodiments of the present invention, $R^3$ is $CH_3$; and all other variables are as defined in Formula (I) or (I-b), or as defined in any one of the embodiments herein.

In certain embodiments of the present invention, $R^4$ is $-NR^{11}R^{12}$ or $-OR^{11}$, wherein $R^{11}$ and $R^{12}$ are optionally taken together with the attached N atom to form a 4-7 membered ring having additional 0-2 heteroatoms selected from O, S, and N, said ring being optionally substituted with one to four $R^{13}$ groups; and all other variables are as defined in Formula (I) or (I-a), or as defined in any one of the embodiments herein.

In certain embodiments of the present invention, $R^4$ is $-NR^{11}R^{12}$ or $-OR^{11}$, wherein $R^{11}$ is alkyl or heterocyclyl, and $R^{12}$ is H or alkyl and said alkyl or heterocyclyl is optionally substituted by one or three $R^{13}$ groups, and wherein $R^{11}$ and $R^{12}$ are optionally taken together with the attached N atom to form a 4-7 membered ring having additional 0-2 heteroatoms selected from O, S, and N, said ring being optionally substituted with one to four $R^{13}$ groups; and all other variables are as defined in Formula (I) or (I-a), or as defined in any one of the embodiments herein.

In certain embodiments of the present invention, $R^4$ is selected from one of the following groups; and all other variables are as defined in Formula (I) or (I-a), or as defined in any one of the embodiments herein:

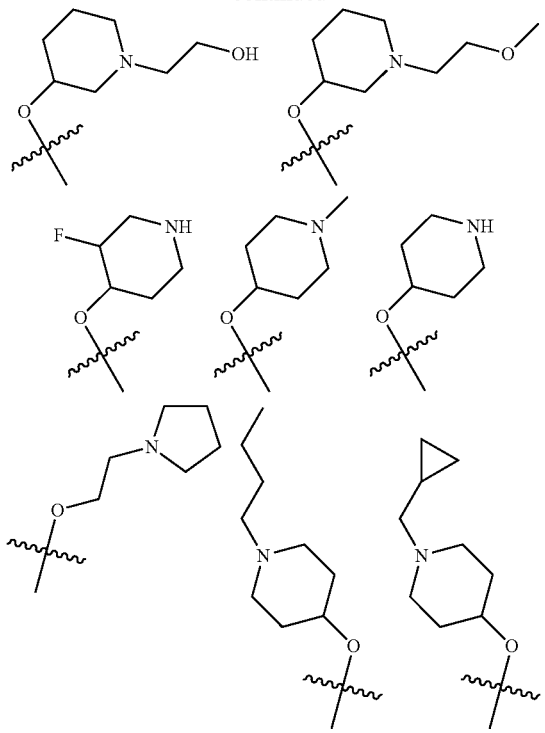

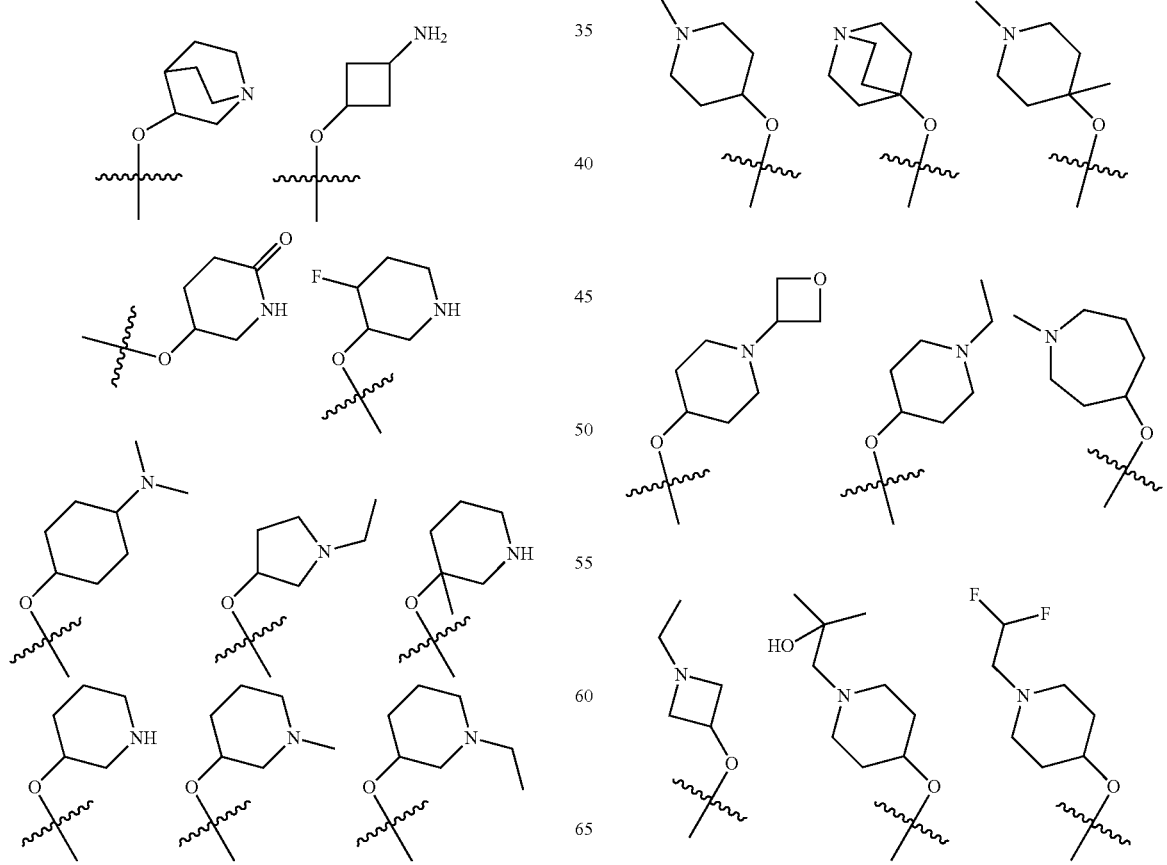

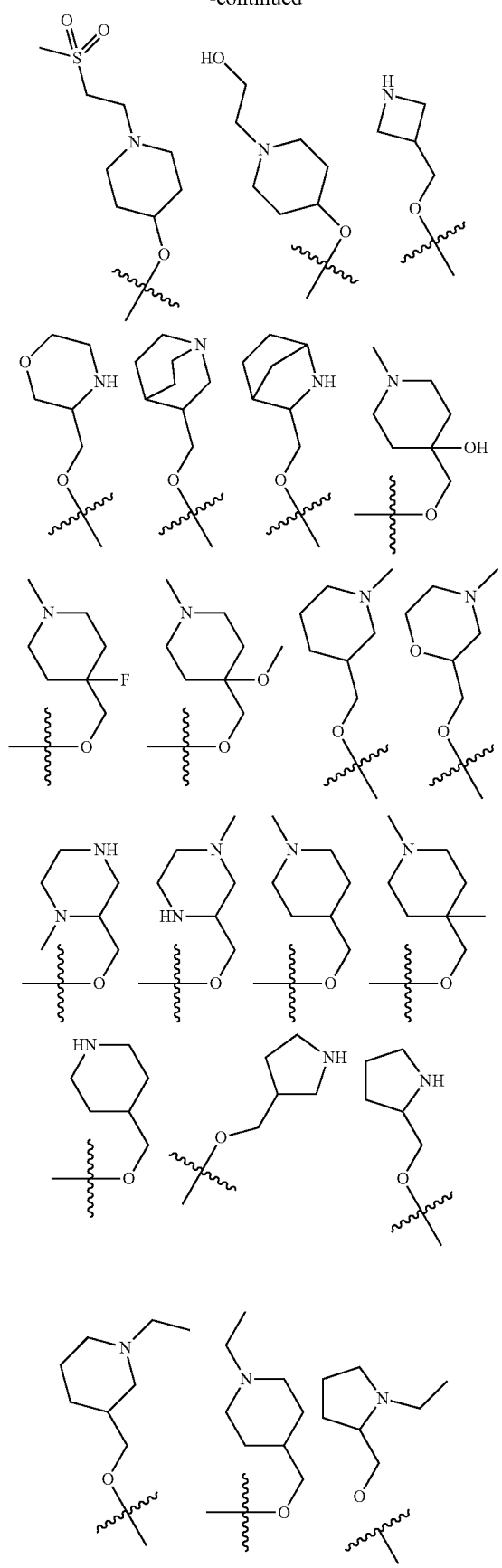
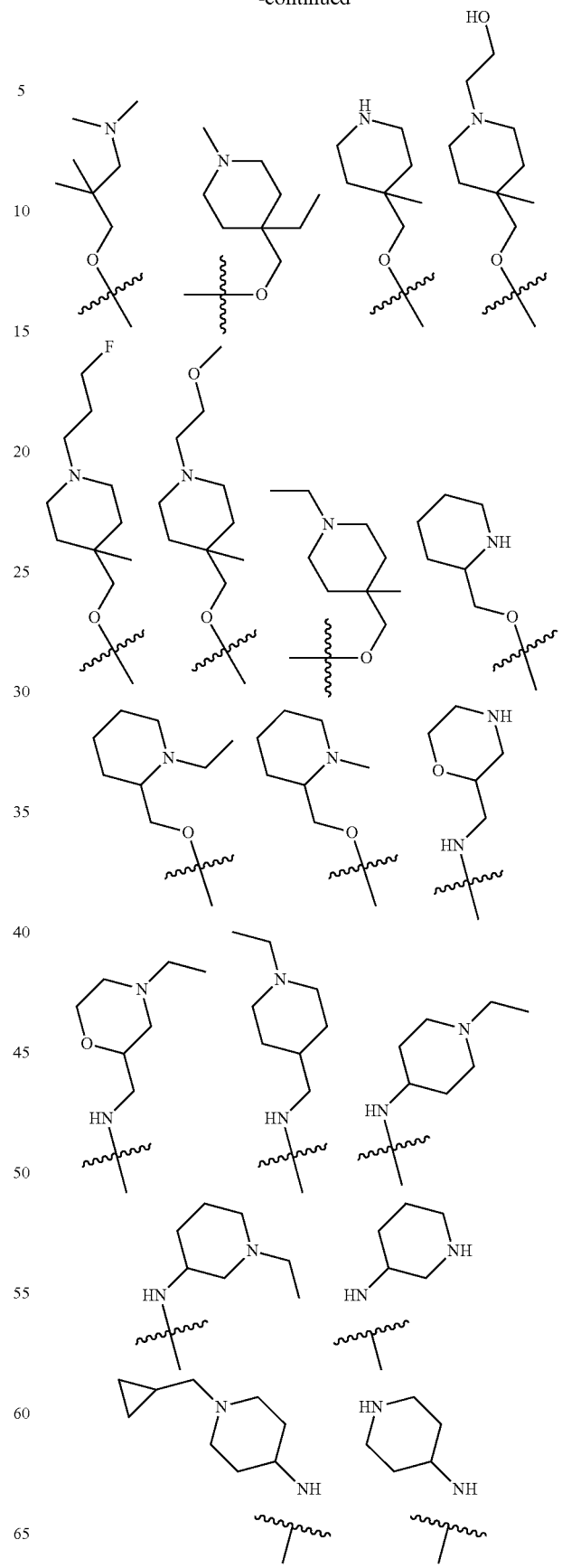

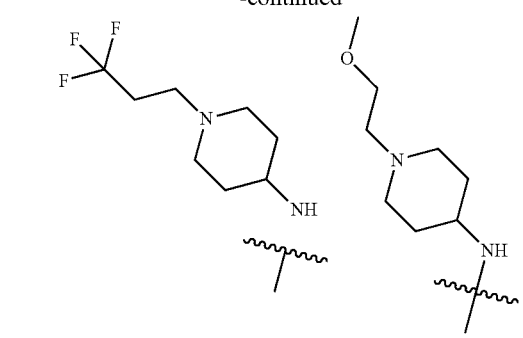
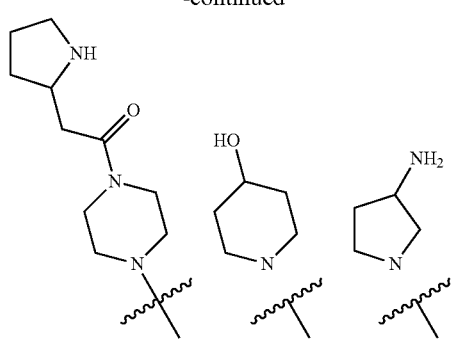

-continued

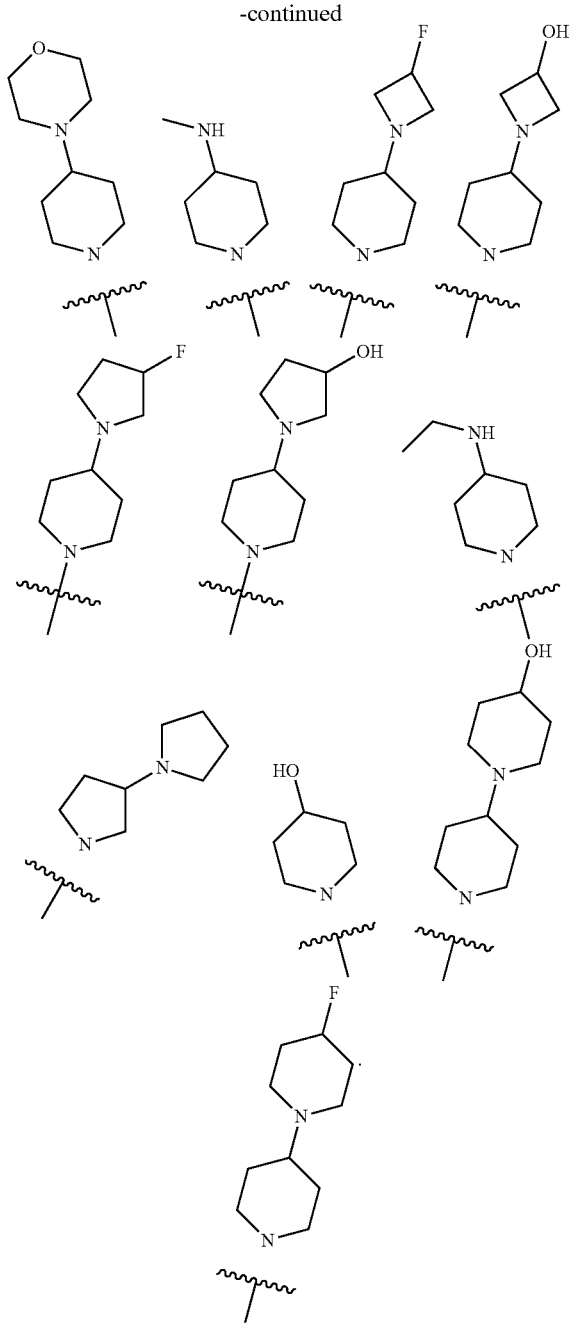

In certain embodiments of the present invention, $R^5$ is —$NR^{11}R^{12}$ or —$OR^{11}$, wherein $R^{11}$ and $R^{12}$ are optionally taken together with the attached N atom to form a 4-7 membered ring having additional 0-2 heteroatoms selected from O, S, and N, said ring being optionally substituted with one to four $R^{13}$ groups; and all other variables are as defined in Formula (I) or (I-a), or as defined in any one of the embodiments herein.

In certain embodiments of the present invention, $R^5$ is —$NR^{11}R^{12}$ or —$OR^{11}$, wherein $R^{11}$ is alkyl or heterocyclyl, and $R^{12}$ is H or alkyl and said alkyl or heterocyclyl is optionally substituted by one or three $R^{13}$ groups, and wherein $R^{11}$ and $R^{12}$ are optionally taken together with the attached N atom to form a 4-7 membered ring having additional 0-2 heteroatoms selected from O, S, and N, said ring being optionally substituted with one to four $R^{13}$ groups; and all other variables are as defined in Formula (I) or (I-a), or as defined in any one of the embodiments herein.

In certain embodiments of the present invention, $R^5$ is selected from one of the following groups; and all other variables are as defined in Formula (I) or (I-b), or as defined in any one of the embodiments herein:

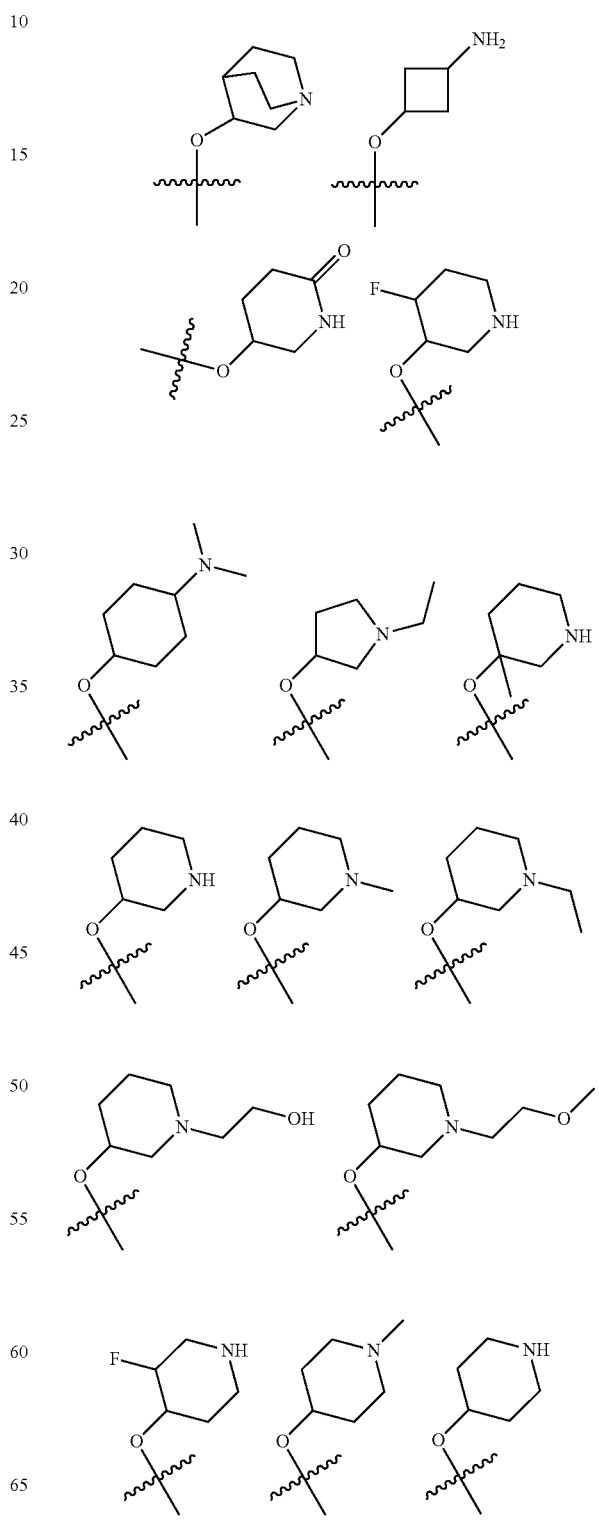

23
-continued
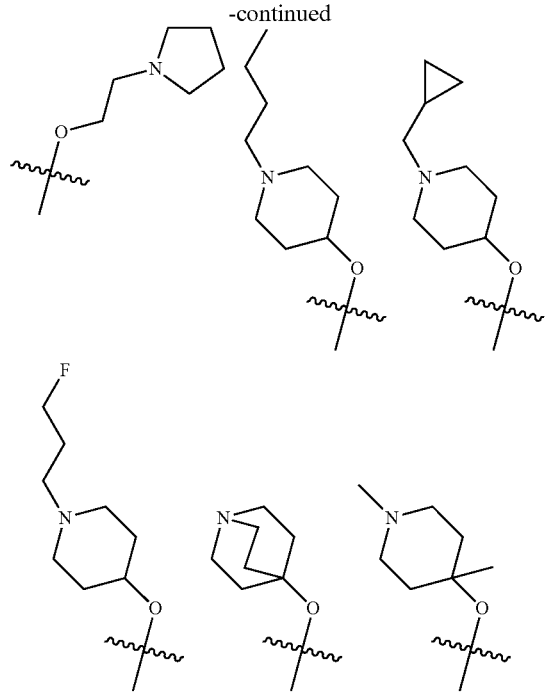
24
-continued
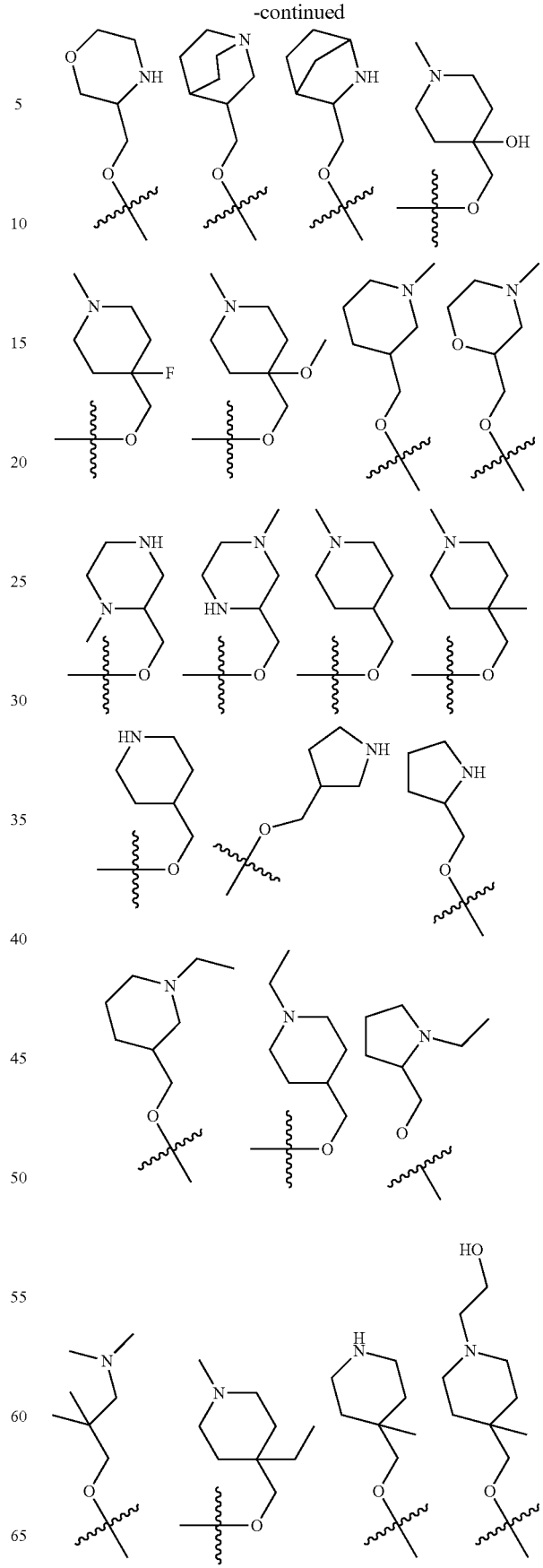

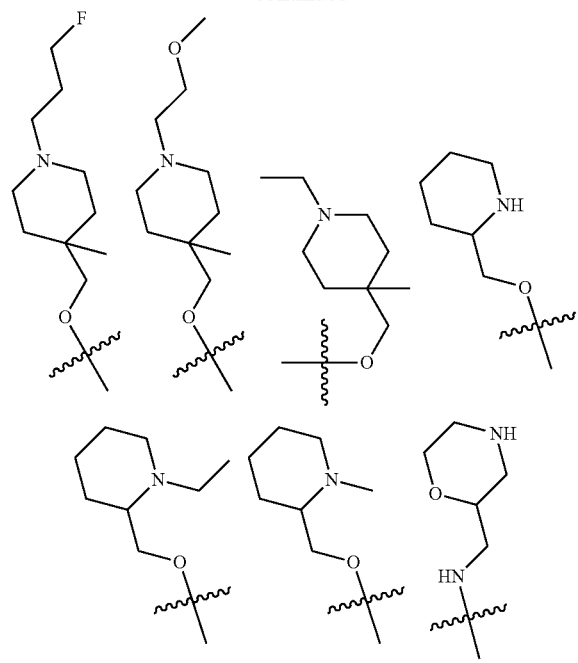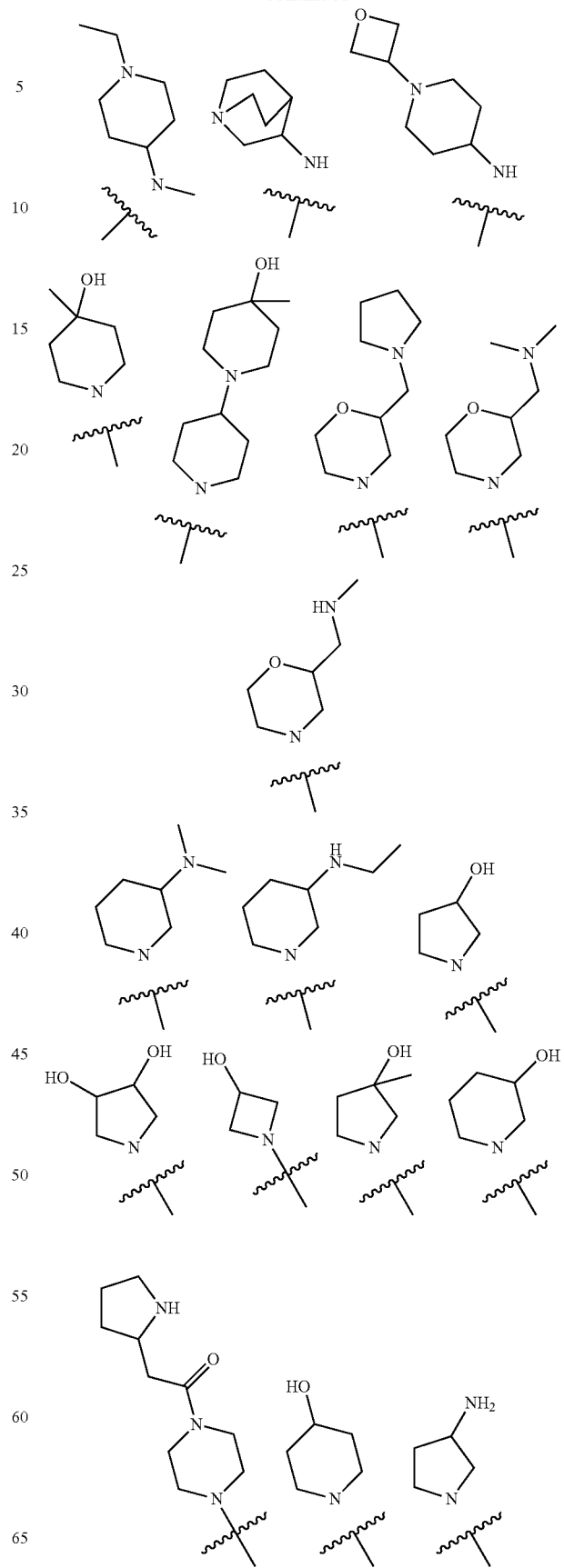

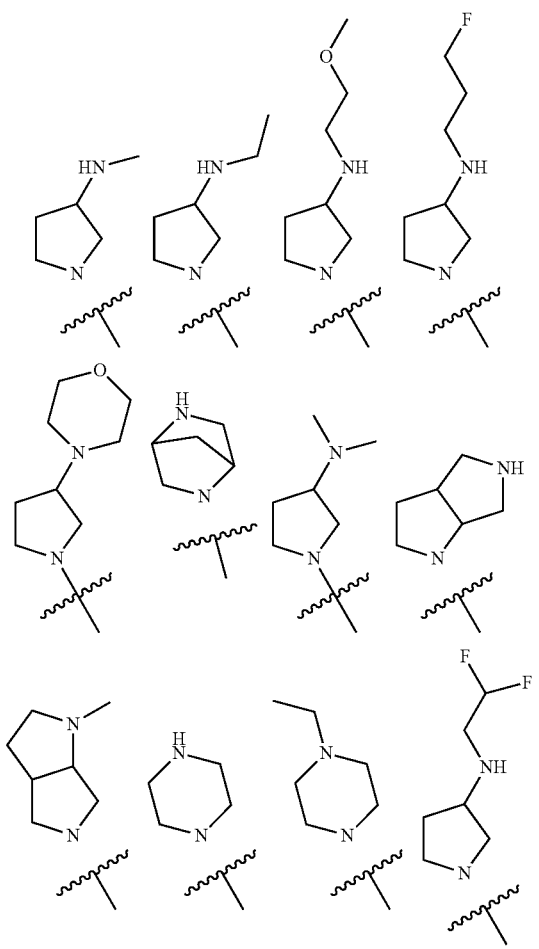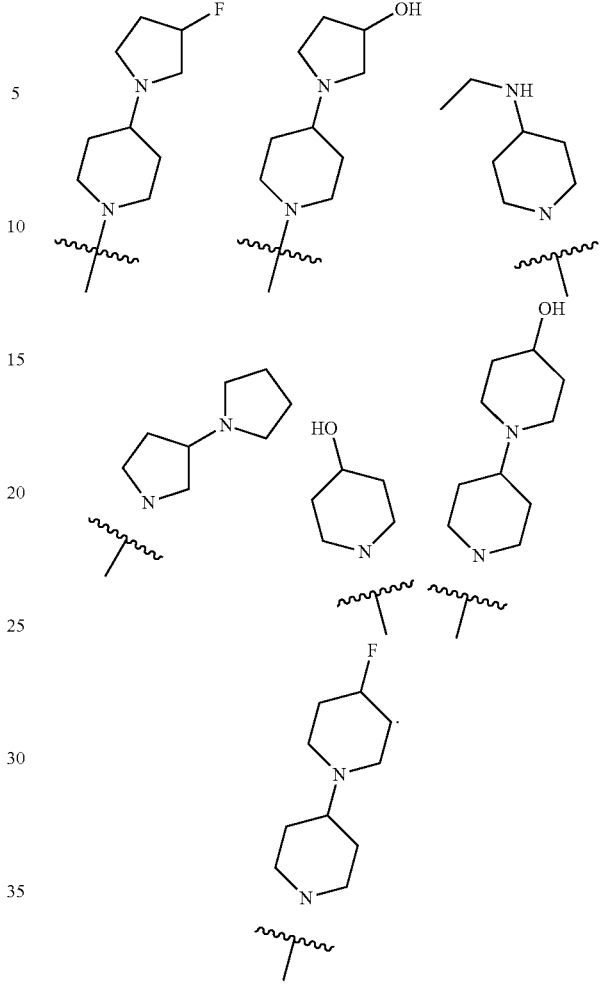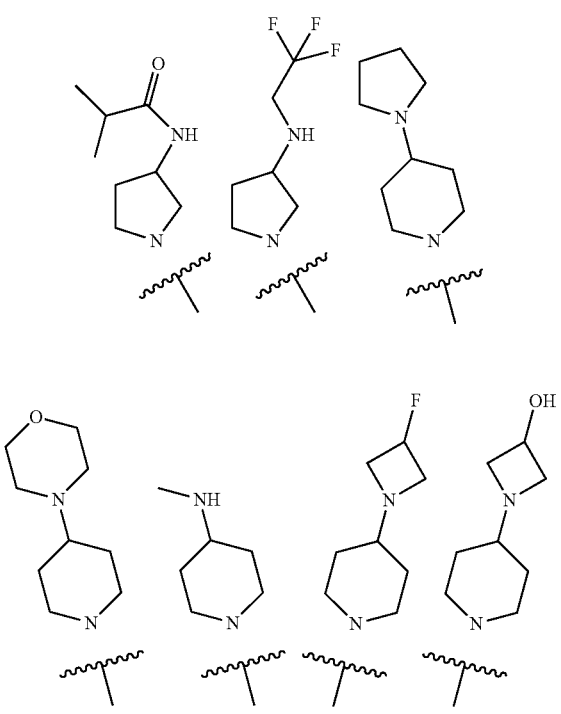

In certain embodiments of the present invention, $R^6$ is H, CN or pyrrolyl optionally substituted with $C_1$-$C_3$ alkyl; and all other variables are as defined in Formula (I), (I-a) or (I-b), or as defined in any one of the embodiments herein. In certain embodiments of the present invention, $R^6$ is CN or pyrrolyl optionally substituted with $C_1$-$C_3$ alkyl; and all other variables are as defined in Formula (I), (I-a) or (I-b), or as defined in any one of the embodiments herein. In certain embodiments of the present invention, $R^6$ is CN; and all other variables are as defined in Formula (I), (I-a) or (I-b), or as defined in any one of the embodiments herein. In certain embodiments of the present invention, $R^6$ is N-methylpyrrolyl or pyrrolyl; and all other all other variables are as defined in Formula (I-a), or as defined in any one of the embodiments herein. In certain embodiments of the present invention, $R^6$ is H; and all other all other variables are as defined in Formula (I), (I-a) or (I-b), or as defined in any one of the embodiments herein.

Another embodiment of the present invention includes any one of the title compounds described here in Examples 1-178 (e.g., any one of the title compounds in Examples 1-32, 35-53, 55-109, 113, 115-116, 119-123, 125, 127-143, 145-146, 149, 153-154, 156, 159-167, 169-171, and 174-176).

In certain embodiments there is provided a compound selected from the group consisting of:
4-(N-(morpholin-2-ylmethyl))-9H-dipyrido[2,3-b;4',3'-d]pyrrole-6-carbonitrile;

4-(azetidin-3-ylmethoxy)-9H-dipyrido[2,3-b;4',3'-d]pyrrole-6-carbonitrile;
(R)-4-(morpholin-2-ylmethoxy)-9H-dipyrido[2,3-b;4',3'-d]pyrrole-6-carbonitrile;
(S)-4-(morpholin-2-ylmethoxy)-9H-dipyrido[2,3-b;4',3'-d]pyrrole-6-carbonitrile;
(R)-4-(quinuclidin-3-yloxy)-9H-dipyrido[2,3-b;4',3'-d]pyrrole-6-carbonitrile;
4-((1s,3s)-cyclobutanamine-3-yloxy)-9H-dipyrido[2,3-b;4',3'-d]pyrrole-6-carbonitrile;
(R)-4-((1-methylpiperazin-2-yl)methoxy)-9H-dipyrido[2,3-b;4',3'-d]pyrrole-6-carbonitrile;
(S)-4-((1-methylpiperazin-2-yl)methoxy)-9H-dipyrido[2,3-b;4',3'-d]pyrrole-6-carbonitrile;
(R)-4-((4-methylpiperazin-2-yl)methoxy)-9H-dipyrido[2,3-b;4',3'-d]pyrrole-6-carbonitrile;
(S)-4-((4-methylpiperazin-2-yl)methoxy)-9H-dipyrido[2,3-b;4',3'-d]pyrrole-6-carbonitrile;
(R)-4-((piperdin-2-one)-5-yloxy)-9H-dipyrido[2,3-b;4',3'-d]pyrrole-6-carbonitrile;
4-((1-methylpiperidin-4-yl)methoxy)-9H-dipyrido[2,3-b;4',3'-d]pyrrole-6-carbonitrile;
4-((1,3-dimethylpiperidin-3-yl)methoxy)-9H-dipyrido[2,3-b;4',3'-d]pyrrole-6-carbonitrile;
4-(2-(pyrrolidin-1-ylmethyl)morpholino)-9H-dipyrido[2,3-b;4',3'-d]pyrrole-6-carbonitrile;
(R)-4-(morpholin-3-ylmethoxy)-9H-dipyrido[2,3-b;4',3'-d]pyrrole-6-carbonitrile;
4-(quinuclidin-3-ylmethoxy)-9H-dipyrido[2,3-b;4',3'-d]pyrrole-6-carbonitrile;
trans-4-(4-fluoropiperidin-3-yloxy)-9H-dipyrido[2,3-b;4',3'-d]pyrrole-6-carbonitrile;
4-((1R,3S,4S)-2-azabicyclo[2.2.1]heptan-3-ylmethoxy)-9H-dipyrido[2,3-b;4',3'-d]pyrrole-6-carbonitrile;
(S)-4-(2-((dimethylamino)methyl)morpholino)-9H-dipyrido[2,3-b;4',3'-d]pyrrole-6-carbonitrile;
(R)-4-2-(dimethylamino)methyl)morpholino-9H-dipyrido[2,3-b;4',3'-d]pyrrole-6-carbonitrile;
(S)-4-(2-((methylamino)methyl)-9H-dipyrido[2,3-b;4',3'-d]pyrrole-6-carbonitrile;
(R)-4-(2-((methylamino)methyl)-9H-dipyrido[2,3-b;4',3'-d]pyrrole-6-carbonitrile;
4-((4-hydroxy-1-methylpiperidin-4-yl)methoxy)-9H-dipyrido[2,3-b;4',3'-d]pyrrole-6-carbonitrile;
4-((4-fluoro-1-methylpiperidin-4-yl)methoxy)-9H-dipyrido[2,3-b;4',3'-d]pyrrole-6-carbonitrile;
4-((4-methoxy-1-methylpiperidin-4-yl)methoxy)-9H-dipyrido[2,3-b;4',3'-d]pyrrole-6-carbonitrile;
(R)-4-(3-(dimethylamino)piperidin-1-yl)-9H-dipyrido[2,3-b;4',3'-d]pyrrole-6-carbonitrile;
(S)-4-(3-(dimethylamino)piperidin-1-yl)-9H-dipyrido[2,3-b;4',3'-d]pyrrole-6-carbonitrile;
4-((1r,4r)-4-(dimethylamino)cyclohexyloxy)-9H-dipyrido[2,3-b;4',3'-d]pyrrole-6-carbonitrile;
(R)-4-((1-methylpiperidin-3-yl)methoxy)-9H-dipyrido[2,3-b;4',3'-d]pyrrole-6-carbonitrile;
(R)-4-(4-methylmorpholin-2-ylmethoxy)-9H-dipyrido[2,3-b;4',3'-d]pyrrole-6-carbonitrile;
(R)-4-(1-ethylpyrrolidin-3-yloxy)-9H-dipyrido[2,3-b;4',3'-d]pyrrole-6-carbonitrile;
(S)-4-((1-ethylpyrrolidin-2-yl)methoxy)-9H-dipyrido[2,3-b;4',3'-d]pyrrole-6-carbonitrile;
(S)-4-(3-(ethylamino)piperidin-1-yl)-9H-dipyrido[2,3-b;4',3'-d]pyrrole-6-carbonitrile;
(R)-4-(3-(ethylamino)piperidin-1-yl)-9H-dipyrido[2,3-b;4',3'-d]pyrrole-6-carbonitrile;
(S)-4-(4-(2-(pyrrolidin-2-yl)acetyl)piperazin-1-yl)-9H-dipyrido[2,3-b;4',3'-d]pyrrole-6-carbonitrile;
(R)-4-(4-(2-(pyrrolidin-2-yl)acetyl)piperazin-1-yl)-9H-dipyrido[2,3-b;4',3'-d]pyrrole-6-carbonitrile;
cis-4-(4-fluoropiperidin-3-yloxy)-9H-dipyrido[2,3-b;4',3'-d]pyrrole-6-carbonitrile;
3-Bromo-4-((1,4-dimethylpiperidin-4-yl)methoxy)-9H-dipyrido[2,3-b;4',3'-d]pyrrole-6-carbonitrile;
3-Chloro-4-((1,4-dimethylpiperidin-4-yl)methoxy)-9H-dipyrido[2,3-b;4',3'-d]pyrrole-6-carbonitrile;
1-[4-(3-Chloro-9H-dipyrido[2,3-b;4',3'-d]pyrrol-4-yl)-piperazin-1-yl]-2-(R)-pyrrolidin-2-yl-ethanone
(S)-3-Chloro-4-(3-hydroxypyrrolidin-1-yl)-9H-dipyrido[2,3-b;4',3'-d]pyrrole-6-carbonitrile;
3-Chloro-4-((3S,4S)-3,4-dihydroxypyrrolidin-1-yl)-9H-dipyrido[2,3-b;4',3'-d]pyrrole-6-carbonitrile;
3-Chloro-4-((3R,4R)-3,4-dihydroxypyrrolidin-1-yl)-9H-dipyrido[2,3-b;4',3'-d]pyrrole-6-carbonitrile;
3-Chloro-4-(3-hydroxyazetidin-1-yl)-9H-dipyrido[2,3-b;4',3'-d]pyrrole-6-carbonitrile;
(S)-3-Chloro-4-(3-hydroxy-3-methylpyrrolidin-1-yl)-9H-dipyrido[2,3-b;4',3'-d]pyrrole-6-carbonitrile;
(R)-3-Chloro-4-(3-hydroxy-3-methylpyrrolidin-1-yl)-9H-dipyrido[2,3-b;4',3'-d]pyrrole-6-carbonitrile;
(S)-3-Chloro-4-(3-hydroxypiperidin-1-yl)-9H-dipyrido[2,3-b;4',3'-d]pyrrole-6-carbonitrile;
(R)-3-Chloro-4-(3-hydroxypiperidin-1-yl)-9H-dipyrido[2,3-b;4',3'-d]pyrrole-6-carbonitrile;
3-Chloro-4-(4-hydroxypiperidin-1-yl)-9H-dipyrido[2,3-b;4',3'-d]pyrrole-6-carbonitrile;
(S)-3-Chloro-4-(3-aminopyrrolidin-1-yl)-9H-dipyrido[2,3-b;4',3'-d]pyrrole-6-carbonitrile;
(S)-3-Chloro-4-(3-(methylamino)pyrrolidin-1-yl)-9H-dipyrido[2,3-b;4',3'-d]pyrrole-6-carbonitrile;
(S)-3-Chloro-4-(3-(ethylamino)pyrrolidin-1-yl)-9H-dipyrido[2,3-b;4',3'-d]pyrrole-6-carbonitrile;
(S)-3-Bromo-4-(3-(ethylamino)pyrrolidin-1-yl)-9H-dipyrido[2,3-b;4',3'-d]pyrrole-6-carbonitrile;
(S)-3-Fluoro-4-(3-(ethylamino)pyrrolidin-1-yl)-9H-dipyrido[2,3-b;4',3'-d]pyrrole-6-carbonitrile;
4-((3-methylpiperidin-3-yloxy)-9H-dipyrido[2,3-b;4',3'-d]pyrrole-6-carbonitrile;
4-(dimethylamino)-2,2-dimethylpropoxy)-9H-dipyrido[2,3-b;4',3'-d]pyrrole-6-carbonitrile;
(S)-4-(piperidin-3-yloxy)-9H-dipyrido[2,3-b;4',3'-d]pyrrole-6-carbonitrile;
4-((4-methylpiperidin-4-yl)methoxy)-9H-dipyrido[2,3-b;4',3'-d]pyrrole-6-carbonitrile;
4-(1-(3-fluoropropyl)-4-methylpiperidin-4-yl)methoxy]-9H-dipyrido[2,3-b;4',3'-d]pyrrole-6-carbonitrile;
4-((1-(2-hydroxyethyl)-4-methylpiperidin-4-yl)methoxy)-9H-dipyrido[2,3-b;4',3'-d]pyrrole-6-carbonitrile;
4-((1-(2-methoxyethyl)-4-methylpiperidin-4-yl)methoxy)-9H-dipyrido[2,3-b;4',3'-d]pyrrole-6-carbonitrile;
4-((1-ethyl-4-methylpiperidin-3-yl)methoxy)-9H-dipyrido[2,3-b;4',3'-d]pyrrole-6-carbonitrile;
(R)-4-(1-methylpiperidin-3-yloxy)-9H-dipyrido[2,3-b;4',3'-d]pyrrole-6-carbonitrile;
4-((R)-1-ethylpiperidin-3-oxy)-9H-dipyrido[2,3-b;4',3'-d]pyrrole-6-carbonitrile;
(R)-4-(1-(2-hydroxyethyl)piperidin-3-yloxy)-9H-dipyrido[2,3-b;4',3'-d]pyrrole-6-carbonitrile;
(R)-4-(1-(2-methoxyethyl)piperidin-3-oxy)-9H-dipyrido[2,3-b;4',3'-d]pyrrole-6-carbonitrile;
4-((4-ethyl-1-methylpiperidin-4-yl)methoxy)-9H-dipyrido[2,3-b;4',3'-d]pyrrole-6-carbonitrile;

4-((1,4-dimethylpiperidin-4-yl)methoxy)-9H-dipyrido[2,3-b;4',3'-d]pyrrole-6-carbonitrile;
(R)-4-(piperidin-2-ylmethoxy)-9H-dipyrido[2,3-b;4',3'-d]pyrrole-6-carbonitrile;
(S)-4-(piperidin-2-ylmethoxy)-9H-dipyrido[2,3-b;4',3'-d]pyrrole-6-carbonitrile;
(R)-4-((1-ethylpiperidin-2-yl)methoxy)-9H-dipyrido[2,3-b;4',3'-d]pyrrole-6-carbonitrile;
(R)-4-((1-methylpiperidin-2-yl)methoxy)-9H-dipyrido[2,3-b;4,3'-d]pyrrole-6-carbonitrile;
(S)-4-(N-(2-methoxyethyl)pyrrolidin-3-amino)-9H-dipyrido[2,3-b;4',3'-d]pyrrole-6-carbonitrile;
(S)-4-(N-(3-fluoropropyl)pyrrolidin-3-amino)-9H-dipyrido[2,3-b;4',3'-d]pyrrole-6-carbonitrile;
(R)-4-(N-(2-methoxyethyl)pyrrolidin-3-amino)-9H-dipyrido[2,3-b;4',3'-d]pyrrole-6-carbonitrile;
(S)-4-(N-ethylpyrrolidin-3-amino)-9H-dipyrido[2,3-b;4',3'-d]pyrrole-6-carbonitrile;
4-(4-(pyrrolidin-3-yl)morpholino)-9H-dipyrido[2,3-b;4',3'-d]pyrrole-6-carbonitrile;
4-(2,5-diazabicyclo[2.2.1]heptan-2-yl)-9H-dipyrido[2,3-b;4',3'-d]pyrrole-6-carbonitrile;
4-(N-methylpyrrolidin-3-amino)-9H-dipyrido[2,3-b;4',3'-d]pyrrole-6-carbonitrile;
(R)-4-(N,N-dimethylpyrrolidin-3-amino)-9H-dipyrido[2,3-b;4',3'-d]pyrrole-6-carbonitrile;
(S)-4-(N,N-dimethylpyrrolidin-3-amino)-9H-dipyrido[2,3-b;4',3'-d]pyrrole-6-carbonitrile;
4-(octahydropyrrolo[3,4-b]pyrrol)-9H-dipyrido[2,3-b;4',3'-d]pyrrole-6-carbonitrile;
4-((3aS,6aS)-1-methyloctahydropyrrolo[3,4-b]pyrrol)-9H-dipyrido[2,3-b;4',3'-d]pyrrole-6-carbonitrile;
4-((R)-piperidin-3-amino)-9H-dipyrido[2,3-b;4',3'-d]pyrrole-6-carbonitrile;
3-chloro-4-piperazin-9H-dipyrido[2,3-b;4',3'-d]pyrrole-6-carbonitrile;
3-Chloro-4-(1-ethylpiperazin)-9H-dipyrido[2,3-b;4',3'-d]pyrrole-6-carbonitrile;
(S)-3-Chloro-4-(N-(3-fluoropropyl)pyrrolidin-3-amino)-9H-dipyrido[2,3-b;4',3'-d]pyrrole-6-carbonitrile;
(S)-3-Chloro-4-(3-(2,2-difluoroethylamino)pyrrolidin-1-yl)-9H-dipyrido[2,3-b;4',3'-d]pyrrole-6-carbonitrile;
(S)-3-Chloro-4-(N-(pyrrolidin-3-yl)isobutyramide)-9H-dipyrido[2,3-b;4',3'-d]pyrrole-6-carbonitrile;
(S)-3-Chloro-4-(N-(2,2,2-trifluoroethyl)pyrrolidin-3-amino)-9H-dipyrido[2,3-b;4',3'-d]pyrrole-6-carbonitrile;
(R)-4-(Piperidin-3-yloxy)-6-(1-methyl-1H-pyrazol-4-yl)-9H-dipyrido[2,3-b;4',3'-d]pyrrole;
1-[4-(9H-Dipyrido[2,3b;4',3'-d]pyrrol-4-yl)-piperazin-1-yl]-2-(R)-pyrrolidin-2-yl-ethanone;
[(S)-1-(9H-Dipyrido[2,3-b;4',3'-d]pyrrol-4-yl)-pyrrolidin-3-yl]-ethyl-amine;
4-(1-Ethyl-piperidin-4-ylamino)-9H-dipyrido[2,3-b;4',3'-d]pyrrole-6-carbonitrile;
4-[(S)-(1-Azabicyclo-[2.2.2]oct-3-yl)oxy]-9H-dipyrido[2,3-b;4',3'-d]pyrrole-6-carbonitrile;
4-((S)-1-Ethylpiperidin-3-ylamino)-9H-dipyrido[2,3-b;4',3'-d]pyrrole-6-carbonitrile;
cis-3-Fluoro-piperidin-4-yloxy)-9H-dipyrido[2,3-b;4',3'-d]pyrrole-6-carbonitrile;
4-(4-Ethylpiperazin-1-yl)-9H-dipyrido[2,3-b;4',3'-d]pyrrole-6-carbonitrile;
4-(4-Pyrrolidin-1-ylpiperidin-1-yl)-9H-dipyrido[2,3-b;4',3'-d]pyrrole-6-carbonitrile;
4-(4-Morpholin-4-yl-piperidin-1-yl)-9H-dipyrido[2,3b;4',3'd]pyrrole-6-carbonitrile;
4-((R)-1-Ethyl-piperidin-3-ylamino)-9H-dipyrido-[2,3b;4',3'-d]pyrrole-6-carbonitrile;
4-(4-Methylaminopiperidin-1-yl)-9H-dipyrido[2,3-b;4',3'-d]pyrrole-6-carbonitrile;
4-((R)-3-Hydroxypyrrolidin-1-yl)-9H-dipyrido[2,3b;4',3'-d]pyrrole-6-carbonitrile;
4-((S)-3-Hydroxypyrrolidin-1-yl)-9H-dipyrido[2,3b;4',3'-d]pyrrole-6-carbonitrile;
Trans-3-Fluoropiperidin-4-yloxy)-9H-dipyrido[2,3-b;4',3'd]pyrrole-6-carbonitrile;
5-(Piperidin-4-ylmethoxy)-9H-dipyrido[2,3-b;4',3'-d]pyrrole-6-carbonitrile;
5-(Pyrrolidin-3-ylmethoxy)-9H-dipyrido[2,3-b;4',3'-d]pyrrole-6-carbonitrile;
5-((S)-Piperidin-3-yloxy)-9H-dipyrido[2,3-b;4,3'-d]pyrrole-6-carbonitrile;
5-((R)-1-Pyrrolidin-2-ylmethoxy)-9H-dipyrido[2,3-b;4',3'-d]pyrrole-6-carbonitrile;
5-[1-(3,3,3-Trifluoro-propyl)-piperidin-4-ylamino]-9H-dipyrido[2,3-b;4',3'-d]pyrrole-6-carbonitrile;
5-((S)-1-Ethyl-piperidin-3-yloxy)-9H-dipyrido[2,3-b;4',3'-d]pyrrole-6 carbonitrile;
5-[1-(2-Methoxy-ethyl)-piperidin-4-ylamino]-9H-dipyrido[2,3-b;4',3'-d]pyrrole-6-carbonitrile;
5-(1-Cyclopropylmethyl-piperidin-4-yloxy)-9H-dipyrido[2,3-b;4',3'-d]pyrrole-6-carbonitrile;
5-(Cis)-3-Fluoro-piperidin-4-yloxy)-9H-dipyrido[2,3b;4',3'-d]pyrrole-6-carbonitrile;
5-((S)-1-Pyrrolidin-2-ylmethoxy)-9H-dipyrido[2,3-b;4',3'-d]pyrrole-6-carbonitrile;
5-[(1-Ethyl-piperidin-4-ylmethyl)-amino]-9H-dipyrido[2,3-b;4',3'-d]pyrrole-6-carbonitrile;
5-[(1-Ethyl-piperidin-4-yl)-methyl-amino]-9H-dipyrido[2,3-b;4',3'-d]pyrrole-6-carbonitrile;
5-(1-Butyl-piperidin-4yloxy)-9H-dipyrido[2,3-b;4',3'-d]pyrrole-6-carbonitrile;
5-(1-Methyl-piperidin-4-yloxy)-9H-dipyrido[2,3-b;4',3'-d]pyrrole-6-carbonitrile;
5-[1-(3,3,3-Trifluoro-propyl)-piperidin-4-ylamino]-9H-dipyrido[2,3-b;4',3'-d]pyrrole-6-carbonitrile;
5-[(S)-(1-Azabicyclo[2.2.2]oct-3-yl)amino]-9H-dipyrido[2,3-b;4',3'-d]pyrrole-6-carbonitrile;
5-(2-Pyrrolidin-1-yl-ethoxy)-9H-dipyrido[2,3-b;4',3'-d]pyrrole-6-carbonitrile;
5-(trans)-3-Fluoro-piperidin-4-yloxy)-9H-dipyrido[2,3-b;4',3'-d]pyrrole-6-carbonitrile;
5-[(4-Ethyl-morpholin-2-ylmethyl)-amino]-9H-dipyrido[2,3-b;4',3'-d]pyrrole-6-carbonitrile;
5-(4-Ethylamino-piperidin-1-yl)-9H-dipyrido[2,3-b;4',3'-d]pyrrole-6-carbonitrile;
5-(1-Oxetan-3-yl-piperidin-4-ylamino)-9H-dipyrido[2,3-b;4',3'-d]pyrrole-6-carbonitrile;
5-(1-Cyclopropylmethyl-piperidin-4-ylamino)-9H-dipyrido[2,3-b;4',3'-d]pyrrole-6-carbonitrile;
5-[1,3']Bipyrrolidinyl-1'-yl-9H-dipyrido[2,3-b;4',3'-d]pyrrole-6-carbonitrile;
5-[1-(3-Fluoro-propyl)-piperidin-4-yloxy]-9H-dipyrido[2,3-b;4',3'-d]pyrrole-6-carbonitrile;
5-[4-(3-Fluoro-azetidin-1-yl)-piperidin-1-yl]-9H-dipyrido[2,3-b;4',3'-d]pyrrole-6-carbonitrile;
5-[4-(3-Hydroxy-azetidin-1-yl)-piperidin-1-yl]-9H-dipyrido[2,3-b;4',3'-d]pyrrole-6-carbonitrile;
5-[4-((S)-3-Fluoro-pyrrolidin-1-yl)-piperidin-1-yl]-9H-dipyrido[2,3-b;4',3'-d]pyrrole-6-carbonitrile;
5-(4-Azetidin-1-yl-piperidin-1-yl)-9H-dipyrido[2,3-b;4',3'-d]pyrrole-6-carbonitrile;

5-[4-((R)-3-Fluoropyrrolidin-1-yl)-piperidin-1-yl]-9H-dipyrido[2,3-b;4',3'-d]pyrrole-6carbonitrile;
5-[4-((S)-3-Hydroxypyrrolidin-1-yl)-piperidin-1-yl]-9H-dipyrido[2,3-b;4',3'-d]pyrrole-6-carbonitrile;
5-[4-((R)-3-Hydroxy-pyrrolidin-1-yl)-piperidin-1-yl]-9H-dipyrido[2,3-b;4',3'-d]pyrrole-6-carbonitrile;
5-(4-Hydroxy-piperidin-1-yl)-9H-dipyrido[2,3-b;4',3'-d]pyrrole-6-carbonitrile;
5-(4-Hydroxy-[1,4']bipiperidinyl-1'-yl)-9H-dipyrido[2,3-b;4',3'-d]pyrrole-6-carbonitrile;
5-(4-Fluoro-[1,4']bipiperidinyl-1'-yl)-9H-dipyrido[2,3-b;4',3'-d]pyrrole-6-carbonitrile;
5-(4-Hydroxy-4-methyl-piperidin-1-yl)-9H-dipyrido[2,3-b;4',3'-d]pyrrole-6-carbonitrile;
5-(1-Aza-bicyclo[2.2.2]oct-4-yloxy)-9H-dipyrido[2,3-b;4',3'-d]pyrrole-6-carbonitrile;
5-(1,4-Dimethyl-piperidin-4-yloxy)-9H-dipyrido[2,3-b;4',3'-d]pyrrole-6-carbonitrile;
5-(4-Hydroxy-4-methyl[1,4']bipiperidinyl-1'-yl)-9H-dipyrido[2,3b;4',3'-d]pyrrole-6-carbonitrile;
3-Bromo-5-(piperidin-4-ylamino)-9H-dipyrido[2,3-b;4',3'-d]pyrrole-6-carbonitrile;
3-Bromo-5-(piperidin-4-yloxy)-9H-dipyrido[2,3-b;4',3'-d]pyrrole-6-carbonitrile;
3-Bromo-5-(1-oxetan-3-yl-piperidin-4-yloxy)-9H-dipyrido[2,3-b;4',3'-d]pyrrole-6-carbonitrile;
3-Bromo-5-(1-ethyl-piperidin-4-ylamino)-9H-dipyrido[2,3-b;4',3'-d]pyrrole-6-carbonitrile;
5-(1-Ethyl-piperidin-4-yloxy)-3-fluoro-9H-dipyrido[2,3-b;4',3'-d]pyrrole-6-carbonitrile;
5-[(S)-(1-Azabicyclo[2.2.2]oct-3-yl)oxy]-3-fluoro-9H-dipyrido[2,3-b;4',3'-d]pyrrole-6-carbonitrile;
3-Fluoro-5-(4-morpholin-4-yl-piperidin-1-yl)-9H-dipyrido[2,3-b;4',3'-d]pyrrole-6-carbonitrile;
3-Chloro-5-(4-morpholin-4-yl-piperidin-1-yl)-9H-dipyrido[2,3-b;4',3'-d]pyrrole-6-carbonitrile;
3-Fluoro-5-(piperidin-4-yloxy)-9H-dipyrido[2,3-b;4',3'-d]pyrrole-6-carbonitrile;
3-Bromo-5-(4-morpholin-4-yl-piperidin-1-yl)-9H-dipyrido[2,3-b;4',3'-d]pyrrole-6-carbonitrile;
5-[(S)-(1-Azabicyclo[2.2.2]oct-3-yl)oxy]-3-chloro-9H-dipyrido[2,3-b;4',3'-d]pyrrole-6-carbonitrile;
3-Chloro-5-(1-ethyl-piperidin-4-ylamino)-9H-dipyrido[2,3-b;4',3'-d]pyrrole-6-carbonitrile;
3-Chloro-5-(4-pyrrolidin-1-yl-piperidin-1-yl)-9H-dipyrido[2,3-b;4',3'-d]pyrrole-6-carbonitrile;
5-(1-Ethyl-piperidin-3-ylmethoxy)-9H-dipyrido[2,3-b;4',3'-d]pyrrole-6-carbonitrile;
5-(1-Ethyl-piperidin-4-ylmethoxy)-9H-dipyrido[2,3-b;4',3'-d]pyrrole-6-carbonitrile;
5-((S)-1-Ethyl-piperidin-3-ylmethoxy)-9H-dipyrido[2,3-b;4',3'-d]pyrrole-6-carbonitrile;
5-(1-Methyl-azepan-4-yloxy)-9H-dipyrido[2,3-b;4',3'-d]pyrrole-6-carbonitrile;
5-[1-(2-Hydroxy-2-methyl-propyl)-piperidin-4-yloxy]-9H-dipyrido[2,3-b;4',3'-d]pyrrole-6-carbonitrile;
5-(1-Ethyl-azetidin-3-yloxy)-9H-dipyrido[2,3-b;4',3'-d]pyrrole-6-carbonitrile;
3-Fluoro-5-(1-methyl-piperidin-4-yloxy)-9H-dipyrido[2,3-b;4',3'-d]pyrrole-6-carbonitrile;
3-Chloro-5-(1-methyl-piperidin-4-yloxy)-9H-dipyrido[2,3-b;4',3'-d]pyrrole-6-carbonitrile;
3-Chloro-5-(1-ethyl-piperidin-4-yloxy)-9H-dipyrido[2,3-b;4',3'-d]pyrrole-6-carbonitrile;
5-(1-Methyl-piperidin-4-ylamino)-9H-dipyrido[2,3-b;4',3'-d]pyrrole-6-carbonitrile;
5-(4-Pyrrolidin-1-yl-piperidin-1-yl)-9H-dipyrido[2,3-b;4',3'-d]pyrrole-6-carbonitrile;
5-(4-Morpholin-4-yl-piperidin-1-yl)-9H-dipyrido[2,3-b;4',3'-d]pyrrole-6-carbonitrile;
5-(Piperidin-4-ylamino)-9H-dipyrido[2,3-b;4',3'-d]pyrrole-6-carbonitrile;
5-Piperazin-1-yl-9H-dipyrido[2,3-b;4',3'-d]pyrrole-6 carbonitrile;
5-[1-(2,2-Difluoroethyl)-piperidin-4-yloxy]-9H-dipyrido[2,3-b;4',3'-d]pyrrole-6-carbonitrile;
5-[1-(2-Methanesulfonylethyl)-piperidin-4-yloxy]-9H-dipyrido[2,3-b;4',3'-d]pyrrole-6-carbonitrile;
5-[1-(2-Hydroxyethyl)-piperidin-4-yloxy]-9H-dipyrido[2,3-b;4',3'-d]pyrrole-6-carbonitrile;
5-(1-Ethyl-piperidin-4-yloxy)-3-methyl-9H-dipyrido[2,3-b;4',3'-d]pyrrole-6-carbonitrile; and
5-(1-Ethyl-piperidin-4-yloxy)-9H-dipyrido[2,3-b;4',3'-d]pyrrole.

In certain embodiments there is provided a compound selected from the group consisting of:
4-(N-(morpholin-2-ylmethyl))-9H-dipyrido[2,3-b;4',3'-d]pyrrole-6-carbonitrile;
4-(azetidin-3-ylmethoxy)-9H-dipyrido[2,3-b;4',3'-d]pyrrole-6-carbonitrile;
(R)-4-(morpholin-2-ylmethoxy)-9H-dipyrido[2,3-b;4',3'-d]pyrrole-6-carbonitrile;
(S)-4-(morpholin-2-ylmethoxy)-9H-dipyrido[2,3-b;4',3'-d]pyrrole-6-carbonitrile;
(R)-4-(quinuclidin-3-yloxy)-9H-dipyrido[2,3-b;4',3'-d]pyrrole-6-carbonitrile;
4-((1s,3s)-cyclobutanamine-3-yloxy)-9H-dipyrido[2,3-b;4',3'-d]pyrrole-6-carbonitrile;
(R)-4-((1-methylpiperazin-2-yl)methoxy)-9H-dipyrido[2,3-b;4',3'-d]pyrrole-6-carbonitrile;
(S)-4-((1-methylpiperazin-2-yl)methoxy)-9H-dipyrido[2,3-b;4',3'-d]pyrrole-6-carbonitrile;
(R)-4-((4-methylpiperazin-2-yl)methoxy)-9H-dipyrido[2,3-b;4',3'-d]pyrrole-6-carbonitrile;
(S)-4-((4-methylpiperazin-2-yl)methoxy)-9H-dipyrido[2,3-b;4',3'-d]pyrrole-6-carbonitrile;
(R)-4-((piperdin-2-one)-5-yloxy)-9H-dipyrido[2,3-b;4',3'-d]pyrrole-6-carbonitrile;
4-((1-methylpiperidin-4-yl)methoxy)-9H-dipyrido[2,3-b;4',3'-d]pyrrole-6-carbonitrile;
4-((1,3-dimethylpiperidin-3-yl)methoxy)-9H-dipyrido[2,3-b;4',3'-d]pyrrole-6-carbonitrile;
4-(2-(pyrrolidin-1-ylmethyl)morpholino)-9H-dipyrido[2,3-b;4',3'-d]pyrrole-6-carbonitrile;
(R)-4-(morpholin-3-ylmethoxy)-9H-dipyrido[2,3-b;4',3'-d]pyrrole-6-carbonitrile;
4-(quinuclidin-3-ylmethoxy)-9H-dipyrido[2,3-b;4',3'-d]pyrrole-6-carbonitrile;
trans-4-(4-fluoropiperidin-3-yloxy)-9H-dipyrido[2,3-b;4,3'-d]pyrrole-6-carbonitrile;
4-((1R,3S,4S)-2-azabicyclo[2.2.1]heptan-3-ylmethoxy)-9H-dipyrido[2,3-b;4',3'-d]pyrrole-6-carbonitrile;
(S)-4-(2-((dimethylamino)methyl)morpholino)-9H-dipyrido[2,3-b;4',3'-d]pyrrole-6-carbonitrile;
(R)-4-(2-((dimethylamino)methyl)morpholino)-9H-dipyrido[2,3-b;4',3'-d]pyrrole-6-carbonitrile;
(S)-4-(2-((methylamino)methyl)-9H-dipyrido[2,3-b;4',3'-d]pyrrole-6-carbonitrile;
(R)-4-(2-((methylamino)methyl)-9H-dipyrido[2,3-b;4',3'-d]pyrrole-6-carbonitrile;
4-((4-hydroxy-1-methylpiperidin-4-yl)methoxy-9H-dipyrido[2,3-b;4',3'-d]pyrrole-6-carbonitrile;

4-((4-fluoro-1-methylpiperidin-4-yl)methoxy)-9H-dipyrido[2,3-b;4',3'-d]pyrrole-6-carbonitrile;
4-((4-methoxy-1-methylpiperidin-4-yl)methoxy)-9H-dipyrido[2,3-b;4',3'-d]pyrrole-6-carbonitrile;
(R)-4-(3-(dimethylamino)piperidin-1-yl)-9H-dipyrido[2,3-b;4',3'-d]pyrrole-6-carbonitrile;
(S)-4-(3-(dimethylamino)piperidin-1-yl)-9H-dipyrido[2,3-b;4',3'-d]pyrrole-6-carbonitrile;
4-((1r,4r)-4-(dimethylamino)cyclohexyloxy)-9H-dipyrido[2,3-b;4',3'-d]pyrrole-6-carbonitrile;
(R)-4-((1-methylpiperidin-3-yl)methoxy)-9H-dipyrido[2,3-b;4',3'-d]pyrrole-6-carbonitrile;
(R)-4-(4-methylmorpholin-2-ylmethoxy)-9H-dipyrido[2,3-b;4',3'-d]pyrrole-6-carbonitrile;
(R)-4-(1-ethylpyrrolidin-3-yloxy)-9H-dipyrido[2,3-b;4',3'-d]pyrrole-6-carbonitrile;
(S)-4-((1-ethylpyrrolidin-2-yl)methoxy)-9H-dipyrido[2,3-b;4',3'-d]pyrrole-6-carbonitrile;
(S)-4-(3-(ethylamino)piperidin-1-yl)-9H-dipyrido[2,3-b;4',3'-d]pyrrole-6-carbonitrile;
(R)-4-(3-(ethylamino)piperidin-1-yl)-9H-dipyrido[2,3-b;4',3'-d]pyrrole-6-carbonitrile;
(S)-4-(4-(2-(pyrrolidin-2-yl)acetyl)piperazin-1-yl)-9H-dipyrido[2,3-b;4',3'-d]pyrrole-6-carbonitrile;
(R)-4-(4-(2-(pyrrolidin-2-yl)acetyl)piperazin-1-yl)-9H-dipyrido[2,3-b;4',3'-d]pyrrole-6-carbonitrile;
cis-4-(4-fluoropiperidin-3-yloxy)-9H-dipyrido[2,3-b;4',3'-d]pyrrole-6-carbonitrile;
3-Bromo-4-((1,4-dimethylpiperidin-4-yl)methoxy)-9H-dipyrido[2,3-b;4',3'-d]pyrrole-6-carbonitrile;
3-Chloro-4-((1,4-dimethylpiperidin-4-yl)methoxy)-9H-dipyrido[2,3-b;4',3'-d]pyrrole-6-carbonitrile;
1-[4-(3-Chloro-9H-dipyrido[2,3-b;4',3'-d]pyrrol-4-yl)-piperazin-1-yl]-2-(R)-pyrrolidin-2-yl-ethanone
(S)-3-Chloro-4-(3-hydroxypyrrolidin-1-yl)-9H-dipyrido[2,3-b;4',3'-d]pyrrole-6-carbonitrile;
3-Chloro-4-((3S,4S)-3,4-dihydroxypyrrolidin-1-yl)-9H-dipyrido[2,3-b;4',3'-d]pyrrole-6-carbonitrile;
3-Chloro-4-((3R,4R)-3,4-dihydroxypyrrolidin-1-yl)-9H-dipyrido[2,3-b;4',3'-d]pyrrole-6-carbonitrile;
3-Chloro-4-(3-hydroxyazetidin-1-yl)-9H-dipyrido[2,3-b;4',3'-d]pyrrole-6-carbonitrile;
(S)-3-Chloro-4-(3-hydroxy-3-methylpyrrolidin-1-yl)-9H-dipyrido[2,3-b;4',3'-d]pyrrole-6-carbonitrile;
(R)-3-Chloro-4-(3-hydroxy-3-methylpyrrolidin-1-yl)-9H-dipyrido[2,3-b;4',3'-d]pyrrole-6-carbonitrile;
(S)-3-Chloro-4-(3-hydroxypiperidin-1-yl)-9H-dipyrido[2,3-b;4',3'-d]pyrrole-6-carbonitrile;
(R)-3-Chloro-4-(3-hydroxypiperidin-1-yl)-9H-dipyrido[2,3-b;4',3'-d]pyrrole-6-carbonitrile;
3-Chloro-4-(4-hydroxypiperidin-1-yl)-9H-dipyrido[2,3-b;4',3'-d]pyrrole-6-carbonitrile;
(S)-3-Chloro-4-(3-aminopyrrolidin-1-yl)-9H-dipyrido[2,3-b;4',3'-d]pyrrole-6-carbonitrile;
(S)-3-Chloro-4-(3-(methylamino)pyrrolidin-1-yl)-9H-dipyrido[2,3-b;4',3'-d]pyrrole-6-carbonitrile;
(S)-3-Chloro-4-(3-(ethylamino)pyrrolidin-1-yl)-9H-dipyrido[2,3-b;4',3'-d]pyrrole-6-carbonitrile;
(S)-3-Bromo-4-(3-(ethylamino)pyrrolidin-1-yl)-9H-dipyrido[2,3-b;4',3'-d]pyrrole-6-carbonitrile;
(S)-3-Fluoro-4-(3-(ethylamino)pyrrolidin-1-yl)-9H-dipyrido[2,3-b;4',3'-d]pyrrole-6-carbonitrile;
4-((3-methylpiperidin-3-yloxy)-9H-dipyrido[2,3-b;4',3'-d]pyrrole-6-carbonitrile;
4-(3-(dimethylamino)-2,2-dimethylpropoxy)-9H-dipyrido[2,3-b;4',3'-d]pyrrole-6-carbonitrile;
(S)-4-(piperidin-3-yloxy)-9H-dipyrido[2,3-b;4',3'-d]pyrrole-6-carbonitrile;
4-((4-methyl piperidin-4-yl)methoxy)-9H-dipyrido[2,3-b;4',3'-d]pyrrole-6-carbonitrile;
4-(1-(3-fluoropropyl)-4-methylpiperidin-4-yl)methoxy]-9H-dipyrido[2,3-b;4',3'-d]pyrrole-6-carbonitrile;
4-((1-(2-hydroxyethyl)-4-methylpiperidin-4-yl)methoxy)-9H-dipyrido[2,3-b;4',3'-d]pyrrole-6-carbonitrile;
4-((1-(2-methoxyethyl)-4-methylpiperidin-4-yl)methoxy)-9H-dipyrido[2,3-b;4',3'-d]pyrrole-6-carbonitrile;
4-((1-ethyl-4-methylpiperidin-4-yl)methoxy)-9H-dipyrido[2,3-b;4',3'-d]pyrrole-6-carbonitrile;
(R)-4-(1-methylpiperidin-3-yloxy)-9H-dipyrido[2,3-b;4',3'-d]pyrrole-6-carbonitrile;
4-((R)-1-ethylpiperidin-3-oxy)-9H-dipyrido[2,3-b;4',3'-d]pyrrole-6-carbonitrile;
(R)-4-(1-(2-hydroxyethyl)piperidin-3-yloxy)-9H-dipyrido[2,3-b;4',3'-d]pyrrole-6-carbonitrile;
(R)-4-(1-(2-methoxyethyl)piperidin-3-oxy)-9H-dipyrido[2,3-b;4',3'-d]pyrrole-6-carbonitrile;
4-((4-ethyl-1-methylpiperidin-4-yl)methoxy)-9H-dipyrido[2,3-b;4',3'-d]pyrrole-6-carbonitrile;
4-((1,4-dimethylpiperidin-4-yl)methoxy)-9H-dipyrido[2,3-b;4',3'-d]pyrrole-6-carbonitrile;
(R)-4-(piperidin-2-ylmethoxy)-9H-dipyrido[2,3-b;4',3'-d]pyrrole-6-carbonitrile;
(S)-4-(piperidin-2-ylmethoxy)-9H-dipyrido[2,3-b;4',3'-d]pyrrole-6-carbonitrile;
(R)-4-((1-ethylpiperidin-2-yl)methoxy)-9H-dipyrido[2,3-b;4',3'-d]pyrrole-6-carbonitrile;
(R)-4-((1-methylpiperidin-2-yl)methoxy)-9H-dipyrido[2,3-b;4',3'-d]pyrrole-6-carbonitrile;
(S)-4-(N-(2-methoxyethyl)pyrrolidin-3-amino)-9H-dipyrido[2,3-b;4',3'-d]pyrrole-6-carbonitrile;
(S)-4-(N-(3-fluoropropyl)pyrrolidin-3-amino)-9H-dipyrido[2,3-b;4',3'-d]pyrrole-6-carbonitrile;
(R)-4-(N-(2-methoxyethyl)pyrrolidin-3-amino)-9H-dipyrido[2,3-b;4',3'-d]pyrrole-6-carbonitrile;
(S)-4-(N-ethylpyrrolidin-3-amino)-9H-dipyrido[2,3-b;4',3'-d]pyrrole-6-carbonitrile;
4-(4-(pyrrolidin-3-yl)morpholino)-9H-dipyrido[2,3-b;4',3'-d]pyrrole-6-carbonitrile;
4-(2,5-diazabicyclo[2.2.1]heptan-2-yl)-9H-dipyrido[2,3-b;4',3'-d]pyrrole-6-carbonitrile;
4-(N-methylpyrrolidin-3-amino)-9H-dipyrido[2,3-b;4',3'-d]pyrrole-6-carbonitrile;
(R)-4-(N,N-dimethylpyrrolidin-3-amino-9H-dipyrido[2,3-b;4',3'-d]pyrrole-6-carbonitrile;
(S)-4-(N,N-dimethylpyrrolidin-3-amino)-9H-dipyrido[2,3-b;4',3'-d]pyrrole-6-carbonitrile;
4-(octahydropyrrolo[3,4-b]pyrrol)-9H-dipyrido[2,3-b;4',3'-d]pyrrole-6-carbonitrile;
4-((3aS,6aS)-1-methyloctahydropyrrolo[3,4-b]pyrrol)-9H-dipyrido[2,3-b;4',3'-d]pyrrole-6-carbonitrile;
4-((R)-piperidin-3-amino)-9H-dipyrido[2,3-b;4',3'-d]pyrrole-6-carbonitrile;
3-chloro-4-piperazin-9H-dipyrido[2,3-b;4',3'-d]pyrrole-6-carbonitrile;
3-Chloro-4-(1-ethylpiperazin)-9H-dipyrido[2,3-b;4',3'-d]pyrrole-6-carbonitrile;
(S)-3-Chloro-4-(N-(3-fluoropropyl)pyrrolidin-3-amino)-9H-dipyrido[2,3-b;4',3'-d]pyrrole-6-carbonitrile;
(S)-3-Chloro-4-(3-(2,2-difluoroethylamino)pyrrolidin-1-yl)-9H-dipyrido[2,3-b;4',3'-d]pyrrole-6-carbonitrile;
(S)-3-Chloro-4-(N-(pyrrolidin-3-yl)isobutyramide)-9H-dipyrido[2,3-b;4',3'-d]pyrrole-6-carbonitrile;

(S)-3-Chloro-4-(N-(2,2,2-trifluoroethyl)pyrrolidin-3-amino)-9H-dipyrido[2,3-b;4',3'-d]pyrrole-6-carbonitrile;
(R)-4-(Piperidin-3-yloxy)-6-(1-methyl-1H-pyrazol-4-yl)-9H-dipyrido[2,3-b;4',3'-d]pyrrole;
1-[4-(9H-Dipyrido[2,3b;4',3'-d]pyrrol-4-yl)-piperazin-1-yl]-2-(R)-pyrrolidin-2-yl-ethanone;
[(S)-1-(9H-Dipyrido[2,3-b;4',3'-d]pyrrol-4-yl)-pyrrolidin-3-yl]-ethyl-amine;
4-(1-Ethyl-piperidin-4-ylamino)-9H-dipyrido[2,3-b;4',3'-d]pyrrole-6-carbonitrile;
4-[(S)-(1-Azabicyclo-[2.2.2]oct-3-yl)oxy]-9H-dipyrido[2,3-b;4',3'-d]pyrrole-6-carbonitrile;
4-((S)-1-Ethylpiperidin-3-ylamino)-9H-dipyrido[2,3-b;4',3'-d]pyrrole-6-carbonitrile;
cis-3-Fluoro-piperidin-4-yloxy)-9H-dipyrido[2,3-b;4',3'-d]pyrrole-6-carbonitrile;
4-(4-Ethylpiperazin-1-yl)-9H-dipyrido[2,3-b;4',3'-d]pyrrole-6-carbonitrile;
4-(4-Pyrrolidin-1-ylpiperidin-1-yl)-9H-dipyrido[2,3-b;4',3'-d]pyrrole-6-carbonitrile;
4-(4-Morpholin-4-yl-piperidin-1-yl)-9H-dipyrido[2,3b;4',3'd]pyrrole-6-carbonitrile;
4-((R)-1-Ethyl-piperidin-3-ylamino)-9H-dipyrido-[2,3b;4',3'-d]pyrrole-6-carbonitrile;
4-(4-Methylaminopiperidin-1-yl)-9H-dipyrido[2,3-b;4',3'-d]pyrrole-6-carbonitrile;
4-((R)-3-Hydroxypyrrolidin-1-yl)-9H-dipyrido[2,3b;4',3'-d]pyrrole-6-carbonitrile;
4-((S)-3-Hydroxypyrrolidin-1-yl)-9H-dipyrido[2,3b;4',3'-d]pyrrole-6-carbonitrile; and
Trans-3-Fluoropiperidin-4-yloxy)-9H-dipyrido[2,3-b;4',3'd]pyrrole-6-carbonitrile.

In certain embodiments there is provided a compound selected from the group consisting of:
5-(Piperidin-4-ylmethoxy)-9H-dipyrido[2,3-b;4',3'-d]pyrrole-6-carbonitrile;
5-(Pyrrolidin-3-ylmethoxy)-9H-dipyrido[2,3-b;4',3'-d]pyrrole-6-carbonitrile;
5-((S)-Piperidin-3-yloxy)-9H-dipyrido[2,3-b;4',3'-d]pyrrole-6-carbonitrile;
5-((R)-1-Pyrrolidin-2-ylmethoxy)-9H-dipyrido[2,3-b;4',3'-d]pyrrole-6-carbonitrile;
5-[1-(3,3,3-Trifluoro-propyl)-piperidin-4-ylamino]-9H-dipyrido[2,3-b;4',3'-d]pyrrole-6-carbonitrile;
5-((S)-1-Ethyl-piperidin-3-yloxy)-9H-dipyrido[2,3-b;4',3'-d]pyrrole-6 carbonitrile;
5-[1-(2-Methoxy-ethyl)-piperidin-4-ylamino]-9H-dipyrido[2,3-b;4',3'-d]pyrrole-6-carbonitrile;
5-(1-Cyclopropylmethyl-piperidin-4-yloxy)-9H-dipyrido[2,3-b;4',3'-d]pyrrole-6-carbonitrile;
5-(Cis)-3-Fluoro-piperidin-4-yloxy)-9H-dipyrido[2,3b;4',3'-d]pyrrole-6-carbonitrile;
5-((S)-1-Pyrrolidin-2-ylmethoxy)-9H-dipyrido[2,3-b;4',3'-d]pyrrole-6-carbonitrile;
5-[(1-Ethyl-piperidin-4-ylmethyl)-amino]-9H-dipyrido[2,3-b;4',3'-d]pyrrole-6-carbonitrile;
5-[(1-Ethyl-piperidin-4-yl)-methyl-amino]-9H-dipyrido[2,3-b;4',3'-d]pyrrole-6-carbonitrile;
5-(1-Butyl-piperidin-4yloxy)-9H-dipyrido[2,3-b;4',3'-d]pyrrole-6-carbonitrile;
5-(1-Methyl-piperidin-4-yloxy)-9H-dipyrido[2,3-b;4',3'-d]pyrrole-6-carbonitrile;
5-[1-(3,3,3-Trifluoro-propyl)-piperidin-4-ylamino]-9H-dipyrido[2,3-b;4',3'-d]pyrrole-6-carbonitrile;
5-[(S)-(1-Azabicyclo[2.2.2]oct-3-yl)amino]-9H-dipyrido[2,3-b;4',3'-d]pyrrole-6-carbonitrile;
5-(2-Pyrrolidin-1-yl-ethoxy)-9H-dipyrido[2,3-b;4',3'-d]pyrrole-6-carbonitrile;
5-(trans)-3-Fluoro-piperidin-4-yloxy)-9H-dipyrido[2,3-b;4',3'-d]pyrrole-6-carbonitrile;
5-[(4-Ethyl-morpholin-2-ylmethyl)-amino]-9H-dipyrido[2,3-b;4',3'-d]pyrrole-6-carbonitrile;
5-(4-Ethylamino-piperidin-1-yl)-9H-dipyrido[2,3-b;4',3'-d]pyrrole-6-carbonitrile;
5-(1-Oxetan-3-yl-piperidin-4-ylamino)-9H-dipyrido[2,3-b;4',3'-d]pyrrole-6-carbonitrile;
5-(1-Cyclopropylmethyl-piperidin-4-ylamino)-9H-dipyrido[2,3-b;4',3'-d]pyrrole-6-carbonitrile;
5-[1,3']Bipyrrolidinyl-1'-yl-9H-dipyrido[2,3-b;4',3'-d]pyrrole-6-carbonitrile;
5-[1-(3-Fluoro-propyl)-piperidin-4-yloxy]-9H-dipyrido[2,3-b;4',3'-d]pyrrole-6-carbonitrile;
5-[4-(3-Fluoro-azetidin-1-yl)-piperidin-1-yl]-9H-dipyrido[2,3-b;4',3'-d]pyrrole-6-carbonitrile;
5-[4-(3-Hydroxy-azetidin-1-yl)-piperidin-1-yl]-9H-dipyrido[2,3-b;4',3'-d]pyrrole-6-carbonitrile;
5-[4-((S)-3-Fluoro-pyrrolidin-1-yl)-piperidin-1-yl]-9H-dipyrido[2,3-b;4',3'-d]pyrrole-6-carbonitrile;
5-(4-Azetidin-1-yl-piperidin-1-yl)-9H-dipyrido[2,3-b;4',3'-d]pyrrole-6-carbonitrile;
5-[4-((R)-3-Fluoropyrrolidin-1-yl)-piperidin-1-yl]-9H-dipyrido[2,3-b;4',3'-d]pyrrole-6carbonitrile;
5-[4-((S)-3-Hydroxypyrrolidin-1-yl)-piperidin-1-yl]-9H-dipyrido[2,3-b;4',3'-d]pyrrole-6-carbonitrile;
5-[4-((R)-3-Hydroxy-pyrrolidin-1-yl)-piperidin-1-yl]-9H-dipyrido[2,3-b;4',3'-d]pyrrole-6-carbonitrile;
5-(4-Hydroxy-piperidin-1-yl)-9H-dipyrido[2,3-b;4',3'-d]pyrrole-6-carbonitrile;
5-(4-Hydroxy-[1,4']bipiperidinyl-1'-yl)-9H-dipyrido[2,3-b;4',3'-d]pyrrole-6-carbonitrile;
5-(4-Fluoro-[1,4']bipiperidinyl-1'-yl)-9H-dipyrido[2,3-b;4',3'-d]pyrrole-6-carbonitrile;
5-(4-Hydroxy-4-methyl-piperidin-1-yl)-9H-dipyrido[2,3-b;4',3'-d]pyrrole-6-carbonitrile;
5-(1-Aza-bicyclo[2.2.2]oct-4-yloxy)-9H-dipyrido[2,3-b;4',3'-d]pyrrole-6-carbonitrile;
5-(1,4-Dimethyl-piperidin-4-yloxy)-9H-dipyrido[2,3-b;4',3'-d]pyrrole-6-carbonitrile;
5-(4-Hydroxy-4-methyl[1,4']bipiperidinyl-1'-yl)-9H-dipyrido[2,3b;4',3'-d]pyrrole-6-carbonitrile;
3-Bromo-5-(piperidin-4-ylamino)-9H-dipyrido[2,3-b;4',3'-d]pyrrole-6-carbonitrile;
3-Bromo-5-(piperidin-4-yloxy)-9H-dipyrido[2,3-b;4',3'-d]pyrrole-6-carbonitrile;
3-Bromo-5-(1-oxetan-3-yl-piperidin-4-yloxy)-9H-dipyrido[2,3-b;4',3'-d]pyrrole-6-carbonitrile;
3-Bromo-5-(1-ethyl-piperidin-4-ylamino)-9H-dipyrido[2,3-b;4',3'-d]pyrrole-6-carbonitrile;
5-(1-Ethyl-piperidin-4-yloxy)-3-fluoro-9H-dipyrido[2,3-b;4',3'-d]pyrrole-6-carbonitrile;
5-[(S)-(1-Azabicyclo[2.2.2]oct-3-yl)oxy]-3-fluoro-9H-dipyrido[2,3-b;4',3'-d]pyrrole-6-carbonitrile;
3-Fluoro-5-(4-morpholin-4-yl-piperidin-1-yl)-9H-dipyrido[2,3-b;4',3'-d]pyrrole-6-carbonitrile;
3-Chloro-5-(4-morpholin-4-yl-piperidin-1-yl)-9H-dipyrido[2,3-b;4',3'-d]pyrrole-6-carbonitrile;
3-Fluoro-5-(piperidin-4-yloxy)-9H-dipyrido[2,3-b;4',3'-d]pyrrole-6-carbonitrile;
3-Bromo-5-(4-morpholin-4-yl-piperidin-1-yl)-9H-dipyrido[2,3-b;4',3'-d]pyrrole-6-carbonitrile;
5-[(S)-(1-Azabicyclo[2.2.2]oct-3-yl)oxy]-3-chloro-9H-dipyrido[2,3-b;4',3'-d]pyrrole-6-carbonitrile;

3-Chloro-5-(1-ethyl-piperidin-4-ylamino)-9H-dipyrido[2,3-b;4',3'-d]pyrrole-6-carbonitrile;
3-Chloro-5-(4-pyrrolidin-1-yl-piperidin-1-yl)-9H-dipyrido[2,3-b;4',3'-d]pyrrole-6-carbonitrile;
5-(1-Ethyl-piperidin-3-ylmethoxy)-9H-dipyrido[2,3-b;4',3'd]pyrrole-6-carbonitrile;
5-(1-Ethyl-piperidin-4-ylmethoxy)-9H-dipyrido[2,3-b;4',3'-d]pyrrole-6-carbonitrile;
5-((S)-1-Ethyl-piperidin-3-ylmethoxy)-9H-dipyrido[2,3-b;4',3'-d]pyrrole-6-carbonitrile;
5-(1-Methyl-azepan-4-yloxy)-9H-dipyrido[2,3-b;4',3'-d]pyrrole-6-carbonitrile;
5-[1-(2-Hydroxy-2-methyl-propy)-piperidin-4-yloxy]-9H-dipyrido[2,3-b;4',3'-d]pyrrole-6-carbonitrile;
5-(1-Ethyl-azetidin-3-yloxy)-9H-dipyrido[2,3-b;4',3'-d]pyrrole-6-carbonitrile;
3-Fluoro-5-(1-methyl-piperidin-4-yloxy)-9H-dipyrido[2,3-b;4',3'-d]pyrrole-6-carbonitrile;
3-Chloro-5-(1-methyl-piperidin-4-yloxy)-9H-dipyrido[2,3-b;4',3'-d]pyrrole-6-carbonitrile;
3-Chloro-5-(1-ethyl-piperidin-4-yloxy)-9H-dipyrido[2,3-b;4',3'-d]pyrrole-6-carbonitrile;
5-(1-Methyl-piperidin-4-ylamino)-9H-dipyrido[2,3-b;4',3'-d]pyrrole-6-carbonitrile;
5-(4-Pyrrolidin-1-yl-piperidin-1-yl)-9H-dipyrido[2,3-b;4',3'-d]pyrrole-6-carbonitrile;
5-(4-Morpholin-4-yl-piperidin-1-yl)-9H-dipyrido[2,3-b;4',3'-d]pyrrole-6-carbonitrile;
5-(Piperidin-4-ylamino)-9H-dipyrido[2,3-b;4',3'-d]pyrrole-6-carbonitrile;
5-Piperazin-1-yl-9H-dipyrido[2,3-b;4',3'-d]pyrrole-6 carbonitrile;
5-[1-(2,2-Difluoroethyl)-piperidin-4-yloxy]-9H-dipyrido[2,3-b;4',3'-d]pyrrole-6-carbonitrile;
5-[1-(2-Methanesulfonylethyl)-piperidin-4-yloxy]-9H-dipyrido[2,3-b;4',3'-d]pyrrole-6-carbonitrile;
5-[1-(2-Hydroxyethyl)-piperidin-4-yloxy]-9H-dipyrido[2,3-b;4',3'-d]pyrrole-6-carbonitrile;
5-(1-Ethyl-piperidin-4-yloxy)-3-methyl-9H-dipyrido[2,3-b;4',3'-d]pyrrole-6-carbonitrile; and
5-(1-Ethyl-piperidin-4-yloxy)-9H-dipyrido[2,3-b;4',3'-d]pyrrole.
In certain embodiments there is provided a compound selected from the group consisting of:
5-(Piperidin-4-ylmethoxy)-9H-dipyrido[2,3-b;4',3'-d]pyrrole-6-carbonitrile;
5-(Pyrrolidin-3-ylmethoxy)-9H-dipyrido[2,3-b;4',3'-d]pyrrole-6-carbonitrile;
5-((S)-Piperidin-3-yloxy)-9H-dipyrido[2,3-b;4',3'-d]pyrrole-6-carbonitrile;
5-((R)-1-Pyrrolidin-2-ylmethoxy)-9H-dipyrido[2,3-b;4',3'-d]pyrrole-6-carbonitrile;
5-((S)-1-Ethyl-piperidin-3-yloxy)-9H-dipyrido[2,3-b;4',3'-d]pyrrole-6 carbonitrile;
5-(1-Cyclopropylmethyl-piperidin-4-yloxy)-9H-dipyrido[2,3-b;4',3'-d]pyrrole-6-carbonitrile;
5-(Cis-3-Fluoro-piperidin-4-yloxy)-9H-dipyrido[2,3b;4',3'-d]pyrrole-6-carbonitrile;
5-((S)-1-Pyrrolidin-2-ylmethoxy)-9H-dipyrido[2,3-b;4',3'-d]pyrrole-6-carbonitrile;
5-(1-Butyl-piperidin-4yloxy)-9H-dipyrido[2,3-b;4',3'-d]pyrrole-6-carbonitrile;
5-(1-Methyl-piperidin-4-yloxy)-9H-dipyrido[2,3-b;4',3'-d]pyrrole-6-carbonitrile;
5-(2-Pyrrolidin-1-yl-ethoxy)-9H-dipyrido[2,3-b;4',3'-d]pyrrole-6-carbonitrile;
5-(trans)-3-Fluoro-piperidin-4-yloxy)-9H-dipyrido[2,3-b;4',3'-d]pyrrole-6-carbonitrile;
5-[1-(3-Fluoro-propyl)-piperidin-4-yloxy]-9H-dipyrido[2,3-b;4',3'-d]pyrrole-6-carbonitrile;
5-(4-Hydroxy-4-methyl-piperidin-1-yl)-9H-dipyrido[2,3-b;4',3'-d]pyrrole-6-carbonitrile;
5-(1-Aza-bicyclo[2.2.2]oct-4-yloxy)-9H-dipyrido[2,3-b;4',3'-d]pyrrole-6-carbonitrile;
5-(1,4-Dimethyl-piperidin-4-yloxy)-9H-dipyrido[2,3-b;4',3'-d]pyrrole-6-carbonitrile;
3-Bromo-5-(piperidin-4-yloxy)-9H-dipyrido[2,3-b;4',3'-d]pyrrole-6-carbonitrile;
3-Bromo-5-(1-oxetan-3-yl-piperidin-4-yloxy)-9H-dipyrido[2,3-b;4',3'-d]pyrrole-6-carbonitrile;
5-(1-Ethyl-piperidin-4-yloxy)-3-fluoro-9H-dipyrido[2,3-b;4',3'-d]pyrrole-6-carbonitrile;
5-[(S)-(1-Azabicyclo[2.2.2]oct-3-yl)oxy]-3-fluoro-9H-dipyrido[2,3-b;4',3'-d]pyrrole-6-carbonitrile;
3-Fluoro-5-(piperidin-4-yloxy)-9H-dipyrido[2,3-b;4',3'-d]pyrrole-6-carbonitrile;
5-[(S)-(1-Azabicyclo[2.2.2]oct-3-yl)oxy]-3-chloro-9H-dipyrido[2,3-b;4',3'-d]pyrrole-6-carbonitrile;
5-(1-Ethyl-piperidin-3-ylmethoxy)-9H-dipyrido[2,3-b;4',3'd]pyrrole-6-carbonitrile;
5-(1-Ethyl-piperidin-4-ylmethoxy)-9H-dipyrido[2,3-b;4',3'-d]pyrrole-6-carbonitrile;
5-((S)-1-Ethyl-piperidin-3-ylmethoxy)-9H-dipyrido[2,3-b;4',3'-d]pyrrole-6-carbonitrile;
5-(1-Methyl-azepan-4-yloxy)-9H-dipyrido[2,3-b;4',3'-d]pyrrole-6-carbonitrile;
5-[1-(2-Hydroxy-2-methyl-propyl)-piperidin-4-yloxy]-9H-dipyrido[2,3-b;4',3'-d]pyrrole-6-carbonitrile;
5-(1-Ethyl-azetidin-3-yloxy)-9H-dipyrido[2,3-b;4',3'-d]pyrrole-6-carbonitrile;
3-Fluoro-5-(1-methyl-piperidin-4-yloxy)-9H-dipyrido[2,3-b;4',3'-d]pyrrole-6-carbonitrile;
3-Chloro-5-(1-methyl-piperidin-4-yloxy)-9H-dipyrido[2,3-b;4',3'-d]pyrrole-6-carbonitrile;
3-Chloro-5-(1-ethyl-piperidin-4-yloxy)-9H-dipyrido[2,3-b;4',3'-d]pyrrole-6-carbonitrile;
5-[1-(2,2-Difluoroethyl)-piperidin-4-yloxy]-9H-dipyrido[2,3-b;4',3'-d]pyrrole-6-carbonitrile;
5-[1-(2-Methanesulfonylethyl)-piperidin-4-yloxy]-9H-dipyrido[2,3-b;4',3'-d]pyrrole-6-carbonitrile;
5-[1-(2-Hydroxyethyl)-piperidin-4-yloxy]-9H-dipyrido[2,3-b;4',3'-d]pyrrole-6-carbonitrile;
5-(1-Ethyl-piperidin-4-yloxy)-3-methyl-9H-dipyrido[2,3-b;4',3'-d]pyrrole-6-carbonitrile; and
5-(1-Ethyl-piperidin-4-yloxy)-9H-dipyrido[2,3-b;4',3'-d]pyrrole.
In certain embodiments there is provided a compound selected from the group consisting of:
5-[1-(3,3,3-Trifluoro-propyl)-piperidin-4-ylamino]-9H-dipyrido[2,3-b;4',3'-d]pyrrole-6-carbonitrile;
5-[1-(2-Methoxy-ethyl)-piperidin-4-ylamino]-9H-dipyrido[2,3-b;4',3'-d]pyrrole-6-carbonitrile;
5-[(1-Ethyl-piperidin-4-ylmethyl)-amino]-9H-dipyrido[2,3-b;4',3'-d]pyrrole-6-carbonitrile;
5-[(1-Ethyl-piperidin-4-yl)-methyl-amino]-9H-dipyrido[2,3-b;4',3'-d]pyrrole-6-carbonitrile;
5-[1-(3,3,3-Trifluoro-propyl)-piperidin-4-ylamino]-9H-dipyrido[2,3-b;4',3'-d]pyrrole-6-carbonitrile;
5-[(S)-(1-Azabicyclo[2.2.2]oct-3-yl)amino]-9H-dipyrido[2,3-b;4',3'-d]pyrrole-6-carbonitrile;
5-[(4-Ethyl-morpholin-2-ylmethyl)-amino]-9H-dipyrido[2,3-b;4',3'-d]pyrrole-6-carbonitrile;

5-(1-Oxetan-3-yl-piperidin-4-ylamino)-9H-dipyrido[2,3-b; 4',3'-d]pyrrole-6-carbonitrile;
5-(1-Cyclopropylmethyl-piperidin-4-ylamino)-9H-dipyrido [2,3-b;4',3'-d]pyrrole-6-carbonitrile;
3-Bromo-5-(piperidin-4-ylamino)-9H-dipyrido[2,3-b;4',3'-d]pyrrole-6-carbonitrile;
3-Bromo-5-(1-ethyl-piperidin-4-ylamino)-9H-dipyrido[2,3-b;4',3'-d]pyrrole-6-carbonitrile;
3-Chloro-5-(1-ethyl-piperidin-4-ylamino)-9H-dipyrido[2,3-b;4',3'-d]pyrrole-6-carbonitrile;
5-(1-Methyl-piperidin-4-ylamino)-9H-dipyrido[2,3-b;4',3'-d]pyrrole-6-carbonitrile; and
5-(Piperidin-4-ylamino)-9H-dipyrido[2,3-b;4',3'-d]pyrrole-6-carbonitrile.

In certain embodiments there is provided a compound selected from the group consisting of:
5-[4-(3-Fluoro-azetidin-1-yl)-piperidin-1-yl]-9H-dipyrido [2,3-b;4',3'-d]pyrrole-6-carbonitrile;
5-[4-(3-Hydroxy-azetidin-1-yl)-piperidin-1-yl]-9H-dipyrido [2,3-b;4',3'-d]pyrrole-6-carbonitrile;
5-[4-((S)-3-Fluoro-pyrrolidin-1-yl)-piperidin-1-yl]-9H-dipyrido[2,3-b;4',3'-d]pyrrole-6-carbonitrile;
5-(4-Azetidin-1-yl-piperidin-1-yl)-9H-dipyrido[2,3-b;4',3'-d]pyrrole-6-carbonitrile;
5-[4-((R)-3-Fluoropyrrolidin-1-yl)-piperidin-1-yl]-9H-dipyrido[2,3-b;4',3'-d]pyrrole-6carbonitrile;
5-[4-((S)-3-Hydroxypyrrolidin-1-yl)-piperidin-1-yl]-9H-dipyrido[2,3-b;4',3'-d]pyrrole-6-carbonitrile;
5-[4-((R)-3-Hydroxy-pyrrolidin-1-yl)-piperidin-1-yl]-9H-dipyrido[2,3-b;4',3'-d]pyrrole-6-carbonitrile;
5-(4-Hydroxy-piperidin-1-yl)-9H-dipyrido[2,3-b;4',3'-d]pyrrole-6-carbonitrile;
5-(4-Hydroxy-[1,4']bipiperidinyl-1'-yl)-9H-dipyrido[2,3-b; 4',3'-d]pyrrole-6-carbonitrile;
5-(4-Fluoro-[1,4']bipiperidinyl-1'-yl)-9H-dipyrido[2,3-b;4', 3'-d]pyrrole-6-carbonitrile;
5-(4-Hydroxy-4-methyl-piperidin-1-yl)-9H-dipyrido[2,3-b; 4',3'-d]pyrrole-6-carbonitrile;
5-(4-Hydroxy-4-methyl[1,4']bipiperidinyl-1'-yl)-9H-dipyrido[2,3b;4',3'-d]pyrrole-6-carbonitrile;
3-Fluoro-5-(4-morpholin-4-yl-piperidin-1-yl)-9H-dipyrido [2,3-b;4',3'-d]pyrrole-6-carbonitrile;
3-Chloro-5-(4-morpholin-4-yl-piperidin-1-yl)-9H-dipyrido [2,3-b;4',3'-d]pyrrole-6-carbonitrile;
3-Bromo-5-(4-morpholin-4-yl-piperidin-1-yl)-9H-dipyrido [2,3-b;4',3'-d]pyrrole-6-carbonitrile;
3-Chloro-5-(4-pyrrolidin-1-yl-piperidin-1-yl)-9H-dipyrido [2,3-b;4',3'-d]pyrrole-6-carbonitrile;
5-(4-Pyrrolidin-1-yl-piperidin-1-yl)-9H-dipyrido[2,3-b;4', 3'-d]pyrrole-6-carbonitrile;
5-(4-Morpholin-4-yl-piperidin-1-yl)-9H-dipyrido[2,3-b;4', 3'-d]pyrrole-6-carbonitrile; and
5-Piperazin-1-yl-9H-dipyrido[2,3-b;4',3'-d]pyrrole-6 carbonitrile.

Synthesis

The present compounds are prepared according to the procedures described below in the schemes and examples, or by methods known in the art. The starting materials and various intermediates may be obtained from commercial sources, prepared from commercially available compounds, or prepared using well known synthetic methods. Accordingly, methods for making the present compounds of Formula (I), (I-a) or (I-b) according to one or more of Schemes 1, 2, 3, 4, 5, 6, 7, 8, 9, 10, 11a, 11b, 11c, 11d, 11c, 11d, 11e, 12, 13, 14, 15, 16, 17, 18, 19, 20, 21, 22, 23, 24, 25, 26, 27 (27-1, 27-2, and 27-3), and/or 28-32 are within the scope of the present invention.

For example, 9H-dipyrido[2,3-b;4',3'-d]pyrrole (also referred to as diazacarbazole herein) compounds of formula (1-4) may be prepared using the synthetic route outlined in Scheme 1.

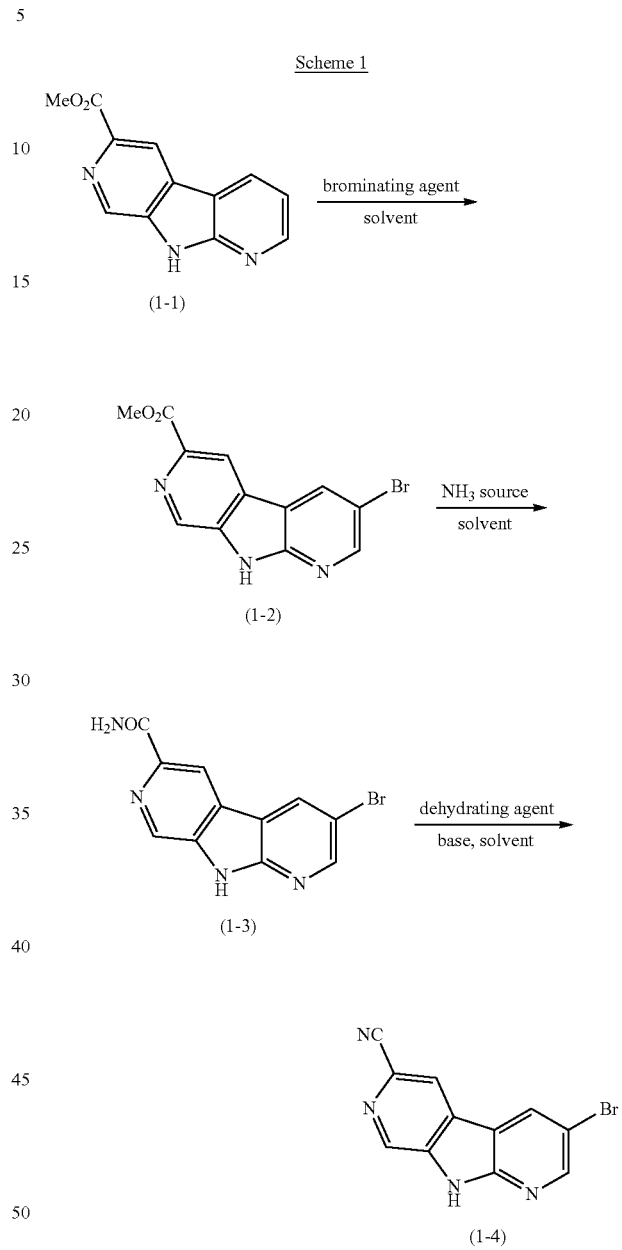

Compounds of formula (1-1) may be prepared using published methods described in the literature. Intermediates of formula (1-1) may then be brominated in the presence of a suitable brominating agent, such as bromine, in a suitable solvent such as acetic acid, at a temperature between 20° C. and 120° C., to obtain compounds of formula (1-2).

Compounds of formula (1-3) can be obtained by reaction of intermediate (1-2) with an appropriate source of ammonia, such as ammonia gas, in a suitable solvent such as methanol, at a temperature between 20° C. and 65° C.

Intermediates of formula (1-3) may then be dehydrated in the presence of a suitable dehydrating agent, such as trifluoroacetic anhydride, in a suitable solvent such as THF, at a temperature from 20° C. to the boiling point of the solvent, to obtain compounds of formula (1-4).

Scheme 2

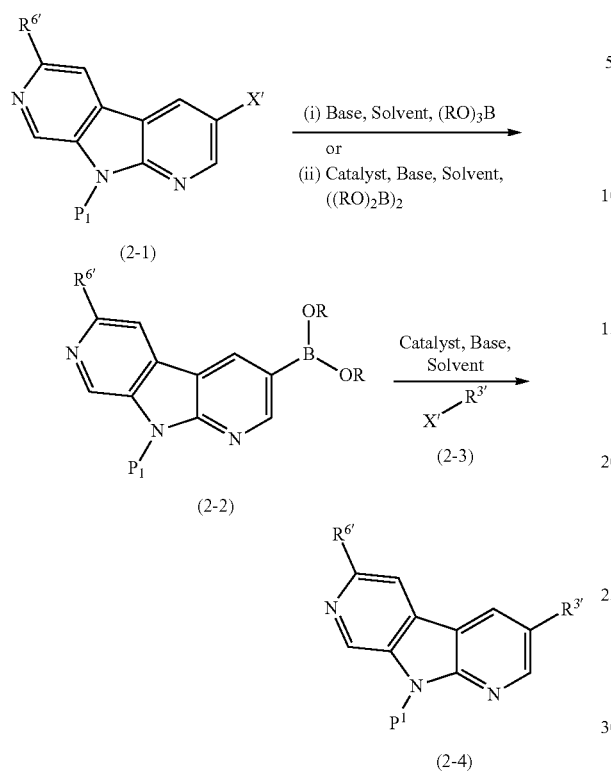

where X' = Cl, Br, I, or OTf

Compounds of formula (2-4) may also be prepared according to the procedure shown in Scheme 2 (wherein $R^{3'}$ is $R^3$ or intermediate moieties that may be manipulated to give $R^3$, and $R^{6'}$ is $R^6$ or intermediate moieties that may be manipulated to give $R^6$). The boronic acid of formula (2-2, where R=H) may be prepared from compounds of formula (2-1) by treatment with a base such as butyllithium in the presence of an alkyl borate such as trimethyl borate in a suitable solvent such as THF at a temperature between −78° C. and ambient temperature.

Alternatively, the boronate ester of formula (2-2, where R=alkyl) may be prepared from compounds of formula (2-1) with the appropriate alkylatodiboron in the presence of a catalyst such as bis(diphenylphosphino)ferrocene palladium (II) dichloride, using a suitable base such as potassium acetate in a solvent such as dioxane at a temperature from room temperature to the reflux temperature of the solvent, or under microwave irradiation at a temperature between 70° C. and 150° C.

Compounds of formula (2-4) may be prepared according to the procedure shown in Scheme 2 by reaction of compounds of formula (2-2) with appropriate halide of formula (2-3) (incorporating appropriate substituents $R^{3'}$), in the presence of a catalyst such as bis(triphenylphosphine)palladium(II)dichloride, with a base such as aqueous sodium carbonate in a suitable co-solvent such as acetonitrile at a temperature from room temperature to the reflux temperature of the solvent, or under microwave irradiation at a temperature between 70° C. and 150° C.

The protecting group ($P_1$) of compounds of formula (2-1), (2-2) and (2-4) may be manipulated at any stage of the synthesis. A protecting group such as SEM (trimethylsilyl ethoxymethyl), can be installed using an alkylating agent such as SEM-chloride, in a solvent such as DMF in the presence of a suitable base such as sodium hydride. Compounds of general formula (2-4) where $P_1$ is a protecting group such as SEM may be de-protected using a reagent such as tetrabutylammonium fluoride in a solvent such as THF at a temperature between −20° C. and 50° C. to provide compounds where $P_1$ is H.

Scheme 3

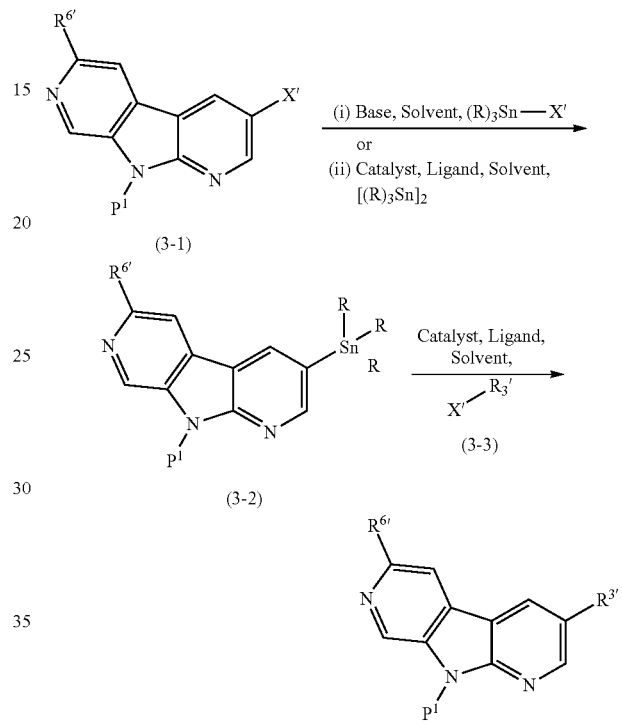

where X' = Cl, Br, I, or OTf

Compounds of general formula (3-4) may also be prepared according to the procedure shown in Scheme 3 (wherein $R^{3'}$ is $R^3$ or intermediate moieties that may be manipulated to give $R^3$, and $R^{6'}$ is $R^6$ or intermediate moieties that may be manipulated to give $R^6$). Stannanes of general formula (3-2) may be prepared from compounds of formula (3-1) with a base and the appropriate tin halide in a suitable solvent such as THF.

Alternatively, stannanes of general formula (3-2) may be prepared from compounds of formula (3-1) with the appropriate alkylditin (containing suitable R groups) in the presence of a catalyst such as tetrakis(triphenylphosphine) palladium(0) in a suitable solvent such as toluene at a temperature from room temperature to the reflux temperature of the solvent, or under microwave irradiation at a temperature between 70° C. and 150° C.

Compounds of general formula (3-4) may be prepared from compounds of general formula (3-2) with the appropriate halide or triflate of formula (3-3), in the presence of a catalyst such as tetrakis(triphenylphosphine) palladium(0) in a suitable solvent such as dioxane at a temperature from room temperature to the reflux temperature of the solvent, or under microwave irradiation at a temperature between 70° C. and 150° C.

Scheme 4

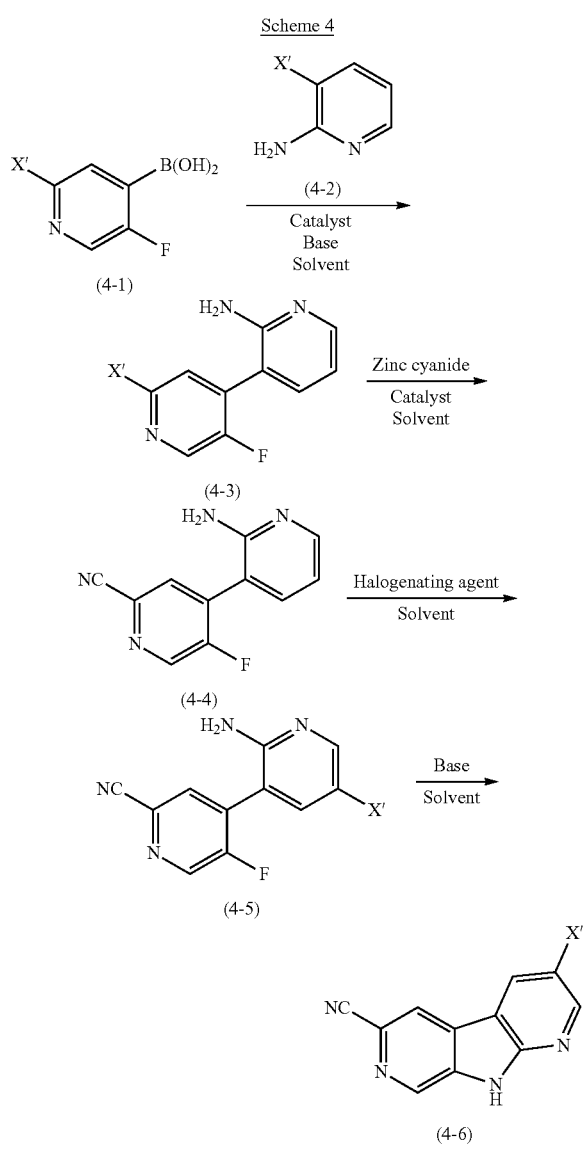

(X' = Br, I, or OTf)

Compounds of general formula (4-6) may be obtained from commercial sources or prepared using published methods described in the literature. Compounds of general formula (4-6) may also be prepared according to the procedure shown in Scheme 4.

Compounds of general formula (4-3) may be obtained from compounds of formula (4-1) by reaction with a halogenated pyridine or triflate of formula (4-2) in the presence of a transition metal catalyst such as bis(triphenylphosphine) palladium(II) dichloride, a base such as aqueous sodium carbonate in a suitable solvent such as acetonitrile at a temperature from room temperature to the reflux temperature of the solvent, or under microwave irradiation at a temperature between 70° C. and 150° C.

The 2-cyanopyridines of formula (4-4) may be prepared from 2-halopyridines of formula (4-3) by reaction with an inorganic cyanide such as zinc cyanide, in the presence of a transition metal catalyst such as tetrakis(triphenylphosphine) palladium(0), in a solvent such as DMF, at a temperature from 50° C. to reflux temperature of the solvent, or under microwave irradiation at a temperature between 70° C. and 200° C. The aminopyridine (4-4) may then be halogenated with a halogenating agent such as N-bromosuccinimide in a solvent such as DMF at a temperature between room temperature and 50° C. to give intermediates of formula (4-5).

Cyclisation of compounds with general formula (4-5) with a suitable base such as sodium hexamethyldisilazide in a suitable solvent such as THF at a temperature between 0° C. and 50° C. may give compounds of general formula (4-6).

Scheme 5

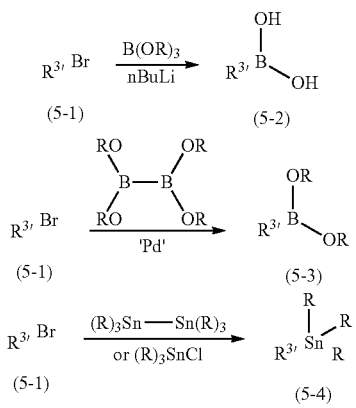

Compounds of general formulae (5-2), (5-3) and (5-4) may be prepared using published methods described in the literature. Compounds of formulae (5-2), (5-3) and (5-4) may also be prepared using the synthetic routes outlined in Scheme 5 (wherein $R^{3'}$ is $R^3$ or intermediate moieties that may be manipulated to give $R^3$).

Compounds of general formula (5-2) may be obtained from compounds of formula (5-1) by reaction with a reagent such as n-butyllithium in a polar aprotic solvent such as THF or diethylether at temperatures between −100° C. and 0° C. and quenched with a boronic ester such as trimethyl borate or triisopropyl borate.

Compounds of general formula (5-3) may be obtained from compounds of formula (5-1) by reaction with a reagent such as bis(pinacolato)diborane in the presence of a catalyst such as [1,1'-bis(diphenylphosphino)ferrocene]dichloropalladium(II), in the presence of a base such as potassium acetate in a suitable solvent such as dioxane, or a mixture of two or more appropriate solvents, at a temperature between room temperature to the reflux temperature of the solvent or solvents, or under microwave irradiation at a temperature between 70° C. and 160° C.

Compounds of general formula (5-4) may be obtained from compounds of formula (5-1) by reaction with a reagent such as hexamethylditin or triethyltin chloride in the presence of a catalyst such as tetrakis(triphenylphosphine)palladium (0), in the presence of a base such as potassium carbonate in a suitable solvent such as DMF, or a mixture of two or more appropriate solvents, at a temperature between room temperature to the reflux temperature of the solvent or solvents, or under microwave irradiation at a temperature between 70° C. and 160° C. Alternatively, these compounds of general formula (5-4) may be obtained from compounds of formula (5-1) by reaction with a reagent such as n-butyllithium in a suitable aprotic solvent such as THF at temperatures between −100° C. and 25° C. and then reacted with a reagent such as hexamethylditin or triethyltin chloride in a suitable aprotic solvent such as THF at temperatures between −100° C. and 50° C.

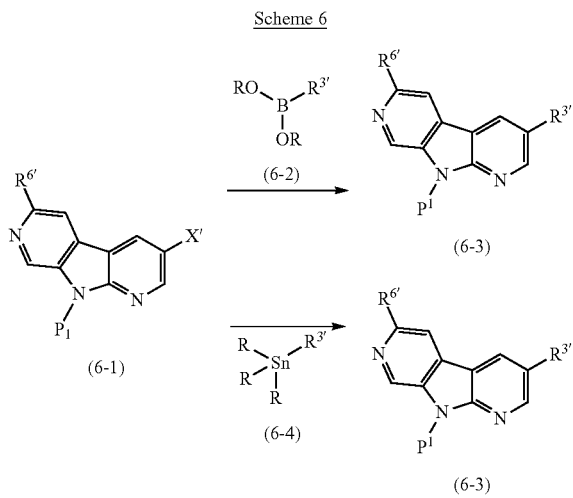

Scheme 6

X' = I, Br, Cl or OTf

Compounds of general formula (6-3) may be prepared using published methods described in the literature. Compounds of formula (6-3) may also be prepared using the synthetic routes outlined in Scheme 6 (wherein $R^{3'}$ is $R^3$ or intermediate moieties that may be manipulated to give $R^3$, and $R^{6'}$ is $R^6$ or intermediate moieties that may be manipulated to give $R^6$). Compounds of general formula (6-3) may be obtained from compounds of formula (6-1) by reaction with a boronic acid or boronate ester of formula (6-2) (incorporating appropriate substituents $R^{3'}$), or by reaction with an aryl or alkyl tin compound of formula (6-4) (incorporating appropriate substituents $R^{3'}$), in the presence of a catalyst such as bis(triphenylphosphine)palladium(II)dichloride, [1,1'-bis(diphenylphosphino)ferrocene]dichloropalladium (II), an aqueous base such as sodium carbonate, in a suitable solvent such as acetonitrile or combination of solvents, at a temperature between room temperature to the reflux temperature of the solvent, or under microwave irradiation at a temperature between 70° C. and 150° C.

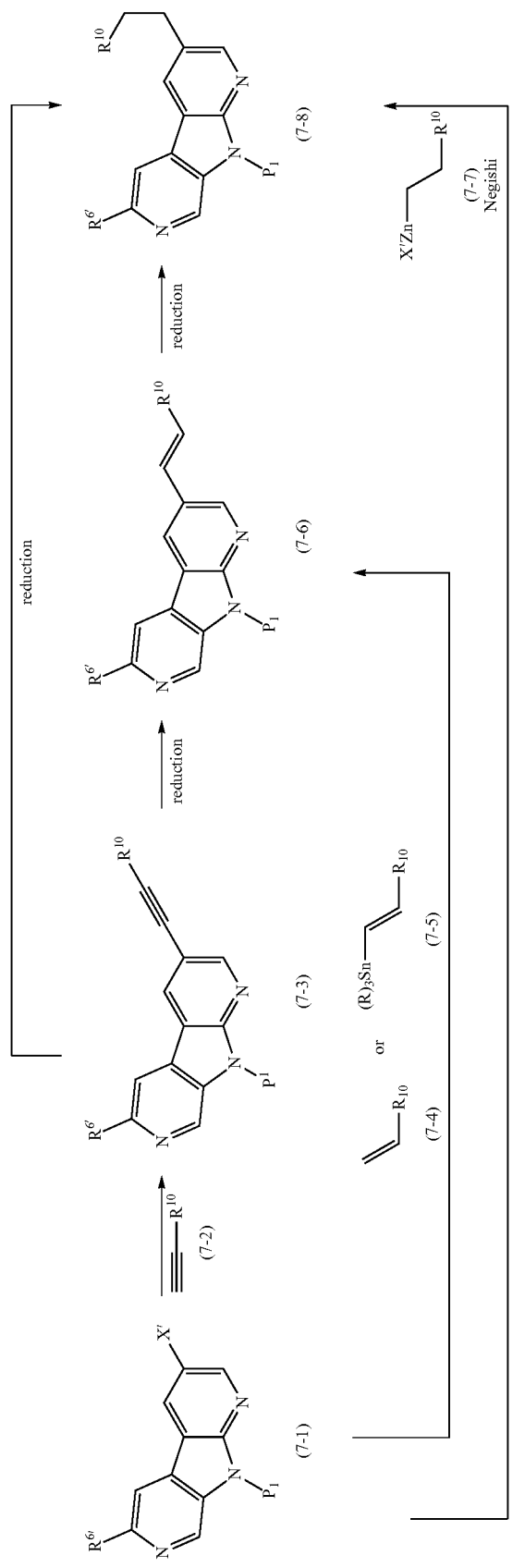

Compounds of general formula (7-8) may be prepared using published methods described in the literature. Compounds of formula (7-8) may also be prepared using the synthetic routes outlined in Scheme 7 (wherein $R^{6'}$ is $R^6$ or intermediate moieties that may be manipulated to give $R^6$). Compounds of general formula (7-3) may be obtained from compounds of general formula (7-1) and a suitable alkyne (7-2) (incorporating a group $R^{10}$ that could be either maintained without modification after coupling, or that could later be modified to give other groups $R^{10}$) by reaction in the presence of a catalyst system such as tetrakis(triphenylphosphine) palladium(0) and copper (I) iodide in the presence of a base such as triethylamine and a suitable solvent such as N,N-dimethylformamide at a temperature between room temperature and the boiling point of the solvent. Such a coupling reaction could also be carried out in the presence of palladium on carbon, triphenylphosphine, copper (I) iodide and triethylamine in the presence of a suitable solvent formula (7-1) by reaction with a vinyl stannane (7-5) (incorporating a group $R^{10}$ that could be either maintained without modification after coupling or that could later be modified to give other groups $R^{10}$) in the presence of a metal species such as tetrakis(triphenylphosphine)palladium (0) in a suitable solvent such as toluene.

Compounds of general formula (7-8) may be obtained from compounds of general formula (7-3) or (7-6) by reaction with hydrogen in the presence of a catalyst such as palladium on carbon or platinum oxide monohydrate in a suitable solvent such as methanol or ethanol.

Compounds of general formula (7-8) may also be obtained by reaction of compounds of general formula (7-1) by reaction with a suitable alkyl zinc reagent (7-7) in the presence of a catalyst such as allyl palladium (II) chloride dimer or bis(tri-tert-butylphosphine)palladium (0) and a suitable solvent such as 1,4-dioxane at a temperature between room temperature and the boiling point of the solvent.

Scheme 8

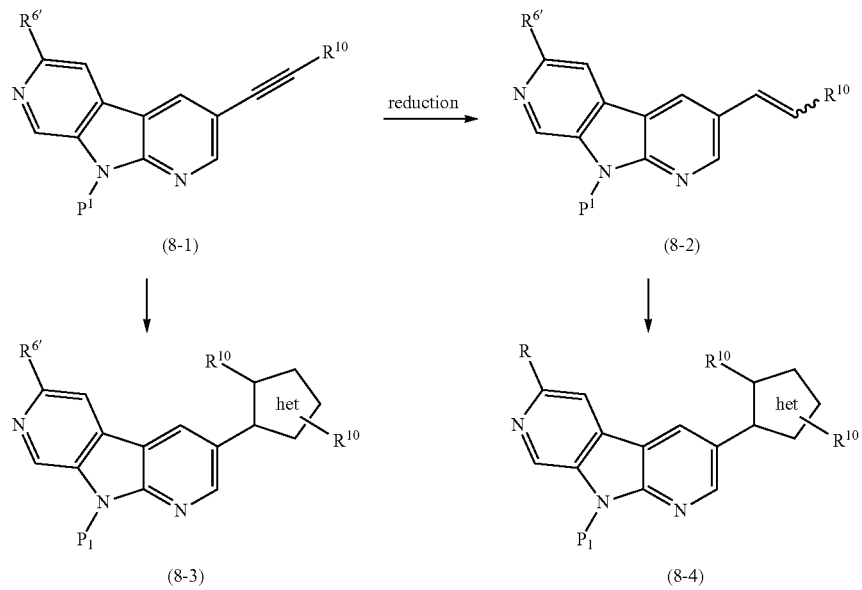

such as acetonitrile at a temperature between room temperature and the reflux temperature of the solvent or solvents, or under microwave irradiation at a temperature between 70° C. and 160° C.

Compounds of general formula (7-6) may be obtained from compounds of general formula (7-3) and hydrogen in the presence of a suitable catalyst such as Lindlar catalyst or palladium on barium sulfate in the presence of quinoline and a suitable solvent such as methanol or ethanol. Compounds of general formula (7-6) may also be obtained by reaction of a compound of general formula (7-1) with a suitable alkene (7-4) (incorporating a group $R^{10}$ that could be either maintained without modification after coupling or that could later be modified to give other groups $R^{10}$) in the presence of a base such as triethylamine or potassium carbonate, a phosphine such as triphenyl phosphine, a metal species such as palladium acetate and a solvent such as acetonitrile at a temperature between room temperature and the boiling point of the solvent. Compounds of general formula (7-6) may also be obtained by the reaction of a compound of general Compounds of general formula (8-3) may be prepared from compounds of general formula (8-1) by reaction with a suitable 1,3-dipole such as trimethylsilylazide in a suitable solvent such as toluene at a temperature between room temperature and the boiling point of the solvent.

Compounds of general formula (8-2) may be obtained from compounds of general formula (8-1) and hydrogen in the presence of a suitable catalyst such as Lindlar catalyst or palladium on barium sulfate in the presence of quinoline and a suitable solvent such as methanol or ethanol.

Compounds of general formula (8-3) may be obtained by reaction of compounds of general formula (8-2) with a suitable 1,3-dipole (or its precursors, incorporating a group $R^{10}$ that could be either maintained without modification after coupling or that could later be modified to give other $R^{10}$ groups) such as N-methoxymethyl-N-(trimethylsilylmethyl) benzylamine and lithium fluoride in a solvent such as acetonitrile with ultrasonic treatment, or nitroethane and phenyl isocyanate in a suitable solvent such as toluene in the presence of a base such as triethylamine at a temperature between 0° C. and the boiling point of the solvent.

Scheme 9

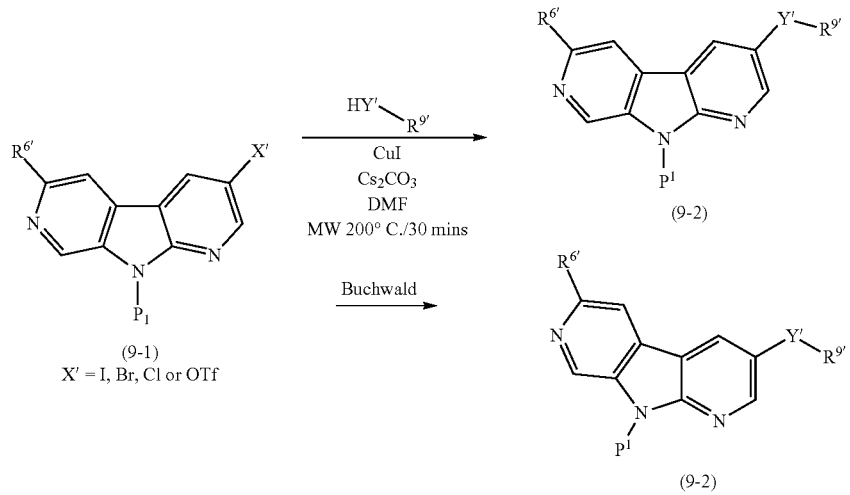

Compounds of general formula (9-2) may be prepared using published methods described in the literature. Compounds of formula (9-2) may be prepared using the synthetic routes outlined in Scheme 9 (wherein R$^{9'}$ is R$^9$ or intermediate moieties that may be manipulated to give R$^9$, and R$^{6'}$ is R$^6$ or intermediate moieties that may be manipulated to give R$^6$).

Compounds of general formula (9-2) may be obtained from compounds of formula (9-1) by reaction with compounds of general formula (HY'—R$^{9'}$) in the presence of reagents such as copper(II) iodide or copper powder in the presence of a base such as cesium carbonate in a suitable solvent such as DMF at a temperature between room temperature and the reflux temperature of the solvent, or under microwave irradiation at a temperature between 70° C. and 240° C., which may be similar to conditions described in the literature by Ullmann.

Compounds of general formula (9-2) may be obtained from compounds of formula (9-1) by reaction with compounds of general formula (HY'—R$^{9'}$) in the presence of a catalyst such as [1,1'-bis(diphenylphosphino)ferrocene]dichloropalladium(II), in the presence of a base such as potassium tert-butoxide in a suitable solvent such as DME, or a mixture of two or more appropriate solvents, at a temperature between room temperature and the reflux temperature of the solvent or solvents, or under microwave irradiation at a temperature between 70° C. and 160° C., which may be similar to conditions described in the literature by Buchwald and Hartwig.

Scheme 10

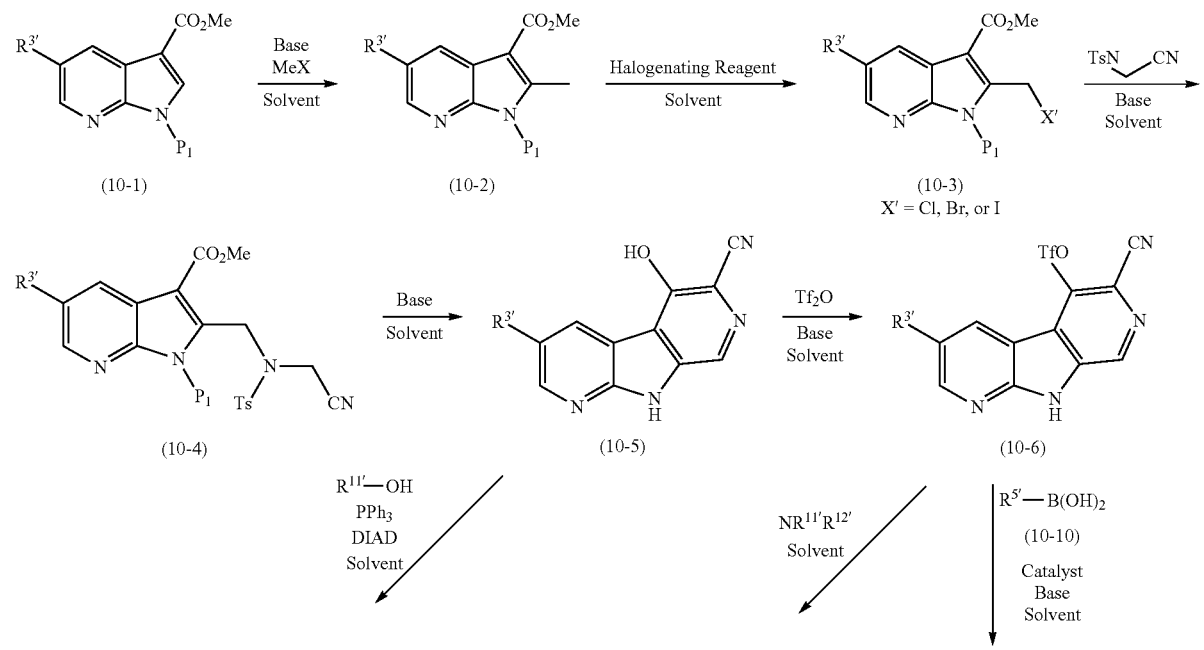

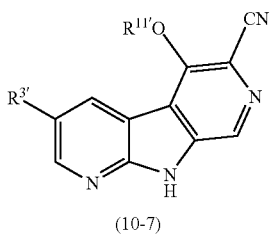 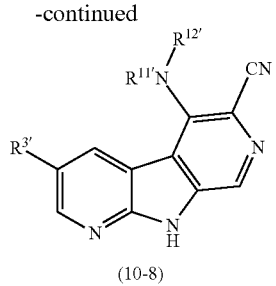 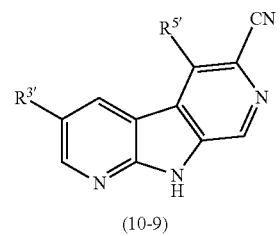

(10-7)  (10-8)  (10-9)

Compounds of general formula (10-7), (10-8) and (10-9) may be prepared using published methods described in the literature (WO2006001754). Compounds of formula (10-7), (10-8) and (10-9) may be prepared using the synthetic routes outlined in Scheme 10 (wherein $R^{3'}$ is $R^3$ or intermediate moieties that may be manipulated to give $R^3$, and $R^{5'}$ is $R^5$ or intermediate moieties that may be manipulated to give $R^5$). Compounds with a general formula (10-2) may be prepared from compounds of formula (10-1) by deprotonation using a suitable base such as lithium diisopropylamide in a suitable solvent such as THF at a temperature between −78° C. and room temperature followed by addition of a suitable methylating agent such as methyl iodide. The intermediate (10-2) may then be brominated with a brominating agent such as N-bromosuccinimide in a solvent such as carbon tetrachloride at a temperature between room temperature and the reflux temperature of the solvent to give compounds of formula (10-3).

Compounds of formula (10-3) may be converted to compounds of formula (10-4) by displacement with tosylaminoacetonitrile using a suitable base such as sodium hydride in a solvent such as DMF at a temperature between −20° C. and 50° C. Intermediates (10-4) may then be cyclised with a suitable base such as lithium hexamethylsilylamide in a solvent such as THF at a temperature between −20° C. and 50° C. to provide compounds of general formula (10-5). The phenol (10-5) may then be reacted with an appropriate alcohol ($R^{11'}OH$) using a phosphine and a coupling reagent such as diisopropylazodicarboxylate in an appropriate solvent such as THF to provide ethers of general formula (10-7).

Alternatively, the phenol intermediate (10-5) may be converted to the triflate using a reagent such as triflic anhydride in the presence of a base such as triethylamine in a suitable solvent such as dichloromethane at a temperature between −50° C. and 20° C. The triflate (10-6) may then be converted to compounds of general formula (10-9) by reaction with a boronic acid or boronate ester of formula (10-10) in the presence of a transition metal catalyst such as bis(triphenylphosphine) palladium(II)dichloride, a base such as aqueous sodium carbonate in a suitable solvent such as acetonitrile at a temperature from room temperature to the reflux temperature of the solvent, or under microwave irradiation at a temperature between 70° C. and 150° C. Alternatively, the triflate may be converted to compounds of general formula (10-8) by displacement with a suitable amine either ($HNR^{11'}R^{12'}$) as solvent or in a solvent such as 2-propanol at a temperature between ambient temperature and the reflux point of the solvent.

Compounds of general formula (10-8) may be obtained from compounds of formula (10-6) by reaction with compounds of general formula ($HNR^{11'}R^{12'}$) in the presence of a catalyst such as [1,1'-bis(diphenylphosphino)ferrocene] dichloropalladium(II), in the presence of a base such as potassium tert-butoxide in a suitable solvent such as DME, or a mixture of two or more appropriate solvents, at a temperature from room temperature to the reflux temperature of the solvent or solvents, or under microwave irradiation at a temperature between 70° C. and 160° C., which may be similar to conditions described in the literature by Buchwald and Hartwig.

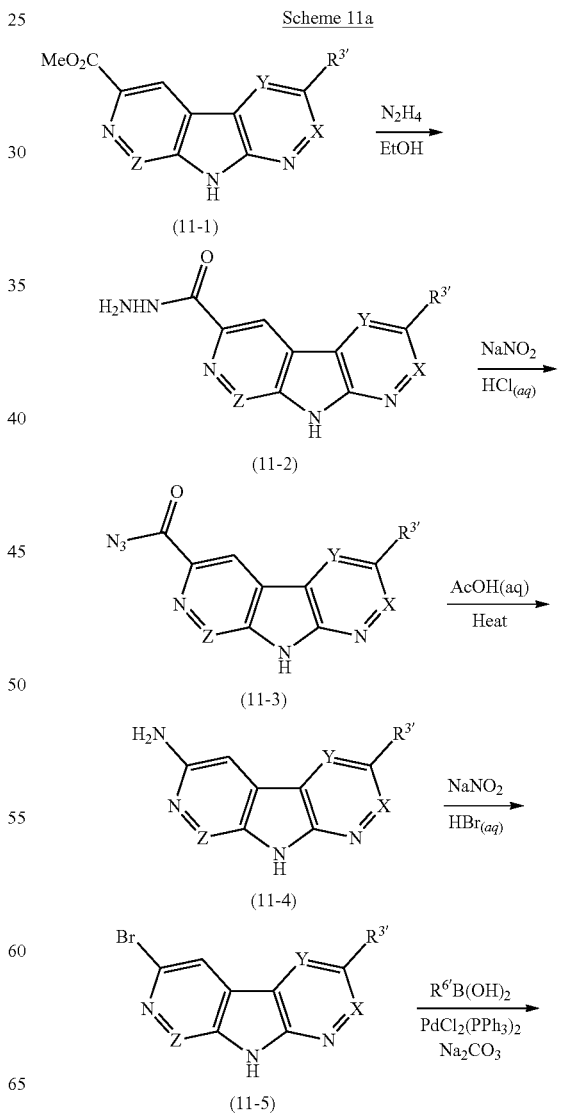

Scheme 11a

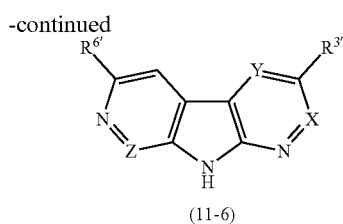

(11-6)

Compounds of general formula (11-6) may be prepared using published methods described in the literature. Compounds of formula (11-6) may be prepared using the synthetic routes outlined in Scheme 11a (wherein $R^{3'}$ is $R^3$ or intermediate moieties that may be manipulated to give $R^3$, and wherein $R^{6'}$ is $R^6$ or intermediate moieties that may be manipulated to give $R^6$). Compounds of the formula (11-1) may be converted via acyl hydrazide formation, diazotization and Curtius rearrangement to give compounds of the formula (11-4), which maybe further converted by Sandmeyer reaction to compounds of the formula (11-5). Similarly, compounds of formula (11-4) may undergo Sandmeyer reaction to provide other 6-substituted derivatives such as 6-fluoro (11-7), 6-chloro (11-8), 6-iodo (11-9), 6-alkylthio (11-10), 6-hydroxy (11-11) and 6-cyano (11-12) as outlined in Scheme 11b.

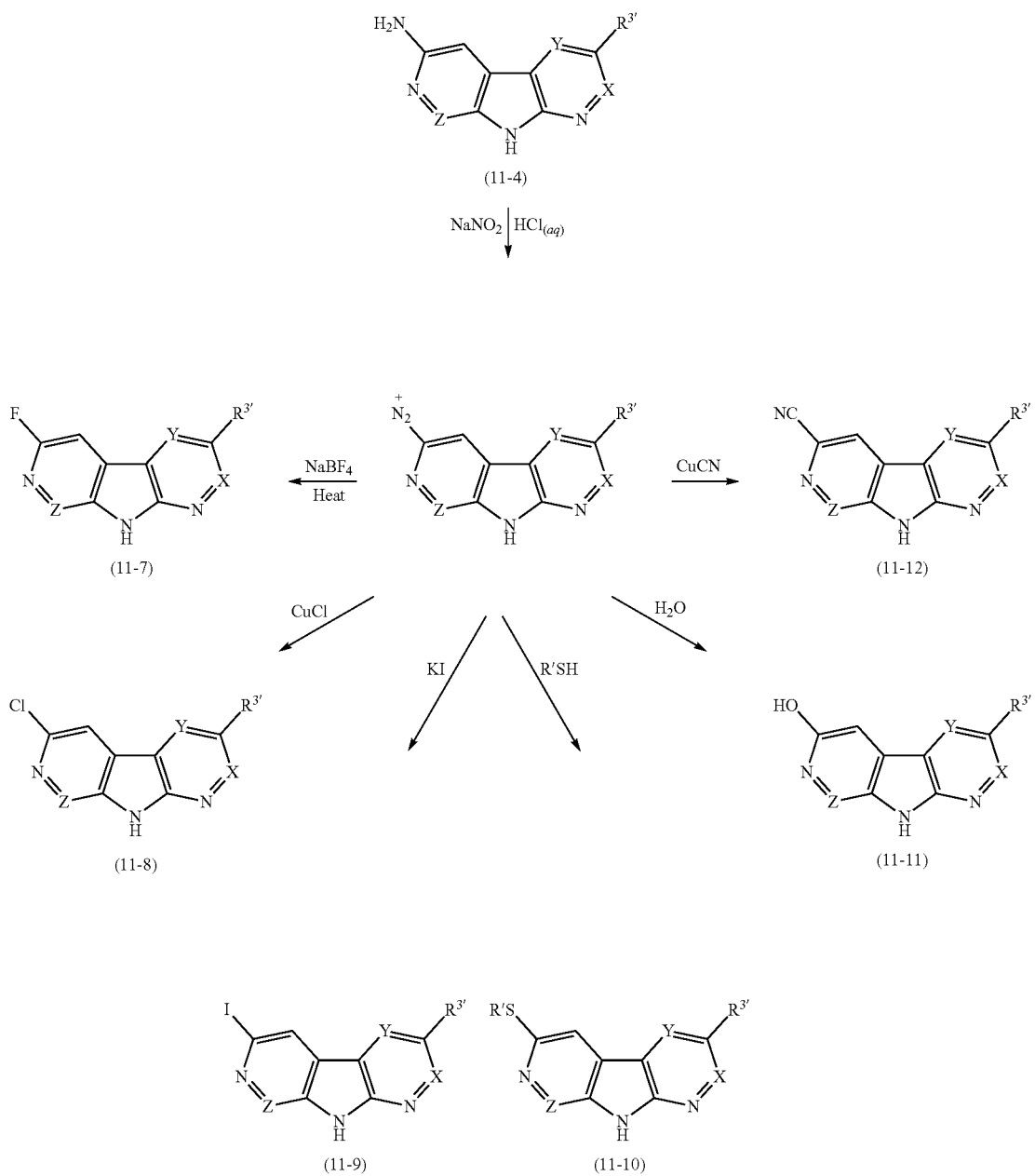

Scheme 11b

Compounds of the formula (11-5) are useful for the introduction of group R⁶ (or group R⁶' which may be converted into group R⁶) in various ways, to generate compounds of the formula (11-6), for example, by coupling with organic boronic acid derivatives in the presence of a palladium catalyst. Similarly, organic stannanes (eg. R⁶'SnR₃), organozinc (R⁶'ZnCl) and other reagents can be used in the place of organic boronic acids. In particular compounds of the formula (11-6) where R⁶' represents such groups as alkyl, cycloalkyl, alkenyl, alkynyl, aryl, heterocyclyl and heteroaryl may be prepared in this manner. Compounds of the formula (11-5) may also be converted into organic boronic acid derivatives of the type (11-13), which may give compounds of the formula (11-6) by coupling with organic halide or triflate derivatives in the presence of a palladium catalyst, as outlined in Scheme 11c. Similarly (11-5) may be converted to an organic stannane, organozinc and other derivatives to be used in the place of organic boronic acids in palladium catalyst-mediated couplings to give compounds of the formula (11-6).

Scheme 11c

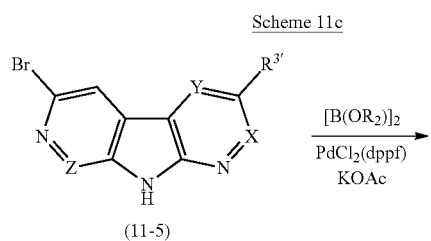

(11-5)

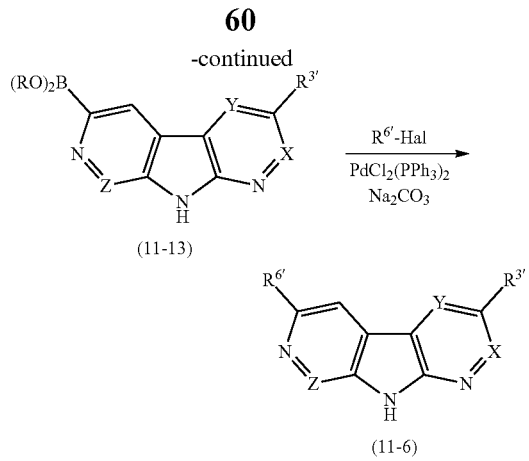

Compounds of general formula (11-5) are useful in the preparation of derivatives through nucleophilic aromatic displacement reactions utilizing nucleophilic reagents R-NuH, which may be facilitated in the presence of base, as outlined in Scheme 11d. Examples of such reagents and reactions are alcohols yielding compounds of the formula (11-14), thiols yielding compounds of the formula (11-15), primary and secondary amines yielding compounds of the formula (11-16), and heterocycles such as imidazole which yields compounds of the formula (11-17). Such displacement reactions may also be facilitated by the presence of a palladium, copper or other catalyst yielding compounds of the general formula (11-18), as outlined in Scheme 11d.

Scheme 11d

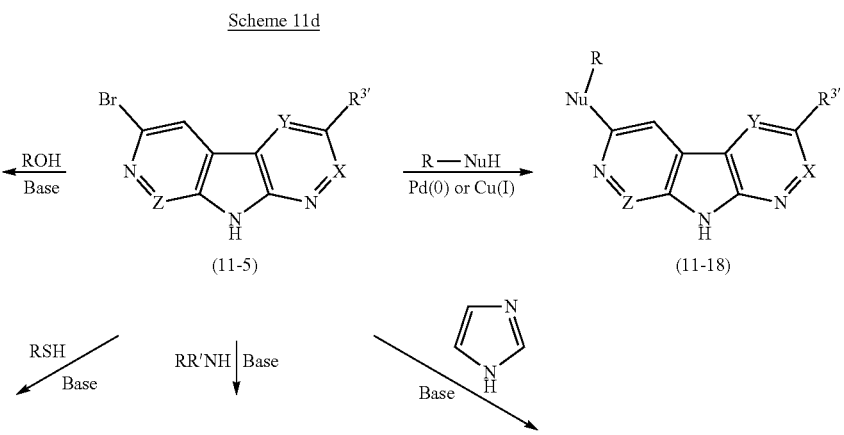

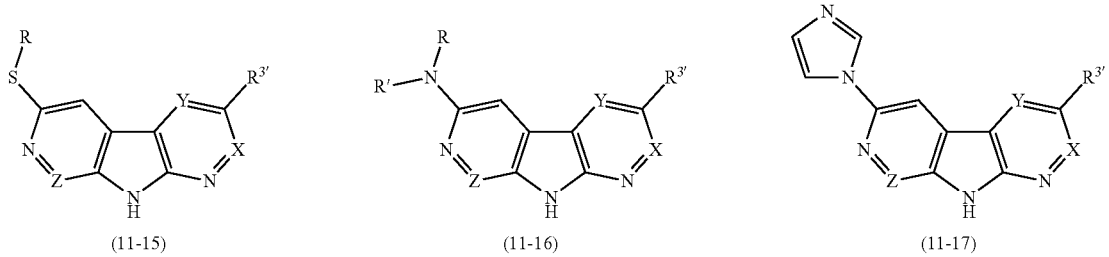

Compounds of general formula (11-5) are useful in the preparation of derivatives through nucleophilic aromatic displacement reactions utilizing nucleophilic reagents R-NuH, which may be facilitated in the presence of base, as outlined in Scheme 11d. Examples of such reagents and reactions are alcohols yielding compounds of the formula (11-14), thiols yielding compounds of the formula (11-15), primary and secondary amines yielding compounds of the formula (11-16), and heterocycles such as imidazole which yields compounds of the formula (11-17). Such displacement reactions may also be facilitated by the presence of a palladium, copper or other catalyst yielding compounds of the general formula (11-18), for example reactions of alcohols and alkyl amines, as outlined in Scheme 11d.

the formula (11-1) may also be subject to partial reduction of the ester function to yield aldehydes of the formula (11-20), for example using hydride transfer reagents such as diisobutylaluminium hydride. Such intermediates as (11-20) may be transformed through nucleophilic addition of organometallic reagents to the aldehyde function, for example ethylmagnesium bromide, to provide secondary alcohols of the formula (11-21). Such benzylic alcohols may further be transformed by O-alkylation, for example utilizing alkyl halide and base, such as transformation of compounds of the formula (11-21) to ether products of the formula (11-22). Aldheydes of the formula (11-20) may also be subject to reductive amination utilizing amines and hydride transfer reagents, for example sodium cyanoborohydride, yielding Scheme 11e

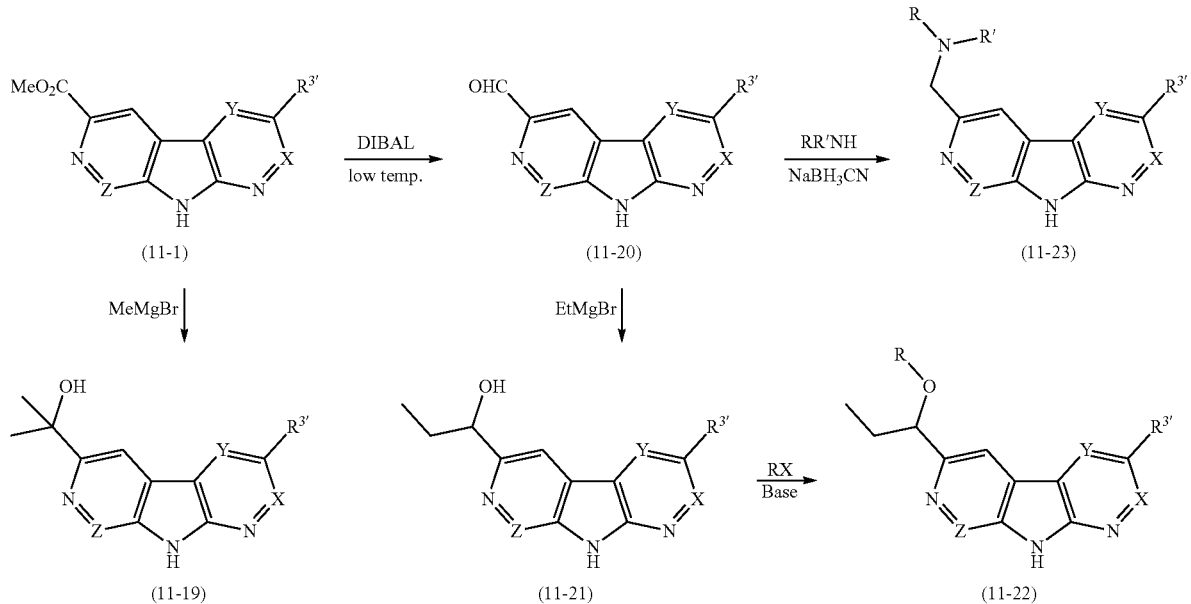

Compounds of the formula (11-1) are also of use as intermediates for the preparation of benzylic alcohols through nucleophilic addition of organometallic or hydride transfer reagents to the ester function, for example methylmagnesium bromide, to provide tertiary alcohols of the formula (11-19), as outlined in Scheme 11e. Compounds of benzylic amines of the general formula (11-22), as outlined in Scheme 11e.

Reagents and conditions given in Schemes 11a, 11b, 11c, 11d and 11e are examples of those that may be used, and comparable methods utilizing alternative reagents can be found in the literature.

Scheme 12

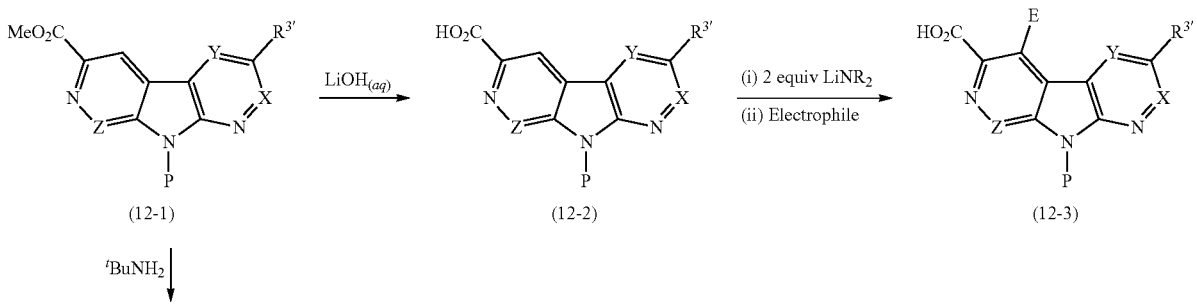

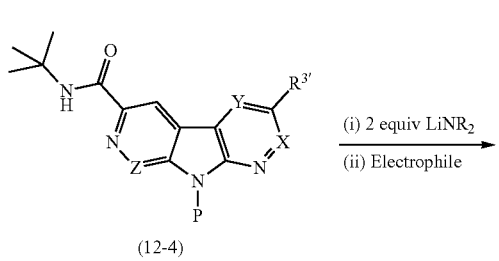

(12-4)

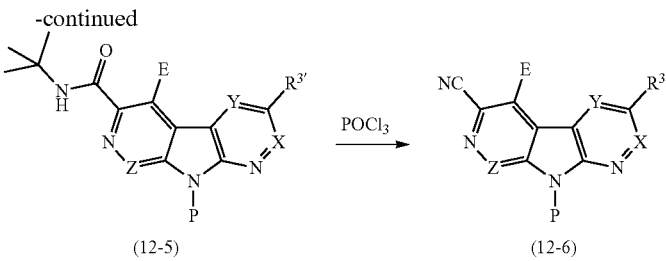

(12-5)    (12-6)

Compounds of general formula (12-1) may be prepared using methods described herein, and compounds of formula (12-6) may be prepared using the synthetic routes outlined in Scheme 12 (wherein $R^{3'}$ is $R^3$ or intermediate moieties that may be manipulated to give $R^3$, and wherein E is a generalized functional group derived from reaction with an electrophilic reagent following suitable work-up procedure, and P is a suitable protecting group). Carboxylic ester compounds of the formula (12-1) may be saponified to generate compounds of the formula (12-2), for example using aqueous lithium hydroxide. Alternatively, compounds of the formula (12-1) may be transformed into carboxamide compounds of the formula (12-4), by treatment for example with neat tert-butylamine. Compounds such as (12-2) may be treated two or more equivalents of with strong base, for example lithium tetramethylpiperidide, and quenched with a variety of electrophilic reagents, to generate derivatives of the general formula (12-3), in which the 5-position has become substituted with a functionality E derived form the electrophilic reagent. Such a transformation is exemplified by in the literature (WO 2003022849). For example, suitable electophilic reagents yielding derivatives with functional groups E include, respectively: ethyl iodide yielding 5-ethyl; formaldehyde yielding 5-hydroymethyl; dimethylformamide yielding 5-formyl; trimethylborate yielding 5-boronic acid ester, which may be further transformed to 5-hydroxy through oxidation using basic hydrogen peroxide. Similarly, carboxamide compounds of the formula (12-4) yield products of the formula (12-5) upon similar treatment, and these products may be further converted to the 6-cyano derivatives of formula (12-6) by treatment with acidic dehydrating agents, for example phosphorous oxychloride.

Reagents and conditions given in Scheme 12 are examples of those that may be used, and comparable methods utilizing alternative reagents can be found in the literature.

Scheme 13

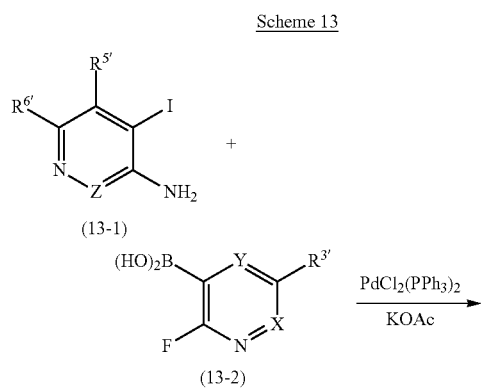

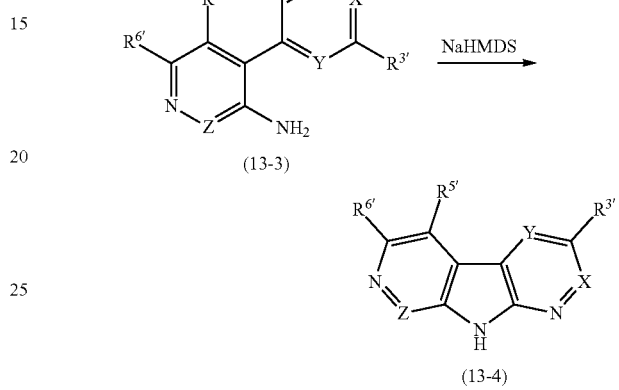

In a similar manner to that outlined in Scheme 14, compounds of the general formula (13-4) may be prepared using the synthetic routes outlined in Scheme 13 (wherein $R^{3'}$ is $R^3$ or intermediate moieties that may be manipulated to give $R^3$, $R^{5'}$ is $R^5$ or intermediate moieties that may be manipulated to give $R^5$, $R^{6'}$ is $R^6$ or intermediate moieties that may be manipulated to give $R^6$, and $R^{8'}$ is $R^8$ or intermediate moieties that may be manipulated to give $R^8$). For example, iodo-amino-heterocycle compounds of the formula (13-4) may be coupled with heterocycle-boronic acids of the formula (13-2) utilizing a suitable palladium catalyst and base, for example dichlorobis(triphenylphosphine)palladium(0) and potassium acetate in a suitable solvent, to yield biaryl compounds of the formula (13-3). Such compounds may be further transformed through treatment with base, for example sodium hexamethyldisilazide in a suitable solvent, to yield tricyclic compounds of the general formula (13-4). Thus further substitution of the tricycle, for example at the 3-, 5-, 6-, and 8-positions, may be achieved through utilizing compounds of the formula (13-1) and (13-2) in which one or more functionality $R^{3'}$, $R^{5'}$, $R^{6'}$ or $R^{8'}$ is already in place.

Compounds of formula (14-7) and (14-9) may be prepared using the synthetic routes outlined in Scheme 14.

Scheme 14

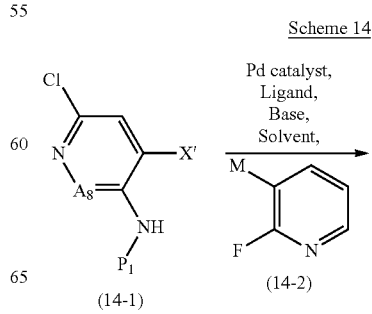

(14-1)    (14-2)

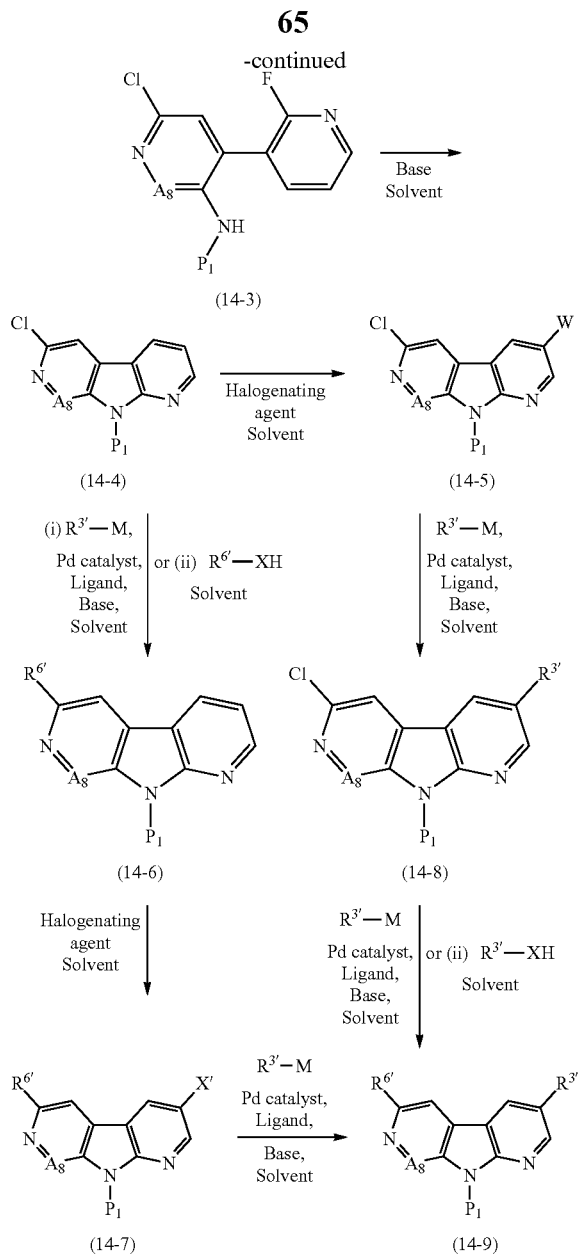

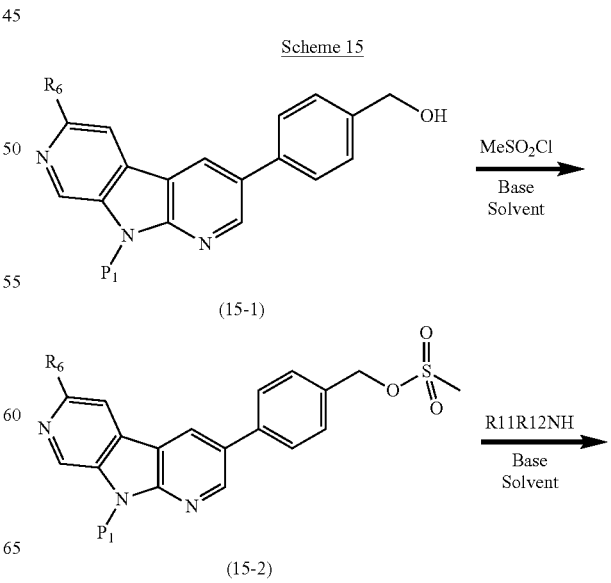

Scheme 15 priate substituents R$^{6'}$), in the presence of a catalyst such as bis(triphenylphosphine) palladium(II) dichloride, a base such as aqueous sodium carbonate in a suitable solvent such as acetonitrile at a temperature between room temperature and the reflux temperature of the solvent, or under microwave irradiation at a temperature between 70° C. and 150° C. Alternatively, Compounds of formula (14-4) may be coupled with an aryl or alkyl tin compound (incorporating appropriate substituents R$^{6'}$), in the presence of a catalyst such as bis(triphenylphosphine) palladium(II) dichloride or [1,1'-bis(diphenylphosphino)ferrocene]dichloropalladium (II), with or without an aqueous base such as sodium carbonate, in a suitable solvent such as acetonitrile at a temperature between room temperature and the reflux temperature of the solvent, or under microwave irradiation at a temperature between 70° C. and 150° C.

Compounds of general formula (14-6) may be obtained from compounds of formula (14-4) by reaction with compounds of general formula (HX—R$_6$') in the presence of a catalyst such as [1,1'-bis(diphenylphosphino)ferrocene]dichloropalladium(II), in the presence of a base such as potassium tert-butoxide in a suitable solvent such as DME, or a mixture of two or more appropriate solvents, at a temperature between room temperature and the reflux temperature of the solvent or solvents, or under microwave irradiation at a temperature between 70° C. to 160° C., as which may be similar to conditions described in the literature by Buchwald and Hartwig.

Intermediates of formula (14-6) may then be halogenated in the presence of a suitable halogenating agent, such as bromine, in a solvent such as acetic acid, at a temperature between 20° C. and 120° C., to obtain compounds of formula (14-7). Compounds of formula (14-7) may then be converted to compounds of formula (14-9) using methods described in Scheme 9.

Alternatively, compounds of formula (14-4) may be halogenated to give compounds of formula (14-5), then converted to compounds of formula (14-8) by reaction with a boronic acid, boronate ester or stannane then converted to compounds of formula (14-9) using similar conditions to those described for the introduction of R$^{3'}$.

Compounds of general formula (14-3) may be obtained from compounds of formula (14-1) by reaction with a boronic acid or boronate ester of formula (14-2), in the presence of a catalyst such as bis(triphenylphosphine)palladium(II) dichloride, a base such as aqueous sodium carbonate in a suitable solvent such as acetonitrile at a temperature between room temperature and the reflux temperature of the solvent, or under microwave irradiation at a temperature between 70° C. and 150° C. Compounds of general formula (14-3) may be cyclised to obtain compounds of formula (14-4) with a suitable base such as sodium hexamethyldisilazane in a suitable solvent such as THF at a temperature between 0° C. and 50° C.

Compounds of general formula (14-4) may then be converted to compounds of general formula (14-6) by reaction with a boronic acid or boronate ester (incorporating appro-

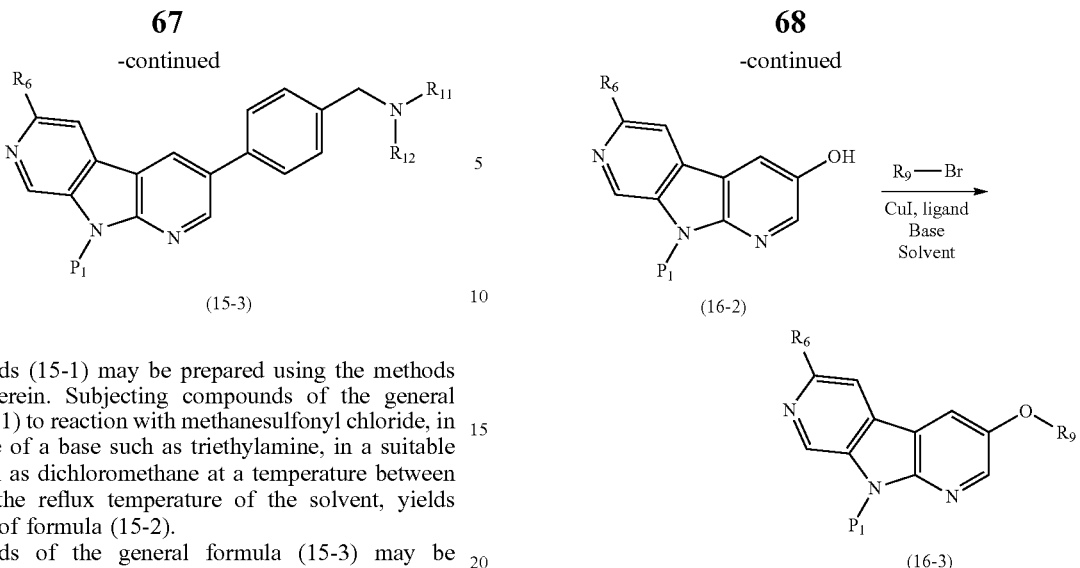

Compounds (15-1) may be prepared using the methods described herein. Subjecting compounds of the general formula (15-1) to reaction with methanesulfonyl chloride, in the presence of a base such as triethylamine, in a suitable solvent such as dichloromethane at a temperature between 0° C. and the reflux temperature of the solvent, yields compounds of formula (15-2).

Compounds of the general formula (15-3) may be obtained from compounds (15-2) by reaction with an amine, in the presence of a base such as triethylamine, in a suitable solvent such as acetonitrile at a temperature between ambient temperature and the reflux temperature of the solvent.

Compounds of general formula (16-3) may be prepared according to the procedure shown in Scheme 16.

Scheme 16

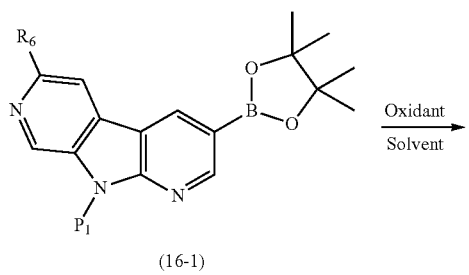

Compounds (16-1) may be prepared using the methods described in Scheme 2. Subjecting compounds of the general formula (16-1) to reaction with an oxidant such as N-methylmorpholine-N-oxide, in a suitable solvent such as tetrahydrofuran, at a temperature between ambient temperature and the reflux temperature of the solvent, yields compound of formula (16-2).

Compounds of the general formula (16-3) may be obtained from compounds (16-2) by reaction with an alkyl halide, in the presence of a catalyst such as copper (I) iodide, a ligand such as N,N-dimethylglycine, a base such as cesium carbonate in a suitable solvent such as dioxane, at a temperature between ambient temperature and reflux temperature of the solvent, or under microwave irradiation at a temperature between 70° C. to 150° C.

Compounds of general formula (17-13) may be prepared according to the procedure shown in Scheme 17.

Scheme 17

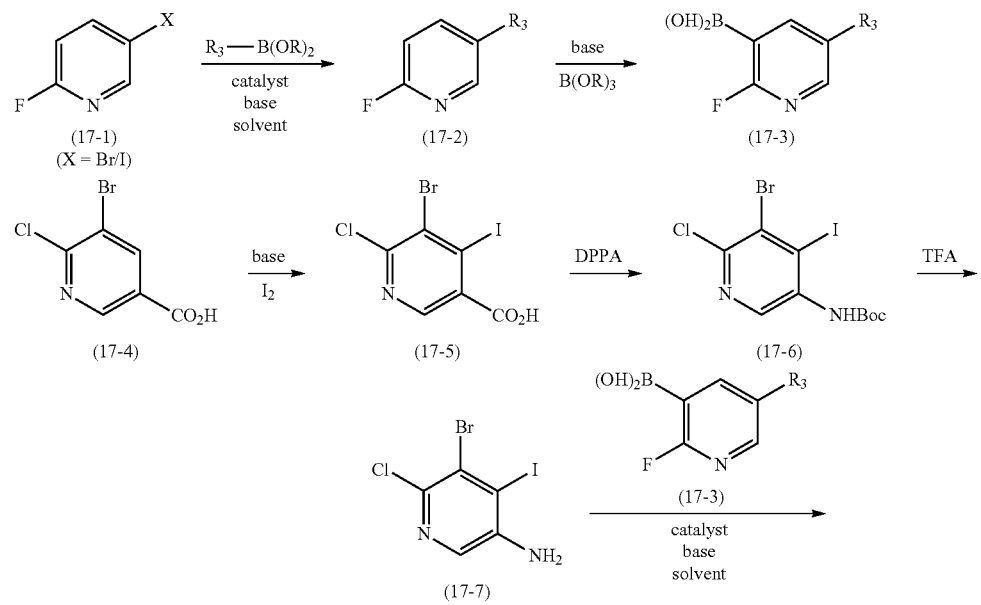

-continued

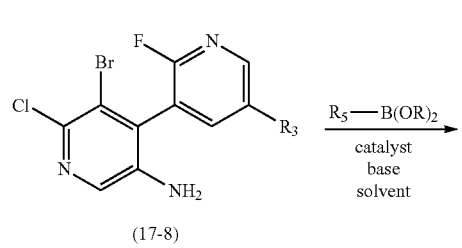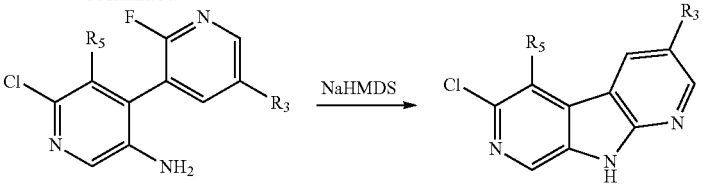

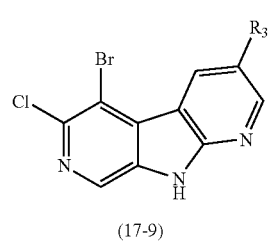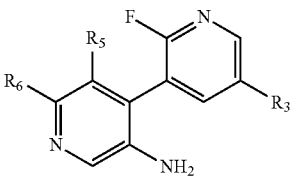

Compounds (17-1) and (17-4) may be obtained from commercial sources or prepared using published methods described in the literature. Compounds of general formula (17-2) may be obtained from compounds of formula (17-1) by reaction with an organometallic reagent such as a boronic acid or ester, in the presence of a transition metal catalyst such as [1,1'-bis(diphenylphosphino)ferrocene]dichloropalladium(II), a base such as aqueous potassium fluoride in a suitable solvent such as acetonitrile at a temperature between ambient temperature and the reflux temperature of the solvent, or under microwave irradiation at a temperature between 70° C. and 150° C.

Compounds of the general formula (17-3) may be obtained from compounds of formula (17-2) by reaction with a base such as lithium diisopropylamide and a boronate source such as triisopropylborate, in a suitable solvent such as THF, at a temperature between −78° C. and ambient temperature.

5-Bromo-6-chloro-4-iodo-nicotinic acid (17-5) may be obtained from 5-bromo-6-chloro-nicotinic acid (17-4) by reaction with a base, such as n-butyl lithium, an amine such as 2,2,6,6-tetramethylpiperidine and an iodine source, such as solid iodine, in a suitable solvent, such as THF at a temperature between −78° C. and ambient temperature. 5-Bromo-6-chloro-4-iodo-pyridin-3-yl)-carbamic acid tert-butyl ester (17-6) may be obtained from 5-bromo-6-chloro-4-iodo-nicotinic acid (17-5) by reaction with diphenylphosphoryl azide in the presence of a base such as triethylamine and tert-butanol, in a suitable solvent such as toluene at a temperature between ambient temperature to reflux temperature of the solvent. 5-Bromo-6-chloro-4-iodo-pyridin-3-ylamine (17-7) may be obtained from 5-bromo-6-chloro-4-iodo-pyridin-3-yl)-carbamic acid tert-butyl ester (17-6) by reaction with trifluoroacetic acid in a suitable solvent such as DCM at a temperature between −10° C. and the reflux temperature of the solvent.

Compounds of general formula (17-8) may be obtained from compounds of formula (17-3) by reaction with 5-bromo-6-chloro-4-iodo-pyridin-3-ylamine (xiii) in the presence of a transition metal catalyst such as [1,1'-bis(diphenylphosphino)ferrocene]dichloropalladium(II), a base such as aqueous potassium fluoride in a suitable solvent such as acetonitrile at a temperature from ambient temperature to the reflux temperature of the solvent, or under microwave irradiation at a temperature between 70° C. and 150° C.

Cyclisation of compounds with general formula (17-8) with a suitable base such as sodium hexamethylsilazide in a suitable solvent such as THF at a temperature between 0° C. and 50° C. yields compounds of general formula (17-9).

Compounds of the general formula (17-10) may be obtained from compounds (17-8) by reaction with an organometallic reagent such as a boronic acid or ester, in the presence of a transition metal catalyst such as [1,1'-bis(diphenylphosphino)ferrocene]dichloropalladium(II), a base such as aqueous potassium fluoride in a suitable solvent such as acetonitrile at a temperature between ambient temperature and the reflux temperature of the solvent, or under microwave irradiation at a temperature between 70° C. and 150° C.

Cyclisation of compounds with general formula (17-10) with a suitable base such as sodium hexamethylsilazide in a suitable solvent such as THF at a temperature between 0° C. and 50° C. yields compounds of general formula (17-12).

Compounds of the general formula (17-13) may be obtained from compounds (17-12) by reaction with an organometallic reagent such as a boronic acid or ester, in the presence of a transition metal catalyst such as [1,1'-bis(diphenylphosphino)ferrocene]dichloropalladium(II), a base such as aqueous potassium fluoride in a suitable solvent such as acetonitrile at a temperature between ambient temperature and the reflux temperature of the solvent, or under microwave irradiation at a temperature between 70° C. and 150° C.

Compounds of the general formula (17-11) may be obtained from compound (17-10) by reaction with an organometallic reagent such as a boronic acid or ester, in the presence of a transition metal catalyst such as [1,1'-bis(diphenylphosphino)ferrocene]dichloropalladium(II), a base such as aqueous potassium fluoride in a suitable solvent such as acetonitrile at a temperature between ambient temperature and the reflux temperature of the solvent, or under microwave irradiation at a temperature between 70° C. and 150° C.

Cyclisation of compounds with general formula (17-11) with a suitable base such as sodium hexamethylsilazide in a suitable solvent such as THF at a temperature between 0° C. and 50° C. may give compounds of general formula (17-13).

Compounds of formula (18-8) may be prepared using the synthetic routes outlined in Scheme 18.

Compounds of the general formula (18-8) may be obtained from compound (18-5) by reaction with an organometallic reagent such as a boronic acid or ester, in the presence of a transition metal catalyst such as [1,1'-bis (diphenylphosphino)ferrocene]dichloropalladium(II), a base such as aqueous sodium carbonate in a suitable solvent such

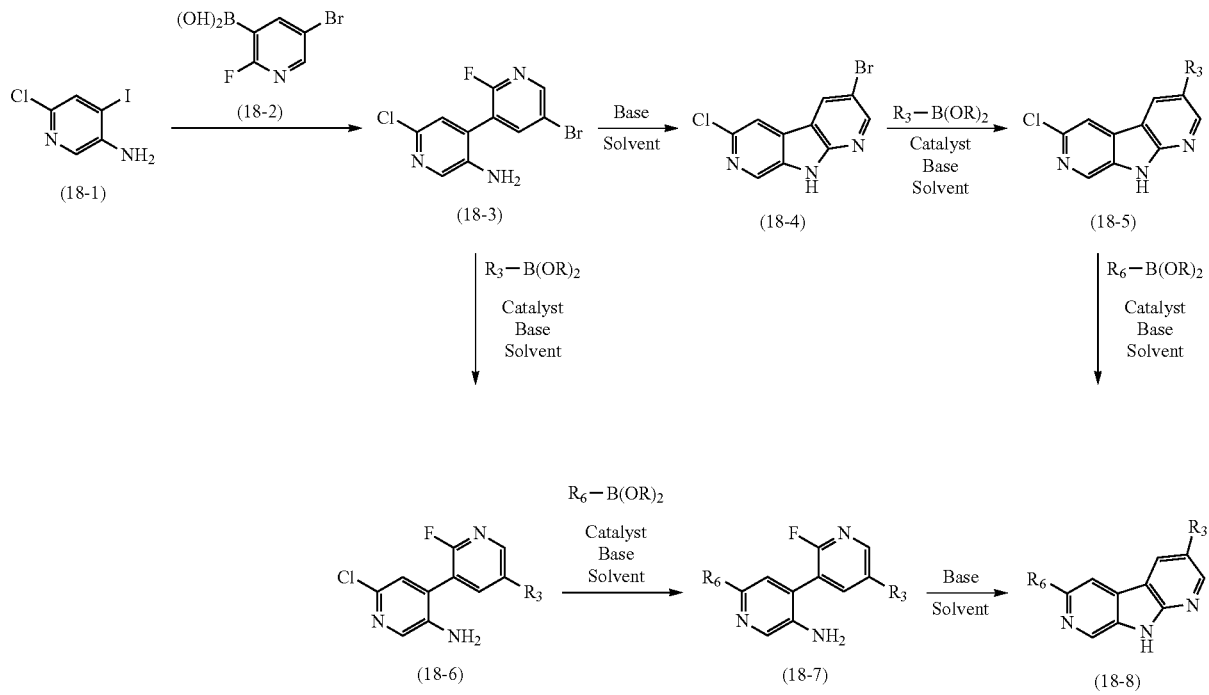

Compounds (18-1) and (18-2) may be obtained from commercial sources, prepared using published methods described in the literature, or from methods described in Scheme 3. 5-Bromo-6'-chloro-2-fluoro-[3,4']bipyridinyl-3'-ylamine (18-3) may be obtained from 5-bromo-2-fluoropyridine-3-boronic acid (18-2) by reaction with 6-chloro-4-iodopyridin-3-ylamine (18-1) in the presence of a transition metal catalyst such as [1,1'-bis(diphenylphosphino)ferrocene]dichloropalladium(II), a base such as aqueous sodium carbonate in a suitable solvent such as acetonitrile at a temperature between ambient temperature and the reflux temperature of the solvent, or under microwave irradiation at a temperature between 70° C. to 150° C.

3-Bromo-6-chloro-1,7-diazacarbazole (18-4) may be obtained from 5-bromo-6'-chloro-2-fluoro-[3,4']bipyridinyl-3'-ylamine (18-3) by cyclisation with a suitable base such as sodium hexamethylsilazide in a suitable solvent such as THF at a temperature between 0° C. and 50° C.

Compounds of the general formula (18-5) may be obtained from compound (18-4) by reaction with an organometallic reagent such as a boronic acid or ester, in the presence of a transition metal catalyst such as [1,1'-bis (diphenylphosphino)ferrocene]dichloropalladium(II), a base such as aqueous sodium carbonate in a suitable solvent such as acetonitrile at a temperature between ambient temperature and the reflux temperature of the solvent, or under microwave irradiation at a temperature between 70° C. and 150° C.

as acetonitrile at a temperature from ambient temperature to the reflux temperature of the solvent, or under microwave irradiation at a temperature between 70° C. to 150° C.

Compounds of the general formula (18-6) may be obtained from compound (18-3) by reaction with an organometallic reagent such as a boronic acid or ester, in the presence of a transition metal catalyst such as [1,1'-bis (diphenylphosphino)ferrocene]dichloropalladium(II), a base such as aqueous sodium carbonate in a suitable solvent such as acetonitrile at a temperature between ambient temperature and the reflux temperature of the solvent, or under microwave irradiation at a temperature between 70° C. and 150° C.

Compounds of the general formula (18-7) may be obtained from compound (18-6) by reaction with an organometallic reagent such as a boronic acid or ester, in the presence of a transition metal catalyst such as [1,1'-bis (diphenylphosphino)ferrocene]dichloropalladium(II), a base such as aqueous sodium carbonate in a suitable solvent such as acetonitrile at a temperature between ambient temperature and the reflux temperature of the solvent, or under microwave irradiation at a temperature between 70° C. and 150° C.

Cyclisation of compounds with general formula (18-7) with a suitable base such as sodium hexamethylsilazide in a suitable solvent such as THF at a temperature between 0° C. and 50° C. may give compounds of general formula (18-8).

Scheme 19

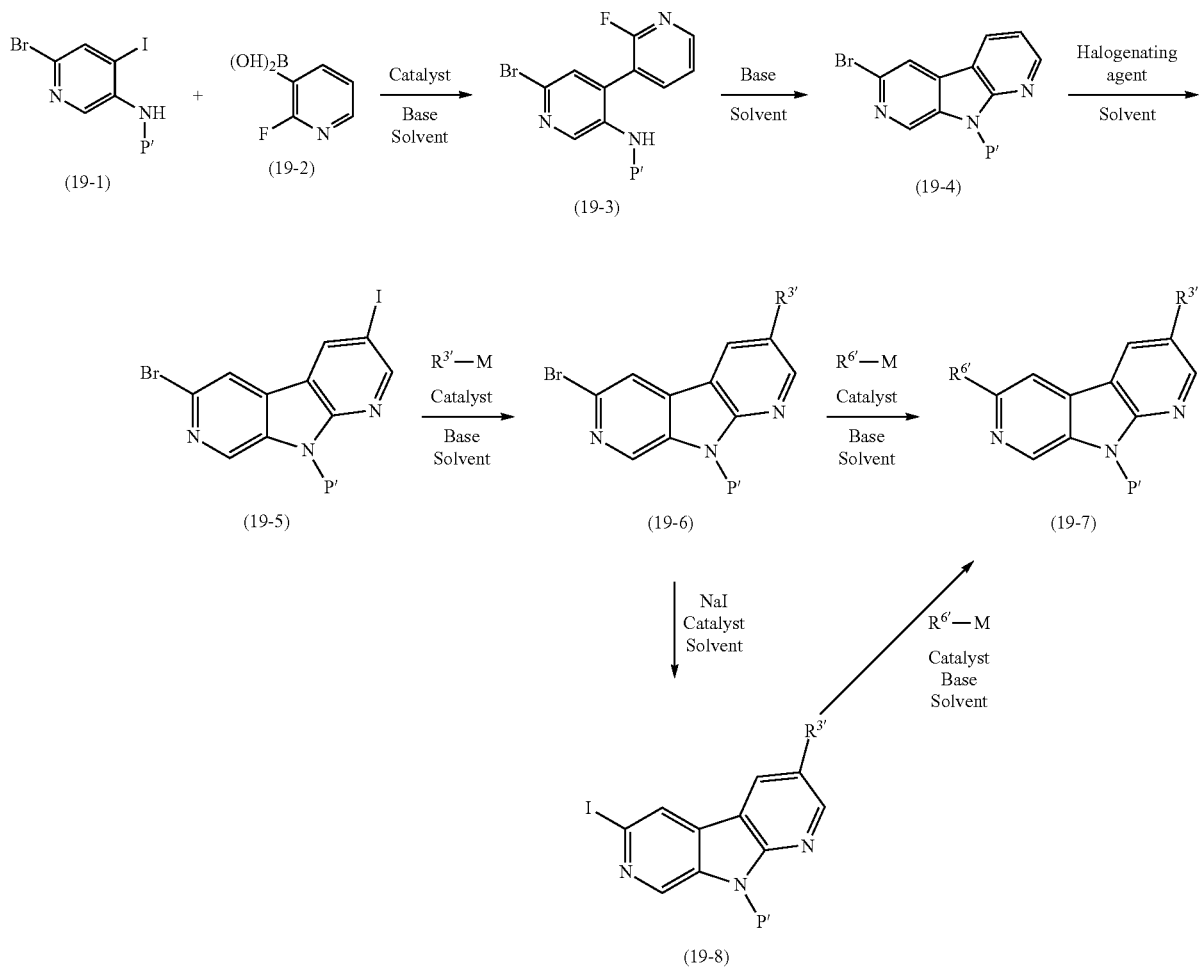

Compounds of formula (19-1) and (19-2) may be synthesized following procedures described in the literature or following the route outlined in scheme 17. Compounds of formula (19-3) may be obtained from compounds of formula (19-1) by reaction with a boronic acid or boronate ester of formula (19-2), in the presence of a catalyst such as bis(triphenylphosphine)palladium(II) dichloride, a base such as aqueous sodium carbonate in a suitable solvent such as acetonitrile at a temperature between room temperature and the reflux temperature of the solvent, or under microwave irradiation at a temperature between 70° C. and 150° C. Compounds of general formula (19-3) may be cyclised to obtain compounds of formula (19-4) with a base such as sodium hexamethyldisilazane in a suitable solvent such as THF at a temperature between 0° C. and 50° C. Intermediates of formula (19-4) may then be halogenated in the presence of a suitable halogenating agent, such as iodine monochloride, in a solvent such as acetic acid, at a temperature between 20° C. and the reflux point of the solvent, to obtain compounds of formula (19-5).

Compounds of formula (19-5) may then be converted to compounds of formula (19-6) by reaction with a boronic acid or boronate ester (incorporating appropriate substituents $R^{3'}$), in the presence of a catalyst such as bis(triphenylphosphine) palladium(II) dichloride, a base such as aqueous sodium carbonate in a suitable solvent such as acetonitrile at a temperature between room temperature and the reflux temperature of the solvent, or under microwave irradiation at a temperature between 70° C. and 150° C. Alternatively, compounds of formula (19-5) may be coupled with an aryl or alkyl tin compound (incorporating appropriate substituents $R^{3'}$), in the presence of a catalyst such as bis(triphenylphosphine) palladium(II) dichloride or [1,1'-bis(diphenylphosphino)ferrocene]dichloropalladium (II), with or without an aqueous base such as sodium carbonate, in a suitable solvent such as acetonitrile at a temperature between room temperature and the reflux temperature of the solvent, or under microwave irradiation at a temperature between 70° C. and 150° C.

Compounds of formula (19-6) may be converted to compounds of formula (19-8) by reaction with an iodine source such as sodium iodide using a copper catalyst such as a combination of copper (I) iodide and N,N'-dimethylethylenediamine in a solvent such as 1,4-dioxane at a temperature between room temperature and the reflux point of the solvent.

Compounds of formula (19-7) may be obtained from compounds of formula (19-6) and (19-8) by reaction with compounds of general formula ($R^{6'}$-M) by reaction with a boronic acid, boronate ester or stannane using similar conditions to those described previously for the introduction of $R^{3'}$.

Scheme 20

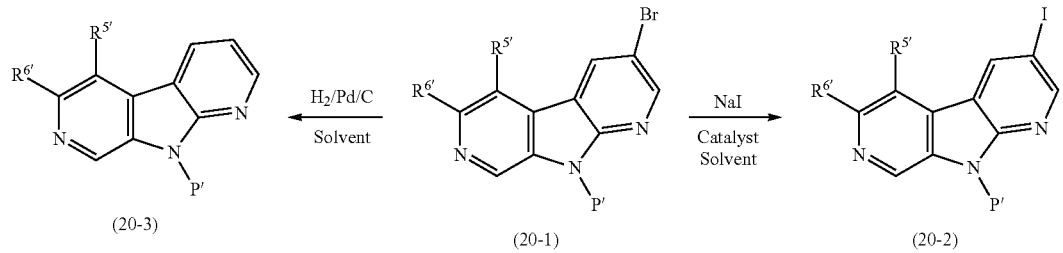

Compounds of formula (20-1) may be synthesized following procedures described in the literature or following routes outlined in schemes 1, 4, 10, 13, 14, 17 and 18. Compounds of formula (20-1) may be converted to compounds of formula (20-2) by reaction with an iodine source such as sodium iodide using a copper catalyst such as a combination of copper (I) iodide and N,N'-dimethylethylenediamine in a solvent such as 1,4-dioxane at a temperature between room temperature and the reflux point of the solvent.

Compounds of formula (20-1) may also be converted to compounds of general formula (20-3) using a catalyst such as palladium in a solvent such as ethanol under an atmosphere of hydrogen at a temperature from room temperature to 50° C.

Scheme 21

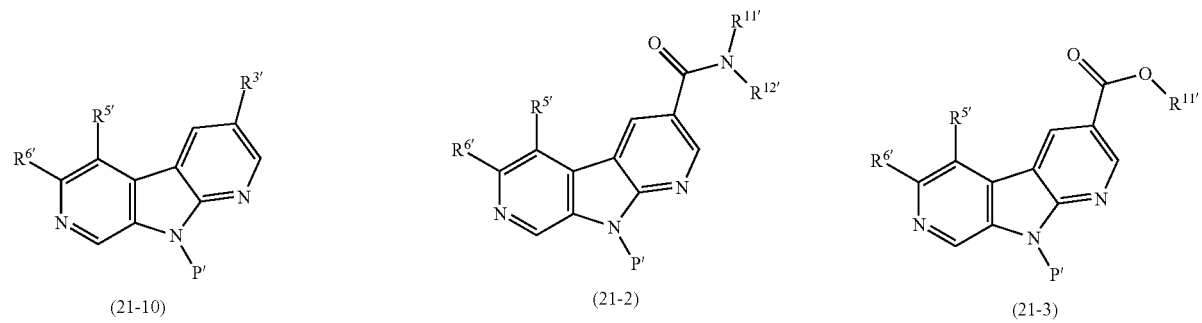

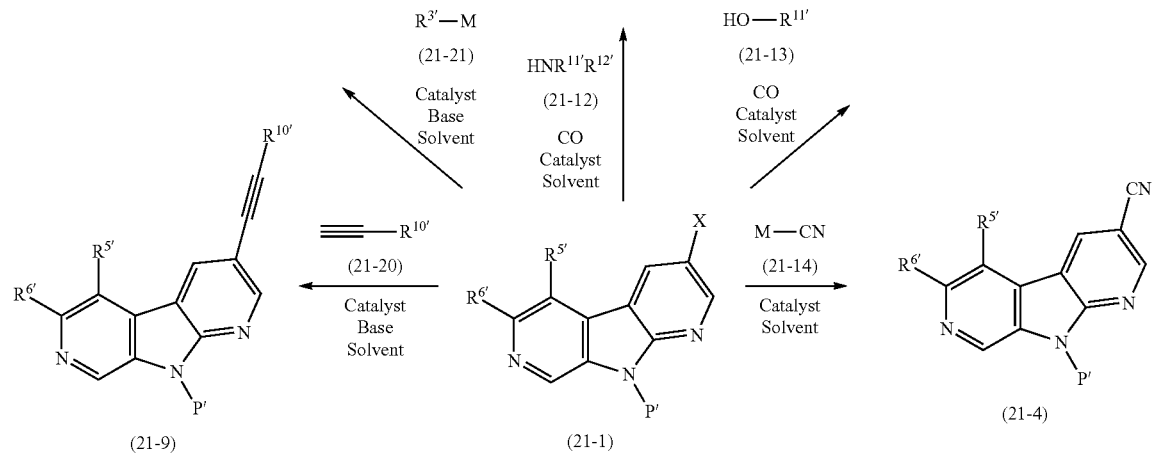

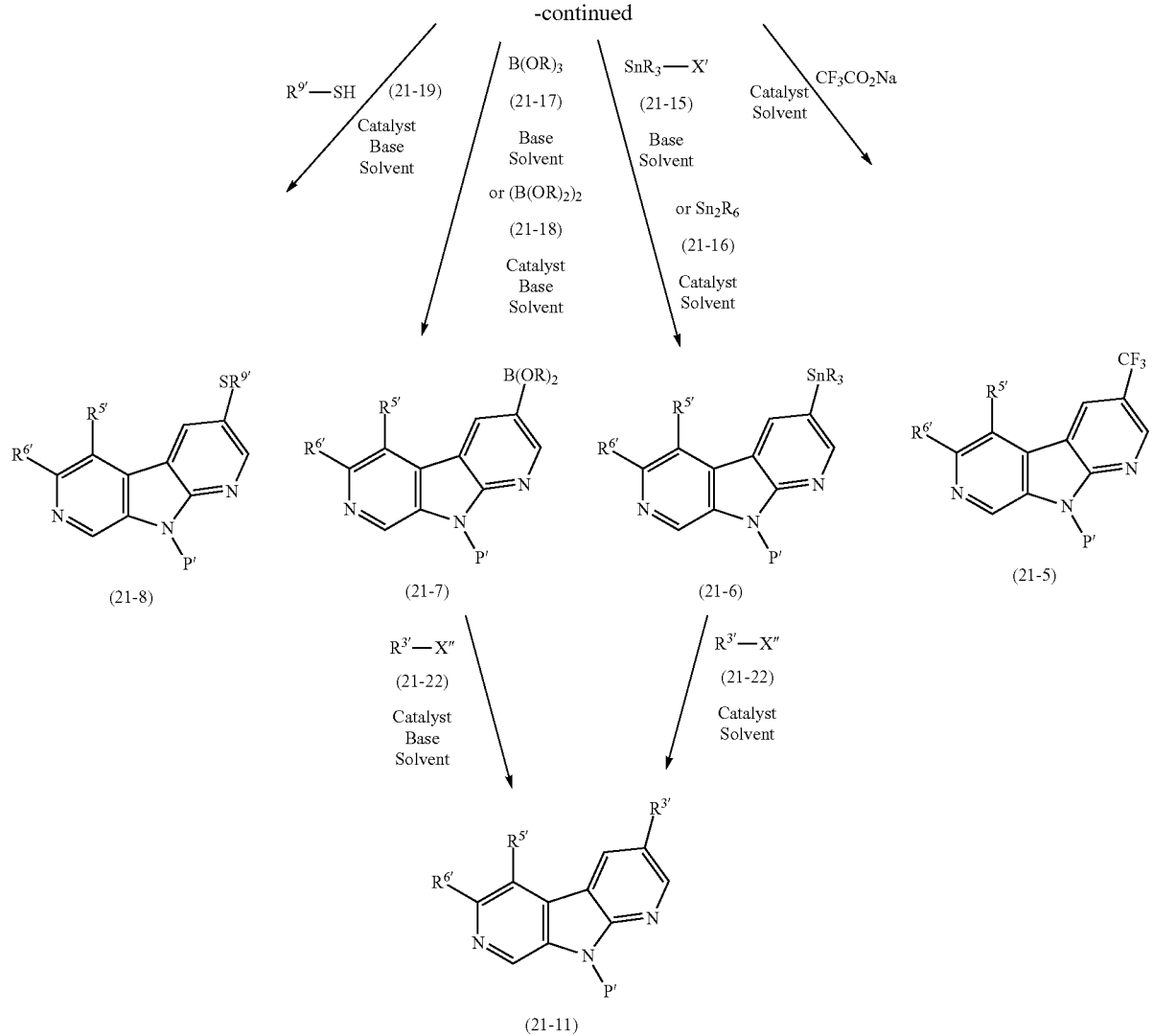

X = Br, I  X' = Cl, Br  X" = Cl, Br, I, OTf

Compounds of formula (21-1) may be synthesized following procedures described in the literature or following routes outlined in schemes 1, 4, 10, 13, 14, 17 and 18. Compounds of formula (21-1) (where X is a leaving group such as Br or I) may be converted to compounds of formula (21-2) using a source of carbon monoxide, such as molybdenum hexacarbonyl in the presence of a catalyst such as Herman's catalyst, containing the appropriate amine (21-12) (HNR$^{11'}$R$^{12'}$), a base such as 1,8-diazabicyclo[5,4,0]undec-7-ene in a solvent such as 1,4-dioxane at a temperature between room temperature and the reflux point of the solvent. Compounds of formula (21-1) may also be converted to compounds of formula (21-3) using a source of carbon monoxide, such as molybdenum hexacarbonyl in the presence of a catalyst such as Herman's catalyst, containing the appropriate alcohol (21-13) (HOR$^{11'}$), a base such as 1,8-diazabicyclo[5,4,0]undec-7-ene in a solvent such as 1,4-dioxane at a temperature between room temperature and the reflux point of the solvent. Compounds of formula (21-1) may be converted to compounds of formula (21-4) using a reagent (21-14) such as zinc (II) cyanide in the presence of a catalyst such as tetrakis(triphenylphosphine)palladium (0) in a solvent such as DMF at a temperature between room temperature and the reflux point of the solvent, or under microwave irradiation at a temperature between 70° C. and 150° C.

Compounds of formula (21-1) may be converted to compounds of formula (21-5) using a reagent such as sodium trifluoroacetate in the presence of a catalyst such as copper (I) iodide in a solvent such as DMF at a temperature between room temperature and the reflux point of the solvent.

Compounds of formula (21-6) may be prepared from compounds of formula (21-1) with a base such as n-butyl-lithium in a solvent such as THF with the appropriate tin halide (21-15) (where X' is a leaving group such as Cl or Br). Alternatively, compounds of formula (21-6) may be prepared from compounds of formula (21-1) with the appropriate alkylditin (21-16) (containing suitable R groups) in the presence of a catalyst such as tetrakis(triphenylphosphine) palladium(0) in a suitable solvent such as toluene at a temperature from room temperature to the reflux temperature of the solvent, or under microwave irradiation at a temperature between 70° C. and 150° C.

Compounds of formula (21-7) may be prepared from compounds of formula (21-1) by treatment with a base such as n-butyllithium in the presence of an alkyl borate (21-17) such as trimethyl borate in a suitable solvent such as THF at a temperature between −78° C. and ambient temperature. Alternatively, compounds of formula (21-7) may be prepared from compounds of formula (21-1) with the appropriate alkylatodiboron (21-18) in the presence of a catalyst such as bis(diphenylphosphino)ferrocene palladium(II) dichloride, using a suitable base such as potassium acetate in a solvent such as dioxane at a temperature from room temperature to the reflux temperature of the solvent, or under microwave irradiation at a temperature between 70° C. and 150° C.

Compounds of formula (21-8) may be obtained from compounds of formula (21-1) by reaction with compounds of formula (21-19) (HSR$^{9'}$) in the presence of a catalyst such as palladium (II) acetate/JOSIPHOS using a base such as potassium tert-butoxide in a suitable solvent such as DME at a temperature from room temperature to the reflux temperature of the solvent or solvents, or under microwave irradiation at a temperature between 70° C. and 160° C.

Compounds of formula (21-9) may be obtained from compounds of formula (21-1) with a suitable alkyne (21-20) (incorporating a R$^{10'}$ group that could be either maintained without modification after coupling, or that could later be modified to give other groups R$^{10}$) by reaction in the presence of a catalyst system such as tetrakis(triphenylphosphine)palladium (0) and copper (I) iodide in the presence of a base such as triethylamine and a suitable solvent such as N,N-dimethylformamide at a temperature between room temperature and the boiling point of the solvent. Such a coupling reaction could also be carried out in the presence of palladium on carbon, triphenylphosphine, copper (I) iodide and triethylamine in the presence of a suitable solvent such as acetonitrile at a temperature between room temperature and the reflux temperature of the solvent or solvents, or under microwave irradiation at a temperature between 70° C. and 160° C.

Compounds of formula (21-1) may be converted to compounds of formula (21-10) by reaction with a boronic acid or boronate ester (21-21) (incorporating appropriate substituents R$^{3'}$), in the presence of a catalyst such as bis(triphenylphosphine)palladium(II) dichloride, a base such as aqueous sodium carbonate in a suitable solvent such as acetonitrile at a temperature between room temperature and the reflux temperature of the solvent, or under microwave irradiation at a temperature between 70° C. and 150° C. Alternatively, compounds of formula (21-1) may be coupled with an aryl or alkyl tin compound (21-21) (incorporating appropriate substituents R$^{3'}$), in the presence of a catalyst such as bis(triphenylphosphine)palladium(II) dichloride or [1,1'-bis(diphenylphosphino) ferrocene]dichloropalladium (II), with or without an aqueous base such as sodium carbonate, in a suitable solvent such as acetonitrile at a temperature between room temperature and the reflux temperature of the solvent, or under microwave irradiation at a temperature between 70° C. and 150° C.

Compounds of formula (21-11) may be prepared from compounds of formula (21-6) with the appropriate halide or triflate of formula (21-22) (R$^{3'}$—X"), in the presence of a catalyst such as tetrakis(triphenylphosphine)palladium(0) in a suitable solvent such as 1,4-dioxane at a temperature from room temperature to the reflux temperature of the solvent, or under microwave irradiation at a temperature between 70° C. and 150° C.

Compounds of formula (21-11) may also be prepared by reaction of compounds of formula (21-7) with appropriate halide of formula (21-22) (R$^{3'}$—X"), (incorporating appropriate substituents R$^{3'}$), in the presence of a catalyst such as bis(triphenylphosphine)palladium(II)dichloride, with a base such as aqueous sodium carbonate in a suitable co-solvent such as acetonitrile at a temperature from room temperature to the reflux temperature of the solvent, or under microwave irradiation at a temperature between 70° C. and 150° C.

Scheme 22

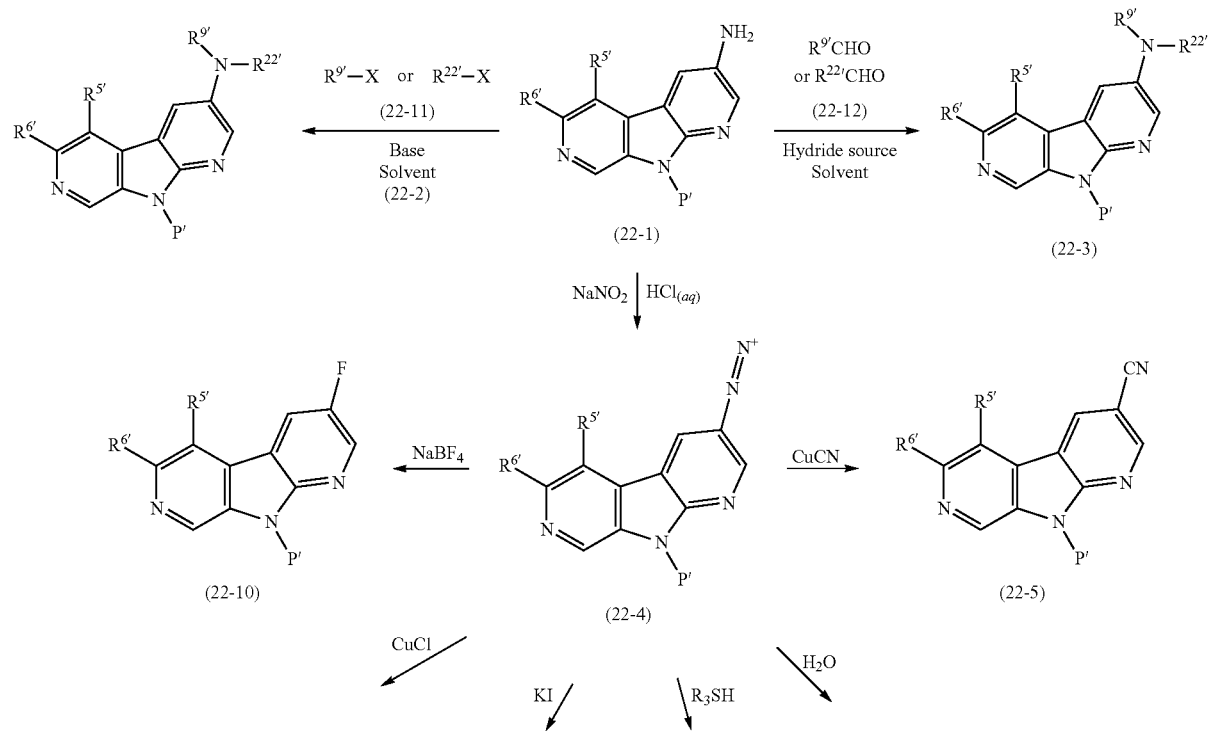

-continued

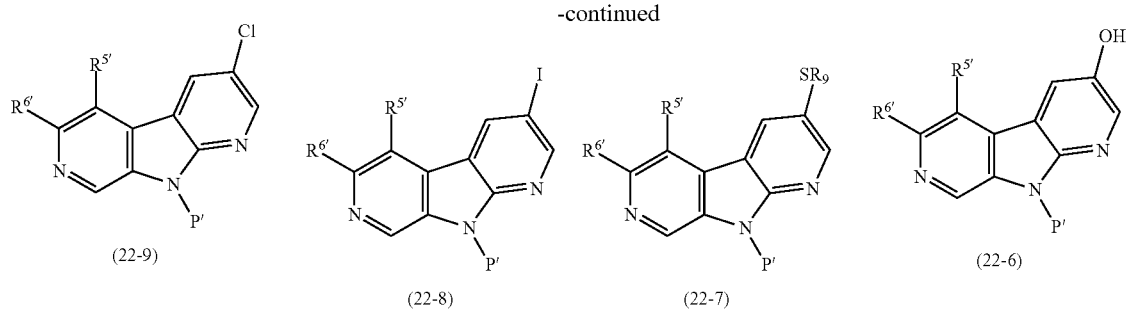

Compounds of formula (22-1) may be synthesized following procedures described in the literature or following routes outlined in scheme 9. Compounds of formula (22-1) may be converted to compounds of formula (22-2) by treatment with a suitable alkylating agent (22-11) $R^{9'}$—X or $R^{22'}$—X (where X is a suitable leaving group such as Cl, Br, I, OMs or OTf) using a suitable base such as cesium carbonate in a solvent such acetonitrile at a temperature between room temperature and the reflux point of the solvent. Alternatively, compounds of formula (22-1) may be converted to compounds of formula (22-3) by reaction with a suitable aldehyde (22-12) $R^{9'}$CHO or $R^{22'}$CHO and a suitable hydride source such as sodium triacetoxyborohydride in a solvent such as 1,2-dichloroethane at a temperature between 0° C. and 50° C.

Compounds of formula (22-1) may also be converted to compounds of formula (22-4) using a reagent such as sodium nitrite in an acidic solution such as aqueous hydrochloric acid, aqueous hydrobromic acid or aqueous sulfuric acid. Compounds of formula (22-4) may then be converted to the fluoro compounds of formula (22-10) with a reagent such as sodium tetrafluoroborate; to the chloro derivatives of formula (22-9) with a reagent such as copper (I) chloride; to the iodo compounds of formula (22-8) with a reagent such as potassium iodide; the alkylthio compounds of formula (22-7) with a reagent such as $NaSR^{9'}$ and the cyano derivatives (22-5) with reagents such as copper (I) cyanide and potassium cyanide all carried out at a temperature between 0° C. and the reflux point of the solvent.

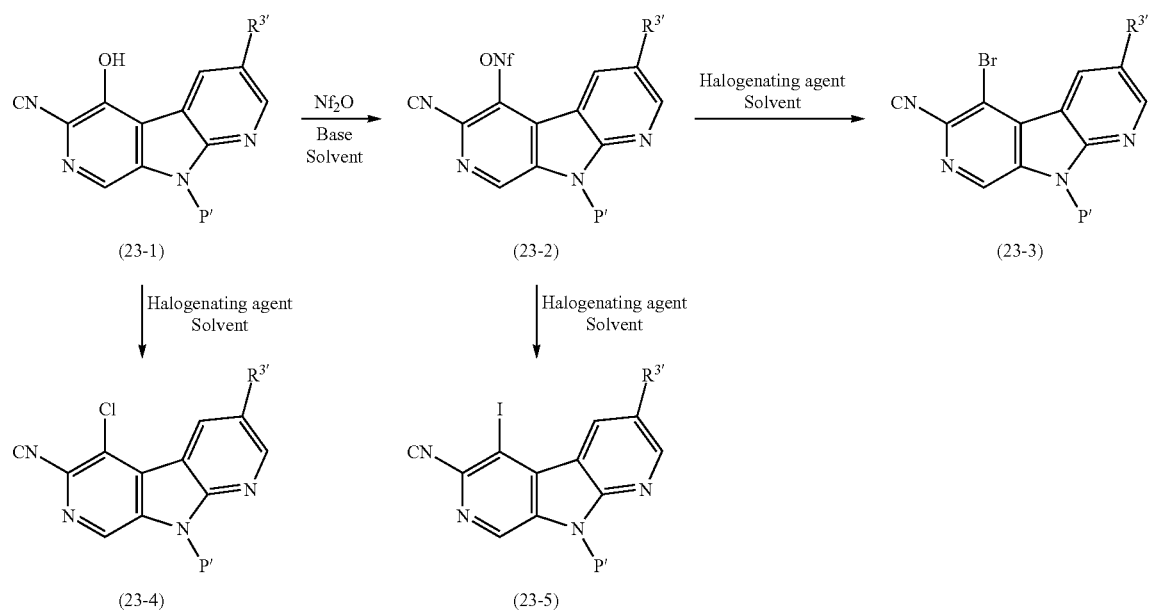

Compounds of formula (23-1) may be synthesized following procedures described in the literature or following the route outlined in scheme 10. Compounds of formula (23-3), (23-4) and (-5) may be prepared using the synthetic route outlined in Scheme 23. Compounds of formula (23-1) may be converted to the compounds of formula (23-4) by reaction with a suitable chloride source such as phosphorus pentachloride in a suitable solvent such as chlorobenzene at a temperature from room temperature to the reflux point of the solvent.

Compounds of formula (23-1) may also be converted to compounds of formula (23-2) using a reagent such as nonafluorobutanesulfonic anhydride in the presence of a base such as pyridine in a suitable solvent such as dichloromethane at a temperature between −50° C. and 20° C. Compounds of formula (23-2) may be converted to compounds of formula (23-3) by reaction with a suitable bromide source such as tetra-n-butylammonium bromide in a solvent such as 1,4-dioxane at a temperature from room temperature to the reflux temperature of the solvent, or under microwave irradiation at a temperature between 70° C. and 150° C.

Compounds of formula (23-2) may be converted to the compounds of formula (23-5) by reaction with a suitable iodide source such as tetra-n-butylammonium iodide in a solvent such as 1,4-dioxane at a temperature from room temperature to the reflux temperature of the solvent, or under microwave irradiation at a temperature between 70° C. and 150° C.

Scheme 24

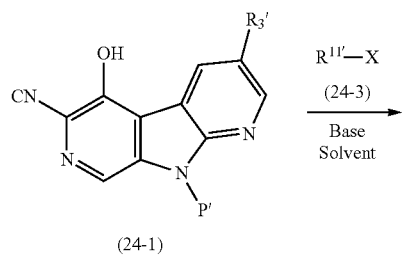

(24-1)

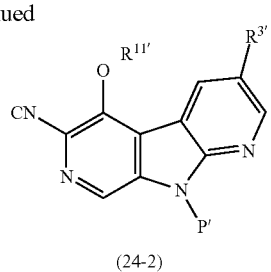

(24-2)

Compounds of formula (24-1) may be synthesized following procedures described in the literature or following the route outlined in scheme 10. Compounds of formula (24-2) may be obtained through alkylation of compounds of formula (24-1) with a suitable alkylating agent (24-3) $R^{11'}$—X (where X is a suitable leaving group such as Cl, Br, I, OMs or OTf) using a suitable base such as cesium carbonate in a solvent such as acetonitrile at a temperature between room temperature and the reflux point of the solvent.

Scheme 25

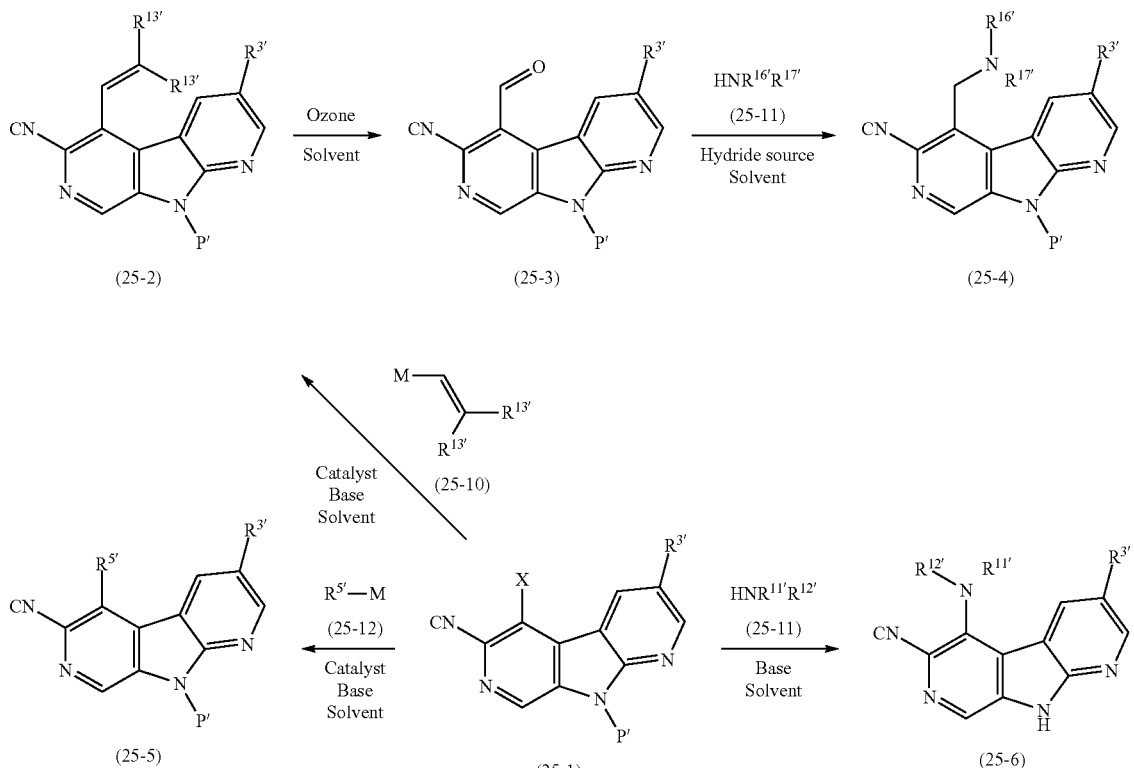

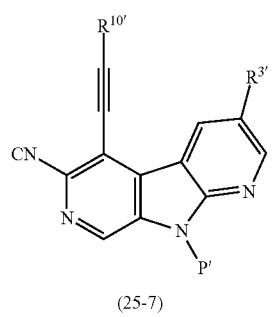

(25-7)

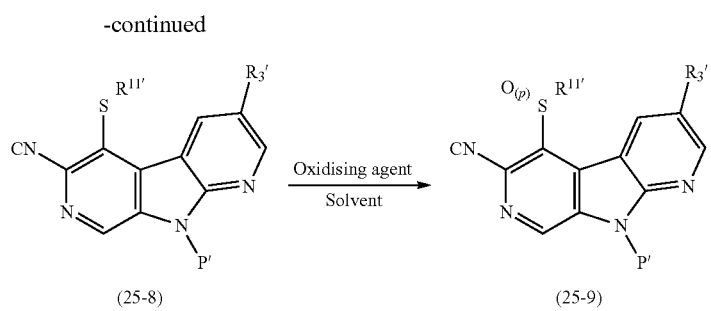

(25-8) → (25-9)

Oxidising agent / Solvent

Compounds of formula (25-1) may be synthesized following procedures described in the literature or following the route outlined in scheme 23. Compounds of formula (25-1) (where X is a leaving group such as Br or I) may be converted to compounds of formula (25-2) by reaction with a suitable alkenyl tin reagent of formula (25-10) such as vinyltributyl tin in the presence of a transition metal catalyst such as tetrakis(triphenylphosphine)palladium(0) in a suitable solvent such as 1,4-dioxane at a temperature between room temperature and the reflux point of the solvent. Compounds of formula (25-2) may be converted to compounds of formula (25-3) by treatment with a reagent such as ozone in a suitable solvent such as methanol at a temperature between −78° C. and room temperature followed by decomposition of the ozonide with a reagent such as dimethylsufide. Compounds of formula (25-3) may be converted to compounds of formula (25-4) by reaction with a suitable amine of formula (25-11) (HNR$^{6'}$R$^{17'}$) and a suitable hydride source such as sodium triacetoxyborohydride in a solvent such as 1,2-dichloroethane at a temperature between 0° C. and 50° C.

Compounds of formula (25-1) (where X is a leaving group such as Br or I) may be converted to compounds of formula (25-5) by reaction with a potassium alkyl trifluoroborate or alkyl borate of formula (25-12) in the presence of a transition metal catalyst such as [1,1'-bis(diphenylphosphino)ferrocene]palladium (II) dichloride, a base such as aqueous potassium carbonate in a suitable solvent such as DMF at a temperature from room temperature to the reflux temperature of the solvent, or under microwave irradiation at a temperature between 70° C. and 150° C. Compounds of formula (25-5) may also be obtained from compounds of formula (25-1) by reaction with an aryl or alkyl tin compound of formula (25-12) (incorporating appropriate substituents R$^{5'}$) in the presence of a catalyst such as bis(triphenyl phosphine)palladium (II) dichloride or [1,1'-bis(diphenylphosphino)ferrocene]dichloropalladium (II), an aqueous base such as sodium carbonate, in a suitable solvent such as acetonitrile or combination of solvents, at a temperature between room temperature to the reflux temperature of the solvent, or under microwave irradiation at a temperature between 70° C. and 150° C.

Alternatively, compounds of formula (25-7) may be obtained from compounds of formula (25-1) (where X is a leaving group such as Br or I) and a suitable alkyne (25-13) (incorporating a R$^{10'}$ group that could be either maintained without modification after coupling, or that could later be modified to give other groups R$^{10}$) by reaction in the presence of a catalyst system such as tetrakis(triphenyl phosphine)palladium(0) and copper (I) iodide in the presence of a base such as triethylamine and a suitable solvent such as N,N-dimethylformamide at a temperature between room temperature and the boiling point of the solvent. Such a coupling reaction could also be carried out in the presence of palladium on carbon, triphenylphosphine, copper (I) iodide and triethylamine in the presence of a suitable solvent such as acetonitrile at a temperature between room temperature and the reflux temperature of the solvent or solvents, or under microwave irradiation at a temperature between 70° C. and 160° C.

Compounds of formula (25-1) (where X is a leaving group such as F, Cl, Br or I) may be converted to compounds of formula (25-6) by displacement with a suitable amine of formula (25-11) (HNR$^{11'}$R$^{12'}$) either as solvent or in a solvent such as NMP at a temperature between ambient temperature and the reflux point of the solvent. Compounds of formula (25-3) may also be obtained from compounds of formula (25-1) (where X is a leaving group such as Br or I) by reaction with compounds of formula (25-11) (HNR$^{11'}$R$^{12'}$) in the presence of a catalyst such as [1,1'-bis(diphenylphosphino) ferrocene]dichloropalladium(II), in the presence of a base such as potassium tert-butoxide in a suitable solvent such as DME, or a mixture of two or more appropriate solvents, at a temperature from room temperature to the reflux temperature of the solvent or solvents, or under microwave irradiation at a temperature between 70° C. and 160° C.

Compounds of formula (25-8) may be obtained from compounds of formula (25-1) (where X is a leaving group such as Br or I) by reaction with compounds of general formula (25-14) (HSR$^{11'}$) in the presence of a catalyst such as palladium(II) acetate/JOSIPHOS in the presence of a base such as potassium tert-butoxide in a suitable solvent such as DME, or a mixture of two or more appropriate solvents, at a temperature from room temperature to the reflux temperature of the solvent or solvents, or under microwave irradiation at a temperature between 70° C. and 160° C.

The sulfide intermediates of formula (25-8) may be converted to sulfoxides and sulfones of formula (25-9) by oxidation with a suitable oxidizing agent such as oxone in a solvent such as acetone at a temperature between 0° C. and 50° C.

Scheme 26

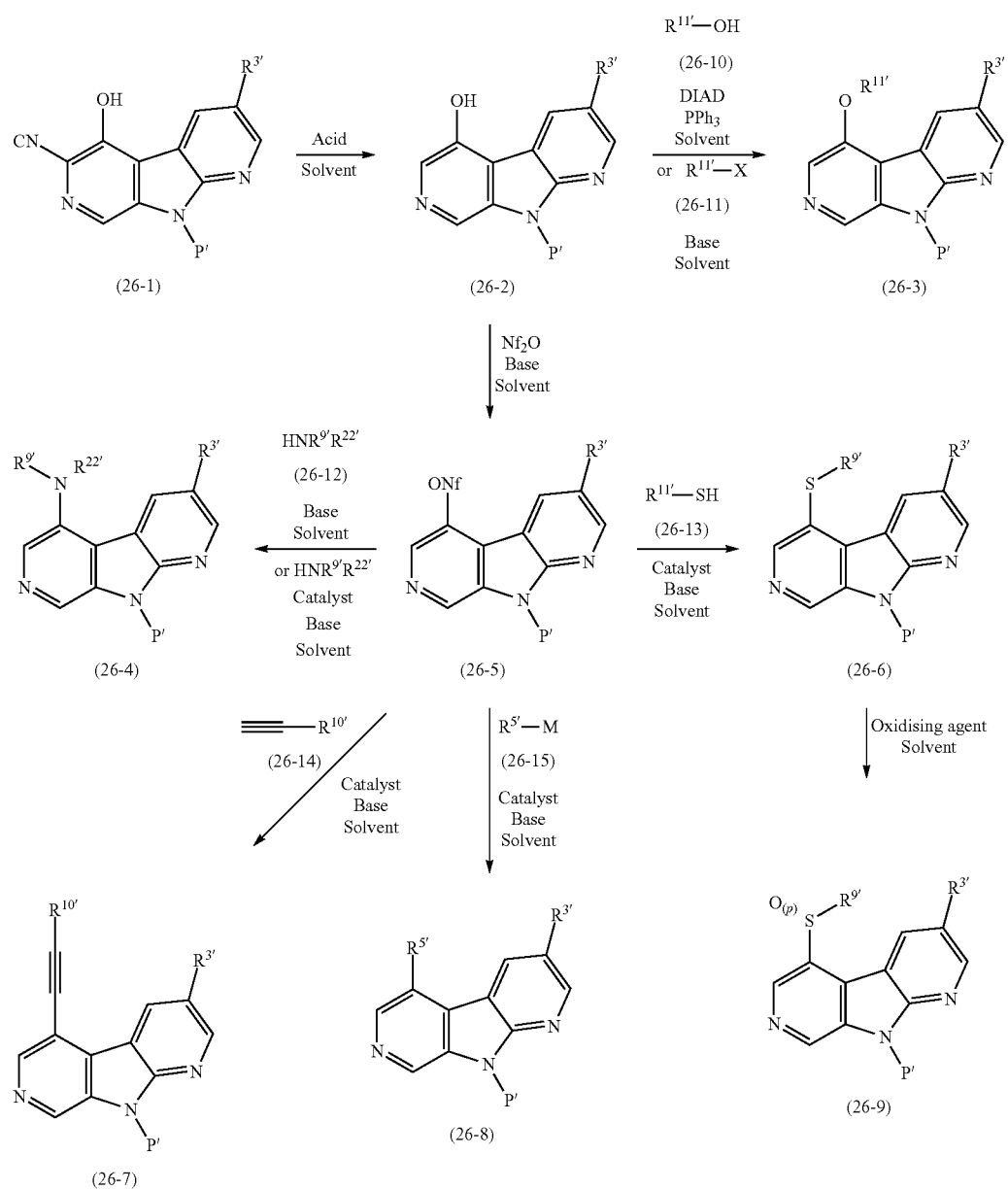

Compounds of formula (26-1) may be synthesized following procedures described in the literature or following the route outlined in scheme 10. Compounds of formula (26-1) may be converted to compounds of formula (26-2) by treatment with an acid such as hydrochloric acid in a solvent such as water at a temperature between room temperature and the reflux point of the solvent, or in a sealed vessel at a temperature between 70° C. and 140° C.

Compounds of formula (26-2) may then be reacted with an appropriate alcohol (26-10) ($R^{11'}$OH) using a phosphine and a coupling reagent such as diisopropylazodicarboxylate in an appropriate solvent such as THF to provide ethers of general formula (26-3). Alternatively, compounds of formula (26-3) may be obtained through alkylation of compounds of general formula (26-2) with a suitable alkylating agent (26-11) $R^{11'}$—X (where X is a suitable leaving group such as Cl, Br, I, OMs or OTf) using a suitable base such as cesium carbonate in a solvent such as acetonitrile at a temperature between room temperature and the reflux point of the solvent.

Compounds of formula (26-2) may also be converted to the nonaflates (26-5) using a reagent such as nonafluorobutanesulfonic anhydride in the presence of a base such as pyridine in a suitable solvent such as dichloromethane at a temperature between −50° C. and 20° C.

Compounds of formula (26-5) may be converted to compounds of formula (26-4) by displacement with a suitable amine of general formula (26-12) (HNR$^{11'}$R$^{12'}$) either as solvent or in a solvent such as NMP at a temperature between ambient temperature and the reflux point of the solvent. Compounds of formula (26-4) may also be obtained from compounds of formula (26-5) by reaction with compounds of general formula (26-12) (HNR$^{11'}$R$^{12'}$) in the presence of a catalyst such as [1,1'-bis(diphenylphosphino) ferrocene]dichloropalladium(II), in the presence of a base such as potassium tert-butoxide in a suitable solvent such as DME, or a mixture of two or more appropriate solvents, at a temperature from room temperature to the reflux temperature of the solvent or solvents, or under microwave irradiation at a temperature between 70° C. and 160° C.

Alternatively, compounds of formula (26-7) may be obtained from compounds of formula (26-5) with a suitable alkyne (26-14) (incorporating a R$^{10'}$ group that could be either maintained without modification after coupling, or that could later be modified to give other groups R$^{10}$) by reaction in the presence of a catalyst system such as tetrakis(triphenylphosphine)palladium (0) and copper (I) iodide in the presence of a base such as triethylamine and a suitable solvent such as N,N-dimethylformamide at a temperature between room temperature and the boiling point of the solvent. Such a coupling reaction could also be carried out in the presence of palladium on carbon, triphenylphosphine, copper (I) iodide and triethylamine in the presence of a suitable solvent such as acetonitrile at a temperature between room temperature and the reflux temperature of the solvent or solvents, or under microwave irradiation at a temperature between 70° C. and 160° C.

The nonaflate intermediates (26-5) may be converted to compounds of formula (26-8) by reaction with a potassium alkyl trifluoroborate or alkyl borate of formula (26-15) in the presence of a transition metal catalyst such as [1,1'-bis(diphenylphosphino)ferrocene]palladium (II) dichloride, a base such as aqueous potassium carbonate in a suitable solvent such as DMF at a temperature from room temperature to the reflux temperature of the solvent, or under microwave irradiation at a temperature between 70° C. and 150° C. Compounds of general formula (26-8) may also be obtained from compounds of formula (26-5) by reaction with an aryl or alkyl tin compound (incorporating appropriate substituents R$^{5'}$), in the presence of a catalyst such as bis(triphenylphosphine)palladium (II) dichloride or [1,1'-bis(diphenylphosphino)ferrocene]dichloropalladium (II), an aqueous base such as sodium carbonate, in a suitable solvent such as acetonitrile or combination of solvents, at a temperature between room temperature to the reflux temperature of the solvent, or under microwave irradiation at a temperature between 70° C. and 150° C.

Compounds of formula (26-6) may be obtained from compounds of formula (26-5) (where X is a leaving group such as Br or I) by reaction with compounds of formula (26-13) (HSR$^{11'}$) in the presence of a catalyst such as palladium (II) acetate/JOSIPHOS in the presence of a base such as potassium tert-butoxide in a suitable solvent such as DME, or a mixture of two or more appropriate solvents, at a temperature from room temperature to the reflux temperature of the solvent or solvents, or under microwave irradiation at a temperature between 70° C. and 160° C.

The sulfide intermediates of formula (26-6) may be converted to sulfoxides and sulfones of formula (26-9) by oxidation with a suitable oxidizing agent such as oxone in a solvent such as acetone at a temperature between 0° C. and 50° C.

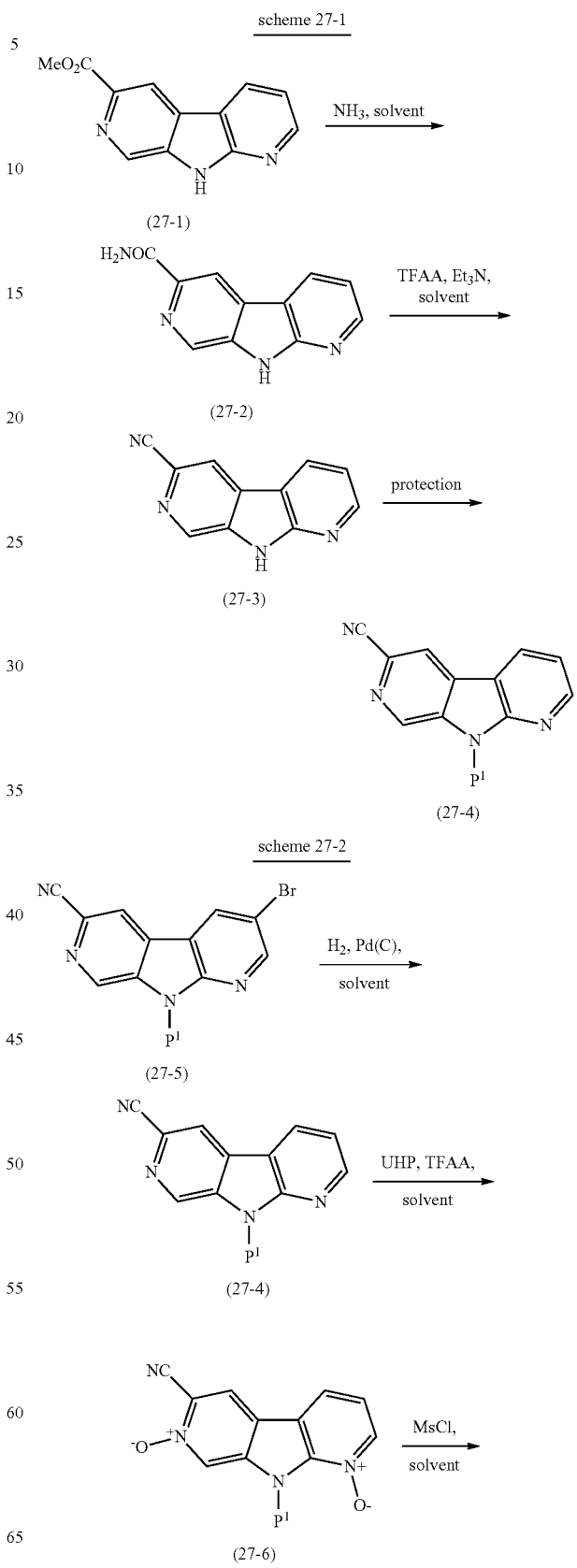

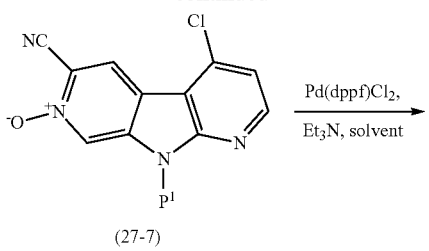

(27-7)

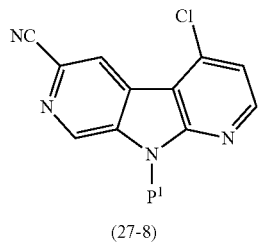

(27-8)

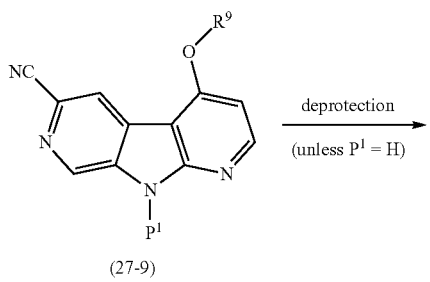

(27-9)

scheme 27-3

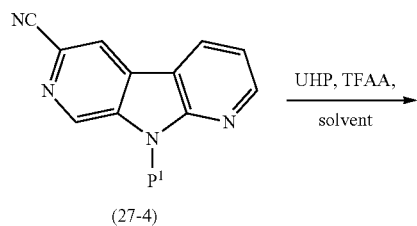

(27-4)

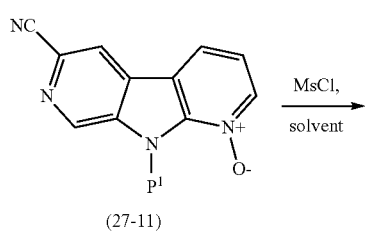

(27-11)

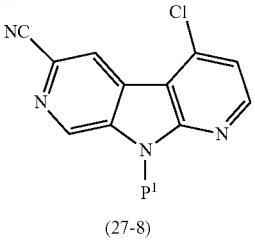

(27-8)

Compounds of formula (27-4) may be synthesized following procedures described in the literature or by the method outlined in Scheme 27-1. Compound (27-1) may be converted to compound (27-2) by treatment with ammonia in a suitable solvent such as methanol by heating in a sealed vessel at a temperature up to 150° C. Compound (27-2) may be converted to compound (27-3) by treatment with a dehydrating agent in a suitable solvent at an appropriate temperature, such as trifluoroacetic acid anhydride in the presence of triethylamine at between 0° C. and ambient temperature. Compound (27-3) may be converted to protected compounds of formula (27-4) by literature methods wherein $P^1$ represents a suitable protecting group, such as the 2-trimethylsilanylethoxy methyl derivative by treatment with 2-trimethylsilanylethoxymethyl chloride and sodium hydride in tetrahydrofuran.

Compounds of formula (27-4) may also be synthesized from compounds of formula (27-5) as outlined in Scheme 27-2, by a literature or other reduction method, such as by hydrogenation in the presence of a carbon-supported palladium catalyst in a suitable solvent such as tetrahydrofuran, or by treatment with zinc powder and ammonium formate in tetrahydrofuran.

Compounds of formula (27-10) may be synthesized from compounds of formula (27-4) as outlined in Scheme 27-2. Compounds of the formula (27-4) may be converted to compounds of formula (27-6) by treatment with an oxidant in a suitable solvent, such as urea-hydrogen peroxide adduct and in chloroform at ambient temperature. Compounds (27-6) may be converted to compounds (27-7) by treatment with an electrophilic agent and chloride source, such as methanesulfonyl chloride in N,N-dimethylformamide at ambient temperature. Compounds (27-7) may be deoxygenated to compounds (27-8) by treatment with a suitable reducing agent, such as triethylamine in the presence of [1,1'-bis(diphenyl phosphino)ferrocene]dichloropalladium (II) in acetonitrile under microwave irradiation.

Compounds of formula (27-8) may also be synthesized by the method outlined in scheme 27-3. Compounds (27-4) may also be converted to compounds of formula (27-11) by treatment with an oxidant in a suitable solvent, such as urea-hydrogen peroxide adduct and in chloroform. Compounds (27-11) may be converted to compounds (27-8) by treatment with a suitable agent such as methanesulfonyl chloride in N,N-dimethylformamide at ambient temperature.

Compounds of formula (27-8) may be converted to compounds of formula (27-9) by treatment with an alcohol, represented by $R^9OH$, in the presence of a suitable base such as sodium hydride, in a suitable solvent such as tetrahydrofuran, at a temperature between ambient temperature and the boiling point of the solvent, or at a temperature in excess of the boiling point of the solvent in a sealed vessel. Compounds of formula (27-9) may be converted to compounds (27-10) by removal of the protecting group represented by $P^1$, such as the 2-trimethylsilanylethoxymethyl protecting group, for example by treatment with tetrabutylammonium fluoride in tetrahydrofuran, or as a further example by treatment with aqueous hydrobromic acid in dioxane followed by treatment with aqueous sodium hydroxide.

a suitable base such as potassium tert-butoxide in a suitable solvent such as tert-butanol at a temperature between room temperature and the reflux point of the solvent.

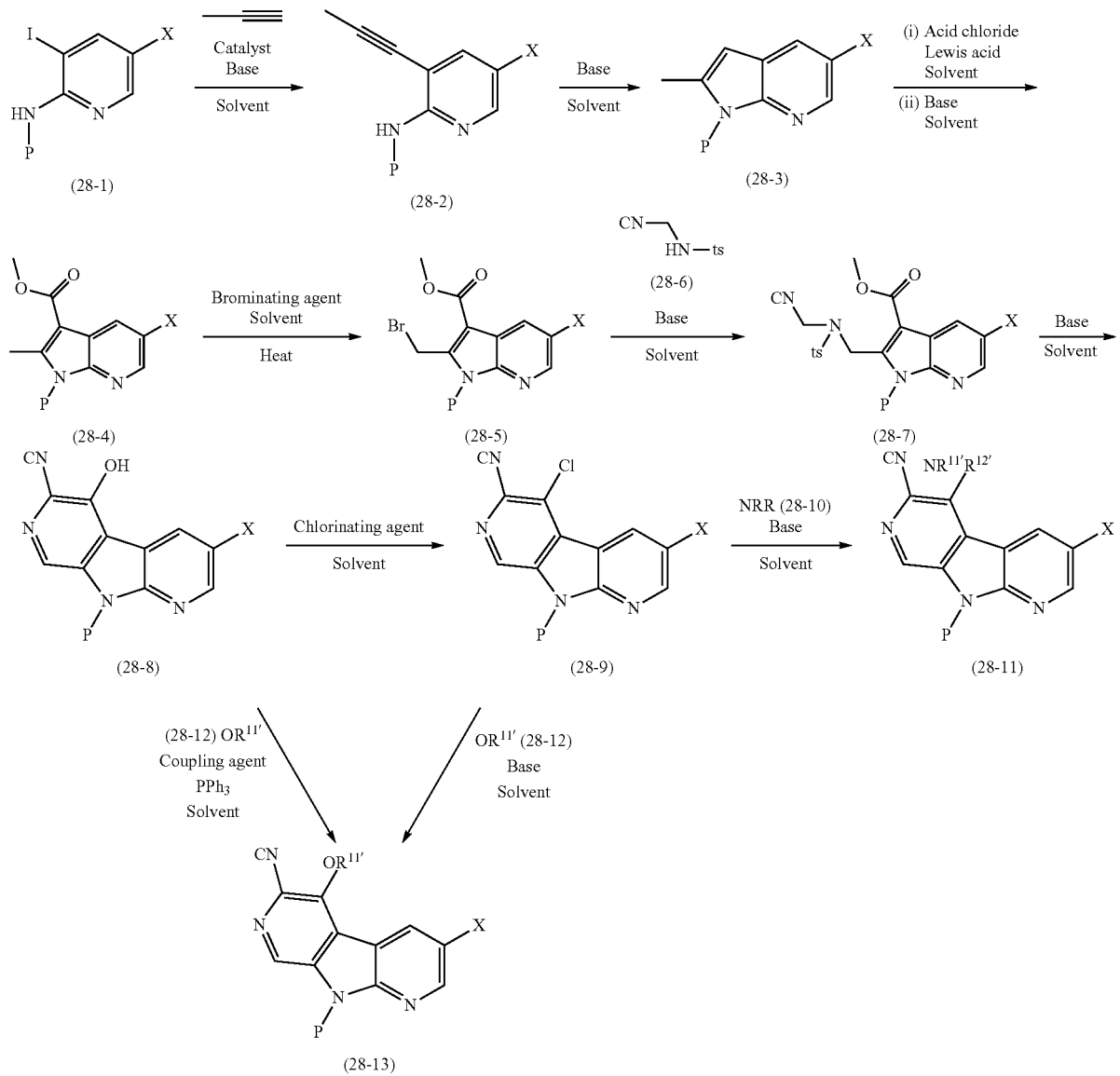

Scheme 28

Compounds of general formula (28-1) may be prepared using published methods described in the literature. Compounds of formula (28-11) and (28-13) may be prepared using the synthetic routes outlined in Scheme 28.

Compounds of general formula (28-2) (where X is H, F, Cl and Br) may be obtained from compounds of general formula (28-1) and propyne by reaction in the presence of a catalyst system such as bis(triphenylphosphine)dichloropalladium(II) and copper (I) iodide in the presence of a base such as triethylamine and a solvent such as THF at a temperature between room temperature and the boiling point of the solvent.

Compounds with a general formula (28-3) may be prepared from compounds of formula (28-2) by treatment with Compounds of general formula (28-3) may then be converted to compounds of general formula (28-4) by treatment with an acid chloride such as trichloroacetyl chloride in the presence of a lewis acid such as aluminum chloride in a suitable solvent such as dichloromethane at a temperature between room temperature and the reflux point of the solvent followed by base hydrolysis using a suitable base such as sodium hydroxide in a suitable solvent such as methanol at a temperature between room temperature and the reflux point of the solvent.

Compounds of general formula (28-4) may then be brominated with a brominating agent such as N-bromosuccinimide in a solvent such as 1,2-dichloroethane at a temperature between room temperature and the reflux temperature of the solvent to give compounds of general formula (28-5). Compounds of general formula (28-5) may be converted to compounds of general formula (28-6) by displacement with tosylaminoacetonitrile (28-6) using a suitable base such as sodium hydride in a solvent such as DMF at a temperature between −20° C. and 50° C. Compounds of general formula (28-7) may then be cyclised with a suitable base such as lithium hexamethylsilylamide in a solvent such as THF at a temperature between −78° C. and room temperature to provide compounds of general formula (28-8). Compounds of general formula (28-8) may then be reacted with an appropriate alcohol (28-12) ($R^{11'}OH$) using a phosphine and a coupling reagent such as diisopropylazodicarboxylate in an appropriate solvent such as THF to provide ethers of general formula (28-13).

Alternatively, compounds of general formula (28-5) may be converted to compounds of general formula (28-9) using a chlorinating agent such as phosphorus pentachloride in suitable solvent such as chlorobenzene or phosphorus oxychloride at a temperature between 50° C. and the reflux point of the solvent.

Compounds of general formula (28-11) may be obtained from compounds of formula (28-9) by reaction with compounds of general formula (28-10) ($HNR^{11'}R^{12'}$) with or without the presence of a base such as N,N-diisopropylethylamine in a suitable solvent such as NMP at a temperature from room temperature to the reflux temperature of the solvent.

Scheme 29

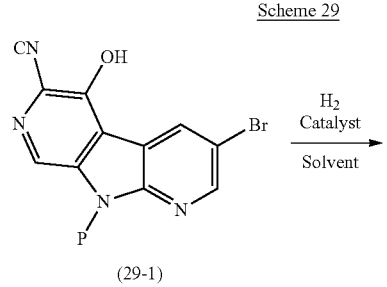

(29-1)

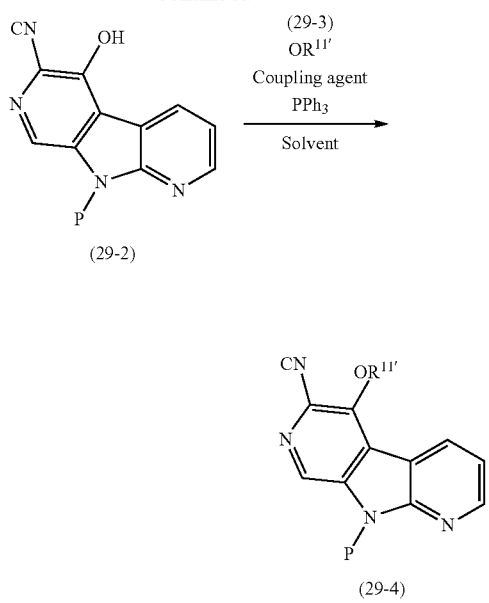

Compounds of general formula (29-1) may be prepared using synthetic routes outlined in Scheme 28. Compounds of formula (29-4) may be prepared using the synthetic routes outlined in Scheme 29.

Compounds of general formula (29-1) may be converted to compounds of general formula (29-2) using a catalyst such as palladium in a solvent such as ethanol under an atmosphere of hydrogen at a temperature from room temperature to 50° C. Compounds of formula (29-2) may then be reacted with an appropriate alcohol (29-3) ($R^{11'}OH$) using a phosphine and a coupling reagent such as diisopropylazodicarboxylate in an appropriate solvent such as THF to provide ethers of general formula (29-4).

Scheme 30

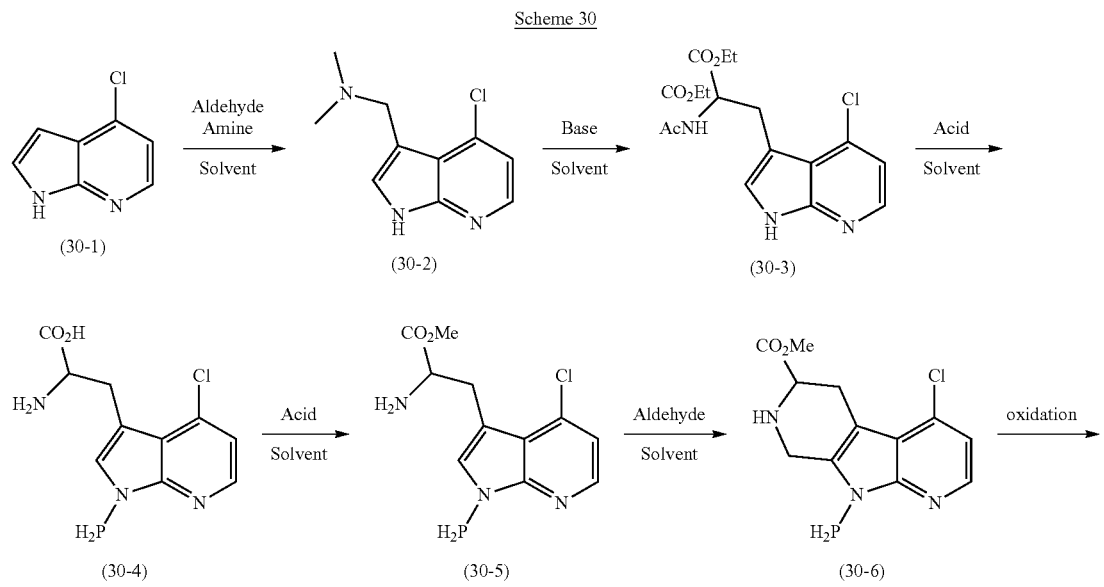

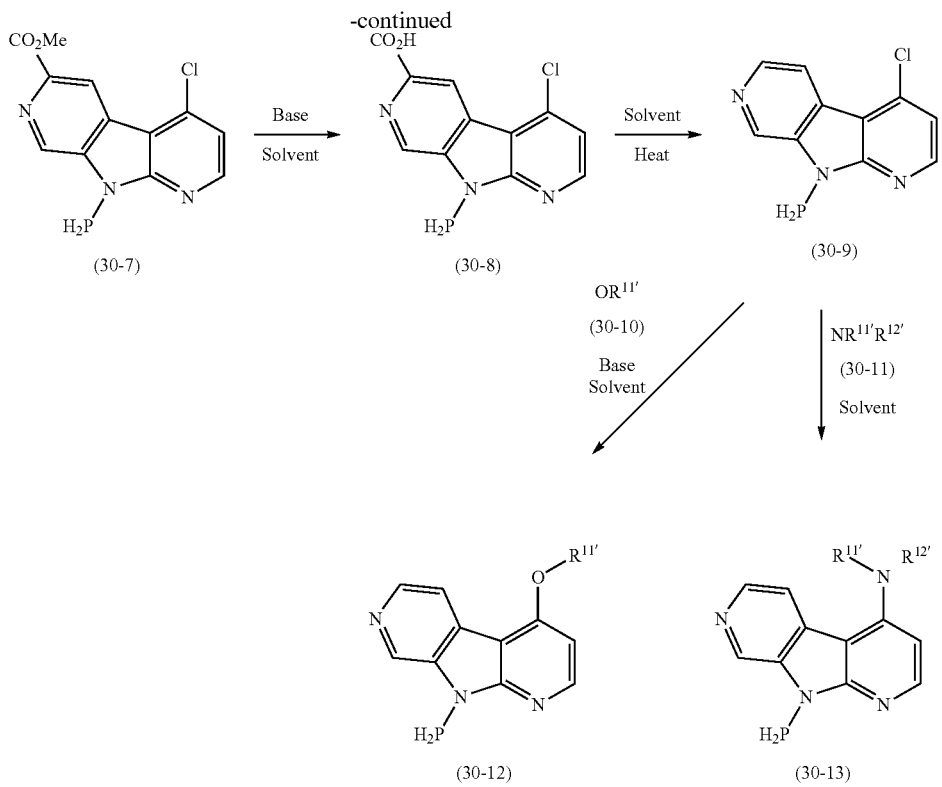

Compounds of general formula (30-1) may be prepared using published methods described in the literature or obtained from commercial sources.

Compounds of general formula (30-2) may be prepared from compounds of general formula (30-1) by treatment with a mixture of an aldehyde such as formaldehyde in the presence of an amine such as dimethylamine in a suitable solvent such as 1-butanol at a temperature between 50° C. and the reflux point of the solvent. Compounds of general formula (30-2) may be converted to compounds of general formula (30-3) by treatment with an acetamidomalonate such as diethylacetamidomalonate in the presence of a base such as sodium hydroxide in a suitable solvent such as xylene at a temperature between 50° C. and the reflux point of the solvent.

Compounds of general formula (30-4) may be obtained from compounds of formula (30-3) by hydrolysis and decarboxylation using a suitable acid such as concentrated hydrochloric acid at a temperature between 50° C. and the reflux point of the solvent. Compounds of general formula (30-5) may be obtained from compounds of general formula (30-4) by treatment with an appropriate acid such as hydrochloric acid in the presence of an alcoholic solvent such as methanol at a temperature between ambient temperature and the reflux point of the solvent. Compounds of general formula (30-5) may be converted to compounds of general formula (30-6) by treatment with an aldehyde such as formaldehyde in a suitable solvent such as pyridine at a temperature between 50° C. and the reflux point of the solvent.

Compounds of general formula (30-7) may be prepared from compounds of general formula (30-6) by oxidation with a suitable oxidizing agent such as selenium dioxide in a suitable solvent such as 1,4-dioxane at a temperature between 50° C. and the reflux point of the solvent. Compounds of general formula (30-7) may then be saponified in the presence of a base, such as lithium hydroxide, in a suitable solvent mixture such as THF and water, at a temperature from 20° C. to 50° C., to obtain compounds of general formula (30-8).

Compounds of general formula (30-9) can be obtained by decarboxylation of compounds of general formula (30-8) by heating in a suitable solvent such as NMP, at a temperature between 100° C. and the boiling point of the solvent.

Compounds of general formula (30-9) may be converted to compounds of general formula (30-13) by displacement with a suitable amine of general formula (30-11) (HNR$^{11'}$R$^{12'}$) either as solvent or in a solvent such as NMP at a temperature between ambient temperature and the reflux point of the solvent. Compounds of general formula (30-13) may also be obtained from compounds of general formula (30-9) by reaction with compounds of general formula (30-11) (HNR$^{11'}$R$^{12'}$) in the presence of a catalyst such as [1,1'-bis(diphenylphosphino)ferrocene]dichloropalladium (II), in the presence of a base such as potassium tert-butoxide in a suitable solvent such as DME, or a mixture of two or more appropriate solvents, at a temperature from room temperature to the reflux temperature of the solvent or solvents, or under microwave irradiation at a temperature between 70° C. and 160° C.

Compounds of general formula (30-12) may be obtained through alkylation of compounds of general formula (30-9) with a suitable alkylating agent (30-10) R$^{11'}$—OH using a suitable base such as cesium carbonate in a solvent such as acetonitrile at a temperature between room temperature and the reflux point of the solvent.

Scheme 31

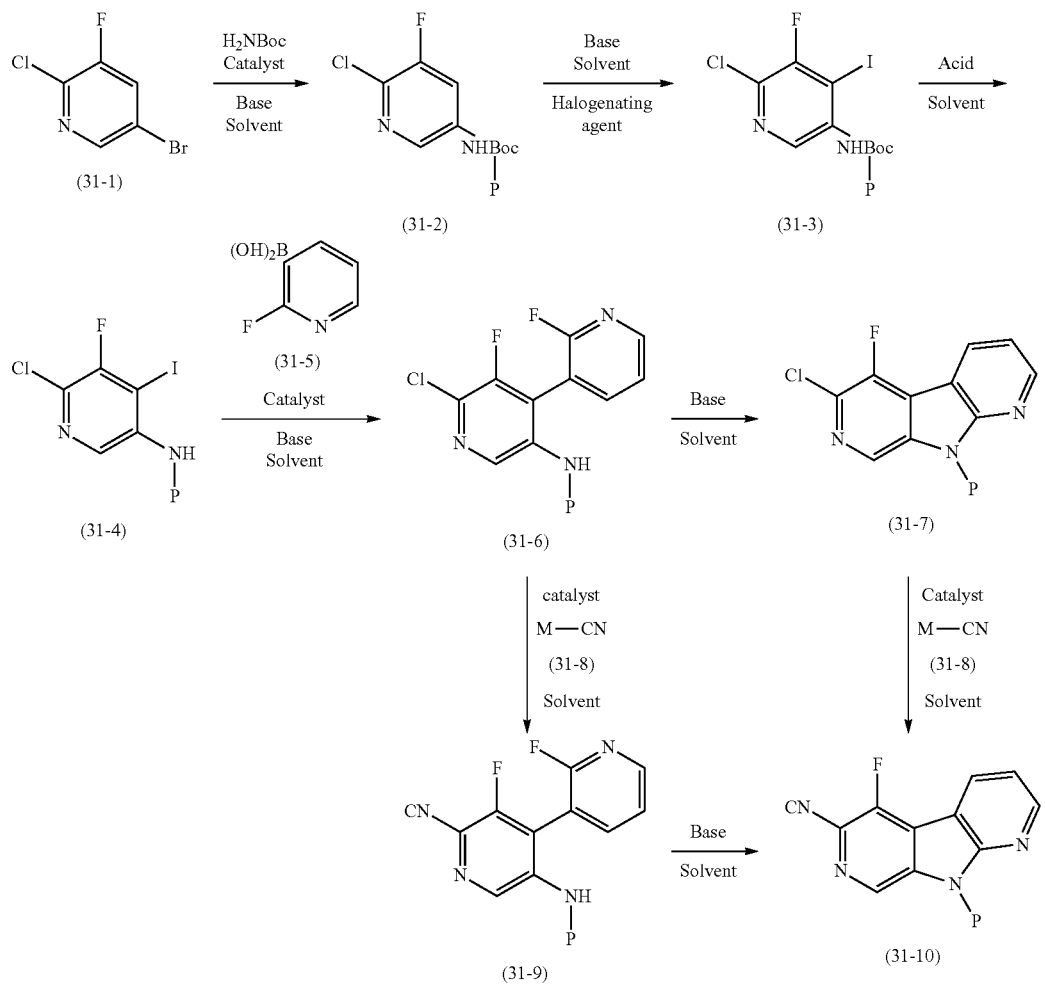

Compounds of general formula (31-1) may be prepared using published methods described in the literature or obtained from commercial sources. Compounds of formula (31-10) may be prepared using the synthetic routes outlined in Scheme 31.

Compounds of general formula (31-2) may be obtained from compounds of general formula (31-1) by reaction with a carbamate such tert-butylcarbamate in the presence of a catalyst such as tris(dibenzylidineacetone)dipalladium(0)/XantPhos, a base such as cesium carbonate in a suitable solvent such as 1,4-dioxane at a temperature of from 50° C. to the reflux temperature of the solvent, or under microwave irradiation at a temperature of from 70° C. to 150° C. Compounds of general formula (31-2) may be deprotonated with a suitable base such as n-butyllithium/TMEDA in a suitable solvent such as diethyl ether at a temperature between −78° C. and −10° C. then halogenated with a suitable halogenating agent such as iodine to obtain compounds of general formula (31-3).

Compounds of general formula (31-3) may be deprotected using an acid such as TFA in a solvent such as dichloromethane to give compounds of general formula (31-4). Compounds of general formula (31-6) may be obtained from compounds of general formula (31-4) by reaction with a boronic acid of general formula (31-5) in the presence of a catalyst such as Amphos2, a base such as aqueous potassium fluoride in a suitable solvent such as acetonitrile at a temperature of from room 50° C. to the reflux temperature of the solvent, or under microwave irradiation at a temperature of from 70° C. to 150° C.

Compounds of general formula (31-6) may be cyclised to obtain compounds of general formula (31-7) with a base such as sodium hexamethyldisilazane in a suitable solvent such as THF at a temperature between 0° C. and 50° C. Compounds of general formula (31-7) may be converted to compounds of general formula (31-10) using a reagent of general formula (31-8) such as zinc (II) cyanide in the presence of a catalyst such as tetrakis(triphenylphosphine) palladium (0) in a solvent such as DMF at a temperature between room temperature and the reflux point of the solvent, or under microwave irradiation at a temperature between 70° C. and 150° C.

Alternatively, compounds of general formula (31-6) may be converted to compounds of general formula (31-9) using a reagent of general formula (31-8) such as zinc (11) cyanide in the presence of a catalyst such as tetrakis(triphenylphosphine)palladium (0) in a solvent such as DMF at a temperature between room temperature and the reflux point of the solvent, or under microwave irradiation at a temperature between 70° C. and 150° C. Compounds of general formula (31-9) may be cyclised to obtain compounds of general formula (31-10) with a base such as sodium hexamethyldisilazane in a suitable solvent such as THF at a temperature between 0° C. and 50° C.

(32-8) using a reagent of general formula (32-4) such as zinc (II) cyanide in the presence of a catalyst such as tetrakis(triphenylphosphine)palladium (0) in a solvent such as DMF at a temperature between room temperature and the reflux

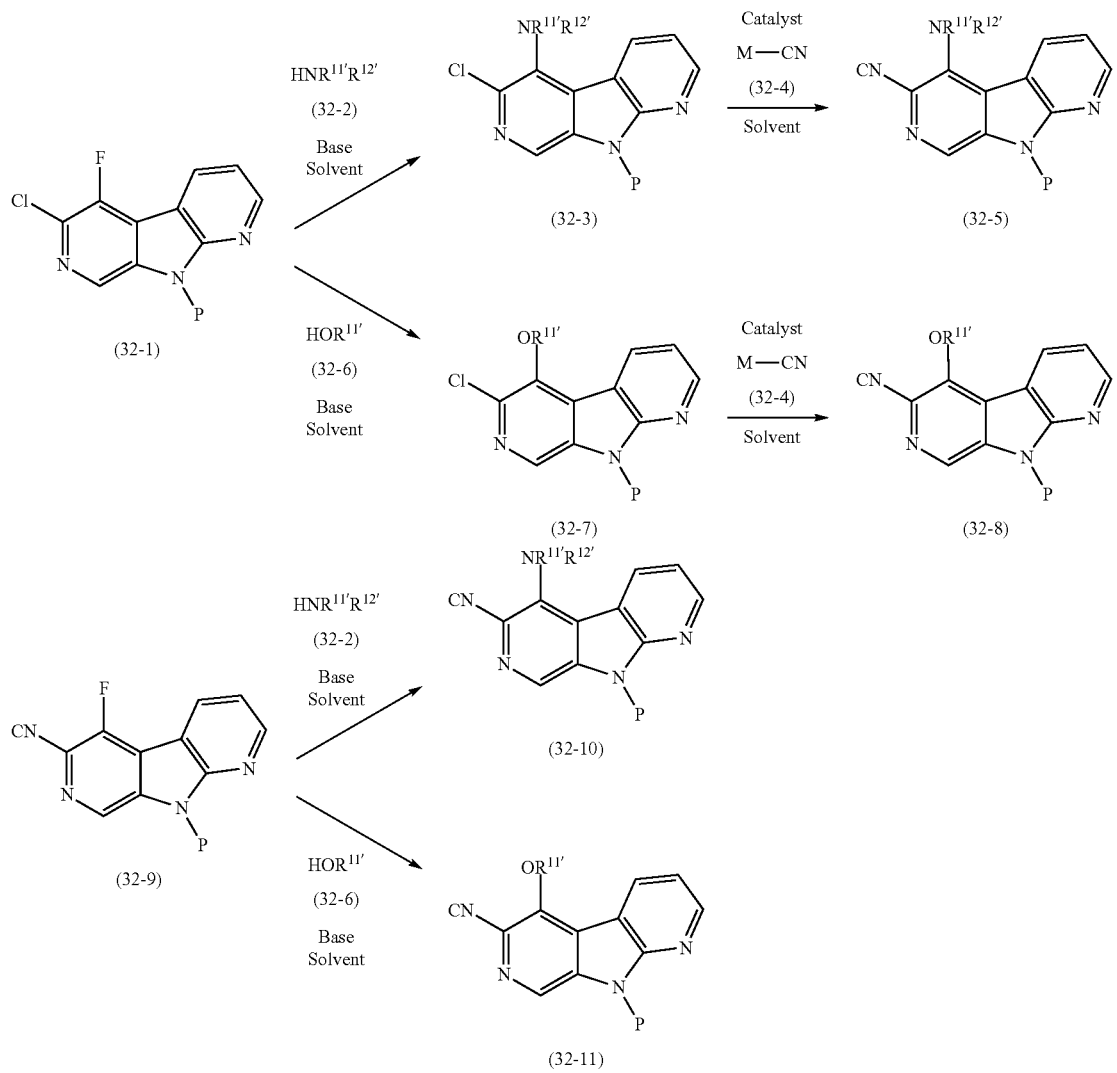

Scheme 32

Compounds of general formula (32-1) and (32-9) may be prepared using the synthetic route outlined in scheme 31. Compounds of general formula (32-5), (32-8), (32-10) and (32-11) may also be prepared using the synthetic route outlined in Scheme 32. Compounds of general formula (32-1) may be converted to compounds of general formula (32-3) by displacement with a suitable amine of general formula (32-2) (HNR$^{11'}$R$^{12'}$) either as solvent or in a solvent such as DMA at a temperature between ambient temperature and the reflux point of the solvent.

Compounds of general formula (32-7) may be obtained through alkylation of compounds of general formula (32-1) with a suitable alkylating agent (32-6) R$^{11'}$—OH using a suitable base such as cesium carbonate in a solvent such as acetonitrile at a temperature between room temperature and the reflux point of the solvent.

compounds of general formula (32-5) and (32-8) may be converted to compounds of general formula (32-5) and point of the solvent, or under microwave irradiation at a temperature between 70° C. and 150° C.

Compounds of general formula (32-9) may be converted to compounds of general formula (32-10) by displacement with a suitable amine of general formula (32-2) (HNR$^{11'}$R$^{12'}$) either as solvent or in a solvent such as DMA at a temperature between ambient temperature and 60° C.

Compounds of general formula (32-11) may be obtained through alkylation of compounds of general formula (32-9) with a suitable alkylating agent (32-6) R$^{11'}$—OH using a suitable base such as sodium hydride in a solvent such as N,N-dimethylformamide at a temperature between 0° C. and the reflux point of the solvent.

It will be appreciated that where appropriate functional groups exist, compounds described in the formulae of Schemes 1-32 or any intermediates used in their preparation may be further derivatised by one or more standard synthetic methods employing substitution, oxidation, reduction, or cleavage reactions. Particular substitution approaches include conventional alkylation, arylation, heteroarylation, acylation, sulfonylation, halogenation, nitration, formylation and coupling procedures.

In a further example primary amine (—$NH_2$) groups may be alkylated using a reductive alkylation process employing an aldehyde or a ketone and a borohydride, for example sodium triacetoxyborohydride or sodium cyanoborohydride, in a solvent such as a halogenated hydrocarbon, for example 1,2-dichloroethane, or an alcohol such as ethanol, where necessary in the presence of an acid such as acetic acid at around ambient temperature. Secondary amine (—NH—) groups may be similarly alkylated employing an aldehyde.

In a further example, primary amine or secondary amine groups may be converted into amide groups (—NHCOR' or —NRCOR') by acylation. Acylation may be achieved by reaction with an appropriate acid chloride in the presence of a base, such as triethylamine, in a suitable solvent, such as dichloromethane, or by reaction with an appropriate carboxylic acid in the presence of a suitable coupling agent such HATU (O-(7-azabenzotriazol-1-yl)-N,N,N',N'-tetramethyluronium hexafluorophosphate) in a suitable solvent such as dichloromethane. Similarly, amine groups may be converted into sulphonamide groups (—$NHSO_2R'$ or —NR"$SO_2R'$) groups by reaction with an appropriate sulphonyl chloride in the presence of a suitable base, such as triethylamine, in a suitable solvent such as dichloromethane. Primary or secondary amine groups can be converted into urea groups (—NHCONR'R" or —NRCONR'R") by reaction with an appropriate isocyanate in the presence of a suitable base such as triethylamine, in a suitable solvent, such as dichloromethane.

An amine (—$NH_2$) may be obtained by reduction of a nitro (—$NO_2$) group, for example by catalytic hydrogenation, using for example hydrogen in the presence of a metal catalyst, for example palladium on a support such as carbon in a solvent such as ethyl acetate or an alcohol e.g. methanol. Alternatively, the transformation may be carried out by chemical reduction using for example a metal, e.g. tin or iron, in the presence of an acid such as hydrochloric acid.

In a further example, amine (—$CH_2NH_2$) groups may be obtained by reduction of nitriles (—CN), for example by catalytic hydrogenation using for example hydrogen in the presence of a metal catalyst, for example palladium on a support such as carbon, or Raney nickel, in a solvent such as an ether e.g. a cyclic ether such as tetrahydrofuran, at a temperature from −78° C. to the reflux temperature of the solvent.

In a further example, amine (—$NH_2$) groups may be obtained from carboxylic acid groups (—$CO_2H$) by conversion to the corresponding acyl azide (—$CON_3$), Curtius rearrangement and hydrolysis of the resultant isocyanate (—N=C=O).

Aldehyde groups (—CHO) may be converted to amine groups (—$CH_2NR'R''$)) by reductive amination employing an amine and a borohydride, for example sodium triacetoxyborohydride or sodium cyanoborohydride, in a solvent such as a halogenated hydrocarbon, for example dichloromethane, or an alcohol such as ethanol, where necessary in the presence of an acid such as acetic acid at around ambient temperature.

In a further example, aldehyde groups may be converted into alkenyl groups (—CH=CHR') by the use of a Wittig or Wadsworth-Emmons reaction using an appropriate phosphorane or phosphonate under standard conditions known to those skilled in the art.

Aldehyde groups may be obtained by reduction of ester groups (such as —$CO_2Et$) or nitriles (—CN) using diisobutylaluminium hydride in a suitable solvent such as toluene. Alternatively, aldehyde groups may be obtained by the oxidation of alcohol groups using any suitable oxidising agent known to those skilled in the art.

Ester groups (—$CO_2R'$) may be converted into the corresponding acid group (—$CO_2H$) by acid- or base-catalused hydrolysis, depending on the nature of R. If R is t-butyl, acid-catalysed hydrolysis can be achieved for example by treatment with an organic acid such as trifluoroacetic acid in an aqueous solvent, or by treatment with an inorganic acid such as hydrochloric acid in an aqueous solvent.

Carboxylic acid groups (—$CO_2H$) may be converted into amides (CONHR' or —CONR'R") by reaction with an appropriate amine in the presence of a suitable coupling agent, such as HATU, in a suitable solvent such as dichloromethane.

In a further example, carboxylic acids may be homologated by one carbon (i.e —$CO_2H$ to —$CH_2CO_2H$) by conversion to the corresponding acid chloride (—COCl) followed by Arndt-Eistert synthesis.

In a further example, —OH groups may be generated from the corresponding ester (e.g. —$CO_2R'$), or aldehyde (—CHO) by reduction, using for example a complex metal hydride such as lithium aluminium hydride in diethyl ether or tetrahydrofuran, or sodium borohydride in a solvent such as methanol. Alternatively, an alcohol may be prepared by reduction of the corresponding acid (—$CO_2H$), using for example lithium aluminium hydride in a solvent such as tetrahydrofuran, or by using borane in a solvent such as tetrahydrofuran.

Alcohol groups may be converted into leaving groups, such as halogen atoms or sulfonyloxy groups such as an alkylsulfonyloxy, e.g. trifluoromethylsulfonyloxy or arylsulfonyloxy, e.g. p-toluenesulfonyloxy group using conditions known to those skilled in the art. For example, an alcohol may be reacted with thioyl chloride in a halogenated hydrocarbon (e.g. dichloromethane) to yield the corresponding chloride. A base (e.g. triethylamine) may also be used in the reaction.

In another example, alcohol, phenol or amide groups may be alkylated by coupling a phenol or amide with an alcohol in a solvent such as tetrahydrofuran in the presence of a phosphine, e.g. triphenylphosphine and an activator such as diethyl-, diisopropyl, or dimethylazodicarboxylate. Alternatively alkylation may be achieved by deprotonation using a suitable base e.g. sodium hydride followed by subsequent addition of an alkylating agent, such as an alkyl halide.

Aromatic halogen substituents in the compounds may be subjected to halogen-metal exchange by treatment with a base, for example a lithium base such as n-butyl or t-butyl lithium, optionally at a low temperature, e.g. around −78° C., in a solvent such as tetrahydrofuran, and then quenched with an electrophile to introduce a desired substituent. Thus, for example, a formyl group may be introduced by using N,N-dimethylformamide as the electrophile. Aromatic halogen substituents may alternatively be subjected to metal (e.g. palladium or copper) catalysed reactions, to introduce, for example, acid, ester, cyano, amide, aryl, heteraryl, alkenyl, alkynyl, thio- or amino substituents. Suitable procedures which may be employed include those described by Heck, Suzuki, Stille, Buchwald or Hartwig.

Aromatic halogen substituents may also undergo nucleophilic displacement following reaction with an appropriate nucleophile such as an amine or an alcohol. Advantageously, such a reaction may be carried out at elevated temperature in the presence of microwave irradiation.

The compounds of the present invention are tested for their capacity to inhibit chk1 activity and activation (primary assays) and for their biological effects on growing cells (secondary assays) as described below. The compounds having $IC_{50}$ of less than 10 µM (more preferably less than 5 µM, even more preferably less than 1 µM, most preferably less than 0.5 µM) in the chk1 activity and activation assay of Example i, and $EC_{50}$ of less than 10 µM (more preferably less than 5 µM, most preferably less than 1 µM) in the cellular assay of Example ii, are useful as chk1 inhibitors.

The present invention includes a composition (e.g., a pharmaceutical composition) comprising a compound of Formula (I), (I-a) and/or (I-b), (and/or solvates, hydrates and/or salts thereof) and a carrier (a pharmaceutically acceptable carrier). The present invention also includes a composition (e.g., a pharmaceutical composition) comprising a compound of Formula (I), (I-a) and/or (I-b) (and/or solvates, hydrates and/or salts thereof) and a carrier (a pharmaceutically acceptable carrier), further comprising a second chemotherapeutic agent such as those described herein. The present invention also includes a composition (e.g., a pharmaceutical composition) comprising a compound of Formula (I), (I-a) and/or (I-b) (and/or solvates, hydrates and/or salts thereof) and a carrier (a pharmaceutically acceptable carrier), further comprising a second chemotherapeutic agent such as a DNA damaging agent including those described herein. The present compositions are useful for inhibiting abnormal cell growth or treating a hyperproliferative disorder such as cancer in a mammal (e.g., human). For example, the present compounds and compositions are useful for treating breast cancer, colorectal cancer, ovarian cancer, non-small cell lung cancer, malignant brain tumors, sarcomas, melanoma, lymphoma, myelomas and/or leukemia in a mammal (e.g., human).

The present invention includes a method of inhibiting abnormal cell growth or treating a hyperproliferative disorder such as cancer in a mammal (e.g., human) comprising administering to said mammal a therapeutically effective amount of a compound of Formula (I), (I-a) and/or (I-b) (and/or solvates, hydrates and/or salts thereof) or a composition thereof. For example, the present invention includes a method of treating breast cancer, colorectal cancer, ovarian cancer, non-small cell lung cancer, malignant brain tumors, sarcomas, melanoma, lymphoma, myelomas and/or leukemia in a mammal (e.g., human), comprising administering to said mammal a therapeutically effective amount of a compound of Formula (I), (I-a) and/or (I-b) (and/or solvates, hydrates and/or salts thereof) or a composition thereof.

The present invention includes a method of inhibiting abnormal cell growth or treating a hyperproliferative disorder such as cancer in a mammal (e.g., human) comprising administering to said mammal a therapeutically effective amount of a compound of Formula (I), (I-a) and/or (I-b) (and/or solvates, hydrates and/or salts thereof) or a composition thereof, in combination with a second chemotherapeutic agent such as those described herein. The present invention also includes a method of inhibiting abnormal cell growth or treating a hyperproliferative disorder such as cancer in a mammal (e.g., human) comprising administering to said mammal a therapeutically effective amount of a compound of Formula (I), (I-a) and/or (I-b) (and/or solvates, hydrates and/or salts thereof) or a composition thereof, in combination with a second chemotherapeutic agent such as a DNA damaging agent including those described herein. For example, the present invention includes a method of treating breast cancer, colorectal cancer, ovarian cancer, non-small cell lung cancer, malignant brain tumors, sarcomas, melanoma, lymphoma, myelomas and/or leukemia in a mammal (e.g., human), comprising administering to said mammal a therapeutically effective amount of a compound of Formula (I), (I-a) and/or (I-b) (and/or solvates, hydrates and/or salts thereof) or a composition thereof, in combination with a second chemotherapeutic agent such as those described herein. The present invention also includes a method of treating breast cancer, colorectal cancer, ovarian cancer, non-small cell lung cancer, malignant brain tumors, sarcomas, melanoma, lymphoma, myelomas and/or leukemia in a mammal (e.g., human), comprising administering to said mammal a therapeutically effective amount of a compound of Formula (I), (I-a) and/or (I-b) (and/or solvates, hydrates and/or salts thereof) or a composition thereof, in combination with a second chemotherapeutic agent such as such as a DNA damaging agent including those described herein.

The present invention includes a method of using the present compounds for in vitro, in situ, and in vivo diagnosis or treatment of mammalian cells, organisms, or associated pathological conditions.

Administration of the compounds of the present invention (hereinafter the "active compound(s)") can be effected by any method that enables delivery of the compounds to the site of action. These methods include oral routes, intraduodenal routes, parenteral injection (including intravenous, subcutaneous, intramuscular, intravascular or infusion), topical, inhalation and rectal administration.

The amount of the active compound administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

The active compound may be applied as a sole therapy or in combination with one or more chemotherapeutic agents, for example those described herein. Such conjoint treatment may be achieved by way of the simultaneous, sequential or separate dosing of the individual components of treatment.

The pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see Remington's Pharmaceutical Sciences, Mack Publishing Company, Ester, Pa., 15.sup.th Edition (1975).

EXAMPLES

Abbreviations

AIBN 2,2'-Azobis(2-methylproprionitrile)
ATP Adenosine-5'-triphosphate
Biotage Pre-packed silica Biotage® SNAP Cartridge for flash chromatography
CDCl$_3$ Deuterated chloroform
CD$_3$OD Deuterated methanol
DCM Dichloromethane
DCE Dichloroethane
DIPEA Diisopropylethylamine
DMAP 4-Dimethylaminopyridine
DMA Dimethylacetamide
DMAP 4-Dimethylaminopyridine
DME 1,2-Dimethoxyethane
DMF Dimethylformamide
DMSO Dimethylsulfoxide
DMSO-d$_6$ Deuterated dimethylsulfoxide
EtOAc Ethyl acetate
EtOH Ethanol
h Hour
HCl Hydrochloric acid
HM-N Isolute® HM-N is a modified form of diatomaceous earth that can efficiently absorb aqueous samples
HOBt 1-Hydroxybenzotriazole
IMS Industrial methylated spirits
HATU O-(7-Azabenzotriazol-1-yl)-N,N,N',N'-tetramethyl uroniumhexafluorophosphate
LCMS Liquid Chromatography Mass Spectroscopy
LDA Lithium diisopropylamide
MeOH Methanol
mmol Millimoles
mol Moles
N Normal (concentration)
NaHCO$_3$ Sodium bicarbonate
NaOH Sodium hydroxide
NBS N-Bromosuccinimide
NMP N-Methyl-2-pyrrolidone
NMR Nuclear magnetic resonance
PyBOP (Benzotriazol-1-yloxy)tripyrrolidinophosphonium hexafluorophosphate
SCX-2 Strong cationic exchange resin
Si-SPE Pre-packed Isolute® silica flash chromatography cartridge
Si-ISCO Pre-packed ISCO® silica flash chromatography cartridge
TBAF Tetrabutylammonium fluoride
THF Tetrahydrofuran
TFA Trifluoroacetic acid
TLC Thin layer chromatography
TMS Trimethylsilyl General Experimental Conditions $^1$H NMR spectra were recorded at ambient temperature using a Varian Unity Inova (400 MHz) spectrometer with a triple resonance 5 mm probe. Chemical shifts are expressed in ppm relative to tetramethylsilane. The following abbreviations have been used: br=broad signal, s=singlet, d=doublet, dd=double doublet, t=triplet, q=quartet, m=multiplet.

High Pressure Liquid Chromatography-Mass Spectrometry (LCMS) experiments to determine retention times ($R_T$) and associated mass ions were performed using one of the following methods.

Method A:

Experiments performed on a Waters Micromass ZQ2000 quadrupole mass spectrometer linked to a Waters Acquity UPLC system with a PDA UV detector using a Acquity UPLC BEH C18 (1.7 □m) 100×2.1 mm column and a 0.4 ml/minute flow rate. The solvent system was 95% water containing 0.1% formic acid (solvent A) and 5% acetonitrile containing 0.1% formic acid (solvent B) for the first 0.40 minutes followed by a gradient up to 5% solvent A and 95% solvent B over the next 7 minutes. The final solvent system was held constant for a further 0.40 minutes.

Method B:

Experiments performed on a Waters Platform LC quadrupole mass spectrometer linked to a Hewlett Packard HP1100 LC system with diode array detector and 100 position autosampler using a Phenomenex Luna C18(2) 30×4.6 mm column and a 1 ml/minute flow rate. The solvent system was 95% water containing 0.1% formic acid (solvent A) and 5% methanol containing 0.1% formic acid (solvent B) for the first 0.50 minutes followed by a gradient up to 5% solvent A and 95% solvent B over the next 4 minutes. The final solvent system was held constant for a further 0.50 minutes.

Method C:

Experiments performed on a Waters Quattro Micro triple quadrupole mass spectrometer linked to a Hewlett Packard HP1100 LC system with diode array detector and 100 position autosampler using a Higgins Clipeus 5 □m C18 100×3 mm column and a 1 ml/minute flow rate. The solvent system was 95% water containing 0.1% formic acid (solvent A) and 5% methanol containing 0.1% formic acid (solvent B) for the first 1.0 minute followed by a gradient up to 5% solvent A and 95% solvent B over the next 20 minutes. The final solvent system was held constant for a further 1.0 minute.

Method D:

Experiments performed on an Agilent 1100 HPLC with Agilent MSD mass spectrometer using ESI as ionization source using an Agilent ZORBAX SB-C18 100×3.0 mm column and a 0.7 ml/minute flow rate. The solvent system was a gradient starting with 95% water with 0.05% TFA (solvent A) and 5% acetonitrile with 0.05% TFA (solvent B), ramping up to 5% solvent A and 95% solvent B over 25 minutes. The final solvent system was held constant for a further 5 minutes.

Method E:

Experiments performed on an Agilent 1100 HPLC with Agilent MSD mass spectrometer using ESI as ionization source using an Agilent ZORBAX SB-C18 30×2.1 mm column and a 0.6 ml/minute flow rate. The solvent system was a gradient starting with 95% water with 0.05% TFA (solvent A) and 5% acetonitrile with 0.05% TFA (solvent B), ramping up to 5% solvent A and 95% solvent B over 9 minutes. The final solvent system was held constant for a further 1 minute.

Method F:

Experiments performed on a Waters Acquity UHPLC with Waters—LCT Premier XE mass spectrometer using ESI as ionization source using an Acquity UPLC BEH C18, 1.7 um, 2.1*50 mm column and a 0.6 ml/minute flow rate. The solvent system was a gradient starting with 98% water with 0.05% TFA (solvent A) and 5% acetonitrile with 0.05% TFA (solvent B), ramping up to 2% solvent A and 98% solvent B over 2.5 minutes. The final solvent system was held constant for a further 1 minute.

Method G:

Experiments performed on a Waters Acquity UHPLC with Waters—LCT Premier XE mass spectrometer using ESI as ionization source using an Acquity UPLC BEH C18, 1.7 um, 2.1*50 mm column and a 0.6 ml/minute flow rate. The solvent system was a gradient starting with 98% water with 0.05% TFA (solvent A) and 5% acetonitrile with 0.05% TFA (solvent B), ramping up to 2% solvent A and 98% solvent B over 17 minutes. The final solvent system was held constant for a further 3 minutes.

Microwave experiments were carried out using a Biotage Initiator 60™ which uses a single-mode resonator and dynamic field tuning. Temperature from 40-250° C. can be achieved, and pressures of up to 30 bar can be reached. Alternatively, a CEM Discover microwave was also used for some of the experiments.

General Methods

Boronic acids and boronate esters were prepared from the appropriate aryl halide intermediate by using the general coupling methods described below. All aryl halide intermediates were either commercially available, prepared using literature methods or could be readily prepared by those skilled in the art. In some cases the intermediate was not isolated, and the coupling reaction performed on the crude boronic acid/boronate ester. Suzuki reactions were performed using either commercially available boronic acids/boronate esters or from compounds prepared using the procedures detailed below. If necessary, any protecting groups were then removed using one of the deprotection conditions described below. Stille reactions were performed using either commercially available stannanes or from compounds prepared using the procedures detailed below. If necessary, any protecting groups were then removed using one of the deprotection conditions described below.

General Boronic Acid/Boronate Ester Preparation Method

Method A:

The appropriate aryl halide (1-3 eq.) was suspended in a mixture of THF under an inert atmosphere then n-butyl lithium (1-3 eq.) was added at −78 OC. After between 5 and 30 minutes at this temperature, trialkylborate (1-3 eq.) was added then the reaction mixture was warmed to ambient temperature and quenched by the addition of ammonium chloride. The resultant residue was purified by one of the general purification methods described below or used crude in the next step.

Method B:

The appropriate aryl halide (1-3 eq.) was suspended in a mixture of dioxane and DMSO before bis(pinacolato)diboron (1-2 eq.), potassium acetate and 1,1'-bis(diphenylphosphino)-ferrocene]dichloropalladium(II) (5-10 mol %) were added and the reaction mixture was then heated with microwave irradiation (100-160° C.) for between 1 and 20 minutes. The resultant residue was purified by one of the general purification methods described below or used crude in the next step.

Method C:

The appropriate (bromomethyl)phenyl boronic acid (1 eq.) was stirred with sodium iodide (0.05 eq.) and potassium carbonate (3.0 eq.) in acetonitrile and the appropriate amine (1.2 eq.) added. The mixture was heated to 50° C. for 2 h and then cooled to ambient temperature or stirred at room temperature until reaction complete, then the volatile components were removed in vacuo and the residue re-suspended in MeOH. The remaining solid was removed by filtration then the methanolic solution was collected and concentrated to dryness under reduced pressure. The resulting boronic acid was used with no further purification.

Method D:

The appropriate electrophile (1-2 eq.) and potassium carbonate (3-5 eq.) were added to 4,4,5,5-tetramethyl-2(1H-pyrazol-4-yl)-1,3,2-dioxaborolane in acetonitrile and the mixture was stirred under reflux for between 1 and 7 days. The residue was purified by one of the general purification methods described below.

Synthesis of Intermediates

Preparation 9-Benzenesulfonyl-3-bromo-5-hydroxy-9H-dipyrido[2,3-b;4',3'-d]pyrrole-6-carbonitrile

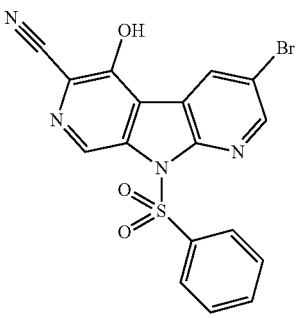 [SMILES: N#Cc1ncc2c(c1O)c1cc(Br)cnc1n2S(=O)(=O)c1ccccc1]

Step 1: 5-Bromo-3-iodo-pyridin-2-ylamine

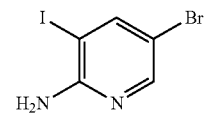

A stirred solution of 5-bromo-pyridin-2-ylamine (50 g, 289 mmol) in 2M sulfuric acid (500 mL) was treated portionwise with potassium iodate (30.8 g, 144 mmol) and the mixture heated to 100° C. A solution of potassium iodide (26.5 g, 160 mmol) in water (50 mL) was added dropwise over ca. 1 hour. The mixture was allowed to stir for a further 30 minutes then cooled to ambient temperature. The pH of the aqueous phase was adjusted to 8-9 and the mixture extracted with ethyl acetate (×3). The combined organic layer was washed with aqueous sodium thiosulfate solution, water and brine, dried (Na$_2$SO$_4$) and evaporated to afford the title compound as a brown solid (77.4 g, 90%). $^1$H NMR (300 MHz, CDCl$_3$): 8.06 (d, J=2.2 Hz, 1H), 7.96 (d, J=2.2 Hz, 1H), 4.96 (s, 2H).

Step 2: 5-Bromo-3-prop-1-ynyl-pyridin-2-ylamine

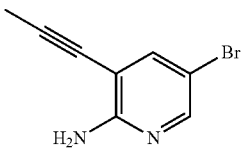

Propyne (28 g, 700 mmol) was condensed into a pre-weighed flask cooled to ca. −40° C. containing THF (150 mL). The solution was added via cannula to a cooled (0-5° C.), degassed mixture of 5-bromo-3-iodo-pyridin-2-ylamine (139 g, 465 mmol), bis(triphenylphosphine)dichloropalladium(0) (16.3 g, 23.2 mmol), copper (I) iodide (5.3 g, 27.9 mmol) and triethylamine (141 g, 194 mL, 1.4 mol) in THF (1.25 L). The mixture was stirred at 0-5° C. for 30 minutes then for a further 30 minutes at ambient temperature. The solid was removed by filtration and the cake washed with THF. The filtrate was diluted with ethyl acetate and extracted with 2M hydrochloric acid (×3). The combined acid extract was washed with diethyl ether and then made basic by careful addition of potassium carbonate then extracted with diethyl ether (×3). The combined organic layer was dried (Na$_2$SO$_4$), filtered and evaporated to afford the title compound as a buff solid (91 g, 93%). $^1$H NMR (400 MHz, CDCl$_3$): 8.01 (d, J=2.4 Hz, 1H), 7.55 (d, J=2.4 Hz, 1H), 4.96 (s, 2H), 2.11 (s, 3H).

Step 3: 5-Bromo-2-methyl-1H-pyrrolo[2,3-b]pyridine

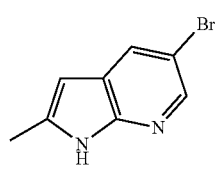

5-Bromo-3-prop-1-ynyl-pyridin-2-ylamine (91 g, 431 mmol) was treated with a 1M solution of potassium tert-butoxide in tert-butanol (700 mL) and the reaction mixture was heated at 85 OC for 1 hour. The mixture was then allowed to cool to ambient temperature and poured onto a 1:1 mixture of water/ice (ca. 1 L). The resultant precipitate was collected by filtration, washed with water and left to air dry. The resultant solid was dissolved in dichloromethane, dried (Na$_2$SO$_4$) and evaporated then triturated with diethyl ether to afford the title compound as a brown solid (88.7 g, 97%). $^1$H NMR (400 MHz, CDCl$_3$): 10.21 (s, 1H), 8.22 (d, J=2.1 Hz, 1H), 7.91 (d, J=2.1 Hz, 1H), 6.13 (s, 1H), 2.52 (s, 3H).

Step 4: 5-Bromo-2-methyl-1H-pyrrolo[2,3-b]pyridine-3-carboxylic acid methyl ester

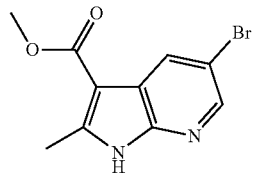

Aluminium trichloride (179 g, 1.34 mol) was added to a mixture of 5-bromo-2-methyl-1H-pyrrolo[2,3-b]pyridine (81 g, 384 mmol) in dichloromethane (1.5 L) and stirred for 50 minutes. Trichloroacetyl chloride (238 g, 147 mL, 1.31 mol) was added and the reaction mixture was left to stir for 18 hours. The reaction mixture was cooled to 0° C. and quenched by the addition of methanol (500 mL). The solvent was evaporated and the resultant residue treated with a mixture of potassium hydroxide (320 g) in methanol (2 L) (caution—exotherm) and the reaction mixture then heated under reflux for 3 hours. The reaction mixture was allowed to cool to ambient temperature then evaporated. The resultant residue was treated with 2M hydrochloric acid to give an acidic mixture. The resulting mixture was extracted with ethyl acetate (×5), the combined organic layer dried (Na$_2$SO$_4$), filtered and evaporated then triturated with diethyl ether to afford the title compound as a buff solid (91 g, 88%). $^1$H NMR (300 MHz, DMSO-d$_6$): 12.63 (s, 1H), 8.31 (s, 2H), 3.83 (s, 3H), 2.68 (s, 3H).

Step 5: 1-Benzenesulfonyl-5-bromo-2-methyl-1H-pyrrolo[2,3-b]pyridine-3-carboxylic acid methyl ester

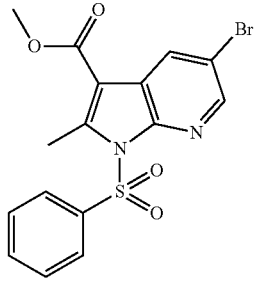 [SMILES: COC(=O)c1c(C)n(S(=O)(=O)c2ccccc2)c2ncc(Br)cc12]

A cooled (0-5° C.) suspension of 5-bromo-2-methyl-1H-pyrrolo[2,3-b]pyridine-3-carboxylic acid methyl ester (85 g, 316 mmol), powdered sodium hydroxide (38.1 g, 953 mmol) and benzyltriethylammonium chloride (1.46 g, 6.3 mmol) in dichloromethane (1 L) was treated over ca. 5 minutes with benzenesulfonyl chloride (69.5 g, 51 mL, 394 mmol). The reaction mixture was allowed to stir at 0-5° C. for 15 minutes then allowed to warm to ambient temperature and stirred for 1 hour.

The solid was removed by filtration through celite and the cake washed with dichloromethane. The filtrate was evaporated and the resultant residue triturated with diethyl ether to afford the title compound as a buff solid (122 g, 94%). ¹H NMR (400 MHz, CDCl₃): 8.43 (d, J=2.3 Hz, 1H), 8.40 (d, J=2.3 Hz, 1H), 8.20-8.16 (m, 2H), 7.65-7.59 (m, 1H), 7.54-7.49 (m, 2H), 3.94 (s, 3H), 3.16 (s, 3H).

Step 6: 1-Benzenesulfonyl-5-bromo-2-bromomethyl-1H-pyrrolo[2,3-b]pyridine-3-carboxylic acid methyl ester

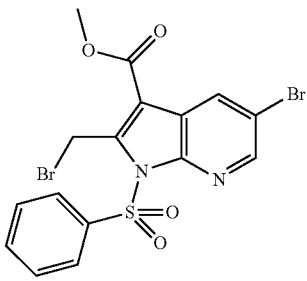 [SMILES: COC(=O)c1c(CBr)n(S(=O)(=O)c2ccccc2)c2ncc(Br)cc12]

A mixture of 1-benzenesulfonyl-5-bromo-2-methyl-1H-pyrrolo[2,3-b]pyridine-3-carboxylic acid methyl ester (121 g, 296 mmol), NBS (63 g, 354 mmol) and 1,1-azobis(cyclohexanecarbonitrile) (14.4 g, 59 mmol) in 1,2-dichloroethane (1.2 L) was heated under reflux for 90 minutes. The reaction mixture was allowed to cool to ambient temperature and washed with saturated aqueous sodium thiosulfate solution. The organic layer was dried (Na₂SO₄) then filtered. The filtrate was stirred with flash silica gel, filtered and the filtrate evaporated under reduced pressure. The resultant residue was triturated with diethyl ether/pentane (1:1) to afford the title compound as a white solid (130 g, 90%). ¹H NMR (400 MHz, CDCl₃): 8.47-8.46 (m, 4H), 7.64-7.64 (m, 1H), 7.54-7.53 (m, 2H), 5.67 (s, 2H), 4.00 (s, 3H).

Step 7: 1-Benzenesulfonyl-5-bromo-2-{[cyanomethyl-(toluene-4-sulfonyl)amino]-methyl}-1H-pyrrolo[2,3-b]pyridine-3-carboxylic acid methyl ester

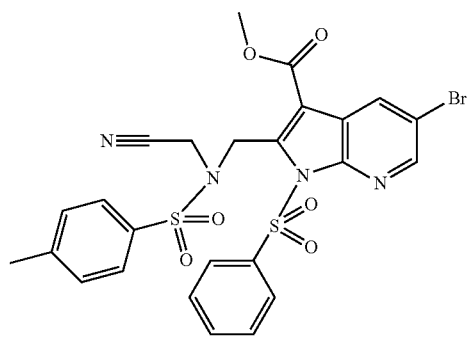 [SMILES: COC(=O)c1c(CN(CC#N)S(=O)(=O)c2ccc(C)cc2)n(S(=O)(=O)c2ccccc2)c2ncc(Br)cc12]

Sodium hydride (11.7 g, 60% dispersion in mineral oil, 293 mmol) was added portionwise to a cooled (0° C.) solution of 1-benzenesulfonyl-5-bromo-2-bromomethyl-1H-pyrrolo[2,3-b]pyridine-3-carboxylic acid methyl ester (130 g, 266 mmol) and N-cyanomethyl-4-methyl-benzenesulfonamide (61.5 g, 293 mmol) in DMF (1.25 L). The reaction mixture was stirred at 0° C. for 15 minutes, then allowed to warm to ambient temperature and stirred for 1 hour. The reaction mixture was poured into a cooled, stirred solution of 2M hydrochloric acid (1.25 L). The resultant precipitate was collected by filtration (slow) and the cake washed with water, followed by methanol and then diethyl ether. The resulting cake was dried to afford the title compound as a grey solid (154 g, 94%). LCMS (Method B): R_T=4.28 min, M+H⁺=617/619. ¹H NMR (400 MHz, CDCl₃): 8.49 (d, J=2.3 Hz, 1H), 8.42 (d, J=2.3 Hz, 1H), 8.33-8.33 (m, 2H), 7.78-7.76 (m, 2H), 7.64-7.64 (m, 1H), 7.55-7.54 (m, 2H), 7.34 (d, J=8.1 Hz, 2H), 5.43 (s, 2H), 4.28 (s, 2H), 3.96 (s, 3H), 2.43 (s, 3H).

Step 8: 9-Benzenesulfonyl-3-bromo-5-hydroxy-9H-dipyrido[2,3-b;4',3'-d]pyrrole-6-carbonitrile

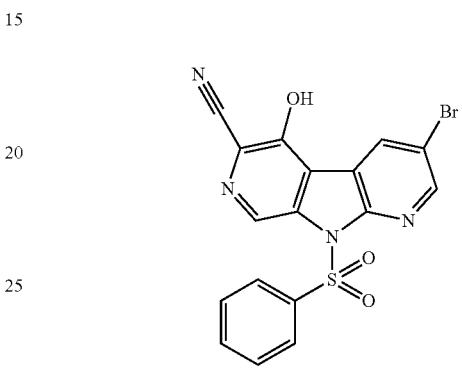

Lithium bis(trimethylsilyl)amide (800 mL of a 1N solution in THF, 800 mmol) was added dropwise to a cooled (−78° C.) suspension of 1-benzenesulfonyl-5-bromo-2-{[cyanomethyl-(toluene-4-sulfonyl)amino]methyl}-1H-pyrrolo[2,3-b]pyridine-3-carboxylic acid methyl ester (154 g, 250 mmol) in dry THF (1.25 L). The reaction mixture was allowed to slowly warm to −10° C. then slowly quenched into cold 1M hydrochloric acid. The layers were separated and the aqueous layer further extracted with THF. The combined organic layer was washed with brine, dried (Na₂SO₄), filtered and evaporated. The resultant residue was triturated with methanol then acetone and air dried to afford the title compound as a beige solid (77.6 g, 72%). LCMS (Method B): R_T=3.83 min, M+H⁺=429/431. ¹H NMR (400 MHz, DMSO-d₆): 9.22 (s, 1H), 8.83 (d, J=2.3 Hz, 1H), 8.81 (d, J=2.3 Hz, 1H), 8.19-8.16 (m, 2H), 7.75-7.74 (m, 1H), 7.65-7.59 (m, 2H).

Preparation of 9-Benzenesulfonyl-5-hydroxy-9H-dipyrido[2,3-b;4',3'-d]pyrrole-6-carbonitrile

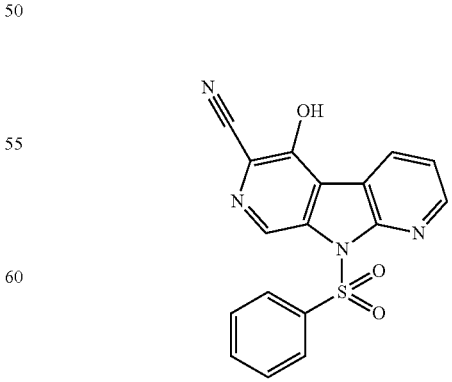

A mixture of 9-benzenesulfonyl-3-bromo-5-hydroxy-9H-dipyrido[2,3-b;4',3'-d]pyrrole-6-carbonitrile (9.91 g, 23.1 mmol), palladium on carbon hydrogenation catalyst (10 wt %, 1.0 g, 0.94 mmol), ethanol (250 mL), ethyl acetate (50 mL), DMF (50 mL) and triethylamine (50 mL) was stirred at room temperature under an atmosphere of hydrogen for 16 hours. The catalyst was removed by filtration through Celite© and the filtrate evaporated to dryness to give a gum, that was mixed with hydrochloric acid (1M, 100 mL) and sonicated in a laboratory ultrasonic cleaning bath for 30 minutes. The resultant solid was collected by filtration, washed with water then dried under vacuum to afford the title compound as a tan coloured solid (7.19 g, 89%). $^1$H NMR (400 MHz, DMSO-$d_6$): 9.27 (s, 1H), 8.71 (dd, J=4.9, 1.7 Hz, 1H), 8.68 (dd, J=7.9, 1.7 Hz, 1H), 8.20-8.20 (m, 2H), 7.74-7.73 (m, 1H), 7.60-7.59 (m, 3H).

Preparation of 9-Benzenesulfonyl-3-bromo-5-chloro-9H-dipyrido[2,3-b;4',3'-d]pyrrole-6-carbonitrile

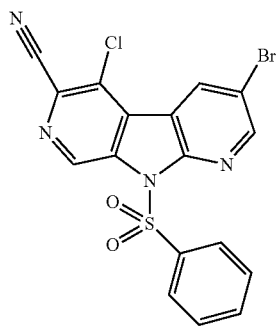 [SMILES: N#Cc1ncc2c(c1Cl)c1cc(Br)cnc1n2S(=O)(=O)c1ccccc1]

A solution of 9-benzenesulfonyl-3-bromo-5-hydroxy-9H-dipyrido[2,3-b;4',3'-d]pyrrole-6-carbonitrile (2.0 g, 4.66 mmol) and phosphorus pentachloride (2.9 g, 14.0 mmol) in chlorobenzene (6 mL) was heated at 105° C. for 1 hour. The reaction mixture was cooled to ambient temperature and the solvent removed in vacuo to afford a residue. The resultant residue was dissolved in dichloromethane (300 mL) and the solution was treated with ice/water (300 mL). The layers were separated and the aqueous layer further extracted with dichloromethane (300 mL). The combined organic layer was washed with brine, dried ($Na_2SO_4$), filtered and evaporated. The resultant residue was triturated with methanol and dried to afford the title compound as a tan solid (1.1 g, 53%). $^1$H NMR (300 MHz, DMSO-$d_6$): 9.70 (s, 1H), 9.06 (d, J=2.2 Hz, 1H), 8.98 (d, J=2.2 Hz, 1H), 8.27-8.22 (m, 2H), 7.77-7.76 (m, 1H), 7.67-7.60 (m, 2H).

Preparation of 9-Benzenesulfonyl-3-fluoro-5-hydroxy-9H-dipyrido[2,3-b;4',3'-d]pyrrole-6-carbonitrile

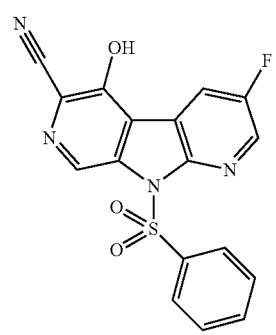 [SMILES: N#Cc1ncc2c(c1O)c1cc(F)cnc1n2S(=O)(=O)c1ccccc1]

Step 1: 5-Fluoro-3-iodo-pyridin-2-ylamine

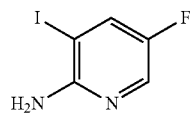

A stirred solution of 5-fluoro-pyridin-2-ylamine (50 g, 0.45 mol) in 2M sulfuric acid (250 mL) was treated portionwise with potassium iodate (48 g, 0.22 mol) and the mixture heated to 100° C. A solution of potassium iodide (41 g, 0.24 mol) in water (100 mL) was added dropwise over ca. 1 hour. The mixture was allowed to stir for a further 30 minutes then cooled to ambient temperature. The pH of the aqueous phase was adjusted to 8-9 and the mixture extracted with ethyl acetate (×3). The combined organic layer was washed with aqueous sodium thiosulfate solution, water and brine, dried ($Na_2SO_4$), filtered and evaporated to afford the title compound as a yellow solid (61.2 g, 58%). $^1$H NMR (400 MHz, $CDCl_3$): 7.94 (d, J=2.7 Hz, 1H), 7.68 (dd, J=7.2, 2.7 Hz, 1H), 4.85 (s, 2H).

Step 2: 5-Fluoro-3-prop-1-ynyl-pyridin-2-ylamine

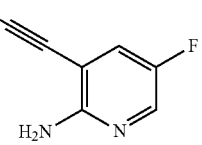

Propyne (15.4 g, 0.39 mol) was condensed into a pre-weighed flask cooled to ca. −40° C. containing THF (80 mL). The solution was added via cannula to a cooled (0-5° C.), degassed mixture of 5-fluoro-3-iodo-pyridin-2-ylamine (61.0 g, 0.26 mol), bis(triphenylphosphine)dichloropalladium(0) (9.0 g, 13.0 mmol), copper (I) iodide (2.95 g, 15.6 mmol) and triethylamine (77.7 g, 107 mL, 0.78 mol) in THF (650 mL). The mixture was stirred at 0-5° C. for 30 minutes then for a further 30 minutes at ambient temperature. The solid was removed by filtration and the cake washed with THF. The filtrate was diluted with ethyl acetate and extracted with 2M hydrochloric acid (×3). The combined acid extract was washed with diethyl ether and then made basic by careful addition of potassium carbonate then extracted with diethyl ether (×3). The combined organic layer was dried ($Na_2SO_4$), filtered and evaporated to afford the title compound as a brown solid (32.2 g, 84%). $^1$H NMR (400 MHz, $CDCl_3$): 7.90 (s, 1H), 7.24 (dd, J=8.4, 2.8 Hz, 1H), 4.84 (s, 2H), 2.11 (s, 3H).

Step 3: 5-Fluoro-2-methyl-1H-pyrrolo[2,3-b]pyridine

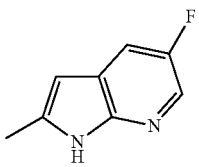

5-Fluoro-3-prop-1-ynyl-pyridin-2-ylamine (14.0 g, 90.0 mmol) was treated with a 1M solution of potassium tert-butoxide in tert-butanol (150 mL) and the reaction mixture was heated at 85 OC for 1 hour. The mixture was then allowed to cool to ambient temperature and poured onto a 1:1 mixture of water/ice (ca. 1 L). The resultant precipitate was collected by filtration, washed with water and left to air dry. The resultant solid was dissolved in dichloromethane, dried (Na$_2$SO$_4$), filtered and evaporated then triturated with diethyl ether to afford the title compound as a buff solid (9.2 g, 66%). $^1$H NMR (300 MHz, CDCl$_3$): 10.61 (s, 1H), 8.12 (s, 1H), 7.51 (dd, J=9.1, 2.3 Hz, 1H), 6.17 (s, 1H), 2.53 (d, J=1.0 Hz, 3H).

Step 4: 5-Fluoro-2-methyl-1H-pyrrolo[2,3-b]pyridine-3-carboxylic acid methyl ester

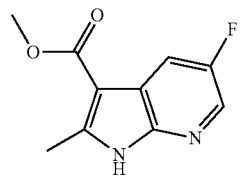

Aluminium trichloride (28.0 g, 209.7 mmol) was added to a mixture of 5-fluoro-2-methyl-1H-pyrrolo[2,3-b]pyridine (9.0 g, 59.9 mmol) in dichloromethane (150 mL) and stirred for 50 minutes. Trichloroacetyl chloride (37 g, 23 mL, 203.7 mmol) was added and the reaction mixture was left to stir for 18 hours. The reaction mixture was cooled to 0° C. and quenched by the addition of methanol (50 mL). The solvent was evaporated and the resultant residue treated with a mixture of potassium hydroxide (50 g) in methanol (150 mL) (caution—exotherm) and the reaction mixture then heated under reflux for 3 hours. The reaction mixture was allowed to cool to ambient temperature then evaporated. The resultant residue was treated with 2M hydrochloric acid to give an acidic mixture. The resulting mixture was extracted with ethyl acetate (×5), the combined organic layer dried (Na$_2$SO$_4$), filtered and evaporated then triturated with diethyl ether to afford the title compound as a buff solid (9.23 g, 74%). $^1$H NMR (400 MHz, DMSO-d$_6$): 12.55 (s, 1H), 8.22 (dd, J=2.8, 1.7 Hz, 1H), 7.95 (dd, J=9.5, 2.8 Hz, 1H), 3.83 (s, 3H), 2.68 (s, 3H).

Step 5: 1-Benzenesulfonyl-5-fluoro-2-methyl-1H-pyrrolo[2,3-b]pyridine-3-carboxylic acid methyl ester

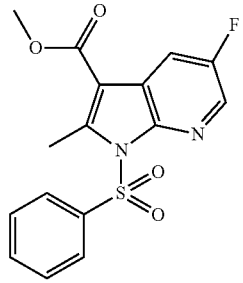 [SMILES: COC(=O)c1c(C)n(S(=O)(=O)c2ccccc2)c2ncc(F)cc12]

A cooled (0-5° C.) suspension of 5-fluoro-2-methyl-1H-pyrrolo[2,3-b]pyridine-3-carboxylic acid methyl ester (9.0 g, 43.2 mmol), powdered sodium hydroxide (5.4 g, 133.9 mmol) and benzyltriethylammonium chloride (0.2 g, 0.86 mmol) in dichloromethane (100 mL) was treated over ca. 5 minutes with benzenesulfonyl chloride (9.5 g, 6.9 mL, 54.0 mmol). The reaction mixture was allowed to stir at 0-5° C. for 20 minutes then allowed to warm to ambient temperature and stirred for 24 hours. The solid was removed by filtration through celite and the cake washed with dichloromethane. The filtrate was evaporated and the resultant residue triturated with diethyl ether to afford the title compound as a cream solid (14.0 g, 93%). $^1$H NMR (400 MHz, CDCl$_3$): 8.27 (dd, J=2.8, 1.1 Hz, 1H), 8.18-8.18 (m, 2H), 7.97 (dd, J=8.7, 2.8 Hz, 1H), 7.61-7.61 (m, 1H), 7.52-7.51 (m, 2H), 3.94 (s, 3H), 3.16 (s, 3H).

Step 6: 1-Benzenesulfonyl-5-fluoro-2-bromomethyl-1H-pyrrolo[2,3-b]pyridine-3-carboxylic acid methyl ester

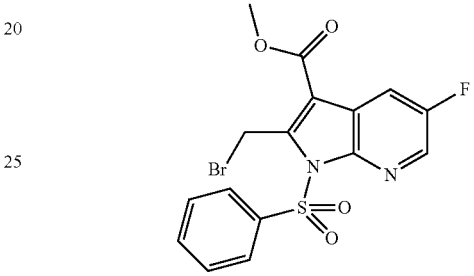

A mixture of 1-benzenesulfonyl-5-fluoro-2-methyl-1H-pyrrolo[2,3-b]pyridine-3-carboxylic acid methyl ester (13.9 g, 39.9 mmol), 1,3-dibromo-5,5-dimethylhydantoin (12.6 g, 39.9 mmol) and 1,1-azobis(cyclohexanecarbonitrile) (1.95 g, 8.0 mmol) in 1,2-dichloroethane (150 mL) was heated under reflux for 90 minutes then stirred at ambient temperature for 16 hours. The reaction mixture was washed with saturated aqueous sodium thiosulfate solution. The organic layer was dried (Na$_2$SO$_4$) then filtered. The filtrate was stirred with flash silica gel, filtered and the filtrate evaporated under reduced pressure. The resultant residue was triturated with diethyl ether/pentane (1:1) to afford the title compound as a cream solid (15.9 g, 93%). $^1$H NMR (400 MHz, CDCl$_3$): 8.47-8.44 (m, 2H), 8.32 (dd, J=2.8, 1.1 Hz, 1H), 8.04 (dd, J=8.5, 2.8 Hz, 1H), 7.64-7.64 (m, 1H), 7.54-7.53 (m, 2H), 5.68 (s, 2H), 4.00 (s, 3H).

Step 7: 1-Benzenesulfonyl-5-fluoro-2-{[cyanomethyl-(toluene-4-sulfonyl)amino]-methyl}-1H-pyrrolo[2,3-b]pyridine-3-carboxylic acid methyl ester

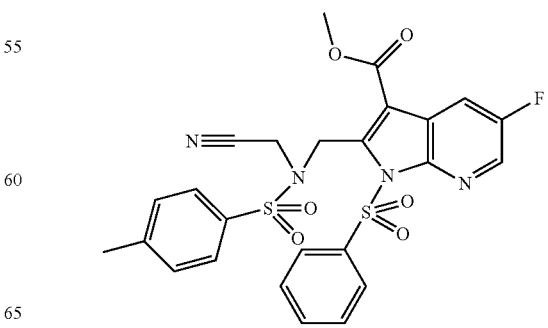

Sodium hydride (1.6 g, 60% dispersion in mineral oil, 40.5 mmol) was added portionwise to a cooled (0° C.) solution of 1-benzenesulfonyl-5-fluoro-2-bromomethyl-1H-pyrrolo[2,3-b]pyridine-3-carboxylic acid methyl ester (15.8 g, 36.9 mmol) and N-cyanomethyl-4-methyl-benzenesulfonamide (8.5 g, 40.5 mmol) in DMF (150 mL). The reaction mixture was stirred at 0° C. for 15 minutes, then allowed to warm to ambient temperature and stirred for 1 hour. The reaction mixture was poured into a cooled, stirred solution of 2M hydrochloric acid (400 mL). The resultant precipitate was collected by filtration (slow) and the cake washed with water, followed by methanol and then diethyl ether. The resulting cake was dried to afford the title compound as a grey solid (16.7 g, 82%). $^1$H NMR (400 MHz, DMSO-$d_6$): 8.49 (dd, J=2.8, 1.2 Hz, 1H), 8.24-8.24 (m, 2H), 8.14 (dd, J=8.8, 2.8 Hz, 1H), 7.75-7.74 (m, 1H), 7.70-7.68 (m, 2H), 7.62-7.62 (m, 2H), 7.39-7.35 (m, 2H), 5.36 (s, 2H), 4.42 (s, 2H), 3.88 (s, 3H), 2.36 (s, 3H).

Step 8: 9-Benzenesulfonyl-3-fluoro-5-hydroxy-9H-dipyrido[2,3-b;4',3'-d]pyrrole-6-carbonitrile

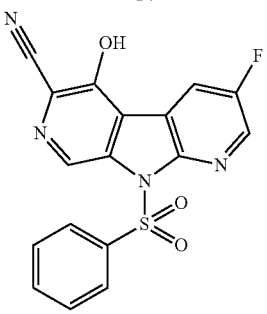

Lithium bis(trimethylsilyl)amide (100 mL of a 1N solution in THF, 100 mmol) was added dropwise to a cooled (−78° C.) suspension of 1-benzenesulfonyl-5-fluoro-2-{[cyanomethyl-(toluene-4-sulfonyl)amino]methyl}-1H-pyrrolo[2,3-b]pyridine-3-carboxylic acid methyl ester (16.5 g, 29.6 mmol) in dry THF (150 mL). The reaction mixture was allowed to slowly warm to −10° C. then slowly quenched into cold 1M hydrochloric acid. The layers were separated and the aqueous layer further extracted with THF. The combined organic layer was washed with brine, dried (Na$_2$SO$_4$), filtered and evaporated. The resultant residue was triturated with methanol then acetone and air dried to afford the title compound as a brown solid (8.2 g, 75%). $^1$H NMR (400 MHz, DMSO-$d_6$): 9.25 (s, 1H), 8.76 (dd, J=2.8, 1.3 Hz, 1H), 8.50 (dd, J=8.2, 2.8 Hz, 1H), 8.20-8.17 (m, 2H), 7.75-7.75 (m, 1H), 7.63-7.62 (m, 2H).

Preparation of 9-Benzenesulfonyl-5-chloro-3-fluoro-9H-dipyrido[2,3-b;4',3'-d]pyrrole-6-carbonitrile

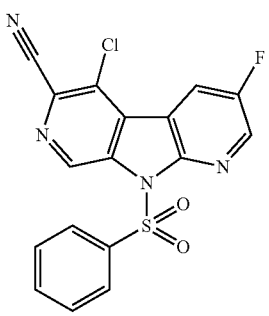 [SMILES: N#Cc1ncc2c(c1Cl)c1cc(F)cnc1n2S(=O)(=O)c1ccccc1]

A solution of 9-benzenesulfonyl-3-fluoro-5-hydroxy-9H-dipyrido[2,3-b;4',3'-d]pyrrole-6-carbonitrile (500 mg, 1.36 mmol) and phosphorus pentachloride (708 mg, 3.4 mmol) in chlorobenzene (1.5 mL) was heated at 110° C. for 1 hour. The reaction mixture was cooled to ambient temperature and then the solvent removed in-vacuo to afford a residue. The resultant residue was dissolved in dichloromethane (50 mL) and then the solution was diluted with ice/water (50 mL). The layers were separated and the aqueous layer further extracted with dichloromethane (50 mL). The combined organic layer was washed with brine, dried (Na$_2$SO$_4$), filtered and evaporated. The resultant residue was triturated with diethyl ether and dried to afford the title compound as a tan solid (320 mg, 65%). $^1$H NMR (400 MHz, CDCl$_3$): 9.81 (s, 1H), 8.69 (d, J=2.8 Hz, 1H), 8.50 (dd, J=7.6, 2.8 Hz, 1H), 8.24 (d, J=8.0 Hz, 2H), 7.65 (t, J=7.5 Hz, 1H), 7.53 (t, J=7.8 Hz, 2H).

Preparation of 9-Benzenesulfonyl-3-chloro-5-hydroxy-9H-dipyrido[2,3-b;4',3'-d]pyrrole-6-carbonitrile

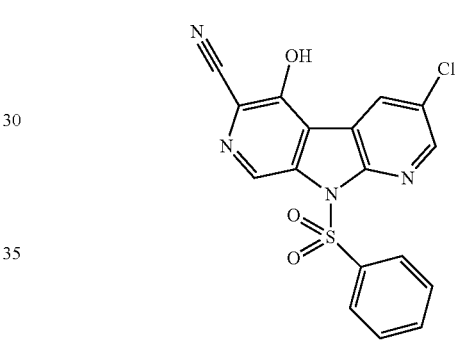

Step 1: 5-Chloro-3-iodo-pyridin-2-ylamine

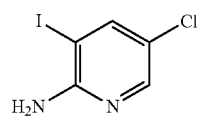

A stirred solution of 5-chloro-pyridin-2-ylamine (51.4 g, 0.40 mol) in 2M sulfuric acid (700 mL) was treated portionwise with potassium iodate (43.7 g, 0.2 mol) and the mixture heated to 100° C. A solution of potassium iodide (36.5 g, 0.55 mol) in water (100 mL) was added dropwise over ca. 1 hour. The mixture was allowed to stir for a further 30 minutes then cooled to ambient temperature. The pH of the aqueous phase was adjusted to 8-9 and the mixture extracted with ethyl acetate (×3). The combined organic layer was washed with aqueous sodium thiosulfate solution, water and brine, dried (Na$_2$SO$_4$), filtered and evaporated to afford the title compound as a tan solid (86.3 g, 84%). LCMS (Method B): R$_T$=3.76 min, M+H$^+$=255/257. $^1$H NMR (400 MHz, CDCl$_3$): 7.98 (d, J=2.3 Hz, 1H), 7.84 (d, J=2.3 Hz, 1H), 5.03 (s, 2H).

Step 2: 5-Chloro-3-prop-1-ynyl-pyridin-2-ylamine

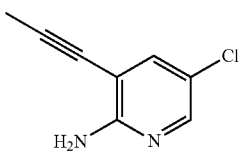

Propyne (35 g, 0.87 mol) was condensed into a pre-weighed flask cooled to ca. −40° C. containing THF (100 mL). The solution was added via cannula to a cooled (0-5° C.), degassed mixture of 5-chloro-3-iodo-pyridin-2-ylamine (81.4 g, 0.32 mol), bis(triphenylphosphine)dichloropalladium(0) (4.49 g, 6.4 mmol), copper (I) iodide (1.46 g, 7.67 mmol) and triethylamine (97.3 g, 134 mL, 0.98 mol) in THF (900 mL). The mixture was stirred at 0-5° C. for 30 minutes then for a further 30 minutes at ambient temperature. The solid was removed by filtration and the cake washed with THF. The filtrate was diluted with ethyl acetate and extracted with 2M hydrochloric acid (×3). The combined acid extract was washed with diethyl ether and then made basic by careful addition of potassium carbonate then extracted with diethyl ether (×3). The combined organic layer was dried ($Na_2SO_4$), filtered and evaporated to afford the title compound as a brown solid (53.8 g, quantitative yield). LCMS (Method B): $R_T$=3.55 min, M+H⁺=167/169. ¹H NMR (300 MHz, $CDCl_3$): 7.92 (d, J=2.5 Hz, 1H), 7.42 (d, J=2.5 Hz, 1H), 5.00 (s, 2H), 2.10 (s, 3H).

Step 3: 5-Chloro-2-methyl-1H-pyrrolo[2,3-b]pyridine

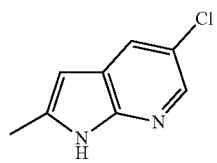

5-Chloro-3-prop-1-ynyl-pyridin-2-ylamine (53.7 g, 0.32 mol) was treated with a 1M solution of potassium tert-butoxide in tert-butanol (515 mL) and the reaction mixture was heated at 85° C. for 1 hour. The mixture was then allowed to cool to ambient temperature and poured onto a 1:1 mixture of water/ice (ca. 1 L). The resultant precipitate was collected by filtration, washed with water and left to air dry. The resultant solid was dissolved in dichloromethane, dried ($Na_2SO_4$), filtered and evaporated then triturated with diethyl ether to afford the title compound as a grey solid (44.8 g, 83%). LCMS (Method B): $R_T$=3.64 min, M+H⁺=167/169. ¹H NMR (400 MHz, DMSO-$d_6$): 8.02 (d, J=2.4 Hz, 1H), 7.83 (d, J=2.4 Hz, 1H), 6.11 (d, J=1.1 Hz, 1H), 2.40 (d, J=1.0 Hz, 3H).

Step 4: 5-Chloro-2-methyl-1H-pyrrolo[2,3-b]pyridine-3-carboxylic acid methyl ester

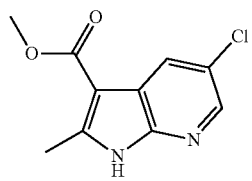

Aluminium trichloride (125 g, 0.94 mol) was added to a mixture of 5-chloro-2-methyl-1H-pyrrolo[2,3-b]pyridine (44.8 g, 0.27 mol) in dichloromethane (1.1 L) and stirred for 50 minutes. Trichloroacetyl chloride (166.2 g, 102 mL, 0.91 mol) was added and the reaction mixture was left to stir for 21 hours. The reaction mixture was cooled to 0° C. and quenched by the addition of methanol (110 mL). The solvent was evaporated and the resultant residue treated with a mixture of potassium hydroxide (226 g) in methanol (900 mL) (caution—exotherm) and the reaction mixture then heated under reflux for 3 hours. The reaction mixture was allowed to cool to ambient temperature then evaporated. The resultant residue was treated with 2M hydrochloric acid to give an acidic mixture. The resulting mixture was extracted with ethyl acetate (×5), the combined organic layer dried ($Na_2SO_4$), filtered and evaporated then triturated with diethyl ether to afford the title compound as a tan solid (57.1 g, 94%). LCMS (Method B): $R_T$=4.15 min, M+H⁺=225. ¹H NMR (400 MHz, DMSO-$d_6$): 8.32 (d, J=0.7 Hz, 1H), 8.23 (d, J=2.4 Hz, 1H), 8.17 (d, J=2.2 Hz, 1H), 3.83 (s, 3H), 2.68 (s, 3H).

Step 5: 1-Benzenesulfonyl-5-chloro-2-methyl-1H-pyrrolo[2,3-b]pyridine-3-carboxylic acid methyl ester

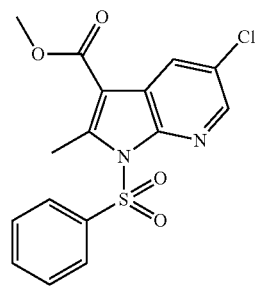 [SMILES: COC(=O)c1c(C)n(S(=O)(=O)c2ccccc2)c2ncc(Cl)cc12]

A cooled (0-5° C.) suspension of 5-chloro-2-methyl-1H-pyrrolo[2,3-b]pyridine-3-carboxylic acid methyl ester (57 g, 0.25 mol), powdered sodium hydroxide (30.45 g, 0.76 mol) and benzyltriethylammonium chloride (1.16 g, 5.1 mmol) in dichloromethane (800 mL) was treated over ca. 5 minutes with benzenesulfonyl chloride (56.1 g, 40.5 mL, 0.32 mol). The reaction mixture was allowed to stir at 0-5° C. for 15 minutes then allowed to warm to ambient temperature and stirred for 24 hours. The solid was removed by filtration through celite and the cake washed with dichloromethane. The filtrate was evaporated and the resultant residue triturated with diethyl ether to afford the title compound as a brown solid (17.5 g, 30%). LCMS (Method B): $R_T$=4.67 min, M+Na⁺=381. ¹H NMR (400 MHz, $CDCl_3$): 8.34 (d, J=2.4 Hz, 1H), 8.25 (d, J=2.4 Hz, 1H), 8.18-8.18 (m, 2H), 7.61-7.61 (m, 1H), 7.51-7.50 (m, 2H), 3.94 (s, 3H), 3.15 (s, 3H).

Step 6: 1-Benzenesulfonyl-5-chloro-2-bromomethyl-1H-pyrrolo[2,3-b]pyridine-3-carboxylic acid methyl ester

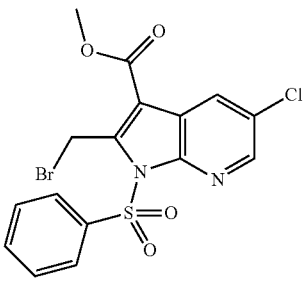 [SMILES: COC(=O)c1c(CBr)n(S(=O)(=O)c2ccccc2)c2ncc(Cl)cc12]

A mixture of 1-benzenesulfonyl-5-chloro-2-methyl-1H-pyrrolo[2,3-b]pyridine-3-carboxylic acid methyl ester (16.9 g, 46.2 mmol), 1,3-dibromo-5,5-dimethylhydantoin (13.21 g, 46.2 mmol) and 1,1-azobis(cyclohexanecarbonitrile) (1.52 g, 9.3 mmol) in 1,2-dichloroethane (200 mL) was heated under reflux for 90 minutes then stirred at ambient temperature for 16 hours. The reaction mixture was washed with saturated aqueous sodium thiosulfate solution. The organic layer was dried ($Na_2SO_4$) then filtered. The filtrate was stirred with flash silica gel, filtered and the filtrate evaporated under reduced pressure. The resultant residue was triturated with diethyl ether/pentane (1:1) to afford the title compound as white solid (13.7 g, 61%). LCMS (Method B): $R_T$=4.35 min, M+H$^+$=443/445/447. $^1$H NMR (400 MHz, CDCl$_3$): 8.46-8.46 (m, 2H), 8.39 (d, J=2.4 Hz, 1H), 8.32 (d, J=2.4 Hz, 1H), 7.64-7.64 (m, 1H), 7.55-7.52 (m, 2H), 5.67 (s, 2H), 4.00 (s, 3H).

Step 7: 1-Benzenesulfonyl-5-chloro-2-{[cyanomethyl-(toluene-4-sulfonyl)amino]-methyl}-1H-pyrrolo[2,3-b]pyridine-3-carboxylic acid methyl ester

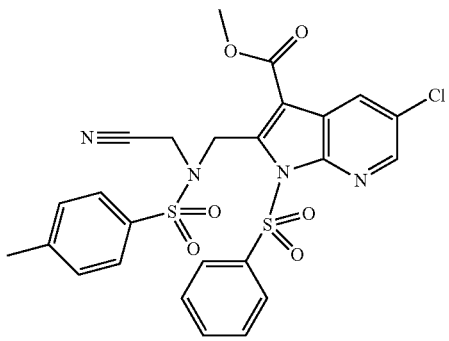 [SMILES: COC(=O)c1c(CN(CC#N)S(=O)(=O)c2ccc(C)cc2)n(S(=O)(=O)c2ccccc2)c2ncc(Cl)cc12]

Sodium hydride (4.1 g, 60% dispersion in mineral oil, 101 mmol) was added portionwise to a cooled (0° C.) solution of 1-benzenesulfonyl-5-chloro-2-bromomethyl-1H-pyrrolo[2,3-b]pyridine-3-carboxylic acid methyl ester (40.8 g, 91.9 mmol) and N-cyanomethyl-4-methyl-benzenesulfonamide (21.3 g, 101 mmol) in DMF (400 mL). The reaction mixture was stirred at 0° C. for 15 minutes, then allowed to warm to ambient temperature and stirred for 1 hour. The reaction mixture was poured into a cooled, stirred solution of 2M hydrochloric acid (400 mL). The resultant precipitate was collected by filtration (slow) and the cake washed with water, followed by methanol and then diethyl ether. The resulting cake was dried to afford the title compound as a tan solid (39.6 g, 75%). LCMS (Method B: $R_T$=4.58 min, M+H$^+$=573/575. $^1$H NMR (400 MHz, CDCl$_3$): 8.40 (d, J=2.4 Hz, 1H), 8.33-8.33 (m, 2H), 8.27 (d, J=2.4 Hz, 1H), 7.78 (d, J=8.2 Hz, 2H), 7.64-7.64 (m, 1H), 7.55-7.54 (m, 2H), 7.34 (d, J=8.1 Hz, 2H), 5.43 (s, 2H), 4.28 (s, 2H), 3.96 (s, 3H), 2.43 (s, 3H).

Step 8: 9-Benzenesulfonyl-3-chloro-5-hydroxy-9H-dipyrido[2,3-b;4',3'-d]pyrrole-6-carbonitrile

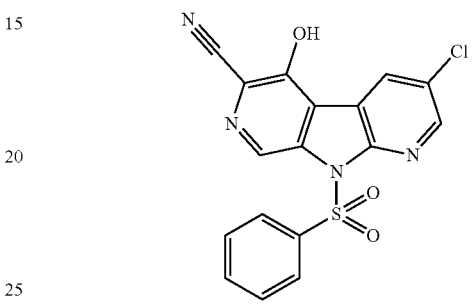

Lithium bis(trimethylsilyl)amide (220 mL of a 1N solution in THF, 220 mmol) was added dropwise to a cooled (−78° C.) suspension of 1-benzenesulfonyl-5-chloro-2-{[cyanomethyl-(toluene-4-sulfonyl)amino]methyl}-1H-pyrrolo[2,3-b]pyridine-3-carboxylic acid methyl ester (39.6 g, 69.1 mmol) in dry THF (350 mL). The reaction mixture was allowed to slowly warm to −10° C. then slowly quenched into cold 1M hydrochloric acid. The layers were separated and the aqueous layer further extracted with THF. The combined organic layer was washed with brine, dried ($Na_2SO_4$), filtered and evaporated. The resultant residue was triturated with methanol then acetone and air dried to afford the title compound as a tan solid (7.37 g, 27%). LCMS (Method B): $R_T$=5.11 min, M+H$^+$=385/387. $^1$H NMR (400 MHz, DMSO-d$_6$): 9.23 (s, 1H), 8.76 (d, J=2.4 Hz, 1H), 8.69 (d, J=2.4 Hz, 1H), 8.19-8.19 (m, 2H), 7.75-7.75 (m, 1H), 7.62-7.61 (m, 2H).

Preparation of 9-Benzenesulfonyl-3,5-dichloro-9H-dipyrido[2,3-b;4',3'-d]pyrrole-6-carbonitrile

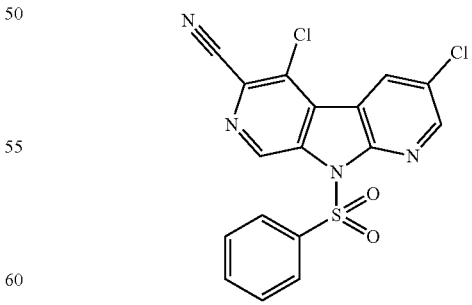

A solution of 9-benzenesulfonyl-3-chloro-5-hydroxy-9H-dipyrido[2,3-b;4',3'-d]pyrrole-6-carbonitrile (1.9 g, 4.94 mmol) and phosphorus pentachloride (3.1 g, 14.8 mmol) in phosphorus oxychloride (8 mL) was heated at 105° C. for 2 hours. The reaction mixture was cooled to ambient temperature and then the solvent removed in-vacuo to afford a residue. The resultant residue was dissolved in dichloromethane (300 mL) and then the solution was diluted with ice/water (300 mL). The layers were separated and the aqueous layer further extracted with dichloromethane. The combined organic layer was washed with brine, dried (Na₂SO₄), filtered and evaporated. The resultant residue was triturated with diethyl ether and dried to afford the title compound as a tan solid (1.17 g, 59%). ¹H NMR (400 MHz, CDCl₃): 9.81 (s, 1H), 8.77 (d, J=2.4 Hz, 1H), 8.75 (d, J=2.4 Hz, 1H), 8.26-8.22 (m, 2H), 7.66-7.66 (m, 1H), 7.53-7.53 (m, 2H).

Preparation of 5-Fluoro-9-(2-trimethylsilanylethoxymethyl)-9H-dipyrido[2,3-b;4'3'-d]pyrrole-6-carbonitrile

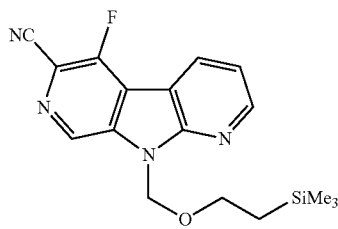 [SMILES: C[Si](C)(C)CCOCn1c2cnc(C#N)c(F)c2c2cccnc21]

Step 1: (6-Chloro-5-fluoropyridin-3-yl)-carbamic acid tert-butyl ester

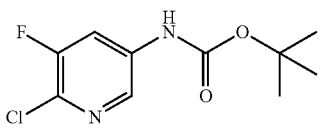 [SMILES: CC(C)(C)OC(=O)Nc1cnc(Cl)c(F)c1]

A degassed mixture of 5-bromo-2-chloro-3-fluoropyridine (22.5 g, 107 mmol), tert-butyl carbamate (13.8 g, 117.5 mmol), tris(dibenzylideneacetone) dipalladium(0) (2.95 g, 3.2 mmol), XantPhos (2.48 g, 4.28 mmol) and cesium carbonate (69.7 g, 214 mmol) in dioxane (340 mL) was heated at 85° C. for 24 hours. The reaction mixture was cooled to ambient temperature and the resultant solid was removed by filtration. The resultant solid was washed with ethyl acetate followed by dichloromethane and the filtrate was combined and concentrated in-vacuo to afford a residue that was purified by flash chromatography (silica: cyclohexane to 25% ethyl acetate/cyclohexane) to afford the title compound as a pale yellow solid (22.6 g, 86%). ¹H NMR (300 MHz, CDCl₃): 8.04 (dd, J=10.1, 2.4 Hz, 1H), 7.98 (d, J=2.4 Hz, 1H), 6.62 (s, 1H), 1.53 (s, 9H).

Step 2: (6-Chloro-5-fluoro-4-iodopyridin-3-yl)-carbamic acid tert-butyl ester

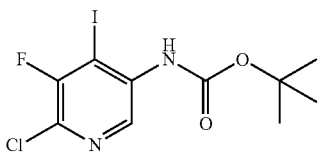 [SMILES: CC(C)(C)OC(=O)Nc1cnc(Cl)c(F)c1I]

nBuLi (107 mL, 2.5 M in hexanes, 268 mmol) was added dropwise to a cooled (−78° C.) solution of (6-chloro-5-fluoro-pyridin-3-yl)-carbamic acid tert-butyl ester (22 g, 89.2 mmol) and N,N,N',N'-tetramethylethylenediamine (40.5 mL, 268 mmol) in anhydrous diethyl ether (400 mL) under an argon atmosphere, ensuring that the internal temperature of the reaction was maintained below −60° C. On complete addition, the reaction mixture was allowed to warm to −20° C. and stirred for 90 minutes. The reaction mixture was cooled to −78° C. and a solution of iodine (70 g, 280 mmol) in THF (125 mL) was added dropwise over 15 minutes. The reaction mixture was allowed to gradually warm to ambient temperature and stirred overnight. The reaction mixture was poured onto 1M HCl (200 mL) and crushed ice (50 g) and the aqueous phase was extracted with ethyl ether (2×200 mL). The combined organic layer was washed with water (200 mL), aqueous potassium carbonate solution (150 mL), aqueous sodium thiosulfate solution (150 mL), and brine (150 mL), dried (Na₂SO₄), filtered and concentrated in-vacuo to afford a residue. The resultant residue was triturated with ethanol and the resultant solid was collected by filtration, washed with pentane and dried in-vacuo to afford the title compound as a white solid (27.2 g, 82%). The trituration liquors were concentrated and purified by flash chromatography (silica: toluene to 5% ethyl acetate/toluene) to afford an additional batch of the title compound as a white solid (4.0 g, 12%). Total yield=31.2 g, 94%. ¹H NMR (400 MHz, CDCl₃): 8.82 (s, 1H), 6.71 (s, 1H), 1.55 (s, 9H).

Step 3: 6-Chloro-5-fluoro-4-iodopyridin-3-ylamine

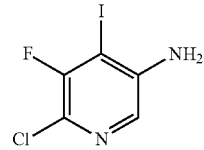

Trifluoroacetic acid (50 mL) was added to a solution of (6-chloro-5-fluoro-4-iodo-pyridin-3-yl)-carbamic acid tert-butyl ester (31 g, 83.2 mmol) in dichloromethane (150 mL) and the resultant reaction mixture was stirred at ambient temperature for 90 minutes. The solvent was evaporated and the resultant residue was treated with ice/water (200 mL), layered with diethyl ether (300 mL) and the pH of the aqueous phase was adjusted to 10 by the addition of solid potassium carbonate solution. The organic phase was separated, dried (Na₂SO₄), filtered and concentrated in-vacuo to afford a residue. The resultant residue was triturated with pentane:diethyl ether (9:1) to afford the title compound as a cream coloured solid (22.3 g, 98%). ¹H NMR (400 MHz, CDCl₃): 7.63 (s, 1H).

Step 4: 6'-Chloro-2,5'-difluoro-[3,4']bipyridinyl-3'-ylamine

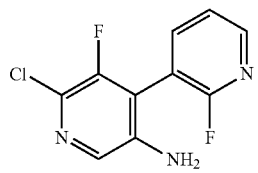 [SMILES: Nc1cnc(Cl)c(F)c1-c1cccnc1F]

A degassed mixture of 6-chloro-5-fluoro-4-iodopyridin-3-ylamine (98.7 g, 362 mmol), 2-fluoropyridine 3-boronic acid (68.3 g, 485 mmol), bis[di-tert-butyl(4-dimethylaminophenyl)phosphine]dichloropalladium(II) (7.7 g, 10.9 mmol) and potassium fluoride (63 g, 1.09 mol) in a mixture of acetonitrile (900 mL) and water (275 mL) was heated at 90° C. for 2 hours. The reaction mixture was allowed to cool to ambient temperature and filtered through Celite© and washed through with ethyl acetate. The filtrate was diluted with ethyl acetate and the organic layer collected, dried (Na$_2$SO$_4$), filtered and concentrated in-vacuo to afford a residue. The resultant residue was triturated with diethyl ether to afford the title compound as a grey solid (65.8 g, 75%). The trituration liquors were concentrated and purified by flash chromatography (silica: dichloromethane to 20% ethyl acetate/dichloromethane) to afford, after trituration with ether, an additional batch of the title compound as a grey solid (9.7 g, 11%). Total yield=75.5 g, 86%. $^1$H NMR (400 MHz, CDCl$_3$): 8.39 (ddd, J=4.9, 2.0, 1.1 Hz, 1H), 7.86-7.84 (m, 2H), 7.39 (ddd, J=7.4, 4.9, 1.9 Hz, 1H).

Step 5: 6-Chloro-5-fluoro-9H-dipyrido[2,3-b;4'3'-d]pyrrole

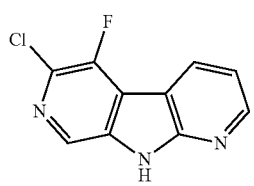 [SMILES: Fc1c(Cl)ncc2[nH]c3ncccc3c12]

A solution of 6'-chloro-2,5'-difluoro-[3,4']bipyridinyl-3'-ylamine (70 g, 290 mmol) in THF (300 mL) was added dropwise to a solution of sodium bis(trimethylsilyl)amide (720 mL, 1M in THF, 720 mmol) at such a rate that the reaction temperature was maintained at 40° C. When the addition was complete the mixture was stirred for ca. 1 hour at ambient temperature. The bulk of the solvent was evaporated in-vacuo and the residue poured into ice-cold 1N hydrochloric acid. The resulting slurry was filtered and the solid washed with water. The filter cake was collected and triturated with acetone followed by diethyl ether to afford the title compound as a beige solid (40.9 g, 64%). The trituration liquors were evaporated and the residue triturated with methanol followed by diethyl ether to afford a second crop of title compound as a brown solid (6.1 g, 10%). Total yield=47 g, 74%. $^1$H NMR (400 MHz, DMSO-d$_6$): 13.24 (s, 1H), 8.91 (d, J=2.5 Hz, 1H), 8.77 (dd, J=4.8, 1.7 Hz, 1H), 8.65 (dd, J=7.9, 1.7 Hz, 1H), 7.50 (dd, J=7.9, 4.8 Hz, 1H).

Step 6: 6-Chloro-5-fluoro-9-(2-trimethylsilanylethoxymethyl)-9H-dipyrido[2,3-b;4'3'-d]pyrrole

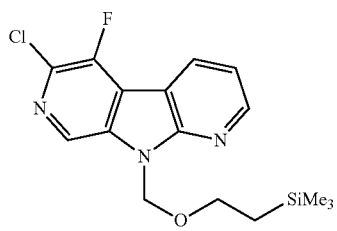 [SMILES: C[Si](C)(C)CCOCn1c2cnc(Cl)c(F)c2c2cccnc21]

A suspension of 6-chloro-5-fluoro-9H-dipyrido[2,3-b;4'3'-d]pyrrole (9 g, 40.6 mmol) in DMF (90 mL) was placed in a cold water bath and treated portionwise with sodium hydride (60% suspension in mineral oil) (1.94 g, 48.5 mmol) keeping the internal temperature at 20-25° C. When gas evolution ceased (ca. 1 hour) the mixture was treated dropwise with 2-(trimethylsilyl)ethoxymethyl chloride (8.1 g, 8.7 mL, 48.5 mmol) keeping the internal temperature at 25-30° C. After stirring for a further 1 hour the mixture was partitioned between ethyl acetate and ice-cold 1N hydrochloric acid. The aqueous phase was further extracted with ethyl acetate and the combined organic phase was washed with water, aqueous potassium carbonate solution, water, and brine, dried (Na$_2$SO$_4$), filtered and evaporated in-vacuo. The residue was triturated with pentane:diethyl ether (ca. 20:1) to afford the title compound as a beige solid (11.4 g, 80%). The trituration liquors were evaporated and purified by chromatography to afford a second crop of title compound (0.85 g, 6%). Total yield=12.3 g, 86%. $^1$H NMR (400 MHz, CDCl$_3$): 8.68-8.68 (m, 2H), 8.52 (dd, J=7.8, 1.7 Hz, 1H), 7.35 (dd, J=7.8, 4.8 Hz, 1H), 5.95 (s, 2H), 3.59 (t, J=8.2 Hz, 2H), 0.92 (t, J=8.2 Hz, 2H), −0.09 (d, J=0.5 Hz, 9H).

Step 7: 5-Fluoro-9-(2-trimethylsilanylethoxymethyl)-9H-dipyrido[2,3-b;4'3'-d]pyrrole-6-carbonitrile

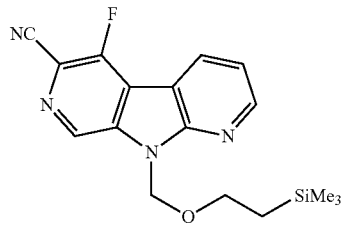 [SMILES: C[Si](C)(C)CCOCn1c2cnc(C#N)c(F)c2c2cccnc21]

A solution of 6-chloro-5-fluoro-9-(2-trimethylsilanylethoxymethyl)-9H-dipyrido[2,3-b;4'3'-d]pyrrole (12.2 g, 34.7 mmol) in DMF (120 mL) was treated with zinc cyanide (4.88 g, 41.7 mmol) and tetrakis(triphenylphosphine)palladium(0) (6 g, 5.2 mmol). The mixture was degassed and stirred under a nitrogen atmosphere at 130° C. for 3 hours. After cooling to ambient temperature the mixture was filtered through Celite© and the filter cake washed with DMF (10 mL). The filtrate was partitioned between ethyl acetate and water and the aqueous phase further extracted with ethyl acetate. The combined organic layer was washed with water (×2) and brine, dried (Na$_2$SO$_4$), filtered and evaporated. The resultant residue was dissolved in dichloromethane, stirred with flash silica gel, filtered to remove the solid and the solid washed well with dichloromethane. The filtrate was evaporated and the resultant residue triturated with pentane:diethyl ether (ca. 4:1) to afford the title compound as a white solid (8.15 g, 68%). The trituration liquors were evaporated and the resultant residue purified by flash chromatography to afford a second crop of title compound (0.92 g, 8%). Total yield=9.07 g, 76%. $^1$H NMR (400 MHz, CDCl$_3$): 8.99 (d, J=2.1 Hz, 1H), 8.75 (dd, J=4.8, 1.7 Hz, 1H), 8.57 (dd, J=7.9, 1.7 Hz, 1H), 7.44 (dd, J=7.9, 4.8 Hz, 1H), 6.02 (s, 2H), 3.63-3.56 (m, 2H), 0.93 (t, J=8.2 Hz, 2H), −0.08 (d, J=0.6 Hz, 9H).

Preparation of 1-Oxetan-3-yl-piperidin-4-ylamine

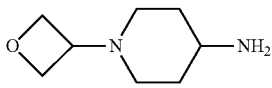

Step 1: (1-Oxetan-3-yl-piperidin-4-yl)-carbamic acid tert-butyl ester

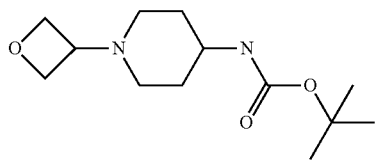 [SMILES: CC(C)(C)OC(=O)NC1CCN(C2COC2)CC1]

To a suspension of piperidin-4-yl-carbamic acid tert-butyl ester (200 mg, 1.0 mmol) in DCE (6 mL) was added oxetanone (60 mg, 0.83 mmol) in DCE (2 mL). After 75 min, sodium triacetoxyborohydride (282 mg, 1.33 mmol) was added in one portion. After 20 hours at ambient temperature, the reaction mixture was loaded directly onto a 5 g SCX-2 cartridge which was washed with methanol, then 2N ammonia in methanol. Concentration of the combined basic fractions in-vacuo followed by flash chromatography of the resultant residue (silica, 5 g column, Si-SPE, 0-10% methanol in dichloromethane) afforded the title compound as a white solid (141 mg, 67%). $^1$H NMR (300 MHz, CDCl$_3$): 4.62-4.61 (m, 4H), 4.44 (s, 1H), 3.46-3.45 (m, 2H), 2.67 (d, J=10.9 Hz, 2H), 2.02-1.88 (m, 4H), 1.44 (s, 9H).

Step 2: 1-Oxetan-3-yl-piperidin-4-ylamine

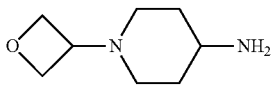 [SMILES: NC1CCN(C2COC2)CC1]

To a solution of (1-oxetan-3-yl-piperidin-4-yl)-carbamic acid tert-butyl ester (134 mg, 0.52 mmol) in dichloromethane (2 mL) was added TFA (2 mL). After 15 minutes at ambient temperature the reaction mixture was concentrated in-vacuo and the residue loaded onto a 5 g SCX-2 cartridge which was washed with methanol, then 2N ammonia in methanol. Concentration of the combined basic fractions in-vacuo afforded the title compound as a colourless gum (82 mg, 100%). $^1$H NMR (400 MHz, CDCl$_3$): 4.63-4.63 (m, 4H), 3.47-3.45 (m, 1H), 2.69-2.68 (m, 3H), 1.90-1.81 (m, 4H), 1.41-1.40 (m, 2H).

Preparation of 1-Oxetan-3-yl-piperidin-4-ol

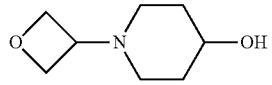 [SMILES: OC1CCN(C2COC2)CC1]

To a suspension of piperidin-4-ol (364 mg, 3.6 mmol) in DCE (30 mL) was added oxetanone (216 mg, 3.0 mmol). After 2 hours, sodium triacetoxyborohydride (1.02 g, 4.8 mmol) was added in one portion. After 20 hours at ambient temperature, the reaction mixture was loaded directly onto a 20 g SCX-2 cartridge which was washed with methanol, then 2N ammonia in methanol. Concentration of the combined basic fractions in-vacuo followed by flash chromatography of the resultant residue (silica, 10 g column, Si-SPE, 0-10% methanol in dichloromethane) afforded the title compound as a colourless oil (285 mg, 52%). $^1$H NMR (300 MHz, CDCl$_3$): 4.64-4.63 (m, 4H), 3.77-3.77 (m, 1H), 3.49-3.47 (m, 1H), 2.65-2.55 (m, 2H), 2.04 (t, J=10.5 Hz, 2H), 1.94-1.93 (m, 2H), 1.62-1.61 (m, 2H), 1.47 (d, J=4.5 Hz, 1H).

Preparation of 4-Methyl-[1,4']bipiperidinyl-4-ol

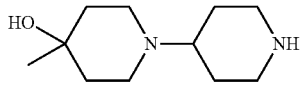

To a suspension of piperidin-4-yl-carbamic acid tert-butyl ester (723 mg, 3.6 mmol) in DCE (20 mL) was added 4-methylpiperidin-4-ol (500 mg, 4.4 mmol). After 30 minutes, sodium triacetoxyborohydride (1.54 g, 7.3 mmol) was added portionwise. After 20 hours at ambient temperature, the reaction mixture was partitioned between saturated aqueous sodium hydrogen carbonate solution (50 mL) and dichloromethane (75 mL). The organic phase was separated, dried (Na$_2$SO$_4$), filtered and evaporated in-vacuo. The resultant residue was purified by flash chromatography (silica, Biotage 100 g column, 0-10% methanol in dichloromethane) to afford crude 4-hydroxy-4-methyl-[1,4']bipiperidinyl-1'-carboxylic acid tert-butyl ester. This crude material was dissolved in dichloromethane (10 mL) and TFA (2 mL) added. After 30 minutes at ambient temperature, the reaction mixture was concentrated in-vacuo and the resultant residue loaded onto a 20 g SCX-2 cartridge which was washed with methanol, then 2N ammonia in methanol. Concentration of the combined basic fractions in-vacuo afforded the title compound as a colourless oil (285 mg, 40% over two steps). $^1$H NMR (300 MHz, CDCl$_3$): 3.15 (d, J=12.3 Hz, 2H), 2.62-2.60 (m, 6H), 2.42-2.39 (m, 1H), 1.84 (d, J=12.6 Hz, 2H), 1.67-1.64 (m, 5H), 1.46-1.44 (m, 2H), 1.24 (s, 3H).

Preparation of (1-Ethyl-piperidin-4-yl)-methylamine

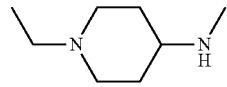

Step 1: (1-Ethylpiperidin-4-yl)-methylcarbamic acid tert-butyl ester

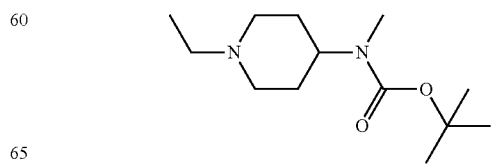

To a solution of methylpiperidin-4-yl-carbamic acid tert-butyl ester (2.0 g, 9.4 mmol) in dichloromethane (50 mL) was added acetaldehyde (1.65 mL, 27.9 mmol). The resultant dark red solution was stirred for 10 minutes, then sodium triacetoxyborohydride (2.97 g, 14.0 mmol) was added portionwise. After 20 hours at ambient temperature, the reaction mixture was partitioned between saturated aqueous sodium hydrogen carbonate solution (100 mL) and dichloromethane (100 mL). The organic layer was separated and the aqueous layer extracted with dichloromethane (3×100 mL). The combined organic layer was (Na$_2$SO$_4$), filtered and concentrated in-vacuo. The resultant residue was purified by flash chromatography (silica, 70 g column, Si-SPE, ethyl acetate followed by 10% methanol in dichloromethane) to afford the title compound as an orange oil (1.64 g, 72%). $^1$H NMR (300 MHz, CDCl$_3$): 3.01 (d, J=11.3 Hz, 2H), 2.74 (s, 3H), 2.41 (q, J=7.2 Hz, 2H), 1.98 (t, J=11.6 Hz, 2H), 1.76-1.72 (m, 5H), 1.46 (s, 9H), 1.08 (t, J=7.2 Hz, 3H).

Step 2: (1-Ethyl-piperidin-4-yl)-methylamine

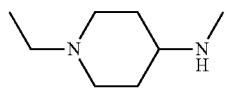

To a solution of (1-ethylpiperidin-4-yl)-methylcarbamic acid tert-butyl ester (1.65 g, 6.8 mmol) in dichloromethane (15 mL) was added TFA (5 mL). After 1 hour at ambient temperature the reaction mixture was concentrated in-vacuo and the residue loaded onto a 70 g SCX-2 cartridge which was washed with methanol, then 2N ammonia in methanol. Concentration of the combined basic fractions in-vacuo afforded the title compound as an orange oil (900 mg, 94%). $^1$H NMR (300 MHz, CD$_3$OD): 2.95 (d, J=11.6 Hz, 2H), 2.48-2.36 (m, 3H), 2.35 (s, 3H), 1.96-1.95 (m, 4H), 1.40-1.38 (m, 2H), 1.09 (t, J=7.2 Hz, 3H).

Preparation of 4-Chloro-9-(2-trimethylsilanyl-ethoxymethyl)-9H-dipyrido[2,3-b;4',3'-d]pyrrole-6-carbonitrile

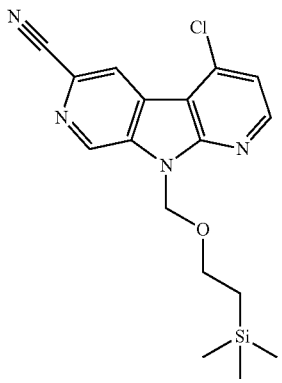 [SMILES: C[Si](C)(C)CCOCn1c2cnc(C#N)cc2c2c(Cl)ccnc21]

Step 1: 9-(2-trimethylsilanyl-ethoxymethyl)-9H-dipyrido[2,3-b;4',3'-d]pyrrole-6-carbonitrile

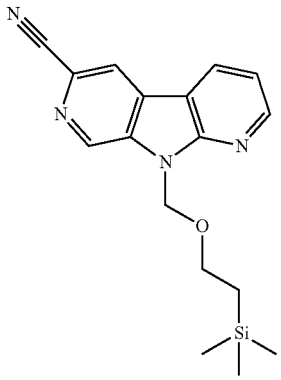 [SMILES: C[Si](C)(C)CCOCn1c2cnc(C#N)cc2c2cccnc21]

A mixture of 3-bromo-9-(2-trimethylsilanyl-ethoxymethyl)-9H-dipyrido[2,3-b;4',3'-d]pyrrole-6-carbonitrile (5.6 g, 14 mmol), ammonium formate (8.8 g, 139 mmol), and zinc (9.1 g, 139 mmol) in tetrahydrofuran (85 mL) was heated at 75° C. for 10 hours. The reaction was allowed to cool, filtered over a pad of Celite, and washed with methylene chloride (200 mL). The filtrate was concentrated in vacuo and then purified by flash chromatography (silica, 120 g, ISCO, 5-45% ethyl acetate in heptane) to afford the title compound as a white solid (3.6 g, 80%). $^1$H NMR (400 MHz, CDCl$_3$) δ 9.17 (s, 1H), 8.73 (dd, J=4.8, 1.5, 1H), 8.46 (dd, J=7.8, 1.5, 1 H), 8.39 (s, 1H), 7.39 (dd, J=7.8, 4.8, 1H), 6.01 (s, 2H), 3.60 (t, J=8.0, 2H), 0.93 (t, J=8.0, 2H), −0.09 (s, 9H).

Step 2: 9-(2-trimethylsilanyl-ethoxymethyl)-9H-dipyrido[2,3-b;4',3'-d]pyrrole-6-carbonitrile-1,7-dioxide

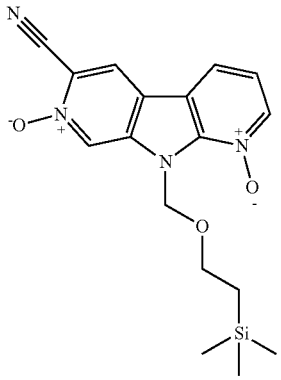

To a suspension of hydrogen peroxide-urea adduct (5.9 g, 62.2 mmol) in chloroform (40 mL) was added trifluoroacetic anhydride (8.7 mL, 61.6 mmol) dropwise over 10 minutes. The reaction mixture was stirred at ambient temperature for 5 minutes and then to this was added 9-(2-trimethylsilanyl-ethoxymethyl)-9H-dipyrido[2,3-b;4',3'-d]pyrrole-6-carbonitrile (2.0 g, 6.0 mmol) as a solution in chloroform (30 mL). Note: an exotherm is observed upon addition of the substrate. The reaction mixture was stirred at ambient temperature for 10 minutes and then at 50° C. for 30 minutes. The reaction mixture was cooled to ambient temperature, treated with saturated sodium thiosulfate solution (20 mL), and diluted with water (50 mL) and methanol (10 mL). The layers were separated and the organic layer was washed with 0.5N hydrochloric acid (50 mL), dried over sodium sulfate, filtered, concentrated in vacuo, and purified by flash chromatography (silica, 80 g, ISCO, 0-10% methanol in dichloromethane) to afford the title compound as a pale yellow solid (930 mg, 40%). ¹H NMR (400 MHz, CDCl₃) δ 8.86 (s, 1H), 8.39 (d, J=6.4, 1H), 8.27 (s, 1H), 7.94 (d, J=8.1, 1H), 7.32 (dd, J=7.9, 6.5, 1H), 6.55 (s, 2H), 3.73 (t, J=8.0, 2H), 0.93 (t, J=8.0, 2H), −0.04 (s, 9H).

Step 3: 4-Chloro-9-(2-trimethylsilanyl-ethoxymethyl)-9H-dipyrido[2,3-b;4',3'-d]pyrrole-6-carbonitrile-7-oxide

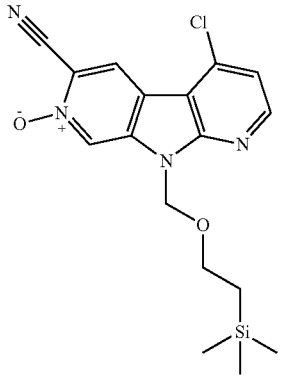

A mixture of 9-(2-trimethylsilanyl-ethoxymethyl)-9H-dipyrido[2,3-b;4',3'-d]pyrrole-6-carbonitrile-1,7-dioxide (2.1 g, 5.9 mmol) in N,N-dimethylformamide (50 mL) was treated with methanesulfonyl chloride (0.78 mL, 10.0 mmol), and the reaction mixture was stirred at ambient temperature for 7 hours. The reaction mixture was then diluted with ethyl acetate (150 mL) and water (200 mL). The layers were separated and the organic layer was dried over sodium sulfate, filtered, concentrated in vacuo, and purified by flash chromatography (silica, 40 g, ISCO, 5-85% ethyl acetate in heptane) to afford the title compound as a 6.5:1 mixture with 2-chloro-9-(2-trimethylsilanyl-ethoxymethyl)-9H-dipyrido[2,3-b;4',3'-d]pyrrole-6-carbonitrile-7-oxide respectively as an off-white solid (1.7 g, 77%). The mixture was triturated in ethyl acetate (10 mL) overnight and the remaining solid was collected by vacuum filtration and washed with ethyl acetate (5 mL) to afford the title compound with >98% purity. ¹H NMR (400 MHz, CDCl₃) δ 8.86 (s, 1H), 8.39 (d, J=6.4, 1H), 8.27 (s, 1H), 7.94 (d, J=8.1, 1H), 7.32 (dd, J=7.9, 6.5, 1H), 6.55 (s, 2H), 3.73 (t, J=8.0, 2H), 0.93 (t, J=8.0, 2H), −0.04 (s, 9H).

Step 4: 4-Chloro-9-(2-trimethylsilanyl-ethoxymethyl)-9H-dipyrido[2,3-b;4',3'-d]pyrrole-6-carbonitrile

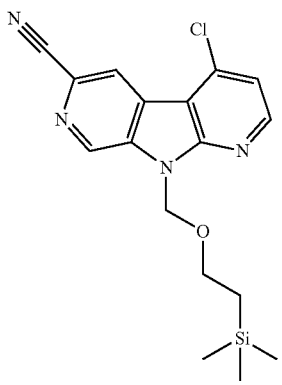 [SMILES: C[Si](C)(C)CCOCn1c2cnc(C#N)cc2c2c(Cl)ccnc21]

A solution of 4-chloro-9-(2-trimethylsilanyl-ethoxymethyl)-9H-dipyrido[2,3-b;4',3'-d]pyrrole-6-carbonitrile-7-oxide (1.3 g, 3.52 mmol) in dichloromethane (11 mL) was treated with phosphorus trichloride (2N solution in dichloromethane, 1.9 mL, 3.9 mmol) and the reaction mixture was stirred at ambient temperature for 2 hours. The reaction mixture was concentrated in vacuo and purified by flash chromatography (silica, 40 g, ISCO, 0-40% ethyl acetate in heptane) to afford the title compound as a white solid (1.2 g, 93%). ¹H NMR (400 MHz, CDCl₃) δ 9.20 (d, J=0.9, 1H), 8.74 (d, J=0.9, 1H), 8.60 (d, J=5.3, 1H), 7.39 (d, J=5.3, 1H), 6.02 (s, 2H), 3.60 (t, J=8.0, 2H), 0.94 (t, J=8.0, 2H), −0.08 (s, 9H).

Preparation of (R)-tert-butyl 3-(hydroxymethyl)-4-methylpiperazine-1-carboxylate

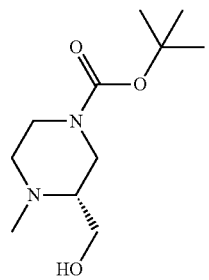 [SMILES: CN1CCN(C(=O)OC(C)(C)C)C[C@@H]1CO]

To a solution of (R)-tert-butyl 3-(hydroxymethyl)piperazine-1-carboxylate (115 mg, 0.53 mmol) in acetonitrile (1.4 mL) and water (0.3 mL) was added Formalin (0.11 mL, 1.6 mmol) followed by sodium triacetoxyborohydride (225 mg, 1.1 mmol). The reaction mixture was stirred for 20 minutes at ambient temperature. The reaction mixture was then basified via the addition of saturated aqueous sodium carbonate solution (1 mL), diluted with methylene chloride (50 mL) and methanol (5 mL), and washed with saturated aqueous sodium bicarbonate solution (2×15 mL). The organic layer was separated, dried over sodium sulfate, and concentrated in vacuo to afford a white crystalline solid, which was used in the next step without any further purification (120 mg, 98%).

Preparation of (S)-tert-butyl 3-(hydroxymethyl)-4-methylpiperazine-1-carboxylate

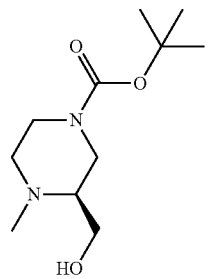 [SMILES: CN1CCN(C(=O)OC(C)(C)C)C[C@H]1CO]

The title compound was prepared following a similar procedure to the previous example using (S)-tert-butyl 3-(hydroxymethyl)piperazine-1-carboxylate.

Preparation of (S)-tert-butyl 2-(hydroxymethyl)-4-methylpiperazine-1-carboxylate

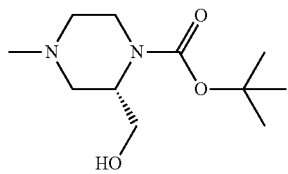 [SMILES: CN1CCN(C(=O)OC(C)(C)C)[C@H](CO)C1]

The title compound was prepared following a similar procedure to the previous example using (S)-tert-butyl 2-(hydroxymethyl)piperazine-1-carboxylate.

Preparation of (R)-tert-butyl 2-(hydroxymethyl)-4-methylpiperazine-1-carboxylate

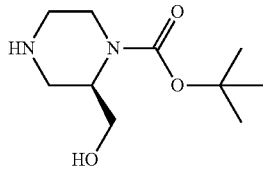

The title compound was prepared following a similar procedure to the previous example using (R)-tert-butyl 2-(hydroxymethyl)piperazine-1-carboxylate.

Preparation of (1R,3S,4S)-2-azabicyclo[2.2.1]heptan-3-ylmethanol

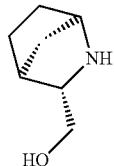

To a slurry of (1R,3S,4S)-2-azabicyclo[2.2.1]heptane-3-carboxylic acid hydrogen chloride (500 mg, 3 mmol) in tetrahydrofuran (4.6 mL) was added lithium tetrahydroaluminate (1N solution in tetrahydrofuran, 5.7 mL, 6 mmol) dropwise over 10 minutes. The reaction mixture was stirred overnight at ambient temperature under an atmosphere of nitrogen. The reaction was quenched with a few drops of water, diluted with diethyl ether (50 mL) and tetrahydrofuran (25 mL). The reaction mixture was basified to a pH of ~11 by the addition of potassium hydroxide pellets and then stirred vigorously for 30 minutes. The reaction mixture was filtered over sodium sulfate, concentrated in vacuo, redissolved in methylene chloride (10 mL), dried once more over sodium sulfate, filtered, and concentrated in vacuo to afford a yellow crystalline solid, which was used in the next step without any further purification (400 mg, 100%).

Preparation of trans-(3S,4S)-tert-butyl 4-fluoro-3-hydroxypiperidine-1-carboxylate

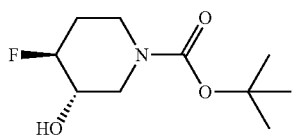

Preparation of the title compound is described in WO2008106692(A1).

Preparation of 4-chloro-9H-dipyrido[2,3-b;4',3'-d]pyrrole

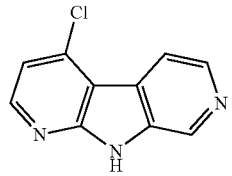 [SMILES: Clc1ccnc2[nH]c3cnccc3c12]

Step 1: Preparation of (4-Chloro-1H-pyrrolo[2,3-b]pyridin-3-ylmethyl)dimethylamine

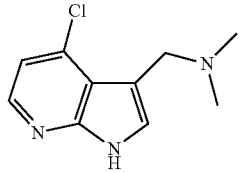

4-Chloro-7-azaindole (7.32 g, 48 mmol), paraformaldehyde (1.59 g, 52.8 mmol) and dimethylamine hydrochloride (4.32 g, 52.8 mmol) were suspended in 1-butanol (30 mL) and the mixture heated under reflux for 2 hours. The mixture was cooled to ambient temperature and diluted with diethyl ether (50 mL). The resultant solid was collected by filtration and washed with diethyl ether and left to air-dry. The solid was dissolved in water (100 mL) and the pH of the solution adjusted to 11 by the portion-wise addition of solid potassium carbonate. The aqueous phase was extracted with dichloromethane (3×40 mL). The combined organic phase was dried (MgSO$_4$), filtered and evaporated to afford the title compound as a pale yellow solid (7.12 g, 70%). $^1$H NMR (300 MHz, CDCl$_3$): 11.19 (s, 1H), 8.15 (d, J=5.2 Hz, 1H), 7.32 (s, 1H), 7.08 (d, J=5.2 Hz, 1H), 3.79 (s, 2H), 2.34 (s, 6H).

Step 2: 2-Acetylamino-2-(4-chloro-1H-pyrrolo[2,3-b]pyridin-3-ylmethyl)malonic acid diethyl ester

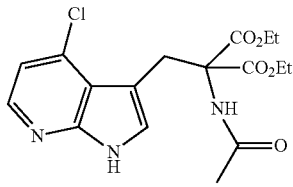 [SMILES: CCOC(=O)C(Cc1c[nH]c2nccc(Cl)c12)(NC(C)=O)C(=O)OCC]

(4-Chloro-1H-pyrrolo[2,3-b]pyridin-3-ylmethyl)dimethylamine (7.1 g, 34 mmol), powdered sodium hydroxide (0.21 g, 5.2 mmol) and diethylacetamidomalonate (8.26 g, 38 mmol) were suspended in xylene (60 mL) and the mixture heated under reflux for 4 hours. The mixture was filtered to remove solid whilst hot and the filtrate allowed to cool to ambient temperature with stirring. The precipitated solid was collected by filtration, washed with xylene then dissolved in dichloromethane and passed through a pad of silica (25 g). The pad was washed with 1:1 ethyl acetate: dichloromethane (100 mL) and ethyl acetate (2×100 mL). The combined filtrate was evaporated and the resultant solid was triturated with ethyl acetate (100 mL). The solid was collected by filtration and left to air dry to afford the title compound as a white solid (8.5 g, 65%). $^1$H NMR (400 MHz, CDCl$_3$): 10.12 (s, 1H), 8.13 (d, J=5.2 Hz, 1H), 7.15 (s, 1H), 7.07 (d, J=5.2 Hz, 1H), 6.71 (s, 1H), 4.23-4.22 (m, 4H), 4.06 (s, 2H), 2.02 (s, 3H), 1.24 (t, J=7.1 Hz, 6H).

Step 3: 2-Amino-3-(4-chloro-1H-pyrrolo[2,3-b]pyridin-3-yl)-propionic acid-hydrochloride salt

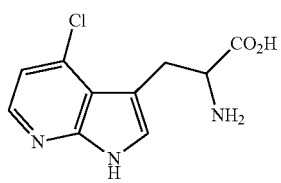 [SMILES: NC(Cc1c[nH]c2nccc(Cl)c12)C(=O)O]

2-Acetylamino-2-(4-chloro-1H-pyrrolo[2,3-b]pyridin-3-ylmethyl)malonic acid diethyl ester (8.5 g, 22.3 mol) was dissolved in concentrated hydrochloric acid (45 mL) and the solution heated at 100° C. for 16 hours. The mixture was allowed to cool to ambient temperature and evaporated in-vacuo. The resultant residue was azeotroped with methanol (100 mL) and toluene (2×100 mL) to afford the crude title compound as a white solid. LCMS (Method B): R$_T$=1.88 min, M+H$^+$=240.

Step 4: 2-Amino-3-(4-chloro-1H-pyrrolo[2,3-b]pyridin-3-yl)-propionic acid methyl ester-hydrochloride salt

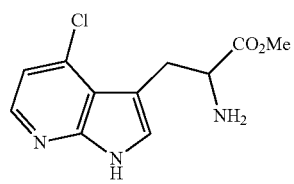 [SMILES: COC(=O)C(N)Cc1c[nH]c2nccc(Cl)c12]

Thionyl chloride (27.5 mL) was added dropwise over 15 minutes to a cooled (0° C.) suspension of 2-amino-3-(4-chloro-1H-pyrrolo[2,3-b]pyridin-3-yl)-propionic acid hydrochloride (7.28 g, 22.3 mmol) in methanol (150 mL). On complete addition, the mixture was heated under reflux for 66 hours. The mixture was allowed to cool to ambient temperature and evaporated. The resultant residue was azeotroped with toluene (2×150 mL) to afford the title compound as a fawn solid (7.7 g, 99%). $^1$H NMR (400 MHz, DMSO-d$_6$): 12.06 (s, 1H), 8.39 (s, 3H), 8.17 (d, J=5.2 Hz, 1H), 7.50 (d, J=2.5 Hz, 1H), 7.19 (d, J=5.2 Hz, 1H), 4.07-4.06 (m, 1H), 3.54 (dd, J=14.9, 5.8 Hz, 1H), 3.30 (dd, J=14.9, 9.0 Hz, 1H).

Step 5: 4-Chloro-6,7,8,9-tetrahydro-5H-dipyrido[2,3-b;4',3'-d]pyrrole-6-carboxylic acid methyl ester

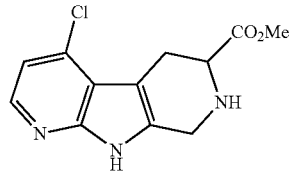 [SMILES: COC(=O)C1Cc2c([nH]c3nccc(Cl)c23)CN1]

A suspension of 2-amino-3-(4-chloro-1H-pyrrolo[2,3-b]pyridin-3-yl)-propionic acid methyl ester (3.5 g, 10 mmol) in pyridine (25 mL) was treated with formaldehyde solution (37% in water, 0.90 mL) and the resulting mixture was heated to 100° C. for 1.25 hours. The mixture was allowed to cool to ambient temperature then evaporated in-vacuo. The resultant residue was treated with saturated aqueous sodium carbonate solution (15 mL) and the resultant solid collected by filtration and washed with water (20 mL). The filtrate was extracted with 20% methanol in dichloromethane (6×25 mL). The combined organic phase was combined with solid and concentrated in-vacuo to afford the title compound as a brown residue (2.1 g, 87%). LCMS (Method B): R$_T$=2.36 min, M+H$^+$=266. $^1$H NMR (400 MHz, DMSO-d$_6$): 11.66 (s, 1H), 8.02 (d, J=5.2 Hz, 1H), 7.06 (d, J=5.1 Hz, 1H), 4.01-3.71 (m, 3H), 3.69 (s, 3H), 3.19 (dd, J=15.4, 4.7 Hz, 1H), 2.94 (dd, J=15.4, 8.9 Hz, 1H).

Step 6: 4-Chloro-9H-dipyrido[2,3-b;4',3'-d]pyrrole-6-carboxylic acid methyl ester

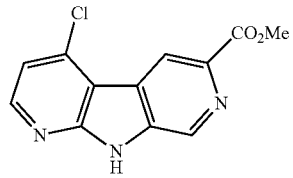 [SMILES: COC(=O)c1cc2c(cn1)[nH]c1nccc(Cl)c12]

A mixture of 4-chloro-6,7,8,9-tetrahydro-5H-dipyrido[2,3-b;4',3'-d]pyrrole-6-carboxylic acid methyl ester (2.1 g, 7.9 mmol) and selenium dioxide (1.20 g, 11.1 mol) in 1,4-dioxane (50 mL) was heated at 100° C. for 3.5 hours. The resulting grey slurry was filtered whilst hot through a pad of celite and the pad washed with hot THF and 25% methanol in dichloromethane. The combined filtrate was concentrated in-vacuo and the resultant residue triturated with methanol (10 mL). The resultant solid was collected by filtration and left to air dry to afford the title compound as an off white solid (1.03 g, 48%). $^1$H NMR (400 MHz, DMSO-d$_6$): 13.02 (s, 1H), 9.06 (d, J=1.1 Hz, 1H), 8.94 (d, J=1.0 Hz, 1H), 8.63 (d, J=5.3 Hz, 1H), 7.54 (d, J=5.3 Hz, 1H), 3.93 (s, 3H).

Step 7: 4-Chloro-9H-dipyrido[2,3-b;4',3'-d]pyrrole-6-carboxylic acid

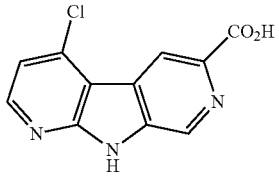 [SMILES: O=C(O)c1cc2c(cn1)[nH]c1nccc(Cl)c12]

A mixture of 4-chloro-9H-dipyrido[2,3-b;4',3'-d]pyrrole-6-carboxylic acid methyl ester (0.73 g, 2.8 mol) and lithium hydroxide (0.38 g, 9.0 mmol) in tetrahydrofuran (15 mL) and water (3 mL) was heated at 50° C. for 1.5 hours. The mixture was allowed to cool to ambient temperature, treated with hydrochloric acid (1M, 9 mL) and evaporated in-vacuo to afford a grey solid (0.68 g, 98%). LCMS (Method B): $R_T$=2.98 min, M+H$^+$=248. $^1$H NMR (400 MHz, DMSO-d$_6$): 12.98 (s, 1H), 9.05 (d, J=1.0 Hz, 1H), 8.95 (d, J=1.0 Hz, 1H), 8.63 (d, J=5.3 Hz, 1H), 7.54 (d, J=5.3 Hz, 1H).

Step 8: 4-Chloro-9H-dipyrido[2,3-b;4',3'-d]pyrrole

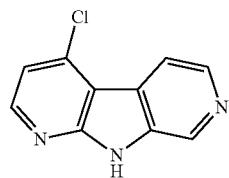 [SMILES: Clc1ccnc2[nH]c3cnccc3c12]

A mixture of 4-chloro-9H-dipyrido[2,3-b;4',3'-d]pyrrole-6-carboxylic acid (390 mg, 1.57 mmol) in N-methylpyrrolidine (8 mL) was heated under reflux for 8 hours. The mixture was allowed to cool to ambient temperature. The compound was used as a solution in NMP for subsequent reactions. LCMS (Method B): $R_T$=2.15 min, M+H$^+$=204.

General Coupling Methods

Method A-1:

A mixture of 4-chloro-9-(2-trimethylsilanyl-ethoxymethyl)-9H-dipyrido[2,3-b;4',3'-d]pyrrole-6-carbonitrile (1 eq.), the appropriate alcohol (2-4 eq.), and sodium hydride as a 60% dispersion in mineral oil (2-8 eq.) in tetrahydrofuran was heated between 25° C. to 55° C. until the reaction deemed complete. The reaction mixture was cooled then diluted with water and extracted with an appropriate solvent. The resultant residue was purified by flash chromatography on silica using either an ethyl acetate in heptane or methanol in dichoromethane gradient. The purified material was then deprotected using the conditions described below.

Method B-1:

A mixture of 4-chloro-9-(2-trimethylsilanyl-ethoxymethyl)-9H-dipyrido[2,3-b;4',3'-d]pyrrole-6-carbonitrile (1 eq.) and the appropriate amine (2-4 eq.) was heated in N,N-dimethylacetamide at between 80° C. to 120° C. until the reaction deemed complete. The reaction mixture was cooled then diluted with water and extracted with an appropriate solvent. The resultant residue was purified by flash chromatography on silica using either an ethyl acetate in heptane or methanol in dichoromethane gradient. The purified material was then deprotected using the conditions described below.

Method C-1:

A mixture of 4-chloro-9-(2-trimethylsilanyl-ethoxymethyl)-9H-dipyrido[2,3-b;4',3'-d]pyrrole-6-carbonitrile (1 eq.), the hydrochloride salt of the appropriate amine (2-4 eq.), and triethylamine (5-10 eq.) was heated in N,N-dimethylacetamide between 80° C. to 120° C. until the reaction deemed complete. The reaction mixture was cooled then diluted with water and extracted with an appropriate solvent. The resultant residue was purified by flash chromatography on silica using either an ethyl acetate in heptane or methanol in dichoromethane gradient. The purified material was then deprotected using the general conditions described below.

Method D-1:

A mixture of 4-chloro-9-(2-trimethylsilanyl-ethoxymethyl)-9H-dipyrido[2,3-b;4',3'-d]pyrrole-6-carbonitrile (1 eq.), the appropriate amine (5 eq.), 4,5-bis(diphenylphosphino)-9,9-dimethylxanthene (0.2 eq), tris(dibenzylideneacetone)dipalladium(0) (0.1 eq.), and cesium carbonate (2 eq.) in 1,4-dioxane was heated between 100° C. to 110° C. until the reaction deemed complete. The reaction mixture was cooled then diluted with water and extracted with an appropriate solvent. The resultant residue was purified by flash chromatography on silica using either an ethyl acetate in heptane or methanol in dichoromethane gradient. The purified material was then deprotected using the conditions described below.

Method E-1:

4-Chloro-9-(2-trimethylsilanyl-ethoxymethyl)-9H-dipyrido[2,3-b;4',3'-dpyrrole-6-carbonitrile (1 eq.) was heated in the appropriate amine (1-5 eq) in DMA between 120° C. to 140° C. until the reaction was deemed complete. The reaction mixture was cooled then diluted with water and extracted with an appropriate solvent. The resultant residue was purified by one of the general purification methods described below.

Method F-1:

4-Chloro-9-(2-trimethylsilanyl-ethoxymethyl)-9H-dipyrido[2,3-b;4',3'-dpyrrole-6-carbonitrile (1 eq.) in THF was heated with the appropriate alcohol (2-5 eq.) and sodium hydride (2-5 eq.) between ambient temperature to 100° C. until the reaction was deemed complete. The reaction mixture was cooled then diluted with water and extracted with an appropriate solvent. The resultant residue was purified by one of the general purification methods described below.

Method A-2.:

The appropriately 3-substituted 9-benzenesulfonyl-5-bromo-9H-dipyrido[2,3-b;4',3'-d]pyrrole-6-carbonitrile (1 eq.) was heated in the appropriate amine (3-5 eq.) and triethylamine (10 eq.) at between 140° C. to 160° C. until the reaction was deemed complete. The reaction mixture was cooled then diluted with water and extracted with an appropriate solvent. The resultant residue was purified by one of the general purification methods described below.

Method B-2:

The appropriately 3-substituted 9-benzenesulfonyl-5-chloro-9H-dipyrido[2,3-b;4',3'-d]pyrrole-6-carbonitrile (1 eq.) or 3-substituted 5-chloro-9H-dipyrido[2,3-b;4',3'-d]pyrrole-6-carbonitrile (1 eq.) was heated in the appropriate amine (3-5 eq.) and triethylamine (10 eq.) between 120° C. to 160° C. until the reaction was deemed complete. The reaction mixture was cooled then diluted with water and extracted with an appropriate solvent. The resultant residue was purified by one of the general purification methods described below.

Method C-2:

A mixture of the appropriately 3-substituted 9-benzenesulfonyl-5-chloro-9H-dipyrido[2,3-b;4',3'-d]pyrrole-6-carbonitrile (1 eq.), the appropriate amine (1-2 eq.), cesium carbonate (1-3 eq.) and sodium iodide (0.5-1 eq.) in DMF were heated with microwave irradiation (100° C. to 160° C.) for between 5 and 15 minutes. The reaction mixture was cooled then diluted with water and extracted with an appropriate solvent. The resultant residue was purified by one of the general purification methods described below.

Method D-2:

5-Fluoro-9-(2-trimethylsilanyl-ethoxymethyl)-9H-dipyrido[2,3-b;4',3'-dpyrrole-6-carbonitrile (1 eq.) or 5-fluoro-9H-dipyrido[2,3-b;4',3'-d]pyrrole-6-carbonitrile (1 eq.) in DMA was heated with the appropriate amine (2-5 eq.) between ambient temperature to 160° C. until the reaction was deemed complete. The reaction mixture was cooled then diluted with water and extracted with an appropriate solvent. The resultant residue was purified by one of the general purification methods described below.

Method E-2:

5-Fluoro-9-(2-trimethylsilanyl-ethoxymethyl)-9H-dipyrido[2,3-b;4',3'-dpyrrole-6-carbonitrile (1 eq.) in NMP was heated with the appropriate alcohol (2-5 eq.) and sodium hydride (2-5 eq.) between ambient temperature to 160 OC until the reaction was deemed complete. The reaction mixture was cooled then diluted with water and extracted with an appropriate solvent. The resultant residue was purified by one of the general purification methods described below.

Method F-2:

A solution of the appropriately 3-substituted 9-benzenesulfonyl-5-hydroxy-9H-dipyrido[2,3-b;4',3'-d]pyrrole-6-carbonitrile (1 eq.), the appropriate alcohol (2-5 eq.) and triphenylphosphine (2-5 eq.) in anhydrous DMF or anhydrous THF was treated dropwise with diethyl azodicarboxylate (2-5 eq.) and the mixture stirred at a temperature between ambient and 50° C. for between 2 and 65 hours. The resultant reaction mixture was diluted with ethyl acetate and washed with brine, dried over anhydrous magnesium sulfate and concentrated in-vacuo. The resultant residue was subjected to purification, by the general methods described below.

Method G-2:

Chloro-9H-dipyrido[2,3-b;4',3'-d]pyrrole (1 eq.) in NMP was heated with the appropriate amine (2-5 eq.) between ambient temperature to 160° C. until the reaction was deemed complete. The reaction mixture was cooled then diluted with water and extracted with an appropriate solvent. The resultant residue was purified by one of the general purification methods described below.

General Hydrogenation Methods

Method A-2:

A solution of the appropriately 5-substituted 9-benzenesulfonyl-3-bromo-9H-dipyrido[2,3-b;4',3'-d]pyrrole-6-carbonitrile (1 eq.) or 5-substituted 3-bromo-9H-dipyrido[2,3-b;4',3'-d]pyrrole-6-carbonitrile (1 eq.) in a mixture of ethanol and tetrahydrofuran (1:1 v/v) was treated with palladium on carbon (10 wt %) then placed under an atmosphere of hydrogen and the reaction mixture was stirred at ambient temperature until the reaction was deemed complete. The reaction mixture was purged with argon then the catalyst was removed by filtration then the filtrate evaporated. The resultant residue was purified by one of the general purification methods described below.

Method B-2:

A solution of the appropriately 5-substituted 9-benzenesulfonyl-3-bromo-9H-dipyrido[2,3-b;4',3'-d]pyrrole-6-carbonitrile (1 eq.) or 5-substituted 3-bromo-9H-dipyrido[2,3-b;4',3'-d]pyrrole-6-carbonitrile (1 eq.) in a mixture of ethanol, dichloromethane, triethylamine and DMF (2:2:1:2 v/v) was treated with palladium on carbon (10 wt %) then placed under an atmosphere of hydrogen and the reaction mixture was stirred at ambient temperature until the reaction was deemed complete. The reaction mixture was purged with argon then the catalyst was removed by filtration then the filtrate evaporated. The resultant residue was purified by one of the general purification methods described below.

General Deprotection Method

Method A-1:

A mixture of the appropriately 4-substituted-9-(2-trimethylsilanyl-ethoxymethyl)-dipyrido[2,3-b;4',3'-d]pyrrole-6-carbonitrile was dissolved in 1,4-dioxane and then treated with 48% $HBr_{(aq)}$ and heated between 50° C. to 75° C. until the reaction deemed complete. The cooled reaction mixture was then basified to pH ~12 by dropwise addition of 6N sodium hydroxide and then immediately acidified to pH ~8-9 by dropwise addition of concentrated hydrochloric acid, producing a cloudy precipitate. The solid was collected by centrifugation, dissolved in dimethylsulfoxide and purified by one of the general methods described below. In some cases, the aqueous supernate was purified by the same method and combined.

Method B-1:

1N TBAF in THF was added to a mixture of the protected substrate in an appropriate solvent. The reaction mixture was stirred between ambient temperature and 55° C. until the reaction was deemed complete. The resultant solution was concentrated in-vacuo before subjecting the crude material to purification by one of the general methods described below.

Method C-1:

6N HCl was added to a mixture of the protected substrate in an appropriate solvent. The reaction mixture was stirred between ambient temperature and 55° C. until the reaction was deemed complete. The resultant solution was concentrated in-vacuo before subjecting the crude material to purification by one of the general methods described below.

Method D-1:

48% Hydrobromic acid was added to a mixture of the protected substrate in acetic acid. The reaction mixture was stirred between ambient temperature and 55° C. until the reaction was deemed complete. The resultant solution was concentrated in-vacuo before subjecting the crude material to purification by one of the general methods described below.

Method A-2:

1N TBAF in THF was added to a mixture of the protected substrate in an appropriate solvent. The reaction mixture was stirred between ambient temperature and 55° C. until the reaction was deemed complete. The resultant solution was concentrated in-vacuo before subjecting the crude material to purification by one of the general methods described below. Alternatively, the crude material was partitioned between water and ethyl acetate and the organic layer was dried, concentrated in-vacuo, before subjecting the crude material to one of the general purification methods described below.

Method B-2:

The tertiary amine was dissolved or suspended in dichloromethane and treated with an excess (at least 2 equivalents) of 1-chloroethyl chloroformate. DIPEA (at least 1 equivalent) was added and the resultant mixture was heated under reflux. When analysis by LCMS showed that starting material (or any 1-chloroethyl carbamate of starting material) had been consumed the solution was cooled and concentrated in-vacuo. The residue was taken up in methanol and heated at reflux until analysis by LCMS showed complete consumption of the intermediates. The reaction mixture was then cooled and concentrated in-vacuo. The residue was subjected to purification by one of the general methods described below.

Method C-2:

2N Ammonia in methanol was added to a mixture of the protected substrate. The reaction mixture was stirred at ambient temperature until the reaction was deemed complete. The resultant solution was concentrated in-vacuo before subjecting the crude material to purification by one of the general methods described below.

Method D-2:

TFA was added to a mixture of the protected substrate in an appropriate solvent at ambient temperature. The mixture was stirred until the reaction was deemed complete. The reaction mixture was concentrated in-vacuo and subjected to purification by one of the general methods described below.

Method E-2:

Triethylamine in methanol was added to a mixture of the protected substrate. The reaction mixture was stirred at ambient temperature until the reaction was deemed complete. The resultant solution was concentrated in-vacuo before subjecting the crude material to purification by one of the general methods described below.

General Reductive Amination/Alkylation Methods

Method A-2:

To a solution of the appropriately 5-substituted 9-benzenesulfonyl-3-bromo-9H-dipyrido[2,3-b;4',3'-d]pyrrole-6-carbonitrile (1 eq.), sodium triacetoxy-borohydride (1-2 eq.) and acetic acid in methanol was added aqueous formaldehyde (2-4 eq.) and the reaction mixture was then stirred at ambient temperature until the reaction was deemed complete. The reaction mixture was concentrated in-vacuo and subjected to purification by one of the general methods described below.

Method B-2:

To a solution of the appropriately 5-substituted 9-benzenesulfonyl-3-bromo-9H-dipyrido[2,3-b;4',3'-d]pyrrole-6-carbonitrile (1 eq.), sodium triacetoxyborohydride (1-2 eq.) and acetic acid in methanol was added acetaldehyde (2-4 eq.) and the reaction mixture was then stirred at ambient temperature until the reaction was deemed complete. The reaction mixture was concentrated in-vacuo and subjected to purification by one of the general methods described below.

Method C-2:

A mixture of the appropriately 5-substituted 9-benzenesulfonyl-9H-dipyrido[2,3-b;4',3'-d]pyrrole-6-carbonitrile (1 eq.), 2,2-dimethyloxirane (1-2 eq.), cesium carbonate (1-3 eq.) in DMF were heated with microwave irradiation (100 OC to 160° C.) for between 5 and 15 minutes. The reaction mixture was cooled then diluted with water and extracted with an appropriate solvent. The resultant residue was purified by one of the general purification methods described below.

General Purification Methods

Method A-1:

Compounds were typically purified by reverse phase HPLC using a Gemini-NX column (10 μm, 3 cm×10 cm) from Phenomenex. Samples were run on a gradient of 5-50%, 5-85%, or 20-60% acetonitrile or methanol in water with 0.1% ammonium hydroxide or 0.1% formic acid over 14 minutes at a flow rate of 60 mL/min. In some cases, pure racemic compounds were resolved using a Berger MG2 semi-prep system using Chiral Technologies AD, OD, OJ, AS, IA, IB, or IB columns (5 μm, 21.2 mm×250 mm) at a flow rate of 50-70 mL/min. Solvents typically used include methanol, ethanol, or IPA with 0.1% triethylamine.

Method A-2:

Biotage, Snap KP-NH, Amino Silica-ISCO, methanol/dichloromethane gradient.

Method B-2:

Si-SPE or Si-ISCO or manual silica column, methanol/dichloromethane gradient.

Method C-2:

A solution of the substrate in methanol was loaded onto an Isolute® SCX-2 cartridge. The cartridge was then washed with methanol before the desired product was eluted using 2N ammonia in MeOH.

Method D-2:

Si-SPE or Si-ISCO, ethyl acetate/methanol gradient

Method E-2:

Si-SPE or Si-ISCO, 2-propanol/dichloromethane gradient

Method F-2:

Biotage, Snap KP-NH, Amino Silica-ISCO, 2-propanol/dichloromethane gradient

Deviations from purification general methods:
[1]triturated in dichloromethane; [2]triturated in methanol; [3]triturated in acetonitrile; [4]triturated in ethyl acetate.

The compounds of the Examples in Table 1 were prepared via one of the general coupling methods, followed by the general deprotection Method A-1 and the general purification Method A-1 described above.

TABLE 1

| Example | Structure/Name | Coupling Method | LCMS $R_T$ (min), M + H+, Method | 1H NMR (ppm) |
|---|---|---|---|---|
| 1 | 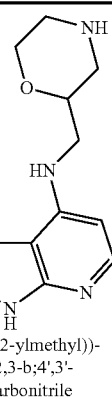<br>4-(N-(morpholin-2-ylmethyl))-9H-dipyrido[2,3-b;4',3'-d]pyrrole-6-carbonitrile | D-1 | 2.397, 309.1, E | 1H NMR (400 MHz, d6-DMSO) δ 12.43 (s, 1H), 9.07 (s, 1H), 8.85 (s, 1H), 8.22 (d, J = 5.8, 1H), 7.01 (t, J = 6.0, 1H), 6.61 (d, J = 5.9, 1H), 3.90 (m, 1H), 3.85 (m, 1H), 3.58 (m, 1H), 3.51 (t, J = 6.0, 2H), 3.20 (m, 1H), 2.98 (m, 1H), 2.87 (m, 1H), 2.73 (m, 1H). |

TABLE 1-continued

| Example | Structure/Name | Coupling Method | LCMS R$_T$ (min), M + H$^+$, Method | $^1$H NMR (ppm) |
|---|---|---|---|---|
| 2 | 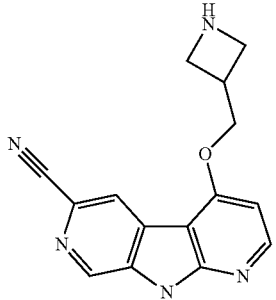<br>4-(azetidin-3-ylmethoxy)-9H-dipyrido[2,3-b;4',3'-d]pyrrole-6-carbonitrile | A-1 | 5.391, 280.1, D | $^1$H NMR (400 MHz, d$_6$-DMSO) δ 8.98 (d, J = 0.9, 1H), 8.57 (d, J = 5.9, 1H), 8.38 (s, 1H), 7.05 (d, J = 5.9, 1H), 4.53 (d, J = 6.3, 2H), 3.97 (t, J = 8.9, 2H), 3.80-3.73 (m, 2H), NH signals not observed |
| 3 | 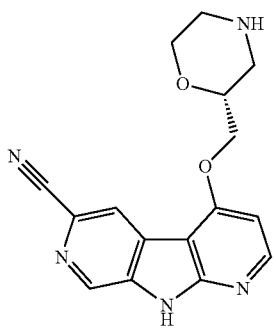 [SMILES: N#Cc1cc2c(cn1)[nH]c1nccc(OC[C@H]3CNCCO3)c12]<br>(R)-4-(morpholin-2-ylmethoxy)-9H-dipyrido[2,3-b;4',3'-d]pyrrole-6-carbonitrile | A-1 | 6.122, 310.1, D | $^1$H NMR (400 MHz, d$_6$-DMSO) δ 8.98 (d, J = 0.9, 1H), 8.54 (d, J = 5.7, 1H), 8.44 (d, J = 0.9, 1H), 7.05 (d, J = 5.8, 1H), 4.40-4.30 (m, 2H), 3.95 (m, 1H), 3.82 (m, 1H), 3.56 (m, 1H), 3.02 (m, 1H), 2.79-2.63 (m, 3H), NH signals not observed. |
| 4 | 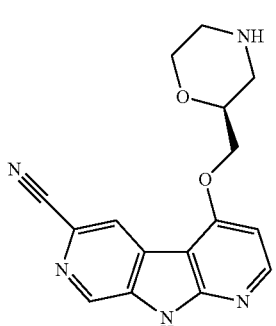<br>(S)-4-(morpholin-2-ylmethoxy)-9H-dipyrido[2,3-b;4',3'-d]pyrrole-6-carbonitrile | A-1 | 5.750, 310.1, D | $^1$H NMR (400 MHz, d$_6$-DMSO) δ 8.95 (s, 1H), 8.52 (d, J = 5.7, 1H), 8.41 (d, J = 0.8, 1H), 6.98 (d, J = 5.7, 1H), 4.33 (3, 2H), 3.98-3.90 (m, 1H), 3.81 (m, 1H), 3.56 (m, 1H), 3.02 (m, 1H), 2.78-2.63 (m, 3H), NH signals not observed. |
| 5 | 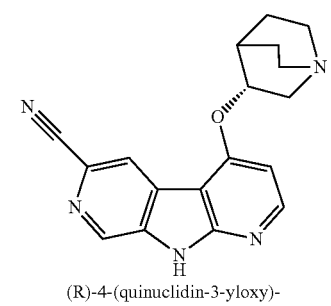<br>(R)-4-(quinuclidin-3-yloxy)-9H-dipyrido[2,3-b;4',3'-d]pyrrole-6-carbonitrile | A-1 | 2.747, 320.1, E | $^1$H NMR (400 MHz, d$_6$-DMSO) δ 12.78 (s, 1H), 8.98 (d, J = 0.9, 1H), 8.53 (s, 1H), 8.52 (d, J = 4.4, 1H), 7.00 (d, J = 5.8, 1H), 5.04-4.95 (m, 1H), 3.48 (m, 1H), 3.07 (m, 2H), 2.95-2.76 (m, 3H), 2.35 (m, 1H), 1.98 (m, 1H), 1.76 (m, 2H), 1.55 (m, 1H). |

TABLE 1-continued

| Example | Structure/Name | Coupling Method | LCMS R_T (min), M + H+, Method | $^1$H NMR (ppm) |
|---|---|---|---|---|
| 6 | 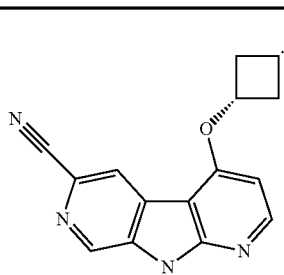<br>4-((1s,3s)-cyclobutanamine-3-yloxy)-9H-dipyrido[2,3-b;4',3'-d]pyrrole-6-carbonitrile | A-1 | 3.147, 280.1, E | $^1$H NMR (400 MHz, d$_6$-DMSO) δ 8.97 (d, J = 0.8, 1H), 8.53 (d, J = 0.8, 1H), 8.51 (d, J = 5.7, 1H), 6.87 (d, J = 5.7, 1H), 4.73 (m, 1H), 3.15-3.05 (m, 1H), 2.96-2.86 (m, 2H), 2.04 (m, 2H), NH signal not observed. |
| 7 | 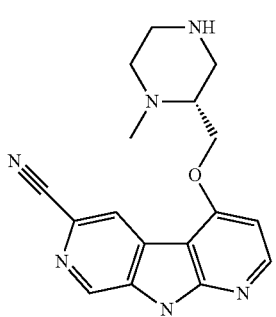<br>(R)-4-((1-methylpiperazin-2-yl)methoxy)-9H-dipyrido[2,3-b;4',3'-d]pyrrole-6-carbonitrile | A-1 | 2.966, 323.1, E | $^1$H NMR (400 MHz, d$_6$-DMSO) δ 8.95 (s, 1H), 8.53 (d, J = 5.7, 1H), 8.44 (s, 1H), 7.01 (d, J = 5.7, 1H), 4.46 (m, 1H), 4.30 (m, 1H), 3.07 (m, 1H), 2.80 (m, 1H), 2.75-2.60 (m, 3H), 2.57-2.52 (m, 1H), 2.43-2.27 (s, 3H), 2.19 (m, 1H), NH signals not observed. |
| 8 | 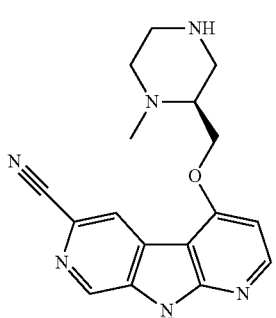<br>(S)-4-((1-methylpiperazin-2-yl)methoxy)-9H-dipyrido[2,3-b;4',3'-d]pyrrole-6-carbonitrile | A-1 | 6.039, 323.1, D | $^1$H NMR (400 MHz, d$_6$-DMSO) δ 8.98 (d, J = 0.9, 1H), 8.55 (d, J = 5.7, 1H), 8.47 (d, J = 0.8, 1H), 7.07 (d, J = 5.8, 1H), 4.47 (dd, J = 10.3, 4.2, 1H), 4.32 (dd, J = 10.2, 5.3, 1H), 3.07 (m, 1H), 2.81 (m, 1H), 2.70 (m, 3H), 2.60-2.53 (m, 1H), 2.34 (s, 3H), 2.23-2.15 (m, 1H), NH signals not observed. |
| 9 | 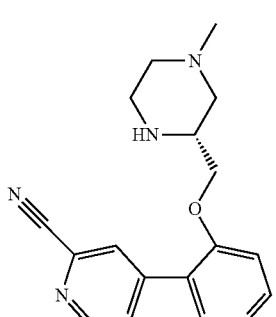<br>(R)-4-((4-methylpiperazin-2-yl)methoxy)-9H-dipyrido[2,3-b;4',3'-d]pyrrole-6-carbonitrile | A-1 | 2.664, 323.1, E | $^1$H NMR (400 MHz, d$_6$-DMSO) δ 8.96 (d, J = 0.8, 1H), 8.53 (m, 2H), 7.03 (d, J = 5.8, 1H), 4.32-4.23 (m, 2H), 2.91 (m, 1H), 2.86-2.74 (m, 2H), 2.60 (m, 1H), 2.19 (s, 3H), 1.98 (m, 1H), 1.90 (m, 1H), NH signals not observed. |

TABLE 1-continued

| Example | Structure/Name | Coupling Method | LCMS R$_T$ (min), M + H$^+$, Method | $^1$H NMR (ppm) |
|---|---|---|---|---|
| 10 | 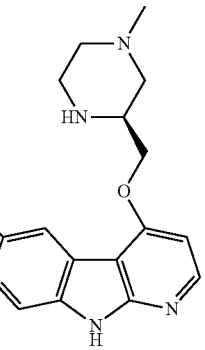<br>(S)-4-((4-methylpiperazin-2-yl)methoxy)-9H-dipyrido[2,3-b;4',3'-d]pyrrole-6-carbonitrile | A | 6.327, 323.1, D | $^1$H NMR (400 MHz, d$_6$-DMSO) δ 8.97 (d, J = 0.9, 1H), 8.55 (m, 2H), 7.05 (d, J = 5.8, 1H), 4.33-4.23 (m, 2H), 2.91 (m, 1H), 2.87-2.74 (m, 2H), 2.60 (m, 1H), 1.98 (td, J = 10.6, 3.0, 1H), 1.91 (t, J = 9.9, 1H), NH signals not observed. |
| 11 | 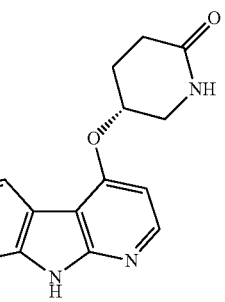<br>(R)-4-((piperdin-2-one)-5-yloxy)-9H-dipyrido[2,3-b;4',3'-d]pyrrole-6-carbonitrile | A-1 | 7.026, 308.0, D | $^1$H NMR (400 MHz, d$_6$-DMSO) δ 12.72 (s, 1H), 8.98 (d, J = 0.8, 1H), 8.56 (d, J = 5.8, 1H), 8.36 (d, J = 0.8, 1H), 7.60 (s, 1H), 7.17 (d, J = 5.9, 1H), 5.33-5.22 (m, 1H), 3.58 (m, 2H), 2.42-2.29 (m, 2H), 2.23 (m, 2H). |
| 12 | 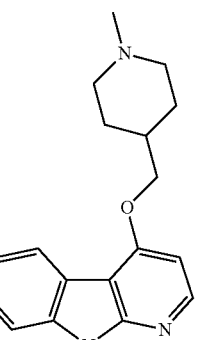<br>4-((1-methylpiperidin-4-yl)methoxy)-9H-dipyrido[2,3-b;4',3'-d]pyrrole-6-carbonitrile | A-1 | 6.510, 322.1, D | $^1$H NMR (400 MHz, d$_6$-DMSO) δ 12.77 (s, 1H), 8.98 (d, J = 0.9, 1H), 8.54 (d, J = 5.7, 1H), 8.42 (d, J = 0.9, 1H), 7.05 (d, J = 5.8, 1H), 4.25 (d, J = 6.3, 2H), 2.91 (m, 2H), 2.26 (s, 3H), 2.07 (m, 2H), 1.99 (m, 1H), 1.88 (m, 2H), 1.47 (m, 2H). |

TABLE 1-continued

| Example | Structure/Name | Coupling Method | LCMS R$_T$ (min), M + H$^+$, Method | $^1$H NMR (ppm) |
|---|---|---|---|---|
| 13 | 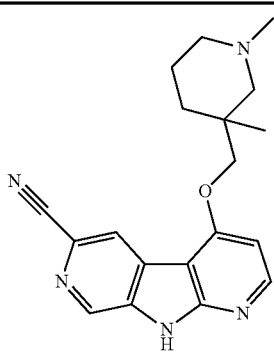<br>4-((1,3-dimethylpiperidin-3-yl)methoxy)-9H-dipyrido[2,3-b;4',3'-d]pyrrole-6-carbonitrile | A-1 | 3.218, 336.1, E | $^1$H NMR (400 MHz, d$_6$-DMSO) δ 12.78 (s, 1H), 8.99 (d, J = 0.8, 1H), 8.54 (d, J = 5.7, 1H), 8.37 (s, 1H), 7.08 (d, J = 5.8, 1H), 4.30 (d, J = 9.2, 1H), 4.22 (d, J = 9.3, 1H), 2.51 (m, 1H), 2.38 (m, 1H), 2.17 (m, 3H), 2.17 (s, 1H), 2.11 (m2, 1H), 1.74-1.55 (m, 3H), 1.34 (m, 1H), 1.19 (s, 3H). |
| 14 | 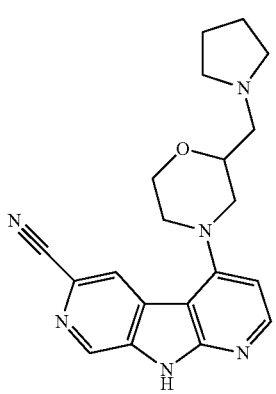 [SMILES: N#Cc1cc2c(cn1)[nH]c1nccc(N3CCOC(CN4CCCC4)C3)c12]<br>4-(2-(pyrrolidin-1-ylmethyl)morpholino)-9H-dipyrido[2,3-b;4',3'-d]pyrrole-6-carbonitrile | B-1 | 6.140, 363.1, D | $^1$H NMR (400 MHz, d$_6$-DMSO) δ 12.82 (s, 1H), 8.98 (s, 1H), 8.50 (d, J = 5.5, 1H), 8.21 (s, 1H), 6.92 (d, J = 5.6, 1H), 4.11 (m, 1H), 4.05 (m, 1H), 3.95 (t, J = 10.4, 1H), 3.78 (d, J = 12.5, 1H), 3.49 (d, J = 11.7, 1H), 3.17-3.06 (m, 1H), 2.78-2.52 (m, 7H), 1.69 (s, 4H). |
| 15 | 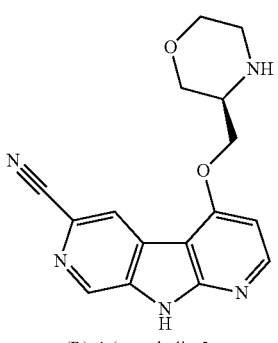<br>(R)-4-(morpholin-3-ylmethoxy)-9H-dipyrido[2,3-b;4',3'-d]pyrrole-6-carbonitrile | A-1 | 6.907, 310.1, D | $^1$H NMR (400 MHz, d$_6$-DMSO) δ 12.78 (s, 1H), 8.97 (d, J = 0.9, 1H), 8.58 (d, J = 0.9, 1H), 8.55 (d, J = 5.7, 1H), 7.05 (d, J = 5.8, 1H), 4.31-4.19 (m, 2H), 3.95 (m, 1H), 3.73 (m, 1H), 3.49-3.42 (m, 2H), 3.41-3.22 (m, 2H), 2.92-2.78 (m, 2H), morpholine NH signal not observed. |

TABLE 1-continued

| Example | Structure/Name | Coupling Method | LCMS R_T (min), M + H+, Method | ¹H NMR (ppm) |
|---|---|---|---|---|
| 16 | 4-(quinuclidin-3-ylmethoxy)-9H-dipyrido[2,3-b;4',3'-d]pyrrole-6-carbonitrile | A-1 | 7.696, 334.1, D | ¹H NMR (400 MHz, d$_6$-DMSO) δ 8.97 (d, J = 0.9, 1H), 8.56 (d, J = 5.7, 1H), 8.40 (d, J = 0.9, 1H), 7.11 (d, J = 5.8, 1H), 4.38 (m, 2H), 3.20-3.12 (m, 1H), 2.78 (m, 4H), 2.61-2.53 (m, 1H), 2.44-2.34 (m, 1H), 1.96 (m, 1H), 1.75 (m, 1H), 1.65 (m, 2H), 1.42 (m, 1H), NH signal not observed. |
| 17 | trans-4-(4-fluoropiperidin-3-yloxy)-9H-dipyrido[2,3-b;4',3'-d]pyrrole-6-carbonitrile | A-1 | 7.490, 312.0, D | ¹H NMR (400 MHz, d$_6$-DMSO) δ 8.97 (d, J = 0.9, 1H), 8.62 (d, J = 0.9, 1H), 8.54 (d, J = 5.8, 1H), 7.15 (d, J = 5.9, 1H), 5.09 (m, 1H), 4.86-4.69 (m, 1H), 3.06-2.94 (m, 1H), 2.69-2.52 (m, 3H), 2.25-2.13 (m, 1H), 1.78-1.61 (m, 1H), NH signals not observed. |
| 18 | 4-((1R,3S,4S)-2-azabicyclo[2.2.1]heptan-3-ylmethoxy)-9H-dipyrido[2,3-b;4',3'-d]pyrrole-6-carbonitrile | A-1 | 1.48 min, 320.18, F | ¹H NMR (400 MHz, d$_6$-DMSO) δ 8.97 (d, J = 0.9, 1H), 8.53 (dd, J = 3.3, 2.3, 2H), 7.01 (d, J = 5.8, 1H), 4.14 (m, 1H), 4.05-3.90 (m, 1H), 3.42 (m, 1H), 2.56-2.49 (m, 1H), 2.44 (m, 1H), 1.64 (m, 3H), 1.55-1.40 (m, 2H), 1.23 (m, 1H), NH signals not observed. |
| 19 | (S)-4-(2-((dimethylamino)methyl)morpholino)-9H-dipyrido[2,3-b;4',3'-d]pyrrole-6-carbonitrile | B-1 | 5.081, 337.2, D | ¹H NMR (400 MHz, d$_6$-DMSO) δ 12.82 (s, 1H), 8.98 (d, J = 0.8, 1H), 8.49 (d, J = 5.6, 1H), 8.23 (d, J = 0.7, 1H), 6.91 (d, J = 5.6, 1H), 4.18-3.99 (m, 2H), 3.93 (m, 1H), 3.81 (d, J = 12.6, 1H), 3.49 (d, J = 12.6, 1H), 3.18-3.01 (m, 1H), 2.64 (m, 1H), 2.41-2.36 (m, 2H), 2.25 (s, 6H). |

TABLE 1-continued

| Example | Structure/Name | Coupling Method | LCMS R$_T$ (min), M + H$^+$, Method | $^1$H NMR (ppm) |
|---|---|---|---|---|
| 20 | (R)-4-(2-((dimethylamino)methyl)morpholino)-9H-dipyrido[2,3-b;4',3'-d]pyrrole-6-carbonitrile | B-1 | 5.081, 337.2, D | $^1$H NMR (400 MHz, d$_6$-DMSO) δ 12.82 (s, 1H), 8.98 (d, J = 0.8, 1H), 8.49 (d, J = 5.6, 1H), 8.23 (d, J = 0.7, 1H), 6.91 (d, J = 5.6, 1H), 4.18-3.99 (m, 2H), 3.93 (m, 1H), 3.81 (d, J = 12.6, 1H), 3.49 (d, J = 12.6, 1H), 3.18-3.01 (m, 1H), 2.64 (m, 1H), 2.41-2.36 (m, 2H), 2.25 (s, 6H). |
| 21 | (S)-4-(2-((methylamino)methyl)-9H-dipyrido[2,3-b;4',3'-d]pyrrole-6-carbonitrile | B-1 | 2.429, 323.2, E | $^1$H NMR (500 MHz, d$_6$-DMSO) δ 8.97 (s, 1H), 8.49 (d, J = 5.5, 1H), 8.20 (s, 1H), 6.92 (d, J = 5.6, 1H), 4.06 (m, 2H), 3.95 (m, 1H), 3.74 (d, J = 12.3, 1H), 3.56 (d, J = 12.8, 1H), 3.16-3.09 (m, 1H), 2.86-2.81 (m, 1H), 2.79 (m, 2H), 2.44 (s, 3H), NH signal not observed. |
| 22 | (R)-4-(2-((methylamino)methyl)-9H-dipyrido[2,3-b;4',3'-d]pyrrole-6-carbonitrile | B-1 | 2.402, 323.2, E | $^1$H NMR (500 MHz, d$_6$-DMSO) δ 8.96 (s, 1H), 8.47 (d, J = 5.5, 1H), 8.20 (s, 1H), 6.90 (d, J = 5.6, 1H), 4.04 (m, 2H), 4.00-3.87 (m, 2H), 3.78 (d, J = 12.6, 1H), 3.53 (d, J = 12.1, 1H), 3.16-3.07 (m, 1H), 2.77 (m, 1H), 2.63 (m, 2H), 2.36 (s, 3H), NH signal not observed. |

TABLE 1-continued

| Example | Structure/Name | Coupling Method | LCMS R_T (min), M + H+, Method | 1H NMR (ppm) |
|---|---|---|---|---|
| 23 | 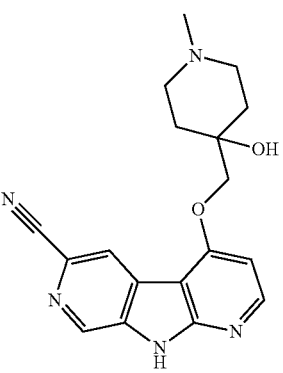 [SMILES: CN1CCC(O)(COc2ccnc3[nH]c4cnc(C#N)cc4c23)CC1] 4-((4-hydroxy-1-methylpiperidin-4-yl)methoxy)-9H-dipyrido[2,3-b;4',3'-d]pyrrole-6-carbonitrile | A-1 | 5.298, 338.2, D | 1H NMR (500 MHz, d6-DMSO) δ 12.75 (s, 1H), 8.97 (d, J = 0.9, 1H), 8.66 (s, 1H), 8.54 (d, J = 5.7, 1H), 7.05 (d, J = 5.8, 1H), 4.92 (s, 1H), 4.16 (s, 2H), 2.61 (m, 2H), 2.42 (m, 2H), 2.26 (s, 3H), 1.77 (m, 4H). |
| 24 | 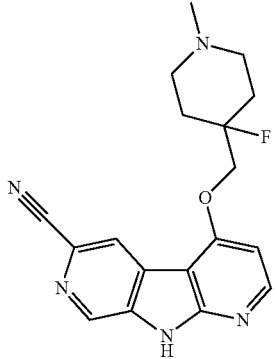 [SMILES: CN1CCC(F)(COc2ccnc3[nH]c4cnc(C#N)cc4c23)CC1] 4-((4-fluoro-1-methylpiperidin-4-yl)methoxy)-9H-dipyrido[2,3-b;4',3'-d]pyrrole-6-carbonitrile | A-1 | 6.49, 340.1, D | 1H NMR (500 MHz, d6-DMSO) δ 8.99 (d, J = 0.9, 1H), 8.57 (d, J = 5.7, 1H), 8.34 (d, J = 0.9, 1H), 7.09 (d, J = 5.8, 1H), 4.53 (s, 1H), 4.49 (s, 1H), 2.68 (m, 2H), 2.25 (m, 2H), 2.23 (s, 3H), 2.04 (m, 2H), 2.00-1.84 (m, 2H), NH signal not observed. |
| 25 | 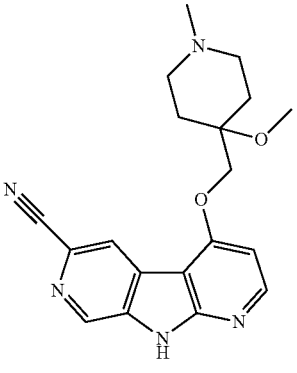 [SMILES: COC1(COc2ccnc3[nH]c4cnc(C#N)cc4c23)CCN(C)CC1] 4-((4-methoxy-1-methylpiperidin-4-yl)methoxy)-9H-dipyrido[2,3-b;4',3'-d]pyrrole-6-carbonitrile | A-1 | 6.34, 352.1, D | 1H NMR (500 MHz, d6-DMSO) δ 8.97 (d, J = 0.9, 1H), 8.55 (d, J = 5.7, 1H), 8.32 (s, 1H), 7.07 (d, J = 5.8, 1H), 4.34 (s, 2H), 3.25 (s, 3H), 2.58-2.50 (m, 2H), 2.25 (m, 2H), 2.20 (s, 3H), 1.93 (m, 2H), 1.81-1.70 (m, 2H), NH signal not observed. |

TABLE 1-continued

| Example | Structure/Name | Coupling Method | LCMS R_T (min), M + H+, Method | 1H NMR (ppm) |
|---|---|---|---|---|
| 26 | 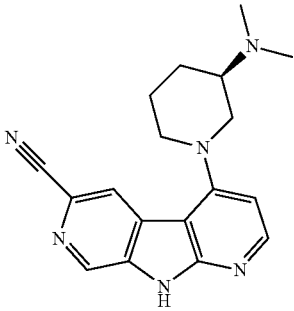 [SMILES: CN(C)[C@@H]1CCCN(c2ccnc3[nH]c4cnc(C#N)cc4c23)C1]<br>(R)-4-3-(dimethylamino)piperidin-1-yl)-9H-dipyrido[2,3-b;4',3'-d]pyrrole-6-carbonitrile | B-1 | 5.363, 321.1, D | 1H NMR (500 MHz, d6-DMSO) δ 12.71 (s, 1H), 8.95 (d, J = 0.7, 1H), 8.44 (d, J = 5.6, 1H), 8.19 (s, 1H), 6.90 (d, J = 5.6, 1H), 3.84 (d, J = 9.8, 1H), 3.60 (d, J = 12.7, 1H), 2.91 (m, 1H), 2.81-2.68 (m, 2H), 2.29 (s, 6H), 2.08 (m, 1H), 1.95 (m, 1H), 1.80 (m, 1H), 1.44 (m, 1H). |
| 27 | 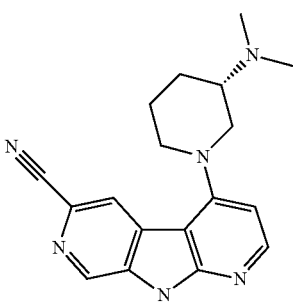<br>(S)-4-3-(dimethylamino)piperidin-1-yl)-9H-dipyrido[2,3-b;4',3'-d]pyrrole-6-carbonitrile | B-1 | 5.350, 321.2, D | 1H NMR (500 MHz, d6-DMSO) δ 12.71 (s, 1H), 8.95 (d, J = 0.7, 1H), 8.44 (d, J = 5.6, 1H), 8.19 (s, 1H), 6.90 (d, J = 5.6, 1H), 3.84 (d, J = 10.6, 1H), 3.60 (d, J = 12.6, 1H), 2.91 (m, 1H), 2.75 (m, 2H), 2.28 (s, 6H), 2.08 (m, 1H), 1.95 (m, 1H), 1.79 (m, 1H), 1.50-1.37 (m, 1H). |
| 28 | 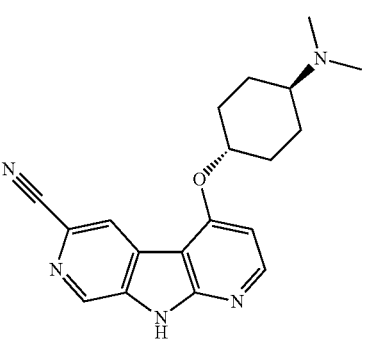 [SMILES: CN(C)[C@H]1CC[C@H](Oc2ccnc3[nH]c4cnc(C#N)cc4c23)CC1]<br>4-((1r,4r)-4-(dimethylamino)cyclohexyloxy)-9H-dipyrido[2,3-b;4',3'-d]pyrrole-6-carbonitrile | A-1 | 6.465, 336.1, A | 1H NMR (500 MHz, d6-DMSO) δ 8.93 (s, 1H), 8.48 (d, J = 5.7, 1H), 8.43 (s, 1H), 7.04 (d, J = 5.8, 1H), 4.74 (m, 1H), 2.28 (m, 3H), 2.21 (s, 6H), 1.90 (m, 2H), 1.73-1.62 (m, 2H), 1.47 (m, 2H), NH signal not observed. |

Example 29

(R)-4-((1-methylpiperidin-3-yl)methoxy)-9H-dipyrido[2,3-b;4',3'-d]pyrrole-6-carbonitrile

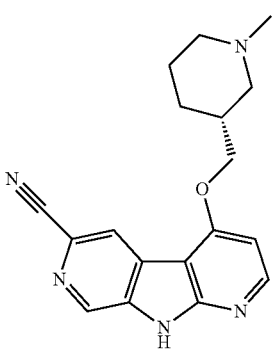 [SMILES: CN1CCC[C@@H](COc2ccnc3[nH]c4cnc(C#N)cc4c23)C1]

Step 1: (R)-tert-butyl 3-((6-cyano-9-((2-(trimethylsilyl)ethoxy)methyl)-9H-[2,3-b;4',3'-d]pyrrol-4-yloxy)methyl)piperidine-1-carboxylate

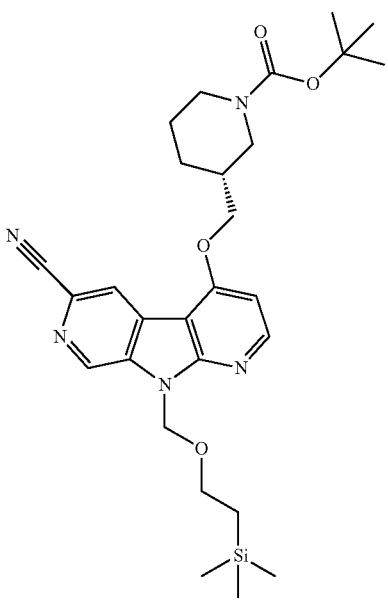 [SMILES: CC(C)(C)OC(=O)N1CCC[C@@H](COc2ccnc3c2c2cc(C#N)ncc2n3COCC[Si](C)(C)C)C1]

To a solution of (R)-tert-butyl 3-(hydroxymethyl)piperidine-1-carboxylate (120 mg, 0.56 mmol) in tetrahydrofuran (1.8 mL) was added sodium hydride as a 60% dispersion in mineral oil (22 mg, 0.56 mmol). The reaction mixture was stirred at ambient temperature for 5 minutes before 4-chloro-9-(2-trimethylsilanyl-ethoxymethyl)-9H-dipyrido[2,3-b;4',3'-d]pyrrole-6-carbonitrile (100 mg, 0.3 mmol) was added in one portion. The reaction mixture was stirred at ambient temperature for 10 minutes before being warmed to 40° C. for 2 hours. The mixture was diluted with water (20 mL) and ethyl acetate (50 mL). The organic layer was separated, dried over sodium sulfate, filtered, concentrated in vacuo, and purified flash chromatography (silica, 4 g, ISCO, 5-75% ethyl acetate in heptane) to afford the title compound as a colorless oil, which was used in the next step without any further purification (105 mg).

Step 2: (R)-4-(piperidin-3-ylmethoxy)-9-((2-(trimethylsilyl ethoxy)methyl)-9H-dipyrido[2,3-b;4',3'-d]pyrrole-6-carbonitrile

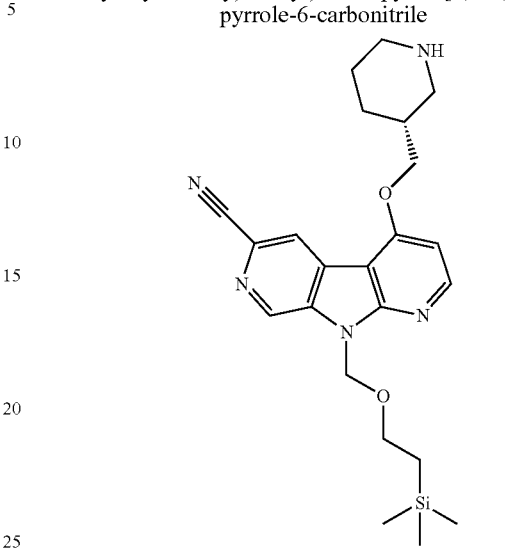

A solution of (R)-tert-butyl 3-((6-cyano-9-((2-(trimethylsilyl)ethoxy)methyl)-9H-[2,3-b;4',3'-d]pyrrol-4-yloxy)methyl)piperidine-1-carboxylate (105 mg, 0.21 mmol) in methylene chloride (2 mL) was treated with trifluoroacetic acid (0.3 mL, 4.0 mmol). The reaction mixture was stirred at ambient temperature for 2 hours and then diluted with methylene chloride (50 mL) and washed with saturated aqueous sodium carbonate solution (10 mL). The organic layer was separated, dried over sodium sulfate, filtered, concentrated in vacuo, and purified flash chromatography (silica, 4 g, ISCO, 0-10% methylene chloride in methanol) to afford the title compound as a yellow foam, which was used in the next step without any further purification (60 mg, 50% over two steps).

Step 3: (R)-4-(1-methylpiperidin-3-ylmethoxy)-9-((2-(trimethylsilyl)ethoxy)methyl)-9H-dipyrido[2,3-b;4',3'-d]pyrrole-6-carbonitrile

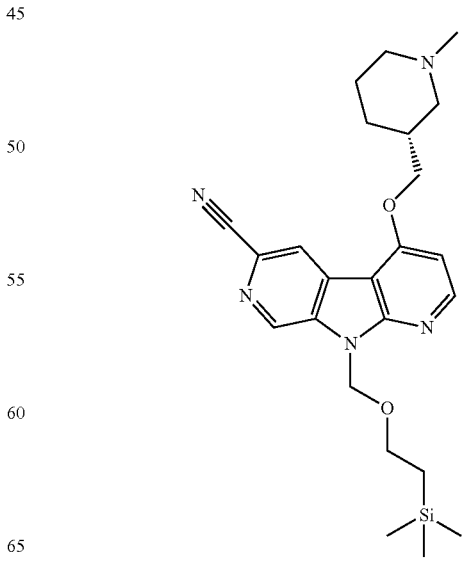

To a solution of (R)-4-(piperidin-3-ylmethoxy)-9-((2-(trimethylsilyl)ethoxy)methyl)-9H-dipyrido[2,3-b;4',3'-d]pyrrole-6-carbonitrile (50 mg, 0.1 mmol) in acetonitrile (0.5 mL) and water (0.1 mL) was added Formalin (0.024 mL, 0.3 mmol) followed by sodium triacetoxyborohydride (48 mg, 0.2 mmol). The reaction mixture was stirred for 20 minutes at ambient temperature and then basified by the addition of saturated aqueous sodium carbonate solution (1 mL), diluted with methylene chloride (50 mL) and methanol (5 mL), and washed with saturated aqueous sodium bicarbonate solution (2×15 mL). The organic layer was separated, dried over sodium sulfate, and concentrated in vacuo to afford a pale yellow solid, which was used in the next step without any further purification (45 mg).

Step 4: (R)-4-((1-methylpiperidin-3-yl)methoxy)-9H-dipyrido[2,3-b;4',3'-d]pyrrole-6-carbonitrile

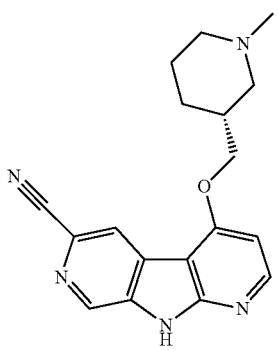

(R)-4-(1-methylpiperidin-3-ylmethoxy)-9-((2-(trimethylsilyl)ethoxy)methyl)-9H-dipyrido[2,3-b;4',3'-d]pyrrole-6-carbonitrile (45 mg, 0.1 mmol) was dissolved in 1,4-dioxane (0.2 mL) and then treated with 48% $HBr_{(aq)}$ (0.2 mL) and heated at 75° C. for 15 minutes. The cooled reaction mixture was then basified to pH ~12 by dropwise addition of 6N sodium hydroxide and then immediately acidified to pH ~8-9 by dropwise addition of concentrated hydrochloric acid, producing a cloudy precipitate. The solid was collected by centrifugation, dissolved in dimethylsulfoxide (2 mL), and purified by preparative HPLC [5-85% methanol in water (0.1% ammonium hydroxide) over 30 min, 35 mL/min] to afford the title compound as a pale yellow solid (26 mg, 70% over two steps). $^1$H NMR (400 MHz, $d_6$-DMSO) δ 8.97 (d, J=0.7, 1H), 8.54 (d, J=5.7, 1H), 8.44 (s, 1H), 7.04 (d, J=5.8, 1H), 4.28 (d, J=6.4, 2H), 2.88 (m, 1H), 2.65 (m, 1H), 2.27 (m, 1H), 2.19 (s, 3H), 1.97 (m, 2H), 1.83 (m, 1H), 1.74-1.66 (m, 1H), 1.59 (m, 1H), 1.28-1.18 (m, 1H), NH signal not observed. LCMS (method D): $R_T$=7.182 min, M+H$^+$=322.1.

Example 30

(R)-4-(4-methylmorpholin-2-ylmethoxy)-9H-dipyrido[2,3-b;4',3'-d]pyrrole-6-carbonitrile

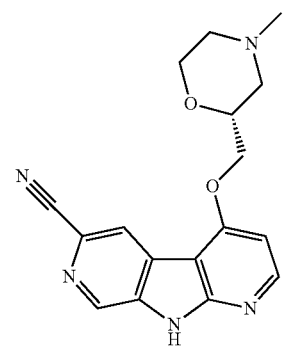 [SMILES: CN1CCO[C@@H](COc2ccnc3[nH]c4cnc(C#N)cc4c23)C1]

The title compound was prepared following a similar procedure to the previous example using (R)-tert-butyl 2-(hydroxymethyl)morpholine-4-carboxylate. $^1$H NMR (400 MHz, $d_6$-DMSO) δ 8.97 (d, J=0.8, 1H), 8.54 (d, J=5.7, 1H), 8.46 (d, J=0.8, 1H), 7.03 (d, J=5.8, 1H), 4.39 (d, J=4.8, 2H), 4.11-4.00 (m, 1H), 3.92-3.84 (m, 1H), 3.64 (m, 1H), 2.90 (m, 1H), 2.66 (m, 1H), 2.24 (s, 3H), 2.11-1.99 (m, 2H), NH signal not observed. LCMS (method D): $R_T$=6.372 min, M+H$^+$=324.0.

Example 31

(R)-4-(1-ethylpyrrolidin-3-yloxy)-9H-dipyrido[2,3-b;4',3'-d]pyrrole-6-carbonitrile The title compound was prepared following a similar procedure to the previous example using (R)-tert-butyl 3-hydroxypyrrolidine-1-carboxylate and acetaldehyde. $^1$H NMR (400 MHz, $d_6$-DMSO) δ 12.75 (s, 1H), 8.97 (d, J=0.9, 1H), 8.53 (d, J=5.7, 1H), 8.50 (d, J=0.9, 1H), 6.96 (d, J=5.8, 1 H), 5.25 (m, 1H), 2.99 (m, 1H), 2.89 (m, 1H), 2.83 (m, 1H), 2.57-2.37 (m, 4H), 2.15-2.05 (m, 1H), 1.07 (t, J=7.2, 3H). LCMS (method E): $R_T$=3.868 min, M+H$^+$=308.1.

Example 32

(S)-4-((1-ethylpyrrolidin-2-yl)methoxy)-9H-dipyrido[2,3-b;4',3'-d]pyrrole-6-carbonitrile

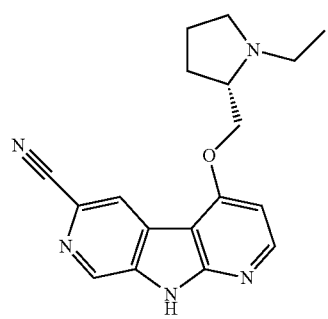 [SMILES: CCN1CCC[C@H]1COc1ccnc2[nH]c3cnc(C#N)cc3c12]

The title compound was prepared following a similar procedure to the previous example using (S)-tert-butyl 2-(hydroxymethyl)pyrrolidine-1-carboxylate and acetaldehyde. $^1$H NMR (400 MHz, $d_6$-DMSO) δ 12.76 (s, 1H), 8.97 (d, J=0.9, 1H), 8.54 (d, J=5.7, 1H), 8.42 (d, J=0.9, 1 H), 7.06 (d, J=5.8, 1H), 4.32 (m, 1H), 4.24-4.13 (m, 1H), 3.10 (m, 1H), 3.07-2.94 (m, 2H), 2.47-2.41 (m, 1H), 2.29 (m, 1H), 2.14-2.00 (m, 1H), 1.83-1.72 (m, 3H), 1.05 (m, 3H). LCMS (method E): $R_T$=3.933 min, M+H$^+$=322.1. LCMS (method D): $R_T$=7.696 min, M+H$^+$=334.1.

Example 33

(S)-tert-butyl 1-(6-cyano-9-((2-(trimethylsilyl)ethoxy)methyl)-9H-dipyrido[2,3-b;4',3'-d]pyrrol-4-yl)piperidin-3-ylcarbamate

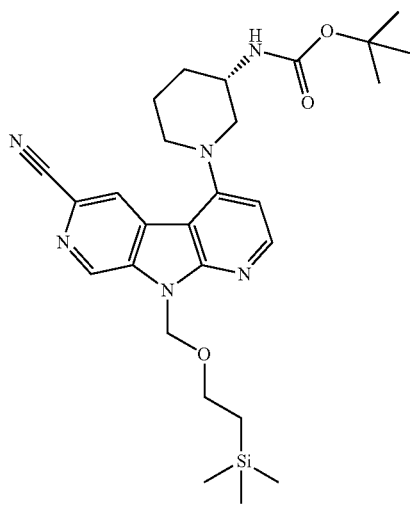 [SMILES: CC(C)(C)OC(=O)N[C@H]1CCCN(c2ccnc3c2c2cc(C#N)ncc2n3COCC[Si](C)(C)C)C1]

A mixture of 4-chloro-9-(2-trimethylsilanyl-ethoxymethyl)-9H-dipyrido[2,3-b;4',3'-d]pyrrole-6-carbonitrile (100 mg, 0.3 mmol) and (S)-tert-butyl piperidin-3-ylcarbamate (167 mg, 0.9 mmol) in N,N-dimethylacetamide (1.3 mL) was heated at 100° C. for 2 hours. The cooled reaction mixture was diluted with ethyl acetate (50 mL) and washed with water (20 mL). The organic layer was separated, dried over sodium sulfate, filtered, concentrated in vacuo, and purified by flash chromatography (silica, 4 g, ISCO, 0-60% ethyl acetate in heptane) to afford the title compound as a white solid, which was used in the next step without any further purification (130 mg, 90%).

Example 34 tert-butyl 4-(6-cyano-9-((2-(trimethylsilyl)ethoxy)methyl)-9H-dipyrido[2,3-b;4',3'-d]pyrrol-4-yl)piperazine-1-carboxylate

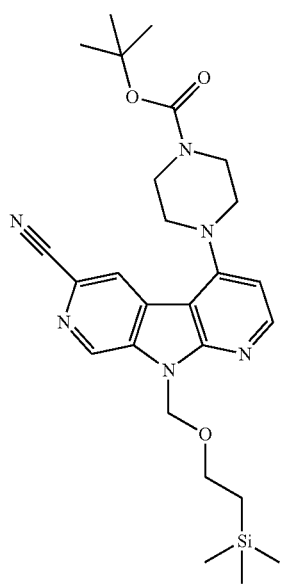 [SMILES: CC(C)(C)OC(=O)N1CCN(c2ccnc3c2c2cc(C#N)ncc2n3COCC[Si](C)(C)C)CC1]

The title compound was prepared following a similar procedure to the previous example using tert-butyl piperazine-1-carboxylate and used in the next step without any further purification.

Example 35

(S)-4-(3-(ethylamino)piperidin-1-yl)-9H-dipyrido[2,3-b;4',3'-d]pyrrole-6-carbonitrile

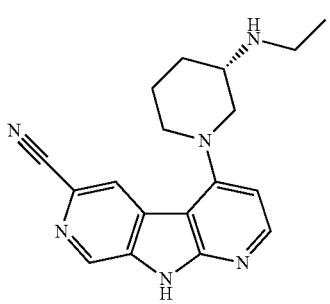 [SMILES: CCN[C@H]1CCCN(c2ccnc3[nH]c4cnc(C#N)cc4c23)C1]

Step 1: (S)-tert-butyl 1-(6-cyano-9-((2-(trimethylsilyl)ethoxy)methyl)-9H-dipyrido[2,3-b;4',3'-d]pyrrol-4-yl)piperidin-3-yl(ethyl)carbamate

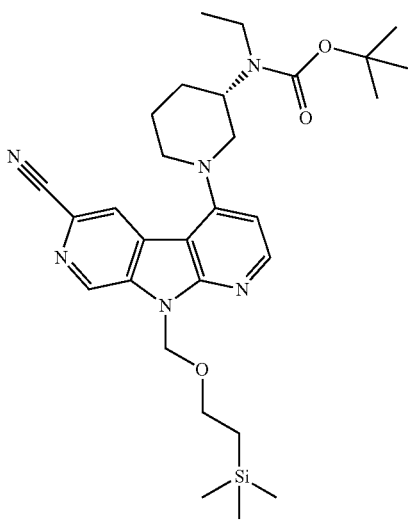 [SMILES: CCN(C(=O)OC(C)(C)C)[C@H]1CCCN(c2ccnc3c2c2cc(C#N)ncc2n3COCC[Si](C)(C)C)C1]

To a solution of (S)-tert-butyl 1-(6-cyano-9-((2-(trimethylsilyl)ethoxy)methyl)-9H-dipyrido[2,3-b;4',3'-d]pyrrol-4-yl)piperidin-3-ylcarbamate (130 mg, 0.25 mmol) in tetrahydrofuran (2 mL) was added sodium hydride as a 60% dispersion in mineral oil (20 mg, 0.5 mmol) followed by iodoethane (0.06 mL, 0.75 mmol) and reaction mixture was stirred overnight at ambient temperature. The reaction was quenched with water (30 μL), diluted with ethyl acetate (50 mL) and washed with water (20 mL). The organic layer was separated, dried over sodium sulfate, filtered, concentrated in vacuo, and purified by flash chromatography (silica, 4 g, ISCO, 0-60% ethyl acetate in heptane) to afford the title compound as a colorless oil, which was used in the next step without any further purification (90 mg).

Step 2: (S)-4-(3-(ethylamino)piperidin-1-yl)-9H-dipyrido[2,3-b;4',3'-d]pyrrole-6-carbonitrile

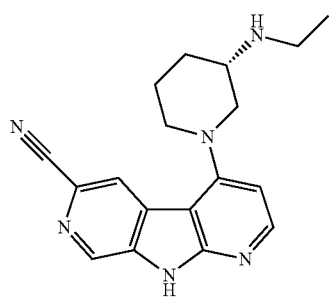 [SMILES: CCN[C@H]1CCCN(c2ccnc3[nH]c4cnc(C#N)cc4c23)C1]

(S)-tert-butyl 1-(6-cyano-9-((2-(trimethylsilyl)ethoxy)methyl)-9H-dipyrido[2,3-b;4',3'-d]pyrrol-4-yl)piperidin-3-yl(ethyl)carbamate (90 mg, 0.15 mmol) was dissolved in 1,4-dioxane (0.3 mL) and then treated with 48% HBr$_{(aq)}$ (0.3 mL) and heated at 75° C. for 15 minutes. The cooled reaction mixture was then basified to pH ~12 by dropwise addition of 6N sodium hydroxide and then immediately acidified to pH ~8-9 by dropwise addition of concentrated hydrochloric acid, producing a cloudy precipitate. The solid was collected by centrifugation, dissolved in dimethylsulfoxide (2 mL), and purified by preparative HPLC [5-85% methanol in water (0.1% ammonium hydroxide) over 30 min, 35 mL/min] to afford the title compound as a white solid (30 mg, 40% over two steps). $^1$H NMR (500 MHz, d$_6$-DMSO) δ 8.94 (s, 1H), 8.45-8.39 (m, 2H), 6.87 (d, J=5.6, 1H), 3.71 (d, J=11.1, 1H), 3.51 (d, J=12.0, 1H), 3.08-2.99 (m, 1H), 2.99-2.90 (m, 1H), 2.80-2.72 (m, 1H), 2.72-2.66 (m, 1H), 2.62 (m, 1H), 2.01 (m, 1H), 1.93 (m, 1H), 1.78 (m, 1H), 1.37 (m, 1H), 1.05 (t, J=7.1, 3H), NH signal not observed. LCMS (Method E): R$_T$=2.576 min, M+H$^+$=321.1.

Example 36

(R)-4-(3-(ethylamino)piperidin-1-yl)-9H-dipyrido[2,3-b;4',3'-d]pyrrole-6-carbonitrile

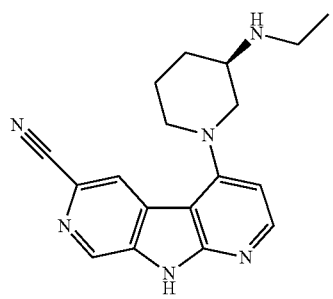 [SMILES: CCN[C@@H]1CCCN(c2ccnc3[nH]c4cnc(C#N)cc4c23)C1]

The title compound was prepared following a similar procedure to the previous example using (R)-tert-butyl piperidin-3-ylcarbamate. $^1$H NMR (500 MHz, d$_6$-DMSO) δ 8.94 (s, 1H), 8.43 (d, J=5.6, 1H), 8.41 (s, 1H), 6.87 (d, J=5.6, 1H), 3.71 (d, J=10.9, 1H), 3.51 (d, J=11.7, 1 H), 3.08-2.99 (m, 1H), 2.94 (m, 1H), 2.80-2.73 (m, 1H), 2.69 (m, 1H), 2.62 (m, 1H), 2.00 (m, 1H), 1.92 (m, 1H), 1.78 (m, 1H), 1.37 (m, 1H), 1.06 (t, J=7.1, 3H), NH signal not observed. LCMS (Method D): R$_T$=5.537 min, M+H$^+$=321.1.

Example 37

(S)-4-(4-(2-(pyrrolidin-2-yl)acetyl)piperazin-1-yl)-9H-dipyrido[2,3-b;4',3'-d]pyrrole-6-carbonitrile

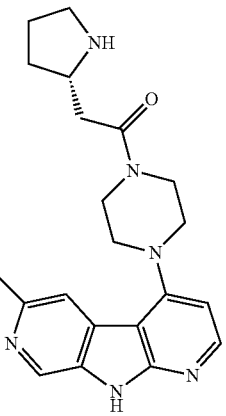

Step 1: 4-(piperazin-1-yl)-9-((2-(trimethylsilyl)ethoxy)methyl)-9H-dipyrido[2,3-b;4',3'-d]pyrrole-6-carbonitrile

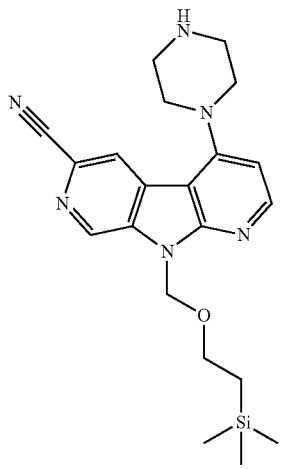 [SMILES: C[Si](C)(C)CCOCn1c2cnc(C#N)cc2c2c(N3CCNCC3)ccnc21]

A solution of tert-butyl 4-(6-cyano-9-((2-(trimethylsilyl)ethoxy)methyl)-9H-dipyrido[2,3-b;4',3'-d]pyrrol-4-yl)piperazine-1-carboxylate (440 mg, 0.8 mmol) in methylene chloride (3 mL) was treated with trifluoroacetic acid (0.6 mL, 8.0 mmol) and the reaction mixture was stirred at ambient temperature for 4 hours. The reaction mixture was diluted with methylene chloride (50 mL) and washed with saturated aqueous sodium carbonate solution (10 mL). The organic layer was separated, dried over sodium sulfate, filtered, concentrated in vacuo, and purified flash chromatography (silica, 4 g, ISCO, 0-10% methylene chloride in methanol) to afford the title compound as a white foam, which was used in the next step without any further purification (200 mg, 60%).

Step 2: (S)-tert-butyl 2-(2-(4-(6-cyano-9-((2-(trimethylsilyl)ethoxymethyl)-9H-dipyrido[2,3-b;4'3'-d]pyrro-4-yl)piperazin-1-yl)-2-oxoethyl)pyrrolidine-1-carboxylate

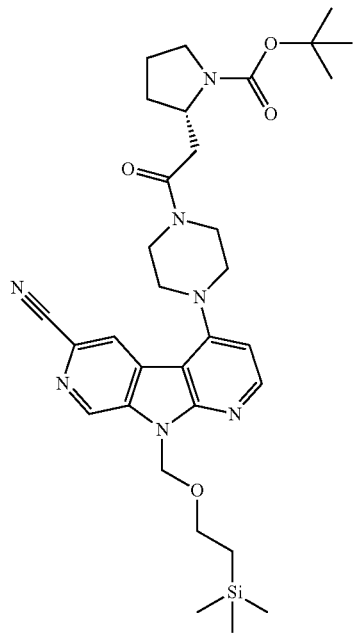 [SMILES: CC(C)(C)OC(=O)N1CCC[C@H]1CC(=O)N1CCN(c2ccnc3c2c2cc(C#N)ncc2n3COCC[Si](C)(C)C)CC1]

A mixture of 4-(piperazin-1-yl)-9-((2-(trimethylsilyl)ethoxy)methyl)-9H-dipyrido[2,3-b;4',3'-d]pyrrole-6-carbonitrile (100 mg, 0.2 mmol), (S)-2-(1-(tert-butoxycarbonyl)pyrrolidin-2-yl)acetic acid (220 mg, 1.0 mmol), 1-hydroxybenzotriazole (50 mg, 0.4 mmol), (3-dimethylamino-propyl)-ethyl-carbodiimide hydrogen chloride (70 mg, 0.4 mmol), and triethylamine (0.1 mL, 0.7 mmol) in methylene chloride (2.5 mL) was stirred at ambient temperature overnight. The reaction mixture was diluted with methylene chloride (50 mL) and washed with saturated aqueous sodium bicarbonate solution (20 mL). The organic layer was separated, dried over sodium sulfate, filtered, concentrated in vacuo, and purified flash chromatography (silica, 4 g, ISCO, 0-70% ethyl acetate in heptane) to afford the title compound as a white foam, which was used in the next step without any further purification (140 mg).

Step 3: (S)-4-(4-(2-(pyrrolidin-2-yl)acetyl)piperazin-1-yl)-9H-dipyrido[2,3-b;4',3'-d]pyrrole-6-carbonitrile

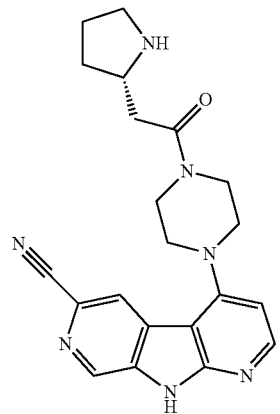 [SMILES: N#Cc1cc2c(cn1)[nH]c1nccc(N3CCN(C(=O)C[C@@H]4CCCN4)CC3)c12]

(S)-tert-butyl 2-(2-(4-(6-cyano-9-((2-(trimethylsilyl)ethoxy)methyl)-9H-dipyrido[2,3-b;4',3'-d]pyrro-4-yl)piperazin-1-yl)-2-oxoethyl)pyrrolidine-1-carboxylate (140 mg, 0.18 mmol) was dissolved in 1,4-dioxane (0.4 mL) and then treated with 48% HBr$_{(aq)}$ (0.4 mL) and heated at 75° C. for 15 minutes. The cooled reaction mixture was then basified to pH ~12 by dropwise addition of 6N sodium hydroxide and then immediately acidified to pH ~8-9 by dropwise addition of concentrated hydrochloric acid, producing a cloudy precipitate. The solid was collected by centrifugation, dissolved in dimethylsulfoxide (2 mL), and purified by preparative HPLC [5-85% methanol in water (0.1% ammonium hydroxide) over 30 min, 35 mL/min] to afford the title compound as a white solid (54 mg, 60% over two steps). $^1$H NMR (500 MHz, d$_6$-DMSO) δ 8.97 (s, 1H), 8.48 (d, J=5.4, 1H), 8.23 (s, 1H), 6.91 (d, J=5.6, 1H), 3.82 (m, J=4.6, 4H), 3.41-3.34 (m, 4H), 2.94-2.85 (m, 1H), 2.80 (m, 1H), 2.65-2.53 (m, 3H), 1.94-1.82 (m, 1H), 1.79-1.59 (m, 2H), 1.34 (m, 1H), NH signal not observed. LCMS (Method D): R$_T$=5.419 min, M+H$^+$=390.2.

Example 38

(R)-4-(4-(2-(pyrrolidin-2-yl)acetyl)piperazin-1-yl)-9H-dipyrido[2,3-b;4',3'-d]pyrrole-6-carbonitrile

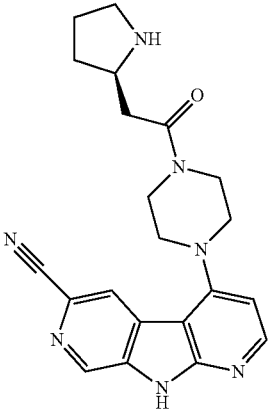 [SMILES: N#Cc1cc2c(cn1)[nH]c1nccc(N3CCN(C(=O)C[C@H]4CCCN4)CC3)c12]

The title compound was prepared following a similar procedure to the previous example using (R)-2-(1-(tert-butoxycarbonyl)pyrrolidin-2-yl)acetic acid. $^1$H NMR (500 MHz, d$_6$-DMSO) δ 8.97 (s, 1H), 8.47 (d, J=5.5, 1H), 8.23 (s, 1H), 6.91 (d, J=5.6, 1H), 3.82 (m, 4H), 3.34 (m, 4H), 2.87 (m, 1H), 2.76 (m, 1H), 2.60-2.52 (m, 3H), 1.86 (m, 1H), 1.75-1.58 (m, 2H), 1.31 (m, 1H), NH signal not observed. LCMS (Method D): R$_T$=5.486 min, M+H$^+$=390.2.

Example 39 cis-4-(4-fluoropiperidin-3-yloxy)-9H-dipyrido[2,3-b;4',3'-d]pyrrole-6-carbonitrile

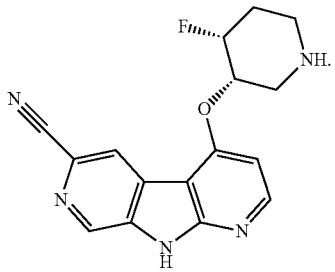 [SMILES: N#Cc1cc2c(cn1)[nH]c1nccc(O[C@H]3CNCC[C@H]3F)c12]

Step 1: 4-hydroxy-9-((2-(trimethylsilyl)ethoxy)methyl)-9H-dipyrido[2,3-b;4',3'-d]pyrrole-6-carbonitrile

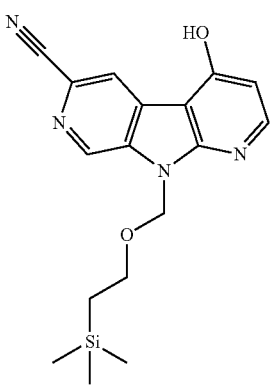 [SMILES: C[Si](C)(C)CCOCn1c2cnc(C#N)cc2c2c(O)ccnc21]

To a solution of 4-chloro-9-(2-trimethylsilanyl-ethoxymethyl)-9H-dipyrido[2,3-b;4',3'-d]pyrrole-6-carbonitrile (100 mg, 0.3 mmol) in tetrahydrofuran (1.8 mL) was added sodium hydride as a 60% dispersion in mineral oil (22 mg, 0.56 mmol) followed by a few drops of water. The reaction mixture was stirred at ambient temperature for 5 minutes and then at 40° C. for 2 hours. The mixture was diluted with water (20 mL) and ethyl acetate (50 mL). The organic layer was separated, dried over sodium sulfate, filtered, concentrated in vacuo, and purified flash chromatography (silica, 4 g, ISCO, 5-100% ethyl acetate in heptane) to afford the title compound as a pale yellow oil, which was used in the next step without any further purification (70 mg).

Step 2: cis-(3S,4R)-tert-butyl 3-(6-cyano-9-((2-(trimethylsilyl)ethoxy)methyl)-9H-dipyrido[2,3-b;4',3'-d]pyrrol-4-yloxy)-4-fluoropiperidine-1-carboxylate

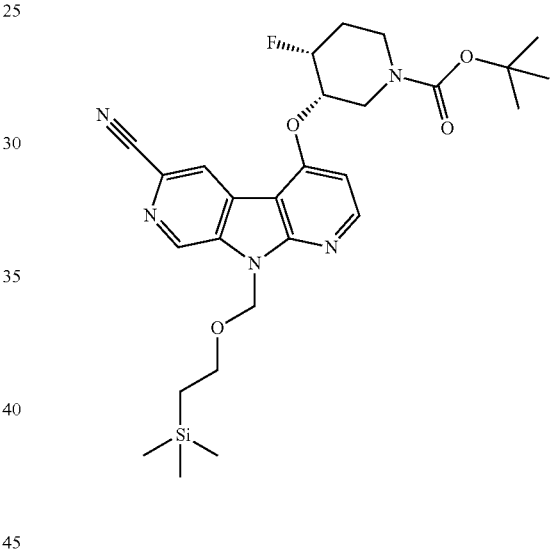

A mixture of 4-hydroxy-9-((2-(trimethylsilyl)ethoxy)methyl)-9H-dipyrido[2,3-b;4',3'-d]pyrrole-6-carbonitrile (70 mg, 0.2 mmol), trans-(3S,4S)-tert-butyl 4-fluoro-3-hydroxypiperidine-1-carboxylate (68 mg, 0.3 mmol), and triphenylphosphine (135 mg, 0.5 mmol) in tetrahydrofuran (1.7 mL) was stirred at ambient temperature. After 3 minutes, the reaction mixture was treated with diisopropyl azodicarboxylate (0.1 mL, 0.5 mmol) and heated at 50° C. for 4 hours. The reaction mixture was diluted with methylene chloride (50 mL) and washed with water (20 mL). The organic layer was separated, dried over sodium sulfate, filtered, concentrated in vacuo, and purified flash chromatography (silica, 4 g, ISCO, 0-70% ethyl acetate in heptane) to afford the title compound as a pale yellow solid, which was used in the next step without any further purification (55 mg).

Step 3: cis-4-(4-fluoropiperidin-3-yloxy)-9H-dipyrido[2,3-b;4',3'-d]pyrrole-6-carbonitrile

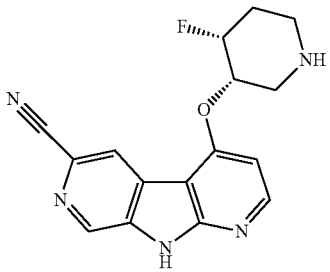 [SMILES: N#Cc1cc2c(cn1)[nH]c1nccc(O[C@H]3CNCC[C@H]3F)c12]

cis-(3S,4R)-tert-butyl 3-(6-cyano-9-((2-(trimethylsilyl)ethoxy)methyl)-9H-dipyrido[2,3-b;4',3'-d]pyrrol-4-yloxy)-4-fluoropiperidine-1-carboxylate (55 mg, 0.1 mmol) was dissolved in 1,4-dioxane (0.2 mL) and then treated with 48% $HBr_{(aq)}$ (0.2 mL) and heated at 75° C. for 15 minutes. The cooled reaction mixture was then basified to pH ~12 by dropwise addition of 6N sodium hydroxide and then immediately acidified to pH ~8-9 by dropwise addition of concentrated hydrochloric acid, producing a cloudy precipitate. The solid was collected by centrifugation, dissolved in dimethylsulfoxide (2 mL), and purified by preparative HPLC [5-85% methanol in water (0.1% ammonium hydroxide) over 30 min, 35 mL/min] to afford the title compound as a white solid (10 mg, 12% over three steps). $^1$H NMR (400 MHz, $d_6$-DMSO) δ 12.90-12.68 (s, 1H), 8.98 (d, J=0.9, 1H), 8.54 (d, J=5.8, 1H), 8.48 (s, 1H), 7.16 (d, J=5.9, 1H), 5.13 (m, 2H), 3.20-3.10 (m, 1H), 2.98 (m, 1H), 2.74-2.62 (m, 2H), 2.06 (m, 1H), 1.93 (m, 1H), piperidine NH not observed. LCMS (Method F): $R_T$=1.47 min, M+H$^+$=312.15.

Example 40

3-Bromo-4-((1,4-dimethylpiperidin-4-yl)methoxy)-9H-dipyrido[2,3-b;4',3'-d]pyrrol-6-carbonitrile

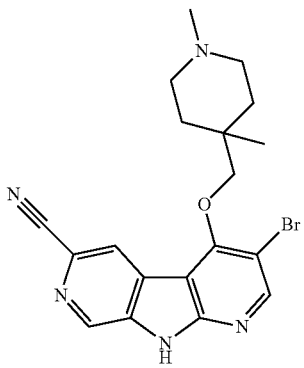 [SMILES: CN1CCC(C)(COc2c(Br)cnc3[nH]c4cnc(C#N)cc4c23)CC1]

A mixture of 4-((1,4-dimethylpiperidin-4-yl)methoxy)-9H-dipyrido[2,3-b;4',3'-d]pyrrole-6-carbonitrile (50 mg, 0.16 mmol), sodium acetate (26 mg, 0.3 mmol), and bromine (32 L, 0.6 mmol) in acetic acid (1 mL) was stirred at ambient temperature for 10 minutes. The reaction mixture was diluted with water (1 mL) and basified to pH ~8 by dropwise addition of 6N sodium hydroxide solution, producing a yellow precipitate. The solid was collected by centrifugation, dissolved in dimethylsulfoxide (2 mL), and purified by preparative HPLC [5-85% methanol in water (0.1% ammonium hydroxide) over 30 min, 35 mL/min] to afford the title compound as a white solid (25 mg, 38%). $^1$H NMR (500 MHz, $d_6$-DMSO) δ 9.02 (d, J=8.7, 1H), 8.70 (d, J=9.9, 1H), 8.43 (s, 1H), 4.21 (s, 2H), 2.81 (m, 2H), 2.62 (m, 2H), 2.45 (s, 3H), 1.97 (m, 2H), 1.68 (m, 2H), 1.30 (s, 3H), NH signal not observed. LCMS (Method D): $R_T$=8.660 min, M+H$^+$=414.0/416.0.

Example 41

3-Chloro-4-((1,4-dimethylpiperidin-4-yl)methoxy)-9H-dipyrido[2,3-b;4',3'-d]pyrrole-6-carbonitrile

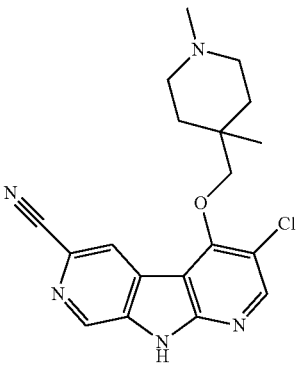 [SMILES: CN1CCC(C)(COc2c(Cl)cnc3[nH]c4cnc(C#N)cc4c23)CC1]

A mixture of 4-((1,4-dimethylpiperidin-4-yl)methoxy)-9H-dipyrido[2,3-b;4',3'-d]pyrrole-6-carbonitrile (50 mg, 0.16 mmol), N-chlorosuccinimide (60 mg, 0.45 mmol) in acetonitrile (0.8 mL) and isopropyl alcohol (0.23 mL) was stirred at 40° C. for 16 hours. The reaction mixture was diluted acetonitrile (1 mL) and the solid was collected by centrifugation, dissolved in dimethylsulfoxide (2 mL), and purified by preparative HPLC [5-85% methanol in water (0.1% ammonium hydroxide) over 30 min, 35 mL/min] to afford the title compound as a white solid (12 mg, 20%). $^1$H NMR (500 MHz, $d_6$-DMSO) δ 9.04 (s, 1H), 8.68 (s, 1H), 8.53 (s, 1H), 4.28 (s, 2H), 2.51-2.46 (m, 2H), 2.28 (m, 2H), 2.22 (s, 3H), 1.82 (m, 2H), 1.51 (m, 2H), 1.19 (s, 3H), NH signal not observed. LCMS (Method D): $R_T$=8.445 min, M+H$^+$=370.1.

Example 42

1-[4-(3-Chloro-9H-dipyrido[2,3-b;4',3'-d]pyrrol-4-yl)-piperazin-1-yl]-2-(R)-pyrrolidin-2-yl-ethanone

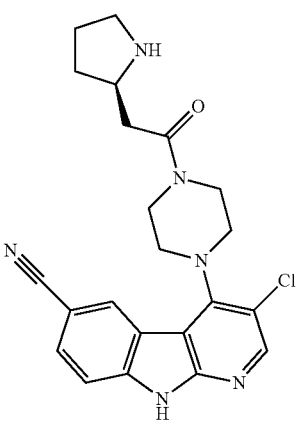 [SMILES: N#Cc1ccc2[nH]c3ncc(Cl)c(N4CCN(C(=O)C[C@H]5CCCN5)CC4)c3c2c1]

The title compound was prepared following a similar procedure to the previous example using 1-[4-(9H-dipyrido[2,3b;4',3'-d]pyrrol-4-yl)-piperazin-1-yl]-2-(R)-pyrrolidin-2-yl-ethanone. $^1$H NMR (400 MHz, CD$_3$OD): 9.17 (s, 1H), 8.76 (d, 1H, J=6.36 Hz), 8.68 (s, 1H), 8.60 (d, 1H, J=6.37 Hz), 3.98-3.96 (m, 3H), 3.89 (t, 2H, J=4.92 Hz), 3.77-3.75 (m, 2H), 3.67 (t, 2H, J=5.15 Hz), 3.33-3.32 (m, 2H), 3.17 (dd, 1H, J=17.53, 3.65 Hz), 2.97 (dd, 1H, J=17.52, 10.07 Hz), 2.30-2.29 (m, 1H), 2.13-2.13 (m, 1H), 2.02-2.01 (m, 1H), 1.81-1.80 (m, 1H). LCMS (Method A): R$_T$=1.84 min, M+H$^+$=399.

Example 43

(S)-3-Chloro-4-(3-hydroxypyrrolidin-1-yl)-9H-dipyrido[2,3-b;4',3'-d]pyrrole-6-carbonitrile

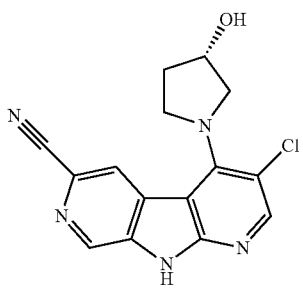 [SMILES: N#Cc1cc2c(cn1)[nH]c1ncc(Cl)c(N3CC[C@H](O)C3)c12]

Step 1: (S)-4-(3-hydroxypyrrolidin-1-yl)-9-((2-(trimethylsilyl)ethoxy)methyl)-9H-dipyrido[2,3-b;4',3'-d]pyrrole-6-carbonitrile

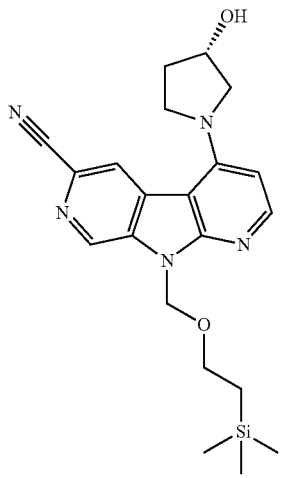 [SMILES: C[Si](C)(C)CCOCn1c2cnc(C#N)cc2c2c(N3CC[C@H](O)C3)ccnc21]

A mixture of 4-chloro-9-(2-trimethylsilanyl-ethoxymethyl)-9H-dipyrido[2,3-b;4',3'-d]pyrrole-6-carbonitrile (130 mg, 0.36 mmol) and (S)-3-hydroxypyrrolidinol (91 mg, 1.04 mmol) in N,N-dimethylacetamide (1.6 mL) was heated at 100° C. for 2 hours. The cooled reaction mixture was diluted with ethyl acetate (50 mL) and washed with water (20 mL). The organic layer was separated, dried over sodium sulfate, filtered, concentrated in vacuo, and purified by flash chromatography (silica, 4 g, ISCO, 0-100% ethyl acetate in heptane) to afford the title compound as a white waxy solid, which was used in the next step without further purification (140 mg, 94%).

Step 2: (S)-3-Chloro-4-(3-hydroxypyrrolidin-1-yl)-9-((2-(trimethylsilyl)ethoxy)methyl)-9H-dipyrido[2,3-b;4',3'-d]pyrrole-6-carbonitrile

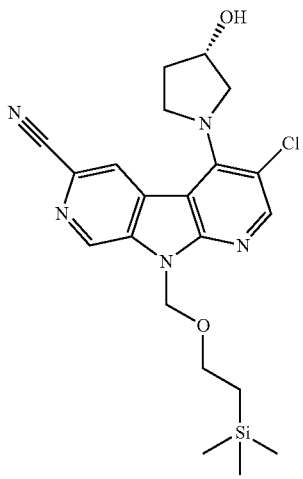 [SMILES: C[Si](C)(C)CCOCn1c2cnc(C#N)cc2c2c(N3CC[C@H](O)C3)c(Cl)cnc21]

A mixture of (S)-4-(3-hydroxypyrrolidin-1-yl)-9-((2-(trimethylsilyl)ethoxy)methyl)-9H-dipyrido[2,3-b;4',3'-d]pyrrole-6-carbonitrile (140 mg, 0.34 mmol) and N-chlorosuccinimide (137 mg, 1.02 mmol) in acetonitrile (1.3 mL) and isopropyl alcohol (0.4 mL) was stirred at 35° C. for 5 hours. The cooled reaction mixture was quenched with saturated aqueous sodium thiosulfate (1 mL), diluted with ethyl acetate (50 mL), and washed with water (20 mL). The organic layer was separated, dried over sodium sulfate, filtered, concentrated in vacuo, and purified by flash chromatography (silica, 4 g, ISCO, 0-50% ethyl acetate in heptane) to afford the title compound as a pale yellow solid, which was used in the next step without any further purification (100 mg).

Step 3: (S)-3-Chloro-4-(3-hydroxypyrrolidin-1-yl)-9H-dipyrido[2,3-b;4',3'-d]pyrrole-6-carbonitrile

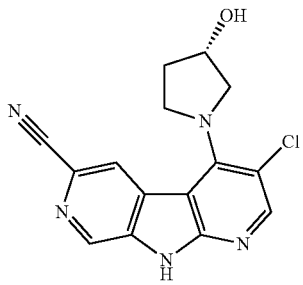 [SMILES: N#Cc1cc2c(cn1)[nH]c1ncc(Cl)c(N3CC[C@H](O)C3)c12]

(S)-3-Chloro-4-(3-hydroxypyrrolidin-1-yl)-9-((2-(trimethylsilyl)ethoxy)methyl)-9H-dipyrido[2,3-b;4',3'-d]pyrrole-6-carbonitrile (100 mg, 0.2 mmol) was dissolved in 1,4-dioxane (0.3 mL) and then treated with 48% HBr$_{(aq)}$ (0.3 mL) and heated at 55° C. for 20 minutes. The cooled reaction mixture was then basified to pH ~12 by dropwise addition of 6N sodium hydroxide and then immediately acidified to pH ~8-9 by dropwise addition of concentrated hydrochloric acid, producing a cloudy precipitate. The solid was collected by centrifugation, dissolved in dimethylsulfoxide (2 mL), and purified by preparative HPLC [5-85% methanol in water (0.1% ammonium hydroxide) over 30 min, 35 mL/min] to afford the title compound as a pale off-white solid (40 mg, 60% over two steps). $^1$H NMR (400 MHz, d$_6$-DMSO) δ 8.95 (s, 1H), 8.56 (s, 1H), 8.45 (s, 1H), 5.27 (s, 1H), 4.54 (s, 1H), 3.88 (m, 1H), 3.78 (dd, J=10.5, 4.6, 1H), 3.66 (td, J=9.0, 4.5, 1H), 3.50 (d, J=10.3, 1H), 2.34-2.19 (m, 1H), 2.06-1.95 (m, 1H), NH signals not observed. LCMS (Method D): R$_T$=8.57 min, M+H$^+$=314.0.

Example 44

3-Chloro-4-((3S,4S)-3,4-dihydroxypyrrolidin-1-yl)-9H-dipyrido[2,3-b;4',3'-d]pyrrole-6-carbonitrile

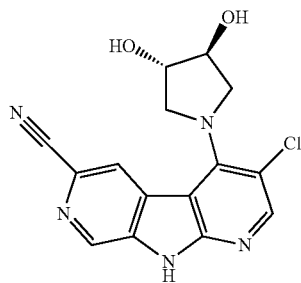 [SMILES: N#Cc1cc2c(cn1)[nH]c1ncc(Cl)c(N3C[C@H](O)[C@@H](O)C3)c12]

The title compound was prepared following a similar procedure to the previous example using (3S,4S)-pyrrolidine-3,4-diol. $^1$H NMR (400 MHz, d$_6$-DMSO) δ 12.85 (s, 1H), 8.95 (s, 1H), 8.65 (s, 1H), 8.45 (s, 1H), 5.42 (d, J=3.1, 2H), 4.20 (s, 2H), 4.00 (dd, J=10.5, 4.2, 2H), 3.50 (d, J=10.8, 2H). LCMS (Method D): R$_T$=6.847 min, M+H$^+$=330.0.

Example 45

3-Chloro-4-((3R,4R)-3,4-dihydroxypyrrolidin-1-yl)-9H-dipyrido[2,3-b;4',3'-d]pyrrole-6-carbonitrile

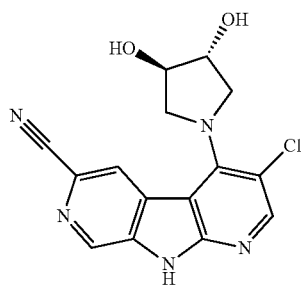 [SMILES: N#Cc1cc2c(cn1)[nH]c1ncc(Cl)c(N3C[C@@H](O)[C@H](O)C3)c12]

The title compound was prepared following a similar procedure to the previous example using (3R,4R)-pyrrolidine-3,4-diol. $^1$H NMR (400 MHz, d$_6$-DMSO) δ 12.88 (s, 1H), 8.95 (s, 1H), 8.65 (s, 1H), 8.45 (s, 1H), 5.44 (d, J=3.1, 2 H), 4.20 (s, 2H), 4.00 (dd, J=10.6, 3.8, 2 H), 3.50 (d, J=10.9, 2H). LCMS (Method D): R$_T$=6.902 min, M+H$^+$=330.0.

Example 46

3-Chloro-4-(3-hydroxyazetidin-1-yl)-9H-dipyrido[2,3-b;4',3'-d]pyrrole-6-carbonitrile

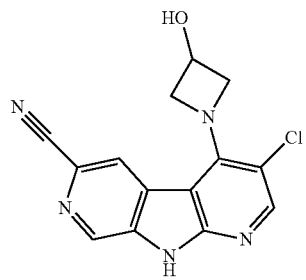 [SMILES: N#Cc1cc2c(cn1)[nH]c1ncc(Cl)c(N3CC(O)C3)c12]

The title compound was prepared following a similar procedure to the previous example using azetidin-3-ol. $^1$H NMR (400 MHz, d$_6$-DMSO) δ 12.63 (s, 1H), 8.84 (s, 1H), 8.48 (s, 1H), 8.20 (s, 1H), 5.75 (d, J=5.2, 1H), 5.05-4.88 (m, 2H), 4.53 (d, J=15.7, 1H), 4.41 (dd, J=9.0, 4.3, 2H). LCMS (Method D): R$_T$=6.880 min, M+H$^+$=300.0.

Example 47

(S)-3-Chloro-4-(3-hydroxy-3-methylpyrrolidin-1-yl)-9H-dipyrido[2,3-b;4',3'-d]pyrrole-6-carbonitrile

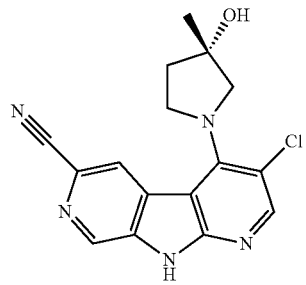 [SMILES: C[C@]1(O)CCN(c2c(Cl)cnc3[nH]c4cnc(C#N)cc4c23)C1]

The title compound was prepared following a similar procedure to the previous example using (S)-3-methylpyrrolidin-3-ol. $^1$H NMR (400 MHz, d$_6$-DMSO) δ 12.88 (s, 1H), 8.96 (s, 1H), 8.60 (s, 1H), 8.46 (s, 1H), 5.14 (s, 1H), 3.95 (dd, J=17.5, 7.9, 1H), 3.71-3.65 (m, 1H), 3.63 (d, J=10.1, 1H), 3.52 (d, J=9.9, 1H), 2.15-2.01 (m, 2H), 1.44 (s, 3H). LCMS (Method G): R$_T$=5.81 min, M+H$^+$=328.12.

Example 48

(R)-3-Chloro-4-(3-hydroxy-3-methylpyrrolidin-1-yl)-9H-dipyrido[2,3-b;4',3'-d]pyrrole-6-carbonitrile

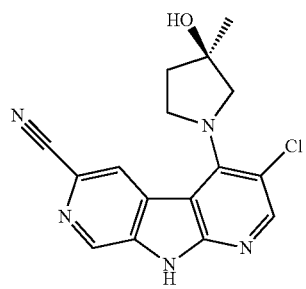 [SMILES: C[C@@]1(O)CCN(c2c(Cl)cnc3[nH]c4cnc(C#N)cc4c23)C1]

The title compound was prepared following a similar procedure to the previous example using (R)-3-methylpyrrolidin-3-ol. ¹H NMR (400 MHz, d₆-DMSO) δ 12.88 (s, 1H), 8.96 (s, 1H), 8.60 (s, 1H), 8.46 (s, 1H), 5.14 (s, 1H), 3.95 (dd, J=17.5, 7.9, 1H), 3.71-3.65 (m, 1H), 3.63 (d, J=10.1, 1H), 3.52 (d, J=10.0, 1H), 2.15-2.02 (m, 2H), 1.44 (s, 3H). LCMS (Method G): R$_T$=5.82 min, M+H⁺=328.12.

Example 49

(S)-3-Chloro-4-(3-hydroxypiperidin-1-yl)-9H-dipyrido[2,3-b;4',3'-d]pyrrole-6-carbonitrile

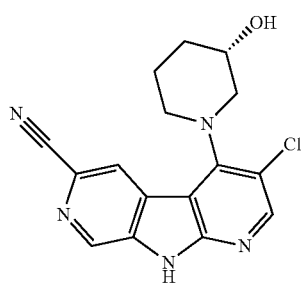 [SMILES: N#Cc1cc2c(cn1)[nH]c1ncc(Cl)c(N3CCC[C@H](O)C3)c12]

The title compound was prepared following a similar procedure to the previous example using (S)-piperidin-3-ol. Proton NMR of this compound shows a mixture of two isomers. ¹H NMR (400 MHz, d₆-DMSO) δ 12.93 (s, 1H), 9.27 (s, 0.2H), 8.97 (s, 0.8H), 8.73 (s, 0.2H), 8.68 (s, 0.8H), 8.57 (s, 0.2H), 8.50 (s, 0.8H), 4.99 (d, J=3.8, 1H), 3.82 (m, 1H), 3.56 (m, 1H), 3.42 (m, 2H), 3.26 (m, 1H), 2.06-1.89 (m, 2H), 1.76 (m, 1H), 1.54 (m, 1H). LCMS (Method D): R$_T$=10.265 min, M+H⁺=328.0.

Example 50

(R)-3-Chloro-4-(3-hydroxypiperidin-1-yl)-9H-dipyrido[2,3-b;4',3'-d]pyrrole-6-carbonitrile

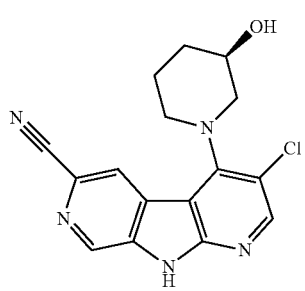 [SMILES: N#Cc1cc2c(cn1)[nH]c1ncc(Cl)c(N3CCC[C@@H](O)C3)c12]

The title compound was prepared following a similar procedure to the previous example using (R)-piperidin-3-ol. Proton NMR of this compound shows a mixture of two isomers. ¹H NMR (400 MHz, d₆-DMSO) δ 13.29-12.45 (s, 1H), 9.27 (s, 0.4H), 8.97 (s, 0.6H), 8.73 (s, 0.4H), 8.67 (s, 0.6H), 8.58 (s, 0.4H), 8.49 (s, 0.6H), 4.99 (s, 1H), 3.86 (m, 1H), 3.55 (m, 1H), 3.43 (m, 2H), 3.26 (m, 1H), 2.06-1.88 (m, 2H), 1.76 (m, 1H), 1.62-1.46 (m, 1H). LCMS (Method D): R$_T$=10.259 min, M+H⁺=328.0.

Example 51

3-Chloro-4-(4-hydroxypiperidin-1-yl)-9H-dipyrido[2,3-b;4',3'-d]pyrrole-6-carbonitrile

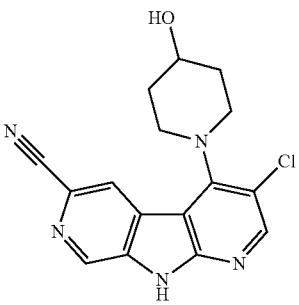 [SMILES: N#Cc1cc2c(cn1)[nH]c1ncc(Cl)c(N3CCC(O)CC3)c12]

The title compound was prepared following a similar procedure to the previous example using piperidin-4-ol. ¹H NMR (400 MHz, d₆-DMSO) δ 12.95 (s, 1H), 8.98 (s, 1H), 8.50 (s, 2H), 4.92 (d, J=4.2, 1H), 3.83 (d, J=4.1, 1H), 3.60 (m, 2H), 3.49 (m, 2H), 1.99 (m, 2H), 1.69 (m, 2H). LCMS (Method D): R$_T$=9.499 min, M+H⁺=328.0.

Example 52

(S)-3-Chloro-4-(3-aminopyrrolidin-1-yl)-9H-dipyrido[2,3-b;4',3'-d]pyrrole-6-carbonitrile

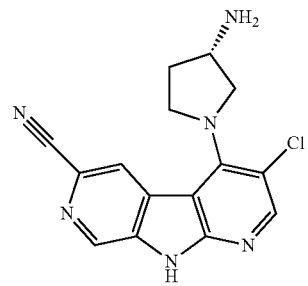 [SMILES: N#Cc1cc2c(cn1)[nH]c1ncc(Cl)c(N3CC[C@H](N)C3)c12]

The title compound was prepared following a similar procedure to the previous example using (S)-tert-butyl pyrrolidin-3-ylcarbamate. ¹H NMR (400 MHz, d₆-DMSO) δ 8.97 (d, J=0.7, 1H), 8.55 (s, 1H), 8.48 (s, 1H), 3.92-3.79 (m, 3H), 3.65 (m, 1H), 3.46 (m, 1H), 2.31 (m, 1H), 1.93 (m, 1H), NH signals not observed. LCMS (Method D): R$_T$=6.620 min, M+H⁺=313.0.

Example 53

(S)-3-Chloro-4-(3-(methylamino)pyrrolidin-1-yl)-9H-dipyrido[2,3-b;4',3'-d]pyrrole-6-carbonitrile

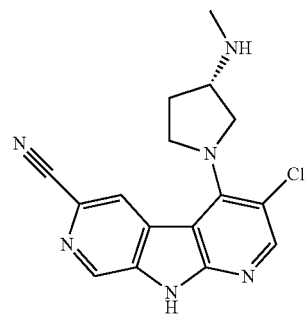 [SMILES: CN[C@H]1CCN(c2c(Cl)cnc3[nH]c4cnc(C#N)cc4c23)C1]

The title compound was prepared following a similar procedure to the previous example using (S)-tert-butyl methyl(pyrrolidin-3-yl)carbamate. ¹H NMR (500 MHz, d₆-DMSO) δ 8.95 (s, 1H), 8.79 (s, 1H), 8.45 (s, 1H), 3.78 (dd, J=14.4, 8.5, 2H), 3.73-3.67 (m, 1H), 3.63 (m, 1H), 3.54 (m, 1H), 3.38 (m, 1H), 2.40 (s, 3H), 2.33-2.23 (m, 2H), 1.89 (m, 1H), NH signals not observed. LCMS (Method D): R$_T$=6.863 min, M+H⁺=327.0.

Example 54

(S)-tert-butyl 1-(6-cyano-9-((2-(trimethylsilyl)ethoxy)methyl)-9H-dipyrido[2,3-b;4',3'-d]pyrrol-4-yl)pyrrolidin-3-yl(ethyl)carbamate

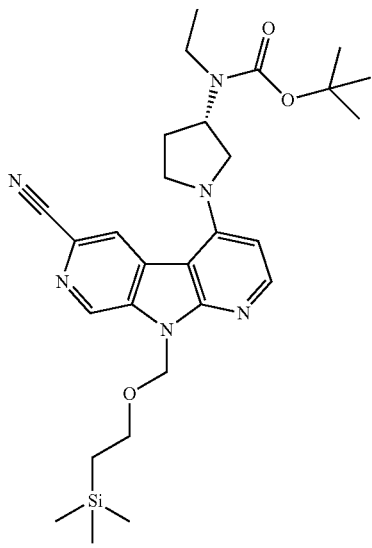 [SMILES: CCN(C(=O)OC(C)(C)C)[C@H]1CCN(c2ccnc3c2c2cc(C#N)ncc2n3COCC[Si](C)(C)C)C1]

Step 1: (S)-tert-butyl 1-(6-cyano-9-((2-(trimethylsilyl)ethoxy)methyl)-9H-dipyrido[2,3-b;4',3'-d]pyrrol-4-yl)pyrrolidin-3-ylcarbamate

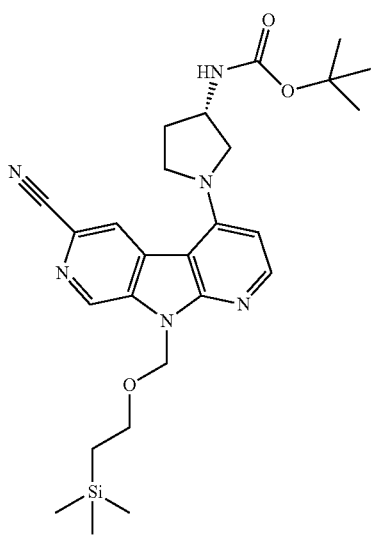 [SMILES: CC(C)(C)OC(=O)N[C@H]1CCN(c2ccnc3c2c2cc(C#N)ncc2n3COCC[Si](C)(C)C)C1]

A mixture of 4-chloro-9-(2-trimethylsilanyl-ethoxymethyl)-9H-dipyrido[2,3-b;4',3'-d]pyrrole-6-carbonitrile (590 mg, 1.6 mmol) and (S)-tert-butyl pyrrolidin-3-ylcarbamate (918 mg, 4.9 mmol) in N,N-dimethylacetamide (7.6 mL) was heated at 100° C. for 2 hours. The cooled reaction mixture was diluted with ethyl acetate (100 mL) and washed with water (40 mL). The organic layer was separated, dried over sodium sulfate, filtered, concentrated in vacuo, and purified by flash chromatography (silica, 12 g, ISCO, 0-90% ethyl acetate in heptane) to afford the title compound as a white solid, which was used in the next step without any further purification (530 mg, 63%).

Step 2: (S)-tert-butyl 1-(6-cyano-9-((2-(trimethylsilyl)ethoxy)methyl)-9H-dipyrido[2,3-b;4',3'-d]pyrrol-4-yl)pyrrolidin-3-yl(ethyl)carbamate

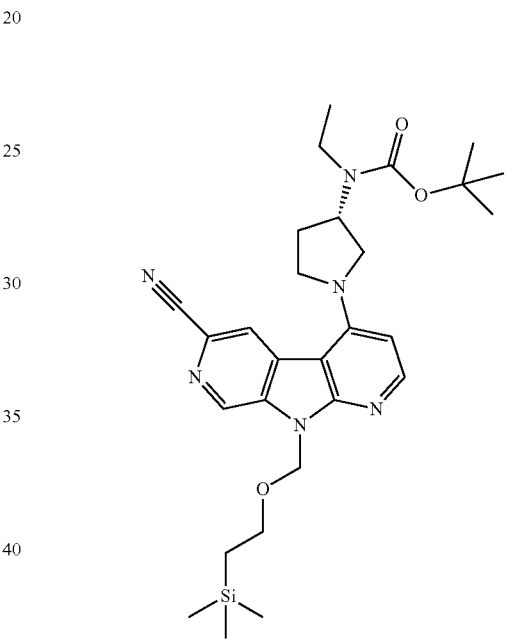

To a solution of (S)-tert-butyl 1-(6-cyano-9-((2-(trimethylsilyl)ethoxy)methyl)-9H-dipyrido[2,3-b;4',3'-d]pyrrol-4-yl)pyrrolidin-3-ylcarbamate (700 mg, 1.0 mmol) in tetrahydrofuran (11 mL) was added sodium hydride as a 60% dispersion in mineral oil (140 mg, 3.4 mmol) followed by iodoethane (0.77 mL, 9.4 mmol) and reaction mixture was stirred overnight at ambient temperature. The reaction was quenched with water (0.1 mL), diluted with ethyl acetate (100 mL) and washed with water (50 mL). The organic layer was separated, dried over sodium sulfate, filtered, concentrated in vacuo, and purified by flash chromatography (silica, 4 g, ISCO, 0-60% ethyl acetate in heptane) to afford the title compound as a white solid, which was used in the next step without any further purification (560 mg. 80%).

Example 55

(S)-3-Chloro-4-(3-(ethylamino)pyrrolidin-1-yl)-9H-dipyrido[2,3-b;4',3'-d]pyrrole-6-carbonitrile

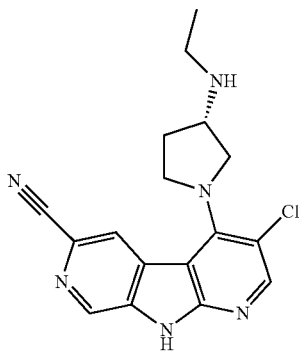 [SMILES: CCN[C@H]1CCN(c2c(Cl)cnc3[nH]c4cnc(C#N)cc4c23)C1]

Step 1: (S)-tert-butyl 1-(3-chloro-6-cyano-9-((2-(trimethylsilyl)ethoxy)methyl)-9H-dipyrido[2,3-b;4',3'-d]pyrrol-4-yl)pyrrolidin-3-yl(ethyl)carbamate

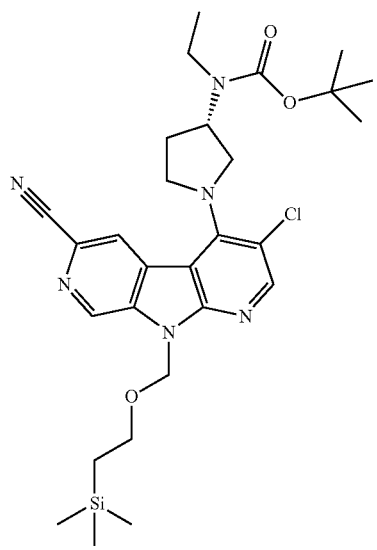 [SMILES: CCN(C(=O)OC(C)(C)C)[C@H]1CCN(c2c(Cl)cnc3c2c2cc(C#N)ncc2n3COCC[Si](C)(C)C)C1]

A mixture of (S)-tert-butyl 1-(6-cyano-9-((2-(trimethylsilyl)ethoxy)methyl)-9H-dipyrido[2,3-b;4',3'-d]pyrrol-4-yl)pyrrolidin-3-yl(ethyl)carbamate (100 mg, 0.2 mmol) and N-chlorosuccinimide (75 mg, 0.56 mmol) in acetonitrile (0.75 mL) and isopropyl alcohol (0.2 mL) was stirred at 35° C. for 5 hours. The cooled reaction mixture was quenched with saturated aqueous sodium thiosulfate, diluted with ethyl acetate (50 mL), and washed with water (20 mL). The organic layer was separated, dried over sodium sulfate, filtered, concentrated in vacuo, and purified by flash chromatography (silica, 4 g, ISCO, 0-50% ethyl acetate in heptane) to afford the title compound as a pale yellow foam, which was used in the next step without any further purification (100 mg).

Step 2: (S)-3-Chloro-4-(3-(ethylamino)pyrrolidin-1-yl)-9H-dipyrido[2,3-b;4',3'-d]pyrrole-6-carbonitrile

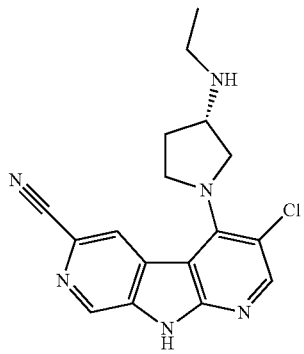 [SMILES: CCN[C@H]1CCN(c2c(Cl)cnc3[nH]c4cnc(C#N)cc4c23)C1]

(S)-tert-butyl 1-(3-chloro-6-cyano-9-((2-(trimethylsilyl)ethoxy)methyl)-9H-dipyrido[2,3-b;4',3'-d]pyrrol-4-yl)pyrrolidin-3-yl(ethyl)carbamate (100 mg, 0.18 mmol) was dissolved in 1,4-dioxane (0.3 mL) and then treated with 48% $HBr_{(aq)}$ (0.3 mL) and heated at 55° C. for 20 minutes. The cooled reaction mixture was then basified to pH ~12 by dropwise addition of 6N sodium hydroxide and then immediately acidified to pH ~8-9 by dropwise addition of concentrated hydrochloric acid, producing a cloudy precipitate. The solid was collected by centrifugation, dissolved in dimethylsulfoxide (2 mL), and purified by preparative HPLC [5-85% methanol in water (0.1% ammonium hydroxide) over 30 min, 35 mL/min] to afford the title compound as a pale yellow solid (40 mg, 60% over two steps). $^1$H NMR (500 MHz, $d_6$-DMSO) δ 8.96 (s, 1H), 8.70 (s, 1H), 8.46 (s, 1H), 3.79 (m, 1H), 3.73 (m, 1H), 3.66-3.60 (m, 1H), 3.55-3.47 (m, 2H), 2.65 (m, 2H), 2.26 (m, 1H), 1.98-1.88 (m, 1H), 1.13 (t, J=7.1, 3H), NH signal not observed. LCMS (Method D): $R_T$=7.287 min, M+H$^+$=341.0.

Example 56

(S)-3-Bromo-4-(3-(ethylamino)pyrrolidin-1-yl)-9H-dipyrido[2,3-b;4',3'-d]pyrrole-6-carbonitrile

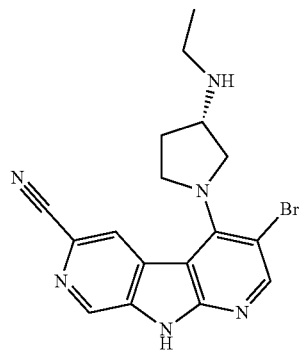 [SMILES: CCN[C@H]1CCN(c2c(Br)cnc3[nH]c4cnc(C#N)cc4c23)C1]

Step 1: (S)-tert-butyl 1-(3-bromo-6-cyano-9-((2-(trimethylsilyl)ethoxy)methyl)-9H-dipyrido[2,3-b;4',3'-d]pyrrol-4-yl)pyrrolidin-3-yl(ethyl)carbamate

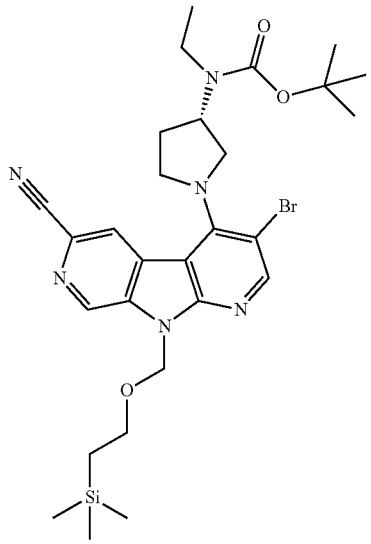 [SMILES: CCN(C(=O)OC(C)(C)C)[C@H]1CCN(c2c(Br)cnc3c2c2cc(C#N)ncc2n3COCC[Si](C)(C)C)C1]

A mixture of (S)-tert-butyl 1-(6-cyano-9-((2-(trimethylsilyl)ethoxy)methyl)-9H-dipyrido[2,3-b;4',3'-d]pyrrol-4-yl)pyrrolidin-3-yl(ethyl)carbamate (125 mg, 0.23 mmol), sodium acetate (38 mg, 0.46 mmol), and bromine (36 μL, 0.7 mmol) in acetic acid (1 mL) was stirred at ambient temperature for 1 minute. The reaction mixture was diluted with ethyl acetate (50 mL), and washed with water (20 mL). The organic layer was separated, dried over sodium sulfate, filtered, concentrated in vacuo, and purified by flash chromatography (silica, 4 g, ISCO, 0-50% ethyl acetate in heptane) to afford the title compound as a pale yellow oil, which was used in the next step without any further purification (65 mg).

Step 2: (S)-3-Bromo-4-(3-(ethylamino)pyrrolidin-1-yl)-9H-dipyrido[2,3-b;4',3'-d]pyrrole-6-carbonitrile

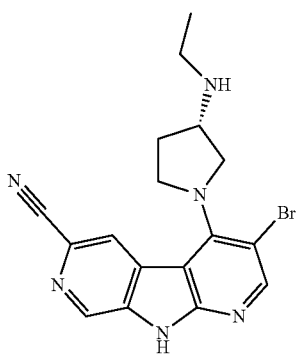 [SMILES: CCN[C@H]1CCN(c2c(Br)cnc3[nH]c4cnc(C#N)cc4c23)C1]

(S)-tert-butyl 1-(3-bromo-6-cyano-9-((2-(trimethylsilyl)ethoxy)methyl)-9H-dipyrido[2,3-b;4',3'-d]pyrrol-4-yl)pyrrolidin-3-yl(ethyl)carbamate (65 mg, 0.1 mmol) was dissolved in 1,4-dioxane (0.3 mL) and then treated with 48% HBr$_{(aq)}$ (0.3 mL) and heated at 55° C. for 20 minutes. The cooled reaction mixture was then basified to pH ~12 by dropwise addition of 6N sodium hydroxide and then immediately acidified to pH ~8-9 by dropwise addition of concentrated hydrochloric acid, producing a cloudy precipitate. The solid was collected by centrifugation, dissolved in dimethylsulfoxide (2 mL), and purified by preparative HPLC [5-85% methanol in water (0.1% ammonium hydroxide) over 30 min, 35 mL/min] to afford the title compound as a pale yellow solid (23 mg, 26% over two steps). $^1$H NMR (500 MHz, d$_6$-DMSO) δ 8.97 (s, 1H), 8.78 (s, 1H), 8.60 (s, 1H), 3.79-3.73 (m, 2H), 3.62-3.51 (m, 3H), 3.43 (m, 1H), 2.72-2.59 (m, 2H), 2.26 (m, 1H), 1.97 (m, 1H), 1.14 (t, J=7.1, 3H), NH signal not observed. LCMS (Method D): R$_T$=7.535 min, M+H$^+$=385.0/387.0.

Example 57

(S)-3-Fluoro-4-(3-(ethylamino)pyrrolidin-1-yl)-9H-dipyrido[2,3-b;4',3'-d]pyrrole-6-carbonitrile

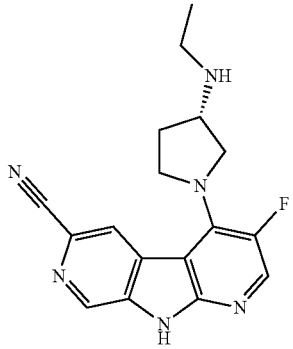 [SMILES: CCN[C@H]1CCN(c2c(F)cnc3[nH]c4cnc(C#N)cc4c23)C1]

Step 1: (S)-tert-butyl 1-(3-fluoro-6-cyano-9-((2-(trimethylsilyl)ethoxy)methyl)-9H-dipyrido[2,3-b;4',3'-d]pyrrol-4-yl)pyrrolidin-3-yl(ethyl)carbamate

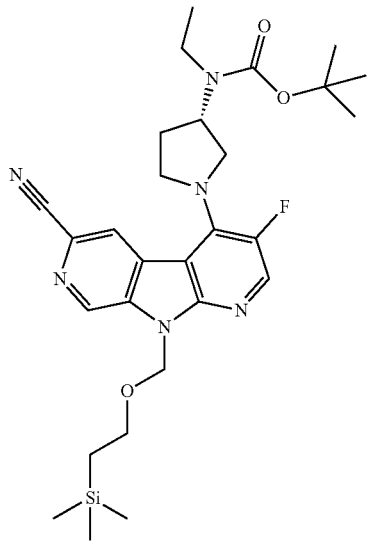 [SMILES: CCN(C(=O)OC(C)(C)C)[C@H]1CCN(c2c(F)cnc3c2c2cc(C#N)ncc2n3COCC[Si](C)(C)C)C1]

A mixture of (S)-tert-butyl 1-(6-cyano-9-((2-(trimethylsilyl)ethoxy)methyl)-9H-dipyrido[2,3-b;4',3'-d]pyrrol-4-yl) pyrrolidin-3-yl(ethyl)carbamate (290 mg, 0.54 mmol) and Selectfluor™ (957 mg, 2.7 mmol) in acetonitrile (4.5 mL) was stirred at 0° C. for 5 minutes. The cooled reaction mixture was quenched with saturated aqueous sodium thiosulfate, diluted with ethyl acetate (50 mL), and washed with water (20 mL). The organic layer was separated, dried over sodium sulfate, filtered, concentrated in vacuo, and purified by flash chromatography (silica, 4 g, ISCO, 0-50% ethyl acetate in heptane) to afford the title compound as a pale yellow foam, which was used in the next step without any further purification (120 mg).

Step 2: (S)-3-Fluoro-4-(3-(ethylamino)pyrrolidin-1-yl)-9H-dipyrido[2,3-b;4',3'-d]pyrrole-6-carbonitrile

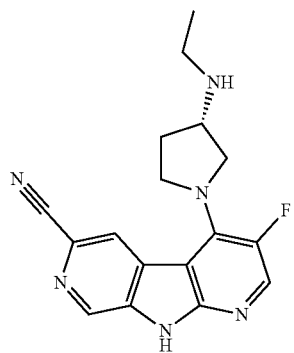 [SMILES: CCN[C@H]1CCN(c2c(F)cnc3[nH]c4cnc(C#N)cc4c23)C1]

(S)-tert-butyl 1-(3-fluoro-6-cyano-9-((2-(trimethylsilyl)ethoxy)methyl)-9H-dipyrido[2,3-b;4',3'-d]pyrrol-4-yl)pyrrolidin-3-yl(ethyl)carbamate (120 mg, 0.2 mmol) was dissolved in 1,4-dioxane (0.3 mL) and then treated with 48% HBr$_{(aq)}$ (0.3 mL) and heated at 55° C. for 20 minutes. The cooled reaction mixture was then basified to pH ~12 by dropwise addition of 6N sodium hydroxide and then immediately acidified to pH ~8-9 by dropwise addition of concentrated hydrochloric acid, producing a cloudy precipitate. The solid was collected by centrifugation, dissolved in dimethylsulfoxide (2 mL), and purified by preparative HPLC [5-85% methanol in water (0.1% ammonium hydroxide) over 30 min, 35 mL/min] to afford the title compound as a pale yellow solid (50 mg, 30% over two steps). $^1$H NMR (500 MHz, d$_6$-DMSO) δ 8.87 (s, 1H), 8.49 (s, 1H), 8.32 (d, J=7.0, 1H), 3.91-3.84 (m, 1H), 3.83-3.76 (m, 2H), 3.58 (m, 1H), 3.43 (m, 1H), 2.67-2.56 (m, 2H), 2.19 (m, 1H), 1.83 (m, 1H), 1.07 (t, J=7.1, 3H), NH signal not observed. LCMS (Method D): R$_T$=6.033 min, M+H$^+$=325.1.

Example 58

4-((3-methylpiperidin-3-yloxy)-9H-dipyrido[2,3-b;4',3'-d]pyrrole-6-carbonitrile

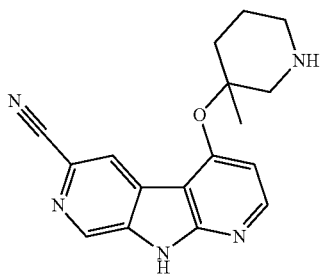 [SMILES: CC1(Oc2ccnc3[nH]c4cnc(C#N)cc4c23)CCCNC1]

Step 1: 4-((3-methylpiperidin-3-yloxy)-9-(2-trimethylsilanyl-ethoxymethyl)-9H-dipyrido[2,3-b;4',3'-d]pyrrole-6-carbonitrile

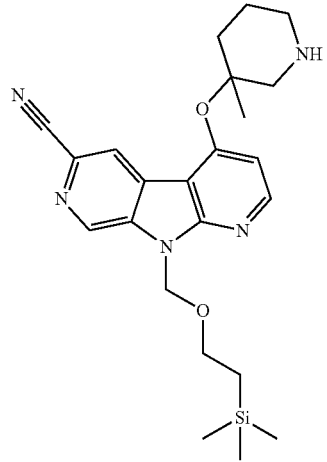 [SMILES: CC1(Oc2ccnc3c2c2cc(C#N)ncc2n3COCC[Si](C)(C)C)CCCNC1]

To a solution of 3-methylpiperidin-3-ol (99 mg, 0.86 mmol) in tetrahydrofuran (3.2 mL) was added sodium hydride as 60% dispersion in mineral oil (35 mg, 0.86 mmol). The reaction mixture was stirred at ambient temperature for 5 minutes before 4-chloro-9-(2-trimethylsilanyl-ethoxymethyl)-9H-dipyrido[2,3-b;4',3'-d]pyrrole-6-carbonitrile (141 mg, 0.39 mmol) was added in one portion and the reaction mixture was stirred at this temperature for 10 minutes before being warmed to 40° C. for 5 hours. The mixture was diluted with water (20 mL) and ethyl acetate (50 mL). The organic layer was separated, dried over sodium sulfate, filtered, concentrated in vacuo, and purified flash chromatography (silica, 40 g, ISCO, 1-20% methanol in methylene chloride) to afford the title compound as an orange solid, which was used in the next step without any further purification (52 mg, 30%).

Step 2: 4-((3-methylpiperidin-3-yloxy)-9H-dipyrido[2,3-b;4',3'-d]pyrrole-6-carbonitrile

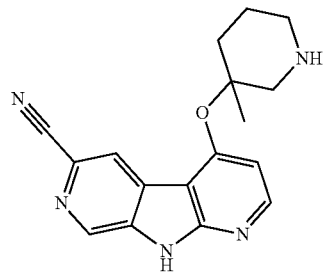 [SMILES: CC1(Oc2ccnc3[nH]c4cnc(C#N)cc4c23)CCCNC1]

4-((3-methylpiperidin-3-yl)methoxy)-9-(2-trimethylsilanyl-ethoxymethyl)-9H-dipyrido[2,3-b;4',3'-d]pyrrole-6-carbonitrile (52 mg, 0.12 mmol) was dissolved in 1,4-dioxane (0.5 mL) and then treated with 48% HBr$_{(aq)}$ (0.5 mL) and heated at 75° C. for 10 minutes. The cooled reaction mixture was then basified to pH ~12 by dropwise addition of 6N sodium hydroxide and then immediately acidified to pH ~8-9 by dropwise addition of concentrated hydrochloric acid, producing a cloudy precipitate. The solid was collected by centrifugation, dissolved in dimethylsulfoxide (2 mL), and purified by preparative HPLC [5-85% methanol in water (0.1% ammonium hydroxide) over 30 min, 35 mL/min] to afford the title compound as an off-white solid (11 mg, 31%). $^1$H NMR (400 MHz, d$_6$-DMSO) δ 12.18 (s, 1H), 8.70 (d, J=0.9, 1 H), 8.51 (d, J=0.9, 1 H), 8.27 (d, J=9.0, 1H), 6.90 (d, J=9.1, 1H), 4.48 (s, 1H), 3.93-3.84 (m, 1H), 3.64 (d, J=13.0, 1H), 3.55-3.40 (m, 2H), 1.79 (m, 1H), 1.67-1.57 (m, 2H), 1.52 (m, 1H), 1.13 (s, 3H). LCMS (Method E): R$_T$=3.73 min, M+H$^+$=308.2.

Example 59

4-(3-(dimethylamino)-2,2-dimethylpropoxy)-9H-dipyrido[2,3-b;4',3'-d]pyrrole-6-carbonitrile

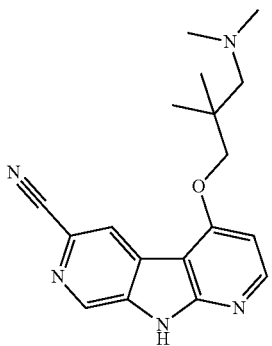 [SMILES: CN(C)CC(C)(C)COc1ccnc2[nH]c3cnc(C#N)cc3c12]

The title compound was prepared following a similar procedure to the previous example with 4-chloro-9-(2-trimethylsilanyl-ethoxymethyl)-9H-dipyrido[2,3-b;4',3'-d]pyrrole-6-carbonitrile, using 3-(dimethylamino)-2,2-dimethylpropan-1-ol. $^1$H NMR (400 MHz, d$_6$-DMSO) δ 12.78 (s, 1H), 8.99 (d, J=0.8, 1H), 8.55 (d, J=5.7, 1H), 8.39 (d, J=0.8, 1H), 7.06 (d, J=5.8, 1H), 4.12 (s, 2H), 2.41 (s, 2H), 2.24 (s, 6H), 1.10 (s, 6H). LCMS (Method E): R$_T$=3.58 min, M+H$^+$=324.1.

Example 60

(S)-4-(piperidin-3-yloxy)-9H-dipyrido[2,3-b;4',3'-d]pyrrole-6-carbonitrile

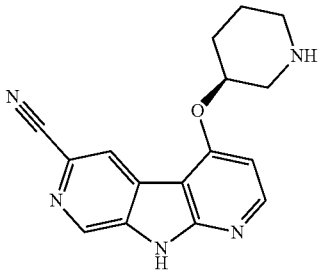 [SMILES: N#Cc1cc2c(cn1)[nH]c1nccc(O[C@H]3CCCNC3)c12]

The title compound was prepared following a similar procedure to the previous example using (S)-piperidin-3-ol. $^1$H NMR (400 MHz, d$_6$-DMSO) δ 8.96 (d, J=0.9, 1H), 8.57 (d, J=0.9, 1H), 8.52 (d, J=5.8, 1H), 7.08 (d, J=5.9, 1H), 4.84-4.74 (m, 1H), 3.22 (m, 1H), 2.93 (m, 1H), 2.89-2.78 (m, 1H), 2.77-2.64 (m, 1H), 2.12 (m, 1H), 1.94-1.85 (m, 1H), 1.85-1.73 (m, 1H), 1.57 (m, 1H). LCMS (Method E): R$_T$=6.98 min, M+H$^+$=294.1.

Example 61

4-((4-methylpiperidin-4-yl)methoxy)-9H-dipyrido[2,3-b;4',3'-d]pyrrole-6-carbonitrile

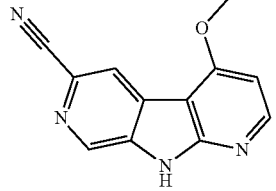

The title compound was prepared following a similar procedure to the previous example using (4-methylpiperidin-4-yl)methanol. $^1$H NMR (400 MHz, d$_6$-DMSO) δ 8.99 (s, 1H), 8.56 (d, J=5.6, 1H), 8.41 (s, 1H), 8.40 (s, 1H), 7.10 (d, J=5.8, 1H), 4.17 (s, 2H), 3.08-2.90 (m, 4H), 1.87-1.71 (m, 2H), 1.59 (m, 2H), 1.24 (s, 3H). LCMS (Method D): R$_T$=7.78 min, M+H$^+$=322.1.

Example 62

4-(1-(3-fluoropropyl)-4-methylpiperidin-4-yl)methoxy]-9H-dipyrido[2,3-b;4',3'-d]pyrrole-6-carbonitrile

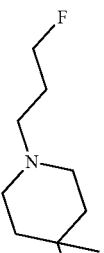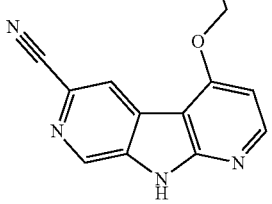

Step 1: tert-butyl 1-benzyl-4-methylpiperidine-4-carboxylate

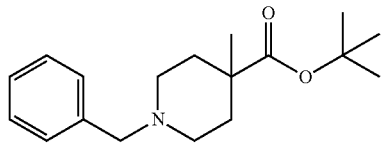 [SMILES: CC(C)(C)OC(=O)C1(C)CCN(Cc2ccccc2)CC1]

To a solution of N,N-diisopropylamine (3.1 mL, 22 mmol) in tetrahydrofuran (60 mL) cooled at −78° C. was added n-butyllithium (2.5N solution in hexanes, 8.9 mL, 22 mmol) dropwise over 5 minutes and the mixture was stirred for 30 minutes at −78° C. A solution of tert-butyl 1-benzylpiperidine-4-carboxylate (5.0 g, 20 mmol) in tetrahydrofuran (40 mL) was then added to the reaction mixture dropwise over 10 min and the temperature was maintained at −78° C. for 30 minutes before methyl iodide (1.3 mL, 21 mmol) was added in one portion. The reaction mixture was warmed to ambient temperature and stirred for 1 hour. The reaction was quenched with water (100 mL) and diluted with ethyl acetate (50 mL). The organic layer was separated and the aqueous layer was extracted with ethyl acetate (3×50 mL). The combined organic portions were dried over sodium sulfate, filtered, concentrated in vacuo, and purified flash chromatography (silica, 40 g, ISCO, 0-100% ethyl acetate in heptanes) to afford the title compound as a colorless oil, which was used in the next step without any further purification (5.3 g, 90%).

Step 2: (1-benzyl-4-methylpiperidin-4-yl)methanol

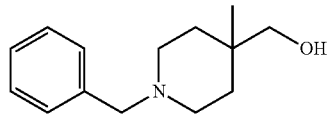 [SMILES: CC1(CO)CCN(Cc2ccccc2)CC1]

A solution of tert-butyl 1-benzyl-4-methylpiperidine-4-carboxylate (4.7 g, 18 mmol) in diethyl ether (47 mL) was cooled at 0° C. and to this was added lithium tetrahydroaluminate (990 mg, 25 mmol) portion-wise. The reaction mixture was warmed to ambient temperature and stirred vigorously for 1 hour. The mixture was then cooled to 0° C. and a 1N solution of sodium hydroxide (6 mL) was added dropwise to the reaction mixture producing a white precipitate. The mixture was filtered and the solids were washed with ethyl acetate (100 mL). The combined filtrate was separated and the aqueous portion was extracted with ethyl acetate (2×50 mL). The combined organic portions were dried over sodium sulfate, filtered, concentrated in vacuo, and purified flash chromatography (silica, 80 g, ISCO, 45-100% ethyl acetate in heptane) to afford the title compound as a white solid, which was used in the next step without any further purification (2.7 g, 67%).

Step 3: (4-methylpiperidin-4-yl)methanol

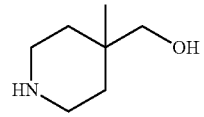

To a solution of (1-benzyl-4-methylpiperidin-4-yl)methanol (2.7 g, 12 mmol) in methanol (34 mL) was added ammonium formate (8.6 g, 135 mmol) followed by palladium on carbon (10% w/w, 3.6 g, 1.7 mmol). The reaction mixture was stirred for 18 hours under a balloon of hydrogen, then degassed, flushed with nitrogen, and filtered over a pad of celite. The solvent was removed in vacuo and the resulting residue was purified by flash chromatography (silica, 40 g, ISCO, 0-20% methanol in methylene chloride) to afford the title compound as a colorless oil, which was used in the next step without any further purification (1.2 g, 76%).

Step 4: 4-((4-methylpiperidin-4-yl)methoxy)-9-(2-trimethylsilanyl-ethoxymethyl)-9H-dipyrido[2,3-b;4',3'-d]pyrrole-6-carbonitrile

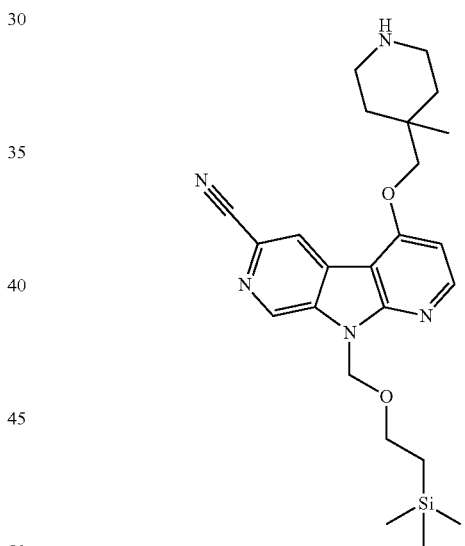

To a solution of (4-methylpiperidin-4-yl)methanol (989 mg, 7.7 mmol) in 1,4-dioxane (18 mL) and N,N-dimethylformamide (12 mL) was added sodium hydride as 60% dispersion in mineral oil (670 mg, 28 mmol). The reaction mixture was stirred at ambient temperature for 5 minutes before 4-chloro-9-(2-trimethylsilanyl-ethoxymethyl)-9H-dipyrido[2,3-b;4',3'-d]pyrrole-6-carbonitrile (428 mg, 1.2 mmol) was added in one portion and the reaction mixture was heated at 40° C. for 18 hours. The cooled reaction mixture was diluted with water (20 mL) and ethyl acetate (50 mL). The organic layer was separated, dried over sodium sulfate, filtered, concentrated in vacuo, and purified flash chromatography (silica, 40 g, ISCO, 1-20% methanol in methylene chloride) to afford the title compound as an off-white solid, which was used in the next step without any further purification (300 mg, 56%).

Step 5: 4-(1-(3-fluoropropyl)-4-methylpiperidin-4-yl)methoxy]-9-(2-trimethylsilanyl-ethoxymethyl)-9H-dipyrido[2,3-b;4',3'-d]pyrrole-6-carbonitrile

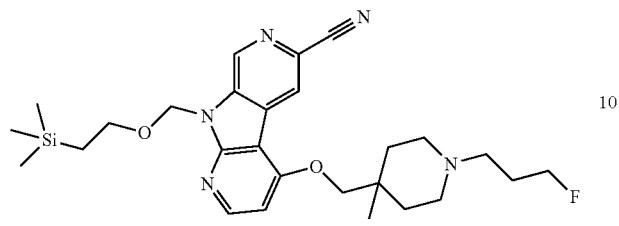

To a solution of 4-((4-methylpiperidin-4-yl)methoxy)-9-(2-trimethylsilanyl-ethoxymethyl)-9H-dipyrido[2,3-b;4',3'-d]pyrrole-6-carbonitrile (77 mg, 0.17 mmol) in 1,4-dioxane (2.6 mL) and N,N-dimethylformamide (0.5 mL) was added sodium hydride as 60% dispersion in mineral oil (20 mg, 0.85 mmol). The reaction mixture was stirred at ambient temperature for 5 minutes before 3-fluoropropyl trifluoromethanesulfonate (46 mg, 0.22 mmol) was added in one portion and the reaction mixture was heated at 40° C. for 18 hours. The cooled reaction mixture was diluted with water (20 mL) and ethyl acetate (50 mL). The organic layer was separated, dried over sodium sulfate, filtered, concentrated in vacuo, and purified flash chromatography (silica, 4 g, ISCO, 1-15% methanol in dichloromethane) to afford the title compound as an oil, which was used in the next step without any further purification (59 mg, 68%).

Step 6: 4-(1-(3-fluoropropyl)-4-methylpiperidin-4-yl)methoxy]-9H-dipyrido[2,3-b;4',3'-d]pyrrole-6-carbonitrile

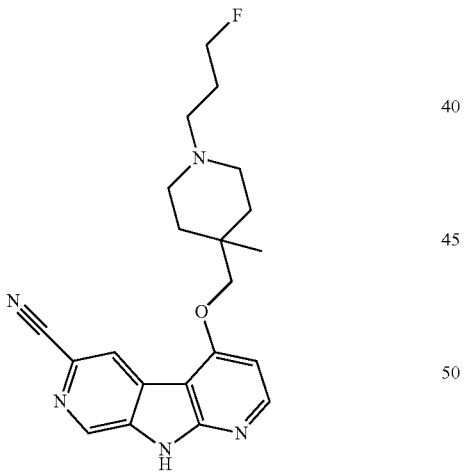

4-(1-(3-fluoropropyl)-4-methylpiperidin-4-yl)methoxy]-9-(2-trimethylsilanyl-ethoxymethyl)-9H-dipyrido[2,3-b;4', 3'-d]pyrrole-6-carbonitrile (59 mg, 0.11 mmol) was dissolved in 1,4-dioxane (0.5 mL) and then treated with 48% HBr$_{(aq)}$ (0.5 mL) and heated at 75° C. for 15 minutes. The cooled reaction mixture was then basified to pH ~12 by dropwise addition of 6N sodium hydroxide and then immediately acidified to pH ~8-9 by dropwise addition of concentrated hydrochloric acid, producing a cloudy precipitate. The solid was collected by centrifugation, dissolved in dimethylsulfoxide (2 mL), and purified by preparative HPLC [5-85% methanol in water (0.1% ammonium hydroxide) over 30 min, 35 mL/min] to afford the title compound (17 mg, 38%). $^1$H NMR (500 MHz, d$_6$-DMSO) δ 8.98 (d, J=0.9, 1H), 8.54 (d, J=5.7, 1H), 8.35 (d, J=0.9, 1H), 7.06 (d, J=5.8, 1H), 4.54 (t, J=6.1, 1H), 4.45 (t, J=6.0, 1H), 4.13 (s, 2H), 2.62-2.55 (m, 2H), 2.42 (t, J=7.1, 2H), 2.33 (m, 2H), 1.86 (m, 2H), 1.78 (m, 2H), 1.54 (m, 2H), 1.20 (s, 3H). LCMS (Method D): R$_T$=7.43 min, M+H$^+$=382.2.

Example 63

4-((1-(2-hydroxyethyl)-4-methylpiperidin-4-yl)methoxy)-9H-dipyrido[2,3-b;4',3'-d]pyrrole-6-carbonitrile

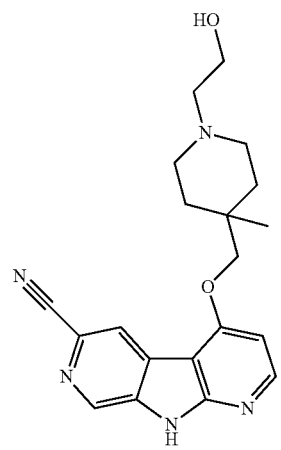 [SMILES: CC1(COc2ccnc3[nH]c4cnc(C#N)cc4c23)CCN(CCO)CC1]

The title compound was prepared following a similar procedure to the previous example using 2-iodoethyl trifluoromethanesulfonate. $^1$H NMR (500 MHz, d$_6$-DMSO) δ 8.99 (s, 1H), 8.55 (d, J=5.7, 1 H), 8.45 (s, 2H), 8.35 (s, 1H), 7.07 (d, J=5.8, 1 H), 4.15 (s, 2H), 3.51 (t, J=6.4, 2H), 2.61 (m, 2H), 2.44 (t, J=6.4, 2H), 2.38 (m, 2H), 1.73 (m, 2H), 1.56 (m, 2H), 1.19 (s, 3H). LCMS (Method D): R$_T$=6.66 min, M+H$^+$=366.0.

Example 64

4-((1-(2-methoxyethyl)-4-methylpiperidin-4-yl)methoxy)-9H-dipyrido[2,3-b;4',3'-d]pyrrole-6-carbonitrile

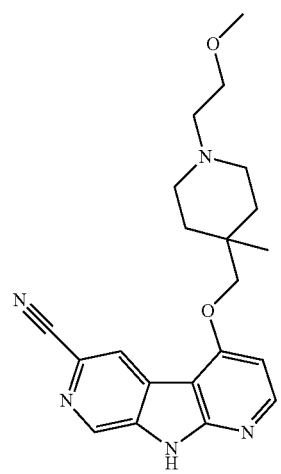 [SMILES: COCCN1CCC(C)(COc2ccnc3[nH]c4cnc(C#N)cc4c23)CC1]

Step 1: 4-((1-(2-methoxyethyl)-4-methylpiperidin-4-yl)methoxy)-9-(2-trimethylsilanyl-ethoxymethyl)-9H-dipyrido[2,3-b;4',3'-d]pyrrole-6-carbonitrile

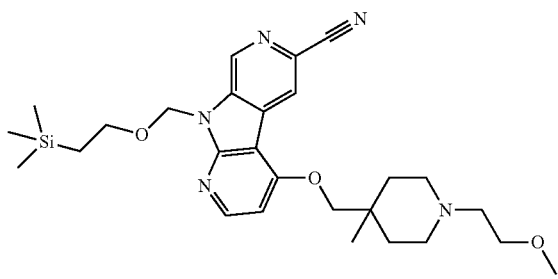

To a solution of 4-((4-methylpiperidin-4-yl)methoxy)-9-(2-trimethylsilanyl-ethoxymethyl)-9H-dipyrido[2,3-b;4',3'-d]pyrrole-6-carbonitrile (74 mg, 0.16 mmol) in acetonitrile (1.7 mL) was added sodium iodide (26 mg, 0.17 mmol) and 1-bromo-2-methoxyethane (16 uL, 0.17 mmol). The reaction mixture was warmed to 50° C. for 18 hours. The mixture was allowed to cool and then 1-bromo-2-methoxyethane (65 uL, 0.69 mmol) and N,N-diisopropylethylamine (29 uL, 0.16 mmol) were added and the mixture was heated at 50° C. for an additional 4 hours. The cooled reaction mixture was diluted with saturated aqueous sodium bicarbonate solution (10 mL), water (20 mL), and methylene chloride (50 mL). The organic layer was separated, dried over sodium sulfate, filtered, concentrated in vacuo, and purified flash chromatography (silica, 4 g, ISCO, 1-20% methanol in dichloromethane) to afford the title compound as an oil, which was used in the next step without any further purification (36 mg, 43%).

Step 2: 4-((1-(2-methoxyethyl)-4-methylpiperidin-4-yl)methoxy)-9H-dipyrido[2,3-b;4',3'-d]pyrrole-6-carbonitrile

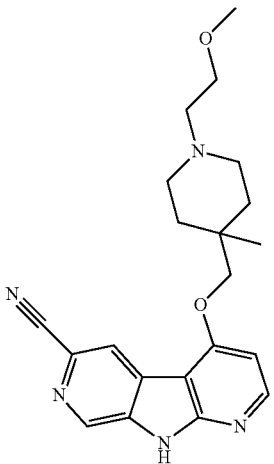 [SMILES: COCCN1CCC(C)(COc2ccnc3[nH]c4cnc(C#N)cc4c23)CC1]

4-((1-(2-methoxyethyl)-4-methylpiperidin-4-yl)methoxy)-9-(2-trimethylsilanyl-ethoxymethyl)-9H-dipyrido[2,3-b;4',3'-d]pyrrole-6-carbonitrile (36 mg, 0.07 mmol) was dissolved in 1,4-dioxane (0.3 mL) and then treated with 48% $HBr_{(aq)}$ (0.3 mL) and heated at 75° C. for 15 minutes. The cooled reaction mixture was then basified to pH ~12 by dropwise addition of 6N sodium hydroxide and then immediately acidified to pH ~8-9 by dropwise addition of concentrated hydrochloric acid, producing a cloudy precipitate. The solid was collected by centrifugation, dissolved in dimethylsulfoxide (1 mL), and purified by preparative HPLC [5-85% methanol in water (0.1% ammonium hydroxide) over 30 min, 35 mL/min] to afford the title compound as a white solid (7 mg, 25%). $^1$H NMR (500 MHz, $d_6$-DMSO) δ 8.99 (s, 1H), 8.55 (d, J=5.7, 1H), 8.35 (s, 1H), 8.31 (s, 1H), 7.08 (d, J=5.8, 1H), 4.13 (s, 2H), 3.44 (t, J=6.4, 2H), 3.24 (s, 3H), 2.66-2.58 (m, 2H), 2.52 (t, J=6.4, 2H), 2.39 (m, 2H), 1.74 (m, 2H), 1.53 (m, 2H), 1.18 (s, 3H). LCMS (Method G): $R_T$=3.92 min, M+H$^+$=380.0.

Example 65

4-((1-ethyl-4-methylpiperidin-4-yl)methoxy)-9H-dipyrido[2,3-b;4',3'-d]pyrrole-6-carbonitrile

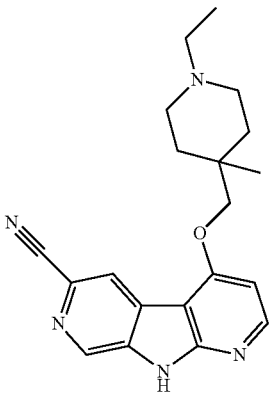 [SMILES: CCN1CCC(C)(COc2ccnc3[nH]c4cnc(C#N)cc4c23)CC1]

Step 1: 4-((1-ethyl-4-methylpiperidin-4-yl)methoxy)-9-(2-trimethylsilanyl-ethoxymethyl)-9H-dipyrido[2,3-b;4',3'-d]pyrrole-6-carbonitrile

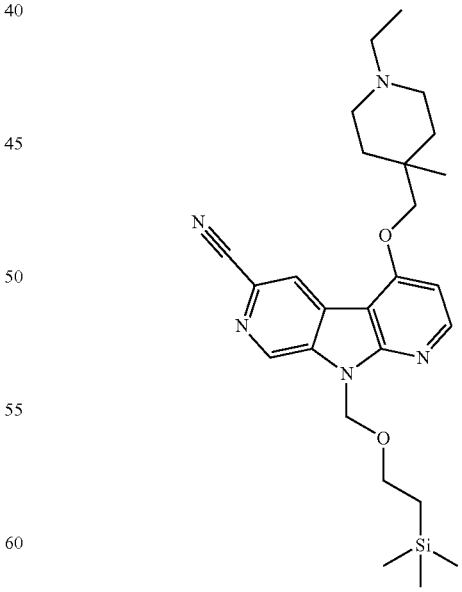

To a solution of 4-((4-methylpiperidin-4-yl)methoxy)-9-(2-trimethylsilanyl-ethoxymethyl)-9H-dipyrido[2,3-b;4',3'-d]pyrrole-6-carbonitrile (75 mg, 0.17 mmol) in methylene chloride (1.1 mL) was added acetaldehyde (14 uL, 0.25 mmol) and sodium triacetoxyborohydride (53 mg, 0.25 mmol), and the mixture was stirred at ambient temperature for 10 minutes. The reaction mixture was diluted with saturated aqueous sodium bicarbonate solution (50 mL) and methylene chloride (50 mL). The organic layer was separated, dried over sodium sulfate, filtered, concentrated in vacuo, and purified flash chromatography (silica, 4 g, ISCO, 0-20% methanol in methylene chloride) to afford the title compound as a yellow solid, which was used in the next step without any further purification (58 mg, 73%).

Step 2: 4-((1-ethyl-4-methylpiperidin-4-yl)methoxy)-9H-dipyrido[2,3-b;4',3'-d]pyrrole-6-carbonitrile

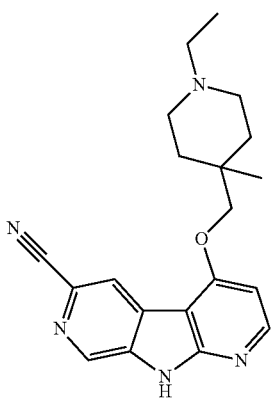 [SMILES: CCN1CCC(C)(COc2ccnc3[nH]c4cnc(C#N)cc4c23)CC1]

4-((1-ethyl-4-methylpiperidin-4-yl)methoxy)-9-(2-trimethylsilanyl-ethoxymethyl)-9H-dipyrido[2,3-b;4',3'-d]pyrrole-6-carbonitrile (58 mg, 0.12 mmol) was dissolved in 1,4-dioxane (0.5 mL) and then treated with 48% HBr$_{(aq)}$ (0.5 mL) and heated at 75° C. for 15 minutes. The cooled reaction mixture was then basified to pH ~12 by dropwise addition of 6N sodium hydroxide and then immediately acidified to pH ~8-9 by dropwise addition of concentrated hydrochloric acid, producing a cloudy precipitate. The solid was collected by centrifugation, dissolved in dimethylsulfoxide (2 mL), and purified by preparative HPLC [5-85% methanol in water (0.1% ammonium hydroxide) over 30 min, 35 mL/min] to afford the title compound as a white solid (13 mg, 30%). $^1$H NMR (400 MHz, d$_6$-DMSO) δ 8.98 (d, J=0.8, 1H), 8.54 (d, J=5.7, 1H), 8.35 (d, J=0.8, 1H), 7.06 (d, J=5.8, 1H), 4.12 (s, 2H), 2.56 (m, 2H), 2.42-2.25 (m, 4H), 1.75 (m, 2H), 1.54 (m, 2H), 1.19 (s, 3H), 1.08-0.97 (m, 3H). LCMS (Method D): R$_T$=8.49 min, M+H$^+$=450.1.

Example 66

(R)-4-(1-methylpiperidin-3-yloxy)-9H-dipyrido[2,3-b;4',3'-d]pyrrole-6-carbonitrile

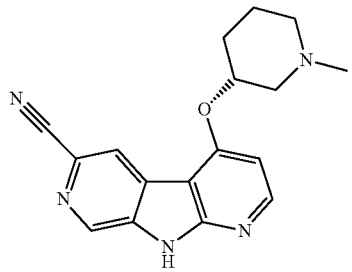

Step 1: (R)-4-(piperidin-3-yloxy)-9-(2-trimethylsilanyl-ethoxymethyl)-9H-dipyrido[2,3-b;4',3'-d]pyrrole-6-carbonitrile

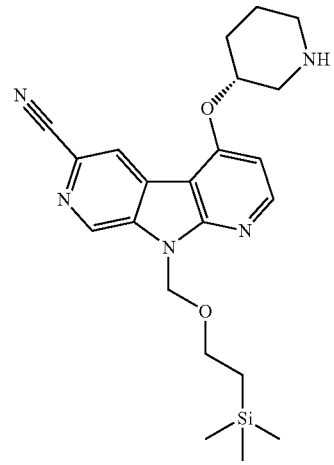 [SMILES: C[Si](C)(C)CCOCn1c2cnc(C#N)cc2c2c(O[C@@H]3CCCNC3)ccnc21]

To a solution of (R)-piperidin-3-ol hydrogen chloride (169 mg, 1.2 mmol) in tetrahydrofuran (4.5 mL) and N,N-dimethylformamide (1 mL) was added sodium hydride as 60% dispersion in mineral oil (200 mg, 5.0 mmol). The reaction mixture was stirred at ambient temperature for 5 minutes before 4-chloro-9-(2-trimethylsilanyl-ethoxymethyl)-9H-dipyrido[2,3-b;4',3'-d]pyrrole-6-carbonitrile (200 mg, 0.56 mmol) was added in one portion and the reaction mixture was stirred at this temperature for 10 minutes before being warmed to 40° C. for 4 hours. The cooled reaction mixture was diluted with water (20 mL) and ethyl acetate (50 mL). The organic layer was separated, dried over sodium sulfate, filtered, concentrated in vacuo, and purified flash chromatography (silica, 40 g, ISCO, 1-20% methanol in methylene chloride) to afford the title compound as a yellow solid, which was used in the next step without any further purification (236 mg, 100%).

Step 2: (R)-4-(1-methylpiperidin-3-yloxy)-9-(2-trimethylsilanyl-ethoxymethyl)-9H-dipyrido[2,3-b;4',3'-d]pyrrole-6-carbonitrile

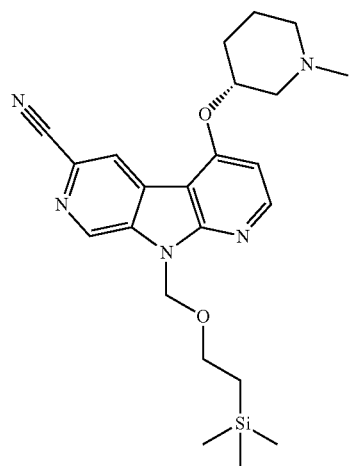 [SMILES: CN1CCC[C@@H](Oc2ccnc3c2c2cc(C#N)ncc2n3COCC[Si](C)(C)C)C1]

To a solution of (R)-4-(1-methylpiperidin-3-yloxy)-9-(2-trimethylsilanyl-ethoxymethyl)-9H-dipyrido[2,3-b;4',3'-d]pyrrole-6-carbonitrile (101 mg, 0.24 mmol) in acetonitrile (1.0 mL) and water (0.21 mL) was added Formalin (20 uL, 0.71 mmol) followed by sodium triacetoxyborohydride (101 mg, 0.48 mmol), and the mixture was stirred at ambient temperature for 20 minutes. The reaction mixture was diluted with saturated aqueous sodium bicarbonate solution (50 mL) and methylene chloride (50 mL). The organic layer was separated, dried over sodium sulfate, filtered, concentrated in vacuo, and purified flash chromatography (silica, 4 g, ISCO, 1-20% methanol in dichloromethane) to afford the title compound as a white solid, which was used in the next step without any further purification (93 mg, 89%).

Step 3: (R)-4-(1-methylpiperidin-3-yloxy)-9H-dipyrido[2,3-b;4',3'-d]pyrrole-6-carbonitrile

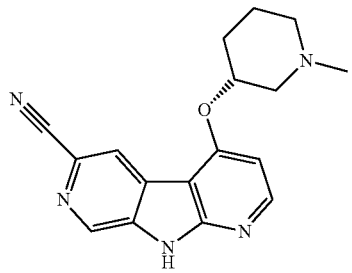

(R)-4-(1-methylpiperidin-3-yloxy)-9-(2-trimethylsilanyl-ethoxymethyl)-9H-dipyrido[2,3-b;4',3'-d]pyrrole-6-carbonitrile (93 mg, 0.21 mmol) was dissolved in 1,4-dioxane (0.5 mL) and then treated with 48% HBr$_{(aq)}$ (0.5 mL) and heated at 75° C. for 15 minutes. The cooled reaction mixture was then basified to pH ~12 by dropwise addition of 6N sodium hydroxide and then immediately acidified to pH ~8-9 by dropwise addition of concentrated hydrochloric acid, producing a cloudy precipitate. The solid was collected by centrifugation, dissolved in dimethylsulfoxide (2 mL), and purified by preparative HPLC [5-85% methanol in water (0.1% ammonium hydroxide) over 30 min, 35 mL/min] to afford the title compound as a white solid (18 mg, 27%). $^1$H NMR (400 MHz, d$_6$-DMSO) δ 12.74 (s, 1H), 8.96 (d, J=0.8, 1H), 8.52 (d, J=5.8, 1H), 8.46 (d, J=0.9, 1H), 7.10 (d, J=5.9, 1H), 4.93-4.82 (m, 1H), 2.93 (m, 1H), 2.57-2.51 (m, 1H), 2.44 (m, 1H), 2.24 (s, 3H), 2.19 (m, 1H), 2.08 (m, 1H), 1.83 (m, 1H), 1.68 (m, 2H). LCMS (Method D): R$_T$=7.08 min, M+H$^+$=308.1.

Example 67

4-((R)-1-ethylpiperidin-3-oxy)-9H-dipyrido[2,3-b;4',3'-d]pyrrole-6-carbonitrile

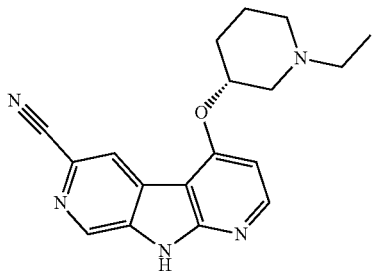 [SMILES: CCN1CCC[C@@H](Oc2ccnc3[nH]c4cnc(C#N)cc4c23)C1]

Step 1: (R)-4-(1-ethylpiperidin-3-yloxy)-9-(2-trimethylsilanyl-ethoxymethyl)-9H-dipyrido[2,3-b;4',3'-d]pyrrole-6-carbonitrile

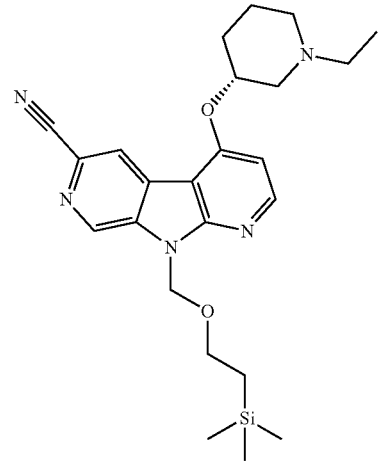 [SMILES: CCN1CCC[C@@H](Oc2ccnc3c2c2cc(C#N)ncc2n3COCC[Si](C)(C)C)C1]

To a solution of (R)-4-(piperidin-3-oxy)-9-(2-trimethylsilanyl-ethoxymethyl)-9H-dipyrido[2,3-b;4',3'-d]pyrrole-6-carbonitrile (84 mg, 0.20 mmol) in acetonitrile (1.0 mL) was added iodoethane (24 uL, 0.30 mmol), and the mixture was heated at 50° C. for 18 hours. The cooled reaction mixture was diluted with saturated aqueous sodium bicarbonate solution (50 mL) and methylene chloride (50 mL). The organic layer was separated, dried over sodium sulfate, filtered, concentrated in vacuo, and purified flash chromatography (silica, 4 g, ISCO, 1-20% methanol in methylene chloride) to afford the title compound as a yellow oil, which was used in the next step without any further purification (46 mg, 51%).

Step 2: (R)-4-(1-ethylpiperidin-3-yloxy)-9H-dipyrido[2,3-b;4',3'-d]pyrrole-6-carbonitrile

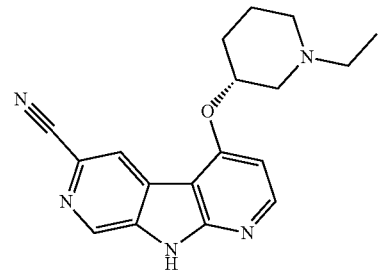 [SMILES: CCN1CCC[C@@H](Oc2ccnc3[nH]c4cnc(C#N)cc4c23)C1]

(R)-4-(1-ethylpiperidin-3-oxy)-9-(2-trimethylsilanyl-ethoxymethyl)-9H-dipyrido[2,3-b;4',3'-d]pyrrole-6-carbonitrile (46 mg, 0.10 mmol) was dissolved in 1,4-dioxane (0.5 mL) and then treated with 48% HBr$_{(aq)}$ (0.5 mL) and heated at 75° C. for 15 minutes. The cooled reaction mixture was then basified to pH ~12 by dropwise addition of 6N sodium hydroxide and then immediately acidified to pH ~8-9 by dropwise addition of concentrated hydrochloric acid, producing a cloudy precipitate. The solid was collected by centrifugation, dissolved in dimethylsulfoxide (2 mL), and purified by preparative HPLC [5-85% methanol in water (0.1% ammonium hydroxide) over 30 min, 35 mL/min] to afford the title compound as a white solid (12 mg, 37%). $^1$H NMR (400 MHz, $d_6$-DMSO) δ 12.78 (s, 1H), 8.96 (d, J=0.9, 1H), 8.54-8.51 (d, J=5.9, 1H), 8.50 (d, J=0.9, 1H), 7.11 (d, J=5.9, 1H), 4.93-4.83 (m, 1H), 2.98 (d, J=8.9, 1 H), 2.61 (m, 1H), 2.52 (m, 2H), 2.44 (q, J=7.2, 2H), 2.26 (t, J=8.8, 1H), 2.07 (m, 1H), 1.86-1.75 (m, 1H), 1.66 (m, 2H), 1.04 (t, J=7.1, 3H). LCMS (Method E): $R_T$=7.33 min, M+H$^+$=322.1.

Example 68

(R)-4-(1-(2-hydroxyethyl)piperidin-3-yloxy)-9H-dipyrido[2,3-b;4',3'-d]pyrrole-6-carbonitrile

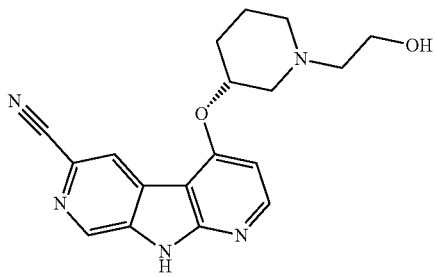

The title compound was prepared following a similar procedure to the previous example using 2-iodoethanol. $^1$H NMR (400 MHz, $d_6$-DMSO) δ 8.95 (d, J=0.8, 1H), 8.50 (d, J=5.8, 1H), 8.47 (d, J=0.8, 1H), 7.06 (d, J=5.9, 1H), 4.84 (m, 1H), 4.37 (s, 1H), 3.53 (t, J=6.2, 2H), 3.08 (m, 1H), 2.67 (m, 1H), 2.54 (m, 3H), 2.32 (m, 1H), 2.09 (m, 1H), 1.85-1.73 (m, 1H), 1.73-1.55 (m, 2H). LCMS (Method G): $R_T$=3.06 min, M+H$^+$=338.1.

Example 69

(R)-4-(1-(2-methoxyethyl)piperidin-3-oxy)-9H-dipyrido[2,3-b;4',3'-d]pyrrole-6-carbonitrile

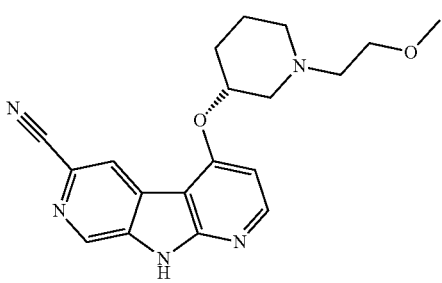

The title compound was prepared following a similar procedure to the previous example using 1-bromo-2-methoxyethane. $^1$H NMR (400 MHz, $d_6$-DMSO) δ 12.73 (s, 1H), 8.97 (s, 1H), 8.52 (d, J=5.6, 1H), 8.50 (s, 1H), 7.10 (d, J=5.8, 1H), 4.87 (s, 1H), 3.48 (m, 2H), 3.24 (s, 3H), 3.00 (m, 1H), 2.65 (m, 3H), 2.38 (m, 1H), 2.04 (m, 1H), 1.85-1.56 (m, 3H). LCMS (Method D): $R_T$=7.09 min, M+H$^+$=352.1.

Example 70

4-((4-ethyl-1-methylpiperidin-4-yl)methoxy)-9H-dipyrido[2,3-b;4',3'-d]pyrrole-6-carbonitrile

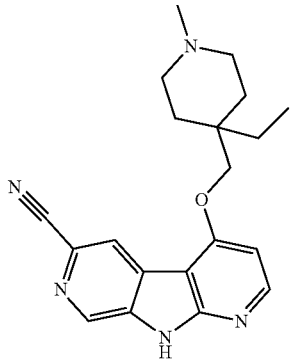 [SMILES: CCC1(COc2ccnc3[nH]c4cnc(C#N)cc4c23)CCN(C)CC1]

Step 1: (4-ethyl-1-methylpiperidin-4-yl)methanol

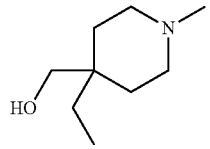

To a stirred suspension of di-tert-butyl 4-ethylpiperidine-1,4-dicarboxylate (1.1 g, 3.7 mmol) in tetrahydrofuran (13 mL) was added lithium tetrahydroaluminate (1.0N solution in tetrahydrofuran, 15 mL, 15 mmol), and the mixture was stirred at ambient temperature for 6 hours. The mixture was diluted with a 1N sodium hydroxide solution (5 mL), filtered over Whatman filter paper, and the solids were washed with ethyl acetate (50 mL). The combined filtrate was separated, and the organic portion was dried over sodium sulfate, filtered, and concentrated in vacuo to afford the title compound as a white solid, which was used in the next step without any further purification (506 mg, 57%).

Step 2: 4-((4-ethyl-1-methylpiperidin-4-yl)methoxy)-9H-dipyrido[2,3-b;4',3'-d]pyrrole-6-carbonitrile

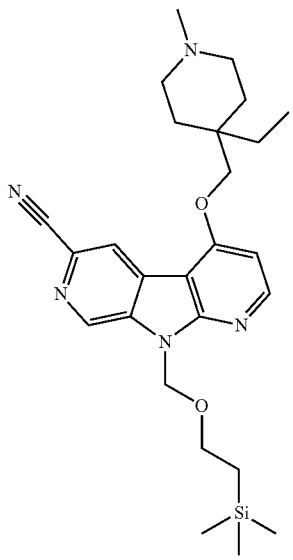 [SMILES: CCC1(COc2ccnc3c2c2cc(C#N)ncc2n3COCC[Si](C)(C)C)CCN(C)CC1]

To a solution of (4-ethyl-1-methylpiperidin-4-yl)methanol (223 mg, 1.4 mmol) in tetrahydrofuran (3.2 mL) was added sodium hydride as 60% dispersion in mineral oil (57 mg, 1.4 mmol). The reaction mixture was stirred at ambient temperature for 5 minutes before 4-chloro-9-(2-trimethylsilanyl-ethoxymethyl)-9H-dipyrido[2,3-b;4',3'-d]pyrrole-6-carbonitrile (150 mg, 0.42 mmol) was added in one portion and the reaction mixture was stirred at this temperature for 10 minutes, and then heated at 40° C. for 4 hours. The mixture was diluted with water (20 mL) and ethyl acetate (50 mL). The organic layer was separated, dried over sodium sulfate, filtered, concentrated in vacuo, and purified flash chromatography (silica, 4 g, ISCO, 0-10% methanol in methylene chloride) to afford the title compound as a white foam, which was used in the next step without any further purification (152 mg, 76%).

Step 3: 4-((4-ethyl-1-methylpiperidin-4-yl)methoxy)-9H-dipyrido[2,3-b;4',3'-d]pyrrole-6-carbonitrile

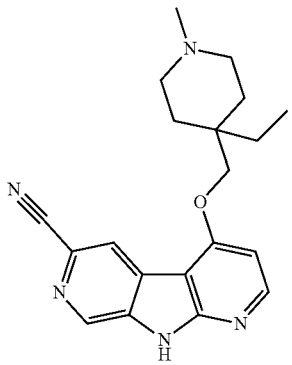 [SMILES: CCC1(COc2ccnc3[nH]c4cnc(C#N)cc4c23)CCN(C)CC1]

4-((4-ethyl-1-methylpiperidin-4-yl)methoxy)-9-(2-trimethylsilanyl-ethoxymethyl)-9H-dipyrido[2,3-b;4',3'-d]pyrrole-6-carbonitrile (152 mg, 0.32 mmol) was dissolved in 1,4-dioxane (0.5 mL) and then treated with 48% $HBr_{(aq)}$ (0.5 mL) and heated at 75° C. for 15 minutes. The cooled reaction mixture was then basified to pH ~12 by dropwise addition of 6N sodium hydroxide and then immediately acidified to pH ~8-9 by dropwise addition of concentrated hydrochloric acid, producing a cloudy precipitate. The solid was collected by centrifugation, dissolved in dimethylsulfoxide (2 mL), and purified by preparative HPLC [5-85% methanol in water (0.1% ammonium hydroxide) over 30 min, 35 mL/min] to afford the title compound as a white solid (44 mg, 40%). $^1$H NMR (500 MHz, $d_6$-DMSO) δ 8.98 (s, 1H), 8.55 (d, J=5.7, 1 H), 8.32 (s, 1H), 7.12 (d, J=5.8, 1H), 4.18 (s, 2H), 2.37 (m, 4H), 2.19 (s, 3H), 1.75-1.68 (m, 2H), 1.67 (m, 2H), 1.65-1.57 (m, 2H), 0.86 (t, J=7.5, 3 H). LCMS (Method D): $R_T$=7.36 min, M+H$^+$=350.2.

Example 71

4-((1,4-dimethylpiperidin-4-yl)methoxy)-9H-dipyrido[2,3-b;4',3'-d]pyrrole-6-carbonitrile

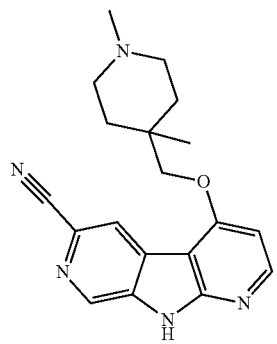 [SMILES: CN1CCC(C)(COc2ccnc3[nH]c4cnc(C#N)cc4c23)CC1]

Step 1: (1,4-dimethylpiperidin-4-yl)methanol

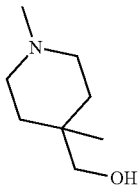

To a stirred suspension of 1,4-dimethylpiperidine-4-carboxylic acid hydrogen chloride (1.00 g, 5.17 mmol) in tetrahydrofuran (18.9 mL) was added lithium tetrahydroaluminate (1.0N solution in tetrahydrofuran, 20.7 mL, 20.7 mmol) dropwise over 5 minutes. The reaction mixture was stirred at ambient temperature for 12 hours and then diluted with water (20 mL), basified to pH ~12 by addition of sodium hydroxide pellets, and then diluted with diethyl ether (100 mL). The organic layer was separated, dried over sodium sulfate, filtered, and concentrated in vacuo to afford the title compound as a colorless oil (543 mg, 73%). $^1$H NMR (400 MHz, $d_6$-DMSO) δ 4.44 (m, 1H), 3.12 (d, J=5.4, 2H), 2.50 (m, 2H), 2.39-2.31 (m, 2H), 2.13 (s, 3H), 2.12-2.09 (m, 1H), 1.42 (m, 2H), 1.16 (m, 2H), 0.82 (s, 3H).

Step 2: 4-((1,4-dimethylpiperidin-4-yl)methoxy)-9H-dipyrido[2,3-b;4',3'-d]pyrrole-6-carbonitrile

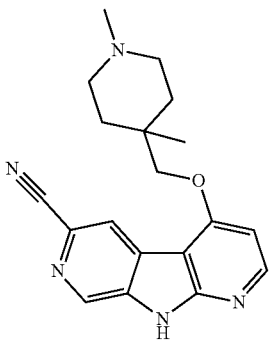 [SMILES: CN1CCC(C)(COc2ccnc3[nH]c4cnc(C#N)cc4c23)CC1]

The title compound was prepared following a similar procedure to the previous example using (1,4-dimethylpiperidin-4-yl)methanol. ¹H NMR (400 MHz, d₆-DMSO) δ 8.99 (d, J=0.8, 1H), 8.55 (d, J=5.7, 1H), 8.35 (d, J=0.9, 1H), 7.08 (d, J=5.8, 1H), 4.13 (s, 2H), 2.54-2.51 (m, 2H), 2.30 (m, 2H), 2.21 (s, 3H), 1.81-1.68 (m, 2H), 1.55 (m, 2H), 1.19 (s, 3H). LCMS (Method D): R$_T$=6.68 min, M+H⁺=336.2.

Example 72

(R)-4-(piperidin-2-ylmethoxy)-9H-dipyrido[2,3-b;4',3'-d]pyrrole-6-carbonitrile

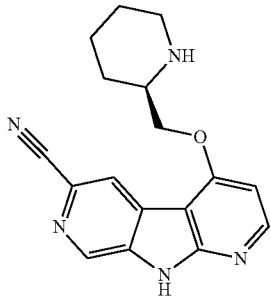

Step 1: (R)-piperidin-2-ylmethanol hydrogen chloride

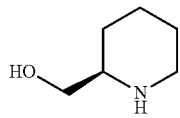

A mixture of (R)-tert-butyl 2-(hydroxymethyl)piperidine-1-carboxylate (840 mg, 3.9 mmol) in 1,4-dioxane (15 mL) was treated with hydrogen chloride (4.0N solution in dioxane, 9.8 mL, 39 mmol), and stirred at ambient temperature for 3 hours. The solvent was evaporated in vacuo to afford the title compound as a white solid (594 mg). ¹H NMR (400 MHz, d₆-DMSO) δ 8.75 (s, 1H), 4.72 (t, J=5.3, 1H), 3.35 (m, 1H), 3.28-3.15 (m, 3H), 2.72 (m, 1H), 2.59-2.52 (m, 1H), 1.88-1.72 (m, 2H), 1.72-1.53 (m, 2H), 1.16 (m, 1H).

Step 2: (R)-4-(piperidin-2-ylmethoxy)-9-(2-trimethylsilanyl-ethoxymethyl)-9H-dipyrido[2,3-b;4',3'-d]pyrrole-6-carbonitrile

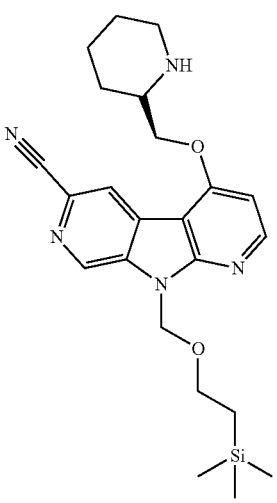

To a solution of (R)-piperidin-2-ylmethanol hydrogen chloride (510 mg, 3.4 mmol) in tetrahydrofuran (12 mL) was added sodium hydride as 60% dispersion in mineral oil (270 mg, 6.8 mmol). The reaction mixture was stirred at ambient temperature for 5 minutes before 4-chloro-9-(2-trimethylsilanyl-ethoxymethyl)-9H-dipyrido[2,3-b;4',3'-d]pyrrole-6-carbonitrile (550 mg, 1.5 mmol) was added in one portion and the reaction mixture was stirred at this temperature for 10 minutes, and then heated at 40° C. for 5 hours. The cooled mixture was diluted with water (20 mL) and ethyl acetate (50 mL). The organic layer was separated, dried over sodium sulfate, filtered, concentrated in vacuo, and purified flash chromatography (silica, 40 g, ISCO, 1-20% methanol in methylene chloride) to afford the title compound as a white solid, which was used in the next step without any further purification (470 mg, 70%).

Step 3: (R)-4-(piperidin-2-ylmethoxy)-9H-dipyrido[2,3-b;4',3'-d]pyrrole-6-carbonitrile

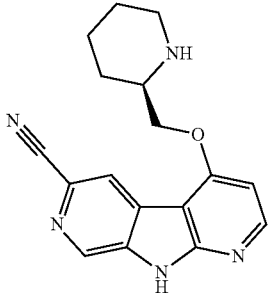 [SMILES: N#Cc1cc2c(cn1)[nH]c1nccc(OC[C@H]3CCCCN3)c12]

(R)-4-(piperidin-2-ylmethoxy)-9-(2-trimethylsilanyl-ethoxymethyl)-9H-dipyrido[2,3-b;4',3'-d]pyrrole-6-carbonitrile (467 mg, 1.1 mmol) was dissolved in 1,4-dioxane (0.5 mL) and then treated with 48% HBr$_{(aq)}$ (0.5 mL) and heated at 75° C. for 15 minutes. The cooled reaction mixture was then basified to pH ~12 by dropwise addition of 6N sodium hydroxide and then immediately acidified to pH ~8-9 by dropwise addition of concentrated hydrochloric acid, producing a cloudy precipitate. The solid was collected by centrifugation, dissolved in dimethylsulfoxide (2 mL), and purified by preparative HPLC [5-85% methanol in water (0.1% ammonium hydroxide) over 30 min, 35 mL/min] to afford the title compound as a white solid (122 mg, 37%). ¹H NMR (400 MHz, d₆-DMSO) δ 8.97 (d, J=0.7, 1H), 8.54 (m, 2H), 7.05 (d, J=5.8, 1H), 4.30-4.18 (m, 2H), 3.11 (m, 1H), 3.03 (m, 1H), 2.69-2.60 (m, 1H), 1.79 (m, 2H), 1.58 (m, 1H), 1.45-1.33 (m, 2H), 1.33-1.21 (m, 1H). LCMS (Method D): R$_T$=7.41 min, M+H⁺=308.1.

Example 73

(S)-4-(piperidin-2-ylmethoxy)-9H-dipyrido[2,3-b;4',3'-d]pyrrole-6-carbonitrile

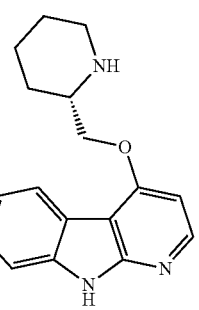

The title compound was prepared following a similar procedure to the previous example using (S)-tert-butyl 2-(hydroxymethyl)piperidine-1-carboxylate. ¹H NMR (400 MHz, d₆-DMSO) δ 8.97 (d, J=0.8, 1H), 8.54 (dd, J=3.3, 2.4, 2H), 7.05 (d, J=5.8, 1H), 4.29-4.17 (m, 2H), 3.08 (m, 1H), 3.03 (m, 1H), 2.70-2.62 (m, 1H), 1.79 (m, 2H), 1.58 (m, 1H), 1.46-1.33 (m, 2H), 1.32-1.19 (m, 1H). LCMS (Method D): $R_T$=7.38 min, M+H⁺=308.1.

Example 74

(R)-4-((1-ethylpiperidin-2-yl)methoxy)-9H-dipyrido[2,3-b;4',3'-d]pyrrole-6-carbonitrile

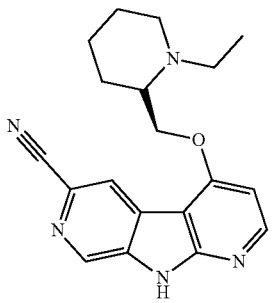

Step 1: (R)-4-((1-ethylpiperidin-2-yl)methoxy)-9-(2-trimethylsilanyl-ethoxymethyl)-9H-dipyrido[2,3-b;4',3'-d]pyrrole-6-carbonitrile

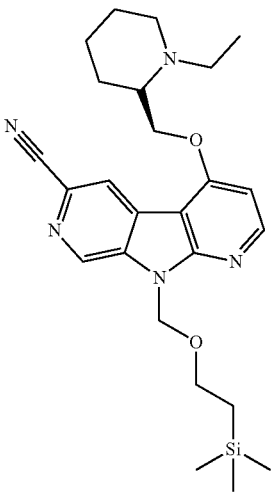

To a solution of (R)-4-(piperidin-2-ylmethoxy)-9-(2-trimethylsilanyl-ethoxymethyl)-9H-dipyrido[2,3-b;4',3'-d]pyrrole-6-carbonitrile (96 mg, 0.22 mmol) in methylene chloride (1.4 mL) was added acetaldehyde (19 uL, 0.33 mmol) followed by sodium triacetoxyborohydride (70 mg, 0.33 mmol), and the reaction mixture was stirred at ambient temperature for 5 minutes. The mixture diluted with saturated aqueous sodium bicarbonate solution (50 mL) and methylene chloride (50 mL). The organic layer was separated, dried over sodium sulfate, filtered, concentrated in vacuo, and purified by flash chromatography (silica, 4 g, ISCO, 1-15% methanol in methylene chloride) to afford the title compound as a yellow solid, which was used in the next step without any further purification (64 mg, 87%).

Step 2: (R)-4-((1-ethylpiperidin-2-yl)methoxy)-9H-dipyrido[2,3-b;4',3'-d]pyrrole-6-carbonitrile

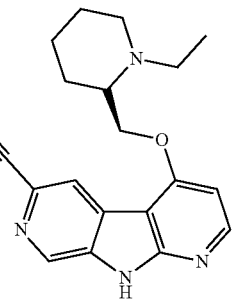

(R)-4-((1-ethylpiperidin-2-yl)methoxy)-9-(2-trimethylsilanyl-ethoxymethyl)-9H-dipyrido[2,3-b;4',3'-d]pyrrole-6-carbonitrile (64 mg, 0.14 mmol) was dissolved in 1,4-dioxane (0.5 mL) and then treated with 48% $HBr_{(aq)}$ (0.5 mL) and heated at 75° C. for 15 minutes. The cooled reaction mixture was then basified to pH ~12 by dropwise addition of 6N sodium hydroxide and then immediately acidified to pH ~8-9 by dropwise addition of concentrated hydrochloric acid, producing a cloudy precipitate. The solid was collected by centrifugation, dissolved in dimethylsulfoxide (2 mL), and purified by preparative HPLC [5-85% methanol in water (0.1% ammonium hydroxide) over 30 min, 35 mL/min] to afford the title compound as a solid (15 mg, 32%). ¹H NMR (500 MHz, d₆-DMSO) δ 12.81 (s, 1H), 8.98 (s, 1H), 8.55 (d, J=5.7, 1H), 8.43 (s, 1H), 7.05 (d, J=5.8, 1H), 4.27 (m, 3H), 3.05 (m, 1H), 2.77 (m, 1H), 2.36 (m, 1H), 2.25 (m, 1H), 1.99 (m, 1H), 1.83 (m, 1H), 1.70 (m, 1H), 1.57 (m, 1H), 1.23 (m, 1H), 1.03 (t, J=7.1, 3H), 0.92 (d, J=6.6, 1H). LCMS (Method D): $R_T$=6.63 min, M+H⁺=336.2.

Example 75

(R)-4-((1-methylpiperidin-2-yl)methoxy)-9H-dipyrido[2,3-b;4',3'-d]pyrrole-6-carbonitrile

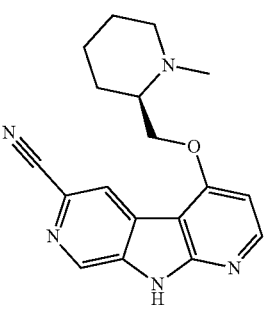 [SMILES: CN1CCCC[C@@H]1COc1ccnc2[nH]c3cnc(C#N)cc3c12]

Step 1: (R)-4-((1-methylpiperidin-2-yl)methoxy)-9-(2-trimethylsilanyl-ethoxymethyl)-9H-dipyrido[2,3-b;4',3'-d]pyrrole-6-carbonitrile

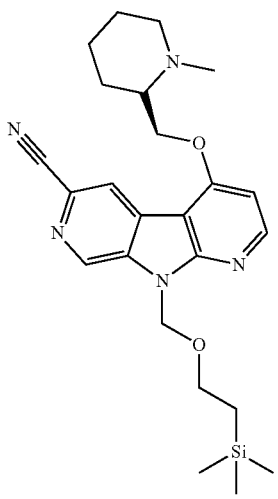

To a solution of (R)-4-(piperidin-2-ylmethoxy)-9-(2-trimethylsilanyl-ethoxymethyl)-9H-dipyrido[2,3-b;4',3'-d]pyrrole-6-carbonitrile (220 mg, 0.50 mmol) in acetonitrile (2.2 mL) and water (0.45 mL) was added Formalin (41 uL, 1.5 mmol) followed by sodium triacetoxyborohydride (210 mg, 1.0 mmol), and the reaction mixture was stirred at ambient temperature for 20 minutes. The mixture diluted with saturated aqueous sodium bicarbonate solution (50 mL) and methylene chloride (50 mL). The organic layer was separated, dried over sodium sulfate, filtered, concentrated in vacuo, and purified flash chromatography (silica, 4 g, ISCO, 1-20% methanol in methylene chloride) to afford the title compound as a yellow solid, which was used in the next step without any further purification (197 mg, 87%).

Step 2: (R)-4-((1-methylpiperidin-2-yl)methoxy)-9H-dipyrido[2,3-b;4',3'-d]pyrrole-6-carbonitrile

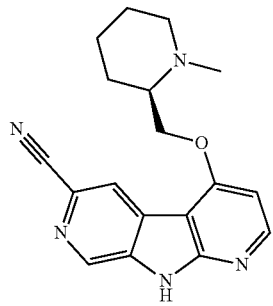 [SMILES: CN1CCCC[C@@H]1COc1ccnc2[nH]c3cnc(C#N)cc3c12]

(R)-4-((1-methylpiperidin-2-yl)methoxy)-9-(2-trimethylsilanyl-ethoxymethyl)-9H-dipyrido[2,3-b;4',3'-d]pyrrole-6-carbonitrile (197 mg, 0.44 mmol) was dissolved in 1,4-dioxane (0.5 mL) and then treated with 48% HBr$_{(aq)}$ (0.5 mL) and heated at 75° C. for 15 minutes. The cooled reaction mixture was then basified to pH ~12 by dropwise addition of 6N sodium hydroxide and then immediately acidified to pH ~8-9 by dropwise addition of concentrated hydrochloric acid, producing a cloudy precipitate. The solid was collected by centrifugation, dissolved in dimethylsulfoxide (2 mL), and purified by preparative HPLC [5-85% methanol in water (0.1% ammonium hydroxide) over 30 min, 35 mL/min] to afford the title compound as a white solid (39 mg, 28%). $^1$H NMR (400 MHz, d$_6$-DMSO) δ 12.80 (s, 1H), 8.98 (d, J=0.9, 1H), 8.55 (d, J=5.7, 1H), 8.47 (d, J=0.9, 1H), 7.07 (d, J=5.8, 1H), 4.39 (ddd, J=35.9, 10.4, 4.4, 2H), 2.84 (m, 1H), 2.34 (s, 3H), 2.16 (td, J=11.4, 3.3, 1H), 1.92-1.82 (m, 1H), 1.76 (m, 1H), 1.62 (m, 1H), 1.58-1.43 (m, 2H), 1.43-1.29 (m, 1H), 1.23 (s, 1H). LCMS (Method D): R$_T$=7.48 min, M+H$^+$=322.1.

Example 76

(S)-4-(N-(2-methoxyethyl)pyrrolidin-3-amino)-9H-dipyrido[2,3-b;4',3'-d]pyrrole-6-carbonitrile

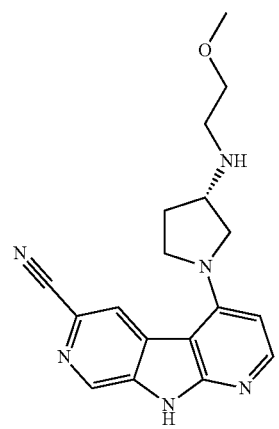 [SMILES: COCCN[C@H]1CCN(c2ccnc3[nH]c4cnc(C#N)cc4c23)C1]

Step 1: (S)-4-(tert-butyl 2-methoxyethyl(pyrrolidin-3-yl)carbamate)-9-(2-trimethylsilanyl-ethoxymethyl)-9H-dipyrido[2,3-b;4',3'-d]pyrrole-6-carbonitrile

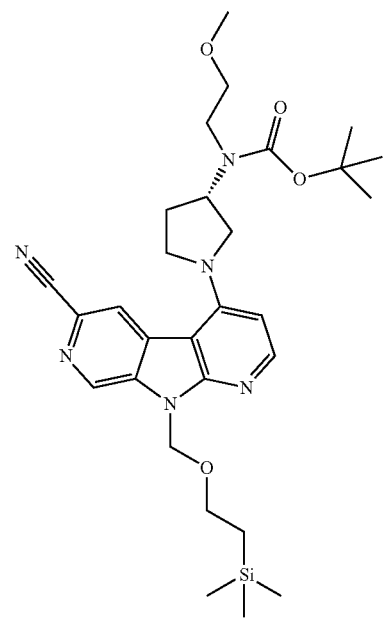 [SMILES: COCCN(C(=O)OC(C)(C)C)[C@H]1CCN(c2ccnc3c2c2cc(C#N)ncc2n3COCC[Si](C)(C)C)C1]

To a solution of (S)-tert-butyl 1-(6-cyano-9-((2-(trimethylsilyl)ethoxy)methyl)-9H-dipyrido[2,3-b;4',3'-d]pyrrol-4-yl)pyrrolidin-3-ylcarbamate (73 mg, 28 mmol) in tetrahydrofuran (17 mL) and N,N-dimethylformamide (0.5 mL) was added sodium hydride as 60% dispersion in mineral oil (34 mg, 1.4 mmol). The reaction mixture was stirred at ambient temperature for 5 minutes before 1-bromo-2-methoxyethane (18 uL, 0.19 mmol) was added and the mixture was heated at 40° C. for 4 hours. The cooled reaction mixture was diluted with water (10 mL) and ethyl acetate (30 mL). The organic layer was separated, dried over sodium sulfate, filtered, concentrated in vacuo, and purified flash chromatography (silica, 4 g, ISCO, 1-100% ethyl acetate in heptane) to afford the title compound as a yellow solid, which was used in the next step without any further purification (58 mg, 71%).

Step 2: (S)-4-(N-(2-methoxyethyl)pyrrolidin-3-amino)-9H-dipyrido[2,3-b;4',3'-d]pyrrole-6-carbonitrile

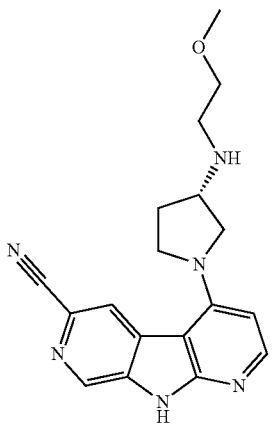 [SMILES: COCCN[C@H]1CCN(c2ccnc3[nH]c4cnc(C#N)cc4c23)C1]

(S)-4-(N-(2-methoxyethyl)pyrrolidin-3-amino)-9-(2-trimethylsilanyl-ethoxymethyl)-9H-dipyrido[2,3-b;4',3'-d]pyrrole-6-carbonitrile (58 mg, 0.10 mmol) was dissolved in 1,4-dioxane (0.5 mL), treated with 48% HBr$_{(aq)}$ (0.5 mL) and heated at 75° C. for 15 minutes. The cooled reaction mixture was then basified to pH ~12 by dropwise addition of 6N sodium hydroxide and then immediately acidified to pH ~8-9 by dropwise addition of concentrated hydrochloric acid, producing a cloudy precipitate. The solid was collected by centrifugation, dissolved in dimethylsulfoxide (2 mL), and purified by preparative HPLC [5-85% methanol in water (0.1% ammonium hydroxide) over 30 min, 35 mL/min] to afford the title compound as a yellow solid (12 mg, 35%). $^1$H NMR (400 MHz, d$_6$-DMSO) δ 8.82 (s, 1H), 8.50 (s, 1H), 8.15 (d, J=5.9, 1H), 6.46 (d, J=6.0, 1H), 3.93 (dd, J=9.8, 5.6, 1H), 3.82 (m, 1H), 3.74-3.66 (m, 1H), 3.59 (dd, J=9.7, 4.0, 1H), 3.48 (s, 1H), 3.41 (t, J=5.5, 2H), 3.24 (s, 3H), 2.77 (m, 2H), 2.16 (m, 1H), 1.94 (m, 1H). LCMS (Method D): R$_T$=6.05 min, M+H$^+$=337.1.

Example 77

(S)-4-(N-(3-fluoropropyl)pyrrolidin-3-amino)-9H-dipyrido[2,3-b;4',3'-d]pyrrole-6-carbonitrile

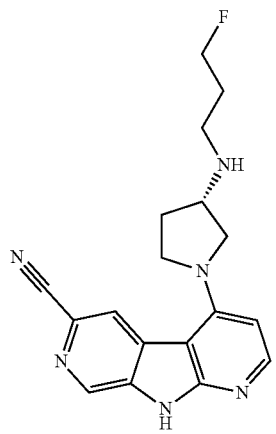 [SMILES: N#Cc1cc2c(cn1)[nH]c1nccc(N3CC[C@H](NCCCF)C3)c12]

The title compound was prepared following a similar procedure to the previous example using 3-fluoropropyl trifluoromethanesulfonate. $^1$H NMR (500 MHz, d$_6$-DMSO) δ 8.83 (s, 1H), 8.49 (s, 1H), 8.18 (d, J=5.9, 1H), 8.13 (s, 1H), 6.50 (d, J=5.9, 1H), 4.57 (t, J=6.0, 1 H), 4.47 (t, J=5.9, 1H), 3.97 (m, 1H), 3.87 (m, 1H), 3.78-3.68 (m, 1H), 3.61 (m, 2H), 2.82 (m, 2H), 2.22 (m, 1H), 2.03 (m, 1H), 1.87 (m, 2H). LCMS (Method D): R$_T$=4.72 min, M+H$^+$=339.1.

Example 78

(R)-4-(N-(2-methoxyethyl)pyrrolidin-3-amino)-9H-dipyrido[2,3-b;4',3'-d]pyrrole-6-carbonitrile

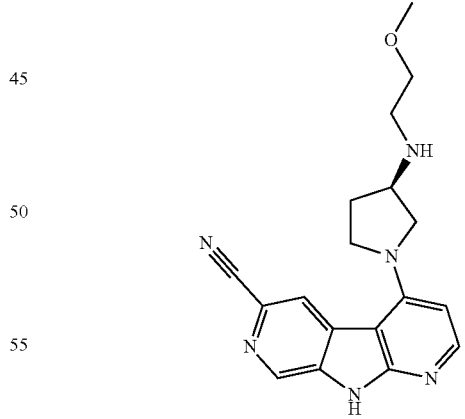

The title compound was prepared following a similar procedure to the previous example using (R)-3-(Boc-amino)pyrrolidine. $^1$H NMR (400 MHz, d$_6$-DMSO) δ 8.79 (s, 1H), 8.46 (s, 1H), 8.13 (d, J=5.9, 1H), 6.41 (d, J=5.9, 1H), 3.90 (dd, J=9.6, 5.6, 1H), 3.79 (m, 1H), 3.68 m, 1H), 3.55 (dd, J=9.7, 4.4, 2H), 3.47-3.41 (m, 1H), 3.42-3.37 (m, 2H), 3.23 (s, 3H), 2.73 (m, 2H), 2.13 (m, 1H), 1.91 (m, 1H). LCMS (Method D): R$_T$=6.03 min, M+H$^+$=337.1.

Example 79

(S)-4-(N-ethylpyrrolidin-3-amino)-9H-dipyrido[2,3-b;4',3'-d]pyrrole-6-carbonitrile

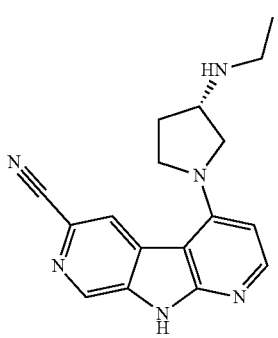 [SMILES: CCN[C@H]1CCN(c2ccnc3[nH]c4cnc(C#N)cc4c23)C1]

Step 1: (S)-4-(N-ethylpyrrolidin-3-amino)-9-(2-trimethylsilanyl-ethoxymethyl)-9H-dipyrido[2,3-b;4',3'-d]pyrrole-6-carbonitrile

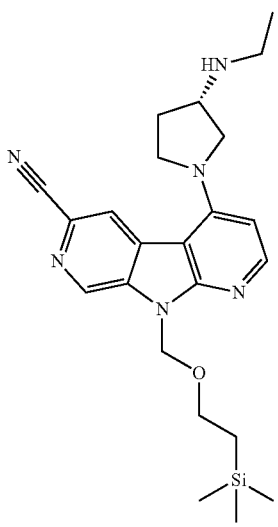 [SMILES: CCN[C@H]1CCN(c2ccnc3c2c2cc(C#N)ncc2n3COCC[Si](C)(C)C)C1]

A mixture of 4-chloro-9-(2-trimethylsilanyl-ethoxymethyl)-9H-dipyrido[2,3-b;4',3'-d]pyrrole-6-carbonitrile (89 mg, 0.25 mmol), (S)-N-ethylpyrrolidin-3-amine (140 mg, 1.23 mmol), 4,5-bis(diphenylphosphino)-9,9-dimethylxanthene (21 mg, 0.037 mmol), cesium carbonate (161 mg, 0.49 mmol), and tris(dibenzylideneacetone)dipalladium(0) (17 mg, 0.018 mmol) was heated in a sealed vial at 110° C. for 2 h. The mixture was diluted with water (20 mL) and ethyl acetate (50 mL). The organic layer was separated, dried over sodium sulfate, filtered, concentrated in vacuo, and purified flash chromatography (silica, 10 g, ISCO, 1-20% methanol in methylene chloride) to afford the title compound as an orange solid, which was used in the next step without any further purification (75 mg, 70%).

Step 2: (S)-4-(N-ethylpyrrolidin-3-amino)-9H-dipyrido[2,3-b;4',3'-d]pyrrole-6-carbonitrile

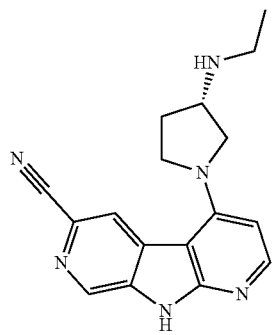 [SMILES: CCN[C@H]1CCN(c2ccnc3[nH]c4cnc(C#N)cc4c23)C1]

(S)-4-(N-ethylpyrrolidin-3-amino)-9-(2-trimethylsilanyl-ethoxymethyl)-9H-dipyrido[2,3-b;4',3'-d]pyrrole-6-carbonitrile (75 mg, 0.17 mmol) was dissolved in 1,4-dioxane (0.5 mL) and then treated with 48% $HBr_{(aq)}$ (0.5 mL) and heated at 75° C. for 15 minutes. The cooled reaction mixture was then basified to pH ~12 by dropwise addition of 6N sodium hydroxide and then immediately acidified to pH ~8-9 by dropwise addition of concentrated hydrochloric acid, producing a cloudy precipitate. The solid was collected by centrifugation, dissolved in dimethylsulfoxide (2 mL), and purified by preparative HPLC [5-85% methanol in water (0.1% ammonium hydroxide) over 30 min, 35 mL/min] to afford the title compound as a tan solid (25 mg, 48%). $^1$H NMR (400 MHz, $d_6$-DMSO) δ 8.81 (s, 1H), 8.50 (s, 1H), 8.14 (d, J=5.9, 1H), 6.46 (d, J=6.0, 1H), 3.91 (dd, J=9.7, 5.6, 1H), 3.83 (m, 1H), 3.71 (m, 1H), 3.53 (dd, J=9.6, 4.3, 1H), 3.43 (m, 1H), 2.59 (m, 2H), 2.13 (m, 1H), 1.96-1.83 (m, 1H), 1.03 (t, J=7.1, 3H). LCMS (Method G): $R_T$=1.97 min, M+H$^+$=307.1.

Example 80

4-(4-(pyrrolidin-3-yl)morpholino)-9H-dipyrido[2,3-b;4',3'-d]pyrrole-6-carbonitrile

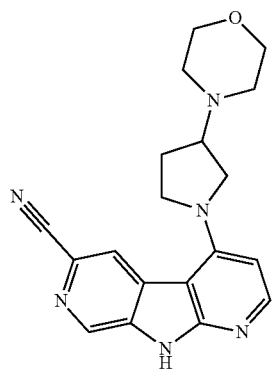 [SMILES: N#Cc1cc2c(cn1)[nH]c1nccc(N3CCC(N4CCOCC4)C3)c12]

The title compound was prepared following a similar procedure to the previous example using 4-(pyrrolidin-3-yl)morpholine. $^1$H NMR (400 MHz, $d_6$-DMSO) δ 12.53 (s, 1H), 8.82 (s, 1H), 8.47 (s, 1H), 8.16 (d, J=5.9, 1H), 6.51 (d, J=6.0, 1H), 3.99-3.88 (m, 1H), 3.79 (m, 2H), 3.68-3.55 (m, 5H), 3.02-2.91 (m, 1H), 2.58-2.41 (m, 4H), 2.27 (m, 1H), 1.94-1.82 (m, 1H). LCMS (Method D): $R_T$=5.16 min, M+H$^+$=349.1.

Example 81

4-(2,5-diazabicyclo[2.2.1]heptan-2-yl)-9H-dipyrido[2,3-b;4',3'-d]pyrrole-6-carbonitrile

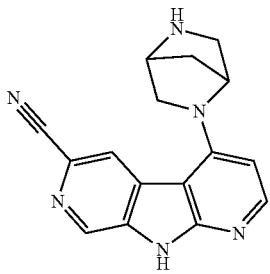 [SMILES: N#Cc1cc2c(cn1)[nH]c1nccc(N3CC4CC3CN4)c12]

The title compound was prepared following a similar procedure to the previous example using tert-butyl 2,5-diazabicyclo[2.2.1]heptane-2-carboxylate. $^1$H NMR (400 MHz, d$_6$-DMSO) δ 8.82 (s, 1H), 8.31 (s, 1H), 8.15 (d, J=5.9, 1H), 6.53 (d, J=5.9, 1H), 4.69 (s, 1H), 4.19 (d, J=6.5, 1H), 3.73 (s, 1H), 3.32 (m, 1H), 3.11 (d, J=9.9, 1H), 3.00 (d, J=9.7, 1H), 1.97 (d, J=9.7, 1H), 1.79 (d, J=9.2, 1H). LCMS (Method D): $R_T$=4.38 min, M+H$^+$=291.1.

Example 82

4-(N-methylpyrrolidin-3-amino)-9H-dipyrido[2,3-b;4',3'-d]pyrrole-6-carbonitrile

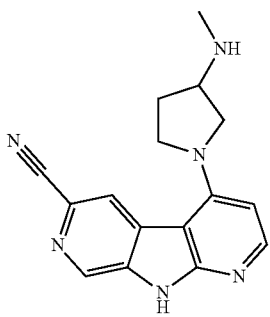 [SMILES: CNC1CCN(c2ccnc3[nH]c4cnc(C#N)cc4c23)C1]

The title compound was prepared following a similar procedure to the previous example using tert-butyl methyl (pyrrolidin-3-yl)carbamate. $^1$H NMR (400 MHz, d$_6$-DMSO) δ 8.81 (s, 1H), 8.49 (s, 1H), 8.14 (d, J=5.9, 1H), 6.45 (d, J=6.0, 1H), 3.91 (m, 1H), 3.83 (m, 1H), 3.73-3.64 (m, 1H), 3.51 (dd, J=9.7, 3.9, 2H), 2.31 (s, 3H), 2.11 (m, 1H), 1.92 (m, 1H). LCMS (Method D): $R_T$=5.38 min, M+H$^+$=293.1.

Example 83

(R)-4-(N,N-dimethylpyrrolidin-3-amino)-9H-dipyrido[2,3-b;4',3'-d]pyrrole-6-carbonitrile

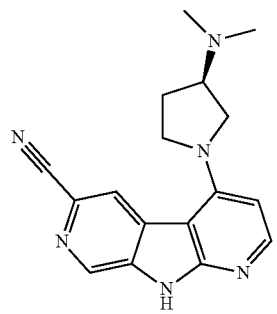 [SMILES: CN(C)[C@@H]1CCN(c2ccnc3[nH]c4cnc(C#N)cc4c23)C1]

The title compound was prepared following a similar procedure to the previous example with 4-chloro-9-(2-trimethylsilanyl-ethoxymethyl)-9H-dipyrido[2,3-b;4',3'-d]pyrrole-6-carbonitrile (101 mg, 0.28 mmol), using (R)—N,N-dimethylpyrrolidin-3-amine. $^1$H NMR (400 MHz, d$_6$-DMSO) δ 8.80 (s, 1H), 8.43 (s, 1H), 8.15 (d, J=5.8, 1H), 6.45 (d, J=5.9, 1 H), 3.88 (m, 1H), 3.77 (m, 2H), 3.65-3.54 (m, 1H), 2.88-2.77 (m, 1H), 2.52 (m, 1H), 2.24 (s, 6H), 1.94-1.80 (m, 1H). LCMS (Method D): $R_T$=4.24 min, M+H$^+$=307.1.

Example 84

(S)-4-(N,N-dimethylpyrrolidin-3-amino)-9H-dipyrido[2,3-b;4',3'-d]pyrrole-6-carbonitrile

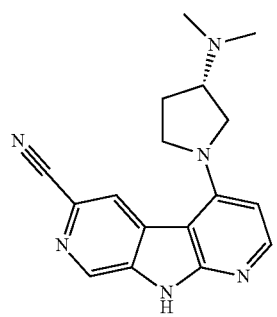 [SMILES: CN(C)[C@H]1CCN(c2ccnc3[nH]c4cnc(C#N)cc4c23)C1]

The title compound was prepared following a similar procedure to the previous example using (S)—N,N-dimethylpyrrolidin-3-amine. $^1$H NMR (400 MHz, d$_6$-DMSO) δ 8.81 (s, 1H), 8.46 (s, 1H), 8.16 (d, J=5.9, 1 H), 6.49 (d, J=5.9, 1H), 3.90 (m, 1H), 3.79 (m, 2H), 3.61 (t, J=8.8, 1H), 2.89-2.77 (m, 1H), 2.52 (m, 1H), 2.24 (s, 6H), 1.95-1.80 (m, 1H). LCMS (Method D): $R_T$=4.17 min, M+H$^+$=307.1.

Example 85

4-(octahydropyrrolo[3,4-b]pyrrol)-9H-dipyrido[2,3-b;4',3'-d]pyrrole-6-carbonitrile

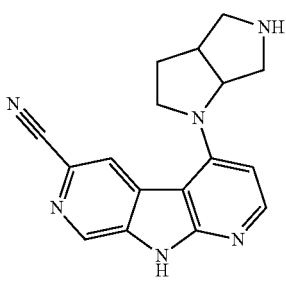 [SMILES: N#Cc1cc2c(cn1)[nH]c1nccc(N3CCC4CNCC43)c12]

The title compound was prepared following a similar procedure to the previous example using tert-butyl hexahydropyrrolo[3,4-b]pyrrole-5(1H)-carboxylate. $^1$H NMR (500 MHz, d$_6$-DMSO) δ 8.85 (s, 1H), 8.49 (s, 1H), 8.24 (s, 1H), 8.20 (d, J=5.9, 1H), 6.63 (d, J=5.9, 1H), 4.65-4.57 (m, 1H), 4.19 (m, 1H), 3.64-3.57 (m, 1H), 3.05 (m, 1H), 2.97 (m, 1H), 2.93-2.84 (m, 2H), 2.78 (d, J=11.9, 1H), 2.09-1.96 (m, 2H). LCMS (Method D): R$_T$=4.57 min, M+H$^+$=305.1.

Example 86

4-((3aS,6aS)-1-methyloctahydropyrrolo[3,4-b]pyrrol)-9H-dipyrido[2,3-b;4',3'-d]pyrrole-6-carbonitrile

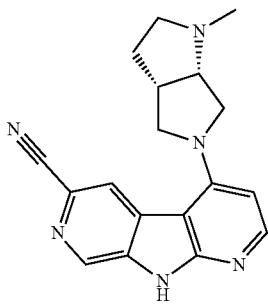 [SMILES: CN1CC[C@H]2CN(c3ccnc4[nH]c5cnc(C#N)cc5c34)C[C@H]21]

The title compound was prepared following a similar procedure to the previous example using (3aS,6aS)-1-methyloctahydropyrrolo[3,4-b]pyrrole. $^1$H NMR (500 MHz, d$_6$-DMSO) δ 12.58 (s, 1H), 8.89 (s, 1H), 8.65 (s, 1H), 8.31 (d, J=5.6, 1H), 6.68 (d, J=5.7, 1H), 3.87 (d, J=11.0, 1H), 3.48 (dd, J=9.7, 7.3, 1H), 3.37 (dd, J=9.8, 2.8, 1H), 3.11-3.01 (m, 2H), 3.01-2.89 (m, 2H), 2.35-2.25 (m, 1H), 2.16-2.06 (m, 1H), 1.74-1.62 (m, 1H). LCMS (Method D): R$_T$=4.28 min, M+H$^+$=319.2.

Example 87

4-((R)-piperidin-3-amino)-9H-dipyrido[2,3-b;4',3'-d]pyrrole-6-carbonitrile

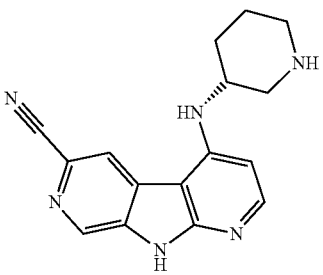

The title compound was prepared following a similar procedure to the previous example using (R)-tert-butyl 3-aminopiperidine-1-carboxylate. $^1$H NMR (400 MHz, d$_6$-DMSO) δ 8.99 (s, 1H), 8.84 (s, 1H), 8.20 (d, J=5.9, 1H), 6.61 (d, J=6.0, 1H), 6.33 (d, J=8.3, 1H), 3.72-3.61 (m, 1H), 3.13 (m, 1H), 2.88 (m, 1H), 2.61 (m, 1H), 2.02 (m, 1H), 1.79-1.65 (m, 2H), 1.52 (m, 1H). LCMS (Method E): R$_T$=3.62 min, M+H$^+$=293.1.

Example 88

3-chloro-4-piperazin-9H-dipyrido[2,3-b;4',3'-d]pyrrole-6-carbonitrile

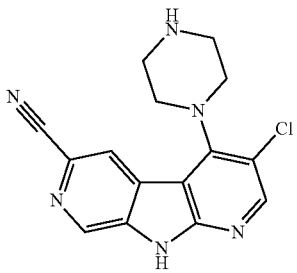

Step 1: 4-(tert-butyl piperazin-1-carboxylate)-9-((2-(trimethylsilyl)ethoxy)methyl)-9H-dipyrido[2,3-b;4',3'-d]pyrrole-6-carbonitrile

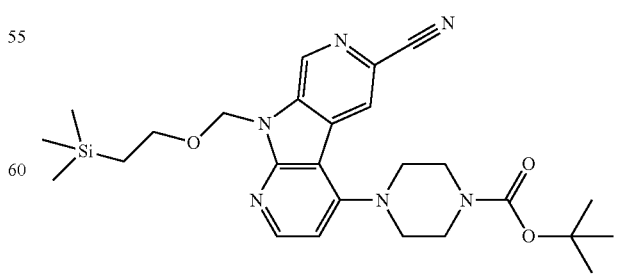

A mixture of 4-chloro-9-(2-trimethylsilanyl-ethoxymethyl)-9H-dipyrido[2,3-b;4',3'-d]pyrrole-6-carbonitrile (126 mg, 0.35 mmol) and tert-butyl piperazine-1-carboxylate (196 mg, 1.05 mmol) in N,N-dimethylacetamide (1.6 mL) was heated at 120° C. for 2 hours. The cooled reaction mixture was diluted with ethyl acetate (50 mL) and washed with water (20 mL). The organic layer was separated, dried over sodium sulfate, filtered, concentrated in vacuo, and purified by flash chromatography (silica, 4 g, ISCO, 0-100% ethyl acetate in heptane) to afford the title compound as a yellow oil, which was used in the next step without any further purification (203 mg, 100%).

Step 2: 3-Chloro-4-(tert-butyl piperazin-1-carboxy-late)-9-((2-(trimethylsilyl)ethoxy)methyl)-9H-dipyrido[2,3-b;4',3'-d]pyrrole-6-carbonitrile

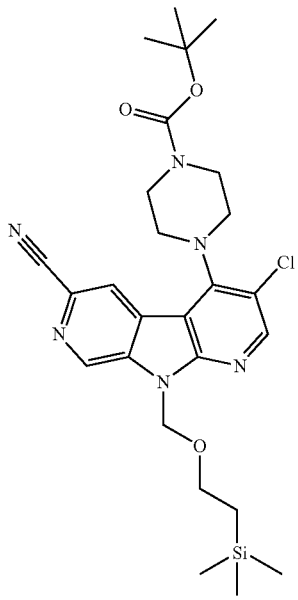 [SMILES: CC(C)(C)OC(=O)N1CCN(c2c(Cl)cnc3c2c2cc(C#N)ncc2n3COCC[Si](C)(C)C)CC1]

A mixture of 4-(tert-butyl piperazin-1-carboxylate)-9-((2-(trimethylsilyl)ethoxy)methyl)-9H-dipyrido[2,3-b;4',3'-d]pyrrole-6-carbonitrile (178 mg, 0.35 mmol) and N-chlorosuccinimide (140 mg, 1.05 mmol) in acetonitrile (1.4 mL) and isopropyl alcohol (0.4 mL) was stirred at 35° C. for 1 hour. The cooled reaction mixture was quenched with saturated aqueous sodium thiosulfate (1 mL), diluted with ethyl acetate (50 mL), and washed with water (20 mL). The organic layer was separated, dried over sodium sulfate, filtered, concentrated in vacuo, and purified by flash chromatography (silica, 4 g, ISCO, 0-100% ethyl acetate in heptane) to afford the title compound as a pale yellow foam, which was used in the next step without any further purification (142 mg, 75%).

Step 3: 3-Chloro-4-piperazin-9H-dipyrido[2,3-b;4',3'-d]pyrrole-6-carbonitrile

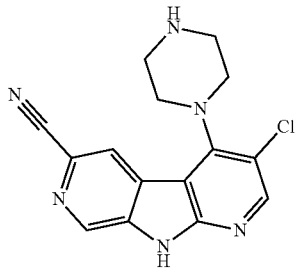 [SMILES: N#Cc1cc2c(cn1)[nH]c1ncc(Cl)c(N3CCNCC3)c12]

3-Chloro-4-(tert-butyl-piperazin-1-carboxylate)-9-((2-(trimethylsilyl)ethoxy)methyl)-9H-dipyrido[2,3-b;4',3'-d]pyrrole-6-carbonitrile (142 mg, 0.26 mmol) was dissolved in 1,4-dioxane (0.4 mL) and then treated with 48% HBr$_{(aq)}$ (0.4 mL) and heated at 60° C. for 20 minutes. The cooled reaction mixture was then basified to pH ~12 by dropwise addition of 6N sodium hydroxide and then immediately acidified to pH ~8-9 by dropwise addition of concentrated hydrochloric acid, producing a cloudy precipitate. The solid was collected by centrifugation, dissolved in dimethylsulfoxide (2 mL), and purified by preparative HPLC [5-85% methanol in water (0.1% ammonium hydroxide) over 30 min, 35 mL/min] to afford the title compound as a light yellow solid (19 mg, 22%). $^1$H NMR (400 MHz, d$_6$-DMSO) δ 8.95 (s, 1H), 8.53 (s, 1H), 8.48 (d, J=6.2, 1H), 3.43 (m, 4H), 3.02-2.97 (m, 4H). LCMS (Method G): R$_T$=3.80 min, M+H$^+$=313.0.

Example 89

3-Chloro-4-(1-ethylpiperazin)-9H-dipyrido[2,3-b;4',3'-d]pyrrole-6-carbonitrile

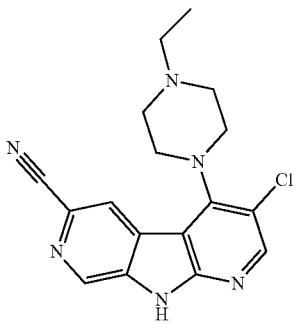 [SMILES: CCN1CCN(c2c(Cl)cnc3[nH]c4cnc(C#N)cc4c23)CC1]

The title compound was prepared following a similar procedure to the previous example using N-ethylpiperazine. $^1$H NMR (400 MHz, d$_6$-DMSO) δ 8.92 (s, 1H), 8.48 (s, 1H), 8.43 (s, 1H), 3.52 (s, 4H), 2.67 (s, 4H), 2.54-2.44 (m, 4H), 1.09 (t, J=7.2, 3H). LCMS (Method D): R$_T$=6.84 min, M+H$^+$=341.0.

Example 90

(S)-3-Chloro-4-(N-(3-fluoropropyl)pyrrolidin-3-amino)-9H-dipyrido[2,3-b;4',3'-d]pyrrole-6-carbonitrile

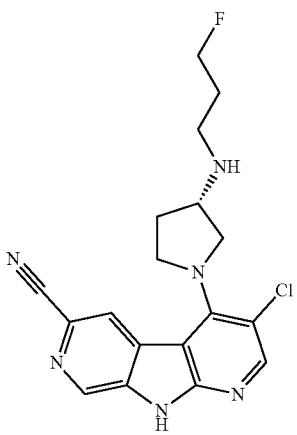 [SMILES: N#Cc1cc2c(cn1)[nH]c1ncc(Cl)c(N3CC[C@H](NCCCF)C3)c12]

Step 1: (S)-Benzyl 3-(tert-butoxycarbonylamino)pyrrolidine-1-carboxylate

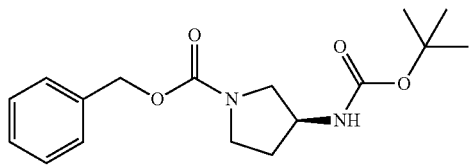 [SMILES: CC(C)(C)OC(=O)N[C@H]1CCN(C(=O)OCc2ccccc2)C1]

A solution of (S)-tert-butyl pyrrolidin-3-ylcarbamate (4.2 g, 22 mmol) in methylene chloride (49 mL) was cooled at 0° C. and treated with pyridine (2.2 mL, 29 mmol) and benzyl chloroformate (3.8 mL, 29 mmol). The mixture was stirred at 0° C. for 30 minutes and then warmed to ambient temperature and stirred for 4 hours. The reaction mixture was diluted with water (100 mL) and methylene chloride (100 mL), the organic layer was separated, dried over sodium sulfate, filtered, concentrated in vacuo, and purified by flash chromatography (silica, 40 g, ISCO, 1-100% ethyl acetate in heptanes) to afford the title compound as a white solid, which was used in the next step without any further purification (5.2 g, 73%).

Step 2: (S)-benzyl 3-(tert-butoxycarbonyl(3-fluoropropyl)amino)pyrrolidine-1-carboxylate

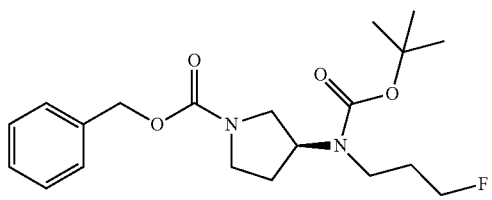 [SMILES: CC(C)(C)OC(=O)N(CCCF)[C@H]1CCN(C(=O)OCc2ccccc2)C1]

To a mixture of (S)-benzyl 3-(tert-butoxycarbonylamino)pyrrolidine-1-carboxylate (400 mg, 1.2 mmol) and 3-fluoropropyl trifluoromethanesulfonate (433 mg, 2.1 mmol) in tetrahydrofuran (10 mL) was added sodium hydride as 60% dispersion in mineral oil (146 mg, 3.6 mmol). The reaction mixture was stirred at ambient temperature for 30 minutes and then diluted with water (20 mL) and methylene chloride (50 mL). The organic layer was separated, dried over sodium sulfate, filtered, concentrated in vacuo, and purified flash chromatography (silica, 40 g, ISCO, 1-20% methanol in methylene chloride) to afford the title compound as a colorless oil, which was used in the next step without any further purification (475 mg, 100%).

Step 3: (S)-tert-butyl 3-fluoropropyl(pyrrolidin-3-yl)carbamate

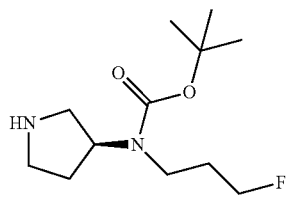 [SMILES: CC(C)(C)OC(=O)N(CCCF)[C@H]1CCNC1]

To a solution of (S)-benzyl 3-(tert-butoxycarbonyl(3-fluoropropyl)amino)pyrrolidine-1-carboxylate (611 mg, 1.6 mmol) in methanol (6.5 mL) was added ammonium formate (1.1 g, 18 mmol) followed palladium on carbon (10% w/w, 479 mg, 0.22 mmol). The reaction mixture was stirred at ambient temperature under a balloon of hydrogen for 1 hour, then degassed and filtered over a pad of celite. The filtrate was concentrated in vacuo to afford a residue, which was used in the next step without any further purification.

Step 4: (S)-4-(benzyl 3-(tert-butoxycarbonyl(3-fluoropropyl)amino)pyrrolidin-1-carboxylate)-9-((2-(trimethylsilyl)ethoxy)methyl)-9H-dipyrido[2,3-b;4',3'-d]pyrrole-6-carbonitrile

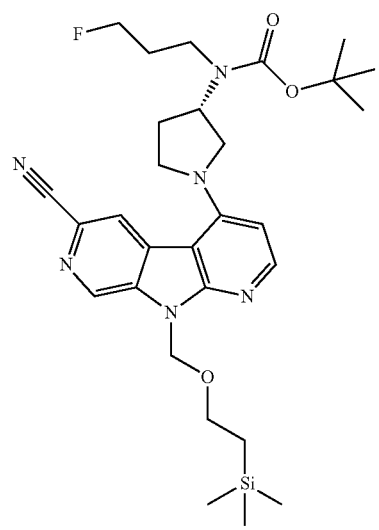 [SMILES: CC(C)(C)OC(=O)N(CCCF)[C@H]1CCN(c2ccnc3c2c2cc(C#N)ncc2n3COCC[Si](C)(C)C)C1]

A mixture of 4-chloro-9-(2-trimethylsilanyl-ethoxymethyl)-9H-dipyrido[2,3-b;4',3'-d]pyrrole-6-carbonitrile (135 mg, 0.38 mmol) and (S)-tert-butyl 3-fluoropropyl (pyrrolidin-3-yl)carbamate (557 mg, 2.3 mmol) in N,N-dimethylacetamide (1.8 mL) was heated at 120° C. for 2 hours. The cooled reaction mixture was diluted with ethyl acetate (50 mL) and washed with water (20 mL). The organic layer was separated, dried over sodium sulfate, filtered, concentrated in vacuo, and purified by flash chromatography (silica, 4 g, ISCO, 0-20% methanol in methylene chloride) to afford the title compound as a yellow oil, which was used in the next step without any further purification (214 mg, 100%).

Step 5: (S)-3-Chloro-4-(benzyl 3-(tert-butoxycarbonyl(3-fluoropropyl)amino) pyrrolidin-1-carboxylate)-9-((2-(trimethylsilyl)ethoxy)methyl)-9H-dipyrido[2,3-b;4',3'-d]pyrrole-6-carbonitrile

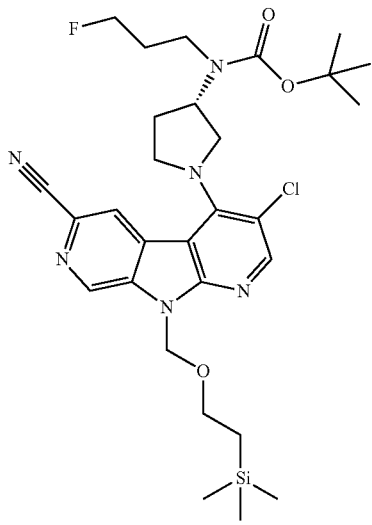 [SMILES: CC(C)(C)OC(=O)N(CCCF)[C@H]1CCN(c2c(Cl)cnc3c2c2cc(C#N)ncc2n3COCC[Si](C)(C)C)C1]

A mixture of (S)-4-(benzyl 3-(tert-butoxycarbonyl(3-fluoropropyl)amino) pyrrolidin-1-carboxylate)-9-((2-(trimethylsilyl)ethoxy)methyl)-9H-dipyrido[2,3-b;4',3'-d]pyrrole-6-carbonitrile (214 mg, 0.38 mmol) and N-chlorosuccinimide (151 mg, 1.1 mmol) in acetonitrile (1.5 mL) and isopropyl alcohol (0.4 mL) was stirred at 35° C. for 1 hour. The cooled reaction mixture was quenched with saturated aqueous sodium thiosulfate, diluted with ethyl acetate (50 mL), and washed with water (20 mL). The organic layer was separated, dried over sodium sulfate, filtered, concentrated in vacuo, and purified by flash chromatography (silica, 4 g, ISCO, 0-100% ethyl acetate in heptane) to afford the title compound as an oil, which was used in the next step without any further purification (125 mg, 55%).

Step 6: (S)-3-Chloro-4-(N-(3-fluoropropyl)pyrrolidin-3-amino)-9H-dipyrido[2,3-b;4',3'-d]pyrrole-6-carbonitrile

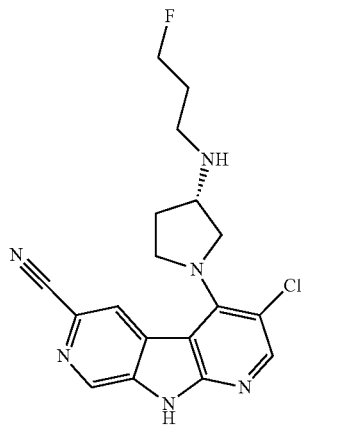 [SMILES: N#Cc1cc2c(cn1)[nH]c1ncc(Cl)c(N3CC[C@H](NCCCF)C3)c12]

(S)-3-chloro-4-(benzyl 3-(tert-butoxycarbonyl(3-fluoropropyl)amino)pyrrolidin-1-carboxylate)-9-((2-(trimethylsilyl)ethoxy)methyl)-9H-dipyrido[2,3-b;4',3'-d]pyrrole-6-carbonitrile (125 mg, 0.21 mmol) was dissolved in 1,4-dioxane (0.4 mL) and then treated with 48% HBr$_{(aq)}$ (0.4 mL) and heated at 60° C. for 20 minutes. The cooled reaction mixture was then basified to pH ~12 by dropwise addition of 6N sodium hydroxide and then immediately acidified to pH ~8-9 by dropwise addition of concentrated hydrochloric acid, producing a cloudy precipitate. The solid was collected by centrifugation, dissolved in dimethylsulfoxide (2 mL), and purified by preparative HPLC [5-85% methanol in water (0.1% ammonium hydroxide) over 30 min, 35 mL/min] to afford the title compound as an off-white solid (18 mg, 23%). $^1$H NMR (400 MHz, d$_6$-DMSO) δ 8.97 (s, 1H), 8.61 (s, 1H), 8.47 (s, 1H), 4.61 (t, J=6.0, 1H), 4.49 (t, J=5.9, 1H), 3.80 (m, 2H), 3.64 (m, 1H), 3.51 (m, 2H), 2.70 (m, 2H), 2.31 (m, 1H), 1.94 (m, 2H), 1.89-1.83 (m, 1H). LCMS (Method E): R$_T$=3.16 min, M+H$^+$=373.1.

Example 91

(S)-3-Chloro-4-(3-(2,2-difluoroethylamino)pyrrolidin-1-yl)-9H-dipyrido[2,3-b;4',3'-d]pyrrole-6-carbonitrile

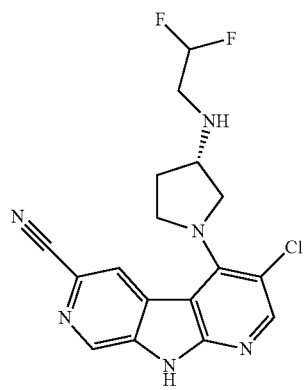 [SMILES: N#Cc1cc2c(cn1)[nH]c1ncc(Cl)c(N3CC[C@H](NCC(F)F)C3)c12]

The title compound was prepared following a similar procedure to the previous example using 2,2-difluoroethyl trifluoromethanesulfonate. $^1$H NMR (400 MHz, d$_6$-DMSO) δ 12.88 (s, 1H), 8.96 (s, 1H), 8.52 (s, 1H), 8.46 (s, 1H), 6.05 (s, 1H), 3.87-3.75 (m, 2H), 3.67-3.54 (m, 2H), 3.48 (m, 1H), 3.00 (m, 2H), 2.51 (m, 1H), 2.27 (m, 1H), 1.95 (m, 1H). LCMS (Method D): R$_T$=7.27 min, M+H$^+$=377.0.

Example 92

(S)-3-Chloro-4-(N-(pyrrolidin-3-yl)isobutyramide)-9H-dipyrido[2,3-b;4',3'-d]pyrrole-6-carbonitrile

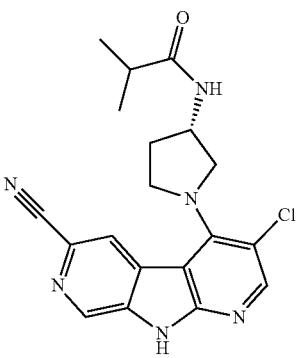 [SMILES: CC(C)C(=O)N[C@H]1CCN(c2c(Cl)cnc3[nH]c4cnc(C#N)cc4c23)C1]

The title compound was prepared following a similar procedure to the previous example using (S)-4-(3-aminopyrrolidin-1-yl)-9-((2-(trimethylsilyl)ethoxy)methyl)-9H-dipyrido[2,3-b;4',3'-d]pyrrole-6-carbonitrile and isobutyryl chloride. ¹H NMR (400 MHz, d₆-DMSO) δ 8.97 (s, 1H), 8.48 (s, 1H), 8.33 (s, 1H), 8.18 (d, J=6.2, 1H), 4.45 (dd, J=11.9, 5.6, 1H), 3.94 (dd, J=9.9, 6.5, 1H), 3.81 (dd, J=16.3, 7.5, 1H), 3.64 (dd, J=15.2, 8.6, 1H), 3.45 (dd, J=10.0, 4.6, 1H), 2.48-2.42 (m, 1H), 2.42-2.29 (m, 1H), 2.11-1.97 (m, 1H), 1.03 (dd, J=16.5, 6.8, 6H). LCMS (Method G): R$_T$=6.53 min, M+H⁺=382.9.

Example 93

(S)-3-Chloro-4-(N-(2,2,2-trifluoroethyl)pyrrolidin-3-amino)-9H-dipyrido[2,3-b;4',3'-d]pyrrole-6-carbonitrile

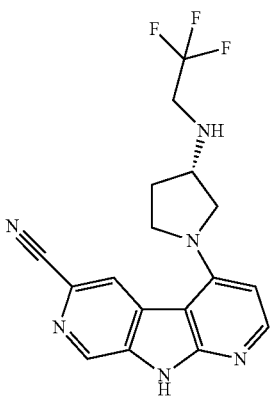 [SMILES: N#Cc1cc2c(cn1)[nH]c1nccc(N3CC[C@H](NCC(F)(F)F)C3)c12]

Step 1: (S)-4-(3-aminopyrrolidin-1-yl)-9-((2-(trimethylsilyl)ethoxy)methyl)-9H-dipyrido[2,3-b;4',3'-d]pyrrole-6-carbonitrile

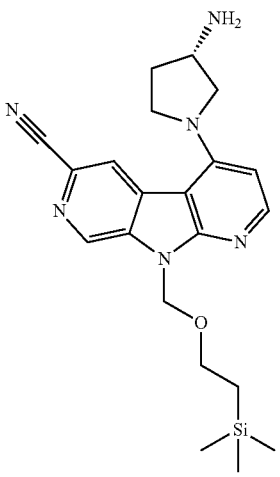 [SMILES: C[Si](C)(C)CCOCn1c2cnc(C#N)cc2c2c(N3CC[C@H](N)C3)ccnc21]

To a solution of (S)-tert-butyl 1-(6-cyano-9-((2-(trimethylsilyl)ethoxy)methyl)-9H-dipyrido[2,3-b;4',3'-d]pyrrol-4-yl)pyrrolidin-3-ylcarbamate (401 mg, 0.79 mmol) in methylene chloride (9.0 mL) was added trifluoroacetic acid (9.0 mL), and the mixture was stirred at ambient temperature for 10 minutes. The solvent was evaporated in vacuo, and the resulting residue was dissolved in methylene chloride and treated with a solution of saturated aqueous sodium bicarbonate solution. The organic layer was separated, dried over sodium sulfate, filtered, concentrated in vacuo to afford the title compound as a yellow foam, which was used in the next step without any further purification (268 mg, 83%).

Step 2: (S)-4-(3-(2,2,2-trifluoroethylamino)pyrrolidin-1-yl)-9-((2-(trimethylsilyl)ethoxy)methyl)-9H-dipyrido[2,3-b;4',3'-d]pyrrole-6-carbonitrile

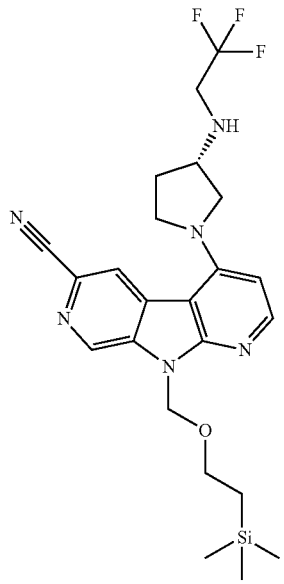 [SMILES: C[Si](C)(C)CCOCn1c2cnc(C#N)cc2c2c(N3CC[C@H](NCC(F)(F)F)C3)ccnc21]

A mixture of (S)-4-(3-aminopyrrolidin-1-yl)-9-((2-(trimethylsilyl)ethoxy)methyl)-9H-dipyrido[2,3-b;4',3'-d]pyrrole-6-carbonitrile (131 mg, 0.32 mmol), 2,2,2-trifluoroethyl trifluoromethanesulfonate (490 mg, 2.1 mmol), and N,N-diisopropylethylamine (365 uL, 2.1 mmol) in methylene chloride (15 mL) was heated at 40° C. for 4 hours. The cooled reaction mixture was diluted with water (20 mL) and methylene chloride (50 mL). The organic layer was separated, dried over sodium sulfate, filtered, concentrated in vacuo, and purified by flash chromatography (silica, 4 g, ISCO, 0-20% methanol in methylene chloride) to afford the title compound as an oil, which was used in the next step without any further purification (156 mg, 100%).

Step 3: (S)-4-(3-(2,2,2-trifluoroethylamino)pyrrolidin-1-yl)-9H-dipyrido[2,3-b;4',3'-d]pyrrole-6-carbonitrile

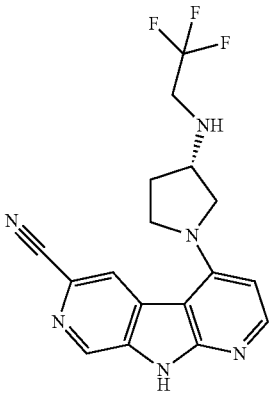 [SMILES: N#Cc1cc2c(cn1)[nH]c1nccc(N3CC[C@H](NCC(F)(F)F)C3)c12]

(S)-4-(3-(2,2,2-trifluoroethylamino)pyrrolidin-1-yl)-9-((2-(trimethylsilyl)ethoxy)methyl)-9H-dipyrido[2,3-b;4',3'-d]pyrrole-6-carbonitrile (156 mg, 0.32 mmol) was dissolved in 1,4-dioxane (0.4 mL) and then treated with 48% HBr$_{(aq)}$ (0.4 mL) and heated at 60° C. for 20 minutes. The cooled reaction mixture was then basified to pH ~12 by dropwise addition of 6N sodium hydroxide and then immediately acidified to pH ~8-9 by dropwise addition of concentrated hydrochloric acid, producing a cloudy precipitate. The solid was collected by centrifugation, dissolved in dimethylsulfoxide (2 mL), and purified by preparative HPLC [5-85% methanol in water (0.1% ammonium hydroxide) over 30 min, 35 mL/min] to afford the title compound as a yellow solid (5.0 mg, 5%). $^1$H NMR (400 MHz, d$_6$-DMSO) δ 8.81 (s, 1H), 8.47 (s, 1H), 8.15 (d, J=5.8, 1H), 6.43 (d, J=5.8, 1H), 3.95 (m, 1H), 3.81 (m, 1H), 3.68 (m, 1H), 3.60-3.50 (m, 2H), 2.81 (m, 1H), 2.14 (m, 1H), 2.02-1.88 (m, 1H). LCMS (Method D): R$_T$=7.71 min, M+H$^+$=361.0.

Example 94

(R)-4-(Piperidin-3-yloxy)-6-(1-methyl-1H-pyrazol-4-yl)-9H-dipyrido[2,3-b;4',3'-d]pyrrole

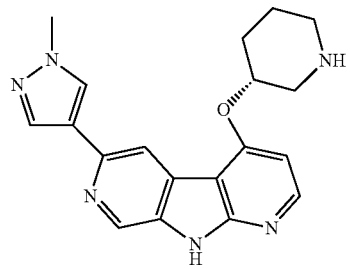 [SMILES: Cn1cc(-c2cc3c(cn2)[nH]c2nccc(O[C@@H]4CCCNC4)c23)cn1]

Step 1: 6-Bromo-3-iodo-9H-dipyrido[2,3-b;4',3'-d]pyrrole

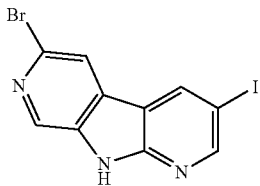 [SMILES: Brc1cc2c(cn1)[nH]c1ncc(I)cc12]

A solution of iodine monochloride (32.5 g, 200 mmol) in acetic acid (120 mL) was added portionwise over 2 h to a mixture of 6-bromo-9H-dipyrido[2,3-b;4',3'-d]pyrrole (5.0 g, 20 mmol) and sodium acetate (18.2 g, 221 mmol) in acetic acid (120 mL) at 100° C. The reaction mixture was cooled to ambient temperature and poured into saturated sodium metabisulfite solution (20% w/w, 400 mL). The resultant precipitate was collected by filtration and the solid was washed with water (50 mL) and diethyl ether (2×50 mL) then dried at 45° C. until constant weight was achieved, to afford the title compound as a grey solid (6.3 g, 83%). $^1$H NMR (DMSO-D$_6$, 300 MHz) 12.49 (s, 1H); 9.14 (d, J=2.1 Hz, 1H); 8.79 (d, J=2.1 Hz, 1H); 8.71 (s, 1H); 8.49 (s, 1H). LCMS (Method B): R$_T$=3.40 min, M+H$^+$=374/376.

Step 2: 3-Bromo-3-iodo-9-(2-trimethylsilanyl-ethoxymethyl)-9H-dipyrido[2,3-b;4',3'-d]pyrrole

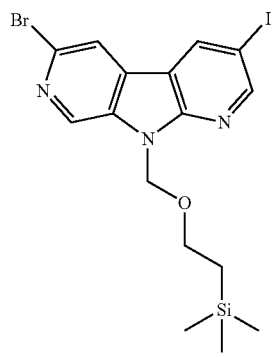 [SMILES: C[Si](C)(C)CCOCn1c2cnc(Br)cc2c2cc(I)cnc21]

To a suspension of 6-bromo-3-iodo-9H-dipyrido[2,3-b;4',3'-d]pyrrole (10 g, 24 mmol) in DMF (100 mL), under an inert atmosphere, was added sodium hydride (1.4 g, 36 mmol) and the reaction mixture was allowed to stir at ambient temperature for 30 minutes. The reaction mixture was cooled to 0° C. and 2-(trimethylsilyl)ethoxymethyl chloride (6.4 mL, 36 mmol) was added dropwise and then the resultant suspension was allowed to warm to room temperature. Water (150 mL) was added to the resultant suspension to quench the reaction, the solvent was removed in vacuo and the resultant residue was purified by flash chromatography (silica, 120 g column, ISCO, 0-15% ethyl acetate in cyclohexane) to afford the title compound as an off-white crystalline solid (7.2 g, 59%). $^1$H NMR (400 MHz, CDCl$_3$) δ 8.94 (s, 1H), 8.88 (d, J=1.9, 1H), 8.74 (d, J=1.9, 1H), 8.16 (s, 1H), 5.98 (s, 2H), 3.70-3.58 (m, 2H), 1.04-0.92 (m, 2H), −0.00 (s, 9H).

Step 3: 6-Bromo-9-((2-(trimethylsilyl)ethoxy)methyl)-9H-dipyrido[2,3-b;4',3'-d]pyrrole

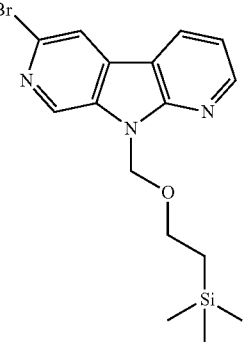

A solution of 6-bromo-3-iodo-9-((2-(trimethylsilyl)ethoxy)methyl)-9H-dipyrido[2,3-b;4',3'-d]pyrrole (3.0 g, 5.95 mmol) in tetrahydrofuran (40 mL) was cooled at −78° C. To this was added isopropylmagnesium chloride (2.0N solution in tetrahydrofuran, 3.12 mL, 6.2 mmol) dropwise over five minutes. The reaction mixture was stirred at this temperature for 1.5 hours and then quenched with saturated aqueous ammonium chloride solution (1 mL). The reaction mixture was then diluted with 25 mL water and extracted with ethyl acetate (150 mL). The organic layer was separated, washed with water (50 mL) then brine (50 mL), dried over sodium sulfate, filtered, and the concentrated in vacuo to afford a yellow oil, which was used in the next step without any further purification (2.2 g, 100%).

Step 4: 6-Bromo-9-(2-trimethylsilanyl-ethoxymethyl)-9H-dipyrido[2,3-b;4',3'-d]pyrrole-1,7-dioxide

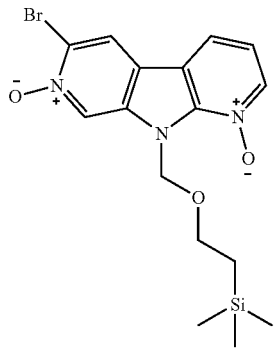 [SMILES: C[Si](C)(C)CCOCn1c2c[n+]([O-])c(Br)cc2c2ccc[n+]([O-])c21]

To a suspension of hydrogen peroxide-urea adduct (4.2 g, 45 mmol) in chloroform (37 mL) was added trifluoroacetic anhydride (6.3 mL, 44.4 mmol) dropwise over 10 minutes. The reaction mixture was stirred at ambient temperature for 5 minutes and then to this was added 6-bromo-9-(2-trimethylsilanyl-ethoxymethyl)-9H-dipyrido[2,3-b;4',3'-d]pyrrole (2.1 g, 5.6 mmol) as a solution in chloroform (15 mL). Note: an exotherm is observed upon addition of the substrate. The reaction mixture was stirred at ambient temperature for 10 minutes and then at 50° C. for 30 minutes. The reaction mixture was cooled to ambient temperature, treated with saturated sodium thiosulfate solution (20 mL), and diluted with water (50 mL) and methanol (10 mL). The layers were separated and the organic layer was washed with 0.5N hydrochloric acid (50 mL), dried over sodium sulfate, filtered, concentrated in vacuo, and purified by flash chromatography (silica, 80 g, ISCO, 0-10% methanol in dichloromethane) to afford the title compound as a pale yellow solid, which was used in the next step without any further purification (1 g, 44%).

Step 5: 6-Bromo-4-chloro-9-(2-trimethylsilanyl-ethoxymethyl)-9H-dipyrido[2,3-b;4',3'-d]pyrrole-7-oxide

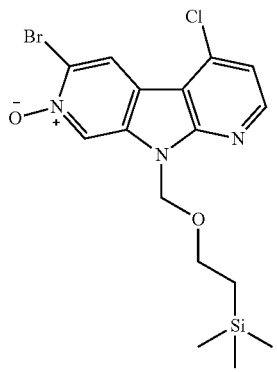 [SMILES: C[Si](C)(C)CCOCn1c2c[n+]([O-])c(Br)cc2c2c(Cl)ccnc21]

A mixture of 6-bromo-9-(2-trimethylsilanyl-ethoxymethyl)-9H-dipyrido[2,3-b;4',3'-d]pyrrole-1,7-dioxide (1 g, 2.4 mmol) in N,N-dimethylformamide (19 mL) was treated with methanesulfonyl chloride (0.38 mL, 4.9 mmol) and the reaction mixture was stirred at ambient temperature for 3 hours. The reaction mixture was then diluted with ethyl acetate (150 mL) and water (200 mL). The layers were separated and the organic layer was dried over sodium sulfate, filtered, concentrated in vacuo, and purified by flash chromatography (silica, 40 g, ISCO, 5-85% ethyl acetate in heptane) to afford the title compound as a 4:1 mixture with 6-bromo-2-chloro-9-(2-trimethylsilanyl-ethoxymethyl)-9H-dipyrido[2,3-b;4',3'-d]pyrrole-7-oxide respectively as an off-white solid (100 mg, 10%). The mixture was used in the next step without any further purification.

Step 6: 6-Bromo-4-chloro-9-(2-trimethylsilanyl-ethoxymethyl)-9H-dipyrido[2,3-b;4',3'-d]pyrrole

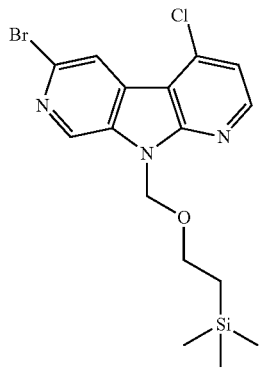 [SMILES: C[Si](C)(C)CCOCn1c2cnc(Br)cc2c2c(Cl)ccnc21]

A solution of 6-bromo-4-chloro-9-(2-trimethylsilanyl-ethoxymethyl)-9H-dipyrido[2,3-b;4',3'-d]pyrrole-7-oxide with 6-bromo-2-chloro-9-(2-trimethylsilanyl-ethoxymethyl)-9H-dipyrido[2,3-b;4',3'-d]pyrrole-7-oxide (4:1, 90 mg, 0.2 mmol), 1,1'-[bis(diphenylphosphino)ferrocene]dichloropalladium(II) (8.5 mg, 0.012 mmol), and triethylamine (0.1 mL, 0.7 mmol) in acetonitrile (1.2 mL) was heated under microwave irradiation at 130° C. for 10 minutes. The cooled reaction mixture was concentrated in vacuo and purified by flash chromatography (silica, 40 g, ISCO, 0-40% ethyl acetate in heptane) to afford the title compound as a 4:1 mixture of the title compound with 6-bromo-2-chloro-9-(2-trimethylsilanyl-ethoxymethyl)-9H-dipyrido[2,3-b;4',3'-d]pyrrole as an off-white solid (60 mg, 70%). The mixture was used in subsequent steps without any further purification.

Step 7: (R)-tert-butyl 3-(6-bromo-9-((2-(trimethylsilyl)ethoxy)methyl)-9H-dipyrido[2,3-b;4',3'-d]pyrrol-4-yloxy)piperidine-1-carboxylate

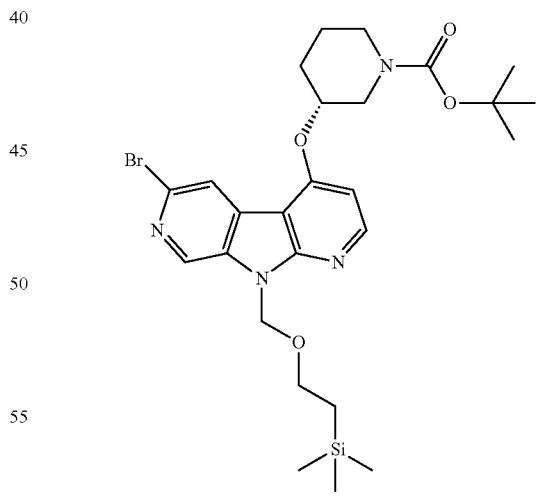

To a solution of (R)-tert-butyl 3-hydroxypiperidine-1-carboxylate (64 mg, 0.32 mmol) in tetrahydrofuran (1.2 mL) was added sodium hydride as 60% dispersion in mineral oil (13 mg, 0.32 mmol). The reaction mixture was stirred at ambient temperature for 5 minutes before a mixture of 6-bromo-4-chloro-9-(2-trimethylsilanyl-ethoxymethyl)-9H-dipyrido[2,3-b;4',3'-d]pyrrole with 6-bromo-2-chloro-9-(2-trimethylsilanyl-ethoxymethyl)-9H-dipyrido[2,3-b;4',3'-d]pyrrole (4:1, 60 mg, 0.1 mmol) was added in one portion, and the reaction mixture was stirred at this temperature for 10 minutes before being warmed to 40° C. for 2 hours. The cooled reaction mixture was then diluted with water (20 mL) and ethyl acetate (50 mL). The organic layer was separated, dried over sodium sulfate, filtered, concentrated in vacuo, and purified flash chromatography (silica, 4 g, ISCO, 0-65% ethyl acetate in heptane) to afford the title compound as a colorless oil, which was used in the next step without any further purification (60 mg, 70%).

Step 8: (R)-tert-butyl 3-(6-(1-methyl-1H-pyrazol-4-yl)-9-((2-(trimethylsilyl)ethoxy)methyl)-9H-dipyrido[2,3-b;4',3'-d]pyrrol-4-yloxy)piperidine-1-carboxylate

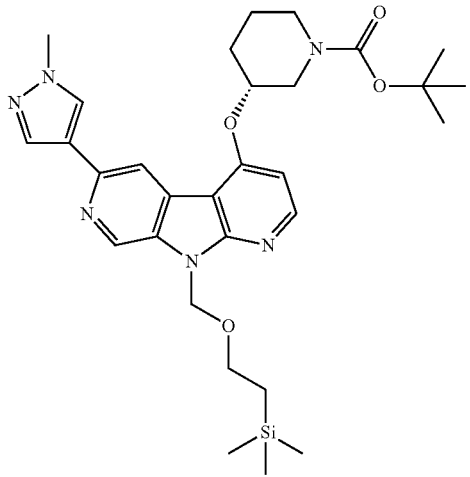 [SMILES: Cn1cc(-c2cc3c4c(O[C@@H]5CCCN(C(=O)OC(C)(C)C)C5)ccnc4n(COCC[Si](C)(C)C)c3cn2)cn1]

A mixture of (R)-tert-butyl 3-(6-bromo-9-((2-(trimethylsilyl)ethoxy)methyl)-9H-dipyrido[2,3-b;4',3'-d]pyrrol-4-yloxy)piperidine-1-carboxylate (50 mg, 0.09 mmol), 1-methyl-4-(4,4,5,5-tetramethyl-1,3,2-dioxaborolan-2-yl)-1H-pyrazole (90 mg, 0.43 mmol), 1,1'-[bis(diphenylphosphino)ferrocene]dichloropalladium(II) (6.3 mg, 0.009 mmol), and saturated aqueous sodium carbonate solution (0.1 mL) in acetonitrile (0.9 mL) was heated under microwave irradiation at 130° C. for 30 minutes. The reaction mixture was concentrated in vacuo, and purified flash chromatography (silica, 4 g, ISCO, 0-90% ethyl acetate in heptane) to afford the title compound as a light brown oil, which was used in the next step without any further purification (50 mg).

Step 9: (R)-4-(Piperidin-3-yloxy)-6-(1-methyl-1H-pyrazol-4-yl)-9H-dipyrido[2,3-b;4',3'-d]pyrrole

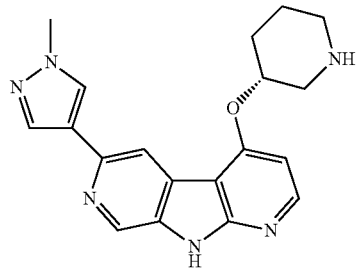 [SMILES: Cn1cc(-c2cc3c(cn2)[nH]c2nccc(O[C@@H]4CCCNC4)c23)cn1]

(R)-tert-butyl 3-(6-(1-methyl-1H-pyrazol-4-yl)-9-((2-(trimethylsilyl)ethoxy)methyl)-9H-dipyrido[2,3-b;4',3'-d]pyrrol-4-yloxy)piperidine-1-carboxylate (50 mg, 0.09 mmol) was dissolved in 1,4-dioxane (0.2 mL) and then treated with 48% HBr$_{(aq)}$ (0.2 mL) and heated at 75° C. for 5 minutes. The cooled reaction mixture was then basified to pH ~12 by dropwise addition of 6N sodium hydroxide and then immediately acidified to pH ~8-9 by dropwise addition of concentrated hydrochloric acid, producing a cloudy precipitate. The solid was collected by centrifugation, dissolved in dimethylsulfoxide (2 mL), and purified by preparative HPLC [5-85% methanol in water (0.1% ammonium hydroxide) over 30 min, 35 mL/min] to afford the title compound as a pale yellow solid (10 mg, 30% over two steps). $^1$H NMR (400 MHz, d$_6$-DMSO) δ 11.95 (s, 1H), 8.77 (s, 1H), 8.39 (d, J=5.7, 1H), 8.21 (s, 1H), 8.12 (s, 1H), 7.94 (s, 1H), 6.95 (d, J=5.9, 1H), 4.77-4.67 (m, 1H), 3.91 (s, 3H), 3.10-3.25 (m, 1H), 2.90-2.83 (m, 2H), 2.67 (m, 1H), 2.19 (m, 1H), 1.91-1.78 (m, 2H), 1.67-1.53 (m, 1H), piperidine NH not observed. LCMS (Method D): R$_T$=5.567 min, M+H$^+$=349.1.

The compounds of the Examples in Table 2 were prepared via one of the general coupling methods, followed by the general deprotection methods and the general purification methods as described above.

TABLE 2

| Example | Structure/Name | Coupling Method | Deprotection Method | Purification Method (s) | LCMS R$_T$, M + H$^+$, Method | $^1$H NMR (ppm) |
|---|---|---|---|---|---|---|
| 95 | 1-[4-(9H-Dipyrido[2,3b;4',3'-d]pyrrol-4-yl)-piperazin-1-yl]-2-(R)-pyrrolidin-2-yl-ethanone | G-2 | D-2 | B-2[3] | 1.42, 365, A | (400 MHz, CD$_3$OD): 9.17 (s, 1H), 8.76 (d, J = 6.4 Hz, 1H), 8.68 (s, 1H), 8.60 (d, J = 6.4 Hz, 1H), 3.98-3.96 (m, 3H), 3.89 (t, J = 4.9 Hz, 2H), 3.77-3.75 (m, 2H), 3.67 (t, J = 5.2 Hz, 2H), 3.33-3.32 (m, 2H), 3.17 (dd, J = 17.5, 3.7 Hz, 1H), 2.97 (dd, J = 17.5, 10.1 Hz, 1H), 2.30-2.29 (m, 1H), 2.13-2.13 (m, 1H), 2.02-2.01 (m, 1H), 1.81-1.80 (m, 1H). |

TABLE 2-continued

| Example | Structure/Name | Coupling Method | Deprotection Method | Purification Method (s) | LCMS R$_T$, M + H$^+$, Method | $^1$H NMR (ppm) |
|---|---|---|---|---|---|---|
| 96 | [(S)-1-(9H-Dipyrido[2,3-b;4',3'-d]pyrrol-4-yl)-pyrrolidin-3-yl]-ethyl-amine | G-2 | D-2 | B-2$^3$ | 0.62, 282, A | (400 MHz, CD$_3$OD): 8.73 (s, 1H), 8.26 (d, J = 5.7 Hz, 1H), 8.11-8.05 (m, 2H), 6.51 (d, J = 6.1 Hz, 1H), 3.97 (dd, J = 9.9, 6.3 Hz, 1H), 3.92-3.91 (m, 1H), 3.80-3.79 (m, 1H), 3.64 (dd, J = 9.8, 6.0 Hz, 1H), 3.55-3.54 (m, 1H), 2.74-2.73 (m, 2H), 2.36-2.35 (m, 1H), 1.98-1.97 (m, 1H), 1.18 (t, J = 7.17 Hz, 3H). |

The compounds of the Examples in Table 3 were prepared via one of the general coupling methods, followed by the general deprotection methods and the general purification methods as described above.

TABLE 3

| Example | Structure/Name | Coupling Method | Deprotection Method | Purification Method (s) | LCMS R$_T$, M + H$^+$, Method | $^1$H NMR (ppm) |
|---|---|---|---|---|---|---|
| 97 | 4-(1-Ethyl-piperidin-4-ylamino)-9H-dipyrido[2,3-b;4',3'-d]pyrrole-6-carbonitrile | E-1 | B-1 | C-2$^3$ | 1.08, 321, C | (300 MHz, DMSO-d$_6$): 12.40 (s, 1H), 9.07 (s, 1H), 8.83 (s, 1H), 8.19 (d, J = 5.9 Hz, 1H), 6.60 (d, J = 6.0 Hz, 1H), 6.39 (d, J = 8.2 Hz, 1H), 3.77-3.52 (m, 1H), 2.94 (d, J = 11.1 Hz, 2H), 2.36 (q, J = 7.2 Hz, 2H), 2.03-2.01 (m, 4H), 1.84-1.76 (m, 2H), 1.03 (t, J = 7.1 Hz, 3H). |
| 98 | 4-[(S)-(1-Azabicyclo-[2.2.2]oct-3-yl)oxy]-9H-dipyrido[2,3-b;4',3'-d]pyrrole-6-carbonitrile | F-1 | B-1 | B-2$^3$ | 4.44, 320, C | (400 MHz, CDCl$_3$): 8.95 (d, J = 1.0 Hz, 1H), 8.47 (d, J = 5.9 Hz, 1H), 8.41 (d, J = 1.0 Hz, 1H), 6.70 (d, J = 5.9 Hz, 1H), 4.84-4.83 (m, 1H), 3.50 (ddd, J = 14.6, 8.0, 2.1 Hz, 1H), 3.14-3.02 (m, 3H), 3.03-2.83 (m, 2H), 2.45-2.42 (m, 1H), 2.18-2.17 (m, 1H), 1.94-1.93 (m, 1H), 1.82-1.68 (m, 2H). |

TABLE 3-continued

| Example | Structure/Name | Coupling Method | Deprotection Method | Purification Method (s) | LCMS R$_T$, M + H$^+$, Method | $^1$H NMR (ppm) |
|---|---|---|---|---|---|---|
| 99 | 4-((S)-1-Ethylpiperidin-3-ylamino)-9H-dipyrido[2,3-b;4',3'-d]pyrrole-6-carbonitrile | E-1 | B-1 | C-2$^3$ | 1.45, 321, C | (400 MHz, DMSO-d$_6$): 12.44 (s, 1H), 8.95 (s, 1H), 8.84 (d, J = 0.9 Hz, 1H), 8.21 (d, J = 5.9 Hz, 1H), 6.60 (d, J = 6.0 Hz, 1H), 6.34 (d, J = 8.5 Hz, 1H), 3.80 (s, 1H), 2.99 (d, J = 10.7 Hz, 1H), 2.77 (d, J = 10.8 Hz, 1H), 2.42 (q, J = 7.2 Hz, 2H), 2.16 (t, J = 10.1 Hz, 1H), 2.07-1.89 (m, 2H), 1.80-1.68 (m, 1H), 1.61-1.59 (m, 2H), 1.04 (t, J = 7.1 Hz, 3H). |
| 100 | cis-3-Fluoro-piperidin-4-yloxy)-9H-dipyrido[2,3-b;4',3'-d]pyrrole-6-carbonitrile | F-1 | C-1 | C-2$^2$ | 4.01, 312, C | (400 MHz, CDCl$_3$): 12.14 (s, 1H), 8.97 (d, J = 1.1 Hz, 1H), 8.51 (d, J = 5.8 Hz, 1H), 8.45 (d, J = 1.1 Hz, 1H), 6.81 (d, J = 5.9 Hz, 1H), 5.09-4.87 (m, 2H), 3.45-3.44 (m, 1H), 3.28-3.18 (m, 1H), 3.08-3.07 (m, 1H), 2.91-2.82 (m, 1H), 2.20-2.09 (m, 2H). |
| 101 | 4-(4-Ethylpiperazin-1-yl)-9H-dipyrido[2,3-b;4',3'-d]pyrrole-6-carbonitrile | E-1 | B-1 | B-2 | 1.91, 307, A | (400 MHz, CD$_3$OD): 8.94 (d, J = 0.9 Hz, 1H), 8.44 (d, J = 5.7 Hz, 1H), 8.21 (d, J = 1.0 Hz, 1H), 6.96 (d, J = 5.7 Hz, 1H), 3.48-3.47 (m, 4H), 2.92-2.80 (m, 4H), 2.63 (q, J = 7.3 Hz, 2H), 1.22 (t, J = 7.2 Hz, 3H). |
| 102 | 4-(4-Pyrrolidin-1-ylpiperidin-1-yl)-9H-dipyrido[2,3-b;4',3'-d]pyrrole-6-carbonitrile | E-1 | B-1 | C-2$^3$ | 1.87, 347, A | (400 MHz, DMSO-d$_6$): 8.95 (d, J = 0.8 Hz, 1H), 8.43 (d, J = 5.6 Hz, 1H), 8.14 (d, J = 1.0 Hz, 1H), 6.88 (d, J = 5.6 Hz, 1H), 3.66 (d, J = 12.5 Hz, 2H), 3.04 (t, J = 11.8 Hz, 2H), 2.57 (s, 4H), 2.31-2.22 (m, 1H), 2.09 (d, J = 12.5 Hz, 2H), 1.76-1.68 (m, 6H). |

TABLE 3-continued

| Example | Structure/Name | Coupling Method | Deprotection Method | Purification Method (s) | LCMS R$_T$, M + H$^+$, Method | $^1$H NMR (ppm) |
|---|---|---|---|---|---|---|
| 103 | 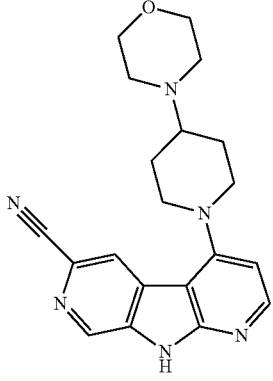 [SMILES: N#Cc1cc2c(cn1)[nH]c1nccc(N3CCC(N4CCOCC4)CC3)c12] 4-(4-Morpholin-4-yl-piperidin-1-yl)-9H-dipyrido[2,3b;4',3'd]pyrrole-6-carbonitrile | E-1 | B-1 | B-2$^1$ | 1.79, 362, A | (400 MHz, DMSO-d$_6$): 8.95 (d, J = 0.9 Hz, 1H), 8.43 (d, J = 5.6 Hz, 1H), 8.15 (d, J = 1.0 Hz, 1H), 6.88 (d, J = 5.6 Hz, 1H), 3.74 (d, J = 12.5 Hz, 2H), 3.62 (t, J = 4.3 Hz, 4H), 2.99 (t, J = 12.2 Hz, 2H), 2.56 (t, J = 4.2 Hz, 4H), 2.44-2.41 (m, 1H), 2.04 (d, J = 12.4 Hz, 2H), 1.87-1.59 (m, 2H). |
| 104 | 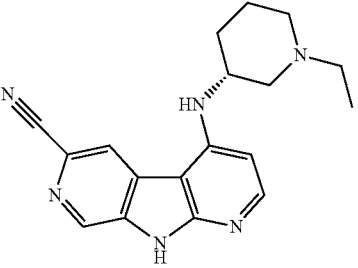 [SMILES: CCN1CCC[C@@H](Nc2ccnc3[nH]c4cnc(C#N)cc4c23)C1] 4-((R)-1-Ethyl-piperidin-3-ylamino)-9H-dipyrido[2,3b;4',3'-d]pyrrole-6-carbonitrile | E-1 | D-1 | C-2$^3$ | 1.68, 321, A | (400 MHz, DMSO-d$_6$): 12.44 (s, 1H), 8.95 (s, 1H), 8.84 (d, J = 0.9 Hz, 1H), 8.21 (d, J = 5.9 Hz, 1H), 6.60 (d, J = 6.0 Hz, 1H), 6.35 (d, J = 8.5 Hz, 1H), 3.87-3.74 (m, 1H), 3.00 (d, J = 10.8 Hz, 1H), 2.77 (d, J = 10.9 Hz, 1H), 2.42 (q, J = 7.2 Hz, 2H), 2.16 (t, J = 10.1 Hz, 1H), 2.07-1.91 (m, 2H), 1.80-1.69 (m, 1H), 1.67-1.56 (m, 2H), 1.04 (t, J = 7.1 Hz, 3H). |
| 105 | 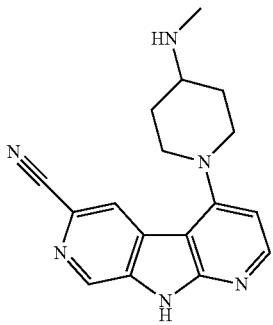 [SMILES: CNC1CCN(c2ccnc3[nH]c4cnc(C#N)cc4c23)CC1] 4-(4-Methylaminopiperidin-1-yl)-9H-dipyrido[2,3-b;4',3'-d]pyrrole-6-carbonitrile | E-1 | C-1 | C-2$^3$ | 1.70, 3.07, A | (400 MHz, CD$_3$OD): 8.93 (d, J = 0.9 Hz, 1H), 8.41 (d, J = 5.7 Hz, 1H), 8.21 (d, J = 1.0 Hz, 1H), 6.94 (d, J = 5.8 Hz, 1H), 3.85 (d, J = 12.9 Hz, 2H), 3.11 (t, J = 12.3 Hz, 2H), 2.79 (s, 1H), 2.51 (s, 3H), 2.23 (d, J = 12.4 Hz, 2H), 1.79-1.69 (m, 2H). |

TABLE 3-continued

| Example | Structure/Name | Coupling Method | Deprotection Method | Purification Method (s) | LCMS R$_T$, M + H$^+$, Method | $^1$H NMR (ppm) |
|---|---|---|---|---|---|---|
| 106 | 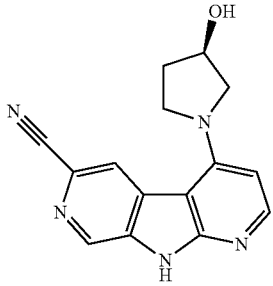 [SMILES: N#Cc1cc2c(cn1)[nH]c1nccc(N3CC[C@@H](O)C3)c12] 4-((R)-3-Hydroxypyrrolidin-1-yl)-9H-dipyrido[2,3b;4',3'-d]pyrrole-6-carbonitrile | E-1 | B-1 | B-2 | 1.93, 280, A | (400 MHz, DMSO-d$_6$): 8.80 (s, 1H), 8.46 (s, 1H), 8.14 (d, J = 5.8 Hz, 1H), 6.42 (d, J = 5.9 Hz, 1H), 4.48 (s, 1H), 4.01 (dd, J = 10.2, 4.3 Hz, 1H), 3.89-3.80 (m, 1H), 3.70-3.62 (m, 1H), 3.53 (d, J = 10.4 Hz, 1H), 3.45-3.20 (2H, obscured by solvent peak), 2.08-2.07 (m, 1H), 2.04-1.94 (m, 1H). |
| 107 | 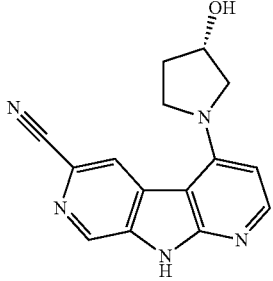 [SMILES: N#Cc1cc2c(cn1)[nH]c1nccc(N3CC[C@H](O)C3)c12] 4-((S)-3-Hydroxypyrrolidin-1-yl)-9H-dipyrido[2,3b;4',3'-d]pyrrole-6-carbonitrile | E-1 | B-1 | B-2 | 1.93, 280, A | (400 MHz, DMSO-d$_6$): 8.79 (s, 1H), 8.43 (s, 1H), 8.14 (d, J = 5.8 Hz, 1H), 6.39 (d, J = 5.6 Hz, 1H), 4.48 (s, 1H), 3.99 (dd, J = 10.2, 4.2 Hz, 1H), 3.88-3.79 (m, 1H), 3.66-3.62 (m, 1H), 3.53 (d, J = 10.6 Hz, 1H), 3.46-3.20 (2H, obscured by solvent peak), 2.08-2.07 (m, 1H), 2.04-1.94 (m, 1H). |
| 108 | 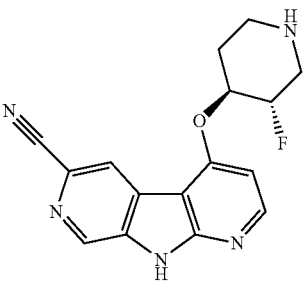 [SMILES: N#Cc1cc2c(cn1)[nH]c1nccc(O[C@H]3CCNC[C@@H]3F)c12] Trans-3-Fluoropiperidin-4-yloxy)-9H-dipyrido[2,3-b;4',3'd]pyrrole-6-carbonitrile | E-1 | B-1, C-1 | C-2$^2$ | 2.05, 312, A | (400 MHz, DMSO-d$_6$): 8.80 (d, J = 1.0 Hz, 1H), 8.36-8.34 (m, 2H), 6.76 (d, J = 5.6 Hz, 1H), 4.80-4.79 (m, 2H), 3.53-3.12 (1H, obscured by solvent peak), 2.93-2.88 (m, 1H), 2.65-2.62 (m, 2H), 2.22-2.19 (m, 1H), 1.68-1.57 (m, 1H). |

The compounds of the Examples in Table 4 were prepared via hydrogenation of the corresponding 3-Br intermediate.

TABLE 4

| Example | Structure/Name | 3-X | Coupling Method | Hydrog'n Method | Deprotection Method | Purification Method | LCMS R_T, M + H+, Method | 1H NMR (ppm) |
|---|---|---|---|---|---|---|---|---|
| 109 | 5-(Piperidin-4-ylmethoxy)-9H-dipyrido[2,3-b;4',3'-d]pyrrole-6-carbonitrile | Br | F-2 | A-2 | C-2, D-2 | C-2[1] | 2.27, 308, A | (400 MHz, CD$_3$OD/CDCl$_3$): 8.73 (s, 1H), 8.66-8.61 (m, 2H), 7.45 (dd, J = 7.9, 4.9 Hz, 1H), 4.46 (d, J = 6.2 Hz, 2H), 3.17 (d, J = 12.6 Hz, 2H), 2.74 (td, J = 12.4, 2.7 Hz, 2H), 2.23-2.20 (m, 1H), 2.02 (d, J = 13.2 Hz, 2H), 1.52 (qd, J = 12.4, 4.0 Hz, 2H). |
| 110 | 5-(Pyrrolidin-3-ylmethoxy)-9H-dipyrido[2,3-b;4',3'-d]pyrrole-6-carbonitrile | Br | F-2 | A-2 | C-2, D-2 | B-2[1] | 2.20, 294, A | (300 MHz, CD$_3$OD/CDCl$_3$): 8.73 (s, 1H), 8.66 (dd, J = 4.9, 1.7 Hz, 1H), 8.62 (dd, J = 7.9, 1.7 Hz, 1H), 7.45 (dd, J = 7.9, 4.9 Hz, 1H), 4.57-4.56 (m, 2H), 3.27-3.26 (m, 1H), 3.03-3.02 (m, 3H), 2.89 (d, J = 9.5 Hz, 1H), 2.16-2.15 (m, 1H), 1.78 (t, J = 6.8 Hz, 1H). |
| 111 | 5-((S)-Piperidin-3-yloxy)-9H-dipyrido[2,3-b;4',3'-d]pyrrole-6-carbonitrile | Br | F-2 | A-2 | C-2, D-2 | C-2[3] | 2.23, 294, A | (400 MHz, CD$_3$OD/CDCl$_3$): 8.75 (s, 1H), 8.66-8.66 (m, 2H), 7.46-7.45 (m, 1H), 4.78-4.77 (m, 1H), 3.35-3.31 (m, 1H), 3.02 (dd, J = 12.5, 8.3 Hz, 1H), 2.91 (d, J = 12.8 Hz, 1H), 2.73 (t, J = 5.5 Hz, 1H), 2.31-2.21 (m, 1H), 1.94-1.93 (m, 2H), 1.59-1.59 (m, 1H). |
| 112 | 5-((R)-1-Pyrrolidin-2-ylmethoxy)-9H-dipyrido[2,3-b;4',3'-d]pyrrole-6-carbonitrile | Br | F-2 | A-2 | C-2, D-2 | C-2 | 2.09, 294, A | (400 MHz, DMSO-d$_6$): 8.80 (dd, J = 7.9, 1.7 Hz, 1H), 8.76 (s, 1H), 8.69 (dd, J = 4.8, 1.7 Hz, 1H), 7.45 (dd, J = 7.9, 4.8 Hz, 1H), 4.33 (d, J = 6.2 Hz, 2H), 3.62-3.61 (m, 1H), 2.86-2.85 (m, 2H), 1.95-1.95 (m, 1H), 1.71-1.70 (m, 2H), 1.56-1.55 (m, 1H). |

TABLE 4-continued

| Example | Structure/Name | 3-X | Coupling Method | Hydrog" Method | Deprotection Method | Purification Method | LCMS $R_T$, M + H$^+$, Method | $^1$H NMR (ppm) |
|---|---|---|---|---|---|---|---|---|
| 113 | 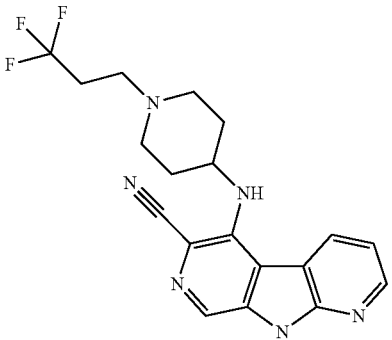 5-[1-(3,3,3-Trifluoro-propyl)-piperidin-4-ylamino]-9H-dipyrido[2,3-b;4',3'-d]pyrrole-6-carbonitrile | Br | B-2 | A-2 | NA | C-2 | 4.81, 389, C | (400 MHz, CD$_3$OD): 8.60 (s, 1H), 8.59 (dd, J = 4.1, 1.5 Hz, 1H), 8.47 (s, 1H), 7.42 (dd, J = 7.7, 5.2 Hz, 1H), 4.14-4.13 (m, 1H), 3.04 (d, J = 11.3 Hz, 2H), 3.03-2.38 (m, 2H), 2.41-2.40 (m, 2H), 2.33-2.30 (m, 2H), 2.25 (d, J = 13.4 Hz, 3H), 1.85-1.83 (m, 2H). |
| 114 | 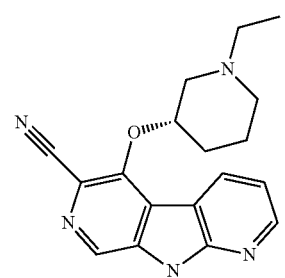 5-((S)-1-Ethyl-piperidin-3-yloxy)-9H-dipyrido[2,3-b;4',3'-d]pyrrole-6-carbonitrile | Br | F-2 | A-2 | E-2 | B-2$^4$ | 4.60, 322, C | (400 MHz. DMSO-d$_6$): 12.92 (s, 1H), 8.78 (s, 1H), 8.74 (dd, J = 7.9, 1.7 Hz, 1H), 8.70 (dd, J = 4.8, 1.6 Hz, 1H), 7.45 (dd, J = 7.9, 4.8 Hz, 1H), 4.82-4.76 (m, 1H), 2.93 (d, J = 11.0 Hz, 1H), 2.56-2.44 (m, 2H), 2.36 (q, J = 7.2 Hz, 2H), 2.26 (t, J = 10.0 Hz, 1H), 2.06-2.00 (m, 1H), 1.87-1.75 (m, 2H), 1.49-1.48 (m, 1H), 0.97 (t, J = 7.2 Hz, 3H). |
| 115 | 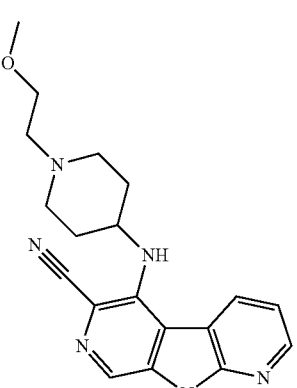 5-[1-(2-Methoxy-ethyl)-piperidin-4-ylamino]-9Hdipyrido[2,3-b;4',3'-d]pyrrole-6-carbonitrile | Br | A-2 | B-2 | NA | C-2$^3$ | 4.64, 351, C | (400 MHz, CD$_3$OD): 8.68 (dd, J = 8.0, 1.5 Hz, 1H), 8.6 (dd, J = 4.9, 1.51 Hz, 1H), 8.4 (s, 1H), 7.43 (dd, J = 8.0, 4.9 Hz, 1H), 4.13-4.12 (m, 1H), 3.55 (t, J = 5.5 Hz, 2H), 3.35 (s, 3H), 3.06-3.03 (m, 2H), 2.63 (t, J = 5.5 Hz, 2H), 2.25 (t, J = 12.0 Hz, 2H), 2.19-2.15 (m, 2H), 1.85 (q, J = 6.1 Hz, 2H). |

TABLE 4-continued

| Example | Structure/Name | 3-X | Coupling Method | Hydrog<sup>n</sup> Method | Deprotection Method | Purification Method | LCMS R<sub>T</sub>, M + H<sup>+</sup>, Method | <sup>1</sup>H NMR (ppm) |
|---|---|---|---|---|---|---|---|---|
| 116 | 5-(1-Cyclopropylmethyl-piperidin-4-yloxy)-9H-dipyrido[2,3-b;4',3'-d]pyrrole-6-carbonitrile | Br | F-2 | A-2 | C-2 | B-2, C-2 | 2.54, 348, A | (400 MHz, CD<sub>3</sub>OD): 8.75 (s, 1H), 8.67-8.67 (m, 2H), 7.46 (dd, J = 7.9, 4.9 Hz, 1H), 4.97-4.87 (m, 1H), 3.17-3.07 (m, 2H), 2.34-2.32 (m, 4H), 2.26-2.16 (m, 2H), 2.13-2.12 (m, 2H), 0.92-0.92 (m, 1H), 0.56-0.55 (m, 2H), 0.16-0.16 (m, 2H). |
| 117 | 5-(Cis)-3-Fluoro-piperidin-4-yloxy)-9H-dipyrido[2,3b;4',3'-d]pyrrole-6-carbonitrile | Br | F-2 | A-2 | E-2 | C-2<sup>3</sup> | 5.13, 312, C | (400 MHz, CDCl<sub>3</sub>): 8.79 (dd, J = 7.9, 1.7 Hz, 1H), 8.76 (s, 1H), 8.63 (dd, J = 4.9, 1.7 Hz, 1H), 7.38 (dd, J = 7.9, 4.9 Hz, 1H), 5.18-4.92 (m, 2H), 3.41-3.41 (m, 1H), 3.21-3.18 (m, 1H), 2.87 (dd, J = 35.6, 14.8 Hz, 1H), 2.78-2.69 (m, 1H), 2.18-2.07 (m, 2H). |
| 118 | 5-((S)-1-Pyrrolidin-2-ylmethoxy)-9H-dipyrido[2,3-b;4',3'-d]pyrrole-6-carbonitrile | Br | F-2 | B-2 | D-2 | A-2 | 2.09, 294, A | (300 MHz. DMSO-d<sub>6</sub>): 8.81 (dd, J = 7.93, 1.70 Hz, 1H), 8.77 (d, J = 0.51 Hz, 1H), 8.69 (dd, J = 4.79, 1.66 Hz, 1H), 7.45 (dd, J = 7.90, 4.79 Hz, 1H), 4.33 (d, J = 6.2 Hz, 2H), 3.62-3.61 (m, 1H), 2.86-2.85 (m, 2H), 1.97-1.93 (m, 1H), 1.67-1.66 (m, 3H). |

TABLE 4-continued

| Example | Structure/Name | Coupling 3-X | Hydrog" Method | Deprotection Method | Purification Method | LCMS $R_T$, M + H+, Method | $^1$H NMR (ppm) |
|---|---|---|---|---|---|---|---|
| 119 | 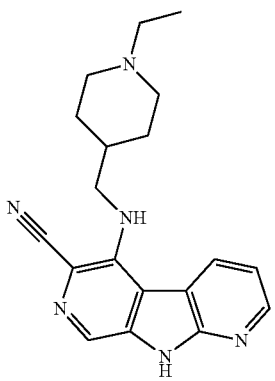 [SMILES: CCN1CCC(CNc2c(C#N)ncc3[nH]c4ncccc4c23)CC1]<br>5-[(1-Ethyl-piperidin-4-ylmethyl)-amino]-9H-dipyrido[2,3-b;4',3'-d]pyrrole-6-carbonitrile | Br | B-2 | B-2 | NA | A-2[2]<br>2.22, 335, A | (300 MHz, DMSO-$d_6$): 8.98 (dd, J = 8.0, 1.5 Hz, 1H), 8.61 (dd, J = 4.8, 1.5 Hz, 1H), 8.40 (s, 1H), 7.42 (dd, J = 8.0, 4.8 Hz, 1H), 6.49 (t, J = 6.5 Hz, 1H), 3.84-3.64 (m, 2H), 3.04-3.04 (m, 2H), 2.89-2.83 (m, 2H), 2.03-2.02 (m, 4H), 1.50-1.45 (m, 2H), 1.19 (t, J = 7.3 Hz, 3H). |
| 120 | 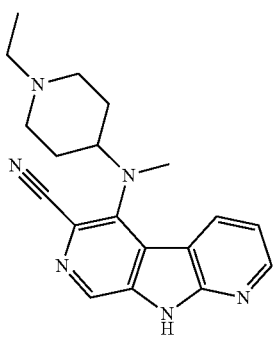 [SMILES: CCN1CCC(N(C)c2c(C#N)ncc3[nH]c4ncccc4c23)CC1]<br>5-[(1-Ethyl-piperidin-4-yl)-methyl-amino]-9H-dipyrido[2,3-b;4',3'-d]pyrrole-6-carbonitrile | Br | A-2 | B-2 | NA | [1]<br>5.16, 335, C | (400 MHz, CD$_3$OD/CDCl$_3$): 8.83 (s, 1H), 8.69-8.67 (m, 2H), 7.48-7.46 (m, 1H), 4.02-3.83 (m, 1H), 3.72-3.53 (m, 2H), 3.24-3.10 (m, 5H), 3.10-2.92 (m, 2H), 2.24-2.10 (m, 4H), 1.35 (t, J = 7.3 Hz, 3H). |

The compounds of the Examples in Table 5 were prepared via the General Methods reported above.

TABLE 5

| Example | Structure/Name | 3-X | Coupling Method | Deprotection Method | Purification Method | LCMS R$_T$, M + H$^+$, Method | $^1$H NMR (ppm) |
|---|---|---|---|---|---|---|---|
| 121 | 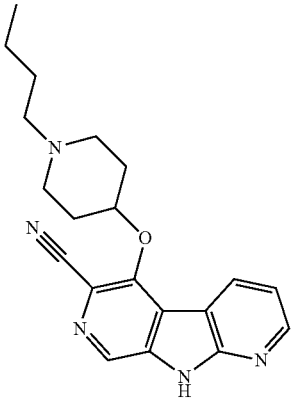 [SMILES: CCCCN1CCC(Oc2c(C#N)ncc3[nH]c4ncccc4c23)CC1]<br>5-(1-Butyl-piperidin-4yloxy)-9H-dipyrido[2,3-b;4',3'-d]pyrrole-6-carbonitrile | H | A-2 | NA | C-2$^3$ | 6.14, 350, C | (300 MHz, CD$_3$OD): 8.74 (s, 1H), 8.67-8.62 (m, 2H), 7.56 (s, 1H), 7.43-7.42 (m, 1H), 4.98-4.89 (m, 1H), 3.05-2.92 (m, 2H), 2.44-2.42 (m, 2H), 2.23-2.16 (m, 6H), 1.52-1.51 (m, 2H), 1.41-1.31 (m, 2H), 0.95 (t, J = 7.3 Hz, 3H). |
| 122 | 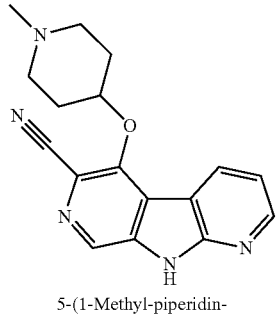<br>5-(1-Methyl-piperidin-4-yloxy)-9H-dipyrido[2,3-b;4',3'-d]pyrrole-6-carbonitrile | H | E-2 | A-2 | B-2$^3$ | 4.87, 308, C | (400 MHz, DMSO-d$_6$): 8.79 (s, 1H), 8.70 (dd, J = 4.8, 1.6 Hz, 1H), 8.59 (dd, J = 7.9, 1.7 Hz, 1H), 7.47 (dd, J = 7.9, 4.8 Hz, 1H), 4.71-4.69 (m, 1H), 2.76 (d, J = 10.9 Hz, 2H), 2.18 (s, 3H), 2.06 (t, J = 10.1 Hz, 4H), 1.96-1.94 (m, 2H). |
| 123 | 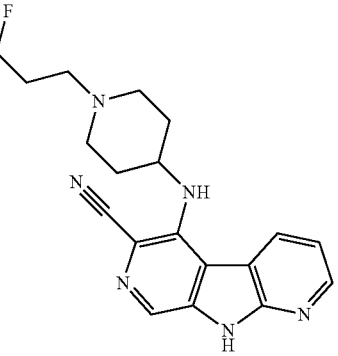<br>5-[1-(3,3,3-Trifluoro-propyl)-piperidin-4-ylamino]-9H-dipyrido[2,3-b;4',3'-d]pyrrole-6-carbonitrile | H | D-2 | NA | B-2$^3$ | 4.81, 389, C | (400 MHz. CD$_3$OD): 8.60 (s, 1H), 8.59 (dd, J = 4.1, 1.5 Hz, 1H), 8.47 (s, 1H), 7.42 (dd, J = 7.7, 5.2 Hz, 1H), 4.14-4.13 (m, 1H), 3.04 (d, J = 11.3 Hz, 2H), 3.03-2.38 (m, 2H), 2.41-2.40 (m, 2H), 2.33-2.30 (m, 2H), 2.25 (d, J = 13.4 Hz, 3H), 1.85-1.83 (m, 2H). |

TABLE 5-continued

| Example | Structure/Name | 3-X | Coupling Method | Deprotection Method | Purification Method | LCMS R$_T$, M + H$^+$, Method | $^1$H NMR (ppm) |
|---|---|---|---|---|---|---|---|
| 124 | 5-[(S)-(1-Azabicyclo[2.2.2]oct-3-yl)amino]-9H-dipyrido[2,3-b;4',3'-d]pyrrole-6-carbonitrile | H | D-2 | NA | C-2$^3$ | 3.99, 319, C | (400 MHz, CD$_3$OD): 8.65 (dd, J = 8.0, 1.5 Hz, 1H), 8.61 (dd, J = 4.9, 1.5 Hz, 1H), 8.47 (s, 1H), 7.45 (dd, J = 8.0, 4.9 Hz, 1H), 4.44 (s, 1H), 3.57 (ddd, J = 14.0, 9.4, 2.3 Hz, 1H), 3.14-3.07 (m, 1H), 2.90-2.89 (m, 4H), 2.11-2.10 (m, 2H), 2.04-1.54 (m, 2H), 1.62-1.61 (m, 1H). |
| 125 | 5-(2-Pyrrolidin-1-yl-ethoxy)-9H-dipyrido[2,3-b;4',3'-d]pyrrole-6-carbonitrile | H | C-2 | C-2 | B-2$^2$ | 4.16, 308, C | (400 MHz, CD$_3$OD): 8.78 (dd, J = 7.9, 1.6 Hz, 1H), 8.74 (s, 1H), 8.65 (dd, J = 4.9, 1.6 Hz, 1H), 7.44 (dd, J = 7.9, 4.9 Hz, 1H), 4.70 (t, J = 5.7 Hz, 2H), 3.15 (t, J = 5.7 Hz, 2H), 2.73-2.72 (m, 4H), 1.83-1.82 (m, 4H). |
| 126 | 5-(trans)-3-Fluoro-piperidin-4-yloxy)-9H-dipyrido[2,3-b;4',3'-d]pyrrole-6-carbonitrile | H | F-2 | E-2 | B-2 | 2.16, 312, A | (400 MHz, DMSO-d$_6$): 8.80 (s, 1H), 8.71 (dd, J = 6.2, 1.7 Hz, 1H), 8.67 (d, J = 8.0 Hz, 1H), 7.47 (dd, J = 7.9, 4.7 Hz, 1H), 4.82-4.81 (m, 2H), 3.25-3.23 (m, 2H), 2.90 (d, J = 13.1 Hz, 1H), 2.42-2.41 (m, 1H), 2.23-2.15 (m, 1H), 1.81 (qd, J = 11.9, 4.4 Hz, 1H). |
| 127 | 5-[(4-Ethyl-morpholin-2-ylmethyl)-amino]-9H-dipyrido[2,3-b;4',3'-d]pyrrole-6-carbonitrile | H | D-2 | NA | C-2 | 2.16, 337, A | (400 MHz, CDCl$_3$): 11.12 (s, 1H), 8.67 (dd, J = 4.9, 1.5 Hz, 1H), 8.55 (s, 1H), 8.39 (dd, J = 8.0, 1.5 Hz, 1H), 7.40 (dd, J = 7.9, 4.9 Hz, 1H), 5.25 (dd, J = 7.1, 4.0 Hz, 1H), 4.10-4.09 (m, 2H), 3.95-3.95 (m, 1H), 3.84 (td, J = 11.3, 2.5 Hz, 1H), 3.72 (ddd, J = 12.7, 8.0, 4.0 Hz, 1H), 2.93 (d, J = 11.3 Hz, 1H), 2.83 (d, J = 11.7 Hz, 1H), 2.48-2.46 (m, 2H), 2.24 (td, J = 11.4, 3.3 Hz, 1H), 2.06 (t, J = 10.7 Hz, 1H), 1.11 (t, J = 7.2 Hz, 3H). |

TABLE 5-continued

| Example | Structure/Name | 3-X | Coupling Method | Deprotection Method | Purification Method | LCMS $R_T$, M + H+, Method | 1H NMR (ppm) |
|---|---|---|---|---|---|---|---|
| 128 | 5-(4-Ethylamino-piperidin-1-yl)-9H-dipyrido[2,3-b;4',3'-d]pyrrole-6-carbonitrile | H | D-2 | D-2, A-2 | B-2 | 2.24, 321, A | (400 MHz, CD3OD): 8.74 (s, 1H), 8.71 (dd, J = 8.0, 1.6 Hz, 1H), 8.64 (dd, J = 4.9, 1.6 Hz, 1H), 7.45 (dd, J = 8.0, 4.9 Hz, 1H), 3.64-3.59 (m, 4H), 3.11-3.00 (m, 1H), 2.94 (q, J = 7.2 Hz, 2H), 2.28-2.19 (m, 2H), 1.92-1.83 (m, 2H), 1.28-1.26 (m, 3H). |
| 129 | 5-(1-Oxetan-3-yl-piperidin-4-ylamino)-9H-dipyrido[2,3-b;4',3'-d]pyrrole-6-carbonitrile | H | D-2 | NA | C-2, D-2 | 2.03, 349, A | (400 MHz, DMSO-d6): 12.68 (s, 1H), 8.78 (dd, J = 8.0, 1.6 Hz, 1H), 8.61 (dd, J = 4.8, 1.5 Hz, 1H), 8.44 (s, 1H), 7.41 (dd, J = 8.0, 4.9 Hz, 1H), 5.72 (d, J = 9.4 Hz, 1H), 4.53 (, J = 6.5 Hz t, 2H), 4.43 (t, J = 6.0 Hz, 2H), 4.00-3.98 (m, 1H), 3.40-3.39 (m, 1H), 2.74 (d, J = 8.9 Hz, 2H), 2.03 (d, J = 10.5 Hz, 2H), 1.99-1.74 (m, 4H). |
| 130 | 5-(1-Cyclopropylmethyl-piperidin-4-ylamino)-9H-dipyrido[2,3-b;4',3'-d]pyrrole-6-carbonitrile | H | D-2 | A-2 | C-2[1] | 2.35, 347, A | (400 MHz. CDCl3): 10.77 (s, 1H), 8.69 (d, J = 4.9 Hz, 1H), 8.59 (s, 1H), 8.31 (d, J = 8.0 Hz, 1H), 7.41 (dd, J = 7.9, 4.9 Hz, 1H), 4.48 (d, J = 9.9 Hz, 1H), 4.17-4.17 (m, 1H), 3.21 (d, J = 11.4 Hz, 2H), 2.36-2.31 (m, 6H), 1.95-1.91 (m, 2H), 0.96-0.96 (m, 1H), 0.60-0.55 (m, 2H), 0.18-0.16 (m, 2H). |

TABLE 5-continued

| Example | Structure/Name | 3-X | Coupling Method | Deprotection Method | Purification Method | LCMS $R_T$, M + H$^+$, Method | $^1$H NMR (ppm) |
|---|---|---|---|---|---|---|---|
| 131 | 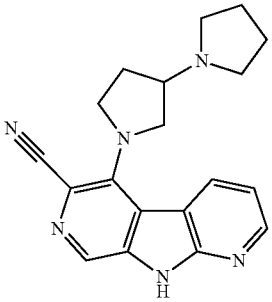 [SMILES: N#Cc1ncc2[nH]c3ncccc3c2c1N1CCC(N2CCCC2)C1] 5-[1,3']Bipyrrolidinyl-1'-yl-9H-dipyrido[2,3-b;4',3'-d]pyrrole-6-carbonitrile | H | D-2 | A-2 | B-2 | 2.20, 333, A | (400 MHz, DMSO-d$_6$): 12.78 (s, 1H), 8.66 (s, 1H), 8.65 (dd, J = 4.8, 1.5 Hz, 1H), 8.48 (dd, J = 8.0, 1.6 Hz, 1H), 7.43 (dd, J = 8.0, 4.8 Hz, 1H), 3.71-3.69 (m, 4H), 3.13 (s, 1H), 2.60 (d, J = 26.2 Hz, 3H), 2.33-2.30 (m, 1H), 2.09-2.07 (m, 1H), 1.76 (s, 4H). |
| 132 | 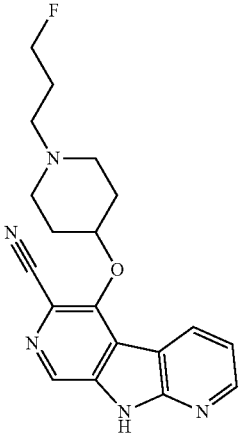 [SMILES: N#Cc1ncc2[nH]c3ncccc3c2c1OC1CCN(CCCF)CC1] 5-[1-(3-Fluoro-propyl)-piperidin-4-yloxy]-9H-dipyrido[2,3-b;4',3'-d]pyrrole-6-carbonitrile | H | E-2 | A-2 | C-2$^3$ | 2.38, 354, A | (300 MHz, CD$_3$OD): 8.75 (s, 1H), 8.68-8.62 (m, 2H), 7.44 (dd, J = 7.9, 5.0 Hz, 1H), 4.96-4.94 (m, 1H), 4.52 (dt, J = 47.3, 5.8 Hz, 2H), 3.06-2.93 (m, 2H), 2.58 (t, J = 7.7 Hz, 2H), 2.35 (t, J = 10.8 Hz, 2H), 2.04-2.03 (m, 6H). |
| 133 | 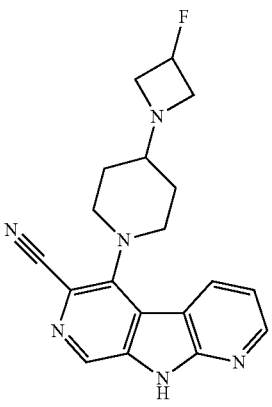 [SMILES: N#Cc1ncc2[nH]c3ncccc3c2c1N1CCC(N2CC(F)C2)CC1] 5-[4-(3-Fluoro-azetidin-1-yl)-piperidin-1-yl]-9H-dipyrido[2,3-b;4',3'-d]pyrrole-6-carbonitrile | H | D-2 | A-2 | B-2$^3$ | 2.22, 351, A | (400 MHz, CD$_3$OD): 8.71 (s, 1H), 8.69 (dd, J = 8.0, 1.6 Hz, 1H), 8.63 (dd, J = 4.9, 1.6 Hz, 1H), 7.44 (dd, J = 8.0, 4.9 Hz, 1H), 5.33-5.04 (m, 1 H), 3.74-3.73 (m, 2H), 3.64-3.56 (m, 2H), 3.52-3.51 (m, 2H), 3.37-3.36 (m, 2H), 2.51-2.50 (m, 1H), 2.09-1.99 (m, 2H), 1.68-1.67 (m, 2H). |

TABLE 5-continued

| Example | Structure/Name | 3-X | Coupling Method | Deprotection Method | Purification Method | LCMS R_T, M + H+, Method | ¹H NMR (ppm) |
|---|---|---|---|---|---|---|---|
| 134 | 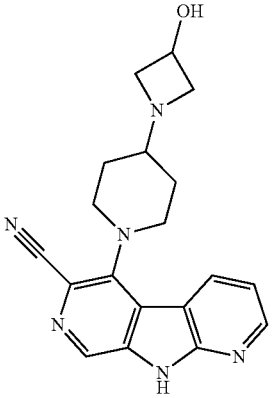 [SMILES: N#Cc1ncc2[nH]c3ncccc3c2c1N1CCC(N2CC(O)C2)CC1]<br>5-[4-(3-Hydroxy-azetidin-1-yl)-piperidin-1-yl]-9H-dipyrido[2,3-b;4',3'-d]pyrrole-6-carbonitrile | H | D-2 | A-2 | A-2³ | 2.13, 349, A | (400 MHz, CD$_3$OD): 8.72 (s, 1H), 8.69 (dd, J = 8.0, 1.6 Hz, 1H), 8.63 (dd, J = 4.9, 1.6 Hz, 1H), 7.44 (dd, J = 8.0, 4.9 Hz, 1H), 4.41 (p, J = 6.3 Hz, 1H), 3.74 (td, J = 6.5, 2.2 Hz, 2H), 3.55-3.54 (m, 4H), 3.02 (td, J = 6.6, 2.1 Hz, 2H), 2.45-2.38 (m, 1H), 2.10-1.99 (m, 2H), 1.67 (q, J = 6.1 Hz, 2H). |
| 135 | 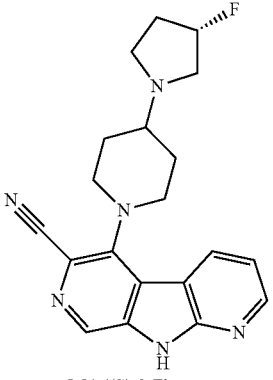<br>5-[4-((S)-3-Fluoro-pyrrolidin-1-yl)-piperidin-1-yl]-9H-dipyrido[2,3-b;4',3'-d]pyrrole-6-carbonitrile | H | D-2 | A-2 | B-2³ | 2.24, 365, A | (300 MHz, CD$_3$OD): 8.74 (s, 1H), 8.72 (dd, J = 8.0, 1.6 Hz, 1H), 8.64 (dd, J = 4.9, 1.6 Hz, 1H), 7.44 (dd, J = 8.0, 4.9 Hz, 1H), 5.27 (dt, J = 55.1, 5.5 Hz, 1H), 3.61-3.58 (m, 4H), 3.14 (s, 2H), 2.84 (ddd, J = 32.0, 11.8, 4.9 Hz, 1H), 2.62 (q, J = 7.9 Hz, 1H), 2.50-2.44 (m, 1H), 2.12-2.07 (m, 6H). |
| 136 | 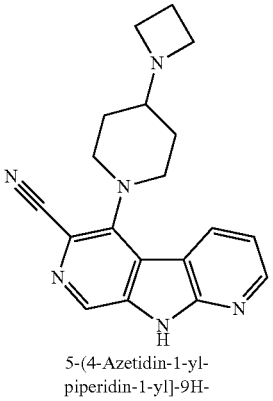<br>5-(4-Azetidin-1-yl-piperidin-1-yl]-9H-dipyrido[2,3-b;4',3'-d]pyrrole-6-carbonitrile | H | D-2 | A-2 | B-2³ | 2.19, 333, A | (400 MHz, CD$_3$OD): 8.73 (s, 1H), 8.64 (t, J = 7.4 Hz, 2H), 7.56 (s, 1H), 7.42 (dd, J = 7.8, 4.8 Hz, 1H), 3.57 (d, J = 13.8 Hz, 4H), 3.39 (t, J = 7.3 Hz, 4H), 2.44 (t, J = 10.4 Hz, 1H), 2.20-2.18 (m, 2H), 2.04 (d, J = 12.5 Hz, 2H), 1.65 (d, J = 12.6 Hz, 2H). |

TABLE 5-continued

| Example | Structure/Name | 3-X | Coupling Method | Deprotection Method | Purification Method | LCMS $R_T$, M + H+, Method | 1H NMR (ppm) |
|---|---|---|---|---|---|---|---|
| 137 | 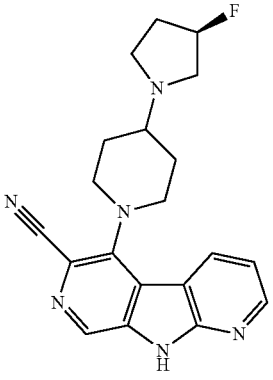 [SMILES: N#Cc1ncc2[nH]c3ncccc3c2c1N1CCC(N2CC[C@@H](F)C2)CC1]<br>5-[4-((R)-3-Fluoropyrrolidin-1-yl)-piperidin-1-yl]-9H-dipyrido[2,3-b;4',3'-d]pyrrole-6-carbonitrile | H | D-2 | A-2 | B-2[3] | 2.24, 365, A | (300 MHz, CD$_3$OD): 8.74 (s, 1H), 8.71 (dd, J = 8.0, 1.6 Hz, 1H), 8.64 (dd, J = 4.9, 1.6 Hz, 1H), 7.43 (dd, J = 8.0, 4.9 Hz, 1H), 5.28 (dt, J = 55.1, 5.4 Hz, 1H), 3.62-2.59 (m, 4H), 3.30-3.15 (m, 2H), 2.87 (ddd, J = 32.0, 11.8, 4.9 Hz, 1H), 2.70-2.60 (m, 1H), 2.58-2.45 (m, 1H), 2.41-1.90 (m, 6H). |
| 138 | 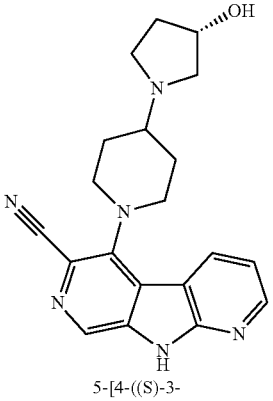<br>5-[4-((S)-3-Hydroxypyrrolidin-1-yl)-piperidin-1-yl]-9H-dipyrido[2,3-b;4',3'-d]pyrrole-6-carbonitrile | Br | B-2 | NA | B-2[3] | 2.11, 363, A | (400 MHz, DMSO-d$_6$): 12.88 (s, 1H), 8.79 (s, 1H), 8.71 (d, J = 4.3 Hz, 1H), 8.59 (d, J = 7.5 Hz, 1H), 7.47 (dd, J = 7.7, 4.8 Hz, 1H), 5.49 (s, 1H), 4.48 (s, 1H), 3.80-3.39 (m, 8H, obscured by solvent peak), 2.38-2.18 (m, 3H), 2.18-1.73 (m, 4H). |
| 139 | 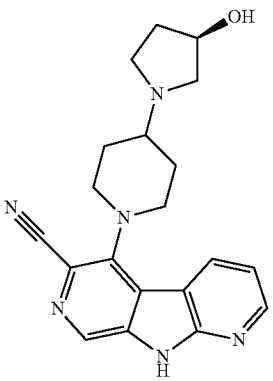 [SMILES: N#Cc1ncc2[nH]c3ncccc3c2c1N1CCC(N2CC[C@@H](O)C2)CC1]<br>5-[4-((R)-3-Hydroxy-pyrrolidin-1-yl)-piperidin-1-yl]-9H-dipyrido[2,3-b;4',3'-d]pyrrole-6-carbonitrile | Br | B-2 | NA | B-2[3] | 2.10, 363, A | (400 MHz, DMSO-d$_6$): 8.80 (s, 1H), 8.72 (dd, J = 4.7, 1.6 Hz, 1H), 8.60 (dd, J = 7.9, 1.7 Hz, 1H), 7.47 (dd, J = 7.9, 4.8 Hz, 1H), 5.67-5.38 (m, 1H), 4.50 (s, 1H), 3.75-3.31 (m, 8H), 2.40-2.21 (m, 3H), 2.09-1.92 (m, 4H). |

TABLE 5-continued

| Example | Structure/Name | 3-X | Coupling Method | Deprotection Method | Purification Method | LCMS $R_T$, M + H+, Method | 1H NMR (ppm) |
|---|---|---|---|---|---|---|---|
| 140 | 5-(4-Hydroxy-piperidin-1-yl)-9H-dipyrido[2,3-b;4',3'-d]pyrrole-6-carbonitrile | H | D-2 | A-2 | E-2[4] | 2.81, 294, A | (400 MHz, CD3OD): 8.72 (dd, J = 8.0, 1.6 Hz, 1H), 8.72 (s, 1H), 8.64 (dd, J = 4.9, 1.6 Hz, 1H), 7.46 (dd, J = 8.0, 4.9 Hz, 1H). 4.09-3.81 (m, 1H), 3.67-3.66 (m, 2H), 3.52-3.50 (m, 2H), 2.20-2.13 (m, 2H), 1.92-1.91 (m, 2H), 1.45 (s, 1H). |
| 141 | 5-(4-Hydroxy-[1,4']bipiperidinyl-1'-yl)-9H-dipyrido[2,3-b;4',3'-d]pyrrole-6-carbonitrile | H | D-2 | A-2 | [2] | 2.14, 377, A | (400 MHz, CD3OD): 8.72 (s, 1H), 8.70 (dd, J = 8.0, 1.6 Hz, 1H), 8.64 (dd, J = 4.9, 1.6 Hz, 1H), 7.46 (dd, J = 8.0, 4.9 Hz, 1H), 3.68-3.64 (m, 3H), 3.61-3.53 (m, 2H), 3.14-2.99 (m, 2H), 2.65 (t, J = 11.2 Hz, 1H), 2.49 (t, J = 10.7 Hz, 2H), 2.17 (d, J = 12.3 Hz, 2H), 1.97-1.95 (m, 4H), 1.66-1.65 (m, 2H). |
| 142 | 5-(4-Fluoro-[1,4']bipiperidinyl-1'-yl)-9H-dipyrido[2,3-b;4',3'-d]pyrrole-6-carbonitrile | H | D-2 | A-2 | E-2[4] | 2.41, 379, A | (400 MHz, CD3OD): 8.77 (s, 1H), 8.72 (dd, J = 8.0, 1.6 Hz, 1H), 8.66 (dd, J = 4.9, 1.6 Hz, 1H), 7.47 (dd, J = 8.0, 4.9 Hz, 1H), 4.96 (d, J = 50.8 Hz, 1H), 3.70-3.68 (m, 4H), 3.46 (s, 5H), 2.37 (d, J = 11.8 Hz, 2H), 2.20-2.20 (m, 6H). |

TABLE 5-continued

| Example | Structure/Name | 3-X | Coupling Method | Deprotection Method | Purification Method | LCMS $R_T$, M + H⁺, Method | ¹H NMR (ppm) |
|---|---|---|---|---|---|---|---|
| 143 | 5-(4-Hydroxy-4-methyl-piperidin-1-yl)-9H-dipyrido[2,3-b;4',3'-d]pyrrole-6-carbonitrile | H | D-2 | A-2 | B-2 | 3.16, 308, A | (400 MHz, DMSO-d₆): 8.73 (s, 1H), 8.67 (dd, J = 4.8, 1.5 Hz, 1H), 8.56 (d, J = 8.0 Hz, 1H), 7.47 (dd, J = 8.0, 4.8 Hz, 1H), 3.70 (td, J = 11.2, 2.8 Hz, 2H), 3.34-3.24 (m, 2H), 1.87-1.85 (m, 2H), 1.75 (d, J = 13.0 Hz, 2H), 1.30 (s, 3H). |
| 144 | 5-(1-Aza-bicyclo[2.2.2]oct-4-yloxy)-9H-dipyrido[2,3-b;4',3'-d]pyrrole-6-carbonitrile | H | D-2 | A-2 | B-2³ | 2.28, 320, A | (300 MHz, DMSO-d₆): 8.83 (s, 1H), 8.78 (dd, J = 8.0, 1.7 Hz, 1H), 8.69 (dd, J = 4.8, 1.6 Hz, 1H), 7.45 (dd, J = 8.0, 4.8 Hz, 1H), 2.88 (t, J = 7.2 Hz, 6H), 1.93 (t, J = 7.2 Hz, 6H). |
| 145 | 5-(1,4-Dimethyl-piperidin-4-yloxy)-9H-dipyrido[2,3-b;4',3'-d]pyrrole-6-carbonitrile | H | E-2 | A-2 | B-2³ | 2.19, 322, A | (400 MHz, DMSO-d₆): 8.81 (s, 1H), 8.70-8.70 (m, 2H), 7.44 (dd, J = 7.9, 4.8 Hz, 1H), 2.72-2.70 (m, 2H), 2.27-2.19 (m, 4H), 2.18 (s, 3H), 1.92-1.89 (m, 2H), 1.34 (s, 3H). |

TABLE 5-continued

| Example | Structure/Name | 3-X | Coupling Method | Deprotection Method | Purification Method | LCMS $R_T$, M + H$^+$, Method | $^1$H NMR (ppm) |
|---|---|---|---|---|---|---|---|
| 146 | 5-(4-Hydroxy-4-methyl[1,4']bipiperidinyl-1'-yl)-9H-dipyrido[2,3 b;4',3'-d]pyrrole-6-carbonitrile | H | D-2 | A-2 | B-2$^3$ | 2.22, 319, A | (400 MHz, DMSO-d$_6$): 8.73 (s, 1H), 8.67 (dd, J = 4.8, 1.5 Hz, 1H), 8.55 (dd, J = 8.0, 1.6 Hz, 1H), 7.49 (dd, J = 8.0, 4.8 Hz, 1H), 4.09 (s, 1 H), 1.99 (d, J = 12.2 Hz, 2H), 3.59 (d, J = 11.8 Hz, 2H), 3.40 (t, J = 11.9 Hz, 2H), 2.60-2.58 (m, 5H), 1.85-1.82 (m, 2H), 1.53-1.47 (m, 4H), 1.12 (s, 3H). |
| 147 | 3-Bromo-5-(piperidin-4-ylamino)-9H-dipyrido[2,3-b;4',3'-d]pyrrole-6-carbonitrile | Br | B-2 | B-2 | C-2$^3$ | 5.66, 370/372, A | (400 MHz, CDCl$_3$/CD$_3$OD): 8.72 (s, 1H), 8.71 (d, J = 2.3 Hz, 1H), 8.68 (d, J = 2.2 Hz, 1H), 3.62-3.57 (m, 4H), 3.05-3.04 (m, 1H), 2.16-2.13 (m, 2H), 1.80-1.79 (m, 2H). |
| 148 | 3-Bromo-5-(piperidin-4-yloxy)-9H-dipyrido[2,3-b;4',3'-d]pyrrole-6-carbonitrile | Br | F-2 | D-2, C-2 | B-2 | 2.55, 372, A | (400 MHz, DMSO-d$_6$): 8.78 (s, 1H), 8.76 (d, 1H, J = 2.3 Hz), 8.58 (d, 1H, J = 2.3 Hz), 4.78-4.77 (m, 1H), 3.08 (dt, 2H, J = 13.0, 4.2 Hz), 2.58 (ddd, 2H, J = 12.8, 10.7, 2.7 Hz), 2.06 (d, 2H, J = 12.1 Hz), 1.85-1.74 (m, 2H). |

TABLE 5-continued

| Example | Structure/Name | 3-X | Coupling Method | Deprotection Method | Purification Method | LCMS $R_T$, M + H$^+$, Method | $^1$H NMR (ppm) |
|---|---|---|---|---|---|---|---|
| 149 | 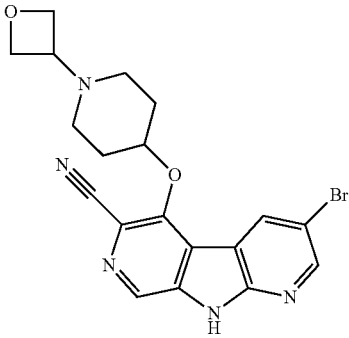 [SMILES: N#Cc1ncc2[nH]c3ncc(Br)cc3c2c1OC1CCN(C2COC2)CC1]<br>3-Bromo-5-(1-oxetan-3-yl-piperidin-4-yloxy)-9H-dipyrido[2,3-b;4',3'-d]pyrrole-6-carbonitrile | Br | F-2 | E-2 | A-2[3] | 2.59, 428, A | (400 MHz, DMSO-d$_6$): 8.80 (d, J = 1.9 Hz, 2H), 8.66 (d, J = 2.3 Hz, 1H), 4.81 (s, 1H), 4.49 (dt, J = 36.1, 6.3 Hz, 4H), 3.43-3.41 (m, 1H), 2.69-2.68 (m, 2H), 2.05-2.02 (m, 6H). |
| 150 | 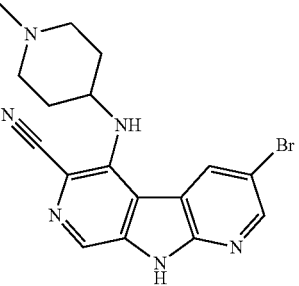<br>3-Bromo-5-(1-ethyl-piperidin-4-ylamino)-9H-dipyrido[2,3-b;4',3'-d]pyrrole-6-carbonitrile | Br | B-2 | NA | B-2 | 2.51, 399/401, A | (400 MHz, CDCl$_3$): 8.62 (d, J = 2.0 Hz, 2H), 8.44 (s, 1H), 4.17 (s, 1H), 3.05 (s, 2H), 2.52 (s, 2H), 2.23 (d, J = 13.0 Hz, 4H), 1.82 (s, 2H), 1.16 (t, J = 7.1 Hz, 3H). |
| 151 | 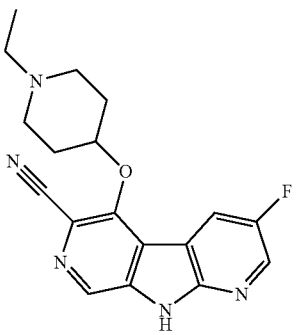 [SMILES: CCN1CCC(Oc2c(C#N)ncc3[nH]c4ncc(F)cc4c23)CC1]<br>5-(1-Ethyl-piperidin-4-yloxy)-3-fluoro-9H-dipyrido[2,3-b;4',3'-d]pyrrole-6-carbonitrile | F | F-2 | E-2 | B-2[3] | 2.41, 340, A | (400 MHz, DMSO-d$_6$): 8.79 (s, 1H), 8.74-8.73 (m, 1H), 8.37 (dd, J = 8.5, 2.8 Hz, 1H), 4.79-4.71 (m, 1H), 2.86-2.82 (m, 2H), 2.34 (q, J = 7.2 Hz, 2H), 2.07-2.04 (m, 4H), 1.97-1.95 (m, 2H), 0.99 (t, J = 7.2 Hz, 3H). |

TABLE 5-continued

| Example | Structure/Name | 3-X | Coupling Method | Deprotection Method | Purification Method | LCMS R_T, M + H+, Method | $^1$H NMR (ppm) |
|---|---|---|---|---|---|---|---|
| 152 | 5-[(S)-(1-Azabicyclo[2.2.2]oct-3-yl)oxy]-3-fluoro-9H-dipyrido[2,3-b;4',3'-d]pyrrole-6-carbonitrile | F | F-2 | E-2 | B-2³ | 2.38, 338, B | (400 MHz, DMSO-d₆): 8.77 (s, 1H), 8.76-8.74 (m, 1H), 8.28 (dd, J = 8.5, 2.8 Hz, 1H), 5.09-5.07 (m, 1H), 3.47-3.21 (m, 1H, obscured by solvent peak), 3.05-3.02 (m, 2H), 2.87-2.76 (m, 1 H), 2.67-2.66 (m, 2H), 2.23-2.22 (m, 1H), 2.05 (s, 1H), 1.69-1.68 (m, 1H), 1.50-1.49 (m, 2H). |
| 153 | 3-Fluoro-5-(4-morpholin-4-yl-piperidin-1-yl)-9H-dipyrido[2,3-b;4',3'-d]pyrrole-6-carbonitrile | F | B-2 | NA | C-2³ | 2.29, 381, A | (400 MHz, DMSO-d₆): 12.96 (s, 1H), 8.75 (s, 1H), 8.73 (dd, J = 2.8, 1.5 Hz, 1H), 8.28 (dd, J = 9.0, 2.8 Hz, 1H), 3.62-3.61 (m, 6H), 3.41 (t, J = 11.7 Hz, 2H), 2.58 (t, J = 4.3 Hz, 4H), 2.50-2.39 (m, 1H), 2.06 (d, J = 12.4 Hz, 2H), 1.76 (qd, J = 11.6, 3.7 Hz, 2H). |
| 154 | 3-Chloro-5-(4-morpholin-4-yl-piperidin-1-yl)-9H-dipyrido[2,3-b;4',3'-d]pyrrole-6-carbonitrile | Cl | B-2 | NA | C-2³ | 2.49, 397/399, A | (400 MHz, DMSO-d₆): 8.75 (s, 1H), 8.71 (d, J = 2.3 Hz, 1H), 8.44 (d, J = 2.4 Hz, 1H), 3.69-3.57 (m, 6H), 3.42 (t, J = 12.2 Hz, 2H), 2.57 (t, J = 4.3 Hz, 4H), 2.46-2.39 (m, 1H), 2.08 (d, J = 12.2 Hz, 2H), 1.72 (qd, J = 11.7, 3.7 Hz, 2H). |

TABLE 5-continued

| Example | Structure/Name | 3-X | Coupling Method | Deprotection Method | Purification Method | LCMS R$_T$, M + H$^+$, Method | $^1$H NMR (ppm) |
|---|---|---|---|---|---|---|---|
| 155 | 3-Fluoro-5-(piperidin-4-yloxy)-9H-dipyrido[2,3-b;4',3'-d]pyrrole-6-carbonitrile | F | F-2 | E-2, D-2 | B-2[4] | 2.30, 312, A | (400 MHz, DMSO-d$_6$): 8.79 (s, 1H), 8.73 (dd, J = 2.8, 1.7 Hz, 1H), 8.31 (dd, J = 8.5, 2.8 Hz, 1H), 4.75-4.74 (m, 1H), 3.09-3.00 (m, 2H), 2.55-2.54 (m, 2H), 2.06-2.05 (m, 2H), 1.85-1.73 (m, 2H). |
| 156 | 3-Bromo-5-(4-morpholin-4-yl-piperidin-1-yl)-9H-dipyrido[2,3-b;4',3'-d]pyrrole-6-carbonitrile | Br | B-2 | E-2 | C-2[4] | 2.51, 441, A | (400 MHz, CDCl$_3$): 8.72 (s, 1H), 8.66-8.65 (m, 2H), 3.83 (s, 4H), 3.70-3.52 (m, 4H), 2.71 (s, 4H), 2.58-2.44 (s, 1H), 2.21 (d, J = 12.2 Hz, 2H), 1.88-1.84 (m, 2H). |
| 157 | 5-[(S)-(1-Azabicyclo[2.2.2]oct-3-yl)oxy]-3-chloro-9H-dipyrido[2,3-b;4',3'-d]pyrrole-6-carbonitrile | Cl | F-2 | E-2 | B-2[4] | 2.61, 354/356, A | (400 MHz, DMSO-d$_6$): 8.77 (s, 1H), 8.73 (d, J = 2.4 Hz, 1H), 8.44 (d, J = 2.4 Hz, 1H), 5.07-5.06 (m, 1H), 3.44-3.20 (m, 1H, obscured by solvent peak), 3.04-2.99 (m, 2H), 2.85-2.82 (m, 1H), 2.74-2.59 (m, 2H), 2.24-2.21 (m, 1H), 2.11-1.99 (m, 1H), 1.70-1.69 (m, 1H), 1.51-1.50 (m, 2H). |

TABLE 5-continued

| Example | Structure/Name | 3-X | Coupling Method | Deprotection Method | Purification Method | LCMS $R_T$, M + H$^+$, Method | $^1$H NMR (ppm) |
|---|---|---|---|---|---|---|---|
| 158 | 3-Chloro-5-(1-ethyl-piperidin-4-ylamino)-9H-dipyrido[2,3-b;4',3'-d]pyrrole-6-carbonitrile | Cl | B-2 | NA | F-2 | 2.47, 355, A | (400 MHz, CD$_3$OD): 8.72 (d, J = 2.3 Hz, 1H), 8.57 (d, J = 2.3 Hz, 1H), 8.42 (s, 1H), 4.18-4.14 (m, 1H), 3.09-3.05 (m, 2H), 2.51 (q, J = 7.3 Hz, 2H), 2.21-2.17 (m, 4H), 1.90-1.81 (m, 2H), 1.15 (t, J = 7.2 Hz, 3H). |
| 159 | 3-Chloro-5-(4-pyrrolidin-1-yl-piperidin-1-yl)-9H-dipyrido[2,3-b;4',3'-d]pyrrole-6-carbonitrile | Cl | B-2 | NA | C-2$^4$ | 2.56, 381/383, A | (400 MHz, CD$_3$OD): 8.73 (s, 1H), 8.63-8.62 (m, 2H), 3.59-3.58 (m, 4H), 2.89-2.66 (m, 4H), 2.48-2.41 (m, 1H), 2.27 (d, J = 12.7 Hz, 2H), 1.91-1.90 (m, 6H). |

The compounds of the Examples in Table 6 were prepared via the General Methods reported above.

TABLE 6

| Example | Structure/Name | 3-X | Coupling Method | Deprotection Method | Reductive Animation Method | Purification Method | LCMS $R_T$, M + H$^+$, Method | $^1$H NMR (ppm) |
|---|---|---|---|---|---|---|---|---|
| 160 | 5-(1-Ethyl-piperidin-ylmethoxy)-9H-dipyrido[2,3-b;4',3' d]pyrrole-6-carbonitrile | H | F-2 | D-2 | B-2 | C$^3$ | 2.39, 336, A | (400 MHz, CDCl$_3$): 8.80 (s, 1H), 8.70 (dd, J = 4.9, 1.6 Hz, 1H), 8.54 (d, J = 7.8 Hz, 1H), 7.37 (dd, J = 7.9, 4.9 Hz, 1H), 4.51 (t, J = 5.8 Hz, 2H), 3.36 (s, 1H), 3.02 (s, 1H), 2.57 (s, 2H), 2.50 (s, 2H), 2.10 (s, 2H), 1.98 (m, 1H), 1.84 (s, 2H), 1.31-1.27 (m, 1H), 1.17 (t, J = 7.0 Hz, 3H). |

TABLE 6-continued

| Example | Structure/Name | 3-X | Coupling Method | Deprotection Method | Reductive Animation Method | Purification Method | LCMS $R_T$, M + H$^+$, Method | $^1$H NMR (ppm) |
|---|---|---|---|---|---|---|---|---|
| 161 | 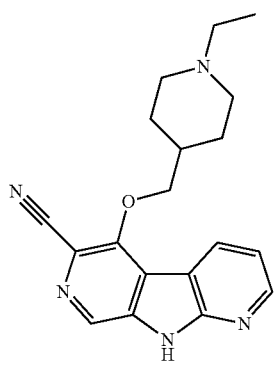 [SMILES: CCN1CCC(COc2c(C#N)ncc3[nH]c4ncccc4c23)CC1] 5-(1-Ethyl-piperidin-4-ylmethoxy)-9H-dipyrido[2,3-b;4',3'-d]pyrrole-6-carbonitrile | H | F-2 | D-2 | B-2 | C-2$^3$ | 2.40, 336, A | (400 MHz, CD$_3$OD): 8.73 (s, 1H), 8.67 (q, J = 1.8 Hz, 1H), 8.65 (s, 1H), 7.46-7.46 (m, 1H), 4.48 (d, J = 6.1 Hz, 2H), 3.16-3.08 (m, 2H), 2.53 (q, J = 7.3 Hz, 2H), 2.22-2.02 (m, 5H), 1.63 (q, J = 12.6 Hz, 2H), 1.15 (t, J = 7.3 Hz, 3H). |
| 162 | 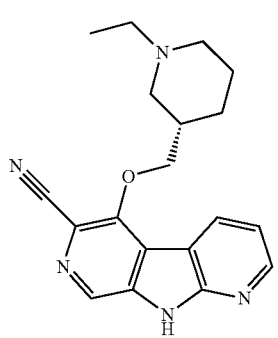 [SMILES: CCN1CCC[C@H](COc2c(C#N)ncc3[nH]c4ncccc4c23)C1] 5-((S)-1-Ethyl-piperidin-3-ylmethoxy)-9H-dipyrido[2,3-b;4',3'-d]pyrrole-6-carbonitrile | H | F-2 | D-2 | B-2 | C-2$^3$ | 2.39, 336, A | (400 MHz, CD$_3$OD): 8.73 (s, 1H), 8.65-8.65 (m, 2H), 7.46 (dd, J = 7.8, 5.0 Hz, 1H), 4.54-4.40 (m, 2H), 3.40-3.29 (m, 1H), 3.00 (d, J = 11.4 Hz, 1H), 2.52-2.52 (m, 2H), 2.40-2.32 (m, 1H), 2.05-2.04 (m, 3H), 1.87-1.80 (m, 1H), 1.74-1.73 (m, 1H), 1.30-1.29 (m, 1H), 1.13 (t, J = 7.3 Hz, 3H). |
| 163 | 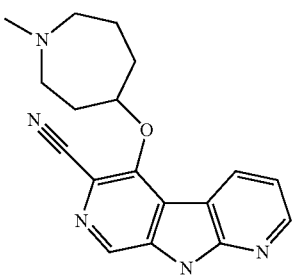 5-(1-Methyl-azepan-4-yloxy)-9H-dipyrido[2,3-b;4',3'-d]pyrrole-6-carbonitrile | H | F-2 | D-2 | A-2 | B-2 | 2.30, 322, A | (400 MHz, DMSO-d$_6$): 8.77 (s, 1H), 8.70 (dd, J = 4.8, 1.6 Hz, 1H), 8.56 (dd, J = 7.9, 1.7 Hz, 1H), 7.47 (dd, J = 7.9, 4.8 Hz, 1H), 4.98-4.97 (m, 1H), 2.68 (ddd, J = 13.4, 7.3, 3.0 Hz, 1H), 2.58 (ddd, J = 12.4, 8.7, 3.4 Hz, 1H), 2.45-2.44 (m, 2H), 2.26 (s, 3H), 2.25-1.99 (m, 4H), 1.83-1.82 (m, 1H), 1.56-1.54 (m, 1H). |

TABLE 6-continued

| Example | Structure/Name | 3-X | Coupling Method | Deprotection Method | Reductive Amination Method | Purification Method | LCMS $R_T$, M + H$^+$, Method | $^1$H NMR (ppm) |
|---|---|---|---|---|---|---|---|---|
| 164 | 5-[1-(2-Hydroxy-2-methyl-propyl)-piperidin-4-yloxy]-9H-dipyrido[2,3-b;4',3'-d]pyrrole-6-carbonitrile | H | F-2 | D-2 | C-2 | B-2[4] | 2.36, 366, A | (400 MHz, DMSO-d$_6$): 8.78 (s, 1H), 8.70 (dd, J = 4.8, 1.6 Hz, 1H), 8.58 (dd, J = 7.9, 1.7 Hz, 1H), 7.48 (dd, J = 7.9, 4.8 Hz, 1H), 5.75 (s, 1H), 4.68-4.66 (m, 1H), 2.99-2.95 (m, 2 H), 2.27 (t, J = 11.2 Hz, 2H), 2.21 (s, 2H), 2.09-1.98 (m, 2H), 2.02-1.90 (m, 2H), 1.09 (s, 6H). |
| 165 | 5-(1-Ethyl-azetidin-3-yloxy)-9H-dipyrido[2,3-b;4',3'-d]pyrrole-6-carbonitrile | H | F-2 | D-2, E-2 | B-2 | B-2[4] | 3.92, 294, A | (400 MHz, DMSO-d$_6$): 8.78 (s, 1H), 8.70 (dd, J = 4.8, 1.7 Hz, 1H), 8.63 (dd, J = 7.9, 1.7 Hz, 1H), 7.46 (dd, J = 7.9, 4.8 Hz, 1H), 5.31-5.30 (m, 1H), 3.69-3.68 (m, 2H), 3.35-3.33 (m, 4H), 0.92 (t, J = 7.2 Hz, 3H). |
| 166 | 3-Fluoro-5-(1-methyl-piperidin-4-yloxy)-9H-dipyrido[2,3-b;4',3'-d]pyrrole-6-carbonitrile | F | F-2 | D-2, E-2 | B-2 | C-2[3] | 2.33, 326, A | (400 MHz, CDCl$_3$): 8.72 (s, 1H), 8.57-8.47 (m, 1H), 8.36-8.22 (m, 1H), 5.10-4.95 (m, 1 H), 3.06-2.77 (s, 2 H), 2.64 (s, 3 H), 2.38-2.24 (m, 4 H), 2.18-2.01 (m, 2 H). |

TABLE 6-continued

| Example | Structure/Name | 3-X | Coupling Method | Deprotection Method | Reductive Animation Method | Purification Method | LCMS $R_T$, M + H$^+$, Method | $^1$H NMR (ppm) |
|---|---|---|---|---|---|---|---|---|
| 167 | 3-Chloro-5-(1-methyl-piperidin-4-yloxy)-9H-dipyrido[2,3-b;4',3'-d]pyrrole-6-carbonitrile | Cl | F-2 | D-2, E-2 | A-2 | B-2[4] | 2.51, 342/344, A | (400 MHz, DMSO-d$_6$): 8.80 (s, 1H), 8.74 (d, J = 2.4 Hz, 1H), 8.53 (d, J = 2.4 Hz, 1H). 4.81-4.76 (m, 1H), 2.75-2.73 (m, 2H), 2.19 (s, 3H), 2.10-2.07 (m, 4H), 2.00-1.89 (m, 2H). |
| 168 | 3-Chloro-5-(1-ethyl-piperidin-4-yloxy)-9H-dipyrido[2,3-b;4',3'-d]pyrrole-6-carbonitrile | Cl | F-2 | D-2, E-2 | B-2 | B-2[4] | 2.62, 356/358, A | (400 MHz, DMSO-d$_6$): 8.80 (s, 1H), 8.73 (d, J = 2.4 Hz, 1H), 8.54 (d, J = 2.4 Hz, 1H), 4.86-4.73 (m, 1H), 2.86-2.81 (m, 2H), 2.35 (q, J = 7.2 Hz, 2H), 2.16-2.01 (m, 4H), 1.96-1.94 (m, 2H), 1.00 (t, J = 7.2 Hz, 3H). |

The compounds of the Examples in Table 7 were prepared by hydrogenation of the corresponding 3-Br analogues.

TABLE 7

| Example | Structure/Name | 3-X | Hydrogenation Method | Deprotection Method | Purification Method(s) | LCMS $R_T$, M + H$^+$, Method | $^1$H NMR (ppm) |
|---|---|---|---|---|---|---|---|
| 169 | 5-(1-Methyl-piperidin-4-ylamino)-9H-dipyrido[2,3-b;4',3'-d]pyrrole-6-carbonitrile | Br | A-2 | NA | [1] | 3.99, 307, C | (400 MHz, CD$_3$OD): 8.69 (dd, J = 8.0, 1.5 Hz, 1H), 8.62 (dd, J = 4.9, 1.5 Hz, 1H), 8.53 (s, 1H), 7.44 (dd, J = 8.0, 4.9 Hz, 1H), 4.35-4.22 (m, 1H), 3.56 (d, J = 12.9 Hz, 2H), 3.23-3.07 (s, 2H), 2.87 (s, 3H), 2.42 (d, J = 14.0 Hz, 2H), 2.10-2.05 (m, 2H). |

TABLE 7-continued

| Example | Structure/Name | 3-X | Hydrogenation Method | Deprotection Method | Purification Method(s) | LCMS $R_T$, M + H+, Method | 1H NMR (ppm) |
|---|---|---|---|---|---|---|---|
| 170 | 5-(4-Pyrrolidin-1-yl-piperidin-1-yl)-9H-dipyrido[2,3-b;4',3'-d]pyrrole-6-carbonitrile | Br | A-2 | NA | 1 | 4.92, 347, C | (400 MHz, CD$_3$OD): 8.77 (s, 1H), 8.72 (dd, J = 8.0, 1.6 Hz, 1H), 8.66 (dd, J = 4.9, 1.6 Hz, 1H), 7.46 (dd. J = 8.0, 4.9 Hz, 1H), 3.67 (dd, J = 8.2, 2.4 Hz, 4H), 3.58-3.36 (s, 5H), 2.45-2.36 (m, 2H), 2.20-2.05 (s, 6H). |
| 171 | 5-(4-Morpholin-4-yl-piperidin-1-yl)-9H-dipyrido[2,3-b;4',3'-d]pyrrole-6-carbonitrile | Br | A-2 | NA | 1 | 4.39, 363, C | (400 MHz, CD$_3$OD): 8.77 (s, 1H), 8.71 (dd, J = 8.0, 1.6 Hz, 1H), 8.66 (dd, J = 4.9, 1.6 Hz, 1H), 7.47 (dd, J = 8.0, 4.9 Hz, 1H), 3.94 (s, 4H), 3.55-3.02 (m, 5H, obscured by solvent peak), 3.73-3.60 (m, 4H), 2.45-2.31 (m, 2H), 2.20-2.00 (m, 2H). |
| 172 | 5-(Piperidin-4-ylamino)-9H-dipyrido[2,3-b;4',3'-d]pyrrole-6-carbonitrile | Br | A-2 | B-2 | B-2[2] | 4.17, 293, C | (400 MHz, CD$_3$OD/CDCl$_3$): 8.69 (dd, J = 8.0, 1.5 Hz, 1H), 8.62 (dd, J = 4.9, 1.5 Hz, 1H), 8.54 (s, 1H), 7.44 (dd, J = 8.0, 4.9 Hz, 1H), 4.35-4.33 (m, 1H). 3.59-3.49 (m, 2H), 3.15 (td, J = 12.9, 3.0 Hz, 2H), 2.50-2.39 (m, 2H), 2.14-2.02 (m, 2H). |

TABLE 7-continued

| Example | Structure/Name | 3-X | Hydrogenation Method | Deprotection Method | Purification Method(s) | LCMS R$_T$, M + H$^+$, Method | $^1$H NMR (ppm) |
|---|---|---|---|---|---|---|---|
| 173 | 5-Piperazin-1-yl-9H-dipyrido[2,3-b;4',3'-d]pyrrole-6-carbonitrile | Br | A-2 | B-2 | 2 | 3.08, 279, C | (400 MHz, CD$_3$OD): 8.98-8.91 (m, 1H), 8.91 (s, 1H), 8.73 (d, J = 5.1 Hz, 1H), 7.63-7.57 (m, 1H), 3.85-3.80 (m, 4H), 3.64-3.59 (m, 4H). |

Example 174

5-[1-(2,2-Difluoroethyl)-piperidin-4-yloxy]-9H-dipyrido[2,3-b;4',3'-d]pyrrole-6-carbonitrile

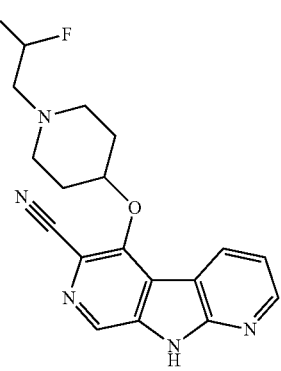

Step 1: 4-(9-Benzenesulfonyl-3-bromo-6-cyano-9H-dipyrido[2,3-b;4',3'-d]pyrrol-5-yloxy)piperidine-1-carboxylic acid tert-butyl ester

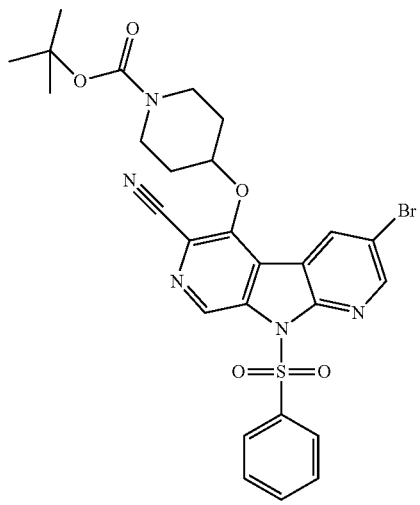 [SMILES: CC(C)(C)OC(=O)N1CCC(Oc2c(C#N)ncc3c2c2cc(Br)cnc2n3S(=O)(=O)c2ccccc2)CC1]

A solution of 9-benzenesulfonyl-3-bromo-5-hydroxy-9H-dipyrido[2,3-b;4',3'-d]pyrrole-6-carbonitrile (15.8 g, 36.8 mmol), 4-hydroxypiperidine-1-carboxylic acid tert-butyl ester (18.5 g, 92.0 mmol) and triphenylphosphine (24.1 g, 92.0 mmol) in anhydrous THF (100 mL) was treated dropwise with diethyl azodicarboxylate (18.1 mL, 92.0 mmol) and the mixture heated to 50° C. for 40 minutes. After this time, the reaction mixture was concentrated in-vacuo and the resultant residue purified by flash chromatography (silica, 2×330 g column, ISCO, 0-10% ethyl acetate in dichloromethane). The resultant product was further purified by trituration with diethyl ether to afford the title compound as an off-white solid (17.6 g, 78%). $^1$H NMR (300 MHz, CDCl$_3$): 9.57 (s, 1H), 8.76 (d, J=2.3 Hz, 1H), 8.57 (d, J=2.3 Hz, 1H), 8.23-8.22 (m, 2H), 7.64-7.63 (m, 1H), 7.53-7.51 (m, 2H), 5.20-5.20 (m, 1H), 4.07 (d, J=13.6 Hz, 2H), 3.06 (t, J=12.1 Hz, 2H), 2.20-2.19 (m, 2H), 1.85-1.85 (m, 2H), 1.47 (s, 9H).

Step 2: 9-Benzenesulfonyl-3-bromo-5-(piperidin-4-yloxy)-9H-dipyrido[2,3-b;4',3'-d]pyrrole-6-carbonitrile

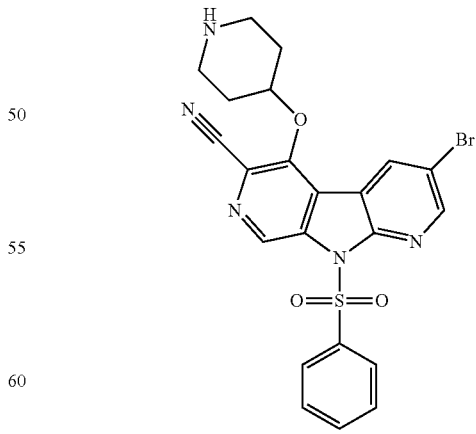

To a solution of 4-(9-benzenesulfonyl-3-bromo-6-cyano-9H-dipyrido[2,3-b;4',3'-d]pyrrol-5-yloxy)piperidine-1-carboxylic acid tert-butyl ester (12.6 g, 20.6 mmol) in dichloromethane (36 mL) was added TFA (36 mL). After 1 hour at ambient temperature the reaction mixture was concentrated in-vacuo and the residue partitioned between saturated aqueous sodium carbonate solution (800 mL) and dichloromethane (2 L). The organic phase was separated, dried (Na₂SO₄), filtered and evaporated in-vacuo to afford the title compound as an off-white solid (8.8 g, 84%) which was used without further purification. $^1$H NMR (300 MHz, DMSO-$d_6$): 9.46 (s, 1H), 8.90 (d, J=2.3 Hz, 1H), 8.64 (d, J=2.3 Hz, 1H), 8.23-8.22 (m, 2H), 7.78 (t, J=7.4 Hz, 1H), 7.64 (t, J=7.8 Hz, 2H), 4.85-4.85 (m, 1H), 3.17 (s, 1H), 3.00 (dt, J=13.0, 4.1 Hz, 2H), 2.50-2.49 (m, 2H obscured by solvent peak), 2.15-1.97 (m, 2H), 1.75-1.75 (m, 2H).

Step 3: 9-Benzenesulfonyl-3-bromo-5-[1-(2,2-difluoroethyl)-piperidin-4-yloxy]-9H-dipyrido[2,3-b;4',3'-d]pyrrole-6-carbonitrile

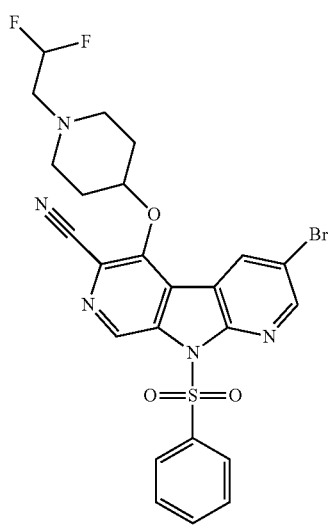 [SMILES: N#Cc1ncc2c(c1OC1CCN(CC(F)F)CC1)c1cc(Br)cnc1n2S(=O)(=O)c1ccccc1]

To a suspension of 9-benzenesulfonyl-3-bromo-5-(piperidin-4-yloxy)-9H-dipyrido[2,3-b;4',3'-d]pyrrole-6-carbonitrile (450 mg, 0.88 mmol) in THF (8 mL) was added 2,2-difluoroethyl trifluoromethanesulfonate (282 mg, 1.32 mmol) in THF (1 mL), followed by DIPEA (250 μL). The resultant reaction mixture was heated at 65° C. for 7 hours, then concentrated in-vacuo. The residue was triturated with ethyl acetate to afford the title compound as a pale yellow solid (485 mg, 96%). $^1$H NMR (300 MHz, DMSO-$d_6$): 9.46 (s, 1H), 8.90 (d, J=2.2 Hz, 1H), 8.70 (d, J=2.3 Hz, 1H), 8.24-8.23 (m, 2H), 7.78 (t, J=7.5 Hz, 1H), 7.64 (t, J=7.8 Hz, 2H), 6.13 (tt, J=55.8, 4.3 Hz, 1H), 4.85-4.85 (m, 1H), 3.17-3.12 (m, 2H), 2.75 (td, J=15.7, 4.3 Hz, 2H), 2.37 (t, J=10.9 Hz, 2H), 2.08-2.07 (m, 2H), 1.96-1.95 (m, 2H).

Step 4: 9-Benzenesulfonoyl-5-[1-(2,2-difluoroethyl)-piperidin-4-yloxy]-9H-dipyrido[2,3-b;4',3'-d]pyrrole-6-carbonitrile

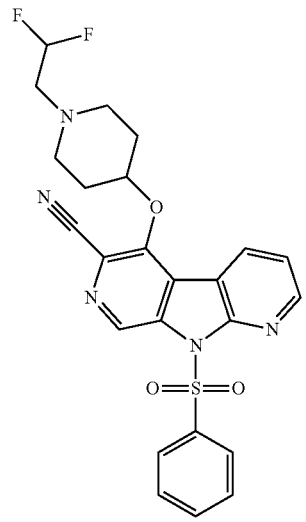 [SMILES: N#Cc1ncc2c(c1OC1CCN(CC(F)F)CC1)c1cccnc1n2S(=O)(=O)c1ccccc1]

A suspension of 9-benzenesulfonyl-3-bromo-5-[1-(2,2-difluoroethyl)-piperidin-4-yloxy]-9H-dipyrido[2,3-b;4',3'-d]pyrrole-6-carbonitrile (240 mg, 0.42 mmol) and palladium on carbon (10 wt %, 50 mg) in industrial methylated spirits (5 mL) and dichloromethane (5 mL) was stirred at ambient temperature under an atmosphere of hydrogen for 5 days. The reaction vessel was purged with nitrogen then the reaction mixture was filtered through a PTFE filter cup. The filtrate was evaporated in-vacuo and the resultant residue purified by flash chromatography (silica, 10 g column, ISCO, 0-2% methanol in dichloromethane) to afford the title compound as an off-white solid (66 mg, 32%). LCMS (Method B): $R_T$=3.74 min, M+H$^+$=518.

Step 5: 5-[1-(2,2-Difluoroethyl)-piperidin-4-yloxy]-9H-dipyrido[2,3-b;4',3'-d]pyrrole-6-carbonitrile To a solution of 9-benzenesulfonyl-5-[1-(2,2-difluoroethyl)-piperidin-4-yloxy]-9H-dipyrido[2,3-b;4',3'-d]pyrrole-6-carbonitrile (68 mg, 0.14 mmol) in methanol (5 mL) was added potassium carbonate (193 mg, 1.4 mmol) and the resultant suspension was heated to 40° C. for 4 hours. After this time, the reaction mixture was loaded directly onto a 5 g SPE NH₂ cartridge, which was eluted with 1:1 methanol:dichloromethane. The appropriate fractions were concentrated in-vacuo and the resultant residue purified by flash chromatography (silica, 10 g column, Si-SPE, 0-4% 2N NH₃ in methanol in dichloromethane) to afford the title compound as a pale yellow solid (36 mg, 73%). LCMS (Method C): $R_T$=6.07 min, M+H⁺=358. ¹H NMR (300 MHz, CD₃OD): 8.74 (s, 1H), 8.64-8.64 (m, 2H), 7.58 (s, 1H), 7.43 (dd, J=7.9, 4.9 Hz, 1H), 5.94 (tt, J=55.8, 4.2 Hz, 1H), 4.93-4.92 (m, 1H), 3.11-2.99 (m, 2H), 2.82 (td, J=15.1, 4.3 Hz, 2H), 2.51-2.51 (m, 2H), 2.15-2.14 (m, 4H).

Example 175

5-[1-(2-Methanesulfonylethyl)-piperidin-4-yloxy]-9H-dipyrido[2,3-b;4',3'-d]pyrrole-6-carbonitrile

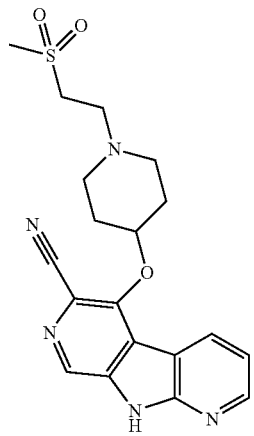 [SMILES: CS(=O)(=O)CCN1CCC(Oc2c(C#N)ncc3[nH]c4ncccc4c23)CC1]

Step 1: 9-Benzenesulfonyl-3-bromo-5-[1-(2-methanesulfonylethyl)-piperidin-4-yloxy]-9H-dipyrido[2,3-b;4',3'-d]pyrrole-6-carbonitrile

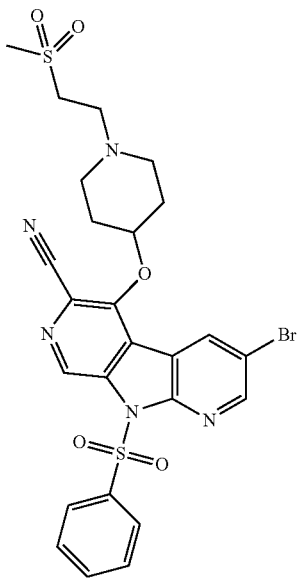 [SMILES: CS(=O)(=O)CCN1CCC(Oc2c(C#N)ncc3c2c2cc(Br)cnc2n3S(=O)(=O)c2ccccc2)CC1]

To a suspension of 9-benzenesulfonyl-3-bromo-5-(piperidin-4-yloxy)-9H-dipyrido[2,3-b;4',3'-d]pyrrole-6-carbonitrile (400 mg, 0.78 mmol) in methanol (10 mL) was added methyl vinyl sulfone (207 mg, 1.95 mmol). The resultant reaction stirred at ambient temperature for 24 hours, then concentrated in-vacuo. The residue was triturated with ethyl acetate to afford the title compound as a pale yellow solid (446 mg, 92%). ¹H NMR (300 MHz, DMSO-d₆): 9.46 (d, J=0.4 Hz, 1H), 8.90 (d, J=2.2 Hz, 1H), 8.67 (d, J=2.3 Hz, 1H), 8.24-8.24 (m, 2H), 7.78 (t, J=7.4 Hz, 1H), 7.64 (t, J=7.8 Hz, 2H), 4.86-4.86 (m, 1H), 3.27 (t, J=7.1 Hz, 2H obscured solvent peak), 3.03 (s, 3H), 2.92-2.80 (m, 2H), 2.73 (t, J=6.8 Hz, 2H), 2.21 (t, J=10.9 Hz, 2H), 2.22-1.98 (m, 2H), 1.92-1.92 (m, 2H).

Step 2: 9-Benzenesulfonyl-5-[1-(2-methanesulfonylethyl)-piperidin-4-yloxy]-9H-dipyrido[2,3-b;4',3'-d]pyrrole-6-carbonitrile

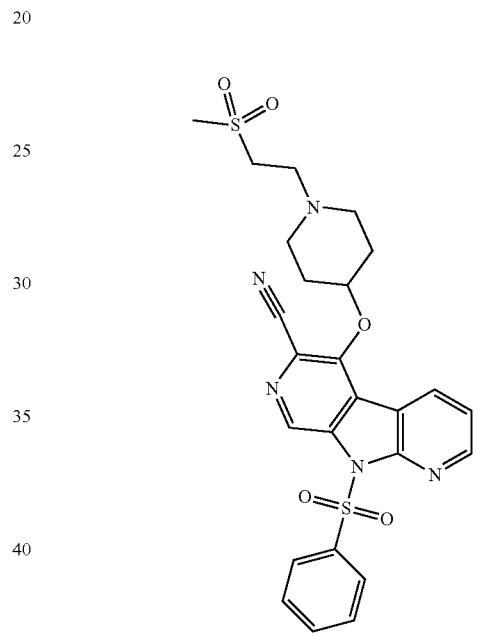

A suspension of 9-benzenesulfonyl-3-bromo-5-[1-(2-methanesulfonyl-ethyl)-piperidin-4-yloxy]-9H-dipyrido[2,3-b;4',3'-d]pyrrole-6-carbonitrile (245 mg, 0.39 mmol) and palladium on carbon (10 wt %, 50 mg) in industrial methylated spirits (5 mL), dichloromethane (5 mL), and triethylamine (3 mL) was stirred at ambient temperature under an atmosphere of hydrogen for 24 hours. The reaction vessel was purged with nitrogen then the reaction mixture was filtered through a PTFE filter cup. The filtrate was evaporated in-vacuo and the resultant residue purified by flash chromatography (silica, 10 g column, ISCO, 0-50% ethyl acetate in dichloromethane) to afford the title compound as an off-white solid (140 mg, 65%). LCMS (Method C): $R_T$=4.97 min, M+H⁺=400. ¹H NMR (300 MHz, DMSO-d₆): 9.49 (s, 1H), 8.76 (dd, J=4.8, 1.6 Hz, 1H), 8.63 (dd, J=7.9, 1.7 Hz, 1H), 8.25-8.24 (m, 2H), 7.76 (t, J=7.4 Hz, 1H), 7.64-7.63 (m, 3H), 4.76-4.75 (m, 1H), 3.26 (t, J=7.4 Hz, 2H obscured by solvent peak), 3.02 (s, 3H), 2.88 (d, J=11.3 Hz, 2H), 2.72 (t, J=6.8 Hz, 2H), 2.14-2.14 (m, 4H), 1.91-1.91 (m, 2H).

Step 3: 5-[1-(2-Methanesulfonylethyl)-piperidin-4-yloxy]-9H-dipyrido[2,3-b;4',3'-d]pyrrole-6-carbonitrile

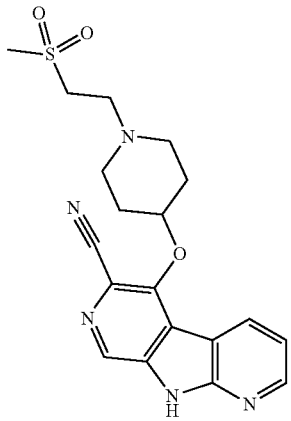 [SMILES: CS(=O)(=O)CCN1CCC(Oc2c(C#N)ncc3[nH]c4ncccc4c23)CC1]

To a solution of 9-benzenesulfonyl-5-[1-(2-methanesulfonylethyl)-piperidin-4-yloxy]-9H-dipyrido[2,3-b;4',3'-d]pyrrole-6-carbonitrile (6138 mg, 0.26 mmol) in methanol (10 mL) was added potassium carbonate (353 mg, 2.6 mmol) and the resultant suspension was heated to 40° C. for 3 hours. After this time, the reaction mixture was loaded directly onto a 5 g SPE NH$_2$ cartridge, which was eluted with 1:1 methanol: dichloromethane. The appropriate fractions were concentrated in-vacuo and the resultant residue purified by flash chromatography (silica, 25 g column, Si-SPE, 0-5% 2N NH$_3$ in methanol in dichloromethane) to afford the title compound as a pale yellow solid (49 mg, 47%). $^1$H NMR (400 MHz, DMSO-d$_6$): 12.96 (s, 1H), 8.79 (s, 1H), 8.71 (dd, J=4.8, 1.6 Hz, 1H), 8.59 (dd, J=7.9, 1.6 Hz, 1H), 7.47 (dd, J=7.9, 4.8 Hz, 1H), 4.87-4.57 (m, 1H), 3.28-3.26 (m, 2H obscured by solvent peak), 3.04 (s, 3H), 3.02-2.77 (m, 2H), 2.73 (t, J=6.8 Hz, 2H), 2.20 (t, J=10.8 Hz, 2H), 2.21-1.97 (m, 2H), 1.96-1.89 (m, 2H).

Example 176

5-[1-(2-Hydroxyethyl)-piperidin-4-yloxy]-9H-dipyrido[2,3-b;4',3'-d]pyrrole-6-carbonitrile

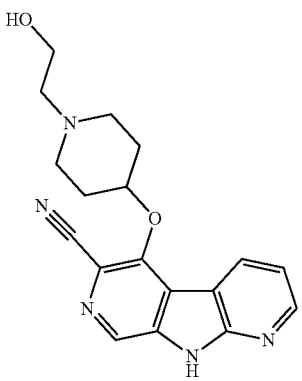 [SMILES: N#Cc1ncc2[nH]c3ncccc3c2c1OC1CCN(CCO)CC1]

Step 1: 9-Benzenesulfonyl-3-bromo-5-{1-[2-(tetrahydropyran-2-yloxy)-ethyl]-piperidin-4-yloxy}-9H-dipyrido[2,3-b;4',3'-d]pyrrole-6-carbonitrile

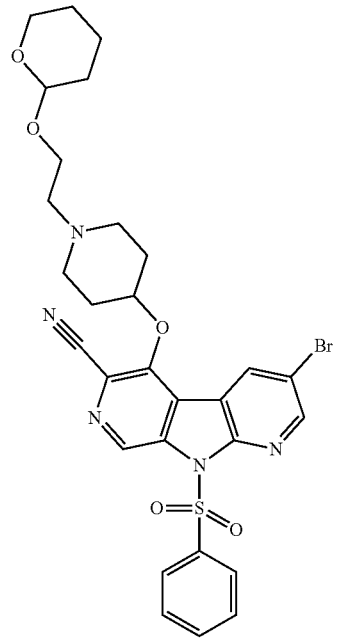 [SMILES: N#Cc1ncc2c(c1OC1CCN(CCOC3CCCCO3)CC1)c1cc(Br)cnc1n2S(=O)(=O)c1ccccc1]

To a suspension of 9-benzenesulfonyl-3-bromo-5-(piperidin-4-yloxy)-9H-dipyrido[2,3-b;4',3'-d]pyrrole-6-carbonitrile (789 mg, 1.54 mmol) in acetonitrile (50 mL) was added sodium iodide (46 mg, 0.31 mmol) and the resultant suspension sonicated for 5 minutes. 2-(2-Bromoethoxy)tetrahydropyran (483 mg, 2.31 mmol) was added and the reaction mixture was heated to 50° C. for 48 hours. The resultant residue was concentrated in-vacuo then dissolved in dichloromethane, diluted with 1N aqueous sodium carbonate (50 mL) and extracted with dichloromethane (3×50 mL). The combined organic layer was dried (Na$_2$SO$_4$), filtered, evaporated in-vacuo and the resultant residue purified by flash chromatography (silica, 40 g column, ISCO, 0-30% ethyl acetate in dichloromethane) to afford the title compound as a pale yellow solid (330 mg, 33%). $^1$H NMR (300 MHz, CDCl$_3$): 9.54 (s, 1H), 8.76 (d, J=2.3 Hz, 1H), 8.65 (d, J=2.3 Hz, 1H), 8.23-8.22 (m, 2H), 7.64-7.64 (m, 1H), 7.53-7.50 (m, 2H), 5.13-5.11 (m, 1H), 4.59 (t, J=3.5 Hz, 1H), 3.87-3.86 (m, 2H), 3.54-3.52 (m, 2H), 2.99 (d, J=11.6 Hz, 2H), 2.67 (t, J=6.0 Hz, 2H), 2.35 (t, J=11.3 Hz, 2H), 2.22 (d, J=12.3 Hz, 2H), 2.03-1.99 (m, 2H), 1.87-1.47 (m, 6H).

Step 2: 9-Benzenesulfonyl-3-bromo-5-[1-(2-hydroxyethyl)-piperidin-4-yloxy]-9H-dipyrido[2,3-b;4',3'-d]pyrrole-6-carbonitrile

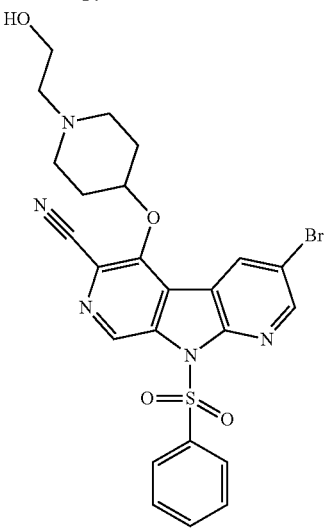

To a solution of 9-benzenesulfonyl-3-bromo-5-{1-[2-(tetrahydropyran-2-yloxy)-ethyl]-piperidin-4-yloxy}-9H-dipyrido[2,3-b;4',3'-d]pyrrole-6-carbonitrile (330 mg, 0.52 mmol) in dichloromethane (5 mL) and methanol (10 mL) was added tosic acid monohydrate (100 mg, 0.52 mmol) and the reaction mixture heated to 40° C. for 4 hours then concentrated in-vacuo. The resultant residue was was taken up in dichloromethane, diluted with saturated aqueous sodium bicarbonate (20 mL) and extracted with dichloromethane (3×20 mL). The combined organic layer was dried (Na$_2$SO$_4$), filtered, evaporated in-vacuo to afford the crude title compound as a pale yellow solid (312 mg) which was used without purification. $^1$H NMR (300 MHz, CDCl$_3$): 9.56 (s, 1H), 8.77 (d, J=2.3 Hz, 1H), 8.63 (d, J=2.3 Hz, 1H), 8.23-8.22 (m, 2H), 7.64-7.63 (m, 1H), 7.52-7.51 (m, 2H), 5.16-5.14 (m, 1H), 3.65 (t, J=5.3 Hz, 2H), 2.96 (m, J=11.5 Hz, 2H), 2.61 (t, J=5.3 Hz, 2H), 2.39 (t, J=11.3 Hz, 2H), 2.25 (m, J=12.5 Hz, 2H), 2.03-2.01 (m, 2H).

Step 3: 9-Benzenesulfonyl-5-[1-(2-hydroxyethyl)-piperidin-4-yloxy]-9H-dipyrido[2,3-b;4',3'-d]pyrrole-6-carbonitrile

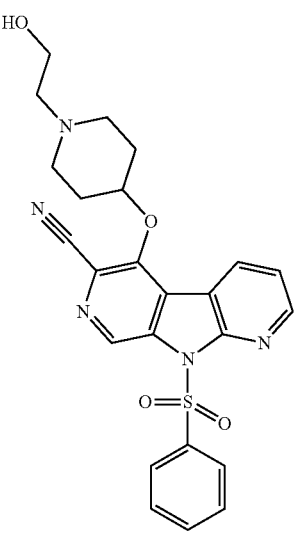 [SMILES: N#Cc1ncc2c(c1OC1CCN(CCO)CC1)c1cccnc1n2S(=O)(=O)c1ccccc1]

A suspension of 9-benzenesulfonyl-3-bromo-5-[1-(2-hydroxyethyl)-piperidin-4-yloxy]-9H-dipyrido[2,3-b;4',3'-d]pyrrole-6-carbonitrile (283 mg, 0.51 mmol) and palladium on carbon (10 wt %, 50 mg) in industrial methylated spirits (3 mL) and dichloromethane (3 mL) was stirred at ambient temperature under an atmosphere of hydrogen for 48 hours. The reaction vessel was purged with nitrogen then the reaction mixture was filtered through a PTFE filter cup. The filtrate was evaporated in-vacuo and the resultant residue purified by flash chromatography (silica, 24 g column, ISCO, 0-30% methanol in dichloromethane) to afford the title compound as an off-white solid (125 mg, 51%). $^1$H NMR (300 MHz, CDCl$_3$): 9.59 (s, 1H), 8.76 (dd, J=4.9, 1.7 Hz, 1H), 8.54 (dd, J=7.9, 1.7 Hz, 1H), 8.27-8.26 (m, 2H), 7.62-7.61 (m, 1H), 7.56-7.44 (m, 3H), 5.04-5.03 (m, 1H), 3.70 (t, J=5.2 Hz, 2H), 3.09-3.09 (m, 2H), 2.69 (t, J=5.2 Hz, 2H), 2.51 (t, J=11.0 Hz, 2H), 2.32-2.25 (m, 2H), 2.12-2.10 (m, 2H).

Step 4: 5-[1-(2-Hydroxyethyl)-piperidin-4-yloxy]-9H-dipyrido[2,3-b;4',3'-d]pyrrole-6-carbonitrile

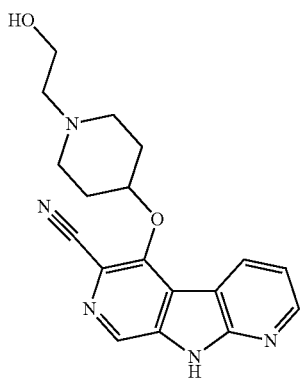 [SMILES: N#Cc1ncc2[nH]c3ncccc3c2c1OC1CCN(CCO)CC1]

A solution of 9-benzenesulfonyl-5-[1-(2-hydroxyethyl)-piperidin-4-yloxy]-9H-dipyrido[2,3-b;4',3'-d]pyrrole-6-carbonitrile (125 mg, 0.26 mmol) and triethylamine (1 mL) in methanol (10 mL) was heated to 60° C. for 3 hours. The mixture was concentrated in-vacuo and the resultant residue purified by flash chromatography (silica, 10 g column, ISCO, 0-8% methanol in dichloromethane). The resultant material was triturated with acetonitrile and methanol to afford the title compound as an off-white solid (40 mg, 45%). LCMS (Method C): R$_T$=4.83 min, M+H$^+$=338.2. $^1$H NMR (400 MHz, DMSO-d$_6$): 8.79 (s, 1H), 8.70 (dd, J=4.8, 1.6 Hz, 1H), 8.59 (dd, J=7.9, 1.7 Hz, 1H), 7.47 (dd, J=7.9, 4.8 Hz, 1H), 4.71-4.69 (m, 1H), 4.38 (s, 1H), 3.49 (s, 2H), 2.93-2.81 (m, 2H), 2.40 (t, J=6.3 Hz, 2H), 2.15 (t, J=11.1 Hz, 2H), 2.06 (d, J=12.0 Hz, 2H), 1.93-1.92 (m, 2H).

Example 177

5-(1-Ethyl-piperidin-4-yloxy)-3-methyl-9H-dipyrido[2,3-b;4',3'-d]pyrrole-6-carbonitrile

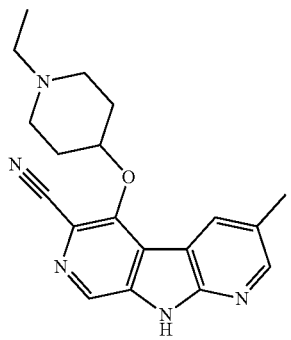 [SMILES: CCN1CCC(Oc2c(C#N)ncc3[nH]c4ncc(C)cc4c23)CC1]

A mixture of 9-benzenesulfonyl-3-bromo-5-(1-ethyl-piperidin-4-yloxy)-9H-dipyrido[2,3-b;4',3'-d]pyrrole-6-carbonitrile (215 mg, 0.40 mmol), trimethylboroxine (167 µL, 1.2 mmol), cesium carbonate (156 mg, 0.48 mmol) and tetrakis(triphenyl-phosphine)palladium(0) (96 mg, 0.04 mmol) in dioxane (2.0 mL) was degassed with argon and heated under microwave irradiation at 100° C. for 90 minutes. The reaction mixture was allowed to cool to ambient temperature, diluted with saturated aqueous ammonium chloride (10 mL) and extracted with dichloromethane (3×10 mL). The combined organic phase was washed with brine (2×10 mL) and concentrated in-vacuo. The resultant residue was diluted with THF (10 mL), 1N aqueous potassium hydroxide (1 mL) added and the reaction mixture was then heated at 50° C. for 1 hour. The solvent was evaporated in-vacuo and the resultant residue was purified by chromatography (silica, 2 g column, Si-SPE, 0-10% 2-propanol in dichloromethane). The appropriate fractions were combined and evaporated in-vacuo and the resultant residue triturated with pentane (2×2 mL) to afford the title compound as an off-white solid (69 mg, 52%). LCMS (Method A): $R_T$=2.46 min, M+H$^+$=336.2. $^1$H NMR (400 MHz, CD$_3$OD): 8.71 (s, 1H), 8.52 (dd, J=2.1, 0.7 Hz, 1H), 8.47 (dd, J=2.1, 0.9 Hz, 1H), 4.91-4.88 (m, 1H), 3.02-2.99 (m, 2H), 2.57 (s, 3H), 2.50 (q, J=7.2 Hz, 2H), 2.26-2.19 (m, 4H), 2.12-2.11 (m, 2H), 1.13 (t, J=7.2 Hz, 3H).

Example 178

5-(1-Ethyl-piperidin-4-yloxy)-9H-dipyrido[2,3-b;4',3'-d]pyrrole

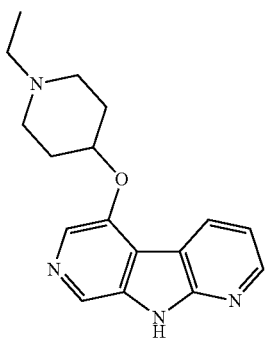 [SMILES: CCN1CCC(Oc2cncc3[nH]c4ncccc4c23)CC1]

Step 1: 3-Bromo-9H-dipyrido[2,3-b;4',3'-d]pyrrol-5-ol

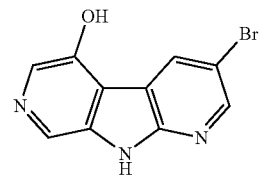

9-Benzenesulfonyl-3-bromo-9H-dipyrido[2,3-b;4',3'-d]pyrrol-5-ol (4.0 g, 9.32 mmol) was dissolved in concentrated hydrochloric acid (100 mL) and heated in an autoclave at 125° C. for 40 hours. The mixture was allowed to cool to ambient temperature then evaporated in-vacuo. The resultant residue was loaded onto a 50 g SCX-2 cartridge which was washed with methanol, then 2N ammonia in methanol. Appropriate fractions were combined and concentrated in-vacuo to afford the title compound as a light brown solid (2.44 g, 99%). LCMS (Method B): $R_T$=2.70 min, M+H$^+$=264/266. $^1$H NMR (400 MHz, DMSO-d$_6$): 12.25 (s, 1H), 8.61 (d, J=2.4 Hz, 1H), 8.58 (d, J=2.4 Hz, 1H), 8.42 (s, 1H), 8.04 (s, 1H).

Step 2: 3-Bromo-5-hydroxy-dipyrido[2,3-b;4',3'-d]pyrrole-9-carboxylic acid benzyl ester

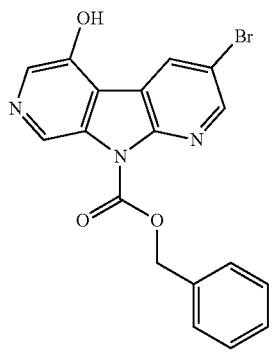 [SMILES: O=C(OCc1ccccc1)n1c2cncc(O)c2c2cc(Br)cnc21]

Sodium hydride (167 mg, 4.17 mmol) was added to a cooled (0° C.) mixture of 3-bromo-9H-dipyrido[2,3-b;4',3'-d]pyrrol-5-ol (1.0 g, 3.79 mmol) in DMF (15 mL). On complete addition the mixture was stirred for 15 minutes then allowed to warm to ambient temperature and stirred for 15 minutes. A solution of benzyl chloroformate (610 mg, 3.6 mmol) in DMF (1 mL) was added and stirring continued for 18 hours. The solvent was evaporated and the resultant residue diluted with water and extracted with dichloromethane (5×50 mL) and ethyl acetate (3×30 mL). The combined organic layer was dried over (Na$_2$SO$_4$), filtered and evaporated to afford a residue. The resultant residue was purified by flash chromatography (silica, 12 g cartridge, ISCO, 0-7% methanol in dichloromethane). The appropriate fractions were collected and evaporated to afford the title compound as a light yellow solid (240 mg, 17%). LCMS (Method B): $R_T$=4.54 min, M+H$^+$=398/400. $^1$H NMR (400 MHz, DMSO-d$_6$): 8.99 (s, 1H), 8.79 (d, J=2.4 Hz, 1H), 8.63 (d, J=2.4 Hz, 1H), 8.23 (s, 1H), 7.63 (d, J=7.5 Hz, 2H), 7.48-7.36 (m, 3H), 5.61 (s, 2H).

Step 3: 3-Bromo-5-(1-tert-butoxycarbonyl-piperidin-4-yloxy)-dipyrido[2,3-b;4',3'-d]pyrrole-9-carboxylic acid benzyl ester

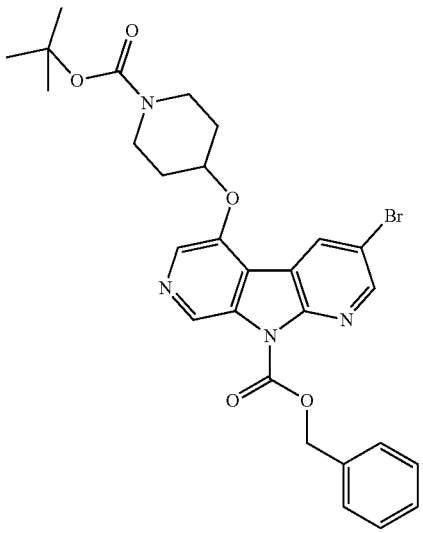 [SMILES: CC(C)(C)OC(=O)N1CCC(Oc2cncc3c2c2cc(Br)cnc2n3C(=O)OCc2ccccc2)CC1]

A solution of 3-bromo-5-hydroxy-dipyrido[2,3-b;4',3'-d]pyrrole-9-carboxylic acid benzyl ester (234 mg, 0.59 mmol), 4-hydroxypiperidine-1-carboxylic acid tert-butyl ester (295 mg, 1.47 mmol) and triphenylphosphine (390 mg, 1.47 mmol) in anhydrous THF (7 mL) was treated dropwise with diethyl azodicarboxylate (295 mg, 1.47 mmol). On complete addition the mixture was heated at 50° C. for 1 hour. The mixture was concentrated in-vacuo and the resultant residue was purified by flash chromatography (silica, 12 g cartridge, ISCO, 0-7% methanol in dichloromethane). The appropriate fractions were collected and evaporated to afford the title compound as an orange oil (0.34 g, 100%). LCMS (Method B): $R_T$=4.76 min, M+H$^+$=581/583. $^1$H NMR (400 MHz, CDCl$_3$): 9.27 (s, 1H), 8.80 (d, J=2.3 Hz, 1H), 8.61 (d, J=2.3 Hz, 1H), 8.32 (s, 1H), 7.60 (d, J=7.3 Hz, 2H), 7.43-7.36 (m, 3H), 5.64 (s, 2H), 4.89 (m, 1H), 3.40-3.39 (m, 2H), 3.02 (ddd, J=13.5, 9.8, 3.4 Hz, 2H), 2.21-1.80 (m, 4H), 1.46 (s, 9H).

Step 4: 3-Bromo-5-(piperidin-4-yloxy)-dipyrido[2,3-b;4',3'-d]pyrrole-9-carboxylic acid benzyl ester

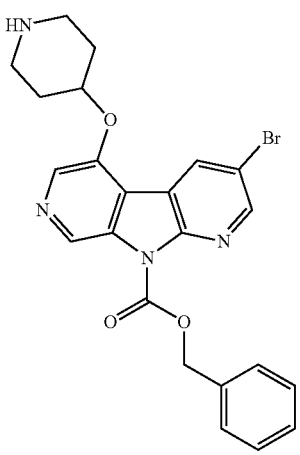 [SMILES: O=C(OCc1ccccc1)n1c2cncc(OC3CCNCC3)c2c2cc(Br)cnc21]

A solution of 3-bromo-5-(1-tert-butoxycarbonyl-piperidin-4-yloxy)dipyrido[2,3-b;4',3'-d]pyrrole-9-carboxylic acid benzyl ester (0.34 g, 0.59 mmol) in triflouroacetic acid (2 mL) and dichloromethane (4 mL) was allowed to stir at ambient temperature for 15 minutes. The solvent was evaporated and the resultant residue was treated with saturated sodium hydrogen carbonate solution (20 mL) and extracted with dichloromethane (3×30 mL). The combined organic phase was dried (Na$_2$SO$_4$), filtered and evaporated to afford a residue. The resultant residue was purified by flash chromatography (silica, 12 g cartridge, ISCO, 0-10% methanol in dichloromethane then 10% 2M NH$_3$ in methanol in dichloromethane). The appropriate fractions were combined and evaporated to afford the title compound as a yellow solid (118 mg, 42%). LCMS (Method B): $R_T$=3.13 min, M+H$^+$=481/483. $^1$H NMR (400 MHz, CDCl$_3$): 9.22 (s, 1H), 8.77 (d, J=2.3 Hz, 1H), 8.62 (d, J=2.4 Hz, 1H), 8.31 (s, 1H), 7.60-7.59 (m, 2H), 7.40-7.40 (m, 3H), 5.63 (s, 2H), 4.86-4.82 (m, 1H), 3.26-3.25 (m, 2H), 2.95-2.94 (m, 2H), 2.29-2.25 (m, 2H), 1.99-1.97 (m, 2H).

Step 5: 3-Bromo-5-(1-ethyl-piperidin-4-yloxy)-dipyrido[2,3-b;4',3'-d]pyrrole-9-carboxylic acid benzyl ester

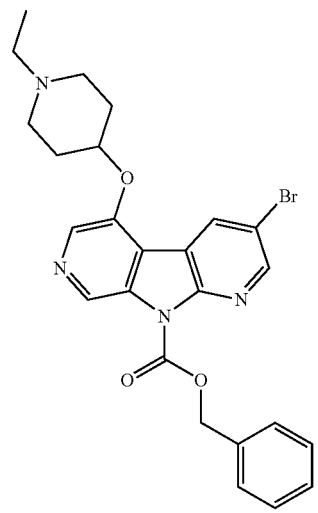 [SMILES: CCN1CCC(Oc2cncc3c2c2cc(Br)cnc2n3C(=O)OCc2ccccc2)CC1]

Acetaldehyde (3M solution in dichloromethane, 0.16 mL, 0.48 mmol) was added to a mixture of 3-bromo-5-(piperidin-4-yloxy)-dipyrido[2,3-b;4',3'-d]pyrrole-9-carboxylic acid benzyl ester (116 mg, 0.24 mmol), sodium triacetoxyborohydride (77 mg, 0.36 mmol) and acetic acid (17 OL, 0.29 mmol) in methanol (3 mL) and dichloromethane (1 mL) and the mixture stirred for 18 hours. The solvent was evaporated and the resultant residue diluted with saturated aqueous sodium hydrogen carbonate solution (20 mL) and extracted with dichloromethane (3×30 mL). The combined organic layer was dried (Na$_2$SO$_4$), filtered and evaporated to give a residue. The resultant residue was purified by flash chromatography (silica, 12 g cartridge, ISCO, 0-8% methanol in dichloromethane). The appropriate fractions were collected and evaporated to afford the title compound as a light yellow solid (75 mg, 61%). LCMS (Method B): $R_T$=3.43 min, M+H$^+$=509/511. $^1$H NMR (400 MHz, CDCl$_3$): 9.23 (s, 1H), 8.77 (d, J=2.3 Hz, 1H), 8.62 (s, 1H), 8.31 (s, 1H), 7.60-7.60 (m, 2H), 7.40-7.40 (m, 3H), 5.63 (s, 2H), 4.85 (s, 1H), 2.91 (br s, 2H), 2.62 (br s, 2H), 2.33 (br s, 2H), 2.14 (br s, 2H), 1.59 (br s, 2H), 1.23 (br s, 3H).

Step 6: 5-(1-Ethyl-piperidin-4-yloxy)-9H-dipyrido[2,3-b;4',3'-d]pyrrole

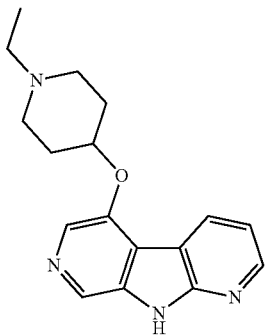 [SMILES: CCN1CCC(Oc2cncc3[nH]c4ncccc4c23)CC1]

A mixture of 3-bromo-5-(1-ethyl-piperidin-4-yloxy)-dipyrido[2,3-b;4',3'-d]pyrrole-9-carboxylic acid benzyl ester (75 mg, 0.15 mmol), palladium on carbon (10 wt %, 10 mg) and triethylamine (0.1 mL) in THF (5 mL) was allowed to stir under an atmosphere of hydrogen for 3 days. The catalyst was removed by filtration through Celite© and the filtrate evaporated to afford a residue. The resultant residue was loaded onto a 2 g SCX-2 cartridge which was washed with methanol, then 2N ammonia in methanol. The basic methanol fractions were evaporated and the resultant residue was purified by flash chromatography (silica, 4 g cartridge, ISCO, 0-7% methanol in dichloromethane). Appropriate fractions were collected and evaporated to afford the title compound as a white solid (33 mg, 75%). LCMS (Method A): $R_T$=1.51 min, M+H$^+$=297. $^1$H NMR (400 MHz, DMSO-$d_6$): 12.13 (s, 1H), 8.53-8.53 (m, 3H), 8.21 (s, 1H), 7.32 (dd, J=7.7, 4.8 Hz, 1H), 4.85-4.84 (m, 1H), 2.70-2.67 (m, 2H), 2.38-2.36 (m, 4H), 2.07-2.06 (m, 2H), 1.88-1.87 (m, 2H), 1.02 (t, J=7.2 Hz, 3H).

Example i

Chk1 and Chk2 Assays (Chk Primary Assays)

Full length human mutant recombinant protein, histidine tagged and expressed in insect cells is used as source of enzymatic activity (Invitrogen, chk1 from product PV3982 and chk2 from product PV3983).

The chk1 AlphaScreen assay is carried out for 30 minutes in the presence of 10 µM ATP using biotinylated Akt substrate-1 peptide (Cell Signalling Technology, product #1065) as a substrate. Phosphorylation of the substrate is detected and quantified using AlphaScreen technology. This consists of an anti-phospho-Akt substrate-1 antibody (Cell Signalling technology Product #9611) and two AlphaScreen beads (Perkin Elmer), one product coated with Protein A which binds the antibody Ig chain (Product 6760137), and one coated with Streptavidin which binds the biotin on the biotinylated Akt substrate peptide-1 (Product 6760002). Chk1 activity results in the production of phosphorylated Akt substrate peptide-1 an event which causes the two bead species to be brought into close proximity in the presence of antibody leading to the generation of luminescence which is detected on a Perkin Elmer reader (Fusion).

The ATP Radiometric ChK1 assay is carried out by incubation for 30 minutes in the presence of 10 µM ATP containing 0.3 µCi $^{33}$P-ATP per sample and using ChKTide (peptide sequence KKKVSRSGLYRSPSMPENLNRPR) as a substrate. Following acidification with 1% phosphoric acid and washing to remove unincorporated ATP, phosphorylation of the substrate is detected and quantified by measurement of radioactivity incorporated using a Perkin Elmer Topcount.

The chk2 AlphaScreen assay is carried out for 30 minutes in the presence of 30 µM ATP using biotinylated tyrosine hydroxylase (ser 40) peptide (Cell Signalling Technology, product #1132) as a substrate. Phosphorylation of the substrate is detected and quantified using AlphaScreen technology. This consists of an anti-phospho-tyrosine hydroxylase (ser 40) peptide antibody (Cell Signalling technology Product #2791) and two AlphaScreen beads (Perkin Elmer), one product coated with Protein A which binds the antibody Ig chain (Product 6760137), and one coated with Streptavidin which binds the biotin on the biotinylated tyrosine hydroxylase (ser 40) peptide (Product 6760002). Chk2 activity results in the production of phosphorylated tyrosine hydroxylase peptide an event which causes the two bead species to be brought into close proximity in the presence of antibody leading to the generation of luminescence which is detected on a Perkin Elmer reader (Fusion).

The ATP Radiometric ChK2 assay is carried out by incubation for 30 minutes in the presence of 30 µM ATP containing 0.3 µCi $^{33}$P-ATP per sample and using ChKTide (peptide sequence KKKVSRSGLYRSPSMPENLNRPR) as a substrate. Following acidification with 1% phosphoric acid and washing to remove unincorporated ATP, phosphorylation of the substrate is detected and quantified by measurement of radioactivity incorporated using a Perkin Elmer Topcount.

Test compounds are diluted in DMSO prior to addition to assay buffer, the final DMSO concentration in the assay is 1%.

The IC$_{50}$ is defined as the concentration at which a given test compound achieved 50% inhibition of the control. IC$_{50}$ values are calculated using the XLfit software package (version 2.0.5).

Tested title compounds of EXAMPLES 1-178 exhibited an IC$_{50}$ of less than 5 µM in the assays described in EXAMPLE i against chk1. For example, EXAMPLES 1-32, 35-50, 53, 55-57, 59-63, 65-73, 75-81, 83-112, and 114-178 exhibited an IC$_{50}$ of less than 5 µM in the assays described in EXAMPLE i against chk1.

Example ii

Cellular Assay (Checkpoint Abrogation)

Compounds are tested in a cellular assay using the human colorectal adenocarcinoma derived cell line HT-29 (ATCC HTB-38).

The cell line is maintained in DMEM/F12 (1:1) media (Invitrogen Gibco, #31331) supplemented with 10% FCS at 37° C. in a 5% CO$_2$ humidified incubator.

Cells are seeded in 96-well plates at 30,000 cells/well and after 24 h they are exposed to 20 nM SN-38 in 0.4% DMSO. One column of 8 wells on each plate was used to generate a maximum signal control. These cells are treated with 0.4% DMSO without SN-38. Cells are grown for a further 16 h, then the media containing DMSO plus or minus SN-38 is removed and replaced with media containing 300 nM nocodazole alone (to determine baseline) or in combination with ten concentrations of chk1 inhibitor (final DMSO concentration is 0.4%). Cells are grown for a further 24 h. The media is removed and replaced with 50 μl lysis buffer containing protease inhibitors and phosphatase inhibitors. This buffer contains detergent to bring about cellular disruption. Following complete cellular disruption, 25 μl lysate is transferred to a MesoScale 96 well 4-spot plate coated with an antibody to Histone H3 (MesoScale Discovery (MSD) Product K110EWA-3) which have been previously blocked with 3% bovine serum albumin in Tris buffered saline. Following the transfer of lysate to the MSD plate, Histone H3 in the lysate is captured on the coated antibody by incubation at room temperature for 2 h. Following the capture step the plate is washed and then incubated with an antibody to phosphorylated Histone H3 which is conjugated with a Sulfo-Tag. This tag gives a signal when in proximity to the electrode on the base of the MSD plate. Binding the tagged antibody to the captured protein allow detection on a MSD reader.

The $EC_{50}$ is defined as the concentration at which a given compound achieves 50% decrease of the measured levels of phospho-Histone H3 within the range of a normal sigmoidal dose response curve compared to the signal generated by 300 nM nocodazole alone. $EC_{50}$ values are calculated using the XLfit software package (version 2.0.5) or Graphpad Prism, (version 3.03) fitting a sigmoidal curve with a variable slope.

Tested title compounds of EXAMPLES 1-178 exhibited an $EC_{50}$ of less than 10 μM in the assay described in EXAMPLE ii. For example, EXAMPLES 1-4, 6-10, 12-15, 17, 19-31, 35-36, 39-50, 53, 55-57, 59-63, 65-67, 70-73, 75-77, 79, 81, 83-92, 94, 96, 100-112, and 114-178 exhibited an $EC_{50}$ of less than 10 μM in the assay described in EXAMPLE ii.

We claim:
1. A compound or a pharmaceutically acceptable salt thereof selected from the group consisting of:

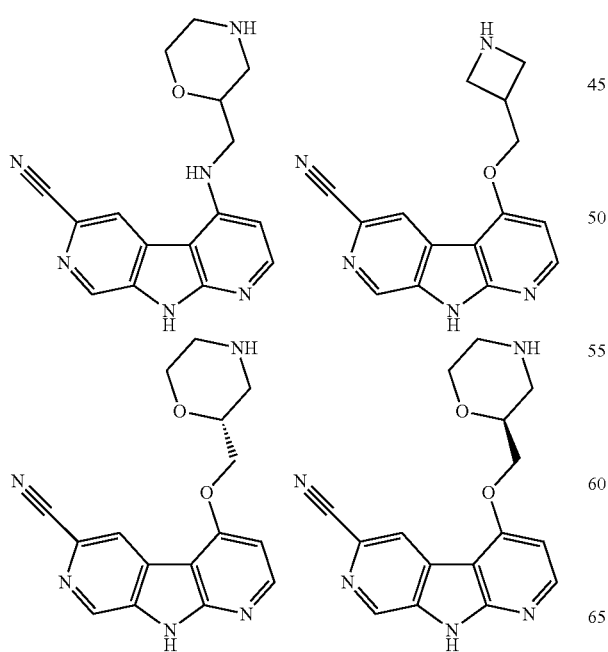

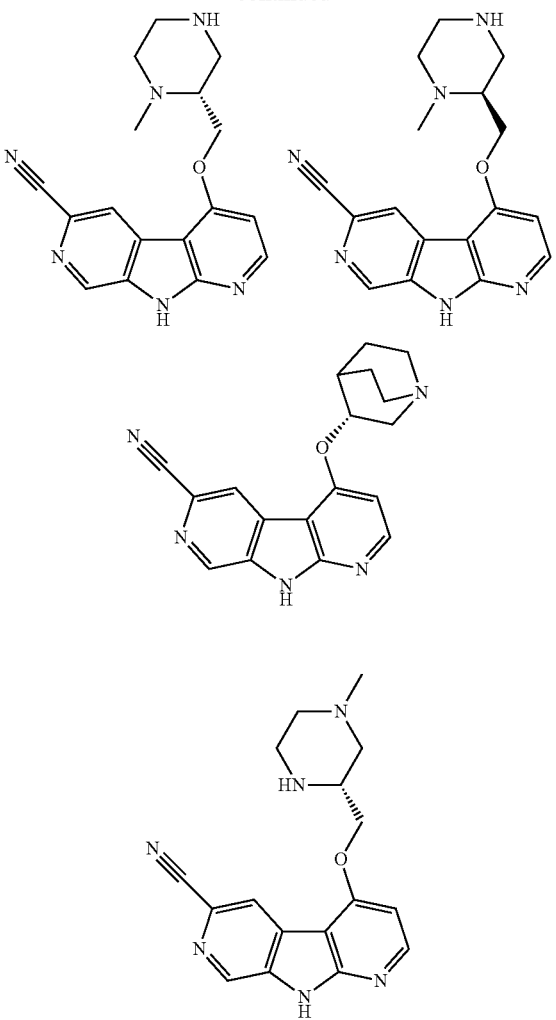

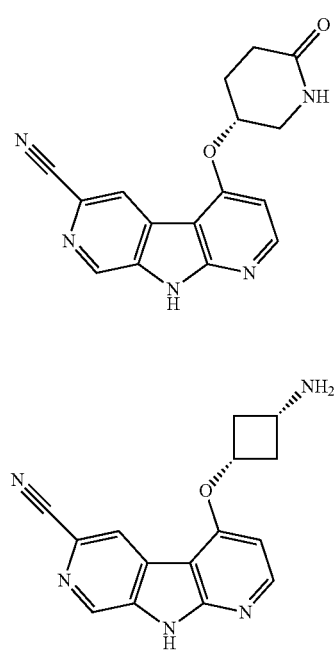

301
-continued
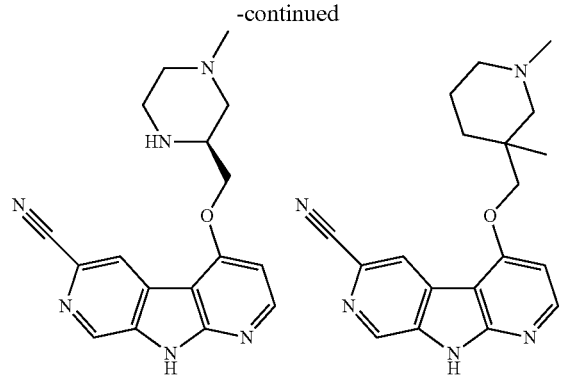
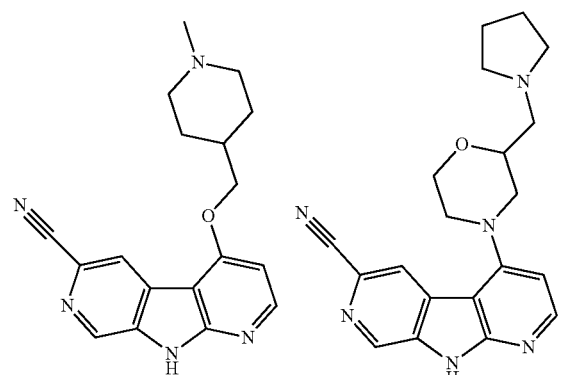
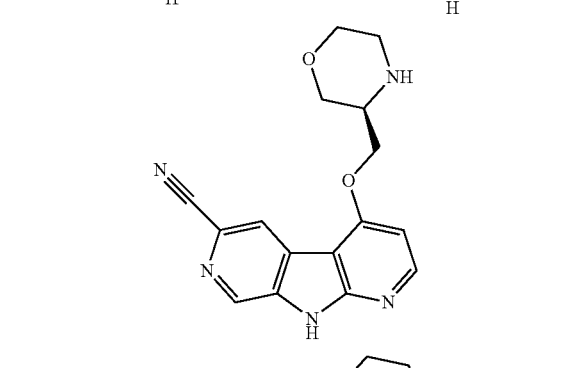
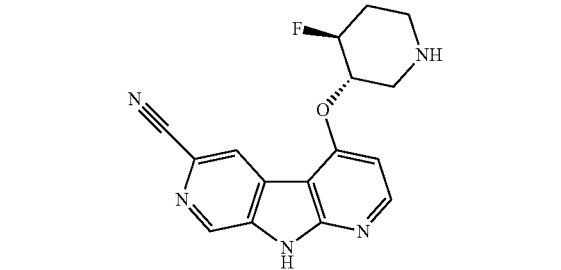
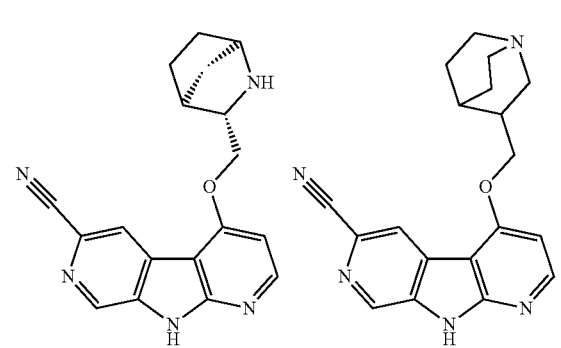
302
-continued
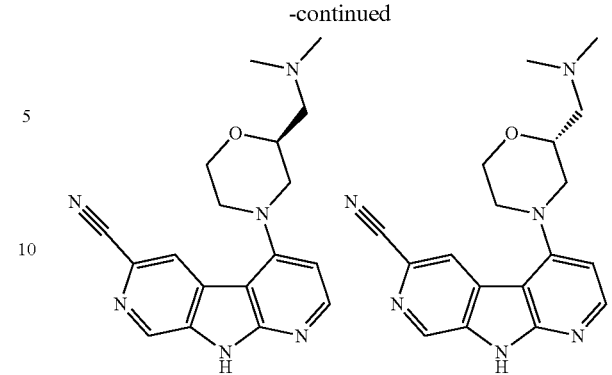
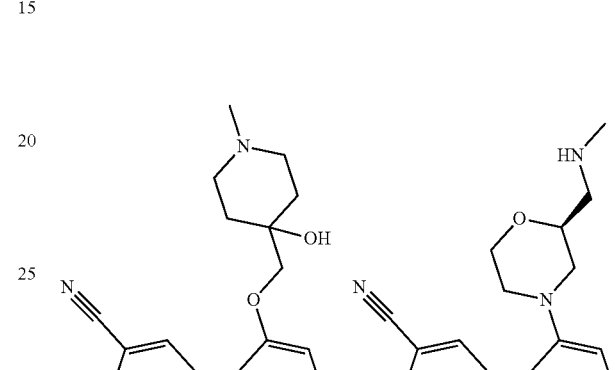
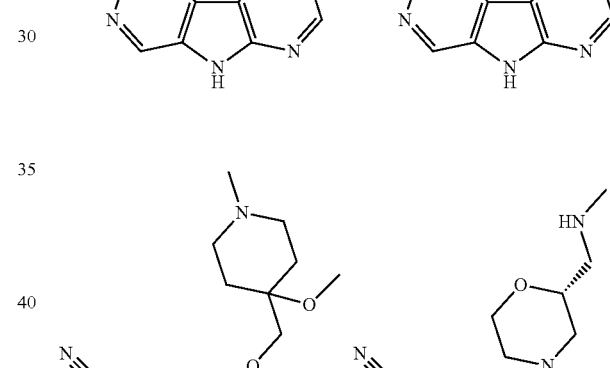
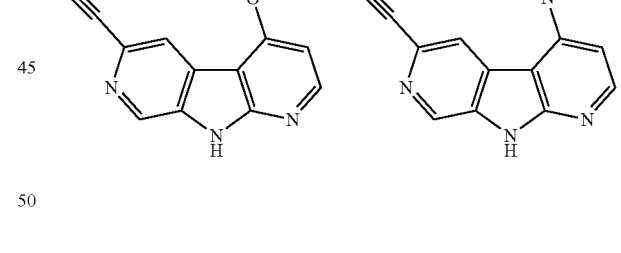
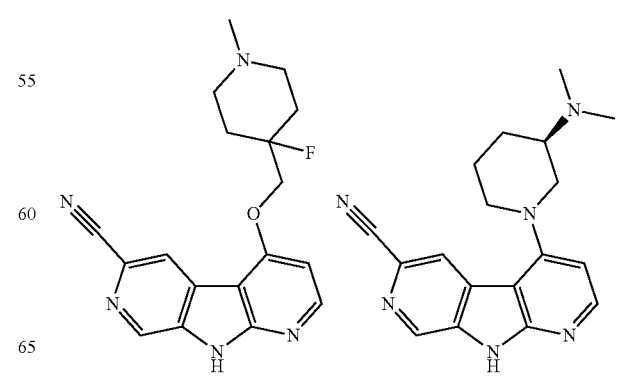

303
-continued
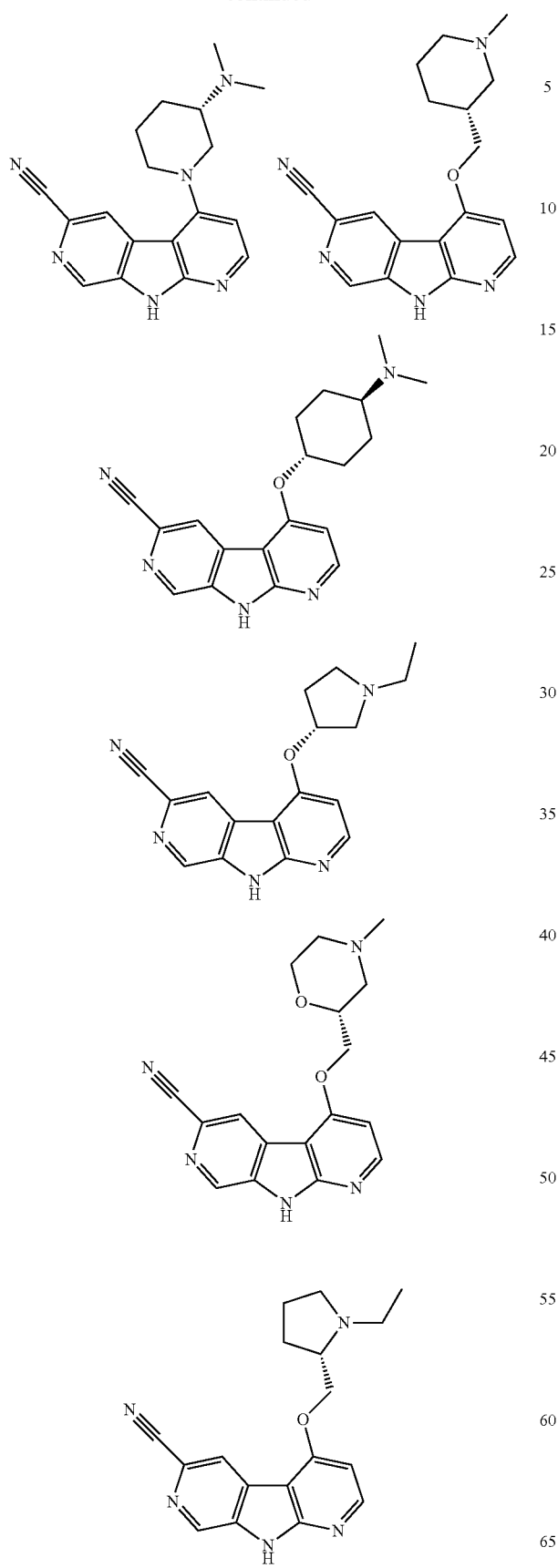
304
-continued
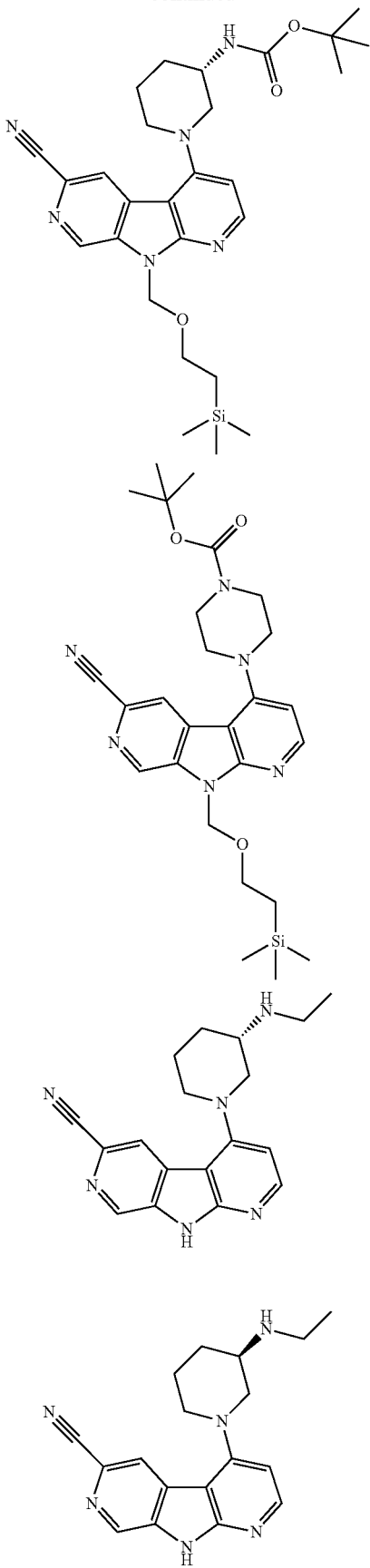

-continued
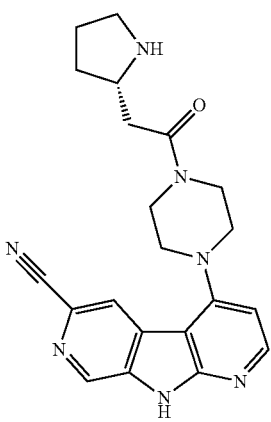
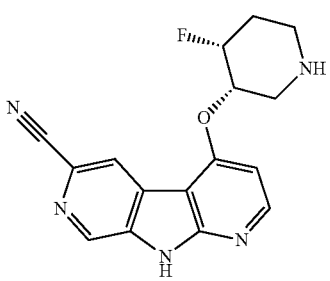
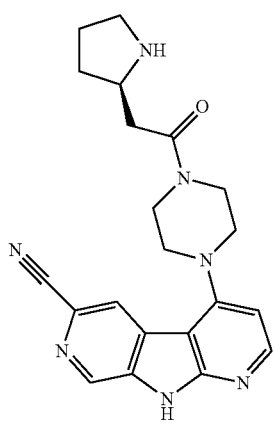
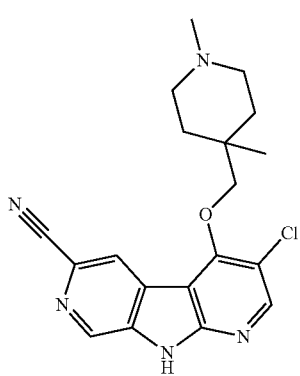
-continued
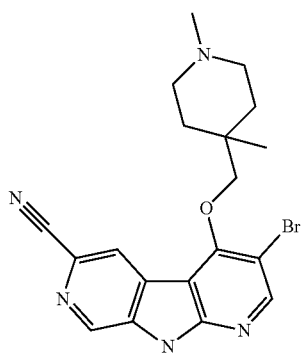
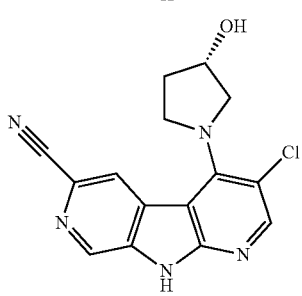
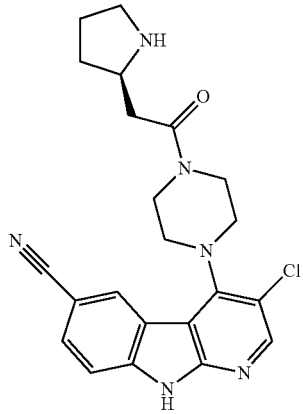
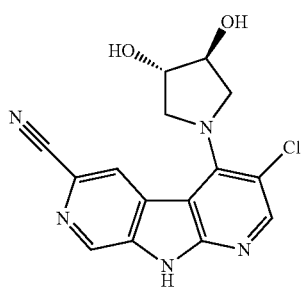
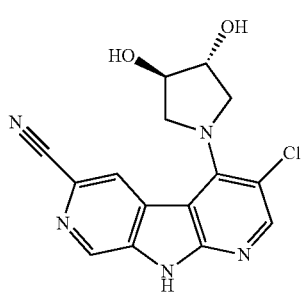

307
-continued
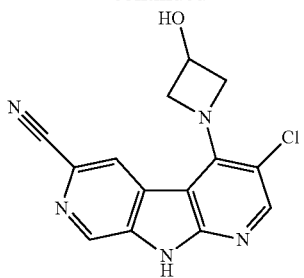
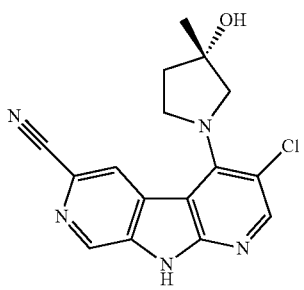
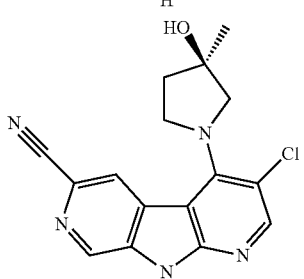
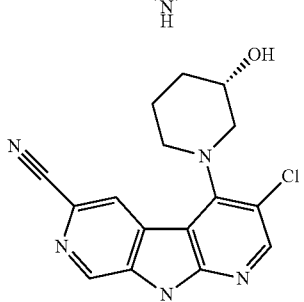
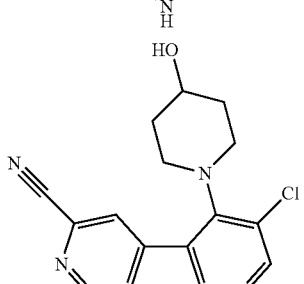
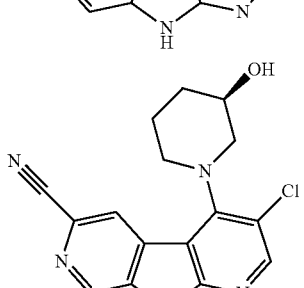
308
-continued
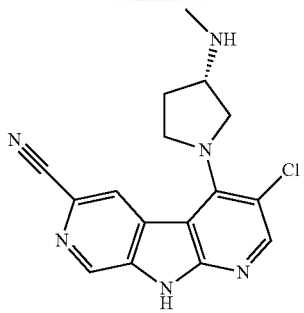
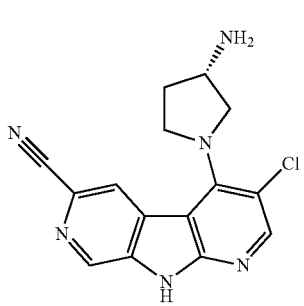
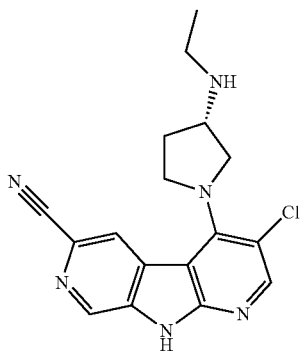
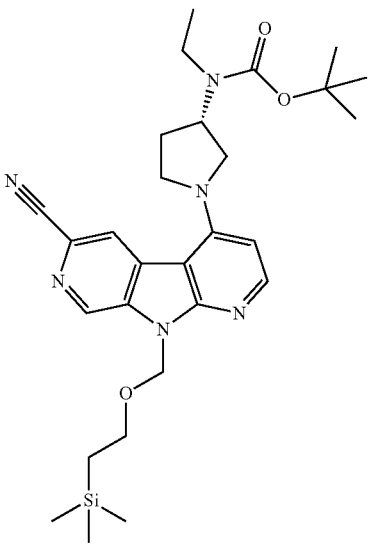

309
-continued
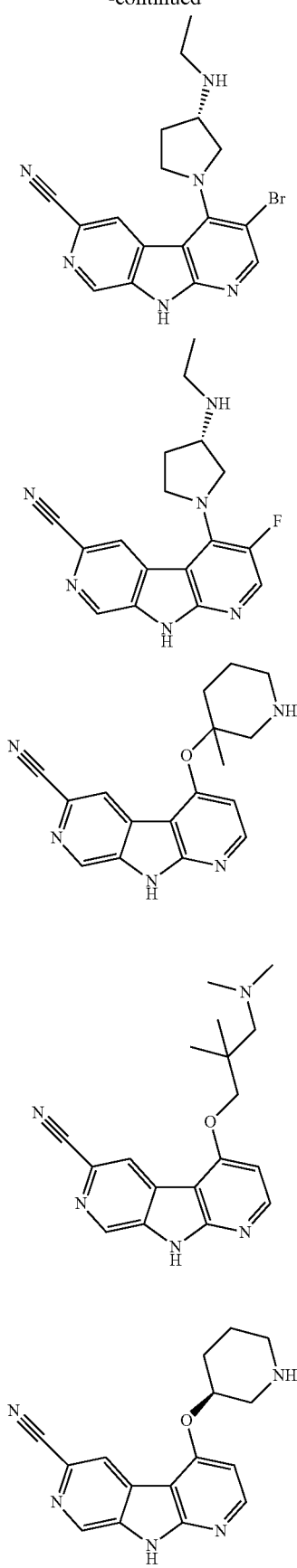
310
-continued
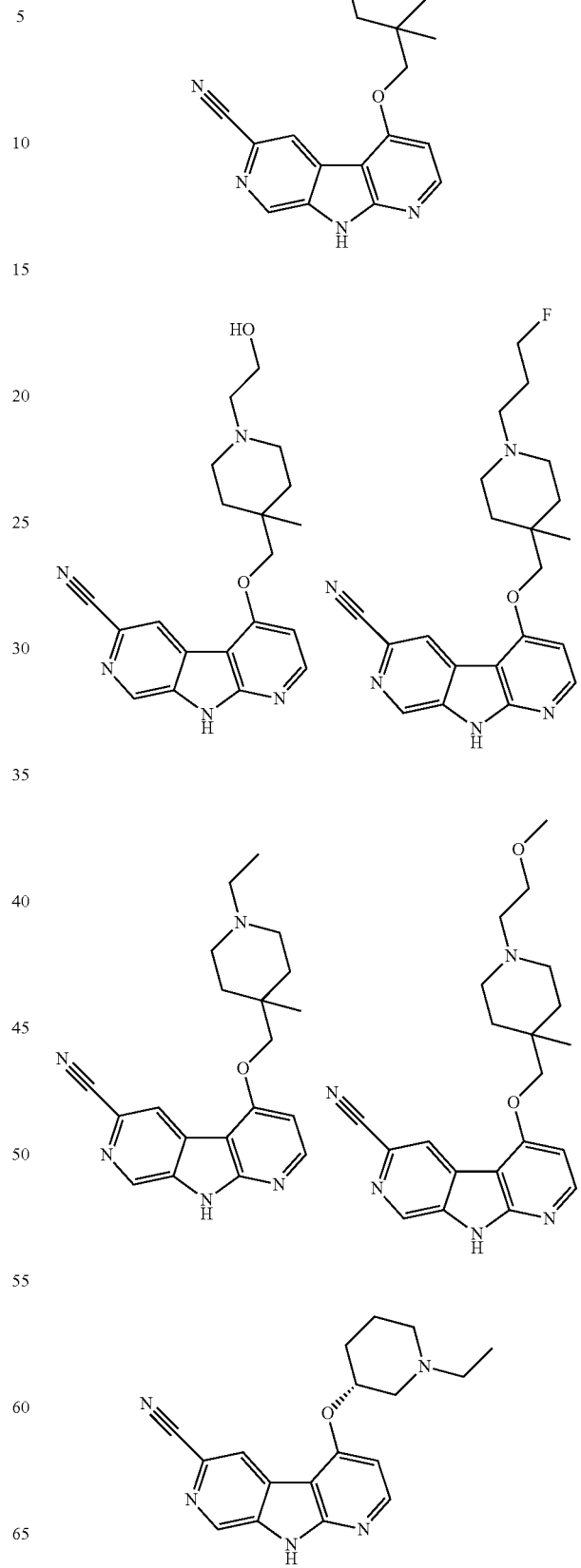

311
-continued
312
-continued
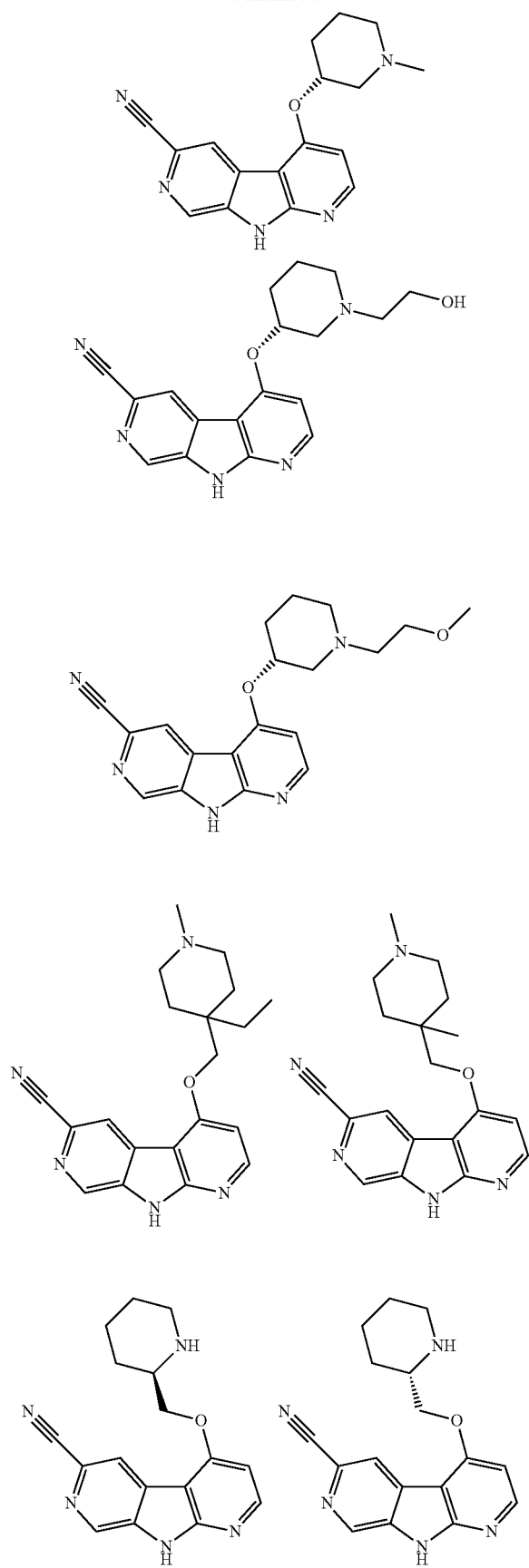
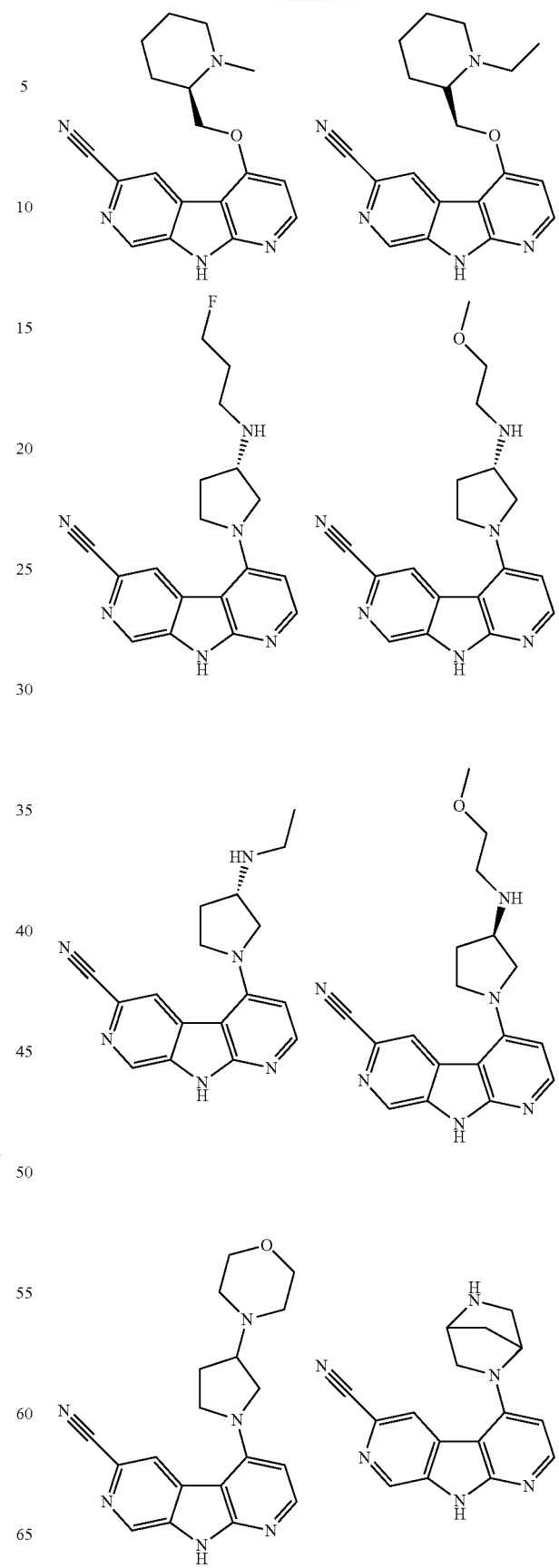

313
-continued
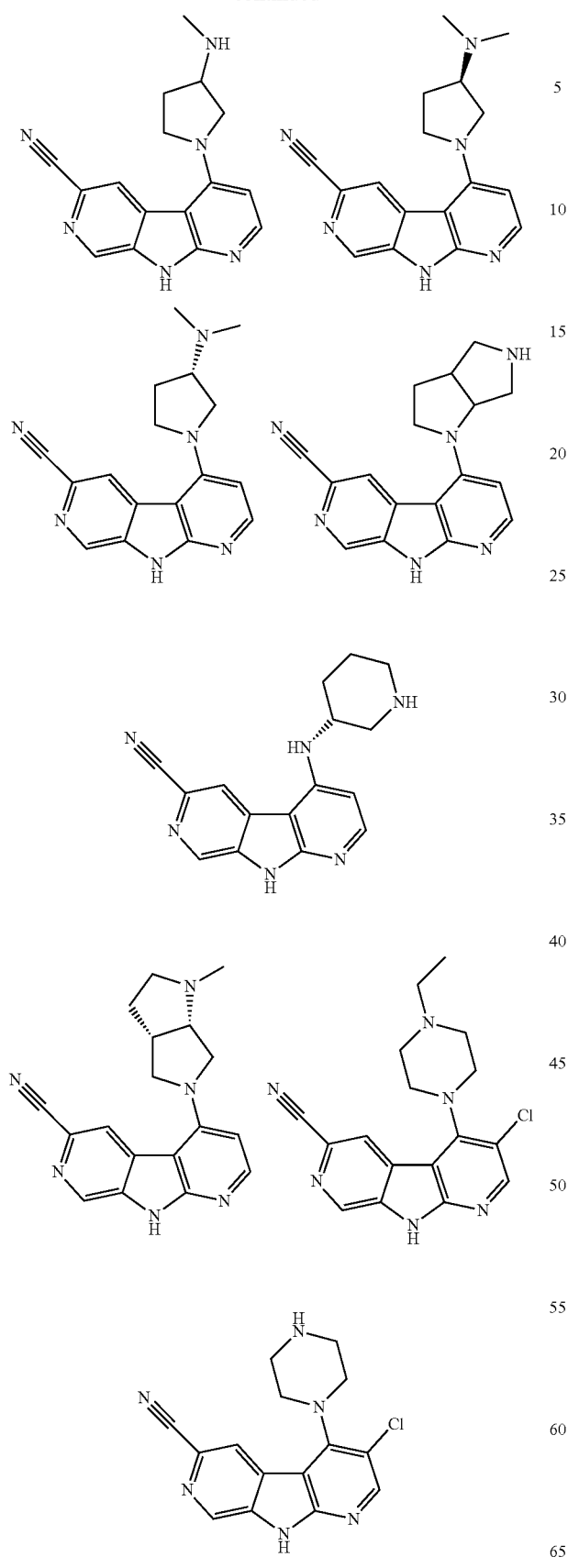
314
-continued
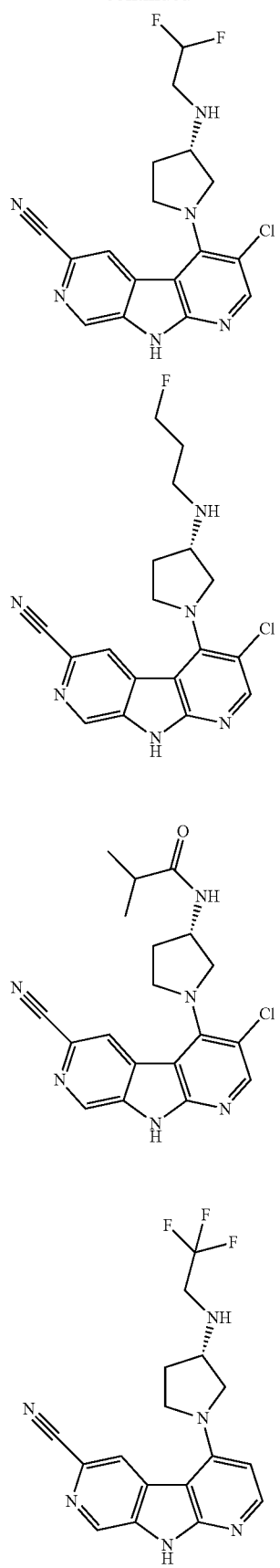

315
-continued
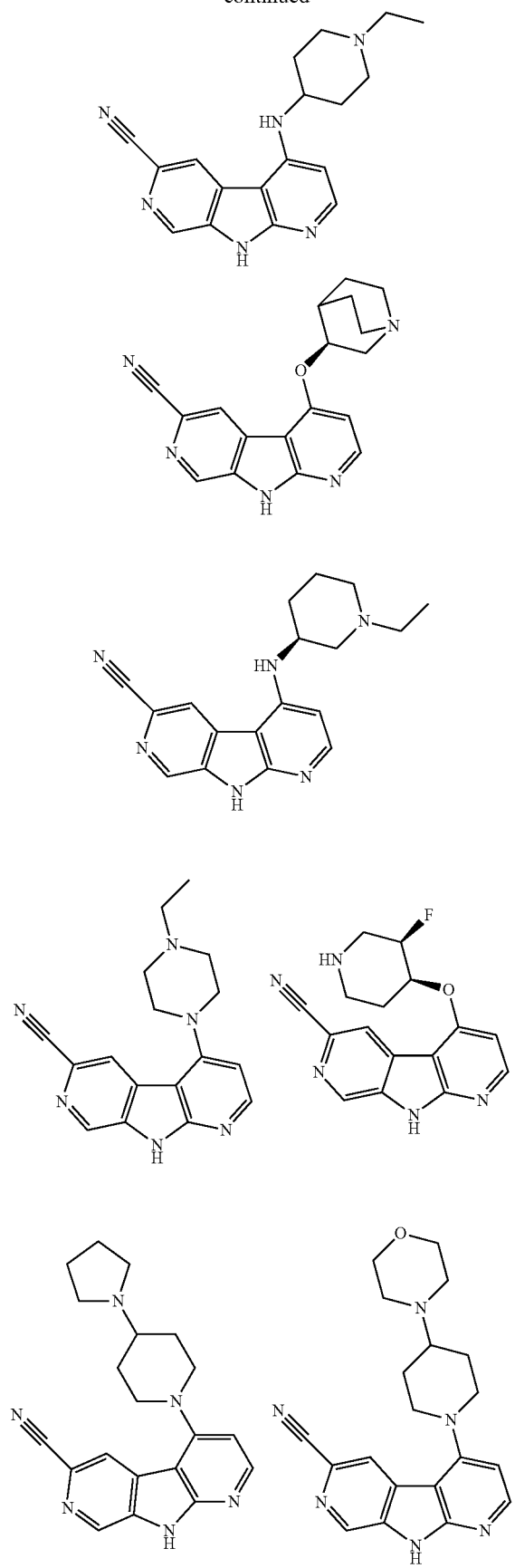
316
-continued
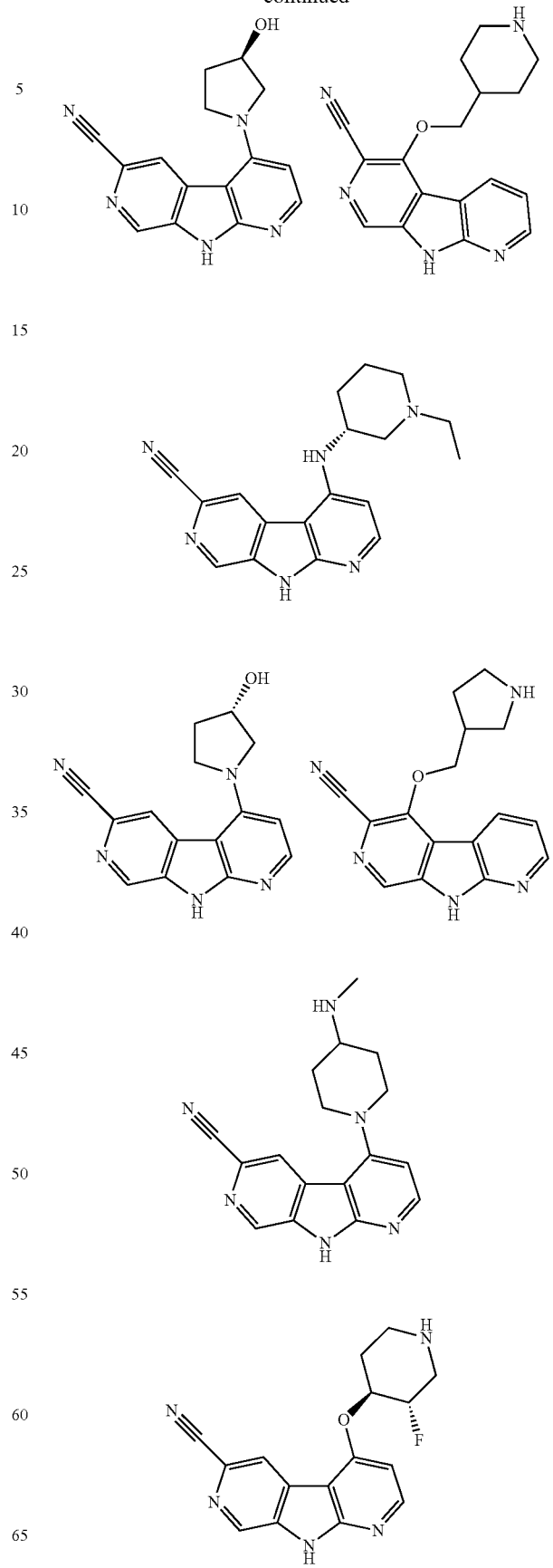

317
-continued
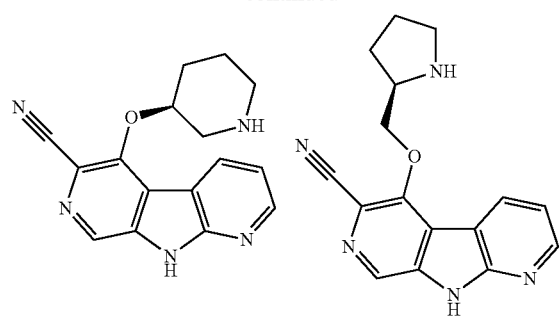
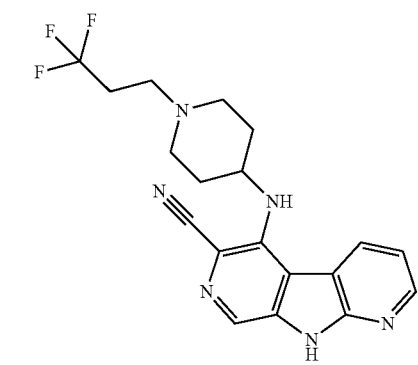
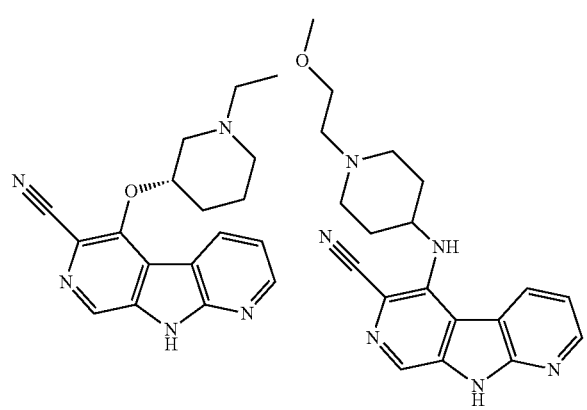
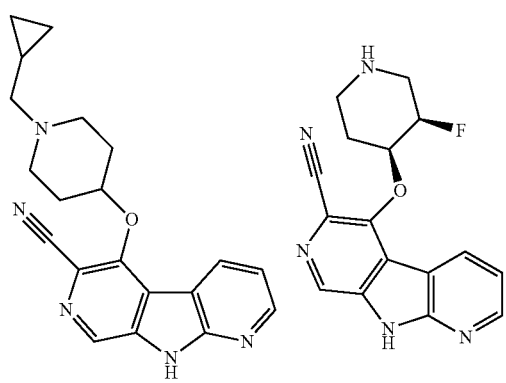
318
-continued
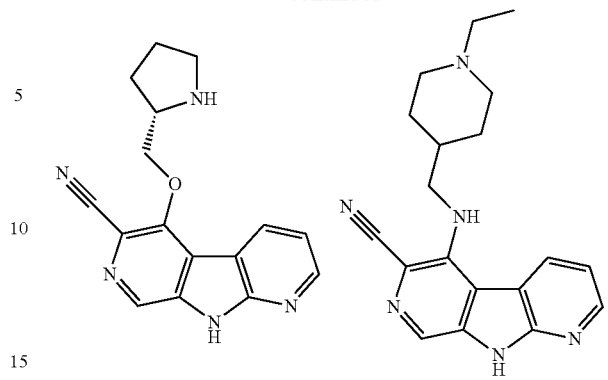
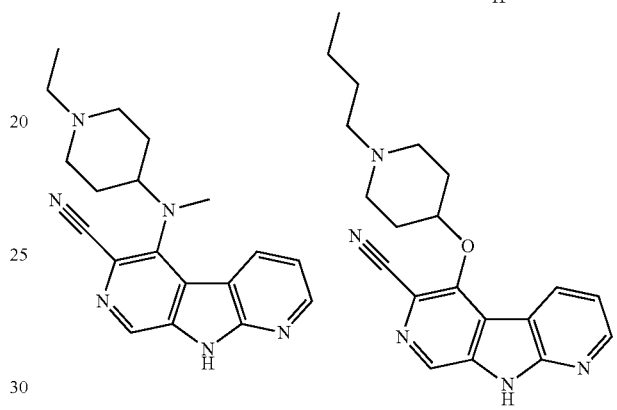
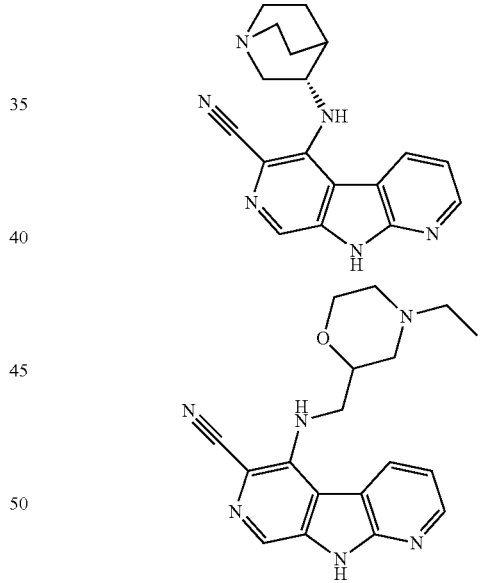
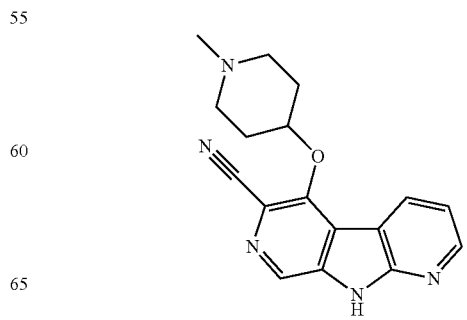

319
-continued
320
-continued
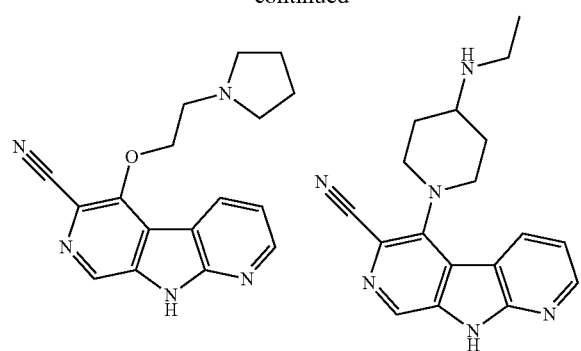
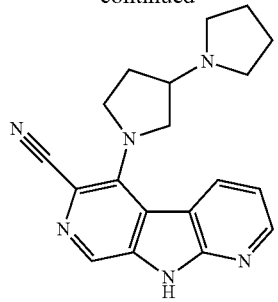
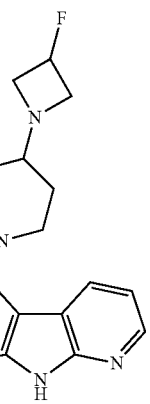
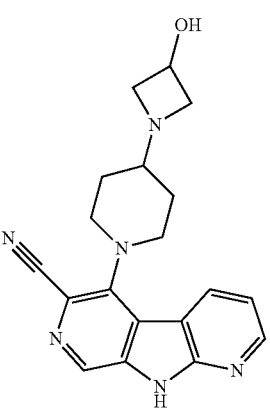
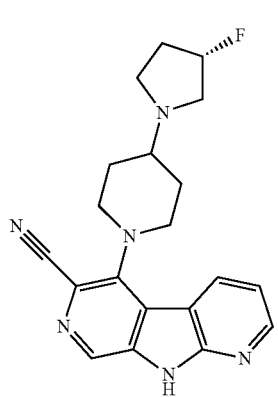
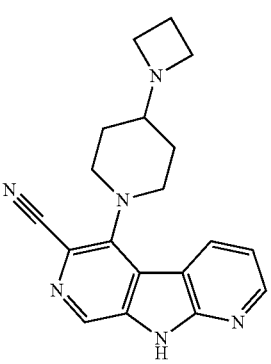
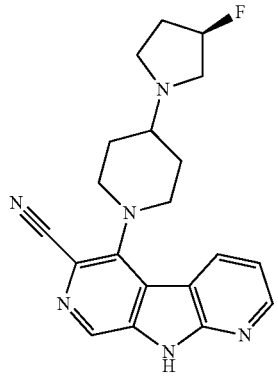

321
-continued
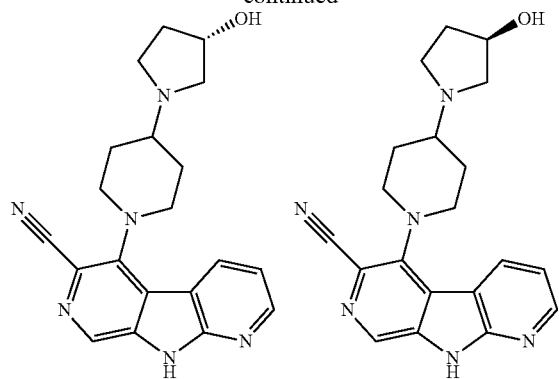
322
-continued
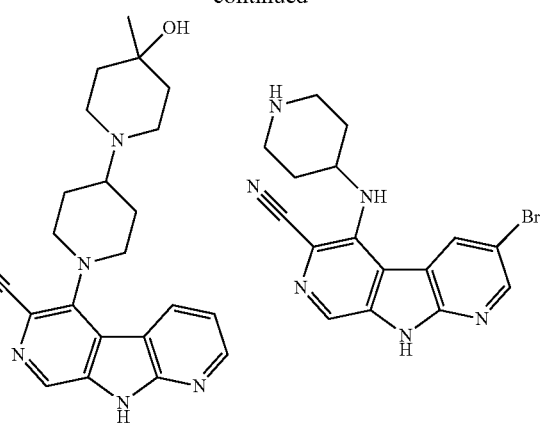
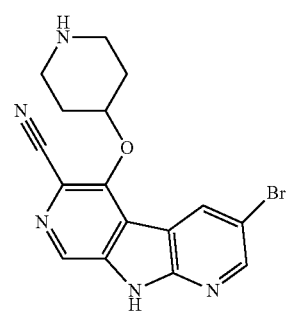
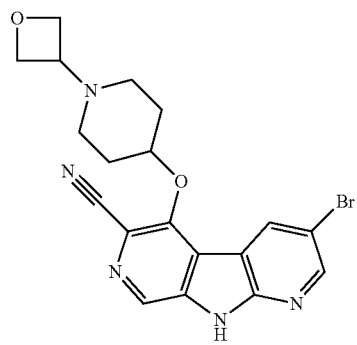
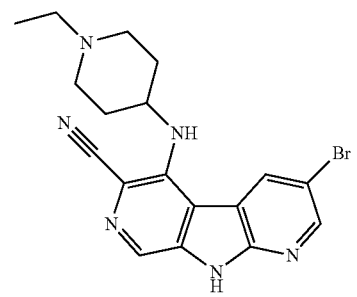
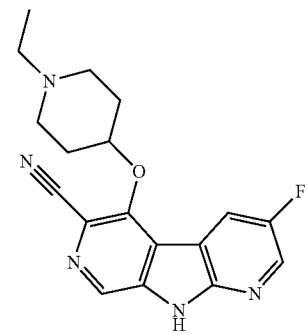

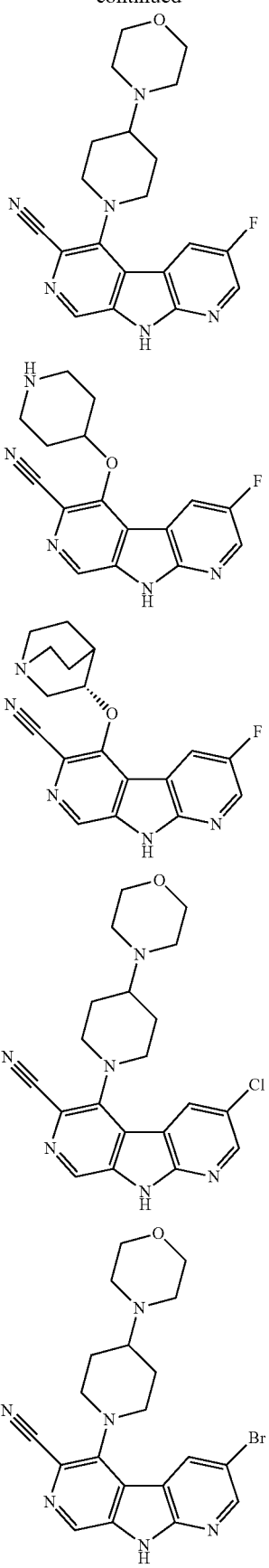
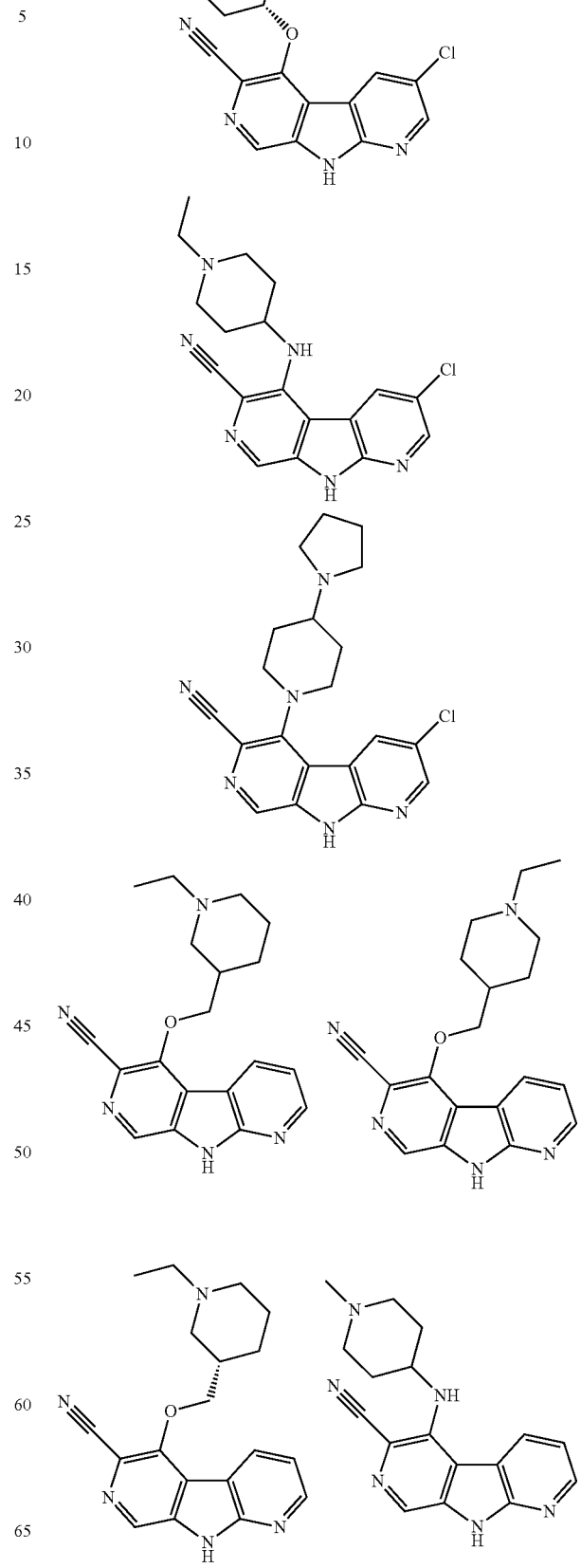

325
-continued
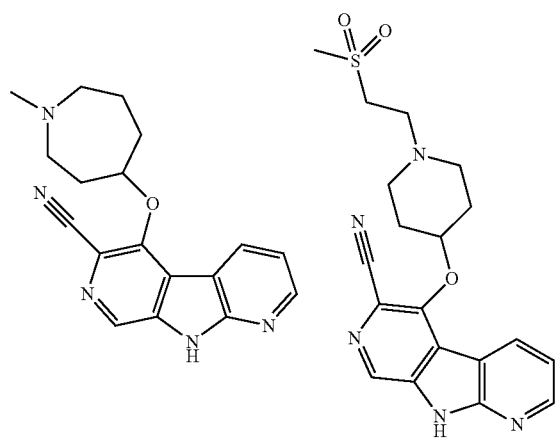
326
-continued
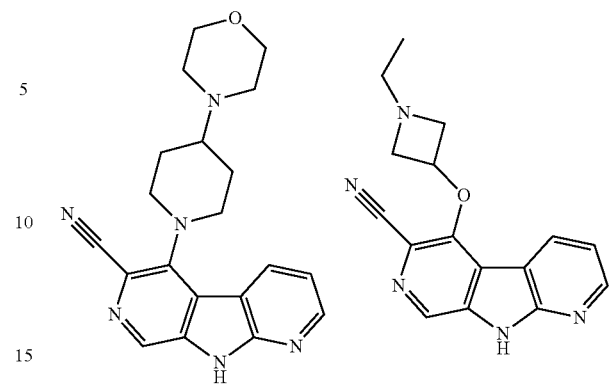
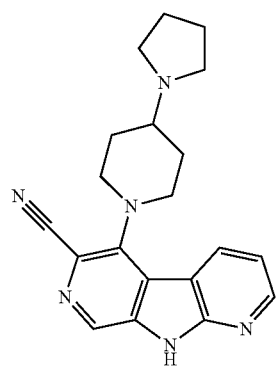
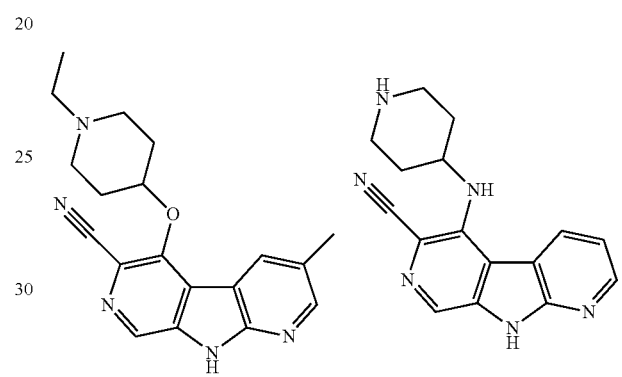
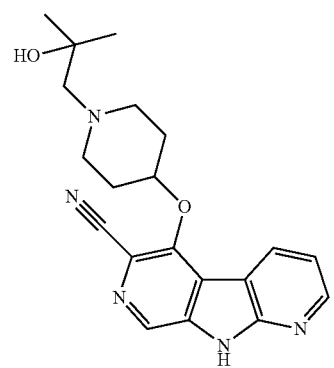
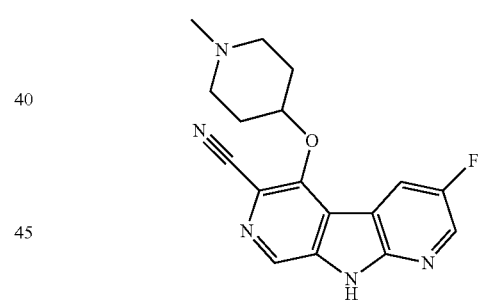
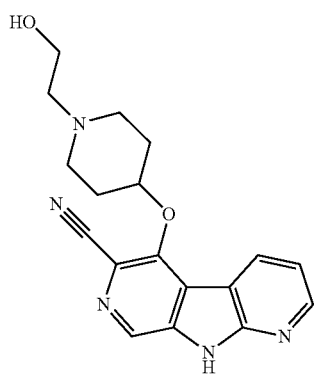
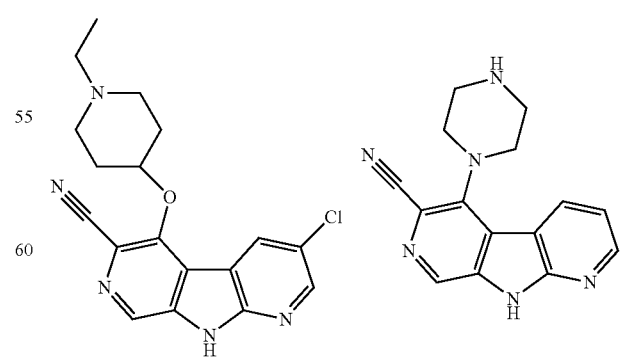

327
-continued

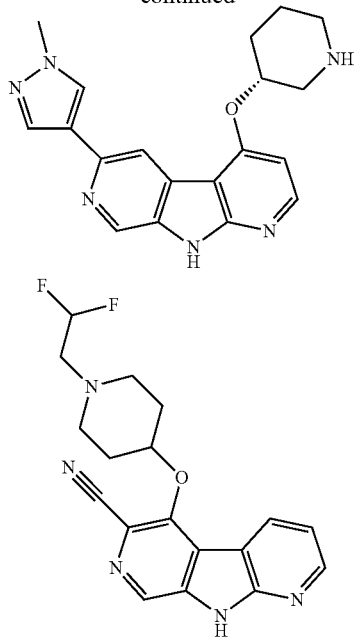

328
-continued

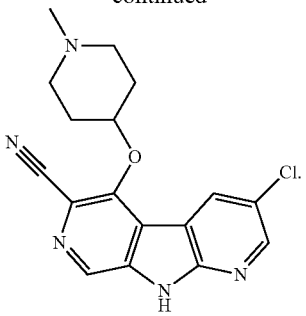

2. A pharmaceutical composition comprising a compound of claim 1 and a pharmaceutically acceptable carrier.

3. The pharmaceutical composition of claim 2, further comprising a second chemotherapeutic agent.

4. The pharmaceutical composition of claim 3, wherein said second chemotherapeutic agent is a DNA damaging agent.

5. The pharmaceutical composition of claim 3, wherein said second chemotherapeutic agent is selected from the group consisting of Gemcitabine, a topoisomer inhibitor, a MEK inhibitor, Irinotecan, SN-38, Xeloda and Ara-C.

* * * * *